(12) United States Patent
Rabea et al.

(10) Patent No.: US 12,378,231 B2
(45) Date of Patent: Aug. 5, 2025

(54) SMALL MOLECULES AS MONOACYLGLYCEROL LIPASE (MAGL) INHIBITORS, COMPOSITIONS AND USE THEREOF

(71) Applicant: APOGEE PHARMACEUTICALS, INC., Burnaby (CA)

(72) Inventors: Safwat Mohamed Rabea, Richmond (CA); David Earl Bogucki, Surrey (CA); Kaiji Hu, Burnaby (CA)

(73) Assignee: APOGEE PHARMACEUTICALS, INC., Burnaby (CA)

( * ) Notice: Subject to any disclaimer, the term of this patent is extended or adjusted under 35 U.S.C. 154(b) by 0 days.

(21) Appl. No.: 18/440,166

(22) Filed: Feb. 13, 2024

(65) Prior Publication Data
US 2024/0294514 A1   Sep. 5, 2024

Related U.S. Application Data

(60) Provisional application No. 63/445,124, filed on Feb. 13, 2023.

(51) Int. Cl.
| | |
|---|---|
| C07D 405/14 | (2006.01) |
| A61K 31/4192 | (2006.01) |
| A61K 31/454 | (2006.01) |
| A61K 31/496 | (2006.01) |
| A61K 31/551 | (2006.01) |
| A61K 45/06 | (2006.01) |
| C07D 401/12 | (2006.01) |
| C07D 471/04 | (2006.01) |
| C07D 491/056 | (2006.01) |

(52) U.S. Cl.
CPC ........ C07D 405/14 (2013.01); A61K 31/4192 (2013.01); A61K 31/454 (2013.01); A61K 31/496 (2013.01); A61K 31/551 (2013.01); A61K 45/06 (2013.01); C07D 401/12 (2013.01); C07D 471/04 (2013.01); C07D 491/056 (2013.01)

(58) Field of Classification Search
CPC .. C07D 405/14; C07D 401/12; C07D 471/04; C07D 491/056; A61K 31/4192; A61K 31/454; A61K 31/496; A61K 31/551; A61K 45/06
See application file for complete search history.

(56) References Cited

U.S. PATENT DOCUMENTS

| | | | |
|---|---|---|---|
| 7,700,368 B2 | 4/2010 | Flockhar et al. | |
| 10,000,450 B2 * | 6/2018 | Kurimura | ............... A61P 25/36 |
| 10,610,520 B2 | 4/2020 | Ikeda et al. | |
| 11,147,805 B2 | 10/2021 | Rashmi et al. | |
| 11,274,101 B2 | 3/2022 | Kamata et al. | |
| 2018/0264121 A1 | 2/2018 | Donaduzzi et al. | |
| 2021/0188798 A1 | 6/2021 | Mueller | |

FOREIGN PATENT DOCUMENTS

| | | |
|---|---|---|
| WO | 0232420 A1 | 4/2002 |
| WO | 2004026802 A1 | 4/2004 |
| WO | 2006116773 A2 | 11/2006 |
| WO | 2009052320 A1 | 4/2009 |
| WO | 2010056309 A2 | 5/2010 |
| WO | 2013098402 A1 | 7/2013 |
| WO | 2014100231 A1 | 6/2014 |
| WO | 2014127458 A1 | 8/2014 |
| WO | 2015003002 A1 | 1/2015 |
| WO | 2015065179 A1 | 5/2015 |
| WO | 2015179559 A2 | 11/2015 |
| WO | 2016014975 A2 | 1/2016 |
| WO | 2017021805 A1 | 2/2017 |

(Continued)

OTHER PUBLICATIONS

Xu et al. Synthesis of Substituted Diarylmethylenepiperidines, a Novel Class of Anti-HIV agents(Bioorganic & Medicinal Chemistry, 10, p. 2807-2816) (Year: 2002).*
Konstantinova et al. Chemoenzymatic Method of 1,2,4-Triazole Nucleoside Synthesis: Possibilities and Limitations (Russian Journal of Bioorganic Chemistry, 39:1, 53-71). (Year: 2013).*
Teixeira et al. Inosine protects against impairment of memory induced by experimental model of Alzheimer disease, (Psychopharmacology, 237: 811-823). (Year: 2020).*
Aubin, A., "Purification of Cannabidiol from Hemp Oil Using the Prep150 LC System." Water Application Notes. http://www.waters.com/waters/webassets. 2015.
Bachovchin, D.A. et al. "The pharmacological landscape and therapeutic potential of serine hydrolases" Nat Rev. Drug Discov, 2012, vol. 11(1), p. 52-68.

(Continued)

Primary Examiner — Joseph K McKane
Assistant Examiner — Meghan C Heasley
(74) Attorney, Agent, or Firm — RAPHAEL BELLUM PLLC

(57) ABSTRACT

Disclosed are compounds of Formula I that are useful as Monoacylglycerol lipase (MAGL) inhibitors

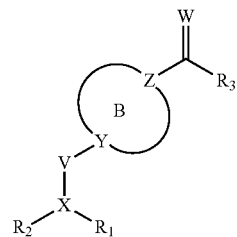

Formula I These compounds may be used in pharmaceutical compositions, formulations, and methods for the treatment of disease states, disorders, and conditions benefited by the inhibition or modulation of MAGL activity, such as, but are not limited to, anxiety and mood disorder, metabolic disorder, a neurodegenerative disorder, mental disorder, brain disorder, pain, inflammatory disorder, cancer, Alzheimer's disease, movement disorders, epilepsy or stroke.

27 Claims, No Drawings

(56) References Cited

FOREIGN PATENT DOCUMENTS

| WO | 2017170830 A1 | 10/2017 |
|---|---|---|
| WO | 2018053447 A1 | 3/2018 |
| WO | 2018093949 A1 | 5/2018 |
| WO | 2018109471 A1 | 6/2018 |
| WO | 2018134695 A1 | 7/2018 |
| WO | 2018134698 A1 | 7/2018 |
| WO | 2018217809 A1 | 11/2018 |
| WO | 2019046318 A1 | 3/2019 |
| WO | 2019046330 A1 | 3/2019 |
| WO | 201906579 A1 | 4/2019 |
| WO | 2019105915 A1 | 6/2019 |
| WO | 2019152917 A1 | 8/2019 |
| WO | 2019180185 A1 | 9/2019 |
| WO | 2019222266 A1 | 11/2019 |
| WO | 2020016710 A1 | 1/2020 |
| WO | 2020035424 A1 | 2/2020 |
| WO | 2020035425 A1 | 2/2020 |
| WO | 2020104494 A1 | 5/2020 |
| WO | 2020154683 A1 | 7/2020 |

OTHER PUBLICATIONS

Bedse et al. "Therapeutic endocannabinoid augmentation for mood and anxiety disorders: comparative profiling of FAAH, MAGL and dual inhibitors" Translational Psychiatry, 2018, vol. 8(1), p. 92.
Blessing et al., "Cannabidiol as a potential treatment for anxiety disorders", Neurotherapeutics, 2015, vol. 12(4), p. 825-836.
Chou, T.C. et al. "CompuSyn for drug combinations: PC software and user's guide, A Computer Program for Quantitation of Synergism and Antagonism in Drug Combinations, and the Determination of IC50 and ED50 and LD50 Values" CompuSyn, PD Science, 2005, p. 7652-1754.
Consroe, P. et al. "Controlled clinical trial of cannabidiol in Huntington's disease" Pharmacol Biochem Behav, 1991, vol. 40(3), p. 701-708.
Cunha, J.M., et al. "Chronic administration of cannabidiol to healthy volunteers and epileptic patients" Pharmacology, 1980, vol. 21(3), p. 175-185.
Deng H, Li W. "Monoacylglycerol lipase inhibitors: modulators for lipid metabolism in cancer malignancy, neurological and metabolic disorders" Acta Pharm Sin B., 2020, vol. 10(4), p. 582-602.
Fu, J., et al. "Drug combination in vivo using combination index method: Taxotere and T607 against colon carcinoma HCT-116 xenograft tumor in nude mice" 2016, vol. 3(3), p. 15-30.
Guindon J, Hohmann AG, "CNS Neurol Disord Drug Targets" 2009, vol. 8(6), p. 403-421.
Huestis, M.A., "Human cannabinoid pharmacokinetics" Chem Biodivers, 2007, vol. 4(8), p. 1770-1804.
Karlsson, M., et al. "cDNA Cloning, Tissue Distribution, and Identification of the Catalytic Triad of Monoglyceride Lipase" Journal of Biological Chemistry, 1997, vol. 272(43), p. 27218-27223.
Kohnz R., et al. "Chemical approaches to therapeutically target the metabolism and signaling of the endocannabinoid 2-AG and eicosanoids" Chem Soc Rev., 2014.
Korhonen, J., et al. "Piperazine and piperidine carboxamides and carbamates as inhibitors of fatty acid amide hydrolase (FAAH) and monoacylglycerol lipase (MAGL)" Bioorganic & Medicinal Chemistry 22, 2014, p. 6694-6705.

Malamas, M.S., et al. "Design and sysnthesis of highly potent and specific ABHD6 inhibitors" ChemMedChem, 2023, vol. 18, e202100406 pp. 1-15.
Narayanaswami K et al. "Stability of *Cannabis sativa* L. samples and their extracts, on prolonged storage in Delhi" United Nations Office on Drugs and Crime (UNODC), 1978.
Pertwee, Handbook of Cannabis. 2014, Oxford: Oxford University Press. 784.
Remington, J.P. et al. "Remington's pharmaceutical sciences" 1990, Easton, PA.: Mack Pub. Co Chapters 89-92.
Remington, J.P. et al. "Remington's pharmaceutical sciences" 1990, Easton, PA.: Mack Pub. Co Chapters 82-88.
Remington, J.P. et al., "Remington's pharmaceutical sciences" 1990, Easton, PA.: Mack Pub. Co Chapters 75-81.
Repetto, M. et al. "Separation of cannabinoids" United Nations Office on Drugs and Crime (UNODC), 1976.
Sciolino et al., "Enhancement of endocannabinoid signaling with JZL 184, an inhibitor of the 2-arachidonoylglycerol hydrolyzing enzume monoacylglycerol lipase, produces anxiolytic effects under conditions of high environmental aversiveness in rats", Pharmacological Research, 2011, vol. 64(3), p. 226-234.
Smith, R.N. et al. "The decomposition of acidic and neutral cannabinoids in organic solvents" Journal of Pharmacy and Pharmacology, 1977, vol. 29(1), p. 286-290.
Stasiulewicz A, et al. "A Guide to Targeting the Endocannabinoid System in Drug Design" Int J Mol Sci., 2020, vol. 21 (8), p. 2778.
Tiwari P, et al. "Phytochemical screening and Extraction: A Review" Internationale Pharmaceutica Sciencia, 2011, vol. 1(1), p. 100-106.
Ulugöl A. "The endocannabinoid system as a potential therapeutic target for pain modulation" Balkan Med J. 2014, vol. 31(2), p. 115-20. doi: 10.5152/balkanmedj.2014.13103. Epub Jun. 1, 2014. PMID: 25207181; PMCID: PMC4115931.
Vuckovic, S. et al. "Cannabinoids and Pain: New insights from old molecules" Frontiers in Pharmacology, 2018, p. 1-19.
Zanfirescu A, et al. "Targeting Monoacylglycerol Lipase in Pursuit of Therapies for Neurological and Neurodegenerative Diseases. Molecules" 2021, vol. 26(18), p. 5668. doi: 10.3390/molecules26185668. PMID: 34577139; PMCID: PMC8468992.
Zuardi, A.W. "Cannabidiol: from an inactive cannabinoid to a drug with wide spectrum of action" Braz J Psychiatr, 2008, vol. 30(3), p. 271-280.
Zuardi, A.W., et al. "Effects of ipsapirone and cannabidiol on human experimental anxiety" J Psychopharmacol, 1993, vol. 7(1 Suppl), p. 82-88.
Narayanaswami, K. et al., "Stability of *Cannabis sativa* L. samples and their extracts, on prolonged storage in Delhi" UNODC—Bulletin of Narcotics, 1978, vol. 4(006), p. 1-12.
Pertwee, R. "Handbook of Cannabis" DOI: 10.1093/acprof:oso/9780199662685.011.0001, 2014.
Gennaro, A. R., "Remington's Pharmaceutical Sciences" Mack Publishing Company, 1990, Chapters 89-92, p. 1633-1712.
Gennaro, A. R., "Remington's Pharmaceutical Sciences" Mack Publishing Company, 1990, Chapters 82-88, p. 1513-1632.
Gennaro, A. R., "Remington's Pharmaceutical Sciences" Mack Publishing Company, 1990, Chapters 75-81, p. 1435-1512.
Repetto, M. et al. "Separation of cannabinoids" UNODC—Bulletin on Narcotics, 1976, vol. 4(007), p. 69-74.
Sciolino, N. R. et al., "Enhancement of endoannabinoid signaling with JZL 184, an inhibitor of the 2-arachidonoylgycerol hydrolyzing enzyme monoacylglycerol lipase, produces anxiolytic effects under conditions of high environmental aversiveness in rats" Pharmacol Res., 2011, vol. 64(3), p. 226-234.

\* cited by examiner

SMALL MOLECULES AS MONOACYLGLYCEROL LIPASE (MAGL) INHIBITORS, COMPOSITIONS AND USE THEREOF

FIELD OF THE INVENTION

The present disclosure relates to novel compounds that are monoacylglycerol lipase (MAGL) inhibitors or modulators, compositions comprising the compounds and uses of the compounds and compositions.

BACKGROUND OF THE INVENTION

Naturally-occurring, plant-derived cannabinoids such as tetrahydrocannabinol (THC), the psychomimetic component found in *Cannabis*, exhibit neuro-behavioral effects by interacting with the (cannabinoid) CB1 receptor. The direct activation of the CB1 receptor by THC and other potent CB1 agonists produces a well-known 'tetrad' of in vivo effects, namely antinociception, hypothermia, hypolocomotion and catalepsy; only antinociception is useful therapeutically, i.e., for alleviating pain (producing analgesia). However, strong CB1 agonists may also give rise to behaviors associated with physical dependence and abuse liability (Vučković S. et al., Front Pharmacol. 2018 November; 9:1259). To date, it has proved difficult to uncouple these beneficial and untoward properties, thus limiting the therapeutic utility of direct CB1 agonists.

The endocannabinoid system (ECS) is comprised of endogenous cannabinoids (called endocannabinoids), the enzymes responsible for the synthesis and degradation of the endocannabinoids (Lu H C, Mackie K., Biol Psychiatry. 2016; 79(7):516-525), as well as the pharmacological targets of the endocannabinoids, the cannabinoid receptors CB1 and CB2. The two primary endocannabinoids are anandamide (AEA) and 2-arachidonoylglycerol (2-AG). Endocannabinoids, such as 2-AG (Sugiura et al., Biochem Biophys Res Commun. 1995 Oct. 4; 215(1):89-97) and AEA, are endogenous agonists of the CB receptors and are produced throughout the brain regions associated with emotionality and are believed to modulate behavioral responses to stress-related conditions (Patel S, Hillard C J., Curr Top Behav Neurosci. 2009; 1:347-371). Inhibition of 2-AG and AEA degradation can increase the endogenous pools of 2-AG and AEA thereby stimulating ECS resulting in diverse physiological effects. 2-AG is metabolized by monoacylglycerol lipase (MAGL) whereas AEA is metabolized by fatty acid amide hydrolase (FAAH). Inhibition of these enzymes increases brain levels of the appropriate endogenous cannabinoid without direct activation of the receptors and associated side effects. Modulation of ECS via inhibition of MAGL can result in diverse physiological processes including, inflammation, pain, anxiety, cognition, neurodegeneration, feeding, metabolic syndromes, wound healing and cough. with therapeutical implications (for example, see; Kohnz R, Chem Soc Rev 2014; Guindon J, Hohmann A G, CNS Neurol Disord Drug Targets. 2009 December; 8(6): 403-21).

MAGL is the main enzyme responsible for the degradation of 2-AG, namely hydrolysis to arachidonic acid (AA) and glycerol (Griebel G et al., (2015). Scientific reports, 5, 7642). Pharmacological inhibition of MAGL leads to analgesic, anti-inflammatory, anxiolytic, and antidepressant effects in both rats and humans (Zanfirescu A et al., Molecules. 2021, 18; 26(18):5668; Stasiulewicz A et al., Int J Mol Sci. 2020 Apr. 16; 21(8):2778; Deng H, Li W., Acta Pharm Sin B. 2020 April; 10(4):582-602). Thus, MAGL is considered a promising target for the treatment of many diseases and conditions involving ECS.

A number of heterocyclic-based compounds have been reported in various publications as MAGL modulators such as Intl. Patent Appl. Nos. WO 2020/104494, WO 2020/104494, WO 2020/035424, WO 2020/035425, WO 2019/065791, and WO 2019/105915. Certain piperazinyl compounds as MAGL modulators are described in Intl. Patent Appl. Nos. WO 2020/104494, WO 2019/180185, WO 2019/222266, WO 2018/217809, and WO 2018/053447. Heterocyclic spiro compounds are described in Intl. Patent Appl. Nos. WO 2018/134698, WO 2019/046318, WO 2019/046330, and WO 2020/016710. Certain carbamate and urea derivatives are described in Intl. Patent Appl. Nos. WO 2020/154683, WO 2018/134695, WO 2018/093949, and WO 2017/021805. However, there remains a desire for potent MAGL modulators with suitable pharmaceutical properties.

SUMMARY OF THE INVENTION

This disclosure relates to novel molecules of formulas I-V, their prodrug forms, pharmaceutically acceptable salts thereof, or combination thereof, process for their preparation, methods, composition and formulation in a delivery system for the prevention and/or treatment of diseases or medical conditions benefited by MAGL inhibition and/or modulation. The composition and/or formulation include disclosed compounds as at least one active ingredient. Furthermore, molecules, pharmaceutical composition and formulation may be combined with one or more therapeutic agents or compounds to prevent and/or treat diseases or medical conditions.

In one aspect, the active ingredient may be compound of Formulas I-V described herein. Compound of Formulas I-V may act as MAGL modulators, inhibitors, or as modulators and inhibitors. Inhibition of MAGL will slow the normal degradation of endogenous endocannabinoid ligand 2-arachidonylglycerol (2-AG) and thereby allow the accumulation of 2-AG. A higher level of 2-AG can induce increased stimulation of cannabinoid receptors CB1 and CB2 and produce diverse physiological effects related to the activation the cannabinoid receptors.

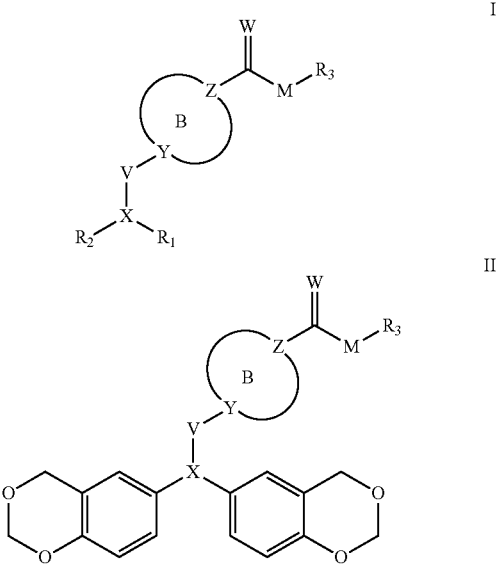

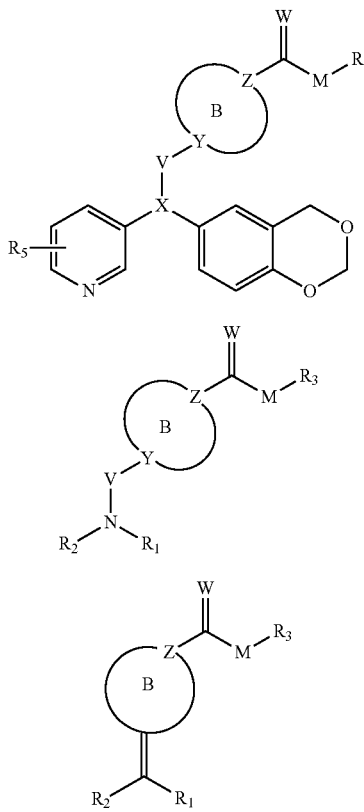

According to an aspect of the invention, there is provided a compound having the Formula I:

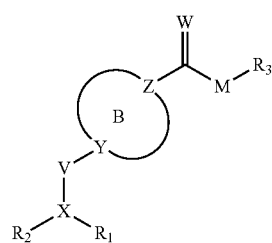

Formula 1 a prodrug thereof, a pharmaceutically acceptable salt thereof, or a pharmaceutically active metabolite thereof,
wherein
a. X is C or N;
b. V is O, N(CH$_3$), or none, wherein when V is none X is directly attached to Y by single or double bond;
c. Y is C or N;
d. Z is C or N;
e. W is O or S;
f. M is O, N, or none, wherein when M is none C=W is directly attached to R$_3$;
g. B is C$_{1-6}$ alkyl, C$_{4-10}$ heterocycloalkyl, C$_{6-12}$ fused heterocycloakyl, C$_{6-12}$ spirocycloalkyl, azetidine, azepanyl, piperazinyl, piperidinyl, diazepanyl, 2-azaspiro[3.3]heptane, 2,5-diazabicyclo[2.2.1]heptane, 8-azabicyclo[3.2.1]octane, 2,6-diazaspiro[3.4]octane, 2,7-diazaspiro[3.5]nonane, 2,7-diazaspiro[4.4]nonane, or 3,9-diazaspiro[5.5]undecane;

h. R$_1$ and R$_2$ are each independently aryl, heteroaryl, heterocyclyl, phenyl, pyridyl, benzo-1,3-dioxanyl, benzo-1,4-dioxanyl, benzofuranyl, dihydrobenzofuranyl, benzopyrazolyl, or quinolinyl, wherein each group may be unsubstituted, monosubstituted or disubstituted with an R$_5$ group; wherein R$_5$ may be one of the following moieties: alkyl, alkoxy, alkenoxy, halogen, cyano, or pyrazolyl.

i. R$_3$ is C$_1$-C$_6$ alkyl, C$_3$-C$_6$ cycloalkyl, C$_4$-C$_8$ heterocloalkyl, aryl, heteroaryl, piperidinyl, piperazinyl, morpholinyl, phenyl, pyridinyl, imidazolyl, pyrazolyl, benzopyrazolyl, triazolyl, benzotriazolyl, pyridotriazolyl, or indanyl; and R$_3$ may be unsubstituted or substituted with R$_4$ group; wherein R$_4$ may be one of the following moieties: F, Cl, Br, CF$_3$, NO$_2$, CN, O, OCH$_3$, OCF$_3$, C$_1$-C$_6$ alkyl, C$_1$-C$_6$ alkyloxy, C$_6$H$_5$, OC$_6$H$_5$, or C(O)OCH$_3$, or wherein M and R$_3$ together form a leaving group.

In some embodiments, R$_1$ and/or R$_2$ is an oxygen-containing heterocyclyl.

In some embodiments, R$_1$ and/or R$_2$ is/are a benzo-dioxanyl. For example, in some embodiments at least one of R$_1$ and R$_2$ may be a benzo-dioxanyl. In some embodiments, R$_1$ and R$_2$ are each independently a benzo-dioxanyl.

In some embodiments, R$_1$ and/or R$_2$ is/are benzo-1,3-dioxanyl. For example, at least one of R$_1$ and R$_2$ may be a benzo-1,3-dioxanyl.

In some embodiments, the compound has Formula II:

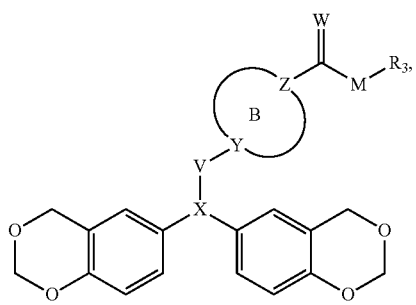

a prodrug thereof, a pharmaceutically acceptable salt thereof, or a pharmaceutically active metabolite thereof.

In some embodiments, R$_1$ is benzo-1,3-dioxanyl; and R$_2$ is aryl, heteroaryl, phenyl, pyridyl, benzo-1,4-dioxanyl, benzofuranyl, dihydrobenzofuranyl, benzopyrazolyl, or quinolinyl, whereingroup may be unsubstituted, monosubstituted or disubstituted with R$_5$ group; wherein R$_5$ may be one of the following moieties: alkyl, alkoxy, alkenoxy, halogen, cyano, or pyrazolyl.

In some embodiments, R$_1$ is benzo-1,3-dioxanyl and R$_2$ is pyridyl and the compound has Formula III

III

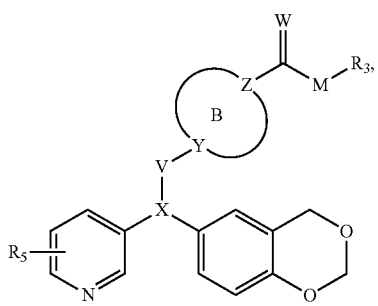

a prodrug thereof, a pharmaceutically acceptable salt thereof, or a pharmaceutically active metabolite thereof.

In some embodiments, X is nitrogen and the compound has Formula IV

IV

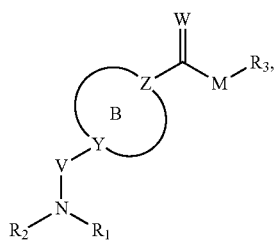

a prodrug thereof, a pharmaceutically acceptable salt thereof, or a pharmaceutically active metabolite thereof.

In some embodiments, X is carbon.

In some embodiments, X and Y are carbon, V is none, and X is directly attached to Y by double bond, the compound having Formula V

V

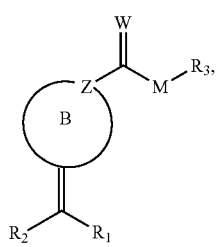

a prodrug thereof, a pharmaceutically acceptable salt thereof, or a pharmaceutically active metabolite thereof.

In some embodiments, Z is nitrogen. In some embodiments, W is O. In some embodiments, W is S. In some embodiments, M is O. In some embodiments, M is N. In some embodiments, V is O.

In some embodiments, B is piperazinyl or piperidinyl.

In some embodiments, $R_3$ represents $C_1$-$C_6$ alkyl, $C_3$-$C_6$ cycloalkyl, $C_4$-$C_8$ heterocycloalkyl, aryl, heteroaryl, piperidinyl, piperazinyl, morpholinyl, phenyl, pyridinyl, imidazolyl, pyrazolyl, benzopyrazolyl, triazolyl, benzotriazolyl, pyridotriazolyl, indanyl; $R_3$ may be unsubstituted or substituted with $R_4$ group; wherein $R_4$ may be one of the following moieties: F, Cl, Br, $CF_3$, $NO_2$, CN, O, $OCH_3$, $OCF_3$, $C_1$-$C_6$ alkyl, $C_1$-$C_6$ alkyloxy, $C_6H_5$, $OC_6H_5$, $C(O)OCH_3$.

In some embodiments, M and $R_3$ together form a leaving group.

In some embodiments, $R_3$ is pyrazolyl, triazolyl, benzo triazolyl, or pyridinyl.

According to another aspect of the disclosure, there is provided a pharmaceutical composition comprising at least one compound described herein and optionally one or more pharmaceutically acceptable excipients or adjuvants.

In some embodiments, the pharmaceutical composition comprises an effective amount of at least one compound described herein, wherein the effective amount is between about 0.0001 to about 1,000 mg.

In some embodiments, the pharmaceutical composition comprises one or more additional therapeutic agent. The additional therapeutic agent may be selected from: FAAH inhibitors, CB1 cannabinoid receptor agonists, CB2 cannabinoid receptor agonists, and phytocannabinoids (e.g., Cannabidiol (CBD), Cannabinol (CBN), Cannabigerol (CBG), Cannabichromene (CBC), Tetrahydrocannabinol (delta-9-THC)), non-steroidal anti-inflammatory drugs (NSAIDs), cyclooxygenase-II (COX-II) inhibitors, antianxiety agents, antidepressants, antiepileptic drugs, anti-Alzheimer's agents, antipsychotic drugs, antihemorrhagic agents, benzodiazepines, acetylcholinesterase inhibitors, alpha-adrenoreceptor antagonists, alpha-adrenergic receptor agonists, β-blockers, angiotensin-converting enzymes inhibitors (ACEI), serotonin (5-HT) reuptake inhibitors, serotonin and noradrenaline reuptake inhibitors (SNRIs), serotonin 1A (5-HT1A) agonists or antagonists, antibody medicament, antirheumatic drug, therapeutic monoclonal antibodies (e.g., trastuzumab, ranibizumab, bevacizumab, panitumumab, cetuximab, rituximab), and anticancer medications.

In some embodiments, the pharmaceutical composition may be formulated for oral, parenteral and/or transmucosal administration.

According to another aspect of the disclosure, there is provided a compound or pharmaceutical composition as described herein, for use as an endocannabinoid hydrolase inhibitor or modulator. The endocannabinoid hydrolase may be a serine hydrolase enzyme. The serine hydrolase enzyme may be a monoacylglycerol lipase (MAGL) enzyme.

According to another aspect of the disclosure, there is provided a compound or pharmaceutical composition as described herein, for use in inhibiting or modulating the activity of MAGL.

According to another aspect of the disclosure, there is provided a compound or pharmaceutical composition as described herein, for use in treating a disease, disorder or condition which benefits from the inhibition or modulation of MAGL activity.

The disease, disorder or condition may be selected from the group consisting of, but not limited to, a neurodegenerative disorder (e.g. multiple sclerosis (MS), Parkinson's disease (PD), Huntington's disease, dementia, Alzheimer's disease, amyotrophic lateral sclerosis (ALS) or Lou Gehrig's disease, epilepsy, fronto-temporal lobar degeneration, a sleep disorder, vascular cognitive impairment, Creutzfeldt-Jakob disease (CJD), or prion disease); primary tauopathies; neuropathy (e.g. diabetic neuropathy, pellagric neuropathy, alcoholic neuropathy, Beriberi neuropathy; cardiovascular disease (e.g., hypertension, dyslipidemia, atherosclerosis, cardiac arrhythmias, or cardiac ischemia); withdrawal syndrome (e.g. alcohol withdrawal syndrome, antidepressant discontinuation syndrome, antipsychotic withdrawal syndrome, benzodiazepine withdrawal syndrome, *cannabis* withdrawal, neonatal withdrawal, nicotine withdrawal, or opioid withdrawal); metabolic disorder (e.g., obesity, fatty liver disease, diabetes, dyslipidemia or hypertriglyceridemia); burning feet syndrome; ischemia (e.g., stroke, hepatic ischemia or reperfusion, CNS ischemia or reperfusion); nausea (e.g., refractory nausea or chemotherapy induced nausea); vomiting or emesis (e.g., chemotherapy induced vomiting); an eating disorder (e.g., anorexia, bulimia, Prader-Willi syndrome and related syndromes); a kidney disease (e.g., acute inflammatory kidney injury and diabetic nephropathy); an eye disease (e.g. glaucoma, ocular hypertension, macular degeneration, abnormal eye neovascularization (e.g. corneal or choroidal neovascularization), or a disease arising from elevated intraocular pressure); a pulmonary, lung or airway disorder (e.g. lung cancers, asthma, cough, allergies, cystic fibrosis, Chronic obstructive pulmonary disease (COPD), chronic bronchitis, interstitial lung disease (ILD), emphysema, pneumonia, tuberculosis, idiopathic pulmonary fibrosis, pulmonary edema, acute respiratory distress syndrome), pulmonary embolism, sarcoidosis, pleural effusion, or mesothelioma); osteoarthritis; osteoporosis; bipolar disease; depression; schizophrenia; sleeping sickness; cerebral palsy; cerebral edema; meningitis; cachexia; sleep apnea; De Vivo disease; spasticity; dystonia; progressive multifocal leukoencephalopathy; dyskinesia; tremor; hearing loss; insomnia; Tourette's syndrome; autism, bladder dysfunction, chronic motor or vocal tic disorder; trichotillomania; cognitive impairment (e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)); an inflammatory disorder (e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, inflammatory bowel disease (IBD), Crohn's disease and ulcerative colitis; Irritable bowel syndrome (IBS), pelvic inflammatory disease, sarcoidosis, HIV encephalitis, rabies, brain abscess, neurotoxicity, neuroinflammation, inflammation in the central nervous system (CNS); an autoimmune disease (e.g., psoriasis, pruritis, lupus erythematosus, Sjogren's syndrome, ankylosing spondylitis, undifferentiated spondylitis, Behcet's disease, hemolytic anemia, graft rejection); a demyelinating disease (e.g., MS, Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis); neuromyelitis optica; a disorder of the immune system (e.g. transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); and Asperger's syndrome.

This summary of the disclosure does not necessarily describe all features of the invention.

DETAILED DESCRIPTION

Features of the invention will become more apparent from the following description which includes a description of example embodiments of the invention.

The present disclosure is directed to the novel compounds of Formula I-V described herein, pharmaceutical derivatives thereof, or a combination thereof. The compounds of Formula I-V according to the present disclosure have intrinsic MAGL inhibitory properties and are therefore useful in the treatment of diseases or medical conditions which benefit from the inhibition of MAGL activity.

According to an aspect of the invention, there is provided a compound of Formula I, wherein,

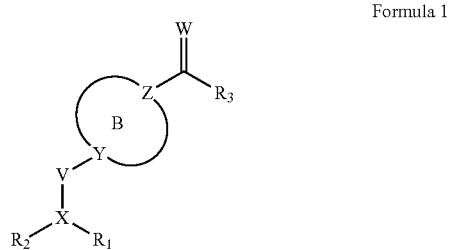

Formula 1 a. a prodrug thereof, a pharmaceutically acceptable salt thereof, or a pharmaceutically active metabolite thereof; wherein
b. B represents $C_{1-3}$ alkyl or $C_{3-6}$ heterocycloalkyl or $C_5$-$C_{10}$ heterobicycloalkyl;
c. V represents nil, alkylene, oxygen or alkylamino;
d. W represents oxygen or sulfur;
e. X represents carbon or nitrogen;
f. Y represents carbon or nitrogen;
g. Z represents carbon or nitrogen;
h. $R_1$ and $R_2$ represent alkyl, heterobicycloalkyl, heteroaromatic, or aromatic ring;
i. $R_3$ represents alkylamino, dialkylamino, piperidinyl, piperazinyl, morpholinyl, alkyloxy, hexafluroalkyloxy, cycloalkyloxy, succinimidyloxy, phenyloxy, pyridyloxy, pyrazolyl, imidazolyl, triazolyl, benzotriazolyl, benzotriazolyloxy, indazolyl, pyridotriazolyl, pyridotriazolyloxy.

$R_1$ and $R_2$ may optionally substituted with $R_5$. $R_5$ may be halogen, alkyl, alkyloxy, haloalkyl, nitrile, or haloalkyloxy.

In one embodiment $R_1$, $R_2$ or $R_1$ and $R_2$ may be 1,3-benzodioxanyl.

Furthermore, $R_3$ may be alkylamino, dialkylamino, piperidinyl, piperazinyl, morpholinyl, alkyloxy, hexafluroalkyloxy, cycloalkyloxy, succinimidyloxy, phenyloxy, pyridyloxy, pyrazolyl, imidazolyl, triazolyl, benzotriazolyl, benzotriazolyloxy, indazolyl, indanoxy, pyridotriazolyl, pyridotriazolyloxy. $R_3$ may be substituted with one or more identical or different $R_4$ groups. $R_4$ may be alkyl, alkyloxy, nitrile aryl, aryloxy, bromo, chloro, cyano, fluoro, nitro, oxo, haloalkyl, haloalkyloxy, fused cycloakyl rings, fused heterocycloakyl rings, fused aryl rings, fused heterocyclic rings, or $COOCH_3$.

$R_4$ may be alkyl, alkyloxy, nitrile, aryl, aryloxy, bromo, chloro, cyano, fluoro, nitro, oxo, haloalkyl, haloalkyloxy, fused cycloakyl rings, fused heterocycloakyl rings, fused aryl rings, fused heterocyclic rings, or $COOCH_3$.

B may be piperazine, piperidine, homopiperazine, azetidine, diazaspiro[3.3]heptane, 2-azaspiro[3.3]heptane or diazabicyclo[2.2.1]heptane.

Furthermore, X is may be carbon. X may be nitrogen. Z may be nitrogen. Z may be carbon. W may be oxygen. W may be sulfur. Y may be carbon. Y may be nitrogen. V may be nil. V may be methylene. V may be oxygen. V may be methylamino.

Furthermore the compound of Formula I may have the formula of formula 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.42a, 2.42b, 2.43a, 2.43b, 2.44a, 2.44b, 2.45a, 2.45b, 2.46a, 2.46b, 2.47a, 2.47b, 2.48a, 2.48b, 2.49a, 2.49b, 2.50a, 2.50b, 2.51a, 2.51b, 2.52a, 2.52b, 2.54a, 2.54b, 2.56a, 2.56b, 2.58a, 2.58b, 2.59a, or 2.59b.

In another aspect, the compound is of Formula I. wherein:
a. $R_1$ and $R_2$ are 1,3-benzodioxanyl;
b. B represents $C_{1-3}$ alkyl or $C_{3-6}$ heterocycloalkyl or $C_5$-$C_{10}$ heterobicycloalkyl;
c. V represents nil, alkylene, oxygen or alkylamino;
d. W represents oxygen or sulfur;
e. X represents carbon or nitrogen;
f. Y represents carbon or nitrogen;
g. Z represents carbon or nitrogen;
h. $R_3$ represents alkylamino, dialkylamino, piperidinyl, piperazinyl, morpholinyl, alkyloxy, hexafluroalkyloxy, cycloalkyloxy, succinimidyloxy, phenyloxy, pyridyloxy, pyrazolyl, imidazolyl, triazolyl, benzotriazolyl, benzotriazolyloxy, indazolyl, indanoxy, pyridotriazolyl, pyridotriazolyloxy whereby the $R_3$ can be substituted with one or more identical or different $R_4$ groups;
i. $R_4$ represents alkyl, alkyloxy, aryl, aryloxy, bromo, chloro, cyano, fluoro, nitro, oxo, trifluoromethyl, fused cycloakyl rings, fused heterocycloakyl rings, fused aryl rings, fused heterocyclic rings, $COOCH_3$.

In another aspect, the compound is of Formula I wherein:
a. $R_1$ and $R_2$ are phenyl that is optionally substituted with $R_5$;
b. B represents $C_{1-3}$ alkyl or $C_{3-6}$ heterocycloalkyl or $C_5$-$C_{10}$ heterobicycloalkyl;
c. V represents nil, alkylene, oxygen or alkylamino;
d. W represents oxygen or sulfur;
e. X represents carbon or nitrogen;
f. Y represents carbon or nitrogen;
g. Z represents carbon or nitrogen;
h. $R_3$ represents alkylamino, dialkylamino, piperidinyl, piperazinyl, morpholinyl, alkyloxy, hexafluroalkyloxy, cycloalkyloxy, succinimidyloxy, phenyloxy, pyridyloxy, pyrazolyl, imidazolyl, triazolyl, benzotriazolyl, benzotriazolyloxy, indazolyl, indanoxy, pyridotriazolyl, pyridotriazolyloxy whereby the $R_3$ can be substituted with one or more identical or different $R_4$ groups;
i. $R_4$ represents alkyl, alkyloxy, nitrile, aryl, aryloxy, bromo, chloro, cyano, fluoro, nitro, oxo, haloalkyl, haloalkyloxy, fused cycloakyl rings, fused heterocycloakyl rings, fused aryl rings, fused heterocyclic rings, $COOCH_3$;
j. $R_5$ represents halogen, alkyl, alkyloxy, haloalkyl, nitrile, haloalkyloxy.

According to another aspect of the disclosure, there is provided a composition, such as a pharmaceutical composition, comprising at least one compound of Formula I described herein and optionally one or more pharmaceutically acceptable excipients or adjuvants.

In some embodiments, the pharmaceutical composition comprises an effective amount of at least one compound. The effective amount may be between about 0.0001 to about 1,000 mg.

In some embodiments, the pharmaceutical composition comprises two or more of the compounds of Formula I described herein. The two or more compounds may be the same compound but in different forms, e.g., compound in the free state and prodrug or the compound, or the two or more compounds may be different compounds.

In some embodiments, the pharmaceutical composition further comprises one or more additional therapeutic agents.

In some embodiments, the one or more additional therapeutic agent may be a mono acyl glycerol lipase (MAGL) inhibitor. The MAGL inhibitor may be a natural MAGL inhibitor, a synthetic MAGL inhibitor or a combination thereof.

In some embodiments, the one or more additional therapeutic agent may comprise a dual monoacylglycerol lipase/fatty acid amide hydrolase/(MAGL/FAAH) inhibitor.

In some embodiments, the one or more additional therapeutic agent may comprise one or more cannabinoids, or a combination of cannabinoids. The one or more cannabinoids may be exogenous cannabinoids (e.g., natural and synthetic cannabinoids) and/or endogenous cannabinoids (e.g., anandamide (AEA) or 2-Arachidonoylglycerol (2-AG)) or a combination thereof. In some embodiments, one or more cannabinoids may comprise cannabidiol (CBD), a prodrug or pharmaceutically acceptable salt thereof.

In some embodiments, the pharmaceutical composition comprises an effective amount of the one or more additional therapeutic agent. The effective amount may be between about 0.0001 to about 1,000 mg.

In some embodiments, the pharmaceutical composition may be formulated for transmucosal, oral, intraperitoneal and/or parenteral delivery.

According to another aspect of the disclosure, there is provided a combination comprising (i) a first compound of Formula I described herein; and (ii) a second compound of Formula I described herein, wherein the first and second compounds are different.

According to another aspect of the disclosure, there is provided a combination comprising (i) a compound of Formula I described herein; and (ii) one or more additional therapeutic agents.

According to another aspect of the disclosure, there is provided a dosage formulation comprising the composition described herein. The dosage formulation may be one selected from the group consisting of: a cream, an emulsion, an ointment, and a spray.

According to another aspect of the disclosure, there is provided a compound as described herein for use as an endocannabinoid hydrolase inhibitor or modulator. The endocannabinoid hydrolase may be a serine hydrolase enzyme. The serine hydrolase enzyme may be a MAGL enzyme.

In some embodiments, the compound of Formula I causes no significant effect on the other brain serine hydrolases (e.g., FAAH). For example, the compound of Formula I selectively inhibits or modulates the serine hydrolase MAGL.

According to another aspect of the disclosure, there is provided a compound as described herein, the composition as described herein or the combination described herein, for use in treating a disease, disorder or condition which benefits from the inhibition or modulation of MAGL activity.

In some embodiments, the disease, disorder or condition which benefits from the inhibition or modulation of MAGL activity is selected from the group consisting of, but are not limited to, a neurodegenerative disorder (e.g., multiple sclerosis (MS), Parkinson's disease (PD), Huntington's disease, dementia, Alzheimer's disease, amyotrophic lateral sclerosis (ALS) or Lou Gehrig's disease, epilepsy, fronto-temporal lobar degeneration, a sleep disorder, vascular cognitive impairment, Creutzfeldt-Jakob disease (CJD), or prion disease); primary tauopathies; neuropathy (e.g., diabetic neuropathy, pellagric neuropathy, alcoholic neuropathy, Beriberi neuropathy); cardiovascular disease (e.g., hypertension, dyslipidemia, atherosclerosis, cardiac arrhythmias, or cardiac ischemia); withdrawal syndrome (e.g., alcohol withdrawal syndrome, antidepressant discontinuation syndrome, antipsychotic withdrawal syndrome, benzodiazepine withdrawal syndrome, *cannabis* withdrawal, neonatal withdrawal, nicotine withdrawal, or opioid withdrawal); metabolic disorder (e.g., obesity, fatty liver disease, diabetes, dyslipidemia or hypertriglyceridemia); burning feet syndrome; ischemia (e.g., stroke, hepatic ischemia or reperfusion, CNS ischemia or reperfusion); nausea (e.g., refractory nausea or chemotherapy induced nausea); vomiting or emesis (e.g., chemotherapy induced vomiting); an eating disorder (e.g., anorexia, bulimia, Prader-Willi syndrome and related syndromes); a kidney disease (e.g., acute inflammatory kidney injury and diabetic nephropathy); an eye disease (e.g., glaucoma, ocular hypertension, macular degeneration, abnormal eye neovascularization (e.g., corneal or choroidal neovascularization), or a disease arising from elevated intraocular pressure); a pulmonary, lung or airway disorder (e.g., lung cancers, asthma, cough, allergies, cystic fibrosis, Chronic obstructive pulmonary disease (COPD), chronic bronchitis, interstitial lung disease (ILD), emphysema, pneumonia, tuberculosis, idiopathic pulmonary fibrosis, pulmonary edema, acute respiratory distress syndrome (pulmonary embolism, sarcoidosis, pleural effusion, or mesothelioma); osteoarthritis; osteoporosis; bipolar disease; depression; schizophrenia; sleeping sickness; cerebral palsy; cerebral edema; meningitis; cachexia; sleep apnea; De Vivo disease; spasticity; dystonia; progressive multifocal leukoencephalopathy; dyskinesia; tremor; hearing loss; insomnia; Tourette's syndrome; autism, bladder dysfunction, chronic motor or vocal tic disorder; trichotillomania; cognitive impairment (e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)); an inflammatory disorder (e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, inflammatory bowel disease (IBD), Crohn's disease and ulcerative colitis; Irritable bowel syndrome (IBS), pelvic inflammatory disease, sarcoidosis, HIV encephalitis, rabies, brain abscess, neurotoxicity, neuroinflammation, inflammation in the central nervous system (CNS)); an autoimmune disease (e.g., psoriasis, pruritus, lupus erythematosus, Sjogren's syndrome, ankylosing spondylitis, undifferentiated spondylitis, Behcet's disease, hemolytic anemia, graft rejection); a demyelinating disease (e.g., MS, Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis); neuromyelitis optica; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome.

Furthermore, the disease or disorder or syndrome is selected from the group consisting of, but are not limited to, a disorder associated with abnormal cell growth or proliferation (e.g., a benign tumor or cancer such as benign skin tumor, brain tumor, papilloma, prostate tumor, cerebral tumor (e.g., glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, prostate cancer, ovarian cancer, cervical cancer, rectal cancer, colon cancer, breast cancer, lung cancer, pancreatic cancer, bladder cancer, brain cancer, glioblastoma (GBM), gastrointestinal cancer, leukemia or blood cancer; traumatic brain injury; non-traumatic brain injury; spinal cord injury; seizures; excitotoxin exposure; stroke (e.g., ischemic stroke; hemorrhagic stroke); subarachnoid hemorrhage; intracerebral hemorrhage; vasospasm; AIDS wasting syndrome; renal ischemia; cerebral ischemia: liver fibrosis, iron overload, cirrhosis of the liver; a liver disorder (e.g., acute liver failure, Alagille syndrome, hepatitis, enlarged liver, Gilbert's syndrome, liver cysts, liver hemangioma, fatty liver disease, steatohepatitis (e.g., nonalcoholic steatohepatitis (NASH)), primary sclerosing cholangitis, fascioliasis, primary biliary cirrhosis, Budd-Chiari syndrome, hemochromatosis, Wilson's disease, or transthyretin-related hereditary amyloidosis), pain (e.g., acute pain; chronic pain; nociceptive pain; neuropathic pain, inflammatory pain; vasoocclusive painful crisis in sickle cell disease; visceral pain; post-operative pain; migraine; lower back pain; joint pain; abdominal pain; chest pain; postmastectomy pain syndrome; menstrual pain; dyspepsia; fibromyalgia; glossopharyngeal neuralgia; endometriosis pain; pain due to physical trauma; skeletal muscle contusion; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, cancer, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, IBS, IBD, cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)).

The compounds of Formula I-V, compositions and formulations may be used in methods for the treatment or prevention of disease states, disorders, and conditions that are mediated by MAGL activity, such as, but not limited to, pain (inflammatory, neuropathic and nociceptive); neurological diseases and disorders such as epilepsy, seizures and stroke; neurological affective disorders such as anxiety, depression, post traumatic stress disorder (PTSD), attention deficit hyperactivity disorder (ADHD), obsessive compulsion (ECD) and mood disorders, neurodegenerative diseases such as Alzheimer's Disease (AD), Parkinson's Disease (PD), Amyotrophic Lateral Sclerosis (ALS) and Multiple Sclerosis (MS); metabolic disorders such as obesity, diabetes and dyslipidemia; inflammatory diseases such as Irritable Bowel Disease (IBD), Crohn's Disease and Colitis, and respiratory diseases such as asthma, Chronic Obsructive Pulmonary Disease (COPD), Idiopathic Pulmonary Fibrotic Disease (IPF), asthma and cough (persistent and chronic, cold-/exercise-mediated).

According to another aspect of the disclosure, there is provided a method for inhibiting or modulating MAGL in a subject, the method may comprise administering an effective amount of a compound, composition or combination described herein to the subject to inhibit or modulate MAGL.

According to another aspect of the disclosure, there is provided a method for treating a disease, disorder or condition which benefits from the inhibition or modulation of MAGL activity in a subject, the method comprising administering an effective amount of a compound, composition, or combination described herein to the subject.

Use of the compound, composition or combination described herein for inhibiting or modulating MAGL in a subject are also provided.

The compound may have the following formula:

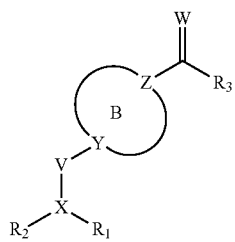

Formula 1 wherein

B represents $C_{1-3}$ alkyl or $C_{3-6}$ heterocycloalkyl or $C_5$-$C_{10}$ heterobicycloalkyl;

V represents nil, alkylene, oxygen or alkylamino;

W represents oxygen or sulfur;

X represents carbon or nitrogen;

Y represents carbon or nitrogen;

Z represents carbon or nitrogen;

$R_1$ and $R_2$ represent alkyl, heterobicycloalkyl, heteroaromatic, or aromatic ring;

$R_3$ represents alkylamino, dialkylamino, piperidinyl, piperazinyl, morpholinyl, alkyloxy, hexafluroalkyloxy, cycloalkyloxy, succinimidyloxy, phenyloxy, pyridyloxy, pyrazolyl, imidazolyl, triazolyl, benzotriazolyl, benzotriazolyloxy, indazolyl, indanoxy, pyridotriazolyl, pyridotriazolyloxy.

In some embodiment $R_1$, $R_2$ or $R_1$ and $R_2$ may be substituted with one or more $R_5$. $R_1/R_2$ can be alkyl, such for example $CH_3$ or $CH_2CH_3$. $R_1/R_2$ can be heterobicycloalkyl, such for example

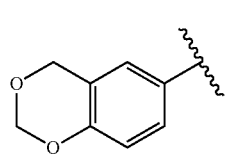 [SMILES: *c1ccc2c(c1)COCO2]

$R_1/R_2$ can be heteroaromatic, such for example

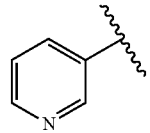 [SMILES: *c1cccnc1]

$R_1/R_2$ can be aromatic, such for example

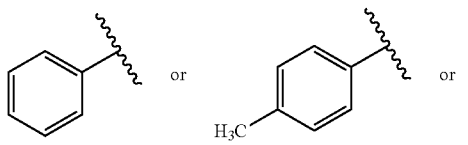 or

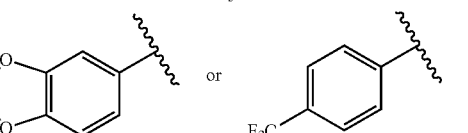 or

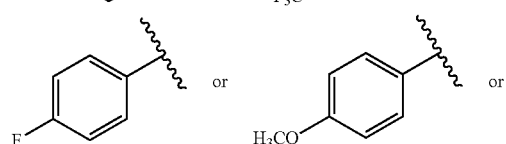 or

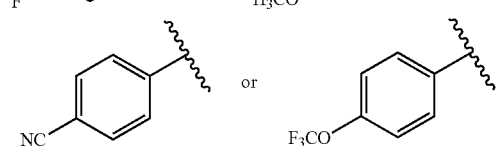 or

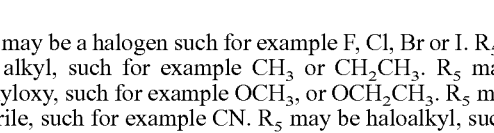 or $R_5$ may be a halogen such for example F, Cl, Br or I. $R_5$ may be alkyl, such for example $CH_3$ or $CH_2CH_3$. $R_5$ may be alkyloxy, such for example $OCH_3$, or $OCH_2CH_3$. $R_5$ may be nitrile, such for example CN. $R_5$ may be haloalkyl, such for example $CF_3$, $CH_2CH_2F$ or $CH_2CF_3$. $R_5$ may be haloalkyloxy, such for example $OCF_3$, $OCH_2CH_2F$ or $OCH_2CF_3$.

In some embodiment, $R_1$, $R_2$ or $R_1$ and $R_2$ may be phenyl, 1,3-benzodioxanyl, 1,4-benzodioxanyl, 1,3-benzodioxolyl, 2,2-difluoro-1,3-benzodioxolyl or 1-methylindazolyl. In one embodiment phenyl is substituted with one or more $R_5$, such for example

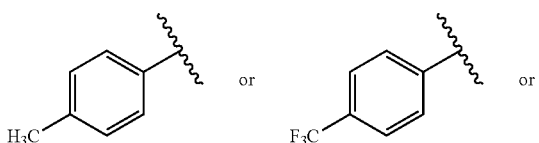 or

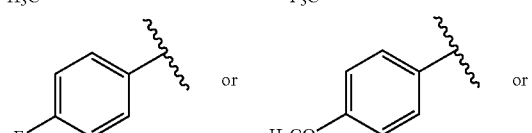 or

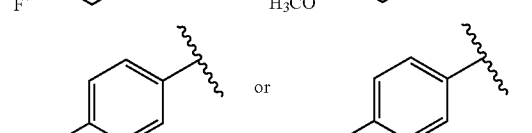 or

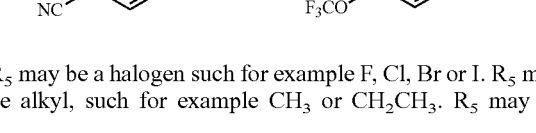 or $R_5$ may be a halogen such for example F, Cl, Br or I. $R_5$ may be alkyl, such for example $CH_3$ or $CH_2CH_3$. $R_5$ may be alkyloxy, such for example OCH$_3$ or OCH$_2$CH$_3$. R$_5$ may be nitrile, such for example CN. R$_5$ may be haloalkyl, such for example CF$_3$, CH$_2$CH$_2$F or CH$_2$CF$_3$. R$_5$ may be haloalkyloxy, such for example OCF$_3$, OCH$_2$CH$_2$F or OCH$_2$CF$_3$.

In some embodiment, R$_3$ may be substituted with one or more identical or different R$_4$ groups, such for example

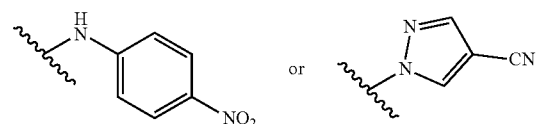

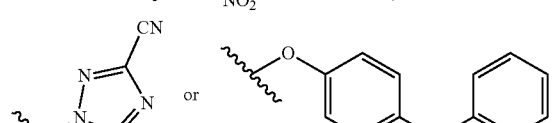

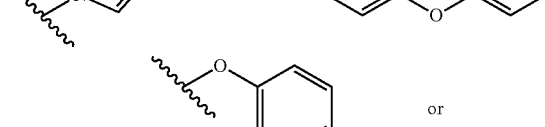

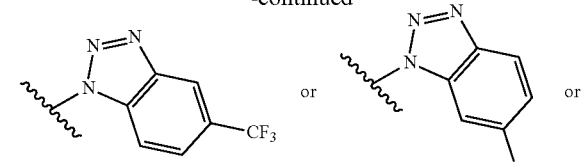

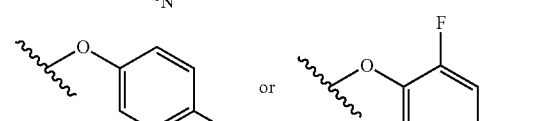

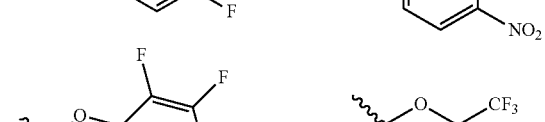

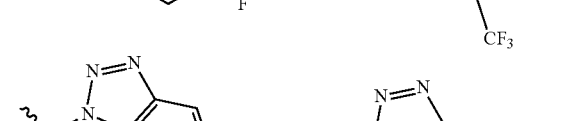


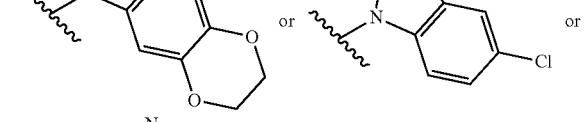

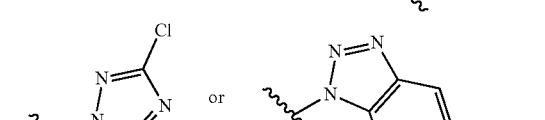

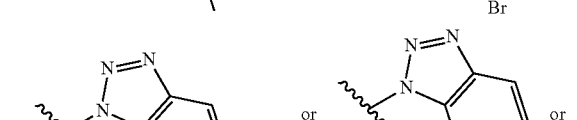

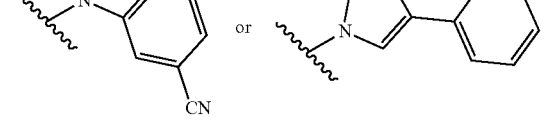

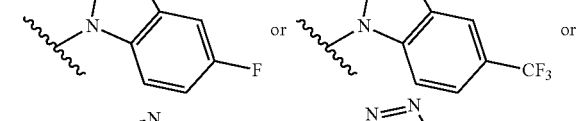

R$_4$ may be a halogen such for example F, Cl, Br or I. R$_4$ may be an alkyl such for example CH$_3$ or CH$_2$CH$_3$. R$_4$ may be an alkyloxy, such for example OCH$_3$ or OCH$_2$CH$_3$. R$_4$ may be nitrile, such for example CN. R$_4$ may be nitro, such for example NO$_2$. R$_4$ may be oxo, such for example O or OH.

R₄ may be haloalkyl, such for example $CF_3$, $CH_2CH_2F$, or $CH_2CF_3$. R₄ may be haloalkyloxy, such for example $OCF_3$, $OCH_2CH_2F$ or $OCH_2CF_3$. R₄ may be aryl, such for example, $C_6H_6$. R₄ may be aryloxy, such for example $OC_6H_6$. Furthermore, R₄ may be a fused cycloakyl rings, fused heterocycloakyl rings, fused aryl rings, fused heterocyclic rings or $COOCH_3$.

In some embodiment, B may be piperazine, piperidine, homopiperazine, azetidine, diazaspiro[3.3]heptane, 2-azaspiro[3.3]heptane or diazabicyclo[2.2.1]heptane.

For example, the compound of Formula I may be one of the following compounds:

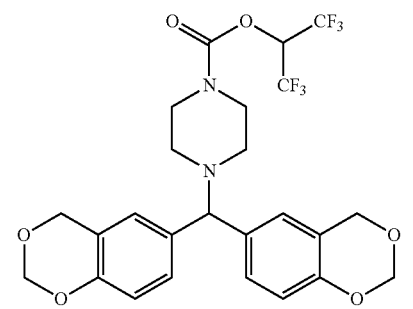

Formula 2.1

1,1,1,3,3,3,-hexafluoropropan-2-yl 4-(bis(4H-benzo[d][1,3]dioxin-6-yl)methyl)piperazine-1-carboxylate

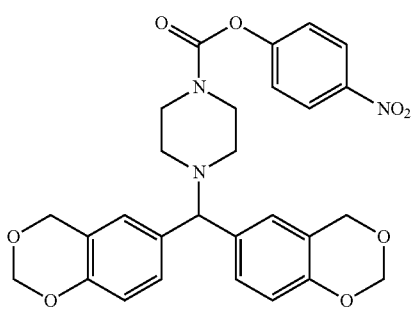

Formula 2.2

4-nitrophenyl 4-(bis(4H-benzo[d][1,3]dioxin-6-yl)methyl)piperazine-1-carboxylate

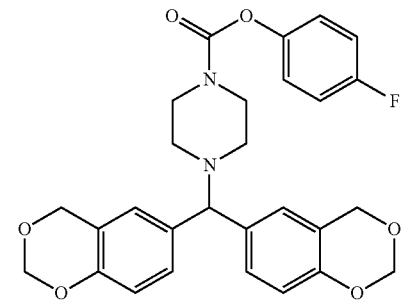

Formula 2.3

4-(bis(4H-benzo[d][1,3]dioxin-6-yl)methyl)piperazine-1-carboxylate

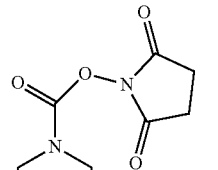

Formula 2.4

2,5-dioxopyrrolidin-1-yl 4-(bis(4H-benzo[d][1,3]dioxin-6-yl)methyl)piperazine-1-carboxylate

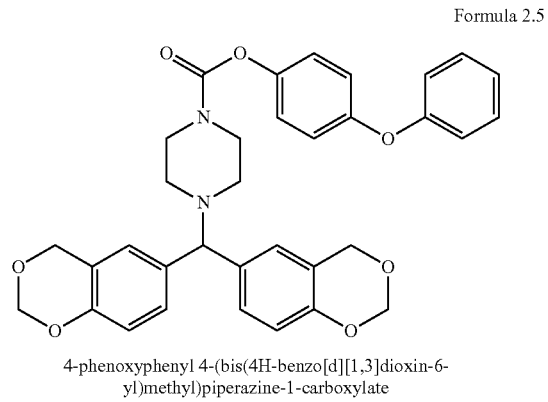

Formula 2.5

4-phenoxyphenyl 4-(bis(4H-benzo[d][1,3]dioxin-6-yl)methyl)piperazine-1-carboxylate

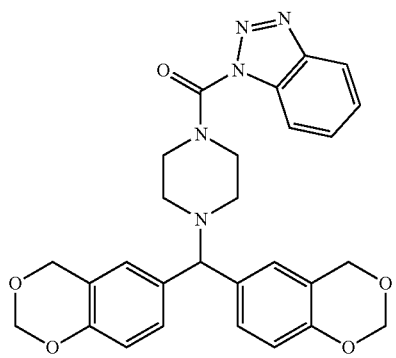

Formula 2.6

(1H-benzo[d][1,2,3]triazol-1-yl)4-(bis(4H-benzo[d][1,3]dioxin-6-yl)methyl)piperazin-1-yl)methanone Formula 2.7

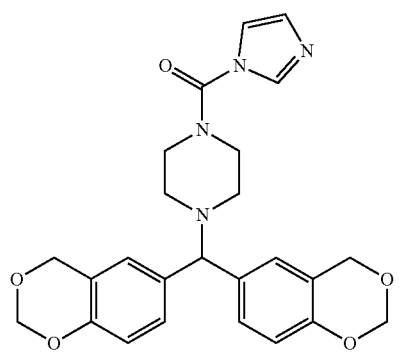

(4-(bis(4H-benzo[d][1,3]dioxin-6-yl)methyl)piperazin-1-yl)(1H-imidazol-1-yl)methanone Formula 2.8

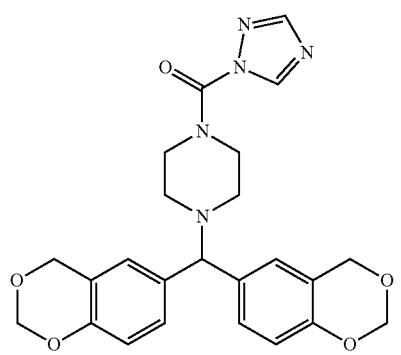

(4-(bis(4H-benzo[d][1,3]dioxin-6-yl)methyl)piperazin-1-yl)(1H-1,2,4-triazol-1-yl)methanone Formula 2.9

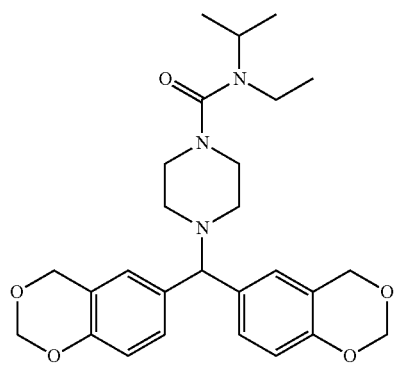

(4-(bis(4H-benzo[d][1,3]dioxin-6-yl)methyl)-N-ethyl-N-isopropylpiperazine-1-carboxamide Formula 2.10

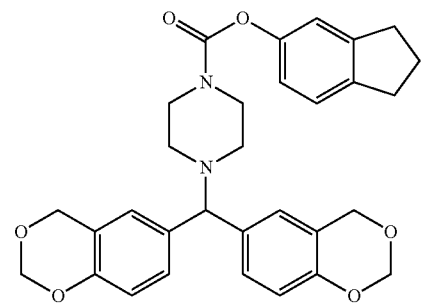

2,3-dihydro-1H-inden-5-yl 4-(bis(4H-benzo[d][1,3]dioxin-6-yl)methyl)piperazine-1-carboxylate Formula 2.11

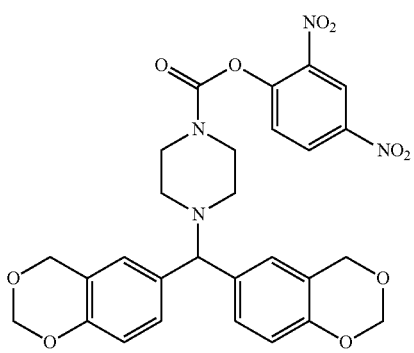

2,4-dinitrophenyl 4-(bis(4H-benzo[d][1,3]dioxin-6-yl)methyl)piperazine-1-carboxylate Formula 2.12

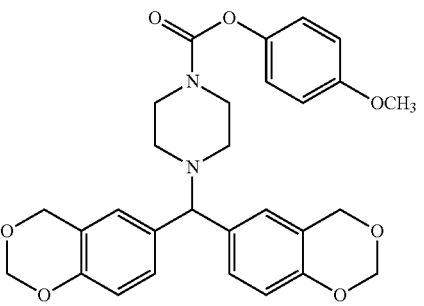

4-methoxyphenyl 4-(bis(4H-benzo[d][1,3]dioxin-6-yl)methyl)piperazine-1-carboxylate Formula 2.13

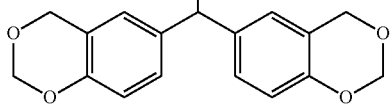

pentan-3-yl 4-(bis(4H-benzo[d][1,3]dioxin-6-yl)methyl)piperazine-1-carboxylate

Formula 2.14

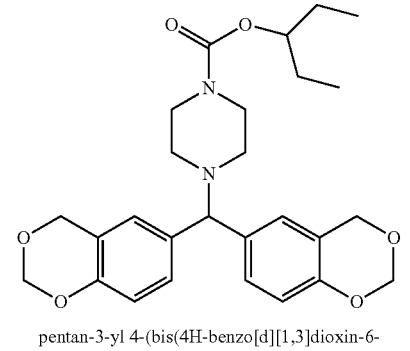

cyclohexyl 4-(bis(4H-benzo[d][1,3]dioxin-6-yl)methyl)piperazine-1-carboxylate

Formula 2.15

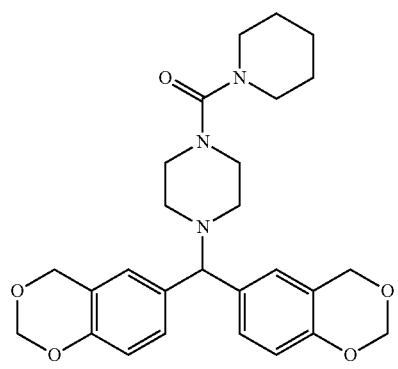

(4-(bis(4H-benzo[d][1,3]dioxin-6-yl)methyl)piperazin-1-yl)(piperidin-1-yl)methanone Formula 2.16

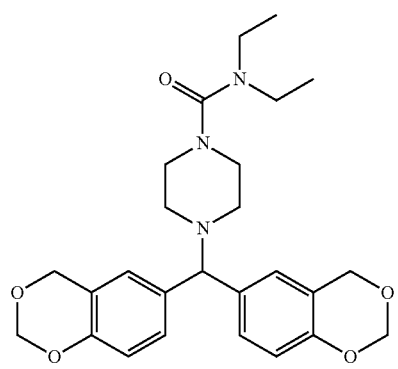

4-(bis(4H-benzo[d][1,3]dioxin-6-yl)methyl)-N,N-diethylpiperazine-1-carboxamide

Formula 2.17

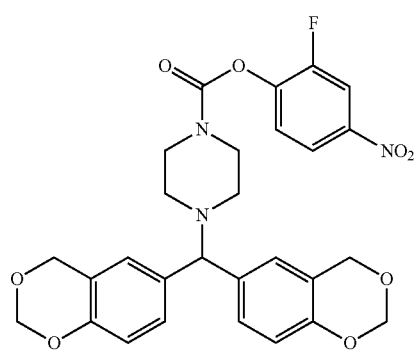

2-fluoro-4-nitrophenyl 4-(bis(4H-benzo[d][1,3]dioxin-6-yl)methyl)piperazine-1-carboxylate Formula 2.18

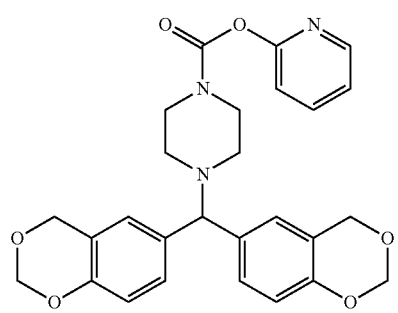

pyridin-2-yl 4-(bis(4H-benzo[d][1,3]dioxin-6-yl)methyl)piperazine-1-carboxylate

Formula 2.19

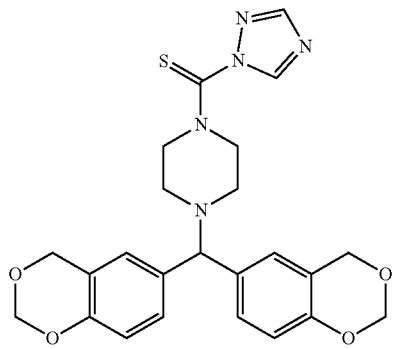

(4-(bis(4H-benzo[d][1,3]dioxin-6-yl)methyl)piperazin-1-yl)(1H-1,2,4-triazol-1-yl)methanethione Formula 2.20

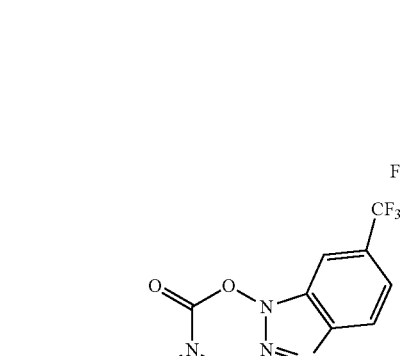

6-(trifluoromethyl-1H-benzo[d][1,2,3]triazol-1-yl 4-(bis(4H-benzo[d][1,3]dioxin-6-yl)methyl)piperazine-1-carboxylate Formula 2.21

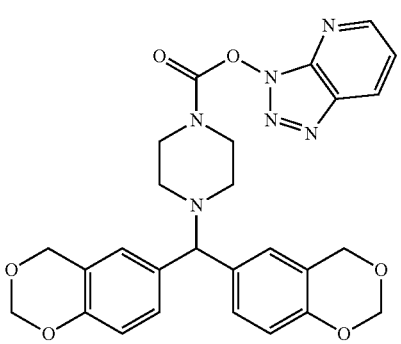

3H-[1,2,3]triazolo[4,5-b]pyridin-3-yl 4-(bis(4H-benzo[d][1,3]dioxin-6-yl)methyl)piperazine-1-carboxylate Formula 2.22

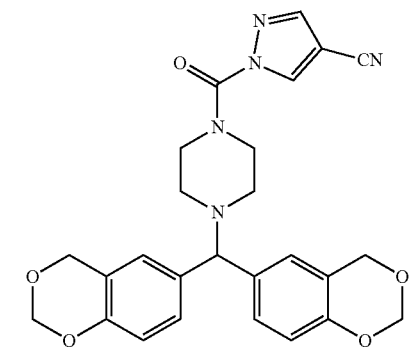

1-(4-(bis(4H-benzo[d][1,3]dioxin-6-yl)methyl)piperazine-1-carbonyl)-1H-pyrazole-4-carbonitrile Formula 2.23

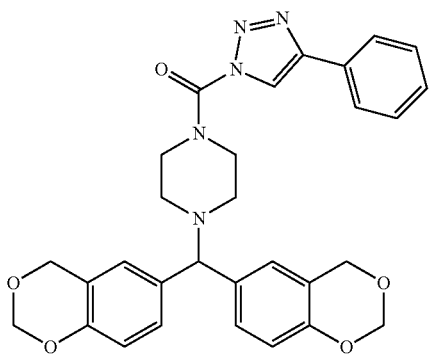

(4-(bis(4H-benzo[d][1,3]dioxin-6-yl)methyl)piperazin-1-yl)(4-phenyl-1H-1,2,3-triazol-1-yl)methanone Formula 2.24

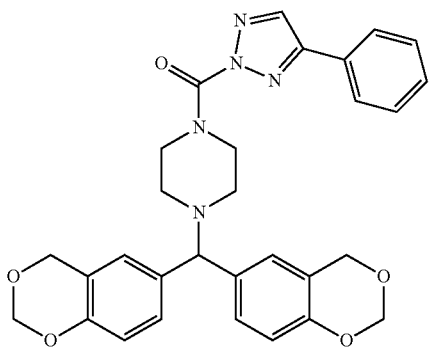

(4-(bis(4H-benzo[d][1,3]dioxin-6-yl)methyl)piperazin-1-yl)(4-phenyl-2H-1,2,3-triazol-2-yl)methanone Formula 2.25

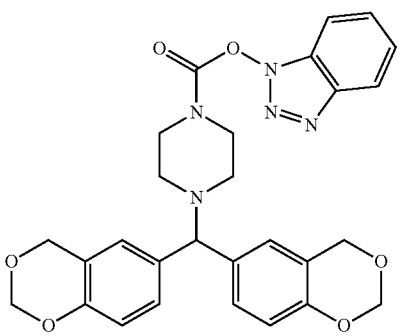

1H-benzo[d][1,2,3]triazol-1-yl 4-(bis(4H-benzo[d][1,3]dioxin-6-yl)methyl)piperazine-1-carboxylate Formula 2.26

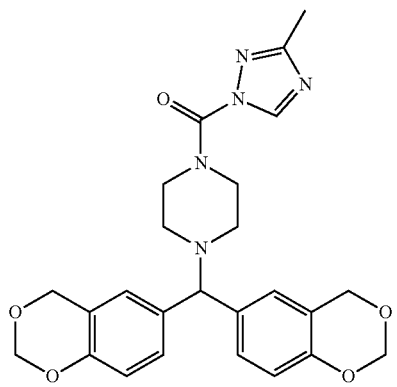

(4-(bis(4H-benzo[d][1,3]dioxin-6-yl)methyl)piperazin-1-yl)(3-methyl-1H-1,2,4-triazol-1-yl)methanone Formula 2.27

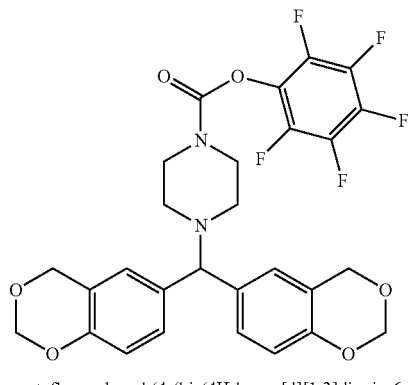

pentafluorophenyl (4-(bis(4H-benzo[d][1,3]dioxin-6-yl)methyl)piperazine-1-carboxylate Formula 2.28

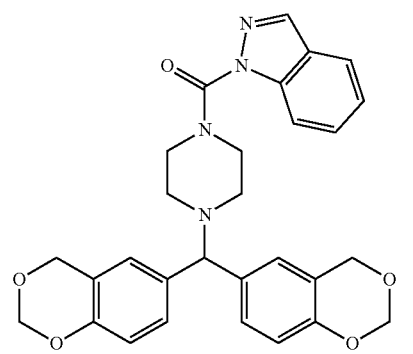

(4-(bis(4H-benzo[d][1,3]dioxin-6-yl)methyl)piperazin-1-yl)(1H-indazol-1-yl)methanone Formula 2.29

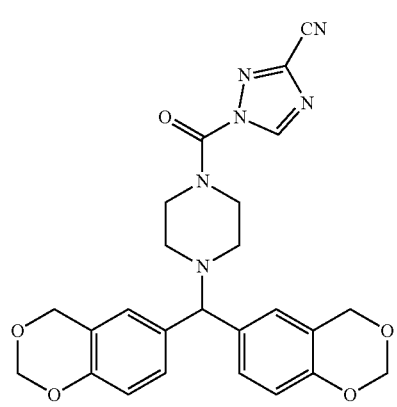

1-(4-(bis(4H-benzo[d][1,3]dioxin-6-yl)methyl)piperazine-1-carbonyl)-1H-1,2,4-triazole-3-carbonitrile Formula 2.30

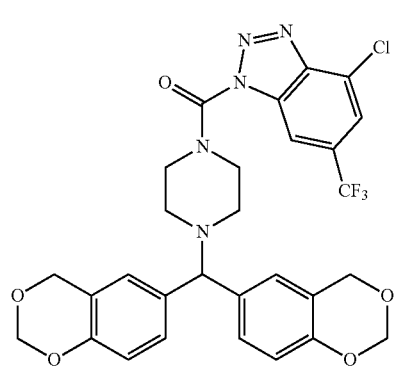

(4-(bis(4H-benzo[d][1,3]dioxin-6-yl)methyl)piperazin-1-yl)(4-chloro-6-(trifluoromethyl)-1H-benzo[d][1,2,3]triazol-1-yl)methanone Formula 2.31

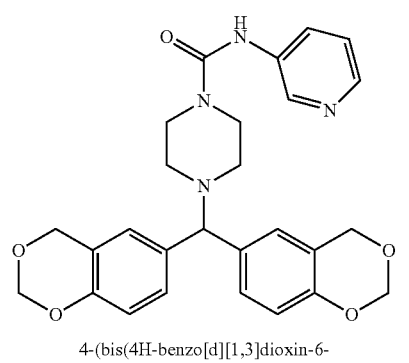

4-(bis(4H-benzo[d][1,3]dioxin-6-yl)methyl)-N-(pyridin-3-yl)piperazine-1-carboxamide Formula 2.32

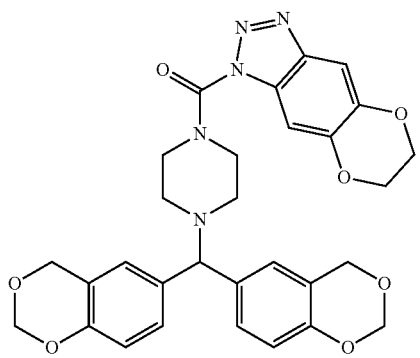

(4-(bis(4H-benzo[d][1,3]dioxin-6-yl)methyl)piperazin-1-yl)(6,7-dihydro-1H-[1,4]dioxino[2′,3′:4,5]benzo[1,2-d][1,2,3]triazol-1-yl)methanone Formula 2.33

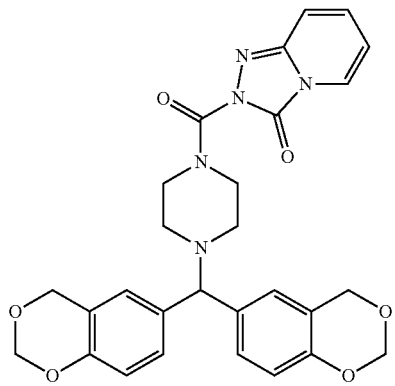

2-(4-(bis(4H-benzo[d][1,3]dioxin-6-yl)methyl)piperazine-1-carbonyl)[1,2,4]triazolo[4,3-a]pyridin-3(2H)-one Formula 2.34

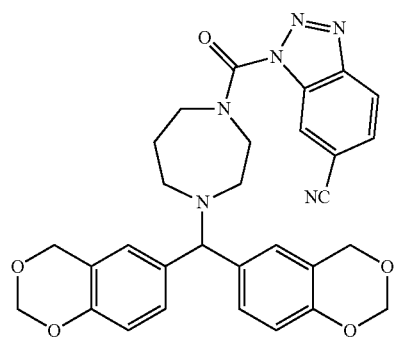

1-(4-(bis(4H-benzo[d][1,3]dioxin-6-yl)methyl)-1,4-diazepane-1-carbonyl)-1H-benzo[d][1,2,3]triazole-6-carbonitrile Formula 2.37

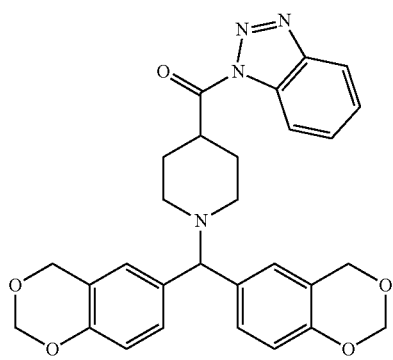

(1H-benzo[d][1,2,3]triazol-1-yl)(1-(bis(4H-benzo[d][1,3]dioxin-6-yl)methyl)piperidin-4-yl)methanone Formula 2.35

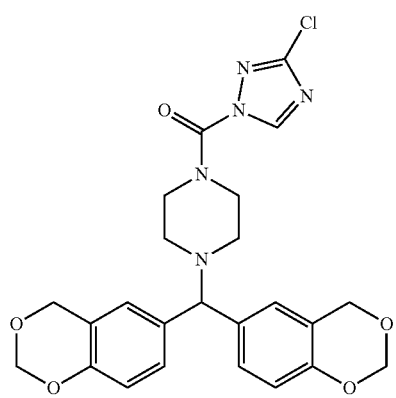

(4-(bis(4H-benzo[d][1,3]dioxin-6-yl)methyl)piperazin-1-yl)(3-chloro-1H-1,2,4-triazol-1-yl)methanone Formula 2.38

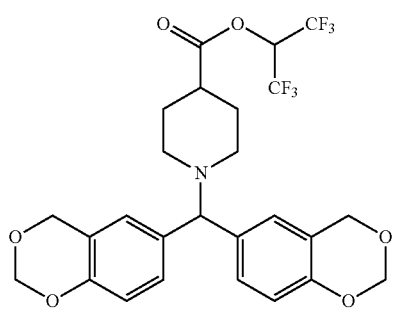

1,1,1,3,3,3-hexafluoropropan-2-yl 1-(bis(4H-benzo[d][1,3]dioxin-6-yl)methyl)piperidine-4-carboxylate Formula 2.36

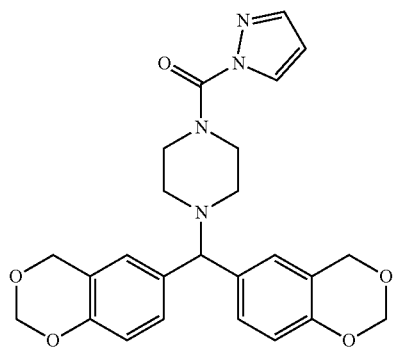

4-(bis(4H-benzo[d][1,3]dioxin-6-yl)methyl)piperazin-1-yl)(1H-pyrazol-1-yl)methanone Formula 2.39

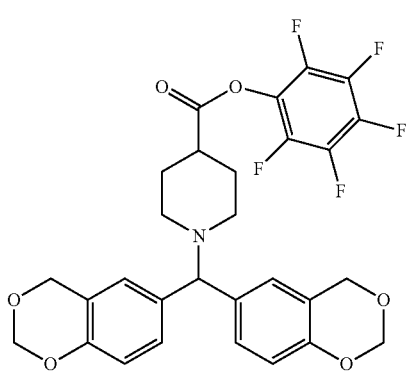

pentafluorophenyl 1-(bis(4H-benzo[d][1,3]dioxin-6-yl)methyl)piperidine-1-carboxylate Formula 2.40

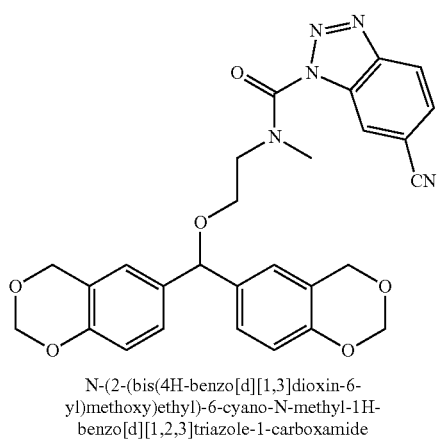

N-(2-(bis(4H-benzo[d][1,3]dioxin-6-yl)methoxy)ethyl)-6-cyano-N-methyl-1H-benzo[d][1,2,3]triazole-1-carboxamide It is further provided, a composition or mixture of compounds of Formula I, For example, the composition or mixture may be the following:

(4-(bis(4H-benzo[d][1,3]dioxin-6-yl)methyl)piperazin-1-yl)
(1H-1,2,3-triazol-1-yl)methanone
and (4-(bis(4H-benzo[d][1,3]dioxin-6-yl)methyl)piperazin-1-yl)
(2H-1,2,3-triazol-2-yl)methanone ((unassigned ratio of 7:4)

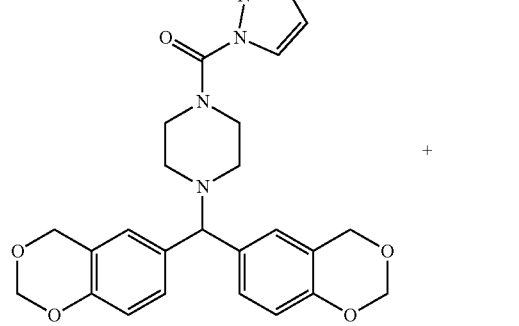

+

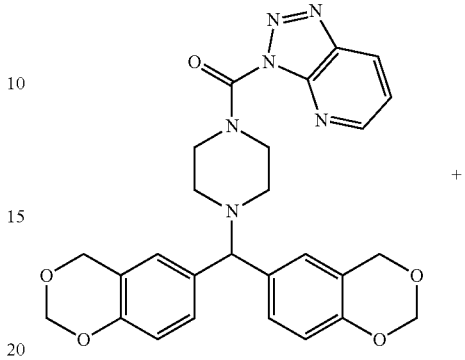

Formula 2.42a + 2.42b (3H-[1,2,3]triazolo[4,5-b]pyridin-3-yl)
(4-(bis(4H-benzo[d][1,3]dioxin-6-yl)methyl)piperazin-1-yl)methanone and (1H-[1,2,3]triazolo[4,5-b]pyridin-1-yl)
(4-(bis(4H-benzo[d][1,3]dioxin-6-yl)methyl)piperazin-1-yl)methanone (unassigned ratio of 5:1)

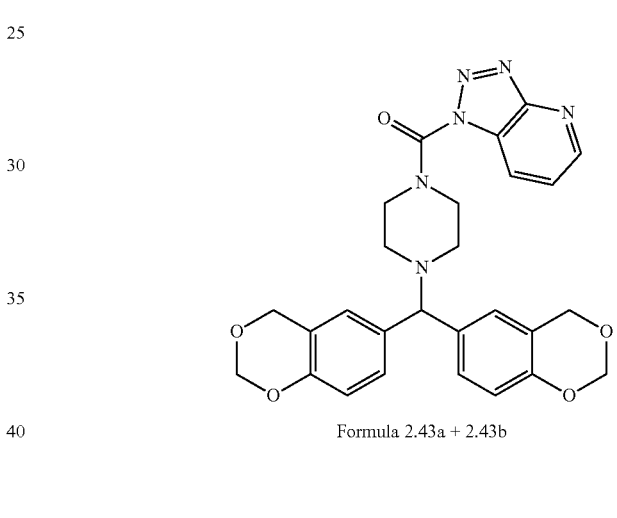

Formula 2.43a + 2.43b (4-(bis(4H-benzo[d][1,3]dioxin-6-yl)methyl)piperazin-1-yl)
(5-chloro-1H-benzo[d][1,2,3]triazol-1-yl)methanone and
(4-(bis(4H-benzo[d][1,3]dioxin-6-yl)methyl)piperazin-1-yl)
(6-chloro-1H-benzo[d][1,2,3]triazol-1-yl)methanone
(unassigned ratio of 5:3)

+

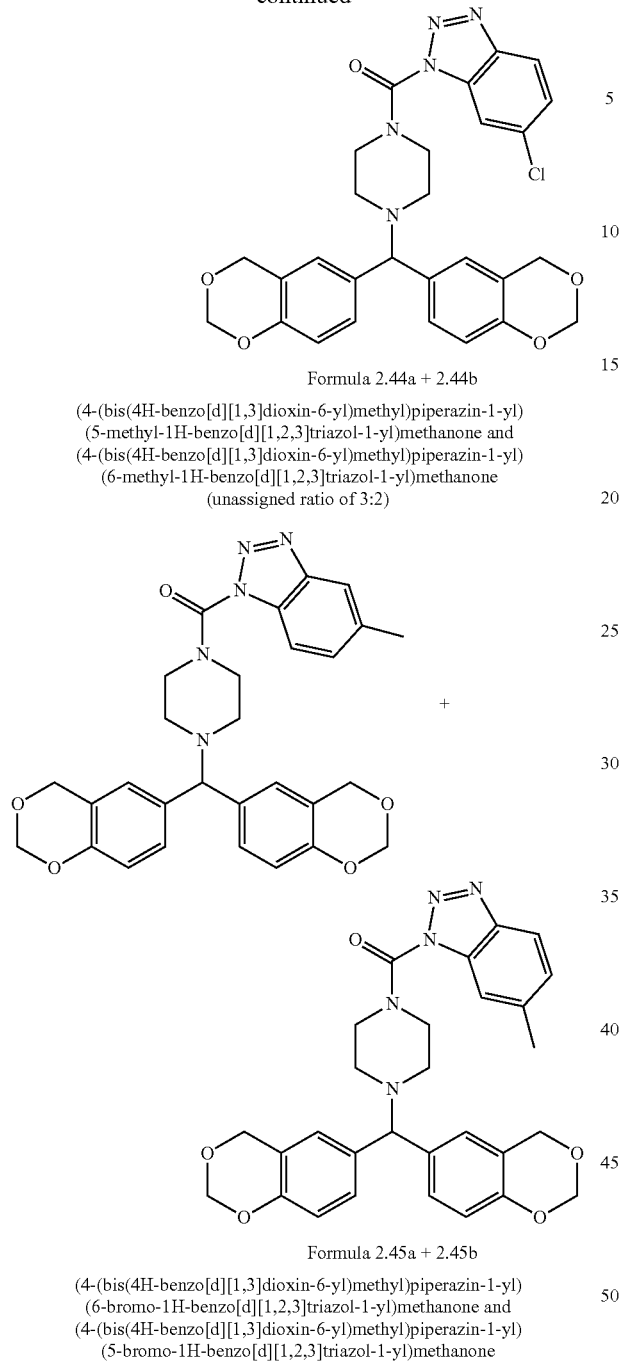

Formula 2.44a + 2.44b (4-(bis(4H-benzo[d][1,3]dioxin-6-yl)methyl)piperazin-1-yl)
(5-methyl-1H-benzo[d][1,2,3]triazol-1-yl)methanone and
(4-(bis(4H-benzo[d][1,3]dioxin-6-yl)methyl)piperazin-1-yl)
(6-methyl-1H-benzo[d][1,2,3]triazol-1-yl)methanone
(unassigned ratio of 3:2)

Formula 2.45a + 2.45b (4-(bis(4H-benzo[d][1,3]dioxin-6-yl)methyl)piperazin-1-yl)
(6-bromo-1H-benzo[d][1,2,3]triazol-1-yl)methanone and
(4-(bis(4H-benzo[d][1,3]dioxin-6-yl)methyl)piperazin-1-yl)
(5-bromo-1H-benzo[d][1,2,3]triazol-1-yl)methanone

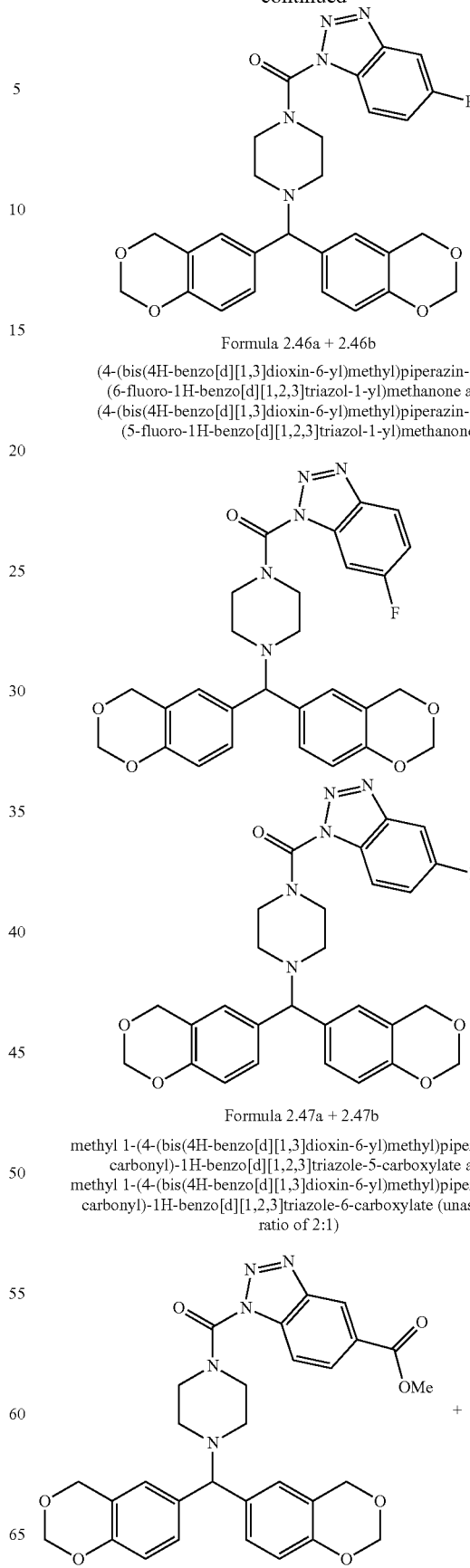

Formula 2.46a + 2.46b (4-(bis(4H-benzo[d][1,3]dioxin-6-yl)methyl)piperazin-1-yl)
(6-fluoro-1H-benzo[d][1,2,3]triazol-1-yl)methanone and
(4-(bis(4H-benzo[d][1,3]dioxin-6-yl)methyl)piperazin-1-yl)
(5-fluoro-1H-benzo[d][1,2,3]triazol-1-yl)methanone Formula 2.47a + 2.47b methyl 1-(4-(bis(4H-benzo[d][1,3]dioxin-6-yl)methyl)piperazine-1-
carbonyl)-1H-benzo[d][1,2,3]triazole-5-carboxylate and
methyl 1-(4-(bis(4H-benzo[d][1,3]dioxin-6-yl)methyl)piperazine-1-
carbonyl)-1H-benzo[d][1,2,3]triazole-6-carboxylate (unassigned
ratio of 2:1)

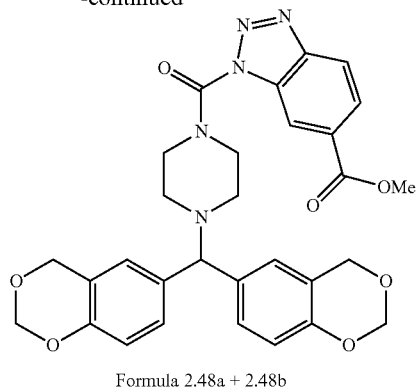

Formula 2.48a + 2.48b (4-(bis(4H-benzo[d][1,3]dioxin-6-yl)methyl)piperazin-1-yl)
(6-trifluoromethyl-1H-benzo[d][1,2,3]triazol-1-yl)methanone and
(4-(bis(4H-benzo[d][1,3]dioxin-6-yl)methyl)piperazin-1-yl)
(5-trifluoromethyl-1H-benzo[d][1,2,3]triazol-1-yl)methanone

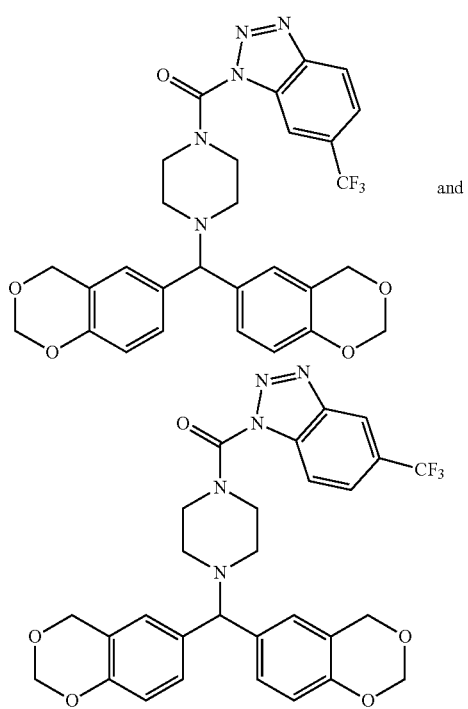

Formula 2.49a + 2.49b (3H-[1,2,3]triazolo[4,5-c]pyridin-3-yl)
(4-(bis(4H-benzo[d][1,3]dioxin-6-yl)methyl)piperazin-1-yl)
methanone and (1H-[1,2,3]triazolo[4,5-c]pyridin-1-yl)
(4-(bis(4H-benzo[d][1,3]dioxin-6-yl)methyl)piperazin-1-yl)
methanone (unassigned ratio of 7:2)

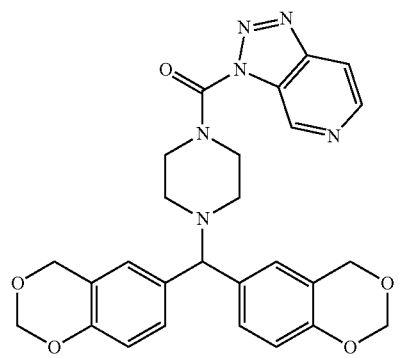

+

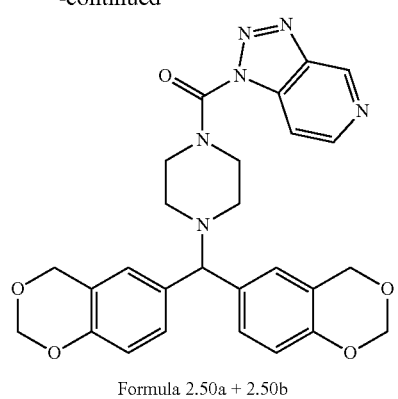

Formula 2.50a + 2.50b 1-(4-(bis(4H-benzo[d][1,3]dioxin-6-yl)methyl)piperazine-1-
carbonyl)-1H-benzo[d][1,2,3]triazole-6-carbonitrile and
1-(4-(bis(4H-benzo[d][1,3]dioxin-6-yl)methyl)piperazine-1-
carbonyl)-1H-benzo[d][1,2,3]triazole-5-carbonitrile

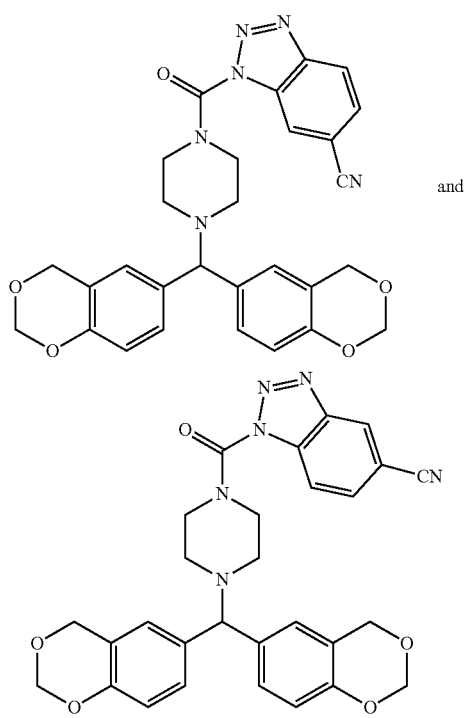

Formula 2.51a + 2.51b 1-(4-(bis(4H-benzo[d][1,3]dioxin-6-yl)methoxy)piperidine-1-
carbonyl)-1H-benzo[d][1,2,3]triazole-6-carbonitrile and
1-(4-(bis(4H-benzo[d][1,3]dioxin-6-yl)methoxy)piperidine-1-
carbonyl)-1H-benzo[d][1,2,3]triazole-5-carbonitrile

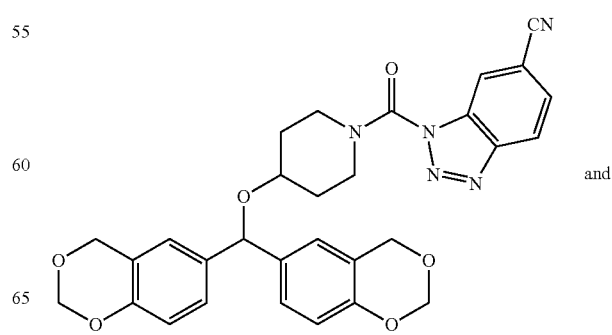

and

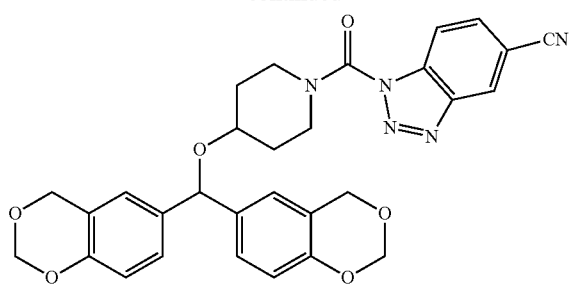

Formula 2.52a + 2.52b 1-(3-(bis(4H-benzo[d][1,3]dioxin-6-yl)methoxy)azetidine-1-carbonyl)-1H-benzo[d][1,2,3]triazole-6-carbonitrile and
1-(3-(bis(4H-benzo[d][1,3]dioxin-6-yl)methoxy)azetidine-1-carbonyl)-1H-benzo[d][1,2,3]triazole-5-carbonitrile
(unassigned ratio of 1:1)

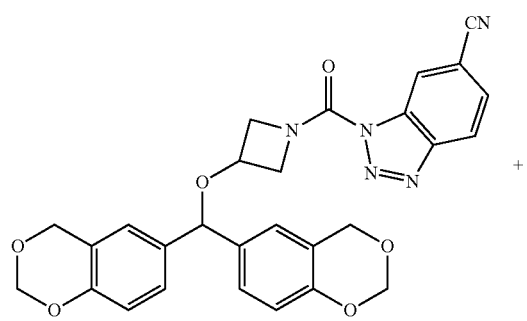

+

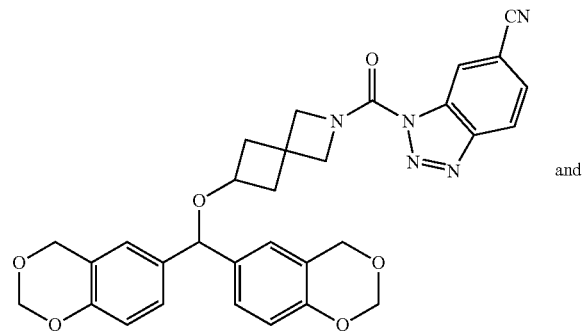

Formula 2.54a + 2.54b 1-(6-(bis(4H-benzo[d][1,3]dioxin-6-yl)methoxy)-2-azaspiro[3.3]heptane-2-carbonyl)-1H-benzo[d][1,2,3]triazole-6-carbonitrile and
1-(6-(bis(4H-benzo[d][1,3]dioxin-6-yl)methoxy)-2-azaspiro[3.3]heptane-2-carbonyl)-1H-benzo[d][1,2,3]triazole-5-carbonitrile

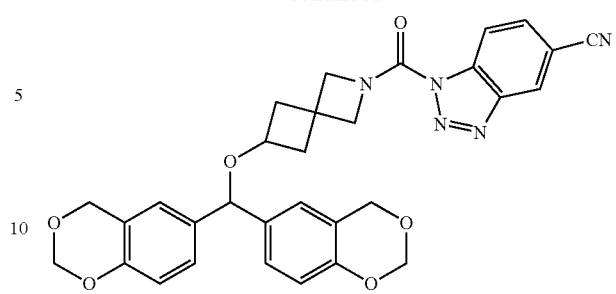

Formula 2.56a + 2.56b 1-(4-(bis(4-fluorophenyl)amino)piperidine-1-carbonyl)-1H-benzo[d][1,2,3]triazole-6-carbonitrile and
1-(4-(bis(4-fluorophenyl)amino)piperidine-1-carbonyl)-1H-benzo[d][1,2,3]triazole-5-carbonitrile

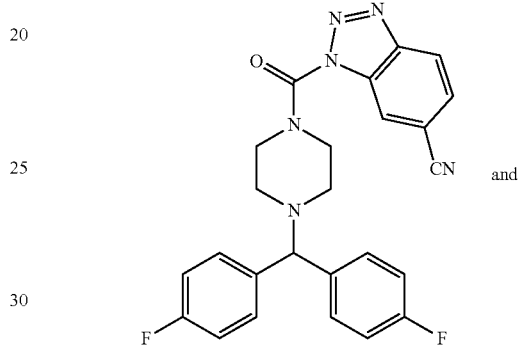

and

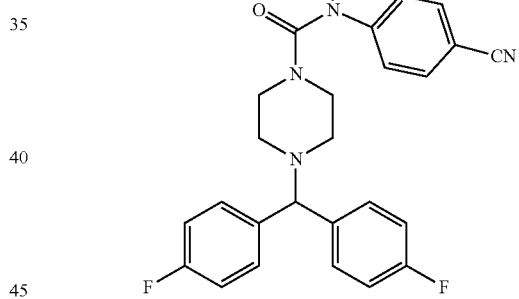

Formula 2.58a + 2.58b 1-((1S,4S)-5-(bis(4H-benzo[d][1,3]dioxin-6-yl)methyl)-2,5-diazabicyclo[2.2.1]heptane-2-carbonyl-1H-benzo[d][1,2,3]triazole-6-carbonitrile and
1-((1S,4S)-5-(bis(4H-benzo[d][1,3]dioxin-6-yl)methyl)-2,5-diazabicyclo[2.2.1]heptane-2-carbonyl-1H-benzo[d][1,2,3]triazole-5-carbonitrile (unassigned ratio of 1:1)

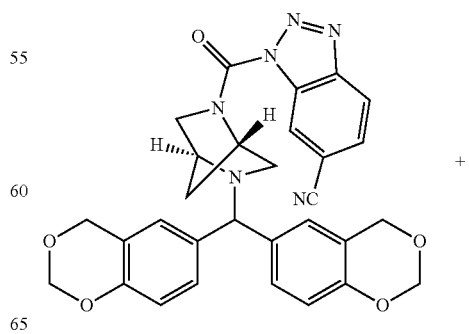

+

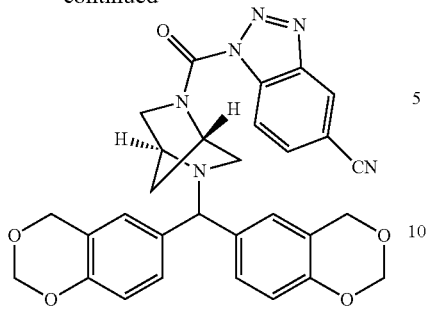

Formula 2.59a + 2.59b

Accordingly, it is also provided a compound that has the formula of formula 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.42a, 2.42b, 2.43a, 2.43b, 2.44a, 2.44b, 2.45a, 2.45b, 2.46a, 2.46b, 2.47a, 2.47b, 2.48a, 2.48b, 2.49a, 2.49b, 2.50a, 2.50b, 2.51a, 2.51b, 2.52a, 2.52b, 2.54a, 2.54b, 2.56a, 2.56b, 2.58a, 2.58b, 2.59a, or 2.59b.

In addition, it is provided compositions or mixtures comprising one or more than one of the compound of formula 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.42a, 2.42b, 2.43a, 2.43b, 2.44a, 2.44b, 2.45a, 2.45b, 2.46a, 2.46b, 2.47a, 2.47b, 2.48a, 2.48b, 2.49a, 2.49b, 2.50a, 2.50b, 2.51a, 2.51b, 2.52a, 2.52b, 2.54a, 2.54b, 2.56a, 2.56b, 2.58a, 2.58b, 2.59a, or 2.59b.

A prodrug of the compound of Formulas I-V, a pharmaceutically acceptable salt thereof, or a pharmaceutically active metabolite thereof are also provided.

The compounds of Formula I-V, their pharmaceutically acceptable derivatives thereof, or combination thereof, may be used in compositions and formulations alone or in combination with an additional therapeutic agent. The compounds of Formulas I-V may target the endocannabinoid system, The compounds of Formulas I may be combined with an additional therapeutic agent, which may be a endocannabinoid system targeting enzyme inhibitor compound, such for example a second MAGL modulator or inhibitor, wherein the second MAGL modulator or inhibitor may be a compounds of Formulas I-V or wherein the second MAGL modulator or inhibitor may be a compound that is not a compound of Formula I-V, but inhibits or modulates MAGL, as described below.

The compounds of Formulas I-V, compositions and formulations may be used in methods for the treatment or prevention of disease states, disorders, and conditions mediated by MAGL activity, such as, but not limited to, anxiety and mood disorder, metabolic disorder, a neurodegenerative disorder, mental disorder, brain disorder, pain, inflammatory disorder, cancer, Alzheimer's disease, movement disorders, epilepsy or stroke.

The present invention relates to compounds of Formula I-V wherein compound has the following formula:

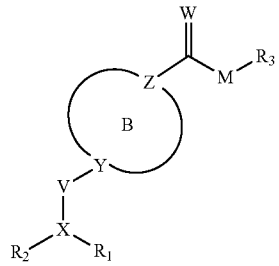

I a prodrug thereof, a pharmaceutically acceptable salt thereof, or a pharmaceutically active metabolite thereof; wherein
a. X represents C or N;
b. V represents O, N(CH$_3$), or none, when V is none X is directly attached to Y by single or double bond;
c. Y represents C or N;
d. Z represents C or N;
e. W represents O or S;
f. M represents O, N, or none, when M is none C=W is directly attached to R$_3$;
g. B represents C$_{1-6}$ alkyl, C$_{4-10}$ heterocycloalkyl, C$_{6-12}$ fused heterocycloakyl, C$_{6-12}$ spirocycloalkyl, azetidine, azepanyl, piperazinyl, piperidinyl, diazepanyl, 2-azaspiro[3.3]heptane, 2,5-diazabicyclo[2.2.1]heptane, 8-azabicyclo[3.2.1]octane, 2,6-diazaspiro[3.4]octane, 2,7-diazaspiro[3.5]nonane, 2,7-diazaspiro[4.4]nonane, 3,9-diazaspiro[5.5]undecane;
h. R$_1$ and R$_2$ may be the same or independent groups represent aryl, heteroaryl, heterocyclyl, phenyl, pyridyl, benzo-1,3-dioxanyl, benzo-1,4-dioxanyl, benzofuranyl, dihydrobenzofuranyl, benzopyrazolyl, quinolinyl. Each group may be unsubstituted, monosubstituted or disubstituted with R$_5$ group; wherein R$_5$ may be one of the following moieties: alkyl, alkoxy, alkenoxy, halogen, cyano, pyrazolyl.
i. R$_3$ represents C$_1$-C$_6$ alkyl, C$_3$-C$_6$ cycloalkyl, C$_4$-C$_8$ heterocycloalkyl, aryl, heteroaryl, piperidinyl, piperazinyl, morpholinyl, phenyl, pyridinyl, imidazolyl, pyrazolyl, benzopyrazolyl, triazolyl, benzotriazolyl, pyridotriazolyl, indanyl; R$_3$ may be unsubstituted or substituted with R$_4$ group; wherein R$_4$ may be one of the following moieties: F, Cl, Br, CF$_3$, NO$_2$, CN, O, OCH$_3$, OCF$_3$, C$_1$-C$_6$ alkyl, C$_1$-C$_6$ alkyloxy, C$_6$H$_5$, OC$_6$H$_5$, C(O)OCH$_3$; or
wherein M and R$_3$ together form a leaving group.

In certain embodiments of Formula I, R$_1$ and R$_2$ independently represent an oxygen-containing heterocyclyl, such as a C$_4$-C$_{10}$ heterocycloalkyl or a C$_{6-12}$ fused heterocycloalkyl.

In certain embodiments of Formula I, R$_1$ and R$_2$ independently represent a benzo-dioxane.

In certain embodiments of Formula I, R$_1$ and R$_2$ independently represent benzo-1,3-dioxane or benzo-1,4-dioxane.

In certain embodiments of Formula I, R$_1$ and R$_2$ independently represent benzo-1,3-dioxane. In certain embodiments of Formula I, R$_1$ and R$_2$ independently represent benzo-1,4-dioxane.

In certain embodiments of Formula I, R$_1$ and/or R$_2$ is fluorophenyl. In certain embodiments of Formula I, R$_1$ and/or R$_2$ is methoxyphenyl. In certain embodiments of Formula I, R$_1$ and/or R$_2$ is trifluoromethylphenyl. In certain embodiments of Formula I, R$_1$ and/or R$_2$ is pyridine. In certain embodiments of Formula I, R$_1$ and/or R$_2$ is (vinyloxy)phenyl. In certain embodiments of Formula I, $R_1$ and/or $R_2$ is dimethoxyphenyl. In certain embodiments of Formula I, $R_1$ and/or $R_2$ is 2,2-difluoro-1,3-benzodioxole. In certain embodiments of Formula I, $R_1$ and/or $R_2$ is benzonitrile. In certain embodiments of Formula I, $R_1$ and/or $R_2$ is dihydrobenzofuran. In certain embodiments of Formula I, $R_1$ and/or $R_2$ is quinoline. In certain embodiments of Formula I, $R_1$ and/or $R_2$ is 1-methyl-1H-indazol. In certain embodiments of Formula I, $R_1$ and/or $R_2$ is methoxypyridine. In certain embodiments of Formula I, $R_1$ and/or $R_2$ is 1-phenyl-1H-pyrazole. In certain embodiments of Formula I, $R_1$ and/or $R_2$ is benzofuran.

In some embodiments, when Y is N, V is a single bond and X is C (CH), i.e. V is nil and Y and X are joined by a single bond.

In some embodiments, Y is N, V is a double bond and X is C, i.e., V is nil and Y and X are joined by a double bond.

In some embodiments, Y is N, V is a single bond and X is N, i.e. V is nil and Y and X are joined by a single bond (hydrazino).

In some embodiments, Y is C (CH), V is a single bond and X is C (CH), i.e. V is nil and Y and X are joined by a single bond.

In some embodiments, Y is C, V is a double bond and X=C, i.e. V is nil and Y and X are joined by a double bond.

In certain embodiment embodiments of Formula I, $R_1$ and $R_2$ are benzo-1,3-dioxane, a compound of Formula II

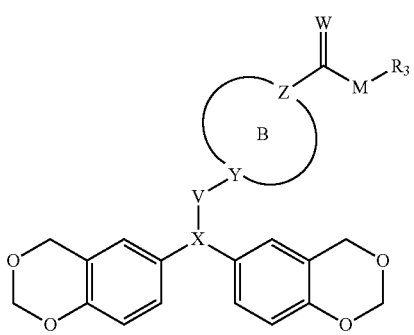

a prodrug thereof, a pharmaceutically acceptable salt thereof, or a pharmaceutically active metabolite thereof.

In some embodiments:
a. X represents C;
b. V represents O, $N(CH_3)$, or none;
c. Y represents C or N;
d. Z represents C or N;
e. W represents O or S;
f. M represents O, N, or none, when M is none C=W is directly attached to $R_3$;
g. B represents azetidinyl, piperazinyl, piperidinyl, azepanyl, diazepanyl, 2-azaspiro[3.3]heptane, 2,5-diazabicyclo[2.2.1]heptane, 2,6-diazaspiro[3.4]octane, 2,7-diazaspiro[3.5]nonane, 2,7-diazaspiro[4.4]nonane, 3,9-diazaspiro[5.5]undecane;
h. $R_3$ represents piperidinyl, piperazinyl, morpholinyl, phenyl, pyridinyl, imidazolyl, pyrazolyl, benzopyrazolyl, triazolyl, benzotriazolyl, pyridotriazolyl, indanyl;
$R_3$ may be unsubstituted or substituted with $R_4$ group; wherein $R_4$ may be one of the following moieties: F, Cl, Br, $CF_3$, $NO_2$, CN, $OCH_3$, $OCF_3$, $C_1$-$C_6$ alkyl, $C_1$-$C_6$ alkyloxy, $C_6H_5$, $OC_6H_5$, $C(O)OCH_3$; or wherein M and $R_3$ together form a leaving group.

Examples of certain useful compounds of Formula II include:

Example 1: (4-(bis(4H-benzo[d][1,3]dioxin-6-yl)methyl)piperazin-1-yl)(1H-pyrazol-1-yl)methanone Example 2: (4-(bis(4H-benzo[d][1,3]dioxin-6-yl)methyl)piperazin-1-yl)(3-chloro-1H-1,2,4-triazol-1-yl)methanone Example 3: 1,1,1,3,3,3-hexafluoropropan-2-yl 4-(bis(4H-benzo[d][1,3]dioxin-6-yl)methyl)piperazine-1-carboxylate Example 4: 4-nitrophenyl 4-(bis(4H-benzo[d][1,3]dioxin-6-yl)methyl)piperazine-1-carboxylate Example 5: 4-fluorophenyl 4-(bis(4H-benzo[d][1,3]dioxin-6-yl)methyl)piperazine-1-carboxylate Example 6: 2,5-dioxopyrrolidin-1-yl 4-(bis(4H-benzo[d][1,3]dioxin-6-yl)methyl)piperazine-1-carboxylate Example 7: 4-phenoxyphenyl 4-(bis(4H-benzo[d][1,3]dioxin-6-yl)methyl)piperazine-1-carboxylate Example 8: (1H-benzo[d][1,2,3]triazol-1-yl)(4-(bis(4H-benzo[d][1,3]dioxin-6-yl)methyl)piperazin-1-yl)methanone Example 9: (4-(bis(4H-benzo[d][1,3]dioxin-6-yl)methyl)piperazin-1-yl)(1H-imidazol-1-yl)methanone Example 10: (4-(bis(4H-benzo[d][1,3]dioxin-6-yl)methyl)piperazin-1-yl)(1H-1,2,4-triazol-1-yl)methanone Example 11: 4-(bis(4H-benzo[d][1,3]dioxin-6-yl)methyl)-N-ethyl-N-isopropylpiperazine-1-carboxamide Example 12: 2,3-dihydro-1H-inden-5-yl 4-(bis(4H-benzo[d][1,3]dioxin-6-yl)methyl)piperazine-1-carboxylate Example 13: 2,4-dinitrophenyl 4-(bis(4H-benzo[d][1,3]dioxin-6-yl)methyl)piperazine-1-carboxylate Example 14: 4-methoxyphenyl 4-(bis(4H-benzo[d][1,3]dioxin-6-yl)methyl)piperazine carboxylate Example 15: pentan-3-yl 4-(bis(4H-benzo[d][1,3]dioxin-6-yl)methyl)piperazine-1-carboxylate Example 16: cyclohexyl 4-(bis(4H-benzo[d][1,3]dioxin-6-yl)methyl)piperazine-1-carboxylate Example 17: (4-(bis(4H-benzo[d][1,3]dioxin-6-yl)methyl)piperazin-1-yl)(piperidin-1-yl)methanone Example 18: 4-(bis(4H-benzo[d][1,3]dioxin-6-yl)methyl)-N,N-diethylpiperazine-1-carboxamide Example 19: 2-fluoro-4-nitrophenyl 4-(bis(4H-benzo[d][1,3]dioxin-6-yl)methyl)piperazine-1-carboxylate Example 20: pyridin-2-yl 4-(bis(4H-benzo[d][1,3]dioxin-6-yl)methyl)piperazine-1-carboxylate Example 21: (4-(bis(4H-benzo[d][1,3]dioxin-6-yl)methyl)piperazin-1-yl)(1H-1,2,4-triazol-1-yl)methanethione Example 22: 6-(trifluoromethyl)-1H-benzo[d][1,2,3]triazol-1-yl 4-(bis(4H-benzo[d][1,3]dioxin-6-yl)methyl)piperazine-1-carboxylate Example 23: 3H-[1,2,3]triazolo[4,5-b]pyridin-3-yl 4-(bis(4H-benzo[d][1,3]dioxin-6-yl)methyl)piperazine-1-carboxylate Example 24: 1-(4-(bis(4H-benzo[d][1,3]dioxin-6-yl)methyl)piperazine-1-carbonyl)-1H-pyrazole-4-carbonitrile Example 25: 4-(bis(4H-benzo[d][1,3]dioxin-6-yl)methyl)piperazin-1-yl)(4-phenyl-1H-1,2,3-triazol-1-yl)methanone Example 26: (4-(bis(4H-benzo[d][1,3]dioxin-6-yl)methyl)piperazin-1-yl)(4-phenyl-2H-1,2,3-triazol-2-yl)methanone Example 27: 1H-benzo[d][1,2,3]triazol-1-yl 4-(bis(4H-benzo[d][1,3]dioxin-6-yl)methyl)piperazine-1-carboxylate Example 28: (4-(bis(4H-benzo[d][1,3]dioxin-6-yl)methyl)piperazin-1-yl)(3-methyl-1H-1,2,4-triazol-1-yl)methanone Example 29: pentaflurophenyl 4-(bis(4H-benzo[d][1,3]dioxin-6-yl)methyl)piperazine-1-carboxylate Example 30: propan-2-one O-(4-(bis(4H-benzo[d][1,3]dioxin-6-yl)methyl)piperazine-1-carbonyl) oxime Example 31: 4-(bis(4H-benzo[d][1,3]dioxin-6-yl)methyl)piperazin-1-yl)(1H-1,2,3-triazol-1-yl)methanone and (4-(bis(4H-benzo[d][1,3]dioxin-6-yl)methyl)piperazin-1-yl)(2H-1,2,3-triazol-2-yl)methanone Example 32: (3H-[1,2,3]triazolo[4,5-b]pyridin-3-yl)(4-(bis(4H-benzo[d][1,3]dioxin-6-yl)methyl)piperazin-1-yl)methanone and (1H-[1,2,3]triazolo[4,5-b]pyridin-1-yl)(4-(bis(4H-benzo[d][1,3]dioxin-6-yl)methyl)piperazin-1-yl)methanone Example 33: 4-(bis(4H-benzo[d][1,3]dioxin-6-yl)methyl)piperazin-1-yl)(5-chloro-1H-benzo[d][1,2,3]triazol-1-yl)methanone and (4-(bis(4H-benzo[d][1,3]dioxin-6-yl)methyl)piperazin-1-yl)(6-chloro-1H-benzo[d][1,2,3]triazol-1-yl)methanone Example 34: 4-(bis(4H-benzo[d][1,3]dioxin-6-yl)methyl)piperazin-1-yl)(5-methyl-1H-benzo[d][1,2,3]triazol-1-yl)methanone and (4-(bis(4H-benzo[d][1,3]dioxin-6-yl)methyl)piperazin-1-yl)(6-methyl-1H-benzo[d][1,2,3]triazol-1-yl)methanone Example 35: (4-(bis(4H-benzo[d][1,3]dioxin-6-yl)methyl)piperazin-1-yl)(1H-indazol-1-yl)methanone Example 36: 1-(4-(bis(4H-benzo[d][1,3]dioxin-6-yl)methyl)piperazine-1-carbonyl)-1H-1,2,4-triazole-3-carbonitrile Example 37: (4-(bis(4H-benzo[d][1,3]dioxin-6-yl)methyl)piperazin-1-yl)(6-bromo-1H-benzo[d][1,2,3]triazol-1-yl)methanone Example 38: (4-(bis(4H-benzo[d][1,3]dioxin-6-yl)methyl)piperazin-1-yl)(5-bromo-1H-benzo[d][1,2,3]triazol-1-yl)methanone Example 39: (4-(bis(4H-benzo[d][1,3]dioxin-6-yl)methyl)piperazin-1-yl)(6-fluoro-1H-benzo[d][1,2,3]triazol-1-yl)methanone Example 40: (4-(bis(4H-benzo[d][1,3]dioxin-6-yl)methyl)piperazin-1-yl)(5-fluoro-1H-benzo[d][1,2,3]triazol-1-yl)methanone Example 41: methyl 1-(4-(bis(4H-benzo[d][1,3]dioxin-6-yl)methyl)piperazine-1-carbonyl)-1H-benzo[d][1,2,3]triazole-5-carboxylate and methyl 1-(4-(bis(4H-benzo[d][1,3]dioxin-6-yl)methyl)piperazine-1-carbonyl)-1H-benzo[d][1,2,3]triazole-6-carboxylate Example 42: (4-(bis(4H-benzo[d][1,3]dioxin-6-yl)methyl)piperazin-1-yl)(4-chloro-6-(trifluoromethyl)-1H-benzo[d][1,2,3]triazol-1-yl)methanone Example 43: 4-(bis(4H-benzo[d][1,3]dioxin-6-yl)methyl)-N-(pyridin-3-yl)piperazine-1-carboxamide Example 44: (4-(bis(4H-benzo[d][1,3]dioxin-6-yl)methyl)piperazin-1-yl)(6-(trifluoromethyl)-1H-benzo[d][1,2,3]triazol-1-yl)methanone Example 45: (4-(bis(4H-benzo[d][1,3]dioxin-6-yl)methyl)piperazin-1-yl)(5-(trifluoromethyl)-1H-benzo[d][1,2,3]triazol-1-yl)methanone Example 46: (4-(bis(4H-benzo[d][1,3]dioxin-6-yl)methyl)piperazin-1-yl)(6,7-dihydro-1H-[1,4]dioxino[2',3':4,5]benzo[1,2-d][1,2,3]triazol-1-yl)methanone Example 47: (3H-[1,2,3]triazolo[4,5-c]pyridin-3-yl)(4-(bis(4H-benzo[d][1,3]dioxin-6-yl)methyl)piperazin-1-yl)methanone and (1H-[1,2,3]triazolo[4,5-c]pyridin-1-yl)(4-(bis(4H-benzo[d][1,3]dioxin-6-yl)methyl)piperazin-1-yl)methanone Example 48: 1-(4-(bis(4H-benzo[d][1,3]dioxin-6-yl)methyl)piperazine-1-carbonyl)-1H-benzo[d][1,2,3]triazole-6-carbonitrile Example 49: 1-(4-(bis(4H-benzo[d][1,3]dioxin-6-yl)methyl)piperazine-1-carbonyl)-1H-benzo[d][1,2,3]triazole-5-carbonitrile Example 50: 2-(4-(bis(4H-benzo[d][1,3]dioxin-6-yl)methyl)piperazine-1-carbonyl)-[1,2,4]triazolo[4,3-a]pyridin-3(2H)-one Example 51: 1-(4-(bis(4H-benzo[d][1,3]dioxin-6-yl)methyl)-1,4-diazepane-1-carbonyl)-1H-benzo[d][1,2,3]triazole-6-carbonitrile Example 52: (1H-benzo[d][1,2,3]triazol-1-yl)(1-(bis(4H-benzo[d][1,3]dioxin-6-yl)methyl)piperidin-4-yl)methanone Example 53: 1,1,1,3,3,3-hexafluoropropan-2-yl 1-(bis(4H-benzo[d][1,3]dioxin-6-yl)methyl)piperidine-4-carboxylate Example 54: pentafluorophenyl 1-(bis(4H-benzo[d][1,3]dioxin-6-yl)methyl)piperidine-4-carboxylate Example 55: N-(2-(4H-benzo[d][1,3]dioxin-6-yl)methoxy)ethyl)-6-cyano-N-methyl-1H-benzo[d][1,2,3]triazole-1-carboxamide Example 56: 1-(4-(bis(4H-benzo[d][1,3]dioxin-6-yl)methoxy)piperidine-1-carbonyl)-1H-benzo[d][1,2,3]triazole-6-carbonitrile Example 57: 1-(4-(bis(4H-benzo[d][1,3]dioxin-6-yl)methoxy)piperidine-1-carbonyl)-1H-benzo[d][1,2,3]triazole-5-carbonitrile Example 58: 1-(3-(bis(4H-benzo[d][1,3]dioxin-6-yl)methoxy)azetidine-1-carbonyl)-1H-benzo[d][1,2,3]triazole-6-carbonitrile and 1-(3-(bis(4H-benzo[d][1,3]dioxin-6-yl)methoxy)azetidine-1-carbonyl)-1H-benzo[d][1,2,3]triazole-5-carbonitrile Example 59: 1-(6-(bis(4H-benzo[d][1,3]dioxin-6-yl)methoxy)-2-azaspiro[3.3]heptane-2-carbonyl)-1H-benzo[d][1,2,3]triazole-6-carbonitrile Example 60: 1-(6-(bis(4H-benzo[d][1,3]dioxin-6-yl)methoxy)-2-azaspiro[3.3]heptane-2-carbonyl)-1H-benzo[d][1,2,3]triazole-5-carbonitrile Example 78: 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-6-carbonitrile and 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-5-carbonitrile Example 79: 1-(9-(bis(4H-benzo[d][1,3]dioxin-6-yl)methyl)-3,9-diazaspiro[5.5]undecane-3-carbonyl)-1H-1,2,4-triazole-3-carbonitrile Example 80: 1-(6-(bis(4H-benzo[d][1,3]dioxin-6-yl)methyl)-2,6-diazaspiro[3.3]heptane-2-carbonyl)-1H-1,2,4-triazole-3-carbonitrile Example 81: meso-1-(5-(bis(4H-benzo[d][1,3]dioxin-6-yl)methyl)octahydropyrrolo[3,4-c]pyrrole-2-carbonyl)-1H-1,2,4-triazole-3-carbonitrile Example 82: 1-(7-(bis(4H-benzo[d][1,3]dioxin-6-yl)methyl)-2,7-diazaspiro[3.5]nonane-2-carbonyl)-1H-1,2,4-triazole-3-carbonitrile Example 83: 1-(2-(bis(4H-benzo[d][1,3]dioxin-6-yl)methyl)-2,7-diazaspiro[3.5]nonane-7-carbonyl)-1H-1,2,4-triazole-3-carbonitrile Example 84: 1-(6-(bis(4H-benzo[d][1,3]dioxin-6-yl)methyl)-2,6-diazaspiro[3.4]octane-2-carbonyl)-1H-1,2,4-triazole-3-carbonitrile Example 85: 1-(7-(bis(4H-benzo[d][1,3]dioxin-6-yl)methyl)-2,7-diazaspiro[4.4]nonane-2-carbonyl)-1H-1,2,4-triazole-3-carbonitrile Example 86: 1-(4-((bis(4H-benzo[d][1,3]dioxin-6-yl)methyl)(methyl)amino)piperidine-1-carbonyl)-1H-benzo[d][1,2,3]triazole-6-carbonitrile and 1-(4-((bis(4H-benzo[d][1,3]dioxin-6-yl)methyl)(methyl)amino)piperidine-1-carbonyl)-1H-benzo[d][1,2,3]triazole-5-carbonitrile Example 129: 1-(4-(bis(4H-benzo[d][1,3]dioxin-6-yl)methyl)piperidine-1-carbonyl)-1H-1,2,4-triazole-3-carbonitrile Example 130: 1-(3-(bis(4H-benzo[d][1,3]dioxin-6-yl)methyl)-8-azabicyclo[3.2.1]octane-8-carbonyl)-1H-1,2,4-triazole-3-carbonitrile Example 131: 1-(4-(bis(4H-benzo[d][1,3]dioxin-6-yl)methyl)azepane-1-carbonyl)-1H-1,2,4-triazole-3-carbonitrile Example 132: 1-(5-(bis(4H-benzo[d][1,3]dioxin-6-yl)methyl)octahydrocyclopenta[c]pyrrole-2-carbonyl)-1H-1,2,4-triazole-3-carbonitrile Example 133: 1-(6-(bis(4H-benzo[d][1,3]dioxin-6-yl)methyl)-2-azaspiro[3.3]heptane-2-carbonyl)-1H-1,2,4-triazole-3-carbonitrile In certain embodiments of Formula I, $R_1$ and $R_2$ are different. In certain embodiments of Formula I, $R_1$ may be an oxygen-containing heterocyclyl such as a benxo-dioxane, such as benzo-1,3-dioxanyl. In certain embodiments of Formula I, $R_2$ may be a heteroaryl, such as an N-containing heteroaryl, such as a pyridyl.

In certain embodiment embodiments of Formula I, $R_1$ is benzo-1,3-dioxanyl and $R_2$ is pyridyl, a compound of Formula III

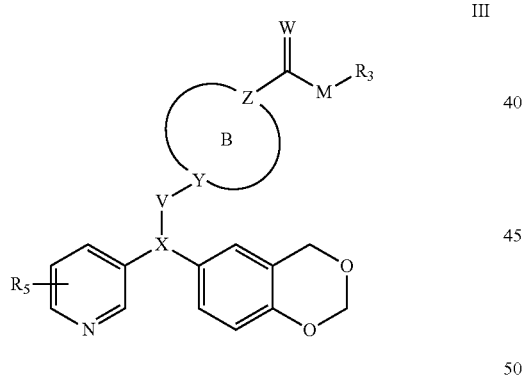

III a prodrug thereof, a pharmaceutically acceptable salt thereof, or a pharmaceutically active metabolite thereof.

In some embodiments:
a. X represents C or N;
b. V represents none, when V is none X is directly attached to Y by single or double bond;
c. Y represents C or N;
d. Z represents C or N;
e. W represents O or S;
f. M represents O, N, or none, when M is none C=W is directly attached to $R_3$;
g. B represents piperazinyl, piperidinyl;
h. $R_5$ represent $C_1$-$C_6$ alkoxy;
i. $R_3$ represents piperidinyl, piperazinyl, morpholinyl, phenyl, pyridinyl, imidazolyl, pyrazolyl, benzopyrazolyl, triazolyl, benzotriazolyl, pyridotriazolyl, indanyl;

$R_3$ may be unsubstituted or substituted with $R_4$ group; wherein $R_4$ may be one of the following moieties: F, Cl, Br, $CF_3$, $NO_2$, CN, $OCH_3$, $OCF_3$, $C_1$-$C_6$ alkyl, $C_1$-$C_6$ alkyloxy, $C_6H_5$, $OC_6H_5$, $C(O)OCH_3$ or wherein M and $R_3$ together form a leaving group.

Examples of certain useful compounds of Formula III include:

Example 118: 1-(4-((4H-benzo[d][1,3]dioxin-6-yl)(6-methoxypyridin-3-yl)methyl)piperazine-1-carbonyl)-1H-1,2,4-triazole-3-carbonitrile Example 119: 1-(4-((4H-benzo[d][1,3]dioxin-6-yl)(6-methoxypyridin-3-yl)methyl)piperazine-1-carbonyl)-1H-pyrazole-4-carbonitrile In some embodiments, in particular embodiments of Formulas I-III, B is:

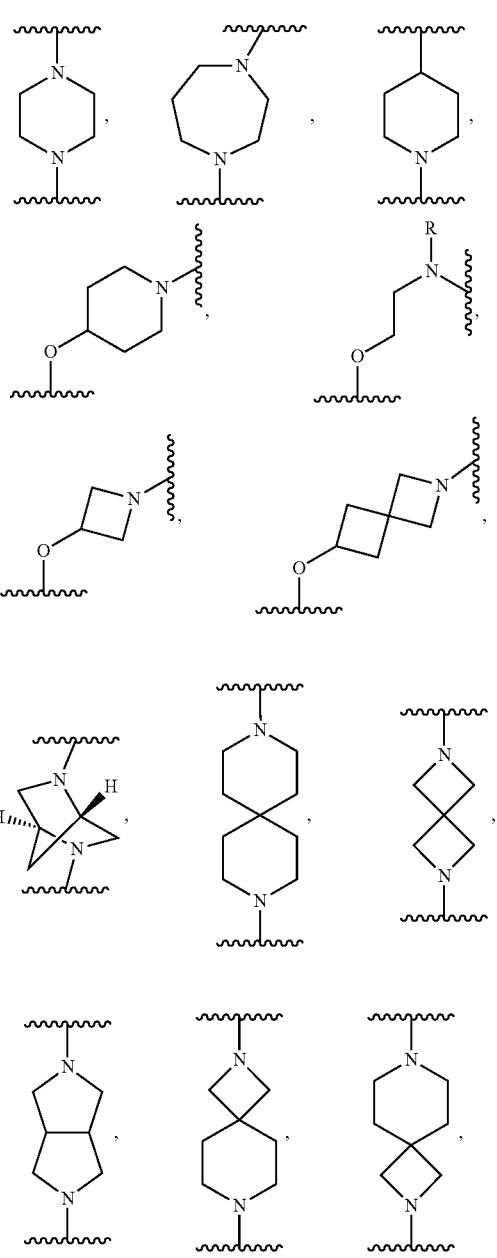

In certain embodiments of Formula I, X is nitrogen.

In certain embodiment embodiments of Formula I, X is nitrogen, a compound of Formula IV.

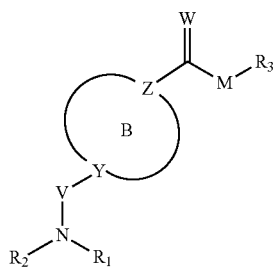

IV a prodrug thereof, a pharmaceutically acceptable salt thereof, or a pharmaceutically active metabolite thereof.

In some embodiments:
a. V represents none, when V is none N is directly attached to Y by single bond;
b. Y represents C;
c. Z represents N;
d. W represents O;
e. M represents O, N, or none, when M is none C=W is directly attached to $R_3$;
f. B represents piperidinyl;
g. $R_1$ and $R_2$ are the same or each independently selected from aryl, heteroaryl, phenyl, pyridyl, benzo-1,3-dioxolyl; each group may be unsubstituted or substituted with $R_5$ group; wherein $R_5$ may be one of the following moieties: F, $CF_3$, $OCH_3$, $OCH=CH_2$;
h. $R_3$ represents phenyl, imidazolyl, pyrazolyl, benzopyrazolyl, triazolyl, benzotriazolyl; each group may be unsubstituted or substituted with $R_4$ group; wherein $R_4$ may be one of the following moieties: F, Cl, Br, $CF_3$, $NO_2$, CN, $OCF_3$, $C_1$-$C_6$ alkyl, $C_1$-$C_6$ alkyloxy; or wherein M and $R_3$ together form a leaving group.

Examples of certain useful compounds of Formula IV include:

Example 61: 1-(4-(bis(4-fluorophenyl)amino)piperidine-1-carbonyl)-1H-benzo[d][1,2,3]triazole-6-carbonitrile Example 62: 1-(4-(bis(4-fluorophenyl)amino)piperidine-1-carbonyl)-1H-benzo[d][1,2,3]triazole-5-carbonitrile Example 63: 1-(4-(benzo[d][1,3]dioxol-5-yl(4-fluorophenyl)amino)piperidine-1-carbonyl)-1H-benzo[d][1,2,3]triazole-6-carbonitrile Example 64: 1-(4-(benzo[d][1,3]dioxol-5-yl(4-fluorophenyl)amino)piperidine-1-carbonyl)-1H-benzo[d][1,2,3]triazole-5-carbonitrile Example 65: 1-(4-((4-fluorophenyl)(4-methoxyphenyl)amino)piperidine-1-carbonyl)-1H-benzo[d][1,2,3]triazole-6-carbonitrile Example 66: 1-(4-((4-fluorophenyl)(4-methoxyphenyl)amino)piperidine-1-carbonyl)-1H-benzo[d][1,2,3]triazole-5-carbonitrile Example 67: 1-(4-(bis(benzo[d][1,3]dioxol-5-yl)amino)piperidine-1-carbonyl)-1H-benzo[d][1,2,3]triazole-6-carbonitrile Example 68: 1-(4-(bis(benzo[d][1,3]dioxol-5-yl)amino)piperidine-1-carbonyl)-1H-benzo[d][1,2,3]triazole-5-carbonitrile Example 69: 1-(4-(benzo[d][1,3]dioxol-5-yl(4-(trifluoromethyl)phenyl)amino)piperidine-1-carbonyl)-1H-benzo[d][1,2,3]triazole-6-carbonitrile Example 70: 1-(4-(benzo[d][1,3]dioxol-5-yl(4-(trifluoromethyl)phenyl)amino)piperidine-1-carbonyl)-1H-benzo[d][1,2,3]triazole-5-carbonitrile Example 71: 1-(4-(benzo[d][1,3]dioxol-5-yl(4-(trifluoromethyl)phenyl)amino)piperidine-1-carbonyl)-1H-1,2,4-triazole-3-carbonitrile Example 72: 1-(4-(benzo[d][1,3]dioxol-5-yl(4-methoxyphenyl)amino)piperidine-1-carbonyl)-1H-benzo[d][1,2,3]triazole-6-carbonitrile Example 73: 1-(4-(benzo[d][1,3]dioxol-5-yl(4-methoxyphenyl)amino)piperidine-1-carbonyl)-1H-benzo[d][1,2,3]triazole-5-carbonitrile Example 74: 1-(4-(benzo[d][1,3]dioxol-5-yl(pyridin-3-yl)amino)piperidine-1-carbonyl)-1H-benzo[d][1,2,3]triazole-6-carbonitrile Example 75: 1-(4-(benzo[d][1,3]dioxol-5-yl(pyridin-3-yl)amino)piperidine-1-carbonyl)-1H-benzo[d][1,2,3]triazole-5-carbonitrile Example 76: 1-(4-((4-fluorophenyl)(4-(vinyloxy)phenyl)amino)piperidine-1-carbonyl)-1H-benzo[d][1,2,3]triazole-6-carbonitrile Example 77: 1-(4-((4-fluorophenyl)(4-(vinyloxy)phenyl)amino)piperidine-1-carbonyl)-1H-benzo[d][1,2,3]triazole-5-carbonitrile In certain embodiments of Formula I, X is carbon. In certain embodiments of Formula I, Y is carbon. In certain embodiments of Formula I, both X and Y are carbon.

In certain embodiments of Formula I, Z is nitrogen.

In certain embodiments of Formula I, V is none.

In certain embodiments of Formula I, X is directly attached to Y by a double bond.

In certain embodiment embodiments of Formula I, X and Y are carbon, Z is nitrogen and V is none, X is directly attached to Y by double bond, a compound of Formula V.

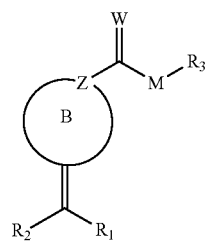

a prodrug thereof, a pharmaceutically acceptable salt thereof, or a pharmaceutically active metabolite thereof.

In some embodiments:
a. W represents O or S;
b. M represents O, N, or none, when M is none C=W is directly attached to $R_3$;
c. B represents piperidinyl, azepanyl, 2-azaspiro[3.3]heptane, azabicyclo[3.2.1]octane, octahydrocyclopenta[c]pyrrole;
d. $R_1$ and $R_2$ are the same or each independently selected from aryl, heteroaryl, benzopyrazolyl, benzo-1,3-dioxolyl; each group may be unsubstituted or substituted with $R_5$ group; wherein $R_5$ may be one of the following moieties: $C_1$-$C_6$ alkyl, $C_1$-$C_6$ alkyloxy;
e. $R_3$ represents phenyl, imidazolyl, pyrazolyl, benzopyrazolyl, triazolyl, benzotriazolyl; each group may be unsubstituted or substituted with $R_4$ group; wherein $R_4$ may be one of the following moieties: F, Cl, Br, $CF_3$, $NO_2$, CN, $OCF_3$, $C_1$-$C_6$ alkyl, $C_1$-$C_6$ alkyloxy; or wherein M and $R_3$ together form a leaving group.

Examples of certain useful compounds of Formula V include:

Example 122: (1H-benzo[d][1,2,3]triazol-1-yl)(4-(bis(1-methyl-1H-indazol-5-yl)methylene)piperidin-1-yl) methanone Example 123: 1-(4-(bis(1-methyl-1H-indazol-5-yl)methylene)piperidine-1-carbonyl)-1H-1,2,4-triazole-3-carbonitrile Example 124: 1-(4-(bis(4H-benzo[d][1,3]dioxin-6-yl)methylene)piperidine-1-carbonyl)-1H-1,2,4-triazole-3-carbonitrile Example 125: 1-(5-(bis(4H-benzo[d][1,3]dioxin-6-yl)methylene)octahydrocyclopenta[c]pyrrole-2-carbonyl)-1H-1,2,4-triazole-3-carbonitrile Example 126: 1-(6-(bis(4H-benzo[d][1,3]dioxin-6-yl)methylene)-2-azaspiro[3.3]heptane-2-carbonyl)-1H-1,2,4-triazole-3-carbonitrile Example 127: 1-(3-(bis(4H-benzo[d][1,3]dioxin-6-yl)methylene)-8-azabicyclo[3.2.1]octane-8-carbonyl)-1H-1,2,4-triazole-3-carbonitrile Example 128: 1-(4-(bis(4H-benzo[d][1,3]dioxin-6-yl)methylene)azepane-1-carbonyl)-1H-1,2,4-triazole-3-carbonitrile Definitions Monoacylglycerol Lipase (MAGL) Inhibitor The compound of Formulas I-V, may modulate, inhibit or modulate and inhibit Monoacylglycerol lipase (MAGL). Accordingly, the compound of Formulas I-V, may be a MAGL inhibitor, a MAGL modulator or a MAGL inhibitor and modulator.

As used herein, the term "modulate", "modulatory", "modulation" or "modulating" refers to a change in the activity e.g., of the MAGL enzyme. As used herein, the term "inhibit", "inhibitory", "inhibition" or "inhibiting" refers to the reduction or suppression of the activity e.g., of the MAGL enzyme or a significant decrease in the baseline activity of a biological activity or process e.g., of the MAGL catalyzed reaction of the MAGL enzyme. The one or more than one inhibition or modulation of the MAGL enzyme may be irreversible or the one or more than one inhibition or modulation of MAGL enzyme may be reversible, therefore the one or more than one MAGL inhibitor or modulator may be an irreversible MAGL inhibitor or modulator, or the MAGL inhibitor or modulator may be a reversible MAGL inhibitor or modulator.

The compound of Formula I-V may be an irreversible MAGL inhibitor or modulator. In one embodiment the compound of Formula I-V may be combined with a reversible MAGL inhibitor or modulator. Furthermore, the compound of Formula I-V may also be combined with a second irreversible MAGL inhibitor or modulator. The second irreversible MAGL inhibitor or modulator may be a compound of Formula I-V or the second MAGL inhibitor or modulator may not be a compound of Formula I-V.

MAGL antagonist compounds which also inhibit other brain serine hydrolases (e.g., FAAH) can interfere with the various biological functions mediated by those other enzymes. Thus, molecules that selectively inhibit the one or more than one MAGL enzyme are desirable. The one or more than one MAGL inhibitor or modulator may specifically inhibit MAGL enzymatic activity while causing no significant effect on the other brain serine hydrolases (e.g., FAAH). Accordingly, the compound may not inhibit brain serine hydrolases (e.g., MAGL). Accordingly, the one or more than one MAGL inhibitor may be a selective MAGL inhibitor or modulator. In an example the MAGL inhibitor or modulator may inhibit or modulate a hydrolase, wherein the hydrolase comprises or consists of MAGL.

Selective MAGL inhibitor or modulator may be defined as the selective pharmacological blockade of MAGL, e.g., that distinguish the endogenous functions of AEA-mediated endocannabinoid pathways.

MAGL inhibitors or modulators are classified as reversible or irreversible. The main difference is that reversible enzyme inhibition inactivates enzymes through non-covalent interaction. In contrast, an irreversible inhibitor inactivate enzyme through covalent binding to form a stable complex with the enzyme. As a result, the enzyme is permanently inactivated or, at best, is slowly reactivated. The compounds described herein may be an irreversible inhibitor or modulator of the MAGL enzyme and this would not show any subsequent competition for binding by accumulated endogenous substrates. Irreversible binding enables and maintains the essential complete inhibition of the enzyme.

This disclosure is also directed to a method of testing the inhibition of MAGL and FAAH enzymes in both in vitro and in vivo systems.

Compounds

The MAGL inhibitor or modulator may be compounds of Formulas I-V, disclosed herein, or a combination thereof.

The term "alkyl", as used herein, refers to a saturated linear or branched-chain monovalent hydrocarbon radical. Unless otherwise specified, an alkyl group contains 1-10 carbon atoms.

Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "cycloalkyl" refers to a fully saturated cyclic hydrocarbon group containing from 3-12 carbon atoms. Examples of cycloalkyl groups include, but are not limited to, cyclobutyl, cyclopentyl, cyclohexyl, cycloheptyl, etc.

The term "heterocycloalkyl" refers to a fully saturated cyclic hydrocarbon group containing one or more heteroatom. The term heterocycloalkyl includes fused, spiro or bridged ring systems. Examples of heterocycloalkyl groups include, but are not limited to, piperazine, piperidine, 2-azaspiro[3.3]heptane, 2,5-diazabicyclo[2.2.1]heptane, 8-azabicyclo[3.2.1]octane, 2,6-diazaspiro[3.4]octane, 2,7-diazaspiro[3.5]nonane, 2,7-diazaspiro[4.4]nonane, 3,9-diazaspiro[5.5]undecane, etc.

The term "heterocyclyl" refers to a cyclic hydrocarbon group containing one or more heteroatom. The cyclic group may be saturated or unsaturated, or may comprise a combination of both saturated and unsaturated rings. The heterocyclic group may be monocyclic, bicyclic or tricyclic. The term "oxygen-containing heterocyclyl" refers to a heterocyclyl ring system containing at least one oxygen molecule. Examples of oxygen-containing heterocyclyl groups include benzopyranyl, benzo-dioxanyl, benzo-1,3-dioxanyl, benzo-1,4-dioxanyl, benzofuranyl, dihydrobenzofuranyl, benzopyrazolyl.

The term "aryl" refers to a carbocyclic ring system wherein at least one ring in the system is aromatic and has a single point of attachment to the rest of the molecule. Unless otherwise specified, an aryl group may be monocyclic, bicyclic or tricyclic.

The term "heteroaryl" as used herein, refers to a ring system in which one or more ring members are an independently selected heteroatom. The term heteroaryl also includes fused, spiro or bridged heterocyclic ring systems. Unless otherwise specified, a heterocycle may be monocyclic, bicyclic or tricyclic.

"Fused" bicyclic ring systems comprise two rings which share two adjoining ring atoms.

"Spiro" bicyclic ring systems share only one ring atom (usually a quaternary carbon atom).

The term "leaving group" or "LG" refers to a group capable of being displaced from the compound in a substitution reaction, such as with a nucleophile. Examples of leaving groups formed by M and $R_3$ together include but are not limited to, for example, when M is O: —O—$C_1$-$C_6$ alkyl, —O—$C_3$-$C_6$ cycloalkyl, —O—$C_4$-$C_8$ heterocycloalkyl, —O-aryl, —O-heteroaryl, —O-phenyl, O-pyridotriazolyl, —O-indanyl; when M is N: —NH-pyridinyl; when M is none: heteroaryl, imidazolyl, pyrazolyl, benzopyrazolyl, triazolyl, benzotriazolyl, pyridotriazolyl pyridinyl, piperidinyl, piperazinyl, morpholinyl.

The compounds of this disclosure include any and all of possible isomers, regioisomers, stereoisomers, enantiomers, diastereomers, racemates, tautomers, free form (e.g., amorphous, polymorphs), pharmaceutically acceptable salts, polymorphs, hydrates, and solvates thereof, as well as isotopic analogs (e.g., deuterium replacing hydrogen) of the above. The disclosed compounds can be also used to prepare prodrugs. Prodrugs are known to those skilled in the art of medicinal chemistry and provide benefits such as increasing bioavailability and prolong the duration of action (half-life).

Compounds of the invention may be synthesized using the conventional methods and utilizing the commercially available reagents and starting materials and/or from compounds described in the chemical literature. "Commercially available chemicals" are obtained from standard commercial sources. It will be readily understood that numerous alterations may be made to the examples and instructions given herein for the synthesis methods and purification of compounds of Formula I-V.

It should also be understood that certain compounds of the disclosure may exist in free state or, where appropriate, as a pharmaceutically acceptable derivative thereof.

The term "pharmaceutically acceptable derivative" includes, but is not limited to, a pharmaceutically acceptable salt, ester, solvate, N-oxide, metabolite or prodrug, which, after being administered to a patient in need thereof, can directly or indirectly provide the compound of the disclosure or a metabolite or residue thereof. Therefore, "the compound of the disclosure" mentioned herein is also intended to cover various derivative forms of the compound.

The compounds used in the reactions described herein are made according to organic synthesis techniques, starting from commercially available chemicals and/or from compounds described in the chemical literature. "Commercially available chemicals" are obtained from standard commercial sources.

Specific and analogous reactants are also identified through the indices of known chemicals prepared by the Chemical Abstract Service of the American Chemical Society.

It will be readily understood that numerous alterations may be made to the examples and instructions given herein for the synthesis methods and purification of compounds of Formula I-V. The synthesis of the compounds of the disclosure is illustrated by the schemes outlined in Example 1 including the preparation of the intermediates and do not limit the scope of the invention in any way.

Pharmaceutically Acceptable Salt

The term "pharmaceutically acceptable salt" as used herein encompasses any and all pharmaceutically acceptable salt forms. Those compounds of the disclosure that are basic in nature are capable of forming acid salts with various pharmacologically accepted anions. The chemical acids which are used as reagents to prepare acid salts of this disclosure include both inorganic and organic acids. In some embodiments, these salts are prepared in situ during the final isolation and purification of the compounds of the disclosure, or by separately reacting a purified compound in its free form with a suitable acid or base, and isolating the salt thus formed. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002 (Stahl & Wermuth 2002 [17]). In some embodiments, the pharmaceutically acceptable salts of the compounds described herein are pharmaceutically acceptable acid addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Prodrugs

In some embodiments, the compounds described herein may exist in prodrug form. The disclosure provides for methods of treating diseases by administering such prodrugs. The disclosure further provides for methods of treating diseases by administering such prodrugs as pharmaceutical compositions.

Metabolites

In some embodiments, the compounds of Formula I-V described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

Combinations

Also contemplated herein are combination therapies, for example, co-administering a disclosed compound of Formula I-V and an additional therapeutic agent, as part of a specific treatment regimen intended to provide the beneficial effect from the co-action of these therapeutic agents.

The combinations may comprise one or more than one endocannabinoid system targeting enzyme inhibitor compound such as a MAGL inhibitor compound described herein. For example, the combinations may comprise: (i) a compound of Formula I-V described herein, a prodrug thereof, pharmaceutically acceptable salt thereof, pharmaceutically active metabolite thereof, or a combination thereof; and (ii) one or more additional therapeutic agents. Alternatively, the combinations may comprise (i) a first compound of Formula I-V described herein, a prodrug thereof, pharmaceutically acceptable salt thereof, pharmaceutically active metabolite thereof, and (ii) a second compound of Formula I-V described herein, a prodrug thereof, pharmaceutically acceptable salt thereof, pharmaceutically active metabolite thereof, wherein the first and second compounds are different. The first and second compounds may be different in the sense that the compounds have a different chemical structure, or may be different in the sense that they are in a different form e.g., a compound in the free form and a prodrug of the same compound, or two different pharmaceutically acceptable salts of the same compound.

The one or more additional therapeutic agent may be selected from the group consisting of, but are not limited to, acetylcholinesterase inhibitors, acetaminophen, Adenosine A2A receptor antagonists, alpha-2-delta inhibitor (e.g., gabapentin or pregabalin), alpha-adrenoreceptor antagonists, alpha-adrenergic receptor agonists (e.g., clonidine or guanfacine), beta3 adrenaline antagonist (e.g., amibegron hydrochloride), amyloid-b (or fragments thereof), amyloid-lowering or -inhibiting agents (including those that reduce amyloid production, accumulation and fibrillization), anti-ADHD drug (e.g., atomoxetine, methylphenidate hydrochloride, methamphetamine, and hydrochloride), anti-Alzheimer's agents (e.g., memantine, Dimebon, donepezil, galanthamine, and rivastigmine), anti-angiogenesis agents (e.g., MMP-2 (matrix-metalloproteinase 2) inhibitors, MMP-9 (matrix-metalloprotienase 9) inhibitors, and COX-11 (cyclooxygenase 11) inhibitors, rapamycin, temsirolimus (CCI-779), everolimus (RAD001), sorafenib, sunitinib, and bevacizumab), anti-anxiety agents (e.g., benzodiazepines: alprazolam, chlordiazepoxide, clonazepam, chlorazepate, diazepam, halazepam, lorazepam, oxazepam, and prazepam; meprobamate), antibody medicament (e.g., antibodies to amyloid-b (or fragments thereof)), anti-cancer agent (chemotherapeutic agents, ablation or other therapeutic hormones, antineoplastic agents, monoclonal antibodies useful against cancers and angiogenesis inhibitors), anti-cytokine drug (e.g., TNF inhibitor, MAP kinase inhibitor), Antidepressants (e.g., imipramine hydrochloride, amitriptyline hydrochloride, desipramine hydrochloride, clomipramine hydrochloride) and atypical antidepressants (e.g., bupropion, lithium, nefazodone, trazodone and viloxazine), anti-epilepsy drug (e.g., lamotrigine, valproate, clonazepam, oxcarbazine, carbamazepine, phenytoin, phenobarbital, primidone, zonisamide, sodium valproate, ethosuximide, diazepam, nitrazepam, clobazam, gabapentin, topiramate, levetiracetam, stiripentol, and rufinamide), anticholinergics (e.g., benztropine, trihexyphenidyl, or procyclidine), anticonvulsants, antihemorrhagic agents (e.g., coagulation factors, activators, or stabilizers) include Factor Xa inhibitors (e.g., rivaroxaban or apixaban) and recombinant Coagulation Factor VIIa (e.g., NovoSeven®), anti-LID (levodopa-induced dyskinesia), antiobesity drug, antipsychotics agents (e.g., paliperidone, bifeprunox, ziprasidone, risperidone, aripiprazole, olanzapine, and quetiapine), anti-pain agents (e.g., aspirin, naproxen, ibuprofen, salsalate, diflunisal, dexibuprofen, enoprofen, ketoprofen, oxaprozin, loxoprofen, indomethacin, tolmetin, sulindac, etodolac, ketorolac, piroxicam, meloxicam, tenoxicam, droxicam, lomoxicam, celecoxib, parecoxib, rimonabant, etoricoxib, morphine, codeine, hydromorphone, hydrocodone, oxymorphone, fentanyl, tramadol, levorphanol, pregabalin, gabapentin, clonidine, neostigmine, baclofen, midazolam, ketamine and/or ziconotide), anti-Parkinson's disease agents (e.g., zonisamide, talipexole, istradefylline, promethazine, L-DOPA (or its methyl or ethyl ester), DOPA decarboxylase inhibitor (e.g., carbidopa), Adenosine A$_{2A}$ receptor antagonist (e.g., Preladenant, benserazide, alpha-methyldopa, monofluoromethyldopa, difluoromethyldopa, brocresine, or m-hydroxybenzylhydrazine), dopamine agonist (e.g., as apomorphine, bromocriptine, cabergoline, dihydrexidine, dihydroergocryptine, fenoldopam, lisuride, pergolide, piribedil, pramipexole, quinpirole, ropinirole, rotigotine, SKF-82958 (GlaxoSmithKline) and sarizotan), monoamine oxidase (MAO) inhibitor (e.g., selegiline, selegiline hydrochloride (L-deprenyl), dimethylselegilene, brofaromine, phenelzine, phenelzine sulfate, tranylcypromine, tranylcypromine sulfate, moclobemide, befloxatone, safinamide, isocarboxazid, nialamide, rasagiline, iproniazide, CHF-3381 (Chiesi Farmaceutici), iproclozide, toloxatone, bifemelane, desoxypeganine, harmine (e.g., telepathine or banasterine), harmaline, linezolid, and pargyline), catechol O-methyltransferase (COMT) inhibitor (e.g., tolcapone, entacapone, and tropolone)), N-methyl-D-aspartate (NMDA) receptor antagonist (e.g., amantadine), anticholinergics (e.g., amitriptyline, butriptyline, benztropine mesylate, trihexyphenidyl, diphenhydramine, orphenadrine, hyoscyamine, atropine, scopolamine, scopolamine methylbromide, dicycloverine, tolterodine, oxybutynin, penthienate bromide, propantheline, cyclizine, imipramine hydrochloride, imipramine maleate, lofepramine, desipramine, doxepin, trimipramine, and glycopyrrolate), antirheumatic drug (e.g., tofacitinib, leflunomide, or methotrexate), anti-schizophrenia agents (e.g., chlorpromazine, haloperidol, sulpiride, clozapine, trifluoperazine hydrochloride, fluphenazine hydrochloride, quetiapine fumarate, risperidone, ziprasidone, risperidone, olanzapine, quetiapine, aripiprazole, asenapine, blonanserin, or iloperidone), apoptosis inhibitor, Autophagy inhibitors (e.g., chloroquine, 3-methyladenine, hydroxychloroquine (Plaquenil™), bafilomycin A1,5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine), beta-adrenergic receptor blocking agents (beta blockers), calcium receptor antagonist, calcium channel, catechol O-methyltransferase (COMT) inhibitors, L-type calcium channel inhibitor, N-type calcium channel inhibitor, cannabinoid receptor (CB1 or CB2) modulator (e.g., CP-55,940 and WIN-55, 0-1812, JWH-133, rimonabant), cannabinoids (exo- or endo-)(e.g., delta-9-THC, nabiximols (Sativex), cannabidiol, AEA, and 2-AG), carbonic anhydrase II inhibitor, CCK antagonist, central nervous system stimulants, cholinesterase inhibitors (e.g., such as rivastigmine, galantamine, and donepezil), corticosteroids, corticotropin releasing factor (CRF) antagonists, COX1 or COX2 inhibitors, dopamine receptor agonists (e.g., bromocriptine, pramipexole, or ropinirole), dopamine receptor antagonists (e.g., haloperidol, pimozide, or fluphenazine), dopamine reuptake inhibitors, dopamine replacement therapy (e.g., levodopa or carbidopa-levodopa), FAAH inhibitor, gamma-aminobutyric acid (GABA) receptor agonists, GAT-1 inhibitor (e.g., tiagabine hydrochloride), glutamate inhibitor (e.g., riluzole), $H_1$ antihistamine (e.g., diphenhydramine, hydroxyzine, cetirizine, loratadine, or desloratadine), heart non-selective beta inhibitor (e.g., propranolol hydrochloride, oxprenolol hydrochloride), histamine H.sub.1 antagonist (e.g., hydroxyzine hydrochloride), histamine 3 (H3) antagonists, 5-HT.sub.2A antagonist, 5-HT.sub.2A inverse agonist, 5-HT.sub.3 antagonist (e.g., cyamemazine), 5-HT4 agonist (e.g., tegaserod or mosapride), immunomodulators, immunosuppressants, interferons, levodopa (or its methyl or ethyl ester), alone or in combination with a DOPA, decarboxylase inhibitor, N-methyl-D-aspartate (NMDA) receptor antagonists, monoamine oxidase (MAO) inhibitors, muscarinic receptor (particularly M1 or M4 subtype) agonists, muscle relaxant (e.g., baclofen and tizanidine), nerve regeneration promoter, neuroleptic (e.g., pimozide, olanzapine, risperidone, or quetiapine), neuronal differentiation promoter, neuroprotective drugs, nicotinic receptor agonists, nicotinic acid receptor agonist, nicotine acetylcholine agonists (e.g., ispronicline, varenicline and MEM 3454), NK-1 receptor antagonists, NMDA receptor antagonists (e.g., memantine), NMDA glycine moiety agonist, non-steroidal anti-inflammatory drug (e.g., such as naproxen, diclofenac, meloxicam, tenoxicam, indomethacin, ibuprofen, celecoxib, rofecoxib, aspirin), norepinephrine (noradrenaline) reuptake inhibitor (e.g., reboxetine mesylate), norepinephrine reuptake inhibitors (e.g., amitriptyline, clomipramine, doxepin, imipramine, trimipramine, dothiepin, butriptyline, iprindole, lofepramine, nortriptyline, protriptyline, amoxapine, desipramine and maprotiline), noradrenaline-dopamine reuptake inhibitor (e.g., bupropion hydrochloride), nucleic acid or nucleic acid derivative, aptamer drug and the like, Opioid (e.g., morphine, codeine, oxycodone, oxymorphone, tramadol, tapentadol, methadone, or fentanyl); opioid antagonist, opioid reuptake inhibitor, peripheral benzodiazepine receptor agonist, phosphodiesterase (PDE) inhibitors, PDE inhibitors (PDE 10 (e.g., PDE10A) inhibitors, PDE1 inhibitors, PDE2, PDE4 inhibitors, PDE5 inhibitors), phosphodiesterase inhibitor, prokinetic agent (e.g., metoclopramide, domperidone, or itopride), quinolines, reversible inhibitors of monoamine oxidase (RIMAs) (e.g., moclobemide), b-secretase inhibitors, g-secretase inhibitors, selective serotonin reuptake inhibitors (SSRIs) (e.g., sertraline, citalopram or escitalopram, fluvoxamine, fluoxetine, paroxetine and their salts thereof, citalopram hydrobromide and escitalopram oxalate), serotonin 1b/1d agonist, Serotonin receptor antagonists ((serotonin (5-hydroxytryptamine) 1A (5-HTiA) receptor antagonists, serotonin (5-hydroxytryptamine) 4 (5-HT4) receptor agonists, serotonin (5-hydroxytryptamine) 6 (5-HT6) receptor antagonists)), serotonin (5-HT) reuptake inhibitors, serotonin and noradrenaline reuptake inhibitors (SNRIs) (e.g., venlafaxine, venlafaxine hydrochloride, duloxetine, milnacipran, clomipramine, duloxetine hydrochloride, and desvenlafaxine hydrochloride), serotonin 1A (5-HT1A) agonists or antagonists, especially 5-HT1A partial agonists (e.g., buspirone, buspirone hydrochloride, tandospirone citrate, osemozotan hydrochloride, flesinoxan, gepirone, and ipsapirone), sex hormone or a derivative thereof (e.g., progesterone, estradiol, estradiol benzoate), sodium channel inhibitor, steroid (e.g., dexamethasone, cortisone acetate), stimulant (e.g., methylphenidate, dextroamphetamine, or lisdexamfetamine), tachykinin antagonist (e.g., MK-869, saredutant), thyroid hormone (T3, T4), TSH, TRH), triptan (e.g., sumatriptan or zolmitriptan), trophic factors, and agents that stimulate production of trophic factors, uridine, vasopressin antagonist, vasopressin V1b antagonist, vasopressin V1a antagonist, and VMAT2 inhibitor (e.g., tetrabenazine).

Furthermore, a compound of Formula I-V described herein, their prodrug forms or a pharmaceutically acceptable salt thereof, or combination thereof, may be co-administered with additional therapeutic agents, such as, but are not limited to a, therapeutic drug for abnormal behavior or suppressant of dromomania due to dementia (e.g., sedatives, antianxiety drug), therapeutic drug for alcoholism, therapeutic drug for alcohol-related syndrome, therapeutic drug for ALS (e.g., riluzole etc., neurotrophic factor), therapeutic drug for autism, therapeutic drug for autonomic ataxia, therapeutic drug for bipolar disorder (e.g., lithium carbonate, sodium valproate, lamotrigine, riluzole, felbamate), therapeutic drug for cerebral infarction, therapeutic drug for chronic fatigue syndrome, therapeutic drug for diabetes, therapeutic drug for dysthymia, therapeutic drug for hypertension, therapeutic drug for hypotension, therapeutic drug for Huntington's disease (e.g., chlorpromazine hydrochloride, haloperidol, and reserpine), therapeutic drug that acts on metabotropic glutamate receptor, therapeutic drug for rheumatism (DMARD), therapeutic drug for fibromyalgia syndrome, therapeutic drug for headache, therapeutic drug for hypersomnia, therapeutic drug for insomnia (e.g., etizolam, zopiclone, triazolam, zolpidem, ramelteon, and indiplon), therapeutic drug for irritable bowel syndrome, therapeutic drug for male and female sexual dysfunction, therapeutic drug for mania, therapeutic drug for metabolic disorders (e.g., pravastatin sodium, atrovastatin, simvastatin, rosuvastatin, clofibrate, fenofibrate, lanifibranor, elafibranor, pioglitazone, saroglitazar, squalene synthetase inhibitor), therapeutic drug for migraine, therapeutic drug for multiple sclerosis (e.g., fingolimod, interferon beta 1b, natalizumab and the like), therapeutic drug for myasthenia gravis, therapeutic drug for quitting smoking, therapeutic drug for pain, therapeutic drug for parathyroid (PTH), therapeutic drug for pathological gambler, therapeutic drug for restless legs syndrome, and therapeutic drug for substance addiction.

In some embodiments, a compound of Formula I-V described herein, or a pharmaceutically acceptable derivative thereof, is co-administered with one or more cannabinoids. The cannabinoids may be exo-cannabinoids, their prodrugs, or a pharmaceutically acceptable salt thereof, but not limited to, Cannabidiol (CBD), Cannabigerol (CBG), Cannabinol (CBN), Cannabichromene (CBC), Abnormal cannabidiol (Abn-CBD), Tetrahydrocannabinol (delta-9-THC) and nabiximols (e.g., Sativex®). In some embodiments, the cannabinoids may be endocannabinoids, their prodrugs, or a pharmaceutically acceptable salt thereof, but not limited to, AEA and 2-AG.

Further MAGL Inhibitor/Modulator

In some embodiments, a compound of Formula I-V described herein, or a pharmaceutically acceptable derivative thereof, is co-administered with a further MAGL inhibitor or modulator, wherein the further MAGL inhibitor or modulator is not a compound of Formula I-V. The further MAGL inhibitor includes but is not limited to, natural MAGL inhibitors/modulators, synthetic MAGL inhibitors/modulators, Dual MAGL/FAAH inhibitors/modulators, or combinations thereof.

MAGL inhibitors and/or modulator may be selected from the list consisting of, without being limited thereto: antagonists against the MAGL enzyme—such as a chemical antagonist, silencing RNA or specific antibody against the MAGL enzyme e.g., a monoclonal antibody.

The term "natural MAGL inhibitor or modulator" refers to a compounds that occur naturally whereas the term "synthetic MAGL inhibitor or modulator" refers to agents that do not occur naturally. "Dual MAGL/FAAH inhibitors/modulators" refer to agents that inhibit or modulate both MAGL and FAAH. The compounds of Formula I-V of the present disclosure are synthetic MAGL inhibitors/modulators, but may be combined with one or more further natural or synthetic MAGL inhibitor/modulator.

Examples of natural MAGL inhibitors, but are not limited to, tanshinone IIA, pristimerin and euphol. Examples of synthetic MAGL inhibitors. Examples of natural FAAH inhibitors include, but are not limited to, Maleimide-based MAGL inhibitors (N-ethylmaleimide (NEM), N-arachidonylmaleimide (NAM), 1-biphenyl-4-ylmethylmaleimide); Natural compounds as MAGL inhibitors (pristimerin and euphol); Disulfide-based MAGL inhibitors (disulfiram and related analogues); Isothiazolinone-based MAGL inhibitors (octhilinone); Carbamate-based MAGL inhibitors (URB602 (104) and URB602 analogues, 4-bisarylcarbinol analogue JZL184, 4-aryloxybenzyl-based analogue JZL195, JZL184, JZL195, KML29, JW642, [2,4-dinitrophenyl-4-benzhydrylpiperazine-1-carbodithioate](CK16), 2,4-dinitrophenyl-4-(4-tert-butylbenzyl)piperazine-1-carbodithioate (CK37), and MJN110); Urea-based MAGL inhibitors (AM6701, SAR629, ML30, JJKK-048, 1,2,4-triazole analogue of JZL184); miscellaneous MAGL inhibitors (OMDM169), silencing RNA and specific antibody against the MAGL enzyme.

In some embodiments, a compound of Formula I-V described herein, or a pharmaceutically acceptable derivative thereof, is co-administered with FAAH inhibitors, their prodrugs, or a pharmaceutically acceptable salt thereof, but are not limited to, natural FAAH inhibitors, and synthetic FAAH inhibitors. Examples of natural FAAH inhibitors include, but are not limited to, Diadzein, biochanin A, Greenstein, Kaempferol, 7-hydroxyflavone and 3,7-dihydroxyflavone. Examples of synthetic FAAH inhibitors include, but are not limited to, AM374, ARN2508, BIA 10-2474, BMS469908, CAY-10402, MP-208, JNJ-245, JNJ-1661010, JNJ-28833155, JNJ-40413269, JNJ42119779, JNJ-42165279, LY-2183240, Cannabidiol, MK-3168, MK-4409, MM-433593, OL92, OL-135, PF-622, PF-750, PF-3845, PF-04457845, RN-450, SA-47, SA-73, SSR-411298, ST-4068, TK-25, JZP327A, URB524, URB597, URB694, URB937, VER-156084 and V158866. Examples of dual FAAH/MAGL inhibitors include, but are not limited to, JZL195.

In some embodiments, compound of Formula I-V described herein, their prodrug forms or a pharmaceutically acceptable salt thereof, or combination thereof, is co-administered with therapeutic monoclonal antibodies such as, but are not limited to, trastuzumab (e.g., anti-HER2), ranibizumab (e.g., anti-VEGF-A), bevacizumab (e.g., anti-VEGF), panitumumab (e.g., anti-EGFR), cetuximab (e.g., anti-EGFR), rituximab (anti-CD20) and antibodies directed to c-MET.

In certain embodiments, a disclosed compound utilized by one or more of the foregoing methods is one of the generics, subgeneric, or specific compounds described herein, such as a compound of Formula I-V.

The disclosed inhibitory compounds can be combined with one or more agents targeting the endogenous cannabinoid system. Such agents include, but not limited to, FAAH inhibitors, CB1 cannabinoid receptor agonists, CB2 cannabinoid receptor agonists, and phytocannabinoids (e.g., Cannabidiol (CBD), Cannabinol (CBN), Cannabinol (CBN), Cannabigerol (CBG), Cannabichromene (CBC), Tetrahydrocannabinol (delta-9-THC)).

The disclosed inhibitory compounds can be combined with one or more additional therapeutic agent may be selected from the group consisting of, but are not limited to, non-steroidal anti-inflammatory drugs (NSAIDs), cyclooxygenase-II (COX-II) inhibitors, anti-anxiety agents, antidepressants, antiepileptic drugs, anti-Alzheimer's agents, antipsychotic drugs, antihemorrhagic agents, benzodiazepines, acetylcholinesterase inhibitors, alpha-adrenoreceptor antagonists, alpha-adrenergic receptor agonists, β-blockers, angiotensin-converting enzymes inhibitors (ACEI), serotonin (5-HT) reuptake inhibitors, serotonin and noradrenaline reuptake inhibitors (SNRIs), serotonin 1A (5-HT1A) agonists or antagonists, antibody medicament, antirheumatic drug, therapeutic monoclonal antibodies (e.g., trastuzumab, ranibizumab, bevacizumab, panitumumab, cetuximab, rituximab), and anticancer medications.

The effective amount of the compound of Formula I-V or the synergistic additional molecule may be between about 0.0001 to about 1,000 mg.

The beneficial effect of the combination includes, but is not limited to, pharmacokinetic or pharmacodynamic co-action resulting from the combination of therapeutic agents. Administration of these therapeutic agents in combination typically is carried out over a defined time period (usually days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

The components of the combination may be administered to a patient simultaneously or sequentially. For example, the components may be present in the same pharmaceutically acceptable carrier and, therefore, are administered simultaneously. Alternatively, the therapeutic ingredients may be present in separate pharmaceutical carriers, such as, conventional oral dosage forms, that are administered either simultaneously or sequentially.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is affected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally, or all therapeutic agents are administered by intravenous injection. Combination therapy also embraces the administration of the therapeutic agents as described above in further combination with other biologically therapeutic ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Compositions

The disclosure is directed to a pharmaceutical formulation comprising at least one compound of Formula I-V. Dosage formulation can be any of a number of dosage forms known in the art. These dosage forms include, but not limited to, tablets, capsules, pills, syrups, suspensions, solutions, powders, granules, creams, emulsions, ointments, sprays, liquids, gels, injectables, patches, microspheres and injectable solutions, and solid lipid nanoparticles, and may comprise drug stabilizers/additives.

The compounds of Formula I-V described herein can be administered to a human patient per se, or in compositions where they are mixed with suitable excipients and/or adjuvants.

The compositions described herein may be pharmaceutical compositions and may include one or more pharmaceutically acceptable excipient or adjuvant.

The term "pharmaceutical composition" refers to a mixture of a compound, formulation or combination of compounds disclosed herein with other chemical components. The pharmaceutical composition facilitates administration of the compound or formulation to an organism. Multiple techniques of administering a compound or formulation exist in the art including, but not limited to, oral, injection, aerosol, parenteral, nasal, ophthalmic and topical administration. Pharmaceutical compositions can also be obtained by reacting compounds or formulations with inorganic or organic acids such as hydrochloric acid, hydrobromic acid, sulfuric acid, nitric acid, phosphoric acid, methane sulfonic acid, ethane sulfonic acid, toluene sulfonic acid, salicylic acid and the like.

The term "excipient" refers to any substance, not itself a therapeutic agent, used as a carrier or vehicle for delivery of a therapeutic agent to a subject or combined with a therapeutic agent (e.g., to create a pharmaceutical composition) to improve its handling or storage properties or to permit or facilitate the formation of a dose unit of the composition. Pharmaceutically acceptable excipients include, by way of illustration and not limitation, diluents, solvents, disintegrants, binders, glidant, lubricants, (physiologically acceptable) surfactant agents, suspending agents, film forming agents, preservatives, sweetening agent, coloring agent, flavoring agents, emulsifying/wetting agent, buffering agents, binders, disintegrants, taste enhancers, thickening agents, penetration enhancers, wetting agents, lubricants, protectives, adsorbents, demulcents, emollients, antioxidants, moisturizers, carriers, buffering agents, solubilizing agents, penetration agents, soothing agents, suspension agents, coating assistants, substances added to mask or counteract a disagreeable odor, fragrances, or taste, substances added to improve appearance or texture of the composition, and combinations thereof. The term "adjuvant" refers to a pharmacological agent that improves the efficacy of the therapeutic agent. Adjuvant includes, by way of illustration and not limitation, painkillers, non-steroidal anti-inflammatory drugs (NSAIDs), and cannabinoid receptor agonists.

The term "solvent" defines a chemical compound that dissolve solute/active pharmaceutical ingredient by breaking of bonds and reducing effective charge on ions thus increasing solute-solvent forces of attraction such as water, alcohol, acetic acid, acetone, ethyl acetates.

The term "diluent" defines chemical compounds known as fillers, make up the bulk of solid unit dosage forms when drug itself is inadequate to produce the volume, the range of diluent may vary from 5%-80% in a pharmaceutical formulation.

Acceptable diluents for therapeutic use are well known in the pharmaceutical art, and are described, for example, in Remington's Pharmaceutical Sciences, 18th Ed., Mack Publishing Co., Easton, Pa. (1990), which is incorporated herein by reference (Remington & Gennaro, 1990 [18]). Preservatives, stabilizers, dyes, sweeteners, fragrances, flavoring agents, and the like may be provided in the pharmaceutical composition. For example, sodium benzoate, and esters of p-hydroxybenzoic acid may be added as preservatives. In addition, antioxidants may be used. In various embodiments, polyoxyethylene sorbitol monooleate, sorbitan fatty acid esters, docusate sodium, Polyoxyethylene castor oil derivatives and the like may be used as surfactant agents; dextrose, lactose, mannitol, sorbitol, starch, sucrose, calcium phosphate, calcium sulphate, calcium carbonate, and the like may be used as diluents; magnesium stearate, stearic acid, Calcium stearate and the like may be used as lubricant; talc, colloidal silicone dioxide, starch and the like may be used as glidant; methyl cellulose, hydroxyethyl cellulose, microcrystalline cellulose and the like may be used as suspending agents; acacia, gelatin, starch paste, polyvinyl pyrrolidone, glucose, carboxymethyl cellulose, povidone and the like may be used as binder and adhesives; starches, clays, cellulose, crosslinked polymers, modified starches, croscarmellose, cross povidone, sodium starch glycolate and the like may be used as disintegrants; hydroxypropyl methyl cellulose (HPMC), synthetic polymers, shellac, povidone, ethyl cellulose and the like may be used as film forming; mannitol, saccharin and the like may be used as sweetening agents; ascorbic acid, sodium bisulphate, thiourea, butyl hydroxy toluene (BHT), tocopherols and the like may be used as antioxidant agents. The term "physiologically acceptable" defines a solvent or diluent that does not abrogate the biological activity and properties of the compound.

The term "surfactant agent" refers to materials that lower the surface tension (or interfacial tension) between two liquids or between a liquid and a solid, may act as wetting agents, emulsifiers, foaming agents, and dispersants, the range of surfactant agent may vary from 0.1%-15% in a pharmaceutical formulation.

The term "disintegrants" can be defined as raw materials that appear in some tablets, they are added to formulations to overcome the cohesive strength imparted during compression, thus facilitating the breakdown of the tablet into granules for ready drug availability once they come in contact with moisture, the range of disintegrant agent may vary from 5%-15% in a pharmaceutical formulation.

The term "lubricants & glidants" refers to materials that reduce friction between the powder mix and the die walls during compression and ejection. They also prevent the mixed powders/granules from sticking to the processing zone of the tablet press especially the punches and die, the range of disintegrant agent may vary from 0.25%-5% in a pharmaceutical formulation The term "binders" refers to polymeric, natural or synthetic materials that impart cohesive qualities to powdered materials used in tablet manufacture. They ensure the tablets remain intact after compression, as well as improve the free-flowing qualities of the powdered materials without retarding disintegration or dissolution, the range of binder may vary from 0.5%-25.0% in a pharmaceutical formulation.

The term "suspending agents" refers to materials that help active pharmaceutical ingredients stay suspended in the formulation and prevent caking at the bottom of the container. One of the properties of a well-formulated suspension is that it can be easily re-suspended by the use of moderate agitation or shaking, the range of suspending agents may vary from 1.0%-10.0% in a pharmaceutical formulation.

The term "film forming agents" refers to materials that help in forming polymer film to the surface of the tablet, the range of film forming agents may vary from 2.0-20.0% weight to the final tablet, it can also be applied to hard gelatin capsules, soft gelatin capsules, and multi particulate systems such as spheroids.

The term "preservatives" refers to materials that act against microorganisms by affecting the various cellular portions of microbial cell and thereby inhibiting their growth, the factors that effect in choosing the antimicrobial preservative include preservative dose, its effect on active ingredient and range of antimicrobial functionality, the range of preservatives may vary from 0.005-1.0% weight to the final The term "sweetening agents" refers to substances designed for oral administration specifically to increase the palatability of the therapeutic agent.

The term "coloring agent" refers to pharmaceutical ingredients that impart the preferred colour to the formulation.

The term "flavoring agents" refers to employed whenever the unpalatable taste of a therapeutic agent is apparent, even in the presence of the sweetening agents.

The term "buffering agent" refers to a compound or a mixture of compounds that, when present in a solution, resists changes in the pH of the solution when small quantities of acid or base are added to the solution such as citrate buffer, acetate buffer, phosphate buffer, and sodium bicarbonate/sodium carbonate buffer which is cover a wide range of pH.

The compositions may be formulated such that they are suitable for oral, ophthalmic, transmucosal, transdermal, buccal, sublingual, injectable, topical, follicular, nasal, ocular, rectal, vaginal, parenteral including but not limited to, intramuscular, subcutaneous, intravenous, intramedullary, as well as intrathecal, direct intraventricular, intraperitoneal, intranasal, or intraocular delivery. In some embodiments, the formulation described herewith may be administered transmucosally or orally. The transmucosal surface may be the sublingual, buccal, nasal, ocular, vaginal, and/or rectal mucosae. Techniques for formulation and administration of the compounds of the instant application may be found in "Remington's Pharmaceutical Sciences," Mack Publishing Co., Easton, Pa., 18th edition, 1990 (Remington & Gennaro, 1990 [18]). The compounds or formulation may also be administered in sustained or controlled release dosage forms, including depot injections, osmotic pumps, pills, transdermal (including electro transport) patches, and the like, for prolonged and/or timed, pulsed administration at a predetermined rate.

The compositions according to the description may be in different dosage forms, in particular a form chosen from the group comprising tablets, capsules, pills, syrups, suspensions, solutions, powders, granules, creams, emulsions, ointments, sprays, liquids, gels, wafers, edibles, injectables, patches, microspheres and injectable solutions, and solid lipid nanoparticles, and may comprise drug stabilizers/additives.

In some embodiments, the compositions described herein are suitable for transdermal administration. Transdermally administrable compositions may be adapted for administration in and/or around the abdomen, back, chest, legs, arms, scalp, or other suitable skin surface and may include formulations in which the compounds of the disclosure are administered in patches, ointments, creams, suspensions, lotions, pastes, gels, sprays, foams or oils. Transdermally administrable compositions include formulations in which the compounds of the disclosure are placed in a glycol or gel formulation.

In some embodiments, the compositions described herein are suitable for topical administration. Topically administrable compositions are adapted for administration in and/or around the abdomen, back, chest, legs, arms, scalp, or other suitable skin surface and may include formulations in which the compounds of the disclosure are compounds of Formula I-V is administered in patches, ointments, creams, suspensions, lotions, pastes, gels, sprays, foams or oils.

In some embodiments, the compositions described herein are suitable for oral administration. Orally administrable compositions include formulations in which the compounds of Formula I-V is administered in tablets, capsules, suspensions, syrups, or liquids. In an additional embodiment, the composition may be formulated as an extended-release or long-acting tablet or capsule. The oral dosage form may be enteric-coated using techniques known to a person of ordinary skill in the art.

In some embodiments, the compositions are formulated for transmucosal administration such as buccal administration. Buccally administrable compositions may include formulations in which the compounds of the disclosure are administered in lozenges, sprays, gels, pastes, dissolvable tablets, or dissolvable strips/films.

In some embodiments, the compositions are formulated for transmucosal administration such as sublingual administration. Sublingually administrable compositions may include formulations in which the compounds of the disclosure are administered in lozenges, sprays, gels, pastes, dissolvable tablets, or dissolvable strips.

In some embodiments, the compositions are formulated for transmucosal administration such as rectal administration. Rectally administrable compositions may include formulations in which the compounds of the disclosure are placed in suppositories, ointments, creams, suspensions, solutions, lotions, pastes, gels, sprays, foams, or oils.

In some embodiments, the compositions described herein are suitable for vaginal administration. Vaginally administrable may include formulations in which the compounds of the disclosure are placed in suppositories, ointments, creams, suspensions, solutions, lotions, pastes, gels, sprays, foams, or oils.

In some embodiments, the compositions described herein are suitable for ocular administration. Ocularly administrable compositions may include formulations in which the compounds of the disclosure are placed in ointments, suspensions, solutions, gels, or sprays.

In some embodiment, the compositions described herein are suitable for nasal administration. Nasally administrable may include formulations in which the compounds of the disclosure are placed in ointments, suspensions, solutions, lotions, pastes, gels, sprays, or mists.

In some embodiments, the compositions described herein are suitable for injectable administration. Injectable administrable compositions may include formulations in which the compounds of the disclosure are administered as an intravenous, intrathecal, subcutaneous, or depot injection.

The pharmaceutical compositions of the present disclosure may be manufactured in a manner that is itself known, e.g., by means of conventional mixing, dissolving, granulating, levigating, emulsifying, suspending, dispersing, encapsulating, tableting, and coating processes.

Pharmaceutical compositions for use in accordance with the present disclosure thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art, e.g., in Remington's Pharmaceutical Sciences, above (Remington & Gennaro, 1990 [18]).

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, propylene glycol, parabens, and the like. In addition, if desired, the injectable pharmaceutical compositions may contain minor amounts of nontoxic auxiliary substances, such as wetting agents, pH buffering agents, chelating agents, antioxidants, dispersing agents, and the like. Physiologically compatible buffers include, but are not limited to, Hanks's solution, Ringer's solution, or physiological saline buffer.

Pharmaceutical formulations for parenteral administration, e.g., by direct injection or continuous infusion, include aqueous solutions of the active compounds in water-soluble form, or oily solution of the active compounds in oil-soluble form. Additionally, suspensions of the active compounds may be prepared as appropriate water or oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For transmucosal administration (buccal and sublingual), various solid dosage forms, such as tablets, troches, lozenges, lozenges-on-a-stick, chewing gums, and buccal patches/films, electrospinned nanofibre coated films, have been used to deliver drugs via the oral mucosal tissue. The pharmaceutical ingredients that can be used in the formulation may include, but are not limited to, dissolution agent, Buffering agents, absorbents, colorants, flavorants, solvents and co-solvents, coating agents, disintegrants, glidants, lubricants, polishing agents, suspending agents, polymers, sweetening agents, binders, and the ingredients may also include anti-fungal preservatives, antimicrobial preservatives, emulsifying agents, antioxidants, plasticizers, surfactants, tonicity agents, and viscosity increasing agents. Formulation of films include strip-forming polymers, plasticizers, sweetening agents, saliva stimulating agent, flavoring agents, coloring agents, stabilizing and thickening agents, permeation enhancers, and superdisintegrants.

A variety of pharmaceutical ingredients can be used as the dissolution agent, depending upon the pharmaceutical agent and other ingredients used in the formulation. The dissolution agents include but are not limited to acacia, alginic acid, carbomer, carboxymethylcellulose, calcium, carboxymethylcellulose sodium, microcrystalline cellulose, cellulose, dextrin, dextrose, ethyl cellulose, fructose, gelatin, guar gum, hydroxypropyl cellulose, hydroxypropyl methylcellulose, lactitol, lactose, lecithin, maltodextrin, mannitol, methylcellulose, poloxamer, polyethylene glycol, polymethacrylates, polyvinyl alcohol, povidone, propylene glycol alginate, sodium alginate, sodium ascorbate, sodium starch glycolate, sorbitol, starch, starch (pregelatinized), and sucrose. Buffering agents (selected from phosphate buffer, carbonate buffer, tris buffer, tartrate buffer, borate buffer, acetate buffer, or maleate buffer) can be used in the formulation. Absorbent agents may include but are not limited to ethanol, methyl pyrrolidone, ethyl acetate, citric acid, propylene glycol, dimethyl sulfoxide, sodium lauryl sulfate and the like. Solvents may include but are not limited to water, alcohol, acetic acid, acetone, ethyl acetates and the like. Co-solvents may include but are not limited to ethanol, sorbitol, glycerin, propylene glycol and the like. Coating agents may include but are not limited to hydroxypropyl methyl cellulose (HPMC), synthetic polymers, polysaccharides, povidone, ethyl cellulose and the like. Disintegrants may include but are not limited to starches, clays, cellulose, cross linked polymers, modified starch, croscarmellose, cross povidone, sodium starch glycolate and the like. Glidants may include but are not limited to colloidal silicone dioxide, asbestos free starch, corn starch and the like. Lubricants may include but are not limited to talc, stearic acid, magnesium stearate, calcium stearate, polyethylene glycol, surfactants, vegetable oil and the like. Polishing agents and plasticizers may include but are not limited to castor oil, diacetylated monoglycerides, polyethylene glycol, polypropylene glycol, triacetin and the like. Suspending agents may include but are not limited to methyl cellulose, hydroxyethyl cellulose, microcrystalline cellulose, and the like. Sweetening agents may include but are not limited to sucrose, sorbitol, saccharin, aspartame, sucralose, and the like. Binders may include but are not limited to acacia, gelatin, starch paste, polyvinyl pyrrolidone, glucose, carboxymethyl cellulose, povidone, and the like. Preservatives may include but are not limited to benzyl alcohol, methyl paraben, butyl paraben, phenol, thiomersal and the like. Emulsifying agents may include but are not limited to agar, alginates, ceatyl Alcohol, cholic acid, desoxycholic acid, glycerol, lecithin, monostearate, propylene glycol, and the like. Antioxidants may include but are not limited to ascorbic acid, sodium bisulphate, thiourea, butyl hydroxy toluene (BHT), tocopherols, and the like. Surfactants may include but are not limited to cremophor or polysorbate, sodium cholate, dodecylmaltoside, and the like. Tonicity agents may include but are not limited to sodium chloride, dextrose, mannitol, and the like. Viscosity increasing agents may include but are not limited to methyl cellulose, sodium CMC, tragacanth, and the like.

For oral administration, the compounds can be formulated readily by combining the active compounds with pharmaceutically acceptable carriers well known in the art. Such carriers enable the compounds of the disclosure to be formulated as tablets, pills, capsules, liquids, gels, syrups, slurries, suspensions, and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets. Suitable excipients are, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or coatings for identification or to characterize different combinations of active compound doses.

Pharmaceutical preparations which can be used orally include capsules made of gelatin, as well as soft, sealed capsules made of gelatin and a plasticizer, such as glycerol or sorbitol. The capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. Further disclosed herein are various pharmaceutical compositions well known in the pharmaceutical art for uses that include intraocular, intranasal, and intra-auricular delivery. Pharmaceutical formulations include aqueous ophthalmic solutions of the active ingredients in water-soluble form, such as eyedrops, or in gellan gum or hydrogels; ophthalmic ointments; ophthalmic suspensions, such as microparticulates, drug-containing small polymeric particles that are suspended in a liquid carrier medium, lipid-soluble formulations, and microspheres; and ocular inserts. Such suitable pharmaceutical formulations are most often formulated to be sterile, isotonic and buffered for stability and comfort.

Pharmaceutical compositions may also include drops and sprays often prepared to simulate in many respects nasal secretions to ensure maintenance of normal ciliary action. As disclosed in Remington's Pharmaceutical Sciences, 18th Ed. [18] which is incorporated herein by reference in its entirety, and well-known to those skilled in the art, suitable formulations are most often isotonic, slightly buffered to maintain a pH of 5.5 to 6.5, and most often include antimicrobial preservatives and appropriate drug stabilizers.

Pharmaceutical formulations for intra-auricular delivery include suspensions and ointments for topical application in the ear. Common solvents for such aural formulations include glycerin and water. For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

For topical administration, the compositions may take the form of solution, ointment, paste, cream, gel, hydrogel, lotion, emulsion, foam, patch, film, aerosol, and the like.

Oil-in-water or water-in-oil emulsions are normally referred to as creams. Especially used for the oily phase are fatty alcohols, e.g., lauryl, cetyl or stearyl alcohol, fatty acids, e.g., palmitic or stearic acid, liquid or solid paraffins, liquid to solid waxes, e.g., isopropyl myristate, natural or partially synthetic fat, e.g., coconut fatty acid triglyceride, hardened oils, e.g., hydrogenated peanut or castor oil, or fatty acid partial esters of glycerol, e.g., glycerol monostearate or glycerol distearate. Suitable emulsifiers are surface-active substances, e.g., nonionic surfactants, e.g., fatty acid esters of polyalcohols or ethylene oxide adducts thereof, such as polyglycerol fatty acid esters or polyoxyethylene sorbitan fatty acid esters, sorbitan fatty acid esters, such as, for example, sorbitan oleate and/or sorbitan isostearate, sterols, also polyoxyethylene fatty alcohol ethers or fatty acid esters, or anionic surfactants such as alkali metal salts of fatty alcohol sulphates, e.g., sodium lauryl sulphate, sodium cetyl sulphate or sodium stearyl sulphate, which are normally used in the presence of said fatty alcohols, e.g., cetyl alcohol or stearyl alcohol. It is possible to add to the aqueous phase inter alia agents which prevent the cream drying out, e.g., polyalcohols such as glycerol, sorbitol, propylene glycol and/or polyethylene glycols, also preservatives etc.

Ointments may be anhydrous and contain as base the paraffins which are suitable for topical use and are liquid at body temperature, especially low-viscosity paraffin, also the natural or partially synthetic fats, e.g., coconut fatty acid triglyceride, hardened oils, e.g., hydrogenated peanut or castor oil, fatty acid partial esters of glycerol, e.g., glycerol monostearate, silicones, e.g., polydimethylsiloxanes, e.g., hexamethyldisiloxane or octamethyltrisiloxane, and, for example, the fatty alcohols increasing the water uptake capacity, and sterols, wool waxes, other emulsifiers and/or other additives.

In the case of gels, especially suitable are transparent hydrogels based on inorganic or organic macromolecules. Macromolecular inorganic components with gel-forming properties are predominantly hydrous or water-absorbing silicates such as aluminium silicates, magnesium-aluminium silicates, or colloidal silica. Examples of macromolecular organic substances used are natural, semisynthetic or synthetic polymers. Natural and semisynthetic polymers such as cellulose, starch, tragacanth, gum arabic, agar-agar, gelatin, alginic acid and salts thereof, lower alkylcellulose, for example methyl- or methylcelluloses, carboxy- or hydroxy-lower-alkylcellulose, e.g., carboxymethyl- or hydroxypropylcellulose. The units of synthetic, get-forming polymers are, for example, unsaturated, substituted aliphatic compounds such as vinyl alcohol, vinylpyrrolidone, acrylic or methacrylic acid. It is possible to add conventional additives such as preservatives to the gels.

Pastes are creams or ointments with the constituents and secretion-absorbing dusting powder constituents such as metal oxides, e.g., titanium oxide or zinc oxide, also talc and/or aluminium silicates, which have the task of binding moisture or secretions.

Spray compositions may be solutions or suspensions of a drug substance in a vehicle optionally containing a polymer which, when sprayed on the surface of the skin, forms a film on the skin. The compositions may comprise up to about 30% of drug substance dissolved or suspended in one or more vehicles, which comprise up to 90% of the composition such as water or a non-aqueous solvent for example nonaqueous vehicles include acetone, isopropyl alcohol, methylene chloride, methyl-ethyl-ketone, absolute alcohol, ethyl acetate and trichloromonofluoromethane, methylene dimethyl ether. The composition may further contain one or more film former such as non-ionic copolymer of methyl methacrylate and butyl methacrylate, a copolymer of dimethylamine ethyl methacrylate and a neutral methacrylic acid ester, polyvinyl acetate, cellulose acetate, polyvinyl alcohol, povidone, povidone vinyl acetate, hydroxypropyl methyl cellulose, hydroxy ethyl cellulose, methyl cellulose and ethyl cellulose, solubilizer such as copolymer of dimethylamine ethyl methacrylate and a neutral methacrylic acid ester, surfactants, for example, sodium lauryl sulphate; polyhydric alcohols, for example, propylene glycol or polyethylene glycol, permeation enhancer such as lipophilic solvent, for example, dimethyl sulfoxide, dimethyl formamide or isopropyl myristate; a surfactant, for example, Tweens or sodium lauryl sulfate; menthol; oleic acid, octyl dimethyl para-amino benzoic acid; mixed esters of capric and caprylic acid; or a polyhydric alcohol, for example, propylene glycol or diethylene glycol monoethyl ether EP, and plasticizer such as triethyl citrate, dimethyl isosorbide, acetyltributyl citrate, castor oil, propylene glycol, and polyethylene glycol.

The composition may contain one or more of these additives in amounts, for example, of up to about 10% film-former, up to about 10% solubilizer, up to about 8% permeation enhancer, and up to about 10% plasticizer. The composition may further comprise up to about 7% (w/w) of one or more water-soluble additives. The drug substance so deposited in the matrix of the film-former may remain solubilized or suspended.

Methods for the preparation of spray dosage forms may be as follows: 1—dissolving the film former in the chosen vehicle with stirring to form a clear solution, then 2—dissolving or suspending the active ingredient and solubilizer(s) along with the permeation enhancer, together with any water-soluble additives required, in the solution prepared in step 1, then 3—adding the plasticizer to the solution in step 2, then 4—fill a conventional aerosol can with the mixture prepared in step 3, and 5—charge the filled can with liquefied propellant.

Foam compositions may comprise water, surfactant, alcohol, and combinations thereof. In some embodiments, the quick-breaking foaming agent can also comprise an emollient, which can also act as a humectant. Suitable emollients include, but are not limited to, polyols such as propylene glycol and glycerol. The amount of emollient used in the quick-breaking foaming agent varies from about 0% to about 20% w/w, in addition, the quick-breaking foaming agent can also comprise a pH adjusting agent such as bicarbonates, carbonates, and hydroxides as alkaline, or such as acid salt as acid, or mixtures thereof. Further, the pH adjusting agent can also be a buffer such as citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like. The pH adjusting agent is present in an amount sufficient to adjust the pH of the composition to between about pH 4.0 to about 9.0, such as about pH 4.0 to about 6.5.

The amount of propellant added to the topical delivery active ingredient composition is up to about 7% of propane/butane propellant. In addition to its function as a propellant and for creating the microstructure of the foam upon dispensing, the hydrocarbon or mixtures thereof helps to dissolve the cetyl alcohol and stearyl alcohol in the aqueous/ethanolic system to produce a clear, homogeneous system in the container. While chlorofluorocarbons (CFCs) can also be used as propellants, due to environmental concerns the desired propellants are hydrocarbons in particular, propane, butane, or a mixture thereof. Other suitable propellants include dimethyl ether and hydrofluorocarbons. An especially desired propellant is a mixture of propane and butane.

Topical solutions composition under the present disclosure are solutions per se or are spray liquids, foams, gels, or fluid gels. Water may be present in the compositions and may include but not limited to polyhydric alcohol, glycol ether, ester of a higher fatty acid and the like. The composition may also comprise a volatile solvent such as ethanol or isopropyl alcohol.

Topical lotion compositions may include fluid or thixotropic emulsions or suspensions intended for external application to the body. The lotion may comprise finely powdered, insoluble solids held dispersion medium such as water, isopropyl alcohol, and alcohol through the use of suspending agents and dispersing agents such as but not limited to hydroxypropyl cellulose, hydroxypropyl methylcellulose, microcrystalline cellulose, alginates, xanthan gum, veegum, hydroxyethyethylcellulose, carbomers, and the like. Preservative agents may include but are not limited to benzyl alcohol, methyl paraben, butyl paraben, phenol, thiomersal and the like.

For buccal administration, the compositions may take the form of tablets, lozenges, patches, films, gels, and the like. The pharmaceutical ingredients that can be used in the formulation may include, but are not limited to water-soluble diluents, binders, disintegrants, lubricants, glidants, solvents, co-solvents, penetration enhancer, flavoring agents, coloring agents, sweeteners, polymeric carrier matrix, surfactant agent, emulsifiers, solubilizing agent, chelating agent, Antioxidants, buffering agents, or the like. Diluents may include but are not limited to sugars, polyols, saccharides, polysaccharides, dextrose, maltitol, maltodextrin, mannitol, polyethylene glycol, sorbitol, sucrose, xylitol, and the like. Binders may include but are not limited to starches, pregelatinize starches, gelatin, polyvinylpyrrolidone, methylcellulose, sodium carboxymethylcellulose, ethyl cellulose, polyacrylamides, polyvinyl alcohols, and the like. Disintegrants may include but are not limited to sodium starch glycolate, crospovidone, croscarmellose sodium, low-substituted hydroxypropyl cellulose, starch, pregelatinized starch, microcrystalline cellulose, and the like. Lubricants may include but are not limited to sodium stearyl fumarate, magnesium stearate, stearic acid, sodium lauryl sulfate, talc, polyethylene glycol, calcium stearate, and the like. Glidants may include but are not limited to, colloidal silicon dioxide, talc, magnesium stearate, magnesium carbonate, and the like. Solvents and co-solvents may include but are not limited to, water, ethanol, propylene glycol, polyol alcohol, polyethylene glycol, substituted polyethylene glycols, and the like. Penetration enhancer may include but are not limited to, anionic surfactants (e.g., sodium lauryl sulphate, sodium dodecyl sulphate), cationic surfactants (e.g., palmitoyl DL camitine chloride, cetylpyridinium chloride), non-ionic surfactants (e.g., polysorbate 80, polyoxyethylene 9-lauryl ether, glyceryl monolaurate, polyoxyalkylenes, polyoxyethylene 20 cetyl ether), lipids (e. g. oleic acid), and the like. Solubilizing agents may include but are not limited to, cetyl alcohol, sodium lauryl sulfate, sorbitan monolaurate, polysorbate, ethoxylated castor oils, and the like. Sweeteners may include but are not limited to, glucose, dextrose, fructose, saccharin, aspartame, Stevia, sucralose, sorbitol, mannitol, xylitol, and the like. Polymeric carrier matrices may include but are not limited to, polyethylene oxide, cellulose or cellulose derivatives, gelatin, hydroxyl propyl methyl cellulose (HPMC), hydroxyl ethyl cellulose (HEC), hydroxyl propyl cellulose (HPC), polyvinyl pyrrolidone (PVP), carboxymethyl cellulose (CMC), polyvinyl alcohol (PVA), sodium alginate, xanthine gum, tragacanth gum, guar gum, acacia gum, methyl methacrylate (MMA) copolymer, and the like. Chelating agents may include but are not limited to, calcium disodium edetate and ethylenediaminetetraacetic acid (EDTA), polysaccharides, histidine, and the like. Antioxidants may include but are not limited to butylhydroxytoluene (BHT), butylated hydroxy anisole (BHA), sodium sulfate, citric acid, sodium metabisulfite, ascorbic acid, tocopherol, tocopherol ester derivatives, and the like. Buffering agents may include but are not limited to phosphate, carbonate, tartrate, borate, citrate, acetate, and malate buffers, and the like.

Also contemplated are enteral pharmaceutical formulations including a disclosed compound and an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastro-intestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydro phthalate, cellulose propionate phthalate, cellulose acetate maleate, cellulose acetate butyrate, cellulose acetate propionate, copolymer of methyl methacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

Therapeutic Uses

This disclosure is also directed to a method of inhibition of MAGL enzyme in both in vitro and in vivo systems. In certain instances, the disclosed compounds can be used as research tools and imaging agents to probe MAGL and related lipase mechanism of catalysis. The compounds of Formula I-V may be reversible or irreversible MAGL inhibitor or modulator. Thus, can be used in the treatment of a disease, disorder or condition which benefits from the inhibition or modulation of MAGL activity in a subject.

As discussed above, the compounds according to the present disclosure have intrinsic MAGL inhibition/modulator properties. 2-AG, which is a substrate of MAGL, is involved in various physiological and pathophysiological conditions including but are not limited to, anxiety and mood disorder, pain, metabolic disorder, a neurodegenerative disorder, mental disorder, brain disorder, pain, inflammatory disorder, cancer, Alzheimer's disease, movement disorders, epilepsy or stroke. Therefore, an MAGL inhibitor is promising as a new therapeutic drug for the treatments of these disorders (Zanfirescu A et al., (2021). Molecules, 26, 5668).

Without wishing to be bound by theory, it is believed that the compounds of Formula I-V described herein may offer an improved therapeutic outcome to subjects with MAGL-related diseases, disorders and conditions, such for example as pain and anxiety disorders.

Without wishing to be bound by theory, it is believed that the combination of one or more than one compound of Formula I-V and one or more than one therapeutic compound may offer an improved therapeutic outcome to subjects with MAGL-related diseases, disorders and conditions, such for example as pain and anxiety disorders.

The terms "MAGL-related diseases, disorder or conditions" and "disease, disorder or condition benefitting from MAGL inhibition" refers to any disease state, disorder or condition in a subject that has a symptom that is caused directly or indirectly by the MAGL enzyme and where a positive therapeutic outcome by inhibition of the MAGL enzyme is expected.

In one aspect, the present disclosure provides compound of Formula I-V, their prodrugs, pharmaceutically acceptable salt thereof or combination thereof, as described herein for use as therapeutically active substance.

The present disclosure also embraces isotopically labelled compounds that are identical to those depicted herein except that one or more atoms are replaced by an atom having atomic mass or mass number different from the atomic mass or mass number usually found in nature. Examples of isotopes that can be incorporated into compounds of the invention include, but are not limited to, isotopes of hydrogen, carbon, nitrogen, oxygen, fluorine, and chlorine, such as $^2$H, $^3$H, $^{13}$C, $^{14}$C, $^{15}$N, $^{17}$O, $^{18}$O, $^{18}$F, and $^{36}$Cl respectively. Isotopically labeled compounds of the present invention can generally be prepared by following methods analogues to those disclosed in the Examples herein by substituting an isotopically labeled reagents for a non-isotopically labeled reagents. Isotopically labeled of the present invention may be useful in metabolic studies, reaction kinetic studies, compound and/or substrate tissue distribution assays, and detection or imaging techniques. Such applications of isotopically labeled compounds are well known to person skill in the art and are therefore within the scope of the present invention.

The compounds may be used to treat a variety of medical conditions (Zanfirescu A et al., Molecules. 2021, 18; 26(18): 5668; Stasiulewicz A et al., Int J Mol Sci. 2020 Apr. 16; 21(8): 2778; Deng H, Li W., Acta Pharm Sin B. 2020 April; 10(4): 582-602) where ECS is involved including but not limited to a neurodegenerative disorder (e.g., Multiple Sclerosis, Parkinson's Disease, Huntington's disease, dementia, Alzheimer's disease, ALS, epilepsy, fronto-temporal lobar degeneration, a sleep disorder, CJD, or prion disease); Primary Tauopathies; neuropathy (e.g., diabetic neuropathy, pellagric neuropathy, alcoholic neuropathy, Beriberi neuropathy; cardiovascular disease (e.g., hypertension, dyslipidemia, atherosclerosis, cardiac arrhythmias, or cardiac ischemia); withdrawal syndrome (alcohol withdrawal syndrome, antidepressant discontinuation syndrome, antipsychotic withdrawal syndrome, benzodiazepine withdrawal syndrome, *cannabis* withdrawal, neonatal withdrawal, nicotine withdrawal, or opioid withdrawal); metabolic disorder (e.g., obesity, diabetes, dyslipidemia); burning feet syndrome; ischemia (stroke, hepatic ischemia or reperfusion, CNS ischemia or reperfusion); nausea (e.g., refractory nausea or chemotherapy induced nausea); vomiting or emesis (e.g., chemotherapy induced vomiting); an eating disorder (e.g., anorexia, bulimia, Prader-Willi syndrome and related syndromes)); a kidney disease (e.g., acute inflammatory kidney injury and diabetic nephropathy); an eye disease (e.g., glaucoma, ocular hypertension, macular degeneration, abnormal eye neovascularization (e.g., corneal or choroidal neovascularization), or a disease arising from elevated intraocular pressure); a pulmonary, lung or airway disorder (e.g., lung cancers, asthma, cough, allergies, cystic fibrosis, COPD, chronic bronchitis, ILD, emphysema, pneumonia, tuberculosis, idiopathic pulmonary fibrosis, pulmonary edema, acute respiratory distress syndrome, pulmonary embolism, sarcoidosis, pleural effusion, or mesothelioma); osteoarthritis; osteoporosis; bipolar disease; depression; schizophrenia; sleeping sickness; cerebral palsy; cerebral edema; meningitis; cachexia; sleep apnea; De Vivo disease; spasticity; dystonia; progressive multifocal leukoencephalopathy; dyskinesia; tremor; hearing loss; insomnia; Tourette's syndrome; Autism, agitation in autism, bladder dysfunction, chronic motor or vocal tic disorder; trichotillomania; cognitive impairment (e.g., cognitive impairment associated with Down's syndrome; cognitive impairment associated with Alzheimer's disease; cognitive impairment associated with PD; MCI, dementia, PCCI, POCD); an inflammatory disorder (e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, inflammatory Bowel Disease (IBD), IBS, pelvic inflammatory disease, sarcoidosis, HIV encephalitis, rabies, brain abscess, neuroinflammation (e.g., MS, Alzheimer's disease, PD, ALS, traumatic brain injury, neurotoxicity, stroke, epilepsy and mental disorders such as anxiety and migraine), inflammation in the CNS; an autoimmune disease (e.g., psoriasis, pruritus, lupus erythematosus, Sjogren's syndrome, ankylosing spondylitis, undifferentiated spondylitis, Behcet's disase, hemolytic anemia, graft rejection); a demyelinating disease (e.g., MS, Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, MAG, peripheral neuropathy, Charcot-Marie-Tooth disease, peripheral neuropathy, myelopathy, optic neuropathy, progressive inflammatory neuropathy, optic neuritis, transverse myelitis); neuromyelitis optica; a disorder of the immune system (e.g., transplant rejection or celiac disease); PTSD; acute stress disorder; panic disorder; substance-induced anxiety; OCD; agoraphobia; specific phobia; social phobia; anxiety disorder; ADD; ADHD; Asperger's syndrome; a disorder associated with abnormal cell growth or proliferation (e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, prostate cancer, breast cancer, lung cancer, bladder cancer, brain cancer, glioblastoma (GBM), gastrointestinal cancer, leukemia or blood cancer); traumatic brain injury; non-traumatic brain injury; spinal cord injury; seizures; excitotoxin exposure; stroke (e.g., ischemic stroke; hemorrhagic stroke); subarachnoid hemorrhage; intracerebral hemorrhage; vasospasm; AIDS wasting syndrome; renal ischemia; cerebral ischemia; liver fibrosis, iron overload, cirrhosis of the liver; a liver disorder (acute liver failure, Alagille syndrome, hepatitis, enlarged liver, Gilbert's syndrome, liver cysts, liver hemangioma, fatty liver disease, steatohepatitis (e.g., NASH), primary sclerosing cholangitis, fascioliasis, primary bilary cirrhosis, Budd-Chiari syndrome, hemochromatosis, Wilson's disease, or transthyretin-related hereditary amyloidosis), a pain (e.g., acute pain; chronic pain; inflammatory pain; vasoocclusive painful crisis in siclle cell disease; visceral pain; post-operative pain; migraine; lower back pain; joint pain; abdominal pain; chest pain; postmastectomy pain syndrome; menstrual pain; dyspepsia; fibromyalgia; glossopharyngeal neuralgia; endometriosis pain; pain due to physical trauma; headache; sinus headache; tension headache arachnoiditis, herpes virus pain, diabetic pain); pain due to a disorder selected from: osteoarthritis, rheumatoid arthritis, osteoarthritis, spondylitis, gout, labor, musculoskeletal disease, cancer, skin disease, toothache, pyresis, burn, sunburn, snake bite, venomous snake bite, spider bite, insect sting, neurogenic bladder, interstitial cystitis, UTI, rhinitis, contact dermatitis/hypersensitivity, itch, eczema, pharyngitis, mucositis, enteritis, IBD, cholecystitis, and pancreatitis; neuropathic pain (e.g., neuropathic low back pain, complex regional pain syndrome, post trigeminal neuralgia, causalgia, toxic neuropathy).

In some embodiments, the disease, illness, disorder or condition is a "mental disorder" or "mental illness" or "brain disorder" or "mental disease" or "psychiatric or neuropsychiatric disease or illness or disorder". As used herein, the term "mental disorder" refers to those provided in Diagnostic and Statistical Manual of Mental Disorders, Fourth Edition, (DSM IV), American Psychological Association (APA). These mental disorders include, but are not limited to affective disorders, neurotic disorders and unspecified depressive disorders. Examples of affective disorders include mood disorders, manic disorder, major depressive disorder and bipolar affective disorder. Mood disorders include, but are not limited to, depressive disorders, dysthymic disorder, bipolar disorders (I and II) and cyclothymic disorders. Examples of neurotic disorders include, but are not limited to, anxiety states, panic disorders, phobias, obsessive-compulsive disorder, post traumatic stress disorder, acute stress disorder, generalized anxiety disorder, attention deficit hyperactivity disorder, Tourette's Syndrome and hysteria. Other conditions include sleep disorders, including breathing related sleep disorders.

In one aspect, the present disclosure is relates with the treatment of humans who suffer from or exhibit mental disorders. The following discussion generally reviews the condition of mental disorders as it is understood in clinical (psychiatric) terms. The following discussion should therefore be considered as a general exposition of the condition to identify the general state of the art.

In some embodiments, the disorder is affective disorder referring to a mental disorder characterized by neuroendocrine dysregulation and by a disturbance in the regulation of mood, behavior, emotions such as sadness, social withdrawal and carbohydrate cravings, and affect. Affective disorders are also referred to herein as mood disorders and include, for example, major depressive disorders, such as melancholic depression, atypical depression as well as chronic mood disorder such as dysthymia and anxiety disorders.

In some embodiments, the disorder is mood disorder typically characterized by pervasive, prolonged, and disabling exaggerations of mood and affect that are associated with behavioral, physiologic, cognitive, neurochemical and psychomotor dysfunctions. The major mood disorders include, but are not limited to, major depressive disorder (also known as unipolar disorder), bipolar disorder (also known as manic depressive illness or bipolar depression), dysthymic disorder cyclothymia and many others. See, e.g., Diagnostic and Statistical Manual of Mental Disorders, Fourth Edition, (DSM IV). Other mood disorders may include, but are not limited to major depressive disorder, psychotic; major depressive disorder, melancholic; major depressive disorder, seasonal pattern; postpartum depression; brief recurrent depression; late luteal phase dysphoric disorder (premenstrual dysphoria); and cyclothymic disorder.

In some embodiments, the disorder is a "major depression disorder," "major depressive disorder," or "unipolar disorder" referring to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability, or persistent physical symptoms that do not respond to treatment, such as headaches digestive disorders, and chronic pain. Various subtypes of depression are described in, e.g., DSM IV.

In some embodiments, the disorder is a "Bipolar disorder", a mood disorder characterized by alternating periods of extreme moods. A person with bipolar disorder experiences cycling of moods that usually swing try being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

In some embodiments, the disorder is a "depression", as used herein includes those described in DSM IV, including, but not limited to, mood disorders, depression clinically diagnosed by professionals, such as psychiatrists, psychotherapists, psychologists, and therapists, as well as depression which may not be clinically diagnosed by a mental health practitioner but may nevertheless still be severe and prolonged. By way of non-limiting examples, clinically diagnosed depression includes dementia, acute depression, schizophrenia, and other clinical depression disorders, classified in DSM IV. The use of the term "depression" herein is intended to embrace clinical and subclinical forms of depression, particularly endogenous depression whose onset is or does not appear to be brought on by any particular event in the subject human's life.

In some embodiments, the disorder is a "Anxiety," "anxiety disorder," and "anxiety-related disorder refer to psychiatric syndromes characterized by a subjective sense of unease, dread, or foreboding, e.g., panic disorder, generalized anxiety disorder, attention deficit disorder, attention deficit hyperactive disorder, obsessive-compulsive disorder, and stress disorders, e.g., acute and post-traumatic. Diagnostic criteria for these disorders are well known to those of skill in the art (see, e.g., *Harrison's Principles of Internal Medicine*, pp. 2486-2490 (Wilson et al., eds., 12th ed. 1991) and DSM IV).

In some embodiments, the disorder is "Anxiety" referring to an emotional state of apprehension or other unease that is distressing or otherwise unpleasant to a person. It is the central feature of various anxiety disorders, including, for example, generalized anxiety disorder, obsessive-compulsive disorder, panic disorder, phobic disorders, and stress disorders. Anxiety may also occur comorbidly with other mental disorders, such as with mixed-anxiety depression, or may be a symptom of them, such as in premenstrual dysphoric syndrome. Anxiety may also occur comorbidly with conditions other than mental disorders, such as with Alzheimer's disease or fibromyalgia, for example.

In some embodiments, the disorder is a Generalized Anxiety Disorder, a syndrome characterized by excessive or chronic anxiety or apprehension concerning two or more of life's circumstances, often with little provocation. The disorder's signs and symptoms include somatic complaints, such as tremor, dyspnea, palpitations, light-headedness, and nausea. It is often accompanied by one or more physical symptoms, such as fatigue, headaches, muscle tension, muscle aches, difficulty swallowing, trembling, twitching, irritability, sweating, hot flashes, restlessness, autonomic hyperactivity, vigilance and scanning, and difficulty concentrating. Acute anxiety attacks (panic disorders) are a defining symptom of anxiety neurosis and are extremely unpleasant for the patient who experiences a subjective fear which arises for no apparent reason. This fear may be a fear of some imminent catastrophe which prevents rational reasoning. Such anxiety disorders have been treated by a combination of psychologic and pharmacologic measures. Psychologic treatments may include insight psychotherapy, supportive psychotherapy and relaxation techniques, such as meditation or hypnosis. Pharmacologic treatments include those medications that lower the stress level of the patient.

In some embodiments, the disorder is a Obsessive-Compulsive Disorder (OCD). the primary symptom is recurrent obsessions (i.e., recurrent and intrusive thoughts, images or urges that cause marked anxiety) and/or compulsions (i.e., repetitive behaviors or mental acts that are performed to reduce the anxiety generated by one's obsessions) of sufficient severity to cause distress, be time consuming or to interfere significantly with a person's normal routine or lifestyle. Anxiety is an associated feature of this disorder: an affected person may, for example, show a phobic avoidance of situations that involve the cause of the obsession. Typical obsessions concern contamination, doubting (including self-doubt) and disturbing sexual or religious thoughts. Typical compulsions include washing, checking, ordering things, and counting.

In some embodiments, the disorder is a panic attack characterized by an intense, often spontaneous episode of anxiety accompanied by one or more cognitive or somatic symptoms. Cognitive symptoms include a fear of dying, fear of going crazy or losing control, feelings of unreality, strangeness, or detachment from the environment. Somatic symptoms include chest pain or discomfort, dizziness, faintness, feeling of choking, flushes or chills, nausea or abdominal distress, numbness or tingling sensations, palpitations or accelerated heart rate, sensations of shortness of breath or smothering, sweating, and trembling or shaking Panic attacks may occur spontaneously, or may occur in connection with other anxiety disorders; a person with claustrophobia, for example, may experience a panic attack when entering an elevator. Panic disorder occurs when a person repeatedly suffers panic attacks.

In some embodiments, the disorder is Agoraphobia, a condition characterized by the feature of anxiety about being in places or situations from which escape might be difficult (or embarrassing) or in which help may not be available in the event of having a panic attack or panic-like symptoms (e.g., fear of having a sudden attack of dizziness or a sudden attack of diarrhea). Agoraphobia occurs in the context of panic disorder with agoraphobia and agoraphobia without history of panic disorder. The essential features of agoraphobia without history of panic disorder are similar to those of panic disorder with agoraphobia except the focus of fear is on the occurrence of incapacitating or extremely embarrassing panic-like symptoms or limited symptom attacks rather than full panic attacks. Almost all individuals (over 95%) who present with agoraphobia also have a current diagnosis (or history) or panic disorder. In contrast, the prevalence of agoraphobia without history of panic disorder in epidemiological samples has been reported to be higher than that for panic disorder with agoraphobia.

In some embodiments, the disorder is a Social Phobia characterized by the persistent fear of social or performance situations in which embarrassment may occur. Typical situations feared or avoided by individuals with social phoebe include parties, meetings, eating in front of others, writing in front of others, public speaking, conversations, meeting new people, and other related situations. Exposure to social or performance situations almost invariably provokes an immediate anxiety response, as well as sweating, trembling, racing or pounding heart beat, mental confusion, and a desire to flee. Social avoidance and isolation can also become extreme, especially in the more generalized condition. Alcohol abuse is more commonly associated with social phobia than any other anxiety disorder, and frequently represents an attempt at self medication of social fears.

In some embodiments, the disorder is a Post-Traumatic Stress Disorder (PTSD). The principal characteristic symptoms involve re-experiencing a traumatic (i.e. psychologically distressing) event, the avoidance of stimuli associated with that event, the numbing of general responsiveness, and increased arousal. The "events" concerned are outside the range of common experiences such as simple bereavement, chronic illness and marital conflict.

In some embodiments, the disorder is a Specific Phobia, which is an anxiety disorder featuring a persistent fear of a circumscribed stimulus, which may be an object or situation, other than fear of having a panic attack or of humiliation or embarrassment in social situations (which falls under social phobia). Examples include phobias of flying, heights, animals, injections, and blood. Simple phobias may be referred to as "specific" phobias and, in the population at large. Exposure to the phobic stimulus will almost invariably lead to an immediate anxiety response.

In some embodiments, the disorder is "other mental disorders" such as psychotic disorders (e.g., schizophrenia, schizoaffective disorder, schizophreniform disorder, delusional disorder, brief psychotic disorder, and shared psychotic disorder), personality disorders, as well as other mental disorders such as substance-related disorders, childhood disorders, dementia, autistic disorder, adjustment disorder, delirium, multi-infarct dementia, and Tourette's disorder as described in DSM IV. Typically, such disorders have a complex genetic and/or a biochemical component.

The above-mentioned disease, disorder, illness or medical condition is treated with some form of counseling or psychotherapy or pharmacotherapy (drug therapy), either singly or in combination.

As used herein, the term "treating" and "treatment" refers to modulating certain areas of the body so that the subject has an improvement in the disease, for example, beneficial or desired clinical results. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

The MAGL inhibitor may be formulated for oral, sublingual, topical, transdermal, transmucosal, or parenteral administration to deliver a therapeutically effective amount of the MAGL inhibitor to the patient in need of treatment. For example, the MAGL inhibitor may be formulated as pills, dragee, tablets, capsules, thin-film, gel, liquids, syrup, hydrogel, edibles, inhalers, injectables (IV, IP, IM, SC, etc.), patch, or epidural. The compounds may be delivered as prodrug, controlled release, or sustained release within the formulation.

The description provides methods for delivering a therapeutic agent to a subject by administering a formulation comprising one or more compound of Formula I-V described herein. The description also provides methods of administering a formulation comprising one or more compound of Formula I-V to a subject comprising the steps of: (a) combining the one or more compound of Formula I-V and/or with a pharmaceutical excipient to form a pharmaceutical composition; (b) creating a dosage form suitable for administration to a subject from the pharmaceutical composition; and (c) administering the dosage form to a subject. For example, the subject may be a mammal such as a human. Furthermore, the subject may also be an animal. For example, the animal may be a domestic animal or a zoo animal. Non-limiting examples of animals include cattle, horse, sheep, goat, fish, birds such as chicken, turkey, duck, or goose, as well as pets, such as dogs, cats, or rodents. Furthermore, the subject can be invertebrates and vertebrates. Furthermore, the subject may be insect, plant or microorganisms, wherein FAAH inhibitor may be used as an insecticide, anti-microbial or growth promoting agents.

Dosages

The compounds or pharmaceutical compositions as described herein may be used to treat a disease, disorder or condition that benefits from the inhibition of MAGL activity in a subject (see "Therapeutic Uses" above). Therefore, the current disclosure also provides a method of treating such a disease, disorder or condition by administering to a subject in need thereof a compound or pharmaceutical composition as described herein. The compositions of the present description may comprise a therapeutically or prophylactically effective amount of one or more than one of the compounds described herein which is an MAGL inhibitor. Further, the formulation may be combined with therapeutically or prophylactically effective amount of one or more additional therapeutic agent mentioned above.

The term "effective amount", "therapeutically effective amount" or "therapeutically and/or prophylactically effective amount" as used herein refers to an amount of compound or agent that is sufficient to elicit the required or desired therapeutic and/or prophylactic response, as the particular treatment context may require. For example, reduction or inhibition of an enzyme or a protein activity, or ameliorate symptoms, alleviate conditions, slow or delay disease progression, or prevent a disease, etc. In one non-limiting embodiment, the term "effective amount" or "therapeutically effective amount" refers to the amount of the compound within the formulation of the present disclosure that, when administered to a cell, or a tissue, or a noncellular biological material, or a medium, is effective to at least partially reducing or inhibiting the activity of MAGL; or at least partially reducing or inhibiting the expression of MAGL. In another non-limiting embodiment, the term "effective amount" or "therapeutically effective amount" refers to the amount of the compound or compounds within a formulation of the present disclosure that, when administered to a subject, is effective to at least partially alleviating, inhibiting, preventing and/or ameliorating symptoms, such as pain in the subject.

A therapeutically effective amount may vary according to factors such as the disease state, age, sex and weight of the subject, and the ability of the perborate salt to elicit a desired response in the subject. Dosage regimens may be adjusted to provide the optimum therapeutic response. A therapeutically effective amount is also one in which any toxic or detrimental effects of the formulation are outweighed by the therapeutically beneficial effects. A "prophylactically effective amount" refers to an amount effective, at dosages and for periods necessary, to achieve the desired prophylactic result, such as the prevention or the prevention of the progression of cancer. Typically, a prophylactic dose is used in subjects before or at an earlier state of disease.

For example, the compositions of the description may comprise between about 0.001% and about 95% by weight of one or more than one compound of Formula I-V. The compositions may comprise between about 0.001% to about 50% (wt/wt) of one or more than one compound of Formula I-V. The compositions may comprise between about 0.001% to about 40% (wt/wt) of one or more than one compound of Formula I-V. The compositions may comprise between about 5% to about 30% (wt/wt) of one or more than one compound of Formula I-V. The compositions may comprise between about 5% to about 20% (wt/wt) of one or more than one compound of Formula I-V. The compositions may comprise between about 10% to about 20% (wt/wt) of one or more than one compound of Formula I-V.

Further, the compositions of the description may comprise between about 0.001% and about 95% by weight of one or more therapeutic agent. The compositions may comprise between about 0.001% to about 50% (wt/wt) of one or more therapeutic agent. The compositions may comprise between about 0.001% to about 40% (wt/wt) of one or more therapeutic agent. The compositions may comprise between about 5% to about 30% (wt/wt) of one or more therapeutic agent. The compositions may comprise between about 5% to about 20% (wt/wt) of one or more therapeutic agent. The compositions may comprise between about 10% to about 20% (wt/wt) of one or more therapeutic agent.

The dose of the one or more than one compound of Formula I-V may comprise from about 0.0001 mg/kg to about 2000 mg/kg or any amount therebetween. For example, the dose of composition may be 0.0001, 0.001, 0.01, 0.1, 1, 5, 10, 15, 25, 50, 100, 150, 250, 500, 750, 1000, 1500, 2000 mg/kg or any amount therebetween. The dose of the one or more therapeutic agent may comprise from about 0.0001 mg/kg to about 2000 mg/kg or any amount therebetween. For example, the dose of composition may be 0.0001, 0.001, 0.01, 0.1, 1, 5, 10, 15, 25, 50 100, 150, 250, 500, 750, 1000, 1500, 2000 mg/kg or any amount therebetween.

Furthermore, the composition comprising the one or more than one compound of Formula I-V may be administered in a dose of from between 0.0001-2000 mg/kg or any amount therebetween. For example, the composition may be administered at 0.0001, 0.001, 0.01, 0.1, 1, 5, 10, 15, 25, 50 100, 150, 250, 500, 750, 1000, 1500, 2000 mg/kg or any amount therebetween.

Further, the composition comprising the one or more than one therapeutic agent may be administered in a dose of from between 0.0001-2000 mg/kg/day or any amount therebetween. For example, the composition may be administered at 0.0001, 0.001, 0.01, 0.1, 1, 5, 10, 15, 25, 50 100, 150, 250, 500, 750, 1000, 1500, 2000 mg/kg/day or any amount therebetween.

The compositions described herein, may comprise an effective amount of one or more than one compound of Formula I-V from about 0.0001 mg to about 2000 mg, or any amount there between. For example the effective amount of the one or more than one compound of Formula I-V may be 0.0001 mg, 0.001 mg, 0.005 mg, 0.009 mg, 0.01 mg, 0.02 mg, 0.03 mg, 0.05 mg, 0.07 mg, 0.09 mg, 0.1 mg, 0.2 mg, 0.5 mg, 1 mg, 2 mg, 3 mg, 4 mg, 5 mg, 10 mg, 20 mg, 30 mg, 40 mg, 50, mg, 100 mg, 200 mg, 300 mg, 400 mg, 500 mg, 600 mg, 700 mg, 800, mg, 900 mg, 1000 mg, 1500 mg, 2000 mg or any amount therebetween.

The compound of Formula I-V or the composition comprising the compound of Formula I-V may be administered in a dose once a day or multiple times a day. For example, the compound of Formula I-V or the composition comprising the compound of Formula I-V may be administered once, twice, three, four, five, or six times a day. Furthermore, therapeutic agent combined with the compound of Formula I-V or the composition comprising the compound of Formula I-V may be administered in a dose once a day or multiple times a day. For example, therapeutic agent combined with the compound of Formula I-V or the composition comprising the compound of Formula I-V may be administered once, twice, three, four, five, or six times a day.

The daily dose may be between 0.0001-20,000 m/day or any amount therebetween. The daily dose may be between 0.0001-20 mg/day or any amount therebetween. In another example, the maximum daily dose may be between 1 mg/day-10 g/day or any amount therebetween.

Furthermore, the compound of Formula I-V or the composition comprising one or more than one compound of Formula I-V may be combined with other molecules, intermediates, prodrugs, drugs or precursors to be administered to a subject in need thereof.

The compositions of the present description may be used alone or in combination with other biologically active ingredients. A composition of the present disclosure, alone or in combination with other active ingredients, may be administered to a subject in a single dose or multiple doses over a period of time.

Treatment Regimen

In some embodiments, the method of treating or use may comprise a protracted or an extended treatment period. For example, the treatment period may be at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months or at least 12 months, or any amount therebetween. For example, the treatment period may be between 1-7 days, 1-14 days, 1-21 days, 1-28 days or 1 month to 1 year or any number of days there between.

The treating may comprise an extended treatment period. For example, the treatment period may be at least 21 days. Furthermore, the treating period may be at least 28 days, 35 day, 42 day or any time therebetween. Furthermore, the extended treatment period may be at least 1 month, 2 months, 3 months, 4 months, 5 months, 6 months.

The treating may comprise a protracted treatment period. For example, the treatment period may be less than 21 days. For example, the treatment period may be between about 1 to about 21 days, or any amount of days therebetween. For example, the treatment period may be 1 day, 2 days, 3 days, 4 days, 5 days, 6 days, 7 days, 8 days, 9 days, 10 days, 12 days, 15 days, 18 days, 21 days or any period therebetween.

As used herein, the terms "comprising," "having," "including" and "containing," and grammatical variations thereof, are inclusive or open-ended and do not exclude additional, un-recited elements and/or method steps. The term "consisting of" when used herein in connection with use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/of" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

These and other objects and features of the present disclosure will be illustrated in the following examples. The examples are not intended to be construed as limiting the scope of the present disclosure. It will be readily understood by the skilled artisan that numerous alterations may be made to the examples and instructions given herein for the purification and formulation of disclosed novel compounds.

EXAMPLES

Example 1: Synthesis of MAGL Inhibitors

These and other objects and features of the present disclosure will be made apparent from the following examples. The following examples, as described, are not intended to be construed as limiting the scope of the present disclosure.

It will be readily understood by the skilled artisan that numerous alterations may be made to the examples and instructions given herein for the purification and formulation of disclosed novel compounds.

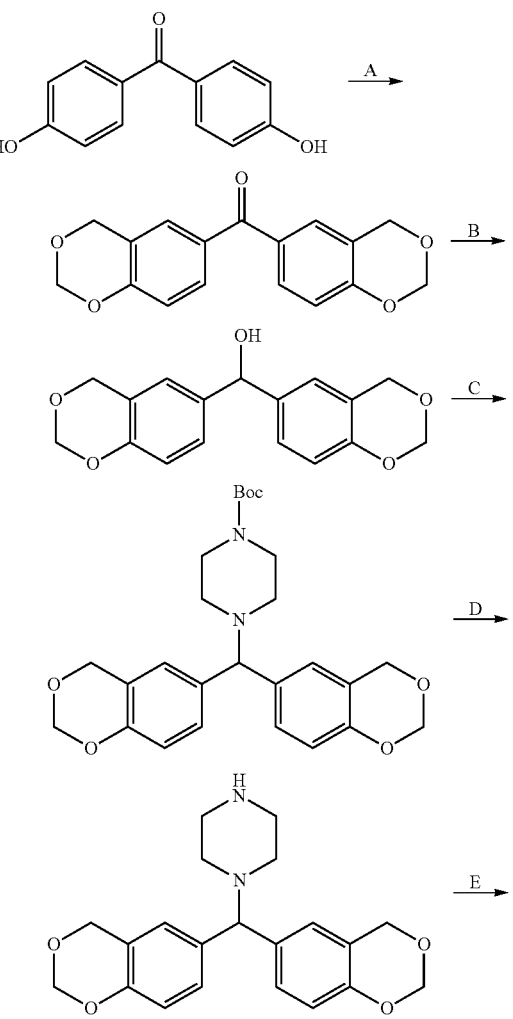

Scheme I:
Synthesis of substituted (4-(bis(4H-benzo[d][1,3]dioxin-6-yl)methyl)piperazin-1-yl)methanone -continued

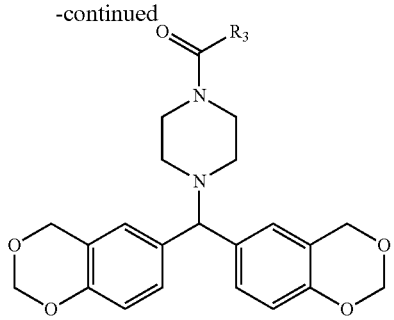

Reagents and conditions: A) HCHO (37%), HClO$_4$/CH$_3$COOH, rt to 75° C., 3 h; B) NaBH$_4$, MeOH/THF (1:1), 60° C., 40 min; C) i) SOCl$_2$, DCM, 0° C. to rt, 3.5 h; ii) 1-Boc-piperazine, DMF, Cs$_2$CO$_3$, 80° C., 16 h; D) TMSI, NMM, DCM, rt, 40 min; E) Method A: i) Triphosgene, DCM, 0° C.; ii) R$_3$—H, Et$_3$N, rt, 3 h; iii) 1-(Bis(4H-benzo[d][1,3]dioxin-6-yl)methyl)piperazine, DCM, rt, 16 h; or Method B: i) Triphosgene, DCM, rt; ii) 1-(Bis(4H-benzo[d][1,3]dioxin-6-yl)methyl)piperazine, Et$_3$N, DCM, rt, 1 h; iii) R$_3$—H, DMAP, DCM, rt, 16 h.

Synthesis of (4-(bis(4H-benzo[d][1,3]dioxin-6-yl)methyl)piperazin-1-yl)(1H-pyrazol-1-yl)methanone (Example-1)

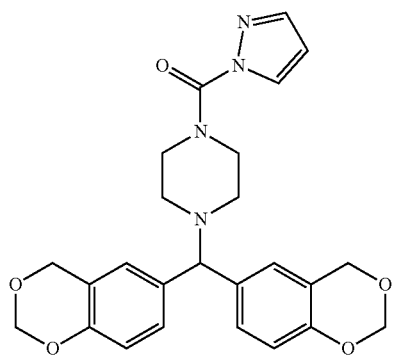 [SMILES: O=C(N1CCN(C(c2ccc3c(c2)COCO3)c2ccc3c(c2)COCO3)CC1)n1cccn1]

Step 1. Preparation of bis(4H-benzo[d][1,3]dioxin-6-yl)methanol

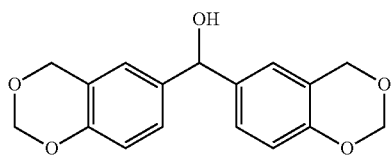 [SMILES: OC(c1ccc2c(c1)COCO2)c1ccc2c(c1)COCO2]

A suspension of 4,4'-dihydroxybenzophenone (9.03 g, 42.2 mmol) in 37% aqueous formaldehyde (119 mL) was stirred at ambient temperature while a solution of 70% aqueous perchloric acid (55 mL) in acetic acid (600 mL) was added dropwise over 2 hours and 35 minutes. The mixture was heated to 75° C. for 3 hours then allowed to cool to ambient temperature and poured into ice-water (1200 mL), giving a colourless precipitate. The precipitate was collected by filtration then partitioned between 10% methanol in dichloromethane (150 mL) and 1N aqueous sodium hydroxide (140 mL). The aqueous phase was extracted with 10% methanol in dichloromethane (2×50 mL) then dichloromethane (50 mL). The combined organic layers were washed with water (600 mL), and the aqueous phase was extracted with 10% methanol in dichloromethane (200 mL). The combined organic layers were dried over anhydrous sodium sulfate, filtered and concentrated in vacuo to provide bis (4H-benzo[d][1,3]dioxin-6-yl)methanone as a colourless solid (6.8 g) that was used in the next step without further purification.

A suspension of the colourless solid from above (6.8 g, 23 mmol) in 50% methanol in tetrahydrofuran (190 mL) was stirred at ambient temperature under nitrogen atmosphere while a portion of sodium borohydride (1.3 g, 34 mmol) was added. The mixture was heated to 60° C. for 10 minutes then the remainder of the sodium borohydride was added portionwise over 40 minutes. Heating was continued for another 40 minutes then the solution was concentrated in vacuo. The residue was dissolved in methanol (38 mL), and the solution was stirred at ambient temperature while water (40 mL) was slowly added to give a cloudy, yellow mixture. The mixture was adjusted to pH 2 by the slow addition of 12N hydrochloric acid followed by 1N hydrochloric acid. The mixture was extracted with dichloromethane (80 mL then 2×50 mL), and the combined organic layers were dried over anhydrous sodium sulfate, filtered and concentrated in vacuo. The residue was purified by column chromatography, eluting with 5% to 15% ethyl acetate in dichloromethane to afford the title compound as a colourless oil (5.0 g, 39% yield).

$^1$H NMR (400 MHz, CDCl$_3$) δ 7.13 (m, 2H), 6.96 (br s, 2H), 6.84 (d, J=8.4 Hz, 2H), 5.70 (d, J=3.3 Hz, 1H), 5.23 (s, 4H), 4.88 (s, 4H), 2.14 (d, J=3.4 Hz, 1H).

Step 2. Preparation of tert-butyl 4-(bis(4H-benzo[d][1,3]dioxin-6-yl)methyl)piperazine-1-carboxylate

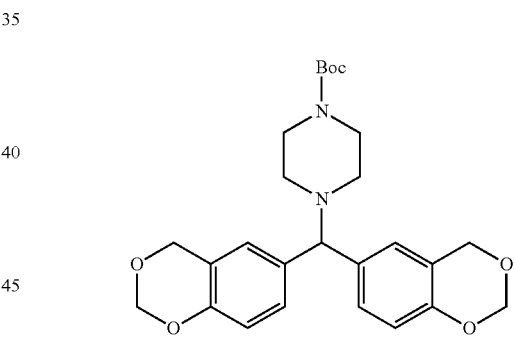

A solution of bis(4H-benzo[d][1,3]dioxin-6-yl)methanol (2.6 g, 8.7 mmol) in anhydrous dichloromethane (22 mL) was cooled to 0° C. under nitrogen atmosphere and thionyl chloride (1.3 mL, 18 mmol) was added dropwise. The solution was stirred at 0° C. for 15 minutes then at ambient temperature for 3.5 hours. The solution was concentrated in vacuo followed by azeotropic removal of thionyl chloride with dichloromethane (2×15 mL). The residue was dissolved in anhydrous N,N-dimethylformamide (29 mL) and cesium carbonate (5.6 g, 17 mmol) was added followed by tert-butyl piperazine-1-carboxylate (1.9 g, 10 mmol). The mixture was heated to 80° C. under nitrogen atmosphere for 16 hours then allowed to cool to ambient temperature. The residue was partitioned between ethyl acetate (100 mL) and water (60 mL), and the organic layer was washed with brine (6×30 mL) then dried over anhydrous sodium sulfate, filtered and concentrated in vacuo. The residue was semi-purified by column chromatography, eluting with 0% to 10% ethyl acetate in dichloromethane to provide a colourless foam (3.7 g). Analysis by ¹H NMR (400 MHz, CDCl₃) indicated that the mixture contained a 5:1 ratio of the title compound and bis(4H-benzo[d][1,3]dioxin-6-yl)methanol, respectively.

¹H NMR (400 MHz, CDCl₃) δ 7.17 (m, 2H), 6.93 (br s, 2H), 6.79 (d, J=8.4 Hz, 2H), 5.20 (s, 4H), 4.86 (s, 4H), 4.04 (s, 1H), 3.40 (m, 4H), 2.29 (m, 4H).

Step 3. Preparation of 1-(bis(4H-benzo[d][1,3]dioxin-6-yl)methyl)piperazine

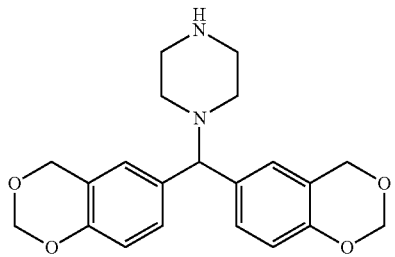 [SMILES: c1cc2c(cc1C(c1ccc3c(c1)COCO3)N1CCNCC1)COCO2]

tert-Butyl 4-(bis(4H-benzo[d][1,3]dioxin-6-yl)methyl)piperazine-1-carboxylate (3.7 g, containing bis(4H-benzo[d][1,3]dioxin-6-yl)methanol as specified above) was dissolved in dichloromethane (78 mL) and stirred at ambient temperature while 4-methylmorpholine (3.5 mL, 32 mmol) was added followed by iodotrimethylsilane (2.8 mL, 20 mmol). The solution was stirred at ambient temperature for 40 minutes then washed with saturated aqueous sodium bicarbonate (60 mL) followed by 1N aqueous sodium thiosulfate (75 mL) and water (40 mL). The organic layer was dried over anhydrous sodium sulfate, filtered and concentrated in vacuo. Toluene (2×30 mL) was used for azeotropic removal of volatiles, and the residue was purified by column chromatography, eluting with 10% ethyl acetate in dichloromethane then 25% methanol in dichloromethane to afford the title compound as a pale foam (2.10 g, 66% yield over 2 steps).

¹H NMR (400 MHz, CDCl₃) δ 7.17 (m, 2H), 6.93 (br s, 2H), 6.79 (d, J=8.4 Hz, 2H), 5.20 (s, 4H), 4.86 (s, 4H), 4.04 (s, 1H), 2.89 (m, 4H), 2.34 (m, 4H) (NH not observed).

Step 4. Preparation of (4-(bis(4H-benzo[d][1,3]dioxin-6-yl)methyl)piperazin-1-yl)(1H-pyrazol-1-yl)methanone (Example-1)

General Procedure A

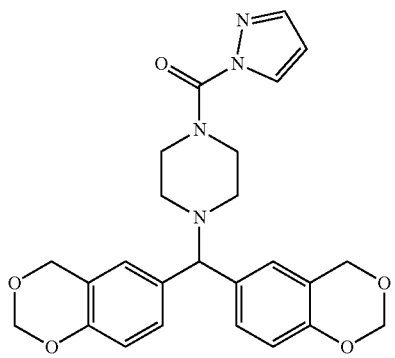 [SMILES: O=C(N1CCN(C(c2ccc3c(c2)COCO3)c2ccc3c(c2)COCO3)CC1)n1cccn1]

Triphosgene (30 mg, 0.10 mmol) was dissolved in anhydrous dichloromethane (0.6 mL), and the solution was cooled to 0° C. under nitrogen atmosphere. Pyrazole (16 mg, 0.24 mmol) was added followed by triethylamine (0.07 mL, 0.5 mmol). The reaction vessel was sealed, and the mixture was stirred at ambient temperature for 3 hours then a solution of 1-(bis(4H-benzo[d][1,3]dioxin-6-yl)methyl)piperazine (74 mg, 0.20 mmol) in anhydrous dichloromethane (1.4 mL) was added. The mixture was sealed and stirred at ambient temperature overnight. The mixture was concentrated in vacuo then purified by column chromatography, eluting with 0% to 10% ethyl acetate in dichloromethane to afford the title compound as a colourless foam (55 mg, 59% yield).

¹H NMR (400 MHz, CDCl₃) δ 8.09 (d, J=2.7 Hz, 1H), 7.59 (br s, 1H), 7.19 (m, 2H), 6.94 (br s, 2H), 6.80 (d, J=8.4 Hz, 2H), 6.34 (m, 1H), 5.21 (s, 4H), 4.87 (s, 4H), 4.10 (s, 1H), 3.90-3.80 (m, 4H), 2.46 (m, 4H); MS (API-ES+) m/z 463.1 (M+1).

Synthesis of (4-(bis(4H-benzo[d][1,3]dioxin-6-yl)methyl)piperazin-1-yl)(3-chloro-1H-1,2,4-triazol-1-yl)methanone (Example-2)

General Procedure B

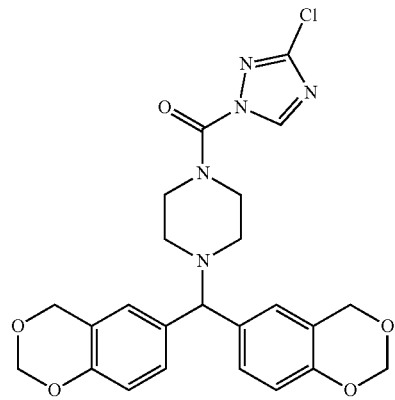

Triphosgene (65 mg, 0.22 mmol) was dissolved in anhydrous dichloromethane (0.5 mL), and the solution was stirred at ambient temperature under nitrogen atmosphere while a solution of 1-(bis(4H-benzo[d][1,3]dioxin-6-yl)methyl)piperazine (81 mg, 0.22 mmol) and triethylamine (0.03 mL, 0.2 mmol) in anhydrous dichloromethane (1.5 mL) was added dropwise. The reaction vessel was sealed, and the mixture was stirred at ambient temperature for 1 hour then concentrated in vacuo. 4-(Dimethylamino)pyridine (27 mg, 0.22 mmol) was added followed by 3-chloro-1,2,4-triazole (23 mg, 0.22 mmol) and anhydrous dichloromethane (2 mL). The mixture was sealed and stirred at ambient temperature overnight. The mixture was concentrated in vacuo then purified by column chromatography, eluting with 0% to 10% ethyl acetate in dichloromethane to afford the title compound as a pale foam (81 mg, 74% yield).

¹H NMR (400 MHz, CDCl₃) δ 8.68 (s, 1H), 7.19 (m, 2H), 6.93 (br s, 2H), 6.81 (d, J=8.4 Hz, 2H), 5.21 (s, 4H), 4.87 (s, 4H), 4.11 (s, 1H), 3.92-3.78 (m, 4H), 2.48 (m, 4H); MS (API-ES+) m/z 498.1/500.1 (³⁵Cl/³⁷Cl) (M+1).

Synthesis of 1,1,1,3,3,3-hexafluoropropan-2-yl 4-(bis(4H-benzo[d][1,3]dioxin-6-yl)methyl)piperazine-1-carboxylate (Example-3)

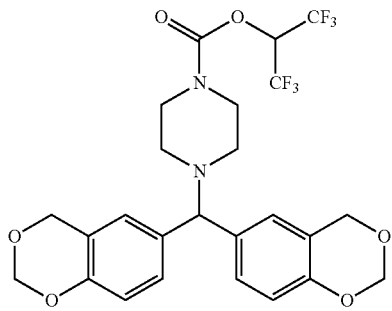 [SMILES: O=C(OC(C(F)(F)F)C(F)(F)F)N1CCN(C(c2ccc3c(c2)COCO3)c2ccc3c(c2)COCO3)CC1]

Following General Procedure A and making non-critical variations as required to replace pyrazole with 1,1,1,3,3,3-hexafluoro-2-propanol, the title compound was obtained as a pale foam (23 mg, 32% yield).

$^1$H NMR (400 MHz, CDCl$_3$) δ 7.17 (m, 2H), 6.92 (br s, 2H), 6.80 (d, J=8.4 Hz, 2H), 5.72 (m, 1H), 5.21 (s, 4H), 4.86 (s, 4H), 4.08 (s, 1H), 3.53 (m, 4H), 2.37 (m, 4H); MS (API-ES+) m/z 563.2 (M+1).

Synthesis of 4-nitrophenyl 4-(bis(4H-benzo[d][1,3]dioxin-6-yl)methyl)piperazine-1-carboxylate (Example-4)

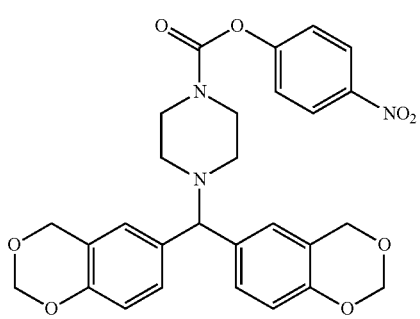 [SMILES: O=C(Oc1ccc([N+](=O)[O-])cc1)N1CCN(C(c2ccc3c(c2)COCO3)c2ccc3c(c2)COCO3)CC1]

Following General Procedure A and making non-critical variations as required to replace pyrazole with 4-nitrophenol, the title compound was obtained as a colorless foam (31 mg, 39% yield).

$^1$H NMR (400 MHz, CDCl$_3$) δ 8.24 (d, J=9.1 Hz, 2H), 7.28 (m, 2H), 7.20 (m, 2H), 6.94 (br s, 2H), 6.82 (d, J=8.4 Hz, 2H), 5.22 (s, 4H), 4.87 (s, 4H), 4.12 (s, 1H), 3.65 (m, 2H), 3.57 (m, 2H), 2.43 (m, 4H); MS (API-ES+) m/z 534.2 (M+1).

Synthesis of 4-fluorophenyl 4-(bis(4H-benzo[d][1,3]dioxin-6-yl)methyl)piperazine-1-carboxylate (Example-5)

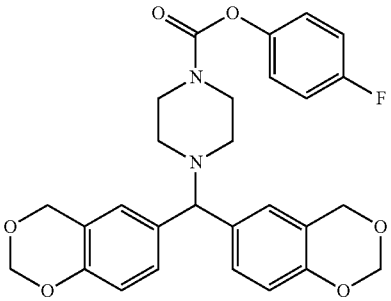

Following General Procedure A and making non-critical variations as required to replace pyrazole with 4-fluorophenol, the title compound was obtained as a light yellow foam (45 mg, 43% yield).

$^1$H NMR (400 MHz, CDCl$_3$) δ 7.20 (m, 2H), 7.03 (m, 4H), 6.94 (br s, 2H), 6.81 (d, J=8.5 Hz, 2H), 5.21 (s, 4H), 4.88 (s, 4H), 4.10 (s, 1H), 3.63 (m, 2H), 3.54 (m, 2H), 2.40 (m, 4H); MS (API-ES+) m/z 507.2 (M+1).

Synthesis of 2,5-dioxopyrrolidin-1-yl 4-(bis(4H-benzo[d][1,3]dioxin-6-yl)methyl)piperazine-1-carboxylate (Example-6)

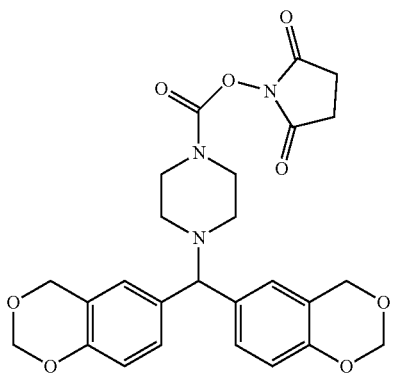 [SMILES: O=C(ON1C(=O)CCC1=O)N1CCN(C(c2ccc3c(c2)COCO3)c2ccc3c(c2)COCO3)CC1]

Following General Procedure A and making non-critical variations as required to replace pyrazole with N-hydroxysuccinimide, the title compound was obtained as a light yellow foam (113 mg, 72% yield).

$^1$H NMR (400 MHz, CDCl$_3$) δ 7.18 (m, 2H), 6.93 (br s, 2H), 6.80 (d, J=8.4 Hz, 2H), 5.21 (s, 4H), 4.87 (s, 4H), 4.10 (s, 1H), 3.62 (m, 2H), 3.51 (m, 2H), 2.81 (s, 4H), 2.42 (m, 4H); MS (API-ES+) m/z 510.1 (M+1).

Synthesis of 4-phenoxyphenyl 4-(bis(4H-benzo[d][1,3]dioxin-6-yl)methyl)piperazine-1-carboxylate (Example-7)

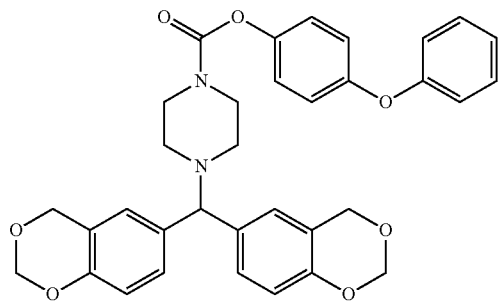 [SMILES: O=C(Oc1ccc(Oc2ccccc2)cc1)N1CCN(C(c2ccc3c(c2)COCO3)c2ccc3c(c2)COCO3)CC1]

Following General Procedure A and making non-critical variations as required to replace pyrazole with 4-phenoxyphenol, the title compound was obtained as a colourless foam (47 mg, 40% yield).

$^1$H NMR (400 MHz, CDCl$_3$) δ 7.32 (m, 2H), 7.20 (m, 2H), 7.10-6.97 (m, 7H), 6.95 (br s, 2H), 6.82 (d, J=8.4 Hz, 2H), 5.22 (s, 4H), 4.88 (s, 4H), 4.11 (s, 1H), 3.64 (m, 2H), 3.56 (m, 2H), 2.41 (m, 4H); MS (API-ES+) m/z 581.2 (M+1).

Synthesis of (1H-benzo[d][1,2,3]triazol-1-yl)(4-(bis(4H-benzo[d][1,3]dioxin-6-yl)methyl)piperazin-1-yl)methanone (Example-8)

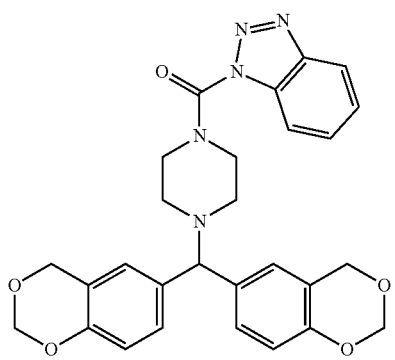 [SMILES: O=C(N1CCN(C(c2ccc3c(c2)COCO3)c2ccc3c(c2)COCO3)CC1)n1nnc2ccccc21]

Following General Procedure A and making non-critical variations as required to replace pyrazole with 1H-benzotriazole, the title compound was obtained as a colourless foam (16 mg, 16% yield).

$^1$H NMR (400 MHz, CDCl$_3$) δ 8.08 (d, J=8.3 Hz, 1H), 7.97 (d, J=8.3 Hz, 1H), 7.59 (m, 1H), 7.44 (m, 1H), 7.21 (m, 2H), 6.96 (br s, 2H), 6.82 (d, J=8.4 Hz, 2H), 5.22 (s, 4H), 4.88 (s, 4H), 4.16 (s, 1H), 3.91 (m, 4H), 2.55 (m, 4H).

Synthesis of (4-(bis(4H-benzo[d][1,3]dioxin-6-yl)methyl)piperazin-1-yl)(1H-imidazol-1-yl)methanone (Example-9)

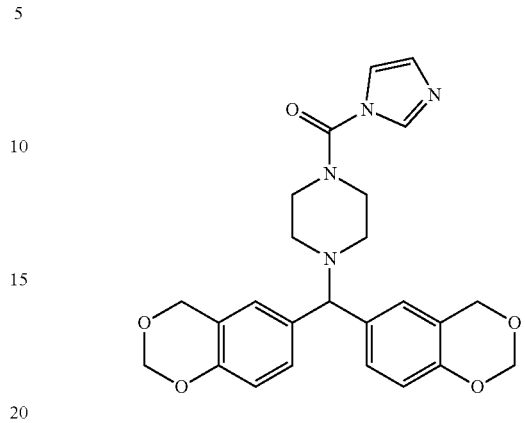

A solution of 1,1'-carbonyldiimidazole (36 mg, 0.22 mmol) in anhydrous dichloromethane (0.5 mL) was cooled to 0° C. under nitrogen atmosphere. A solution of 1-(bis(4H-benzo[d][1,3]dioxin-6-yl)methyl)piperazine (74 mg, 0.20 mmol) in anhydrous dichloromethane (0.5 mL) was added and stirred at 0° C. for 1 hour. The reaction vessel was sealed, and the mixture was stirred at ambient temperature for 3 days then concentrated in vacuo. The residue was purified by column chromatography, eluting with 0% to 90% ethyl acetate in dichloromethane to afford the title compound as a yellow foam (72 mg, 77% yield).

$^1$H NMR (400 MHz, CDCl$_3$) δ 7.84 (s, 1H), 7.17 (m, 3H), 7.06 (s, 1H), 6.92 (br s, 2H), 6.81 (d, J=8.4 Hz, 2H), 5.21 (s, 4H), 4.86 (s, 4H), 4.11 (s, 1H), 3.61 (m, 4H), 2.43 (m, 4H); MS (API-ES+) m/z 463.1 (M+1).

Synthesis of (4-(bis(4H-benzo[d][1,3]dioxin-6-yl)methyl)piperazin-1-yl)(1H-1,2,4-triazol-1-yl)methanone (Example-10)

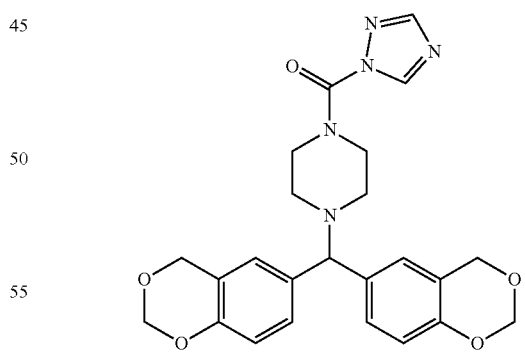

Following General Procedure A and making non-critical variations as required to replace pyrazole with 1,2,4-1H-triazole, the title compound was obtained as a pale foam (12 mg, 13% yield).

$^1$H NMR (400 MHz, CDCl$_3$) δ 8.77 (s, 1H), 7.95 (s, 1H), 7.19 (m, 2H), 6.93 (br s, 2H), 6.81 (d, J=8.4 Hz, 2H), 5.21 (s, 4H), 4.87 (s, 4H), 4.11 (s, 1H), 3.95-3.75 (m, 4H), 2.47 (m, 4H); MS (API-ES+) m/z 464.2 (M+1).

Synthesis of 4-(bis(4H-benzo[d][1,3]dioxin-6-yl)methyl)-N-ethyl-N-isopropylpiperazine-1-carboxamide (Example-11)

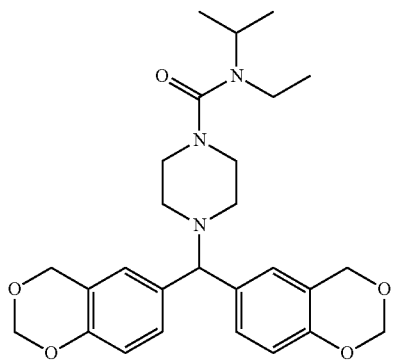 [SMILES: CCN(C(=O)N1CCN(C(c2ccc3c(c2)COCO3)c2ccc3c(c2)COCO3)CC1)C(C)C]

Triphosgene (31 mg, 0.10 mmol) was dissolved in anhydrous dichloromethane (0.5 mL), and the solution was stirred at ambient temperature under nitrogen atmosphere while a solution of cyclohexanol (34 mg, 0.34 mmol) in anhydrous dichloromethane (0.8 mL) was added followed by N,N-diisopropylethylamine (0.12 mL, 0.69 mmol). The reaction vessel was sealed, and the mixture was stirred at ambient temperature overnight then a solution of 1-(bis(4H-benzo[d][1,3]dioxin-6-yl)methyl)piperazine (97 mg, 0.26 mmol) in anhydrous dichloromethane (1.3 mL) was added. The mixture was sealed and stirred at ambient temperature overnight. The mixture was concentrated in vacuo then purified by column chromatography, eluting with 0% to 20% ethyl acetate in dichloromethane to afford the title compound as a light yellow foam (73 mg, 57% yield).

$^1$H NMR (400 MHz, CDCl$_3$) δ 7.18 (m, 2H), 6.94 (br s, 2H), 6.79 (d, J=8.4 Hz, 2H), 5.20 (s, 4H), 4.86 (s, 4H), 4.04 (s, 1H), 3.77 (m, 1H), 3.21 (m, 4H), 3.07 (q, J=7.0 Hz, 2H), 2.34 (m, 4H), 1.11 (d, J=6.6 Hz, 6H), 1.05 (t, J=7.0 Hz, 3H); MS (API-ES+) m/z 482.2 (M+1).

Synthesis of 2,3-dihydro-1H-inden-5-yl 4-(bis(4H-benzo[d][1,3]dioxin-6-yl)methyl)piperazine-1-carboxylate (Example-12)

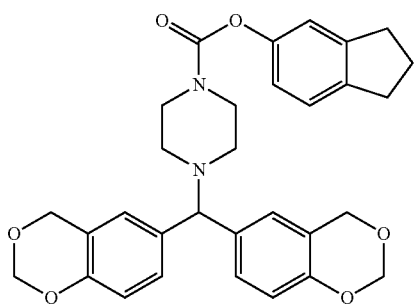 [SMILES: O=C(Oc1ccc2c(c1)CCC2)N1CCN(C(c2ccc3c(c2)COCO3)c2ccc3c(c2)COCO3)CC1]

Following General Procedure A and making non-critical variations as required to replace pyrazole with 5-indanol, the title compound was obtained as a colourless foam (21 mg, 20% yield).

$^1$H NMR (400 MHz, CDCl$_3$) δ 7.19 (m, 2H), 7.15 (d, J=8.1 Hz, 1H), 6.94 (m, 3H), 6.81 (m, 3H), 5.21 (s, 4H), 4.88 (s, 4H), 4.10 (s, 1H), 3.63 (m, 2H), 3.54 (m, 2H), 2.87 (m, 4H), 2.39 (m, 4H), 2.07 (p, J=7.5 Hz, 2H); MS (API-ES+) m/z 529.2 (M+1).

Synthesis of 2,4-dinitrophenyl 4-(bis(4H-benzo[d][1,3]dioxin-6-yl)methyl)piperazine-1-carboxylate (Example-13)

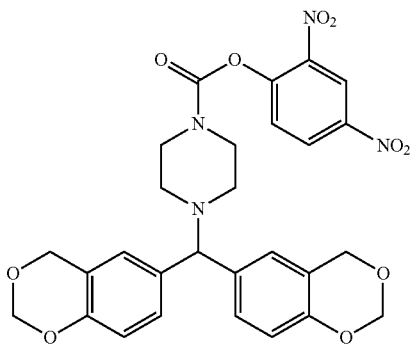 [SMILES: O=C(Oc1ccc([N+](=O)[O-])cc1[N+](=O)[O-])N1CCN(C(c2ccc3c(c2)COCO3)c2ccc3c(c2)COCO3)CC1]

Following General Procedure A and making non-critical variations as required to replace pyrazole with 2,4-dinitrophenol, the title compound was obtained as a yellow foam (32 mg, 29% yield).

$^1$H NMR (400 MHz, CDCl$_3$) δ 8.93 (d, J=2.7 Hz, 1H), 8.48 (dd, J=9.1, 2.7 Hz, 1H), 7.53 (d, J=8.9 Hz, 1H), 7.21 (m, 2H), 6.95 (br s, 2H), 6.82 (d, J=8.4 Hz, 2H), 5.22 (s, 4H), 4.88 (s, 4H), 4.13 (s, 1H), 3.70 (m, 2H), 3.56 (m, 2H), 2.46 (m, 4H); MS (API-ES+) m/z 579.1 (M+1).

Synthesis of 4-methoxyphenyl 4-(bis(4H-benzo[d][1,3]dioxin-6-yl)methyl)piperazine-1-carboxylate (Example-14)

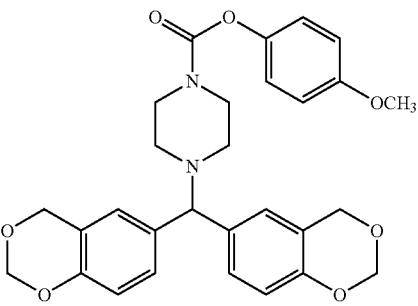 [SMILES: COc1ccc(OC(=O)N2CCN(C(c3ccc4c(c3)COCO4)c3ccc4c(c3)COCO4)CC2)cc1]

Following General Procedure A and making non-critical variations as required to replace pyrazole with 4-methoxyphenol, the title compound was obtained as a colourless foam (12 mg, 12% yield).

$^1$H NMR (400 MHz, CDCl$_3$) δ 7.20 (m, 2H), 7.00 (m, 2H), 6.95 (br s, 2H), 6.85 (m, 2H), 6.81 (d, J=8.4 Hz, 2H), 5.21 (s, 4H), 4.88 (s, 4H), 4.10 (s, 1H), 3.78 (s, 3H), 3.63 (m, 2H), 3.54 (m, 2H), 2.40 (m, 4H); MS (API-ES+) m/z 519.2 (M+1).

Synthesis of pentan-3-yl 4-(bis(4H-benzo[d][1,3]dioxin-6-yl)methyl)piperazine-1-carboxylate (Example-15)

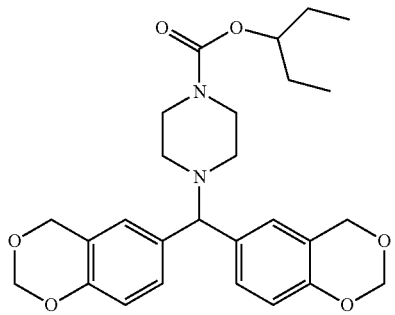 [SMILES: CCC(CC)OC(=O)N1CCN(C(c2ccc3c(c2)COCO3)c2ccc3c(c2)COCO3)CC1]

Following General Procedure A and making non-critical variations as required to replace pyrazole with 3-pentanol, the title compound was obtained as a colourless foam (17 mg, 17% yield).

$^1$H NMR (400 MHz, CDCl$_3$) δ 7.17 (m, 2H), 6.93 (br s, 2H), 6.79 (d, J=8.4 Hz, 2H), 5.20 (s, 4H), 4.86 (s, 4H), 4.63 (p, J=6.1 Hz, 1H), 4.04 (s, 1H), 3.46 (m, 4H), 2.31 (m, 4H), 1.55 (m, 4H), 0.87 (t, J=7.4 Hz, 6H); MS (API-ES+) m/z 483.2 (M+1).

Synthesis of cyclohexyl 4-(bis(4H-benzo[d][1,3]dioxin-6-yl)methyl)piperazine-1-carboxylate (Example-16)

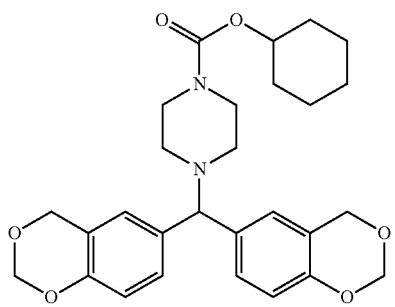 [SMILES: O=C(OC1CCCCC1)N1CCN(C(c2ccc3c(c2)COCO3)c2ccc3c(c2)COCO3)CC1]

Following General Procedure A and making non-critical variations as required to replace pyrazole with cyclohexanol, the title compound was obtained as a colourless foam (44 mg, 40% yield).

$^1$H NMR (400 MHz, CDCl$_3$) δ 7.17 (m, 2H), 6.93 (br s, 2H), 6.79 (d, J=8.4 Hz, 2H), 5.20 (s, 4H), 4.86 (s, 4H), 4.66 (m, 1H), 4.05 (s, 1H), 3.45 (m, 4H), 2.30 (m, 4H), 1.80-1.32 (m, 10H); MS (API-ES+) m/z 495.2 (M+1).

Synthesis of (4-(bis(4H-benzo[d][1,3]dioxin-6-yl)methyl)piperazin-1-yl)(piperidin-1-yl)methanone (Example-17)

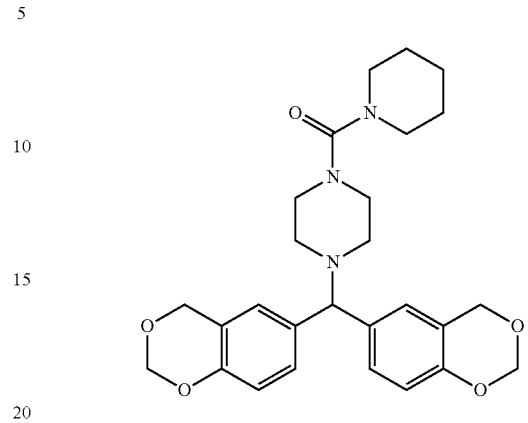

Following General Procedure A and making non-critical variations as required to replace pyrazole with piperidine, the title compound was obtained as a colourless foam (32 mg, 33% yield).

$^1$H NMR (400 MHz, CDCl$_3$) δ 7.17 (m, 2H), 6.93 (br s, 2H), 6.79 (d, J=8.4 Hz, 2H), 5.20 (s, 4H), 4.86 (s, 4H), 4.05 (s, 1H), 3.22 (m, 4H), 3.15 (m, 4H), 2.33 (m, 4H), 1.55 (m, 6H); MS (API-ES+) m/z 480.2 (M+1).

Synthesis of 4-(bis(4H-benzo[d][1,3]dioxin-6-yl)methyl)-N,N-diethylpiperazine-1-carboxamide (Example-18)

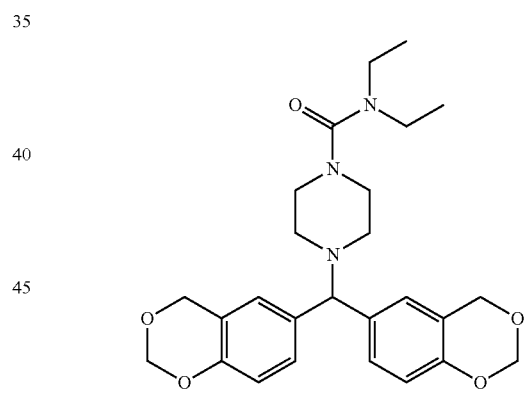

Triphosgene (24 mg, 0.081 mmol) was dissolved in anhydrous dichloromethane (1 mL), and the solution was cooled to 0° C. under nitrogen atmosphere. 1-Hydroxy-7-azabenzotriazole (36 mg, 0.26 mmol) was added followed by triethylamine (0.07 mL, 0.5 mmol), and the mixture was stirred at 0° C. for 1 hour. The reaction vessel was sealed, and the mixture was stirred at ambient temperature for 55 minutes then a solution of 1-(bis(4H-benzo[d][1,3]dioxin-6-yl)methyl)piperazine (74 mg, 0.20 mmol) in anhydrous dichloromethane (1 mL) was added. The mixture was sealed and stirred at ambient temperature for 2 hours. The mixture was concentrated in vacuo then purified by column chromatography, eluting with 0% to 30% ethyl acetate in dichloromethane to afford the title compound as a yellow foam (17 mg, 18% yield).

$^1$H NMR (400 MHz, CDCl$_3$) δ 7.17 (m, 2H), 6.94 (br s, 2H), 6.79 (d, J=8.4 Hz, 2H), 5.20 (s, 4H), 4.86 (s, 4H), 4.04

(s, 1H), 3.19 (m, 8H), 2.34 (m, 4H), 1.08 (t, J=7.0 Hz, 6H); MS (API-ES+) m/z 468.2 (M+1).

Synthesis of 2-fluoro-4-nitrophenyl 4-(bis(4H-benzo[d][1,3]dioxin-6-yl)methyl)piperazine-1-carboxylate (Example-19)

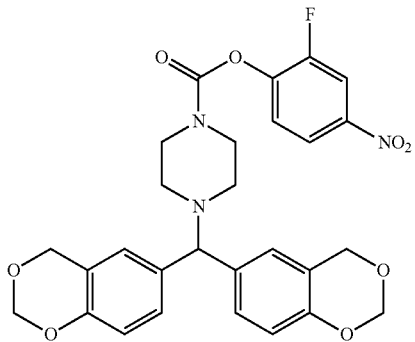

Following General Procedure A and making non-critical variations as required to replace pyrazole with 2-fluoro-4-nitrophenol, the title compound was obtained as a yellow foam (60 mg, 54% yield).

$^1$H NMR (400 MHz, CDCl$_3$) δ 8.05 (m, 2H), 7.41 (m, 1H), 7.20 (m, 2H), 6.94 (br s, 2H), 6.82 (d, J=8.4 Hz, 2H), 5.22 (s, 4H), 4.88 (s, 4H), 4.12 (s, 1H), 3.68 (m, 2H), 3.57 (m, 2H), 2.43 (m, 4H); MS (API-ES+) m/z 552.1 (M+1).

Synthesis of pyridin-2-yl 4-(bis(4H-benzo[d][1,3]dioxin-6-yl)methyl)piperazine-1-carboxylate (Example-20)

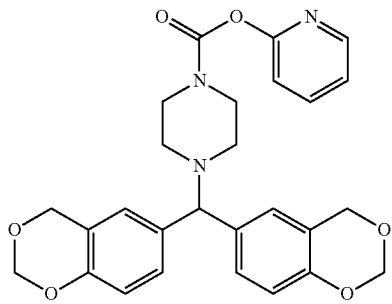 [SMILES: O=C(Oc1ccccn1)N1CCN(C(c2ccc3c(c2)COCO3)c2ccc3c(c2)COCO3)CC1]

Following General Procedure A and making non-critical variations as required to replace pyrazole with 2-hydroxypyridine, the title compound was obtained as a colourless foam (27 mg, 21% yield).

$^1$H NMR (400 MHz, CDCl$_3$) δ 8.36 (m, 1H), 7.76 (m, 1H), 7.19 (m, 3H), 7.09 (d, J=8.2 Hz, 1H), 6.94 (br s, 2H), 6.81 (d, J=8.4 Hz, 2H), 5.21 (s, 4H), 4.88 (s, 4H), 4.11 (s, 1H), 3.68 (m, 2H), 3.57 (m, 2H), 2.41 (m, 4H); MS (API-ES+) m/z 490.2 (M+1).

Synthesis of (4-(bis(4H-benzo[d][1,3]dioxin-6-yl)methyl)piperazin-1-yl)(1H-1,2,4-triazol-1-yl)methanethione (Example-21)

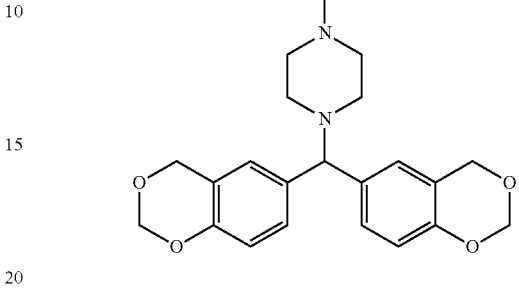

Following General Procedure A and making non-critical variations as required to replace pyrazole with 1,2,4-1H-triazole and triphosgene with thiophosgene, the title compound was obtained as an orange foam (10 mg, 9% yield).

$^1$H NMR (400 MHz, CDCl$_3$) δ 8.85 (s, 1H), 7.94 (s, 1H), 7.19 (m, 2H), 6.93 (br s, 2H), 6.81 (d, J=8.4 Hz, 2H), 5.21 (s, 4H), 4.86 (s, 4H), 4.21 (m, 2H), 4.12 (s, 1H), 3.82 (m, 2H), 2.59-2.49 (m, 4H); MS (API-ES+) m/z 480.1 (M+1).

Synthesis of 6-(trifluoromethyl)-1H-benzo[d][1,2,3]triazol-1-yl 4-(bis(4H-benzo[d][1,3]dioxin-6-yl)methyl)piperazine-1-carboxylate (Example-22)

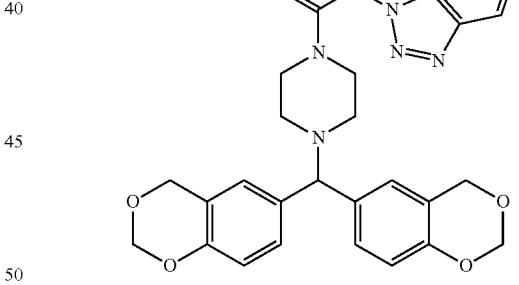

1-Hydroxy-6-(trifluoromethyl)benzotriazole (630 mg, 3.10 mmol) was stirred in diethyl ether (22 mL) at ambient temperature while trichloromethyl chloroformate (0.09 mL, 0.7 mmol) was added. The mixture was stirred at ambient temperature for 10 minutes then more trichloromethyl chloroformate (0.10 mL, 0.8 mmol) was added. The mixture was heated to reflux under nitrogen atmosphere for 1 hour then allowed to cool to ambient temperature. A solid was collected by filtration and rinsed with diethyl ether to presumably provide bis(6-(trifluoromethyl)-1H-benzo[d][1,2,3]triazol-1-yl) carbonate as a colourless solid (389 mg) that was used in the next step without further purification.

A suspension of the solid from above (136 mg) in anhydrous acetonitrile (2 mL) was stirred at ambient temperature while a solution of 1-(bis(4H-benzo[d][1,3]dioxin-6-yl)methyl)piperazine (77 mg, 0.21 mmol) in anhydrous dichloromethane (1 mL) was added. The mixture was stirred at ambient temperature for 1.5 hours then concentrated in vacuo. The residue was purified by column chromatography, eluting with 0% to 25% ethyl acetate in hexanes to afford the title compound as a colourless foam (39 mg, 31% yield).

$^1$H NMR (400 MHz, CDCl$_3$) δ 8.18 (d, J=8.8 Hz, 1H), 7.82 (s, 1H), 7.64 (d, J=8.7 Hz, 1H), 7.22 (m, 2H), 6.96 (br s, 2H), 6.84 (d, J=8.4 Hz, 2H), 5.22 (s, 4H), 4.89 (s, 4H), 4.17 (s, 1H), 3.83 (m, 2H), 3.61 (m, 2H), 2.53 (m, 4H); MS (API-ES+) m/z 598.2 (M+1).

Synthesis of 3H-[1,2,3]triazolo[4,5-b]pyridin-3-yl 4-(bis(4H-benzo[d][1,3]dioxin-6-yl)methyl)piperazine-1-carboxylate (Example-23)

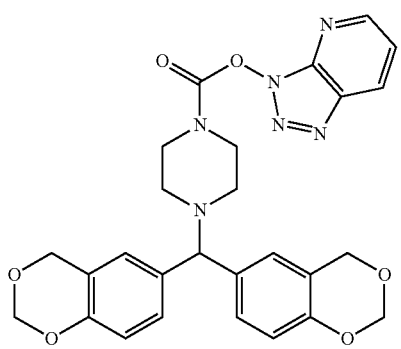

1-Hydroxy-7-azabenzotriazole (505 mg, 3.7 mmol) was stirred as a suspension in 50% diethyl ether in toluene (40 mL) at ambient temperature while trichloromethyl chloroformate (0.22 mL, 1.8 mmol) was added. The mixture was heated to reflux under nitrogen atmosphere for 1.25 hours then allowed to cool to ambient temperature. A solid was collected by filtration and rinsed with diethyl ether to presumably provide 3H-[1,2,3]triazolo[4,5-b]pyridin-3-yl carbonochloridate hydrochloride as a pale solid (302 mg) that was used in the next step without further purification.

A suspension of the solid from above (108 mg) in anhydrous dichloromethane (2 mL) was stirred at ambient temperature while a solution of 1-(bis(4H-benzo[d][1,3]dioxin-6-yl)methyl)piperazine (77 mg, 0.21 mmol) in anhydrous dichloromethane (1 mL) was added followed by the dropwise addition of triethylamine (0.06 mL, 0.4 mmol). The mixture was stirred at ambient temperature for 1.5 hours then concentrated in vacuo. The residue was purified by column chromatography, eluting with 0% to 60% ethyl acetate in hexanes to afford the title compound as a colourless foam (48 mg, 43% yield).

$^1$H NMR (400 MHz, CDCl$_3$) δ 8.74 (m, 1H), 8.41 (m, 1H), 7.43 (dd, J=8.4, 4.3 Hz, 1H), 7.21 (m, 2H), 6.96 (br s, 2H), 6.83 (d, J=8.7 Hz, 2H), 5.22 (s, 4H), 4.89 (s, 4H), 4.16 (s, 1H), 3.85 (m, 2H), 3.60 (m, 2H), 2.52 (m, 4H); MS (API-ES+) m/z 531.2 (M+1).

Synthesis of 1-(4-(bis(4H-benzo[d][1,3]dioxin-6-yl)methyl)piperazine-1-carbonyl)-1H-pyrazole-4-carbonitrile (Example-24)

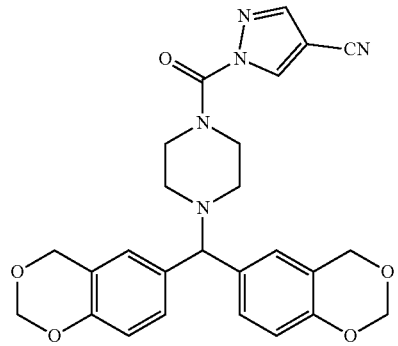 [SMILES: N#Cc1cnn(C(=O)N2CCN(C(c3ccc4c(c3)COCO4)c3ccc4c(c3)COCO4)CC2)c1]

Following General Procedure A and making non-critical variations as required to replace pyrazole with 4-cyanopyrazole, the title compound was obtained as a light yellow foam (55 mg, 52% yield).

$^1$H NMR (400 MHz, CDCl$_3$) δ 8.50 (s, 1H), 7.83 (s, 1H), 7.19 (m, 2H), 6.93 (br s, 2H), 6.81 (d, J=8.4 Hz, 2H), 5.21 (s, 4H), 4.86 (s, 4H), 4.10 (s, 1H), 3.82 (m, 4H), 2.47 (m, 4H); MS (API-ES+) m/z 488.2 (M+1).

Synthesis of (4-(bis(4H-benzo[d][1,3]dioxin-6-yl)methyl)piperazin-1-yl)(4-phenyl-1H-1,2,3-triazol-1-yl)methanone (Example-25) and (4-(bis(4H-benzo[d][1,3]dioxin-6-yl)methyl)piperazin-1-yl)(4-phenyl-2H-1,2,3-triazol-2-yl)methanone (Example-26)

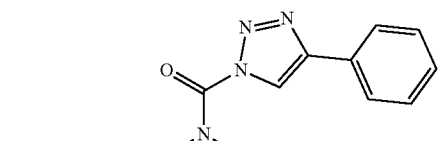

and

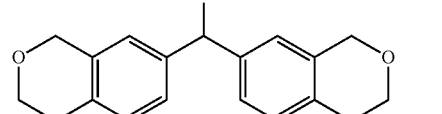
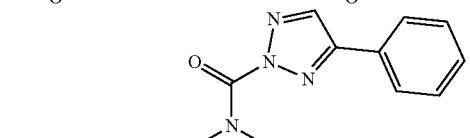

Following General Procedure B and making non-critical variations as required to replace 3-chloro-1,2,4-triazole with 4-phenyl-1H-1,2,3-triazole, the title compounds were each isolated as a pale foam (38 mg, 38% yield) and a pale foam (47 mg, 47% yield), respectively.

The structure of (4-(bis(4H-benzo[d][1,3]dioxin-6-yl)methyl)piperazin-1-yl)(4-phenyl-1H-1,2,3-triazol-1-yl)methanone was tentatively assigned.

$^1$H NMR (400 MHz, CDCl$_3$) δ 8.33 (s, 1H), 7.85 (m, 2H), 7.45 (m, 2H), 7.37 (m, 1H), 7.20 (m, 2H), 6.94 (br s, 2H), 6.82 (d, J=8.4 Hz, 2H), 5.22 (s, 4H), 4.88 (s, 4H), 4.14 (s, 1H), 3.99 (m, 2H), 3.81 (m, 2H), 2.52 (m, 4H); MS (API-ES+) m/z 540.2 (M+1).

The structure of (4-(bis(4H-benzo[d][1,3]dioxin-6-yl)methyl)piperazin-1-yl)(4-phenyl-2H-1,2,3-triazol-2-yl)methanone was tentatively assigned.

$^1$H NMR (400 MHz, CDCl$_3$) δ 8.03 (s, 1H), 7.83 (m, 2H), 7.43 (m, 3H), 7.20 (m, 2H), 6.95 (br s, 2H), 6.81 (d, J=8.4 Hz, 2H), 5.21 (s, 4H), 4.87 (s, 4H), 4.13 (s, 1H), 3.79 (m, 4H), 2.50 (m, 4H); MS (API-ES+) m/z 540.2 (M+1).

Synthesis of 1H-benzo[d][1,2,3]triazol-1-yl 4-(bis(4H-benzo[d][1,3]dioxin-6-yl)methyl)piperazine-1-carboxylate (Example-27)

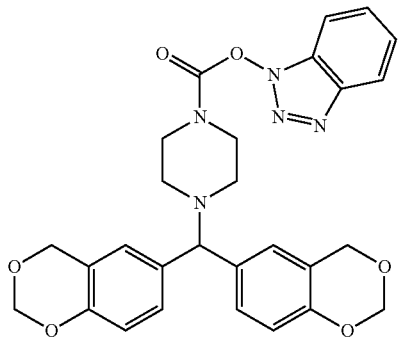 [SMILES: O=C(On1nnc2ccccc21)N1CCN(C(c2ccc3c(c2)COCO3)c2ccc3c(c2)COCO3)CC1]

1-Hydroxybenzotriazole (701 mg, 5.19 mmol) was stirred as a suspension in toluene (20 mL) at ambient temperature while trichloromethyl chloroformate (0.31 mL, 2.6 mmol) was added. The mixture was heated to reflux under nitrogen atmosphere for 1.5 hours then allowed to cool to ambient temperature. Diethyl ether (10 mL) was added, and the precipitate was collected by filtration and rinsed with diethyl ether to presumably provide bis(1H-benzo[d][1,2,3]triazol-1-yl) carbonate as a colourless solid (363 mg) that was used in the next step without further purification.

A suspension of the solid from above (101 mg) in anhydrous dichloromethane (0.6 mL) was stirred at ambient temperature while a solution of 1-(bis(4H-benzo[d][1,3]dioxin-6-yl)methyl)piperazine (74 mg, 0.20 mmol) in anhydrous dichloromethane (1.4 mL) was added followed by the dropwise addition of triethylamine (0.03 mL, 0.2 mmol). The mixture was stirred at ambient temperature overnight then concentrated in vacuo. The residue was purified by column chromatography, eluting with 0% to 40% ethyl acetate in hexanes to afford the title compound as a colourless foam (75 mg, 71% yield).

$^1$H NMR (400 MHz, CDCl$_3$) δ 8.04 (d, J=8.4 Hz, 1H), 7.54 (m, 1H), 7.48 (d, J=8.2 Hz, 1H), 7.41 (m, 1H), 7.22 (m, 2H), 6.96 (br s, 2H), 6.83 (d, J=8.4 Hz, 2H), 5.22 (s, 4H), 4.89 (s, 4H), 4.16 (s, 1H), 3.82 (m, 2H), 3.60 (m, 2H), 2.51 (m, 4H); MS (API-ES+) m/z 530.2 (M+1).

Synthesis of (4-(bis(4H-benzo[d][1,3]dioxin-6-yl)methyl)piperazin-1-yl)(3-methyl-1H-1,2,4-triazol-1-yl)methanone (Example-28)

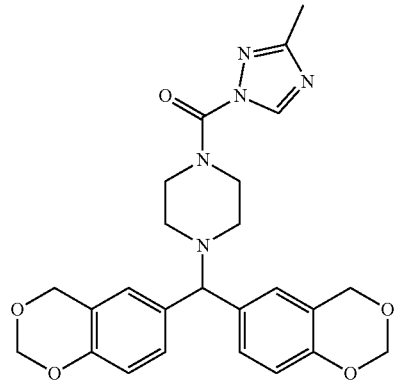 [SMILES: Cc1ncn(C(=O)N2CCN(C(c3ccc4c(c3)COCO4)c3ccc4c(c3)COCO4)CC2)n1]

Following General Procedure B and making non-critical variations as required to replace 3-chloro-1,2,4-triazole with 3-methyl-1H-1,2,4-triazole, the title compound was obtained as a colourless foam (11 mg, 11% yield).

$^1$H NMR (400 MHz, CDCl$_3$) δ 8.65 (s, 1H), 7.19 (m, 2H), 6.94 (br s, 2H), 6.81 (d, J=8.4 Hz, 2H), 5.21 (s, 4H), 4.87 (s, 4H), 4.10 (s, 1H), 3.86 (m, 4H), 2.46 (m, 4H), 2.39 (s, 3H).

Synthesis of pentafluorophenyl 4-(bis(4H-benzo[d][1,3]dioxin-6-yl)methyl)piperazine-1-carboxylate (Example-29)

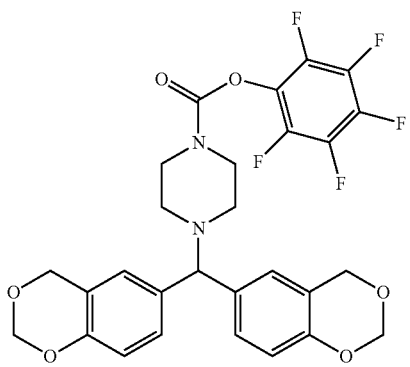 [SMILES: O=C(Oc1c(F)c(F)c(F)c(F)c1F)N1CCN(C(c2ccc3c(c2)COCO3)c2ccc3c(c2)COCO3)CC1]

Following General Procedure A and making non-critical variations as required to replace pyrazole with pentafluorophenol, the title compound was obtained as a colourless foam (66 mg, 56% yield).

$^1$H NMR (400 MHz, CDCl$_3$) δ 7.20 (m, 2H), 6.94 (br s, 2H), 6.82 (d, J=8.4 Hz, 2H), 5.21 (s, 4H), 4.87 (s, 4H), 4.11 (s, 1H), 3.67 (m, 2H), 3.56 (m, 2H), 2.43 (m, 4H); MS (API-ES+) m/z 579.1 (M+1).

Synthesis of propan-2-one O-(4-(bis(4H-benzo[d][1,3]dioxin-6-yl)methyl)piperazine-1-carbonyl) oxime (Example-30)

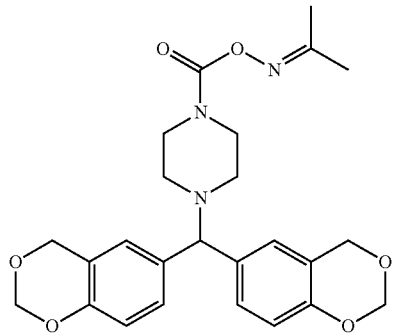 [SMILES: CC(C)=NOC(=O)N1CCN(C(c2ccc3c(c2)COCO3)c2ccc3c(c2)COCO3)CC1]

Step 1. Preparation of propan-2-one oxime

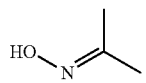

Sodium carbonate (1.44 g, 13.6 mmol) was added portionwise to a stirred solution of acetone (0.50 mL, 6.8 mmol) and hydroxylamine hydrochloride (0.71 g, 10 mmol) in water (7 mL) at ambient temperature. The reaction vessel was sealed, and the solution was stirred for 3 days then extracted with diethyl ether (3×12 mL). The combined organic layers were washed with brine (10 mL) then dried over anhydrous sodium sulfate, filtered and concentrated in vacuo to afford the title compound as a colourless foam (350 mg, 70% yield) that was used in the next step without further purification.

$^{1}$H NMR (400 MHz, CDCl$_3$) δ 8.01 (s, 1H), 1.90 (s, 3H), 1.89 (s, 3H).

Synthesis of (4-(bis(4H-benzo[d][1,3]dioxin-6-yl)methyl)piperazin-1-yl)(1H-1,2,3-triazol-1-yl)methanone and (4-(bis(4H-benzo[d][1,3]dioxin-6-yl)methyl)piperazin-1-yl)(2H-1,2,3-triazol-2-yl)methanone (unassigned ratio of 7:4) (Example-31)

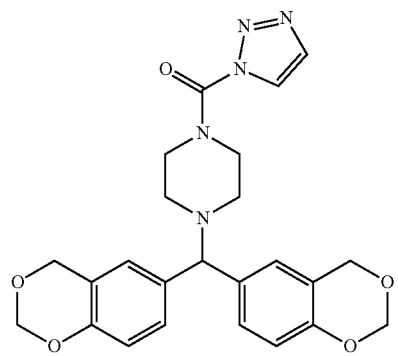

+

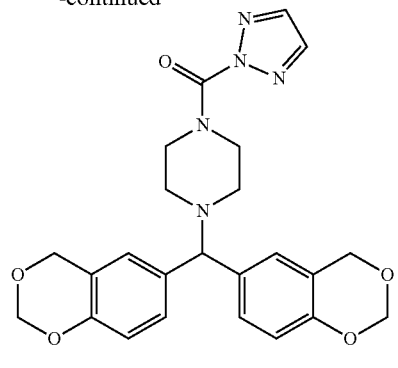

Following General Procedure B and making non-critical variations as required to replace 3-chloro-1,2,4-triazole with 1H-1,2,3-triazole, the title compounds were obtained as a mixture in an unassigned ratio of 7:4 as a colourless foam (105 mg, 86% yield).

$^{1}$H NMR (400 MHz, CDCl$_3$) δ 8.14 (m, 1H), 7.78 (s, 2H), 7.70 (m, 1H), 7.19 (m, 4H), 6.93 (br s, 4H), 6.81 (m, 4H), 5.21 (m, 8H), 4.87 (s, 8H), 4.13 (s, 1H), 4.11 (s, 1H), 3.93-3.69 (m, 8H), 2.50 (m, 8H); MS (API-ES+) m/z 464.2 (M+1).

Synthesis of (3H-[1,2,3]triazolo[4,5-b]pyridin-3-yl)(4-(bis(4H-benzo[d][1,3]dioxin-6-yl)methyl)piperazin-1-yl)methanone and (1H-[1,2,3]triazolo[4,5-b]pyridin-1-yl)(4-(bis(4H-benzo[d][1,3]dioxin-6-yl)methyl)piperazin-1-yl)methanone (unassigned ratio of 5:1) (Example-32)

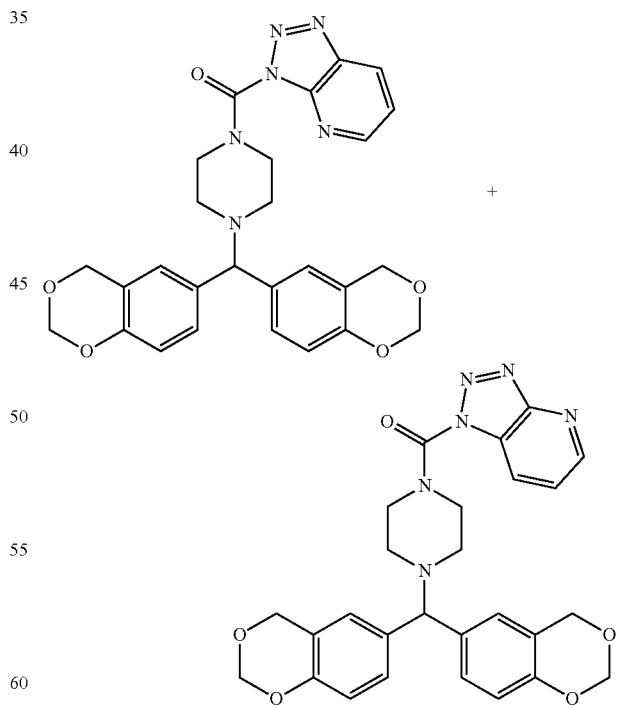

Following General Procedure B and making non-critical variations as required to replace 3-chloro-1,2,4-triazole with 1H-1,2,3-triazolo[4,5-b]pyridine, the title compounds were obtained as a mixture in an unassigned ratio of 5:1 as a pale foam (81 mg, 75% yield).

¹H NMR (400 MHz, CDCl₃) δ 8.91 (m, 1H), 8.80 (m, 1H), 8.37 (m, 1H), 8.30 (m, 1H), 7.55 (dd, J=8.5, 4.4 Hz, 1H), 7.44 (dd, J=8.7, 4.1 Hz, 1H), 7.21 (m, 4H), 6.95 (m, 4H), 6.82 (m, 4H), 5.22 (s, 4H), 5.21 (s, 4H), 4.88 (s, 4H), 4.87 (s, 4H), 4.16 (s, 1H), 4.15 (s, 1H), 4.06-3.89 (m, 8H), 2.56 (m, 8H); MS (API-ES+) m/z 515.2 (M+1).

Synthesis of (4-(bis(4H-benzo[d][1,3]dioxin-6-yl)methyl)piperazin-1-yl)(5-chloro-1H-benzo[d][1,2,3]triazol-1-yl)methanone and (4-(bis(4H-benzo[d][1,3]dioxin-6-yl)methyl)piperazin-1-yl)(6-chloro-1H-benzo[d][1,2,3]triazol-1-yl)methanone (unassigned ratio of 5:3) (Example-33)

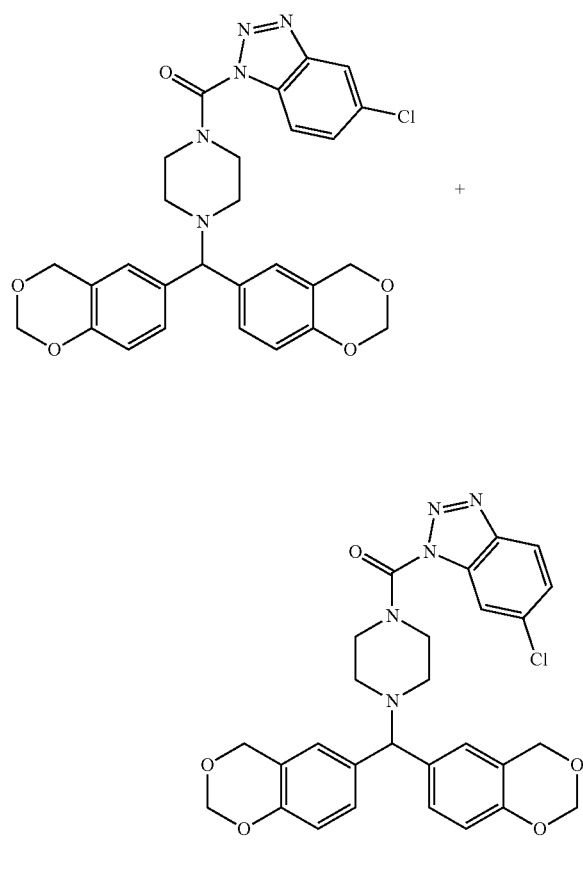

Following General Procedure B and making non-critical variations as required to replace 3-chloro-1,2,4-triazole with 5-chloro-1H-benzotriazole, the title compounds were obtained as a mixture in an unassigned ratio of 5:3 as a colourless foam (59 mg, 54% yield).

¹H NMR (400 MHz, CDCl₃) δ 8.06 (d, J=1.8 Hz, 1H), 8.02 (d, J=1.8 Hz, 1H), 7.99 (d, J=8.8 Hz, 1H), 7.93 (d, J=8.8 Hz, 1H), 7.56 (dd, J=8.8, 1.8 Hz, 1H), 7.41 (dd, J=8.8, 1.8 Hz, 1H), 7.21 (m, 4H), 6.95 (br s, 4H), 6.82 (d, J=8.4 Hz, 4H), 5.21 (s, 8H), 4.88 (s, 8H), 4.15 (s, 2H), 3.91 (m, 8H), 2.55 (m, 8H); MS (API-ES+) m/z 548.1/550.1 (³⁵Cl/³⁷Cl) (M+1).

Synthesis of (4-(bis(4H-benzo[d][1,3]dioxin-6-yl)methyl)piperazin-1-yl)(5-methyl-1H-benzo[d][1,2,3]triazol-1-yl)methanone and (4-(bis(4H-benzo[d][1,3]dioxin-6-yl)methyl)piperazin-1-yl)(6-methyl-1H-benzo[d][1,2,3]triazol-1-yl)methanone (unassigned ratio of 3:2) (Example-34)

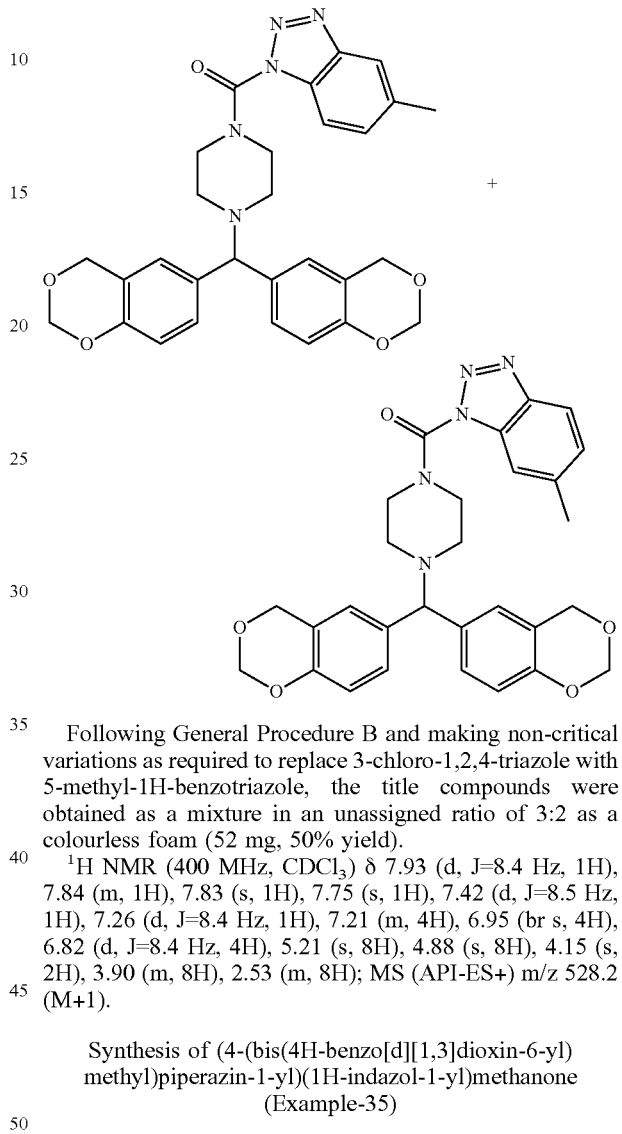

Following General Procedure B and making non-critical variations as required to replace 3-chloro-1,2,4-triazole with 5-methyl-1H-benzotriazole, the title compounds were obtained as a mixture in an unassigned ratio of 3:2 as a colourless foam (52 mg, 50% yield).

¹H NMR (400 MHz, CDCl₃) δ 7.93 (d, J=8.4 Hz, 1H), 7.84 (m, 1H), 7.83 (s, 1H), 7.75 (s, 1H), 7.42 (d, J=8.5 Hz, 1H), 7.26 (d, J=8.4 Hz, 1H), 7.21 (m, 4H), 6.95 (br s, 4H), 6.82 (d, J=8.4 Hz, 4H), 5.21 (s, 8H), 4.88 (s, 8H), 4.15 (s, 2H), 3.90 (m, 8H), 2.53 (m, 8H); MS (API-ES+) m/z 528.2 (M+1).

Synthesis of (4-(bis(4H-benzo[d][1,3]dioxin-6-yl)methyl)piperazin-1-yl)(1H-indazol-1-yl)methanone (Example-35)

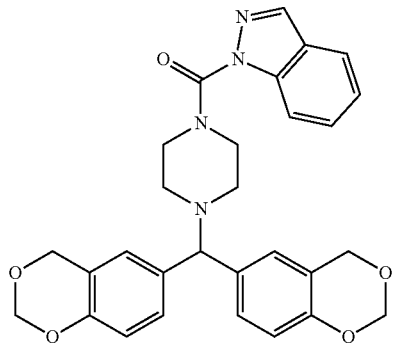 [SMILES: O=C(N1CCN(C(c2ccc3c(c2)COCO3)c2ccc3c(c2)COCO3)CC1)n1ncc2ccccc21]

Following General Procedure B and making non-critical variations as required to replace 3-chloro-1,2,4-triazole with indazole, the title compound was obtained as a colourless foam (15 mg, 15% yield).

$^1$H NMR (400 MHz, CDCl$_3$) δ 8.06 (d, J=8.5 Hz, 1H), 8.04 (s, 1H), 7.71 (d, J=8.0 Hz, 1H), 7.49 (m, 1H), 7.27 (m, 1H), 7.21 (m, 2H), 6.96 (br s, 2H), 6.81 (d, J=8.4 Hz, 2H), 5.21 (s, 4H), 4.87 (s, 4H), 4.12 (s, 1H), 3.84 (m, 4H), 2.50 (m, 4H); MS (API-ES+) m/z 513.1 (M+1).

Synthesis of 1-(4-(bis(4H-benzo[d][1,3]dioxin-6-yl)methyl)piperazine-1-carbonyl)-1H-1,2,4-triazole-3-carbonitrile (Example-36)

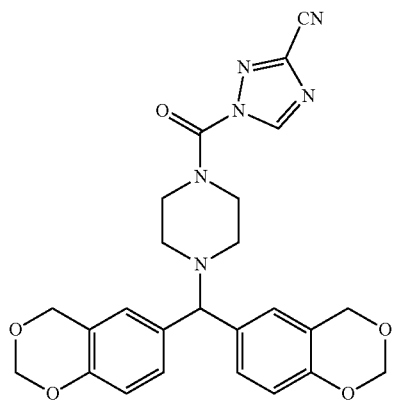 [SMILES: N#Cc1ncn(C(=O)N2CCN(C(c3ccc4c(c3)COCO4)c3ccc4c(c3)COCO4)CC2)n1]

Following General Procedure B and making non-critical variations as required to replace 3-chloro-1,2,4-triazole with 4H-1,2,4-triazole-3-carbonitrile, the title compound was obtained as a colourless foam (40 mg, 43% yield).

$^1$H NMR (400 MHz, CDCl$_3$) δ 8.84 (s, 1H), 7.19 (m, 2H), 6.93 (br s, 2H), 6.82 (d, J=8.4 Hz, 2H), 5.21 (s, 4H), 4.87 (s, 4H), 4.12 (s, 1H), 3.90 (m, 2H), 3.76 (m, 2H), 2.50 (m, 4H); MS (API-ES+) m/z 511.2 (M+23).

Synthesis of (4-(bis(4H-benzo[d][1,3]dioxin-6-yl)methyl)piperazin-1-yl)(6-bromo-1H-benzo[d][1,2,3]triazol-1-yl)methanone (Example-37) and (4-(bis(4H-benzo[d][1,3]dioxin-6-yl)methyl)piperazin-1-yl)(5-bromo-1H-benzo[d][1,2,3]triazol-1-yl)methanone (Example-38)

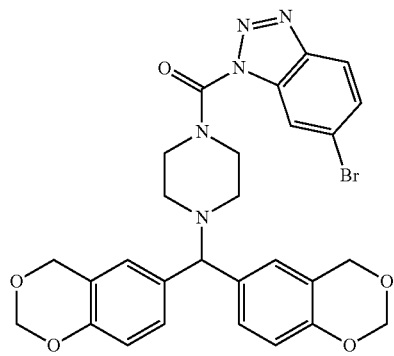

and

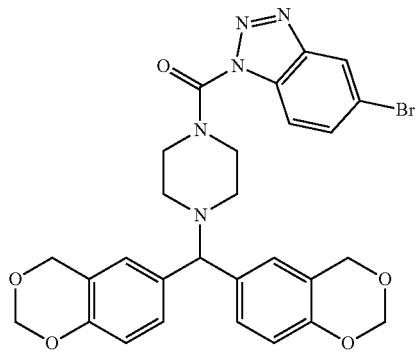

Following General Procedure B and making non-critical variations as required to replace 3-chloro-1,2,4-triazole with 5-bromo-1H-benzotriazole, the title compounds were each isolated as a colourless foam (19 mg, 17% yield) and a colourless foam (14 mg, 12% yield), respectively.

The structure of (4-(bis(4H-benzo[d][1,3]dioxin-6-yl)methyl)piperazin-1-yl)(6-bromo-1H-benzo[d][1,2,3]triazol-1-yl)methanone was tentatively assigned.

$^1$H NMR (400 MHz, CDCl$_3$) δ 8.20 (d, J=1.7 Hz, 1H), 7.93 (d, J=8.7 Hz, 1H), 7.55 (dd, J=8.7, 1.6 Hz, 1H), 7.21 (m, 2H), 6.95 (br s, 2H), 6.82 (d, J=8.4 Hz, 2H), 5.21 (s, 4H), 4.88 (s, 4H), 4.15 (s, 1H), 3.90 (m, 4H), 2.54 (m, 4H); MS (API-ES+) m/z 592.1/594.1 ($^{79}$Br/$^{81}$Br) (M+1).

The structure of (4-(bis(4H-benzo[d][1,3]dioxin-6-yl)methyl)piperazin-1-yl)(5-bromo-1H-benzo[d][1,2,3]triazol-1-yl)methanone was tentatively assigned.

$^1$H NMR (400 MHz, CDCl$_3$) δ 8.24 (d, J=1.7 Hz, 1H), 7.87 (d, J=8.8 Hz, 1H), 7.68 (dd, J=8.8, 1.7 Hz, 1H), 7.21 (m, 2H), 6.95 (br s, 2H), 6.82 (d, J=8.4 Hz, 2H), 5.21 (s, 4H), 4.88 (s, 4H), 4.15 (s, 1H), 3.91 (m, 4H), 2.55 (m, 4H); MS (API-ES+) m/z 592.1/594.1 ($^{79}$Br/$^{81}$Br) (M+1).

Synthesis of (4-(bis(4H-benzo[d][1,3]dioxin-6-yl)methyl)piperazin-1-yl)(6-fluoro-1H-benzo[d][1,2,3]triazol-1-yl)methanone (Example-39) and (4-(bis(4H-benzo[d][1,3]dioxin-6-yl)methyl)piperazin-1-yl)(5-fluoro-1H-benzo[d][1,2,3]triazol-1-yl)methanone (Example-40)

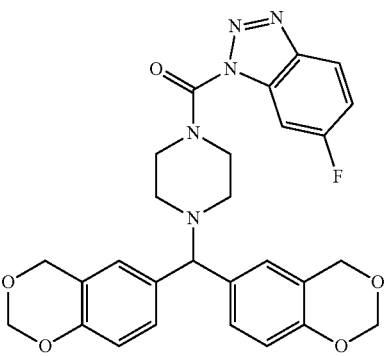

and

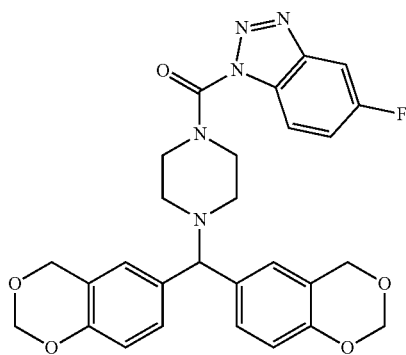

Following General Procedure B and making non-critical variations as required to replace 3-chloro-1,2,4-triazole with 5-fluoro-1H-benzotriazole, the title compounds were each isolated as a pale foam (43 mg, 42% yield) and a yellow foam (15 mg, 15% yield), respectively.

The structure of (4-(bis(4H-benzo[d][1,3]dioxin-6-yl)methyl)piperazin-1-yl)(6-fluoro-1H-benzo[d][1,2,3]triazol-1-yl)methanone was tentatively assigned.

$^1$H NMR (400 MHz, CDCl$_3$) δ 8.03 (dd, J=9.0, 4.5 Hz, 1H), 7.66 (dd, J=8.3, 2.3 Hz, 1H), 7.21 (m, 3H), 6.96 (br s, 2H), 6.82 (d, J=8.4 Hz, 2H), 5.21 (s, 4H), 4.88 (s, 4H), 4.15 (s, 1H), 3.92 (m, 4H), 2.55 (m, 4H); $^{19}$F NMR (376 MHz, CDCl$_3$) δ −108.91 (s, 1F); MS (API-ES+) m/z 532.1 (M+1).

The structure of (4-(bis(4H-benzo[d][1,3]dioxin-6-yl)methyl)piperazin-1-yl)(5-bromo-1H-benzo[d][1,2,3]triazol-1-yl)methanone was tentatively assigned.

$^1$H NMR (400 MHz, CDCl$_3$) δ 7.96 (dd, J=9.1, 4.4 Hz, 1H), 7.70 (dd, J=8.0, 2.3 Hz, 1H), 7.37 (td, J=8.9, 2.3 Hz, 1H), 7.21 (m, 2H), 6.95 (br s, 2H), 6.82 (d, J=8.4 Hz, 2H), 5.22 (s, 4H), 4.88 (s, 4H), 4.15 (s, 1H), 3.91 (m, 4H), 2.55 (m, 4H); MS (API-ES+) m/z 532.1 (M+1).

Synthesis of methyl 1-(4-(bis(4H-benzo[d][1,3]dioxin-6-yl)methyl)piperazine-1-carbonyl)-1H-benzo[d][1,2,3]triazole-5-carboxylate and methyl 1-(4-(bis(4H-benzo[d][1,3]dioxin-6-yl)methyl)piperazine-1-carbonyl)-1H-benzo[d][1,2,3]triazole-6-carboxylate (unassigned ratio of 2:1) (Example-41)

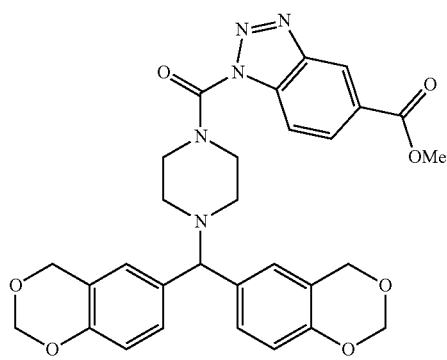

+

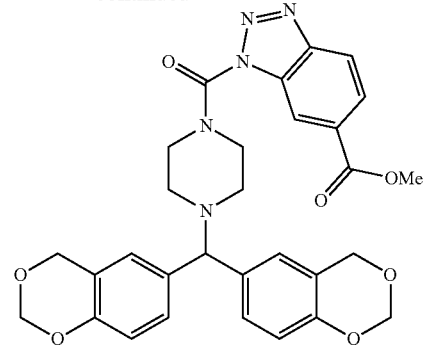

Following General Procedure A and making non-critical variations as required to replace pyrazole with methyl 1H-1,2,3-benzotriazole-5-carboxylate, the title compounds were obtained as a mixture in an unassigned ratio of 2:1 as a yellow foam (148 mg, 73% yield).

$^1$H NMR (400 MHz, CDCl$_3$) δ 8.80 (s, 1H), 8.69 (m, 1H), 8.28 (m, 1H), 8.12 (m, 2H), 8.01 (d, J=8.7 Hz, 1H), 7.21 (m, 4H), 6.96 (br s, 4H), 6.82 (d, J=8.4 Hz, 4H), 5.22 (s, 8H), 4.88 (s, 8H), 4.16 (s, 2H), 3.99 (s, 3H), 3.97 (s, 3H), 3.91 (m, 8H), 2.56 (m, 8H); MS (API-ES+) m/z 572.1 (M+1).

Synthesis of (4-(bis(4H-benzo[d][1,3]dioxin-6-yl)methyl)piperazin-1-yl)(4-chloro-6-(trifluoromethyl)-1H-benzo[d][1,2,3]triazol-1-yl)methanone (Example-42)

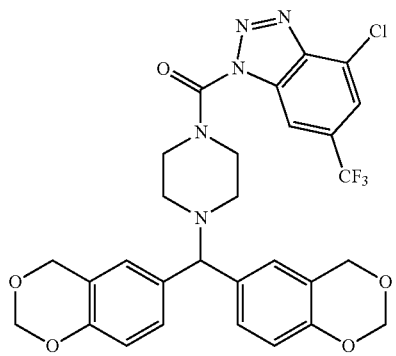 [SMILES: O=C(N1CCN(C(c2ccc3c(c2)COCO3)c2ccc3c(c2)COCO3)CC1)n1nnc2c(Cl)cc(C(F)(F)F)cc21]

Following General Procedure A and making non-critical variations as required to replace pyrazole with 4-chloro-6-(trifluoromethyl)-1,2,3-benzotriazole, the title compound was obtained as a yellow foam (62 mg, 50% yield).

$^1$H NMR (400 MHz, CDCl$_3$) δ 8.25 (s, 1H), 7.69 (s, 1H), 7.21 (m, 2H), 6.95 (br s, 2H), 6.83 (d, J=8.4 Hz, 2H), 5.22 (s, 4H), 4.88 (s, 4H), 4.16 (s, 1H), 3.92 (m, 4H), 2.56 (m, 4H); $^{19}$F NMR (376 MHz, CDCl$_3$) δ −61.93 (s, 3F); MS (API-ES+) m/z 638.0 ($^{35}$Cl) (M+23).

Synthesis of 4-(bis(4H-benzo[d][1,3]dioxin-6-yl)methyl)-N-(pyridin-3-yl)piperazine-1-carboxamide (Example-43)

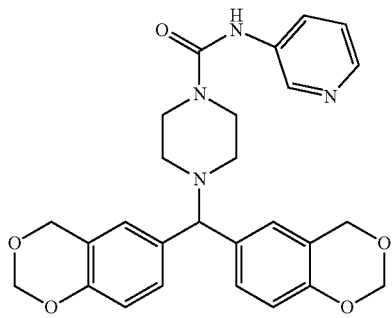 [SMILES: O=C(Nc1cccnc1)N1CCN(C(c2ccc3c(c2)COCO3)c2ccc3c(c2)COCO3)CC1]

Following General Procedure A and making non-critical variations as required to replace pyrazole with 3-aminopyridine, the title compound was obtained as a yellow foam (73 mg, 75% yield).

$^1$H NMR (400 MHz, CDCl$_3$) δ 8.40 (d, J=2.7 Hz, 1H), 8.26 (m, 1H), 7.96 (m, 1H), 7.21 (m, 3H), 6.94 (br s, 2H), 6.81 (d, J=8.4 Hz, 2H), 6.42 (s, 1H), 5.21 (s, 4H), 4.87 (s, 4H), 4.09 (s, 1H), 3.50 (m, 4H), 2.41 (m, 4H); MS (APCI+) m/z 489.1 (M+1).

Synthesis of (4-(bis(4H-benzo[d][1,3]dioxin-6-yl)methyl)piperazin-1-yl)(6-(trifluoromethyl)-1H-benzo[d][1,2,3]triazol-1-yl)methanone (Example-44) and (4-(bis(4H-benzo[d][1,3]dioxin-6-yl)methyl)piperazin-1-yl)(5-(trifluoromethyl)-1H-benzo[d][1,2,3]triazol-1-yl)methanone (Example-45)

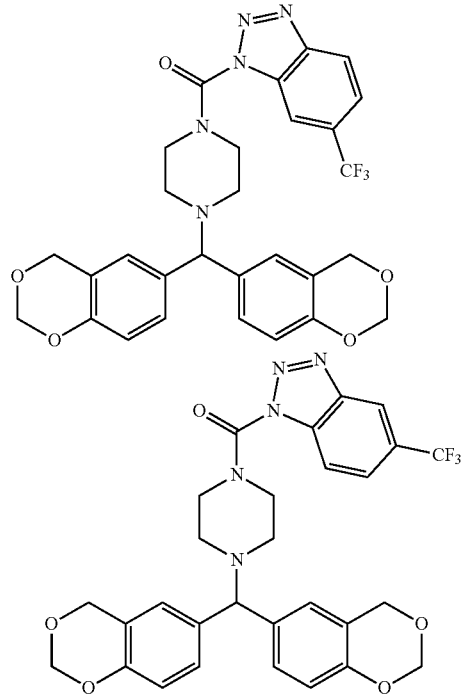

and

Following General Procedure A and making non-critical variations as required to replace pyrazole with 5-(trifluoromethyl)-1H-benzo-1,2,3-triazole, the title compounds were each isolated as a yellow foam (16 mg, 13% yield) and a yellow foam (17 mg, 13% yield), respectively.

The structure of (4-(bis(4H-benzo[d][1,3]dioxin-6-yl)methyl)piperazin-1-yl)(6-(trifluoromethyl)-1H-benzo[d][1,2,3]triazol-1-yl)methanone was tentatively assigned.

$^1$H NMR (400 MHz, CDCl$_3$) δ 8.35 (s, 1H), 8.20 (d, J=8.6 Hz, 1H), 7.69 (d, J=8.7 Hz, 1H), 7.21 (m, 2H), 6.96 (br s, 2H), 6.82 (d, J=8.4 Hz, 2H), 5.22 (s, 4H), 4.88 (s, 4H), 4.16 (s, 1H), 3.93 (m, 4H), 2.56 (m, 4H); MS (API-ES+) m/z 582.1 (M+1).

The structure of (4-(bis(4H-benzo[d][1,3]dioxin-6-yl)methyl)piperazin-1-yl)(5-(trifluoromethyl)-1H-benzo[d][1,2,3]triazol-1-yl)methanone was tentatively assigned.

$^1$H NMR (400 MHz, CDCl$_3$) δ 8.40 (s, 1H), 8.11 (d, J=8.7 Hz, 1H), 7.83 (d, J=8.7 Hz, 1H), 7.21 (m, 2H), 6.96 (br s, 2H), 6.82 (d, J=8.4 Hz, 2H), 5.22 (s, 4H), 4.88 (s, 4H), 4.16 (s, 1H), 3.92 (m, 4H), 2.56 (m, 4H); $^{19}$F NMR (376 MHz, CDCl$_3$) δ −61.60 (s, 3F); MS (API-ES+) m/z 582.1 (M+1).

Synthesis of (4-(bis(4H-benzo[d][1,3]dioxin-6-yl)methyl)piperazin-1-yl)(6,7-dihydro-1H-[1,4]dioxino[2',3':4,5]benzo[1,2-d][1,2,3]triazol-1-yl)methanone (Example-46)

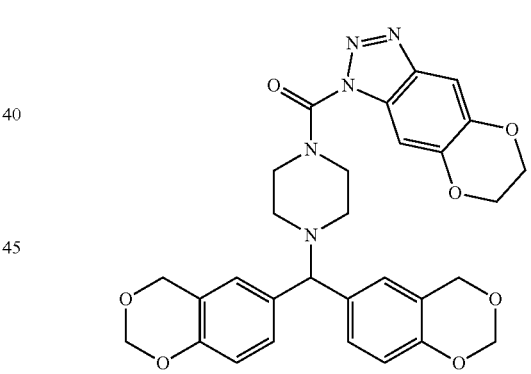

Following General Procedure A and making non-critical variations as required to replace pyrazole with 6,7-dihydro-1H-[1,4]dioxino[2,3-f][1,2,3]benzotriazole, the title compound was obtained as a yellow foam (22 mg, 23% yield).

$^1$H NMR (400 MHz, CDCl$_3$) δ 7.47 (s, 1H), 7.41 (s, 1H), 7.20 (m, 2H), 6.95 (br s, 2H), 6.82 (d, J=8.4 Hz, 2H), 5.21 (s, 4H), 4.88 (s, 4H), 4.32 (m, 4H), 4.14 (s, 1H), 3.89 (m, 4H), 2.52 (m, 4H); MS (API-ES+) m/z 572.1 (M+1).

Synthesis of (3H-[1,2,3]triazolo[4,5-c]pyridin-3-yl)
(4-(bis(4H-benzo[d][1,3]dioxin-6-yl)methyl)piper-
azin-1-yl)methanone and (1H-[1,2,3]triazolo[4,5-c]
pyridin-1-yl)(4-(bis(4H-benzo[d][1,3]dioxin-6-yl)
methyl)piperazin-1-yl)methanone (unassigned ratio
of 7:2) (Example-47)

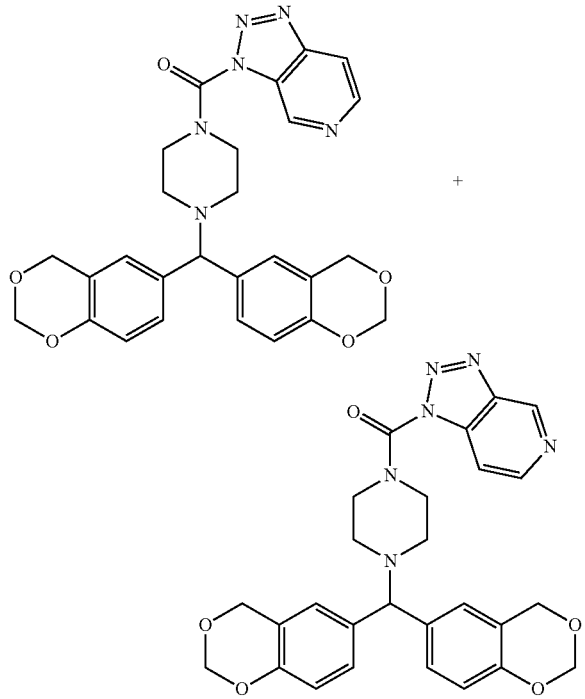

Following General Procedure B and making non-critical variations as required to replace 3-chloro-1,2,4-triazole with 3H-[1,2,3]triazolo[4,5-c]pyridine, the title compounds were obtained as a mixture in an unassigned ratio of 7:2 as a yellow foam (26 mg, 27% yield).
¹H NMR (400 MHz, CDCl₃) δ 9.50 (s, 1H), 9.49 (s, 1H), 8.69 (d, J=5.7 Hz, 1H), 8.64 (d, J=5.7 Hz, 1H), 7.99 (d, J=5.7 Hz, 1H), 7.90 (d, J=5.8 Hz, 1H), 7.21 (d, J=8.1 Hz, 4H), 6.96 (br s, 4H), 6.82 (d, J=8.4 Hz, 4H), 5.22 (s, 8H), 4.88 (s, 8H), 4.16 (s, 2H), 3.93 (m, 8H), 2.56 (m, 8H); MS (APCI+) m/z 515.2 (M+1).

Synthesis of 1-(4-(bis(4H-benzo[d][1,3]dioxin-6-yl)
methyl)piperazine-1-carbonyl)-1H-benzo[d][1,2,3]
triazole-6-carbonitrile (Example-48) and 1-(4-(bis
(4H-benzo[d][1,3]dioxin-6-yl)methyl)piperazine-1-
carbonyl)-1H-benzo[d][1,2,3]triazole-5-carbonitrile
(Example-49)

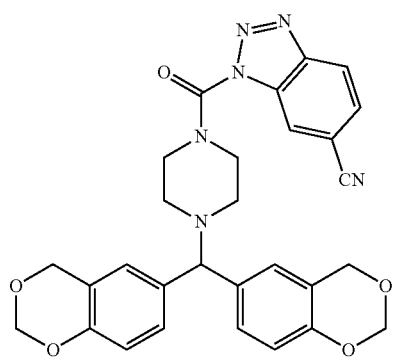

and

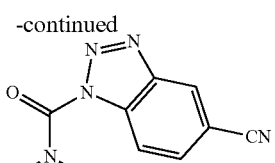

Following General Procedure B and making non-critical variations as required to replace 3-chloro-1,2,4-triazole with 1H-1,2,3-benzotriazole-5-carbonitrile, the title compounds were each isolated as a colourless foam (43 mg, 41% yield) and a pale foam (62 mg, 59% yield), respectively.

The structure of 1-(4-(bis(4H-benzo[d][1,3]dioxin-6-yl)methyl)piperazine-1-carbonyl)-1H-benzo[d][1,2,3]triazole-6-carbonitrile was tentatively assigned.
¹H NMR (400 MHz, CDCl₃) δ 8.41 (s, 1H), 8.19 (d, J=8.5 Hz, 1H), 7.68 (m, 1H), 7.21 (m, 2H), 6.96 (br s, 2H), 6.83 (d, J=8.4 Hz, 2H), 5.22 (s, 4H), 4.88 (s, 4H), 4.16 (s, 1H), 3.93 (m, 4H), 2.56 (m, 4H); MS (API-ES+) m/z 539.1 (M+1).

The structure of 1-(4-(bis(4H-benzo[d][1,3]dioxin-6-yl)methyl)piperazine-1-carbonyl)-1H-benzo[d][1,2,3]triazole-5-carbonitrile was tentatively assigned.
¹H NMR (400 MHz, CDCl₃) δ 8.46 (s, 1H), 8.11 (d, J=8.6 Hz, 1H), 7.81 (m, 1H), 7.21 (m, 2H), 6.95 (br s, 2H), 6.82 (d, J=8.4 Hz, 2H), 5.22 (s, 4H), 4.88 (s, 4H), 4.16 (s, 1H), 3.91 (m, 4H), 2.56 (m, 4H); MS (API-ES+) m/z 539.2 (M+1).

Synthesis of 2-(4-(bis(4H-benzo[d][1,3]dioxin-6-yl)
methyl)piperazine-1-carbonyl)-[1,2,4]triazolo[4,3-a]
pyridin-3(2H)-one (Example-50)

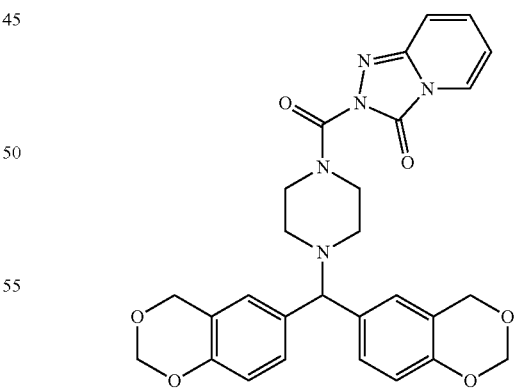

Following General Procedure B and making non-critical variations as required to replace 3-chloro-1,2,4-triazole with 1,2,4-triazolo[4,3-a]pyridin-3(2H)-one, the title compound was obtained as a light yellow foam (12 mg, 11% yield).
¹H NMR (400 MHz, CDCl₃) δ 7.69 (d, J=7.1 Hz, 1H), 7.19 (m, 2H), 7.14 (m, 1H), 7.07 (d, J=9.5 Hz, 1H), 6.93 (br s, 2H), 6.80 (d, J=8.4 Hz, 2H), 6.48 (m, 1H), 5.21 (s, 4H), 4.87 (s, 4H), 4.11 (s, 1H), 3.72 (m, 2H), 3.58 (m, 2H), 2.47 (m, 4H); MS (API-ES+) m/z 530.2 (M+1).

Synthesis of 1-(4-(bis(4H-benzo[d][1,3]dioxin-6-yl)methyl)-1,4-diazepane-1-carbonyl)-1H-benzo[d][1,2,3]triazole-6-carbonitrile (Example-51)

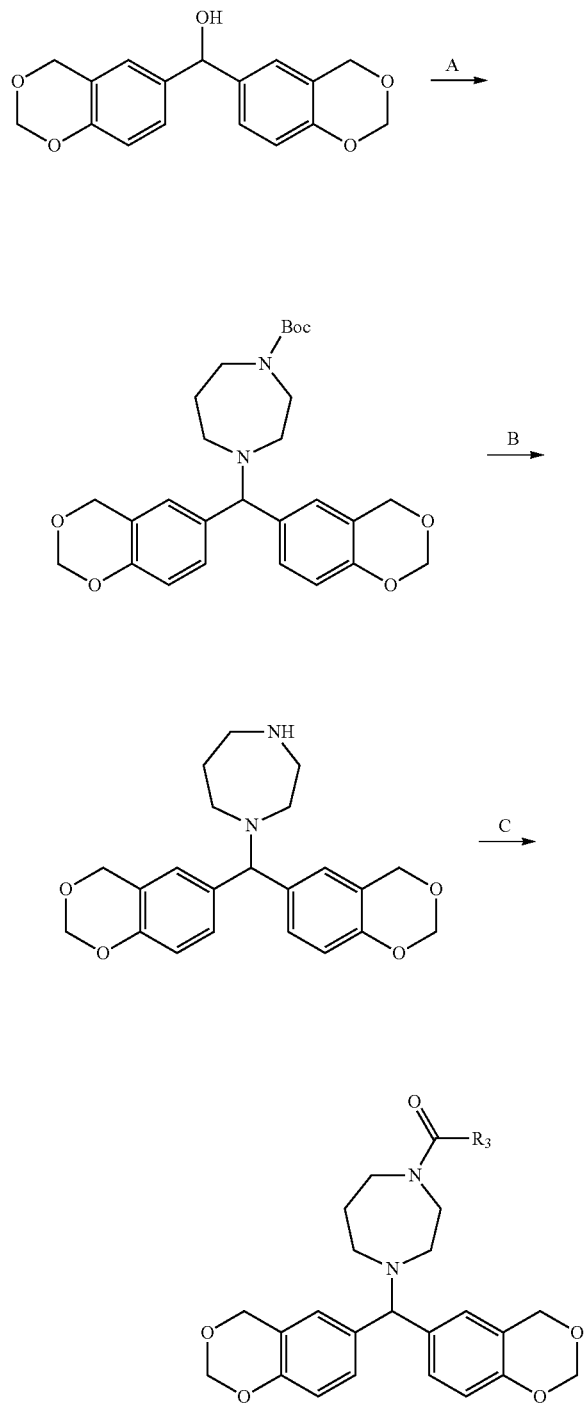

Reagents and conditions: A) i) SOCl₂, DCM, 0° C. to rt, 3 h; ii) 1-Boc-homopiperazine, Cs₂CO₃, DMF, 80° C., 15 h; B) TMSI, NMM, DCM, rt, 50 min; C) i) Triphosgene, DCM, 0° C.; ii) 1-(Bis(4H-benzo[d][1,3]dioxin-6-yl)methyl)-1,4-diazepane, Et₃N, DCM, 0° C. to rt, 2 h; iii) R₃—H, DMAP, THF, rt, 20 h.

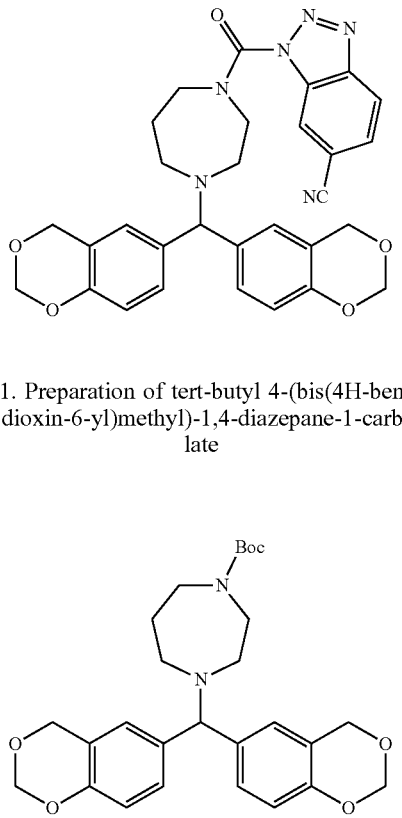

Step 1. Preparation of tert-butyl 4-(bis(4H-benzo[d][1,3]dioxin-6-yl)methyl)-1,4-diazepane-1-carboxylate A solution of bis(4H-benzo[d][1,3]dioxin-6-yl)methanol (797 mg, 2.65 mmol) in anhydrous dichloromethane (6.6 mL) was cooled to 0° C. under nitrogen atmosphere and thionyl chloride (0.39 mL, 5.3 mmol) was added dropwise. The solution was stirred at 0° C. for 10 minutes then at ambient temperature for 3 hours. The solution was concentrated in vacuo followed by azeotropic removal of thionyl chloride with dichloromethane (2×10 mL). The residue was dissolved in anhydrous N,N-dimethylformamide (4.4 mL) and cesium carbonate (1.73 g, 5.31 mmol) was added followed by a solution of tert-butyl 1,4-diazepane-1-carboxylate (638 mg, 3.19 mmol) in anhydrous N,N-dimethylformamide (4.4 mL). The mixture was heated to 80° C. under nitrogen atmosphere for 15 hours then allowed to cool to ambient temperature. The residue was partitioned between ethyl acetate (40 mL) and water (20 mL), and the organic layer was washed with brine (5×20 mL) then dried over anhydrous sodium sulfate, filtered and concentrated in vacuo. The residue was semi-purified by column chromatography, eluting with 0% to 7% ethyl acetate in dichloromethane to provide a colourless foam (976 mg). Analysis by ¹H NMR (400 MHz, CDCl₃) indicated that the mixture contained a 5:2 ratio of the title compound and bis(4H-benzo[d][1,3]dioxin-6-yl)methanol, respectively.

¹H NMR (400 MHz, CDCl₃) δ 7.17 (m, 2H), 6.93 (br s, 2H), 6.79 (d, J=8.5 Hz, 2H), 5.21 (s, 4H), 4.86 (s, 4H), 4.42 (s, 0.5H), 4.40 (s, 0.5H), 3.50-3.35 (m, 4H), 2.56 (m, 4H), 1.70 (m, 2H), 1.47 (s, 4.5H), 1.46 (s, 4.5H) (2 conformational isomers observed in a ratio of 1:1).

Step 2. Preparation of 1-(bis(4H-benzo[d][1,3]dioxin-6-yl)methyl)-1,4-diazepane

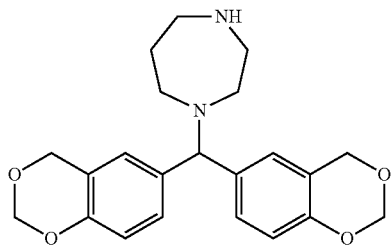

tert-Butyl 4-(bis(4H-benzo[d][1,3]dioxin-6-yl)methyl)-1,4-diazepane-1-carboxylate (972 mg, containing bis(4H-benzo[d][1,3]dioxin-6-yl)methanol as specified above) was dissolved in dichloromethane (20 mL) and stirred at ambient temperature while 4-methylmorpholine (0.89 mL, 8.1 mmol) was added followed by iodotrimethylsilane (0.72 mL, 5.1 mmol). The solution was stirred at ambient temperature for 50 minutes then washed with saturated aqueous sodium bicarbonate (20 mL) followed by 1N aqueous sodium thiosulfate (30 mL) and water (20 mL). The organic layer was dried over anhydrous sodium sulfate, filtered and concentrated in vacuo. Toluene (3×10 mL) was used for azeotropic removal of volatiles, and the residue was purified by column chromatography, eluting with 80% ethyl acetate (containing 10% triethylamine and 10% isopropanol) in dichloromethane to afford the title compound as a yellow foam (540 mg, 53% yield over 2 steps).

$^1$H NMR (400 MHz, CDCl$_3$) δ 7.19 (m, 2H), 6.96 (br s, 2H), 6.78 (d, J=8.3 Hz, 2H), 5.20 (s, 4H), 4.86 (s, 4H), 4.45 (s, 1H), 2.99 (m, 2H), 2.85 (m, 2H), 2.60 (m, 4H), 1.69 (m, 2H) (NH not observed).

Step 3. Preparation of 1-(4-(bis(4H-benzo[d][1,3]dioxin-6-yl)methyl)-1,4-diazepane-1-carbonyl)-1H-benzo[d][1,2,3]triazole-6-carbonitrile (Example-51)

General Procedure C

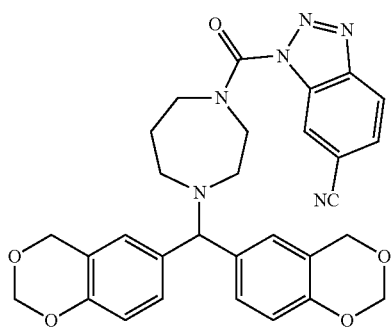 [SMILES: N#Cc1ccc2nnn(C(=O)N3CCCN(C(c4ccc5c(c4)COCO5)c4ccc5c(c4)COCO5)CC3)c2c1]

Triphosgene (70 mg, 0.24 mmol) was dissolved in anhydrous dichloromethane (0.7 mL), and the solution was cooled to 0° C. under nitrogen atmosphere. A solution of 1-(bis(4H-benzo[d][1,3]dioxin-6-yl)methyl)-1,4-diazepane (90 mg, 0.24 mmol) and triethylamine (0.03 mL, 0.2 mmol) in anhydrous dichloromethane (1.7 mL) was added dropwise. The reaction vessel was sealed, and the mixture was stirred at ambient temperature for 2 hours then concentrated in vacuo. Anhydrous tetrahydrofuran (2.4 mL) was added followed by 4-(dimethylamino)pyridine (29 mg, 0.24 mmol) and 1H-1,2,3-benzotriazole-5-carbonitrile (34 mg, 0.24 mmol). The mixture was sealed and stirred at ambient temperature for 20 hours. The mixture was concentrated in vacuo then purified by column chromatography, eluting with 30% to 40% ethyl acetate in hexanes to afford the title compound as a yellow foam (17 mg, 13% yield).

The structure of 1-(4-(bis(4H-benzo[d][1,3]dioxin-6-yl)methyl)-1,4-diazepane-1-carbonyl)-1H-benzo[d][1,2,3]triazole-6-carbonitrile was tentatively assigned.

$^1$H NMR (400 MHz, CDCl$_3$) δ 8.48 (s, 0.5H), 8.46 (s, 0.5H), 8.21 (d, J=8.5 Hz, 1H), 7.69 (d, J=8.6 Hz, 1H), 7.21 (d, J=7.9 Hz, 1H), 7.14 (d, J=8.1 Hz, 1H), 6.95 (br s, 1H), 6.88 (br s, 1H), 6.82 (d, J=8.3 Hz, 1H), 6.75 (d, J=8.5 Hz, 1H), 5.22 (s, 2H), 5.20 (s, 2H), 4.87 (s, 2H), 4.82 (s, 2H), 4.48 (s, 0.5H), 4.44 (s, 0.5H), 3.99-3.83 (m, 4H), 2.85 (m, 2H), 2.69 (m, 2H), 2.01 (m, 2H) (2 conformational isomers observed in a ratio of 1:1); MS (API-ES+) m/z 553.1 (M+1).

Scheme III: Synthesis of substituted (1-(bis(4H-benzo[d][1,3]dioxin-6-yl)methyl)piperidin-4-yl)methanone

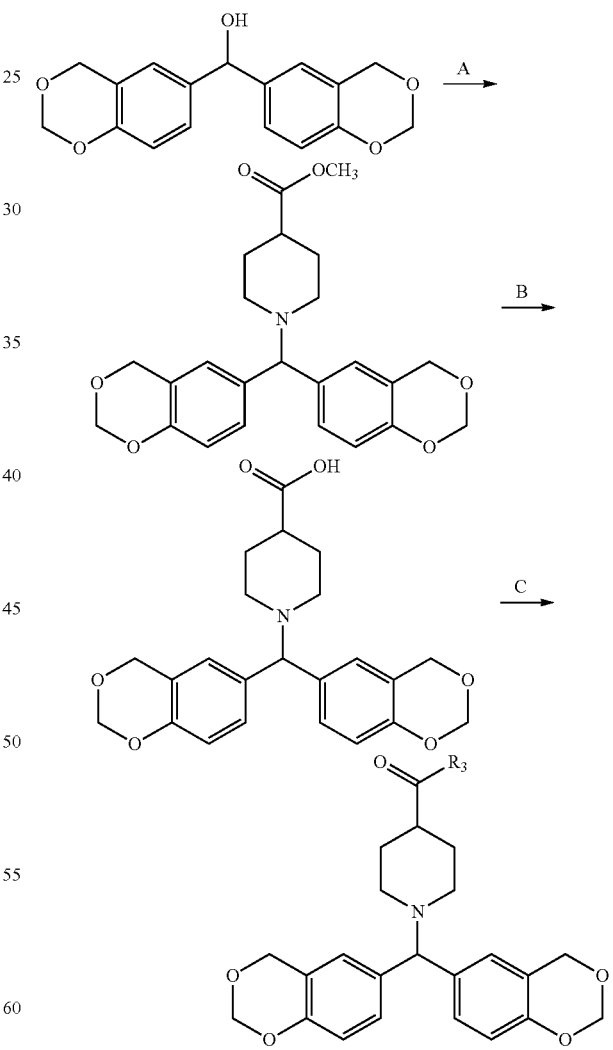

Reagents and conditions: A) i) SOCl$_2$, DCM, 0° C. to rt, 2.8 h; ii) Methyl isonipecotate, Cs$_2$CO$_3$, DMF, 75° C., 15 h; B) i) LiOH, THF/H$_2$O, 60° C., 17 h, ii) HCl (aq); C) Method A: i) R$_3$-H, SOCl$_2$, DCM, rt, 30 min, ii) 1-(Bis(4H-benzo[d][1,3]dioxin-6-yl)methyl)piperidine-4-carboxylic acid rt, 2 h; or Method B: R$_3$-H, DMAP, EDC, THF, rt, 3 h.

113

Synthesis of (1H-benzo[d][1,2,3]triazol-1-yl)(1-(bis(4H-benzo[d][1,3]dioxin-6-yl)methyl)piperidin-4-yl)methanone (Example-52)

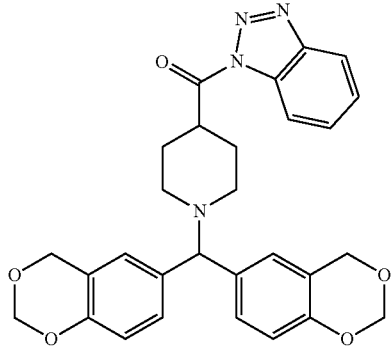 [SMILES: O=C(C1CCN(C(c2ccc3c(c2)COCO3)c2ccc3c(c2)COCO3)CC1)n1nnc2ccccc21]

Step 1. Preparation of methyl 1-(bis(4H-benzo[d][1,3]dioxin-6-yl)methyl)piperidine-4-carboxylate

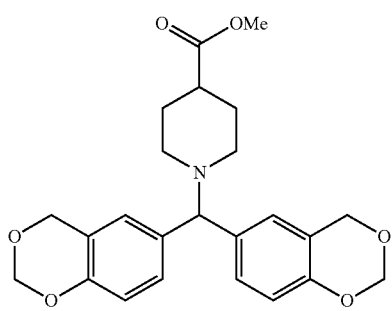

A solution of bis(4H-benzo[d][1,3]dioxin-6-yl)methanol (906 mg, 3.02 mmol) in anhydrous dichloromethane (7.5 mL) was cooled to 0° C. under nitrogen atmosphere and thionyl chloride (0.31 mL, 4.2 mmol) was added dropwise. The solution was stirred at 0° C. for 10 minutes then at ambient temperature for 2.8 hours. The solution was concentrated in vacuo followed by azeotropic removal of thionyl chloride with dichloromethane (2×20 mL). The residue was dissolved in anhydrous N,N-dimethylformamide (5 mL) and cesium carbonate (1.97 g, 6.05 mmol) was added followed by a solution of methyl isonipecotate (518 mg, 3.62 mmol) in anhydrous N,N-dimethylformamide (5 mL). The mixture was heated to 75° C. under nitrogen atmosphere for 15 hours then allowed to cool to ambient temperature. The residue was partitioned between ethyl acetate (40 mL) and water (30 mL), and the organic layer was washed with brine (5×20 mL) then dried over anhydrous sodium sulfate, filtered and concentrated in vacuo. The residue was semi-purified by column chromatography, eluting with 0% to 15% ethyl acetate in dichloromethane to provide a colourless foam (1.0 g). Analysis by $^1$H NMR (400 MHz, CDCl$_3$) indicated that the mixture contained a 2:1 ratio of the title compound and bis(4H-benzo[d][1,3]dioxin-6-yl)methanol, respectively.

$^1$H NMR (400 MHz, CDCl$_3$) δ 7.14 (m, 2H), 6.92 (br s, 2H), 6.78 (d, J=8.4 Hz, 2H), 5.20 (s, 4H), 4.86 (s, 4H), 4.07 (s, 1H), 3.67 (s, 3H), 2.81 (m, 2H), 2.28 (m, 1H), 1.89-1.73 (m, 6H).

114

Step 2. Preparation of (1H-benzo[d][1,2,3]triazol-1-yl)(1-(bis(4H-benzo[d][1,3]dioxin-6-yl)methyl)piperidin-4-yl)methanone (Example-52)

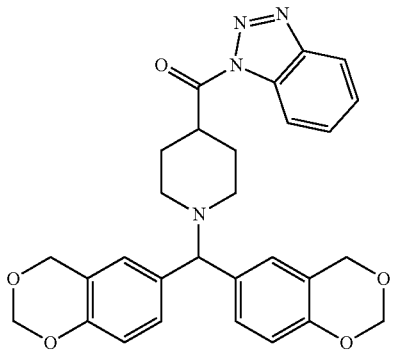 [SMILES: O=C(C1CCN(C(c2ccc3c(c2)COCO3)c2ccc3c(c2)COCO3)CC1)n1nnc2ccccc21]

A solution of methyl 1-(bis(4H-benzo[d][1,3]dioxin-6-yl)methyl)piperidine-4-carboxylate (1.0 g, containing bis(4H-benzo[d][1,3]dioxin-6-yl)methanol as specified above) was dissolved in tetrahydrofuran (47 mL) and stirred at ambient temperature while lithium hydroxide (301 mg, 12.6 mmol) was added followed by water (5.6 mL). The mixture was heated to 60° C. for 17 hours then concentrated in vacuo. The residue was diluted with water (10 mL) and cooled to 0° C. then adjusted to pH 2 using 1N hydrochloric acid. The mixture was extracted with 10% methanol in dichloromethane (4×25 mL) and dichloromethane (3×20 mL) then the combined organic extracts were dried over anhydrous sodium sulfate, filtered and concentrated in vacuo. The residue was dissolved in a minimum amount of 1% methanol in dichloromethane then allowed to stand at ambient temperature until crystals formed. The crystals were collected by filtration and rinsed with dichloromethane to provide 1-(bis(4H-benzo[d][1,3]dioxin-6-yl)methyl)piperidine-4-carboxylic acid as a colourless solid (548 mg) that was used in the next step without further purification.

General Procedure D

A solution of 1H-benzotriazole (98 mg, 0.82 mmol) in anhydrous dichloromethane (1.0 mL) was stirred at ambient temperature under nitrogen atmosphere while thionyl chloride (0.02 mL, 0.3 mmol) was added dropwise. The reaction vessel was sealed, and the mixture was stirred at ambient temperature for 30 minutes then 1-(bis(4H-benzo[d][1,3]dioxin-6-yl)methyl)piperidine-4-carboxylic acid was added. The mixture was sealed and stirred at ambient temperature for 2 hours then diluted with dichloromethane (40 mL) and washed with 1N aqueous sodium hydroxide (3×10 mL). The organic layer was dried over anhydrous sodium sulfate, filtered and concentrated in vacuo, and the residue was purified by column chromatography, eluting with 0% to 4% ethyl acetate in dichloromethane to afford the title compound as a colourless foam (60 mg, 25% yield over 3 steps).

$^1$H NMR (400 MHz, CDCl$_3$) δ 8.30 (d, J=8.3 Hz, 1H), 8.12 (d, J=8.3 Hz, 1H), 7.66 (m, 1H), 7.51 (m, 1H), 7.19 (m, 2H), 6.97 (br s, 2H), 6.81 (d, J=8.4 Hz, 2H), 5.22 (s, 4H), 4.88 (s, 4H), 4.18 (s, 1H), 3.88 (m, 1H), 3.00 (m, 2H), 2.05 (m, 6H); MS (API-ES+) m/z 513.2 (M+1).

Synthesis of 1,1,1,3,3,3-hexafluoropropan-2-yl 1-(bis(4H-benzo[d][1,3]dioxin-6-yl)methyl)piperidine-4-carboxylate (Example-53)

General Procedure E

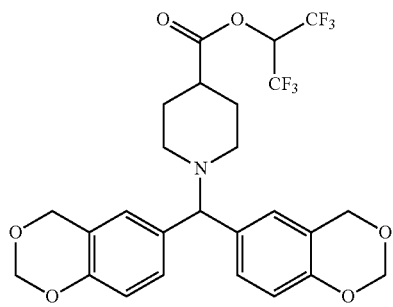 [SMILES: O=C(OC(C(F)(F)F)C(F)(F)F)C1CCN(C(c2ccc3c(c2)COCO3)c2ccc3c(c2)COCO3)CC1]

A suspension of 1-(bis(4H-benzo[d][1,3]dioxin-6-yl)methyl)piperidine-4-carboxylic acid (77 mg, 0.19 mmol) in anhydrous tetrahydrofuran (0.9 mL) was stirred at ambient temperature while 4-(dimethylamino)pyridine (32 mg, 0.26 mmol) was added followed by 1,1,1,3,3,3-hexafluoro-2-propanol (0.06 mL, 0.6 mmol) and N-(3-dimethylaminopropyl)-N'-ethylcarbodiimide hydrochloride (65 mg, 0.34 mmol). The reaction vessel was sealed, and the mixture was stirred at ambient temperature for 3 hours then concentrated in vacuo. The residue was purified by column chromatography, eluting with 0% to 1% ethyl acetate in dichloromethane to afford the title compound as a colourless foam (69 mg, 66% yield).

$^1$H NMR (400 MHz, CDCl$_3$) δ 7.15 (m, 2H), 6.92 (br s, 2H), 6.79 (d, J=8.4 Hz, 2H), 5.76 (hept, J=6.0 Hz, 1H), 5.21 (s, 4H), 4.86 (s, 4H), 4.08 (s, 1H), 2.83 (m, 2H), 2.51 (m, 1H), 1.95-1.77 (m, 6H); MS (API-ES+) m/z 562.1 (M+1).

Synthesis of pentafluorophenyl 1-(bis(4H-benzo[d][1,3]dioxin-6-yl)methyl)piperidine-4-carboxylate (Example-54)

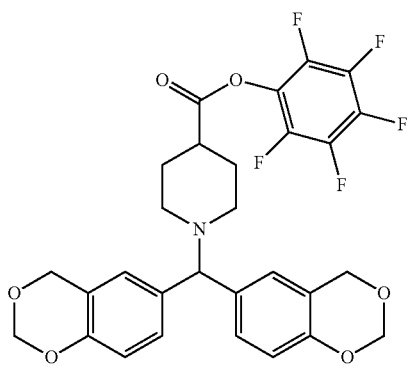

Following General Procedure E and making non-critical variations as required to replace 1,1,1,3,3,3-hexafluoro-2-propanol with pentafluorophenol, the title compound was obtained as a colourless foam (33 mg, 33% yield).

$^1$H NMR (400 MHz, CDCl$_3$) δ 7.17 (m, 2H), 6.94 (br s, 2H), 6.80 (d, J=8.4 Hz, 2H), 5.21 (s, 4H), 4.87 (s, 4H), 4.10 (s, 1H), 2.86 (m, 2H), 2.69 (m, 1H), 2.04-1.87 (m, 6H); $^{19}$F NMR (376 MHz, CDCl$_3$) δ −153.12 (m, 2F), 158.11 (t, J=21.7 Hz, 1F), −162.35 (m, 2F); MS (API-ES+) m/z 578.1 (M+1).

Scheme IV: Synthesis of substituted 2-(bis(4H-benzo[d][1,3]dioxin-6-yl)methoxy)-N-methylethan-1-amine

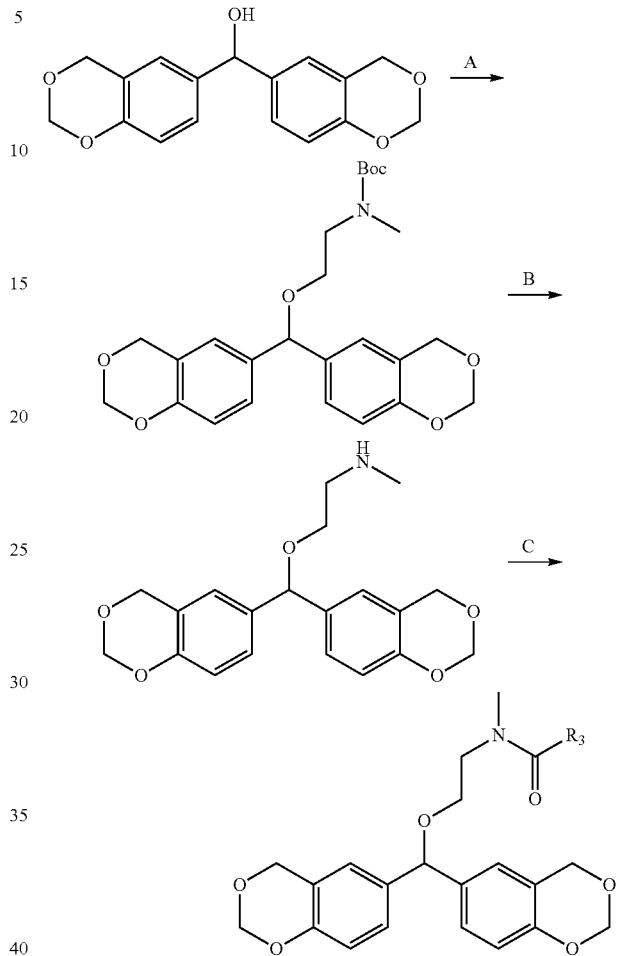

Reagents and conditions: A) i) SOCl$_2$, DCM, 0° C. to rt, 3.5 h; ii) HOCH$_2$CH$_2$N(CH$_3$)Boc, Cs$_2$CO$_3$, DMF, 80° C., 17 h; B) TMSI, NMM, DCM, rt, 1 h; C) i) Triphosgene, DCM, 0° C.; ii) 2-(Bis(4H-benzo[d][1,3]dioxin-6-yl)methoxy)-N-methylethan-1-amine, Et$_3$N, DCM, 0° C. to rt, 2 h; iii) R$_3$-H, DMAP, THF, rt.

Synthesis of N-(2-(bis(4H-benzo[d][1,3]dioxin-6-yl)methoxy)ethyl)-6-cyano-N-methyl-1H-benzo[d][1,2,3]triazole-1-carboxamide (Example-55)

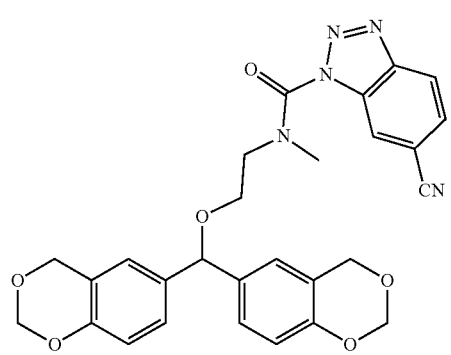 [SMILES: CN(CCOC(c1ccc2c(c1)COCO2)c1ccc2c(c1)COCO2)C(=O)n1nnc2ccc(C#N)cc21]

Step 1. Preparation of tert-butyl (2-(bis(4H-benzo[d][1,3]dioxin-6-yl)methoxy)ethyl)(methyl)carbamate

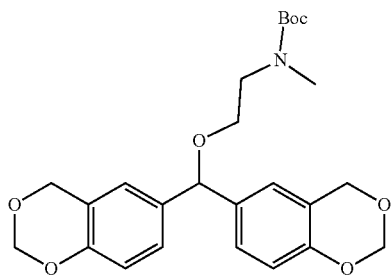 [SMILES: CN(CCOC(c1ccc2c(c1)COCO2)c1ccc2c(c1)COCO2)C(=O)OC(C)(C)C]

A solution of bis(4H-benzo[d][1,3]dioxin-6-yl)methanol (526 mg, 1.75 mmol) in anhydrous dichloromethane (6 mL) was cooled to 0° C. under nitrogen atmosphere and thionyl chloride (0.26 mL, 3.6 mmol) was added dropwise. The solution was stirred at 0° C. for 20 minutes then the reaction vessel was sealed, and the solution was stirred at ambient temperature for 3.5 hours. The solution was concentrated in vacuo followed by azeotropic removal of thionyl chloride with dichloromethane (2×10 mL). The residue was dissolved in anhydrous N,N-dimethylformamide (6 mL) and cesium carbonate (1.14 g, 3.50 mmol) was added followed by tert-butyl N-(2-hydroxyethyl)-N-methylcarbamate (460 mg, 2.63 mmol). The mixture was heated to 80° C. under nitrogen atmosphere for 17 hours then allowed to cool to ambient temperature. The residue was partitioned between ethyl acetate (35 mL) and water (10 mL), and the organic layer was washed with brine (5×12 mL) then dried over anhydrous sodium sulfate, filtered and concentrated in vacuo. The residue was semi-purified by column chromatography, eluting with 5% ethyl acetate in dichloromethane to provide a colourless oil (512 mg). Analysis by $^1$H NMR (400 MHz, CDCl$_3$) indicated that the mixture contained a 5:1 ratio of the title compound and bis(4H-benzo[d][1,3]dioxin-6-yl)methanol, respectively.

$^1$H NMR (400 MHz, CDCl$_3$) δ 7.08 (d, J=8.2 Hz, 2H), 6.88 (br s, 2H), 6.82 (d, J=8.5 Hz, 2H), 5.23 (s, 1H), 5.22 (s, 4H), 4.87 (s, 4H), 3.45 (m, 4H), 2.92 (s, 3H), 1.45 (s, 4.5H), 1.38 (s, 4.5H) (2 conformational isomers observed in a ratio of 1:1).

Step 2. Preparation of 2-(bis(4H-benzo[d][1,3]dioxin-6-yl)methoxy)-N-methylethan-1-amine

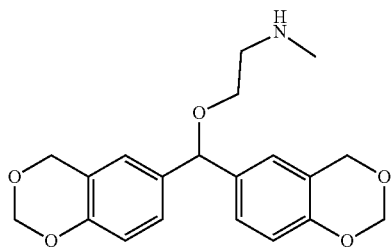 [SMILES: CNCCOC(c1ccc2c(c1)COCO2)c1ccc2c(c1)COCO2]

tert-Butyl (2-(bis(4H-benzo[d][1,3]dioxin-6-yl)methoxy)ethyl)(methyl)carbamate (506 mg, containing bis(4H-benzo[d][1,3]dioxin-6-yl)methanol as specified above) was dissolved in dichloromethane (11 mL) and stirred at ambient temperature while 4-methylmorpholine (0.49 mL, 4.5 mmol) was added followed by iodotrimethylsilane (0.39 mL, 2.7 mmol). The solution was stirred at ambient temperature for 1 hour then washed with saturated aqueous sodium bicarbonate (15 mL) followed by 1N aqueous sodium thiosulfate (30 mL) and water (20 mL). The organic layer was dried over anhydrous sodium sulfate, filtered and concentrated in vacuo. Toluene (2×10 mL) was used for azeotropic removal of volatiles, and the residue was purified by column chromatography, eluting with 0% to 10% ethyl acetate in dichloromethane then 20% methanol in dichloromethane to afford the title compound as a yellow oil (304 mg, 49% yield over 2 steps).

$^1$H NMR (400 MHz, CDCl$_3$) δ 7.09 (m, 2H), 6.93 (br s, 2H), 6.82 (d, J=8.4 Hz, 2H), 5.22 (s, 4H), 5.21 (s, 1H), 4.88 (s, 4H), 3.57 (t, J=5.1 Hz, 2H), 2.85 (t, J=5.2 Hz, 2H), 2.48 (s, 3H) (NH not observed).

Step 3. Preparation of N-(2-(bis(4H-benzo[d][1,3]dioxin-6-yl)methoxy)ethyl)-6-cyano-N-methyl-1H-benzo[d][1,2,3]triazole-1-carboxamide (Example-55)

General Procedure F

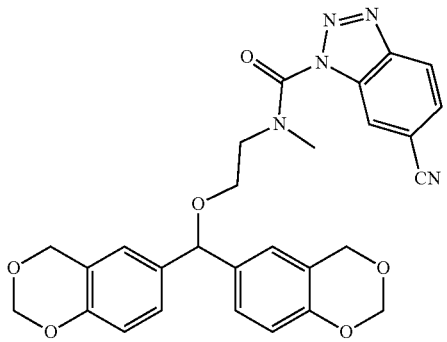 [SMILES: CN(CCOC(c1ccc2c(c1)COCO2)c1ccc2c(c1)COCO2)C(=O)n1nnc2ccc(C#N)cc21]

Triphosgene (74 mg, 0.25 mmol) was dissolved in anhydrous dichloromethane (0.7 mL), and the solution was cooled to 0° C. under nitrogen atmosphere. A solution of 2-(bis(4H-benzo[d][1,3]dioxin-6-yl)methoxy)-N-methylethan-1-amine (89 mg, 0.25 mmol) and triethylamine (0.03 mL, 0.2 mmol) in anhydrous dichloromethane (1.8 mL) was added dropwise. The reaction vessel was sealed, and the mixture was stirred at ambient temperature for 2 hours then concentrated in vacuo. Anhydrous tetrahydrofuran (2.5 mL) was added followed by 4-(dimethylamino)pyridine (30 mg, 0.25 mmol) and 1H-1,2,3-benzotriazole-5-carbonitrile (36 mg, 0.25 mmol). The mixture was sealed and stirred at ambient temperature for 3 days. The mixture was concentrated in vacuo then purified by column chromatography, eluting with 30% to 40% ethyl acetate in hexanes to afford the title compound as a colourless foam (21 mg, 16% yield).

The structure of N-(2-(bis(4H-benzo[d][1,3]dioxin-6-yl)methoxy)ethyl)-6-cyano-N-methyl-1H-benzo[d][1,2,3]triazole-1-carboxamide was tentatively assigned.

$^1$H NMR (400 MHz, CDCl$_3$) δ 8.25 (br s, 1H), 8.18 (d, J=8.6 Hz, 1H), 7.66 (d, J=8.6 Hz, 1H), 6.95-6.74 (m, 6H), 5.22 (s, 4H), 5.16 (br s, 1H), 4.82 (s, 4H), 4.02 (m, 2H), 3.71 (m, 2H), 3.37 (br s, 3H); MS (API-ES+) m/z 528.1 (M+1).

Scheme V: Synthesis of substituted (4-(bis(4H-benzo[d][1,3]dioxin-6-yl)methoxy)piperidin-1-yl)methanone

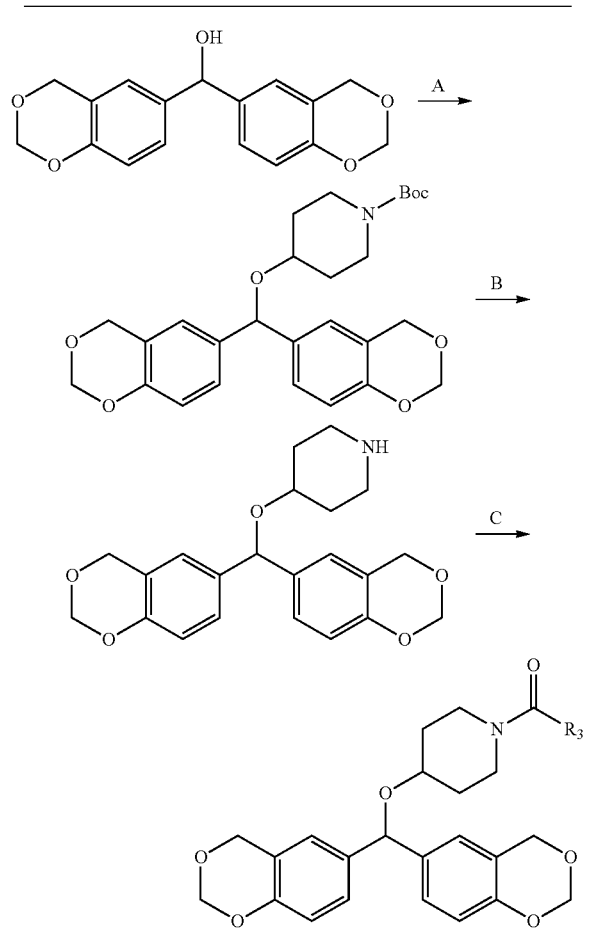

Reagents and conditions: A) i) SOCl₂, DCM, 0° C. to rt, 3 h; ii) tert-Butyl 4-hydroxypiperidine-1-carboxylate, Cs₂CO₃, DMF, 80° C., 17 h; B) TMSI, NMM, DCM, rt, 1 h; C) i) Triphosgene, DCM, 0° C.; ii) 4-(Bis(4H-benzo[d][1,3]dioxin-6-yl)methoxy)piperidine, Et₃N, DCM, 0° C. to rt, 1.5 h; iii) R₃-H, DMAP, THF, rt.

Synthesis of 1-(4-(bis(4H-benzo[d][1,3]dioxin-6-yl)methoxy)piperidine-1-carbonyl)-1H-benzo[d][1,2,3]triazole-6-carbonitrile (Example-56) and 1-(4-(bis(4H-benzo[d][1,3]dioxin-6-yl)methoxy)piperidine-1-carbonyl)-1H-benzo[d][1,2,3]triazole-5-carbonitrile (Example-57)

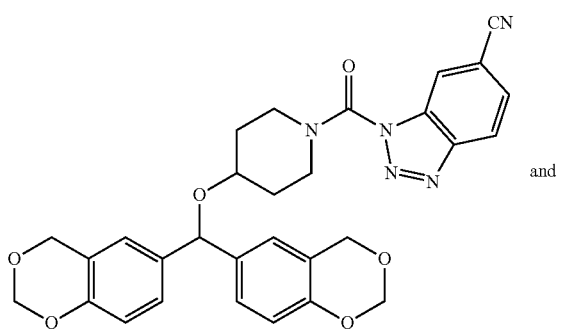

and

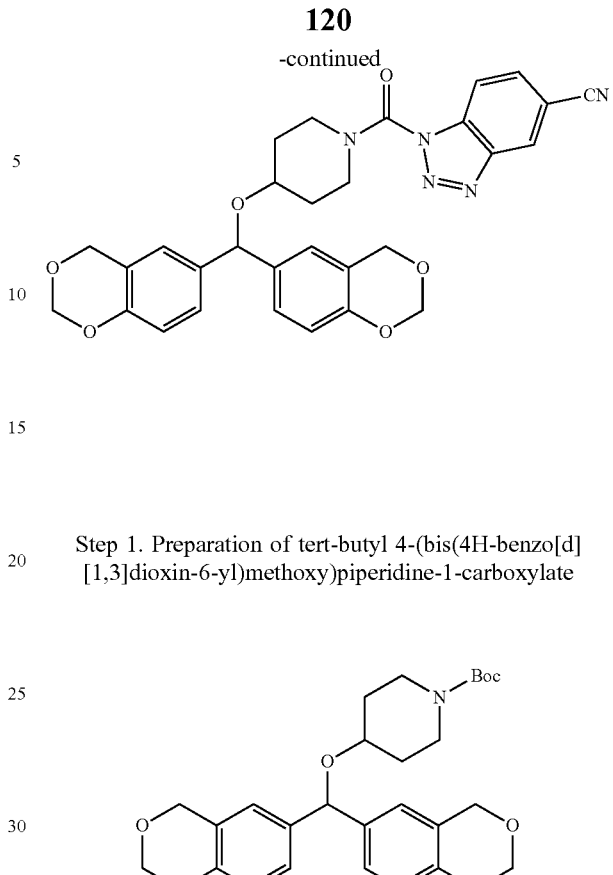

Step 1. Preparation of tert-butyl 4-(bis(4H-benzo[d][1,3]dioxin-6-yl)methoxy)piperidine-1-carboxylate A solution of bis(4H-benzo[d][1,3]dioxin-6-yl)methanol (513 mg, 1.71 mmol) in anhydrous dichloromethane (5.7 mL) was cooled to 0° C. under nitrogen atmosphere and thionyl chloride (0.25 mL, 3.4 mmol) was added dropwise. The solution was stirred at 0° C. for 20 minutes then the reaction vessel was sealed, and the solution was stirred at ambient temperature for 3 hours. The solution was concentrated in vacuo followed by azeotropic removal of thionyl chloride with dichloromethane (2×10 mL). The residue was dissolved in anhydrous N,N-dimethylformamide (5.7 mL) and cesium carbonate (1.11 g, 3.41 mmol) was added followed by tert-butyl 4-hydroxypiperidine-1-carboxylate (516 mg, 2.56 mmol). The mixture was heated to 80° C. under nitrogen atmosphere for 17 hours then allowed to cool to ambient temperature. The residue was partitioned between ethyl acetate (40 mL) and water (10 mL), and the organic layer was washed with brine (5×12 mL) then dried over anhydrous sodium sulfate, filtered and concentrated in vacuo. The residue was semi-purified by column chromatography, eluting with 7% ethyl acetate in dichloromethane to provide a colourless foam (406 mg). Analysis by $^1$H NMR (400 MHz, CDCl₃) indicated that the mixture contained a 10:1 ratio of the title compound and bis(4H-benzo[d][1,3]dioxin-6-yl)methanol, respectively.

$^1$H NMR (400 MHz, CDCl₃) δ 7.09 (m, 2H), 6.89 (br s, 2H), 6.82 (d, J=8.4 Hz, 2H), 5.36 (s, 1H), 5.23 (s, 4H), 4.87 (s, 4H), 3.75 (m, 2H), 3.52 (m, 1H), 3.08 (m, 2H), 1.79 (m, 2H), 1.58 (m, 2H), 1.45 (s, 9H).

Step 2. Preparation of 4-(bis(4H-benzo[d][1,3]di-oxin-6-yl)methoxy)piperidine

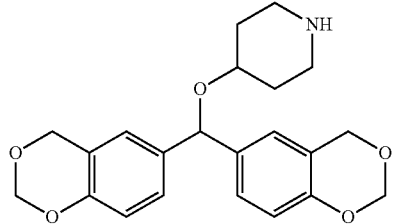 [SMILES: c1cc2c(cc1C(OC1CCNCC1)c1ccc3c(c1)COCO3)COCO2]

tert-Butyl 4-(bis(4H-benzo[d][1,3]dioxin-6-yl)methoxy)piperidine-1-carboxylate (403 mg, containing bis(4H-benzo[d][1,3]dioxin-6-yl)methanol as specified above) was dissolved in dichloromethane (8 mL) and stirred at ambient temperature while 4-methylmorpholine (0.37 mL, 3.4 mmol) was added followed by iodotrimethylsilane (0.30 mL, 2.1 mmol). The solution was stirred at ambient temperature for 1 hour then diluted with dichloromethane (40 mL) and washed with saturated aqueous sodium bicarbonate (15 mL) followed by 1N aqueous sodium thiosulfate (25 mL) and water (20 mL). The organic layer was dried over anhydrous sodium sulfate, filtered and concentrated in vacuo. The residue was purified by column chromatography, eluting with 10% ethyl acetate in dichloromethane then 20% methanol in dichloromethane to afford the title compound as a colourless oil (227 mg, 35% yield over 2 steps).

$^1$H NMR (400 MHz, CDCl$_3$) δ 7.09 (m, 2H), 6.89 (br s, 2H), 6.82 (d, J=8.5 Hz, 2H), 5.37 (s, 1H), 5.23 (s, 4H), 4.88 (s, 4H), 3.47 (m, 1H), 3.12 (m, 2H), 2.65 (m, 2H), 1.92 (m, 2H), 1.58 (m, 2H) (NH not observed).

Step 3. Preparation of 1-(4-(bis(4H-benzo[d][1,3]dioxin-6-yl)methoxy)piperidine-1-carbonyl)-1H-benzo[d][1,2,3]triazole-6-carbonitrile (Example-56) and 1-(4-(bis(4H-benzo[d][1,3]dioxin-6-yl)methoxy)piperidine-1-carbonyl)-1H-benzo[d][1,2,3]triazole-5-carbonitrile (Example-57)

General Procedure G

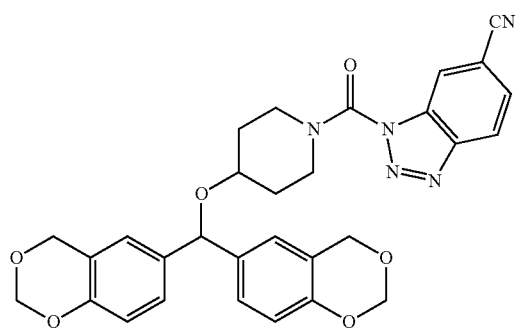

and

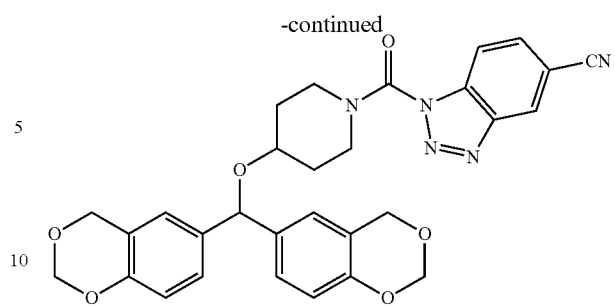

Triphosgene (58 mg, 0.20 mmol) was dissolved in anhydrous dichloromethane (0.5 mL), and the solution was cooled to 0° C. under nitrogen atmosphere. A solution of 4-(bis(4H-benzo[d][1,3]dioxin-6-yl)methoxy)piperidine (75 mg, 0.20 mmol) and triethylamine (0.03 mL, 0.2 mmol) in anhydrous dichloromethane (1.5 mL) was added dropwise. The reaction vessel was sealed, and the mixture was stirred at ambient temperature for 1.5 hours then concentrated in vacuo. Anhydrous tetrahydrofuran (2 mL) was added followed by 4-(dimethylamino)pyridine (24 mg, 0.20 mmol) and 1H-1,2,3-benzotriazole-5-carbonitrile (28 mg, 0.19 mmol). The mixture was sealed and stirred at ambient temperature for 3 days. The mixture was concentrated in vacuo then purified by column chromatography, eluting with 30% ethyl acetate in hexanes to afford the title compounds as a colourless foam (20 mg, 19% yield) and a colourless foam (27 mg, 25% yield), respectively.

The structure of 1-(4-(bis(4H-benzo[d][1,3]dioxin-6-yl)methoxy)piperidine-1-carbonyl)-1H-benzo[d][1,2,3]triazole-6-carbonitrile was tentatively assigned.

$^1$H NMR (400 MHz, CDCl$_3$) δ 8.40 (br s, 1H), 8.20 (d, J=8.6 Hz, 1H), 7.68 (m, 1H), 7.12 (m, 2H), 6.91 (br s, 2H), 6.85 (d, J=8.4 Hz, 2H), 5.40 (s, 1H), 5.24 (s, 4H), 4.89 (s, 4H), 4.05 (m, 2H), 3.80 (m, 3H), 2.00 (m, 2H), 1.93 (m, 2H); MS (API-ES+) m/z 554.1 (M+1).

The structure of 1-(4-(bis(4H-benzo[d][1,3]dioxin-6-yl)methoxy)piperidine-1-carbonyl)-1H-benzo[d][1,2,3]triazole-5-carbonitrile was tentatively assigned.

$^1$H NMR (400 MHz, CDCl$_3$) δ 8.48 (s, 1H), 8.10 (d, J=8.6 Hz, 1H), 7.81 (m, 1H), 7.12 (m, 2H), 6.91 (br s, 2H), 6.85 (d, J=8.4 Hz, 2H), 5.39 (s, 1H), 5.24 (s, 4H), 4.88 (s, 4H), 4.04 (m, 2H), 3.79 (m, 3H), 2.00 (m, 2H), 1.92 (m, 2H); MS (API-ES+) m/z 554.1 (M+1).

Scheme VI: Synthesis of substituted (3-(bis(4H-benzo[d][1,3]dioxin-6-yl)methoxy)azetidin-1-yl)methanone

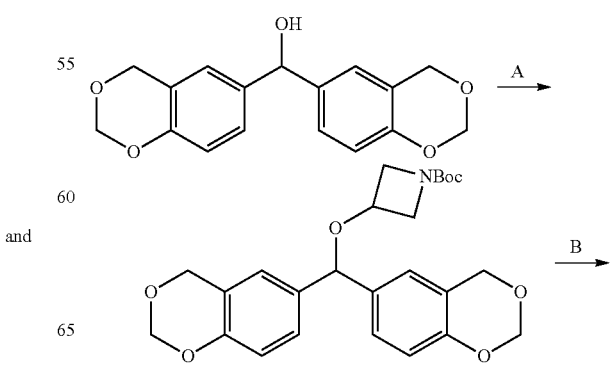

-continued

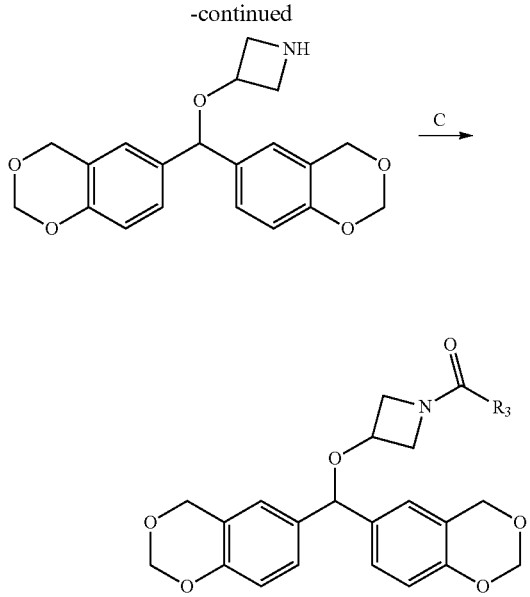

Reagents and conditions: A) i) SOCl₂, DCM, 0° C. to rt, 3 h; ii) tert-Butyl 3-hydroxyazetidine-1-carboxylate, Cs₂CO₃, DMF, 80° C., 20 h; B) TMSI, NMM, DCM, rt, 1 h; C) i) Triphosgene, DCM, 0° C.; ii) 3-(Bis(4H-benzo[d][1,3]dioxin-6-yl)methoxy)azetidine, Et₃N, DCM, 0° C. to rt, 3 h; iii) R₃-H, DMAP, THF, rt.

Synthesis of 1-(3-(bis(4H-benzo[d][1,3]dioxin-6-yl)methoxy)azetidine-1-carbonyl)-1H-benzo[d][1,2,3]triazole-6-carbonitrile and 1-(3-(bis(4H-benzo[d][1,3]dioxin-6-yl)methoxy)azetidine-1-carbonyl)-1H-benzo[d][1,2,3]triazole-5-carbonitrile (unassigned ratio of 1:1) (Example-58)

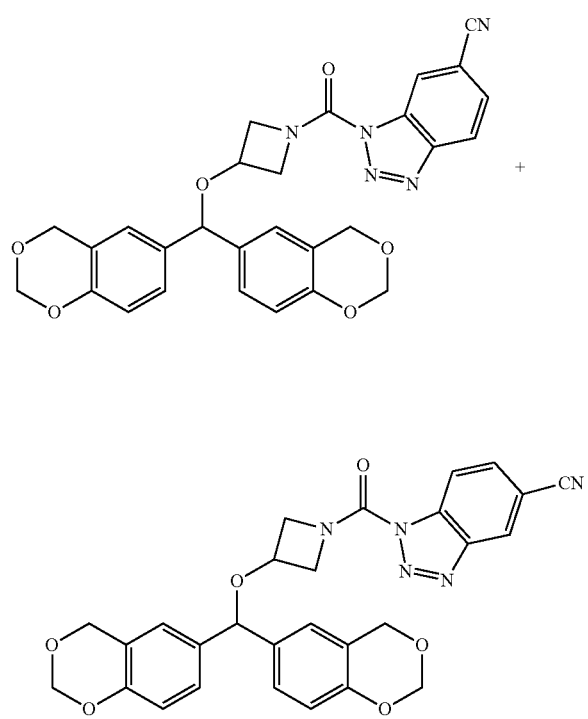

Step 1. Preparation of tert-butyl 3-(bis(4H-benzo[d][1,3]dioxin-6-yl)methoxy)azetidine-1-carboxylate

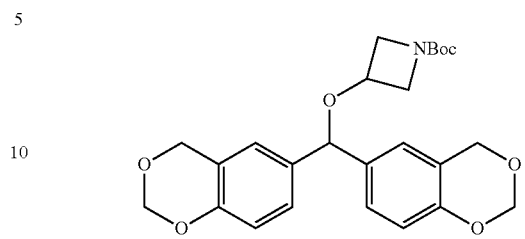

A solution of bis(4H-benzo[d][1,3]dioxin-6-yl)methanol (0.54 g, 1.8 mmol) in anhydrous dichloromethane (6 mL) was cooled to 0° C. under nitrogen atmosphere and thionyl chloride (0.26 mL, 3.6 mmol) was added dropwise. The solution was stirred at 0° C. for 20 minutes then the reaction vessel was sealed, and the solution was stirred at ambient temperature for 3 hours. The solution was concentrated in vacuo followed by azeotropic removal of thionyl chloride with dichloromethane (2×10 mL). The residue was dissolved in anhydrous N,N-dimethylformamide (6 mL) and cesium carbonate (1.17 g, 3.59 mmol) was added followed by tert-butyl 3-hydroxyazetidine-1-carboxylate (0.47 g, 2.7 mmol). The mixture was heated to 80° C. under nitrogen atmosphere for 20 hours then allowed to cool to ambient temperature. The residue was partitioned between ethyl acetate (30 mL) and water (10 mL), and the organic layer was washed with brine (5×10 mL) then dried over anhydrous sodium sulfate, filtered and concentrated in vacuo. The residue was semi-purified by column chromatography, eluting with 5% ethyl acetate in dichloromethane to provide a colourless foam (359 mg). Analysis by ¹H NMR (400 MHz, CDCl₃) indicated that the mixture contained a 5:3 ratio of the title compound and bis(4H-benzo[d][1,3]dioxin-6-yl)methanol, respectively.

¹H NMR (400 MHz, CDCl₃) δ 7.06 (m, 2H), 6.89 (br s, 2H), 6.83 (d, J=8.5 Hz, 2H), 5.23 (s, 4H), 5.16 (s, 1H), 4.88 (s, 4H), 4.26 (m, 1H), 3.97 (dd, J=9.3, 6.6 Hz, 2H), 3.84 (dd, J=9.4, 4.6 Hz, 2H), 1.42 (s, 9H).

Step 2. Preparation of 3-(bis(4H-benzo[d][1,3]dioxin-6-yl)methoxy)azetidine

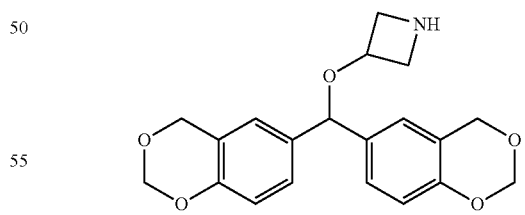

tert-Butyl 3-(bis(4H-benzo[d][1,3]dioxin-6-yl)methoxy)azetidine-1-carboxylate (355 mg, containing bis(4H-benzo[d][1,3]dioxin-6-yl)methanol as specified above) was dissolved in dichloromethane (7.8 mL) and stirred at ambient temperature while 4-methylmorpholine (0.34 mL, 3.1 mmol) was added followed by iodotrimethylsilane (0.28 mL, 2.0 mmol). The solution was stirred at ambient temperature for 55 minutes then diluted with dichloromethane (40 mL) and washed with saturated aqueous sodium bicarbonate (15 mL) followed by 1N aqueous sodium thiosulfate (20 mL) and water (2×20 mL). The organic layer was dried over anhydrous sodium sulfate, filtered and concentrated in vacuo. The residue was purified by column chromatography, eluting with 20% to 25% methanol in dichloromethane to afford the title compound as a pale solid (107 mg, 17% yield over 2 steps).

$^1$H NMR (400 MHz, CDCl$_3$) δ 7.03 (m, 2H), 7.01 (m, 2H), 6.87 (br s, 2H), 6.86 (br s, 2H), 6.82 (d, J=8.1 Hz, 2H), 6.81 (d, J=8.3 Hz, 2H), 5.23 (s, 4H), 5.22 (s, 4H), 5.17 (s, 1H), 5.14 (s, 1H), 4.87 (s, 4H), 4.86 (s, 4H), 4.51 (m, 1H), 4.20 (m, 1H), 3.91 (d, J=6.8 Hz, 4H), 3.55 (m, 2H), 3.25 (s, 2H), 3.05 (m, 2H) (2 conformational isomers observed in a ratio of 1:1).

Step 3. Preparation of 1-(3-(bis(4H-benzo[d][1,3]dioxin-6-yl)methoxy)azetidine-1-carbonyl)-1H-benzo[d][1,2,3]triazole-6-carbonitrile and 1-(3-(bis(4H-benzo[d][1,3]dioxin-6-yl)methoxy)azetidine-1-carbonyl)-1H-benzo[d][1,2,3]triazole-5-carbonitrile (unassigned ratio of 1:1) (Example-58)

General Procedure H

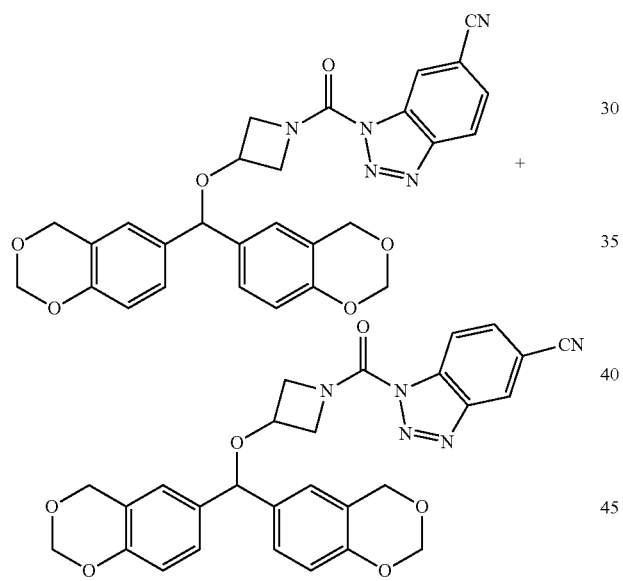

Triphosgene (86 mg, 0.29 mmol) was dissolved in anhydrous dichloromethane (0.9 mL), and the solution was cooled to 0° C. under nitrogen atmosphere. A solution of 3-(bis(4H-benzo[d][1,3]dioxin-6-yl)methoxy)azetidine (103 mg, 0.290 mmol) and triethylamine (0.04 mL, 0.3 mmol) in anhydrous dichloromethane (2 mL) was added dropwise. The reaction vessel was sealed, and the mixture was stirred at ambient temperature for 3 hours then concentrated in vacuo.

Anhydrous tetrahydrofuran (2.9 mL) was added followed by 4-(dimethylamino)pyridine (35 mg, 0.29 mmol) and 1H-1,2,3-benzotriazole-5-carbonitrile (42 mg, 0.29 mmol). The mixture was sealed and stirred at ambient temperature for 19 hours. The mixture was concentrated in vacuo then purified by column chromatography, eluting with 30% ethyl acetate in hexanes to afford the title compounds as a mixture in an unassigned ratio of 1:1 as a colourless foam (95 mg, 63% yield).

$^1$H NMR (400 MHz, CDCl$_3$) δ 8.66 (s, 1H), 8.47 (s, 1H), 8.38 (d, J=8.7 Hz, 1H), 8.20 (d, J=8.6 Hz, 1H), 7.82 (d, J=8.7 Hz, 1H), 7.69 (d, J=8.6 Hz, 1H), 7.10 (d, J=8.5 Hz, 4H), 6.92 (br s, 4H), 6.86 (d, J=8.5 Hz, 4H), 5.27 (s, 2H), 5.24 (s, 8H), 4.92 (m, 2H), 4.89 (s, 8H), 4.72 (m, 2H), 4.51 (m, 2H), 4.41 (m, 2H), 4.24 (m, 2H); MS (API-ES+) m/z 526.1 (M+1).

Scheme VII: Synthesis of substituted (6-(bis(4H-benzo[d][1,3]dioxin-6-yl)methoxy)-2-azaspiro[3.3]heptan-2-yl)methanone

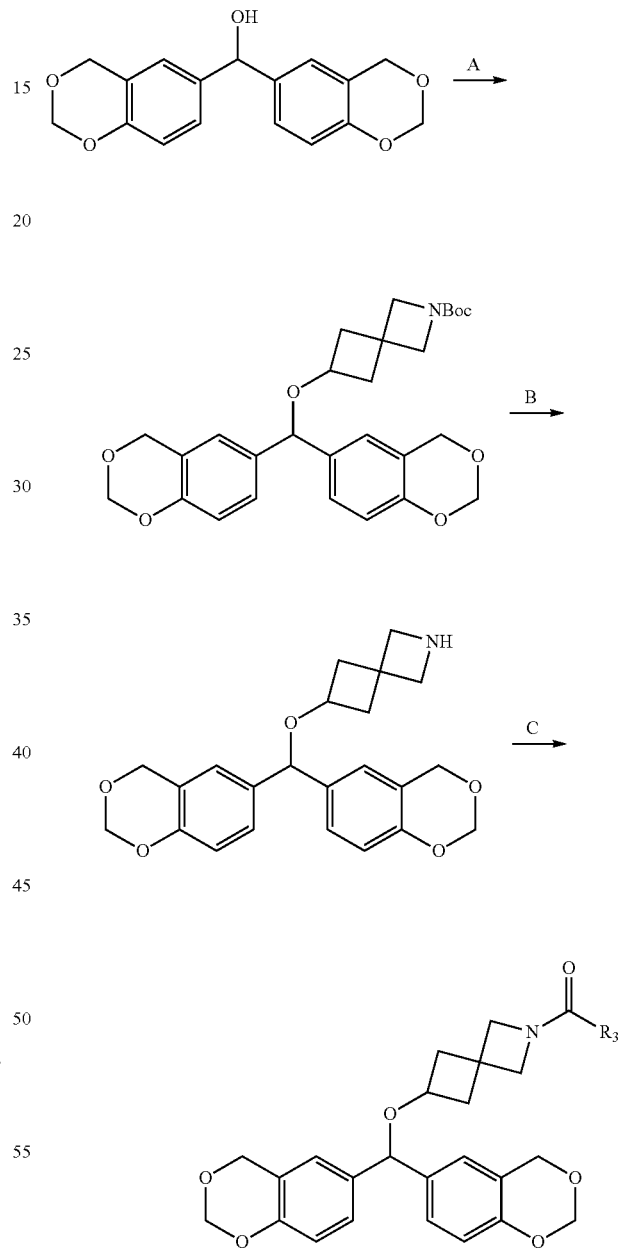

Reagents and conditions: A) i) SOCl$_2$, DCM, 0° C. to rt, 3 h; ii) tert-Butyl 6-hydroxy-2-azaspiro[3.3]heptane-2-carboxylate, Cs$_2$CO$_3$, DMF, 80° C., 15 h; B) TMSI, NMM, DCM, rt, 1 h; C) i) Triphosgene, DCM, 0° C.; ii) 6-(Bis(4H-benzo[d][1,3]dioxin-6-yl)methoxy)-2-azaspiro[3.3]heptane, Et$_3$N, DCM, 0° C. to rt, 2 h; iii) R$_3$-H, DMAP, THF, rt.

Synthesis of 1-(6-(bis(4H-benzo[d][1,3]dioxin-6-yl)methoxy)-2-azaspiro[3.3]heptane-2-carbonyl)-1H-benzo[d][1,2,3]triazole-6-carbonitrile (Example-59) and 1-(6-(bis(4H-benzo[d][1,3]dioxin-6-yl)methoxy)-2-azaspiro[3.3]heptane-2-carbonyl)-1H-benzo[d][1,2,3]triazole-5-carbonitrile (Example-60)

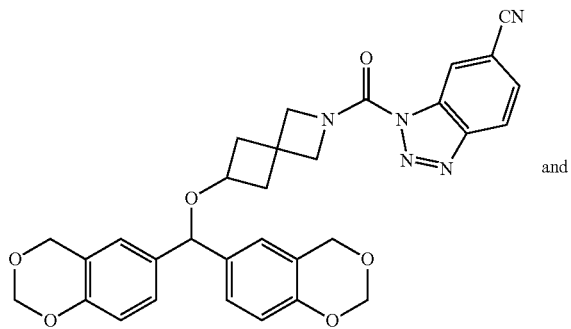

and

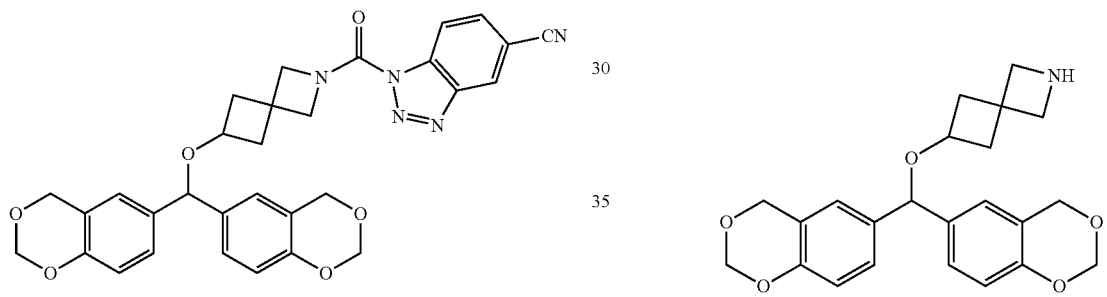

Step 1. Preparation of tert-butyl 6-(bis(4H-benzo[d][1,3]dioxin-6-yl)methoxy)-2-azaspiro[3.3]heptane-2-carboxylate A solution of bis(4H-benzo[d][1,3]dioxin-6-yl)methanol (520 mg, 1.73 mmol) in anhydrous dichloromethane (6 mL) was cooled to 0° C. under nitrogen atmosphere and thionyl chloride (0.25 mL, 3.4 mmol) was added dropwise. The solution was stirred at 0° C. for 35 minutes then the reaction vessel was sealed, and the solution was stirred at ambient temperature for 3 hours. The solution was concentrated in vacuo followed by azeotropic removal of thionyl chloride with dichloromethane (2×10 mL). The residue was dissolved in anhydrous N,N-dimethylformamide (6 mL) and cesium carbonate (1.13 g, 3.47 mmol) was added followed by tert-butyl 6-hydroxy-2-azaspiro[3.3]heptane-2-carboxylate (554 mg, 2.60 mmol). The mixture was heated to 80° C. under nitrogen atmosphere for 15 hours then allowed to cool to ambient temperature. The residue was partitioned between ethyl acetate (40 mL) and water (10 mL), and the organic layer was washed with brine (5×12 mL) then dried over anhydrous sodium sulfate, filtered and concentrated in vacuo. The residue was semi-purified by column chromatography, eluting with 5% ethyl acetate in dichloromethane to provide a colourless foam (545 mg). Analysis by $^1$H NMR (400 MHz, CDCl$_3$) indicated that the mixture contained a 5:2 ratio of the title compound and bis(4H-benzo[d][1,3]dioxin-6-yl)methanol, respectively.

$^1$H NMR (400 MHz, CDCl$_3$) δ 7.05 (m, 2H), 6.87 (br s, 2H), 6.82 (d, J=8.7 Hz, 2H), 5.22 (s, 4H), 5.13 (s, 1H), 4.87 (s, 4H), 3.84 (m, 1H), 3.83 (d, J=8.5 Hz, 4H), 2.39 (m, 2H), 2.15 (m, 2H), 1.41 (s, 9H).

Step 2. Preparation of 6-(bis(4H-benzo[d][1,3]dioxin-6-yl)methoxy)-2-azaspiro[3.3]heptane

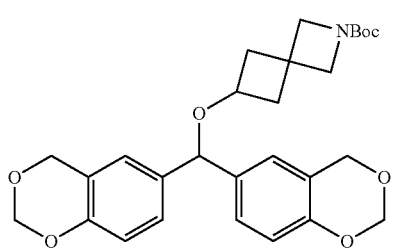 [SMILES: CC(C)(C)OC(=O)N1CC2(CC(OC(c3ccc4c(c3)COCO4)c3ccc4c(c3)COCO4)C2)C1]

tert-Butyl 6-(bis(4H-benzo[d][1,3]dioxin-6-yl)methoxy)-2-azaspiro[3.3]heptane-2-carboxylate (541 mg, containing bis(4H-benzo[d][1,3]dioxin-6-yl)methanol as specified above) was dissolved in dichloromethane (11 mL) and stirred at ambient temperature while 4-methylmorpholine (0.48 mL, 4.4 mmol) was added followed by iodotrimethylsilane (0.39 mL, 2.7 mmol). The solution was stirred at ambient temperature for 1 hour then diluted with dichloromethane (40 mL) and washed with saturated aqueous sodium bicarbonate (20 mL) followed by 1N aqueous sodium thiosulfate (20 mL) and water (2×20 mL). The organic layer was dried over anhydrous sodium sulfate, filtered and concentrated in vacuo. The residue was purified by column chromatography, eluting with 5% to 10% methanol (containing 10% aqueous ammonium hydroxide) in dichloromethane to afford the title compound as a colourless foam (241 mg, 35% yield over 2 steps).

$^1$H NMR (400 MHz, CDCl$_3$) δ 7.05 (m, 2H), 6.86 (br s, 2H), 6.81 (d, J=8.5 Hz, 2H), 5.22 (s, 4H), 5.13 (s, 1H), 4.87 (s, 4H), 3.82 (m, 1H), 3.65 (d, J=8.3 Hz, 4H), 2.44 (m, 2H), 2.12 (m, 2H) (NH not observed).

Step 3. Preparation of 1-(6-(bis(4H-benzo[d][1,3]dioxin-6-yl)methoxy)-2-azaspiro[3.3]heptane-2-carbonyl)-1H-benzo[d][1,2,3]triazole-6-carbonitrile (Example-59) and 1-(6-(bis(4H-benzo[d][1,3]dioxin-6-yl)methoxy)-2-azaspiro[3.3]heptane-2-carbonyl)-1H-benzo[d][1,2,3]triazole-5-carbonitrile (Example-60)

General Procedure I

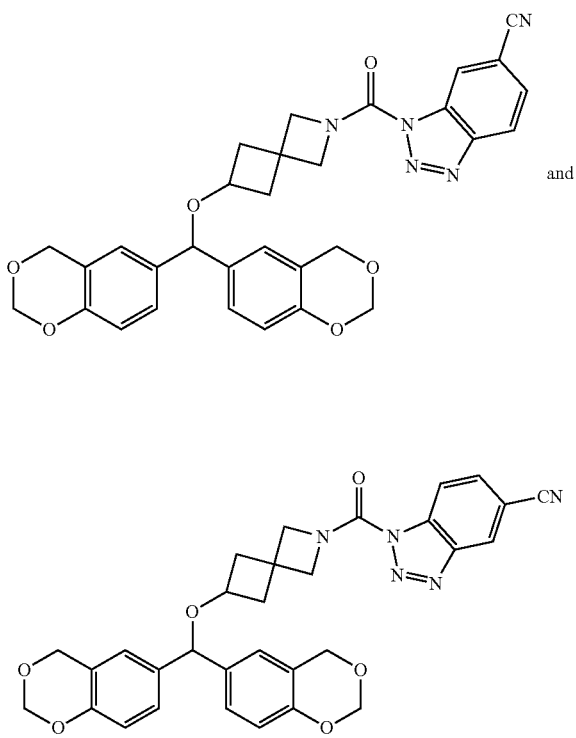

and

Triphosgene (60 mg, 0.20 mmol) was dissolved in anhydrous dichloromethane (0.5 mL), and the solution was cooled to 0° C. under nitrogen atmosphere. A solution of 6-(bis(4H-benzo[d][1,3]dioxin-6-yl)methoxy)-2-azaspiro[3.3]heptane (80 mg, 0.20 mmol) and triethylamine (0.03 mL, 0.2 mmol) in anhydrous dichloromethane (1.5 mL) was added dropwise. The reaction vessel was sealed, and the mixture was stirred at ambient temperature for 2 hours then concentrated in vacuo. Anhydrous tetrahydrofuran (2 mL) was added followed by 4-(dimethylamino)pyridine (25 mg, 0.20 mmol) and 1H-1,2,3-benzotriazole-5-carbonitrile (29 mg, 0.20 mmol). The mixture was sealed and stirred at ambient temperature for 21 hours. The mixture was concentrated in vacuo then purified by column chromatography, eluting with 30% ethyl acetate in hexanes to afford the title compounds as a colourless foam (13 mg, 11% yield) and a colourless foam (24 mg, 21% yield), respectively.

The structure of 1-(6-(bis(4H-benzo[d][1,3]dioxin-6-yl)methoxy)-2-azaspiro[3.3]heptane-2-carbonyl)-1H-benzo[d][1,2,3]triazole-6-carbonitrile was tentatively assigned.

$^1$H NMR (400 MHz, CDCl$_3$) δ 8.66 (s, 1H), 8.19 (m, 1H), 7.68 (d, J=8.6 Hz, 1H), 7.07 (m, 2H), 6.89 (br s, 2H), 6.84 (d, J=8.4 Hz, 2H), 5.23 (s, 4H), 5.17 (s, 1H), 4.88 (s, 4H), 4.73 (d, J=6.1 Hz, 2H), 4.27 (d, J=10.6 Hz, 2H), 3.95 (m, 1H), 2.53 (m, 2H), 2.30 (m, 2H); MS (API-ES+) m/z 566.1 (M+1).

The structure of 1-(6-(bis(4H-benzo[d][1,3]dioxin-6-yl)methoxy)-2-azaspiro[3.3]heptane-2-carbonyl)-1H-benzo[d][1,2,3]triazole-5-carbonitrile was tentatively assigned.

$^1$H NMR (400 MHz, CDCl$_3$) δ 8.46 (m, 1H), 8.38 (m, 1H), 7.81 (d, J=8.6 Hz, 1H), 7.07 (m, 2H), 6.89 (br s, 2H), 6.84 (d, J=8.4 Hz, 2H), 5.23 (s, 4H), 5.17 (s, 1H), 4.88 (s, 4H), 4.73 (d, J=6.2 Hz, 2H), 4.27 (d, J=10.6 Hz, 2H), 3.95 (m, 1H), 2.52 (m, 2H), 2.30 (m, 2H); MS (API-ES+) m/z 566.1 (M+1).

Scheme VIII: Synthesis of substituted (4-(bis(4-fluorophenyl)amino)piperidin-1-yl)methanone

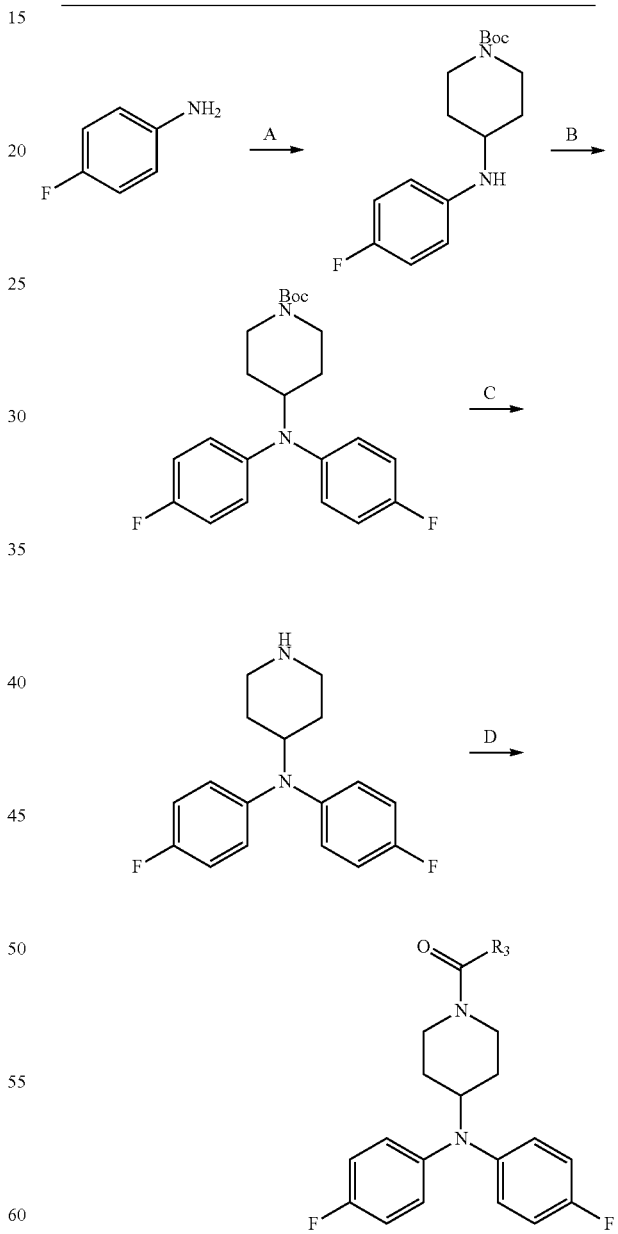

Reagents and conditions: A) i) 1-(tert-Butoxycarbonyl)-4-piperidone, NaBH(OAc)$_3$, AcOH, rt, 3 d; B) Method A: R$_2$-I, BINAP, Pd(OAc)$_2$, KOtBu, toluene, 110° C., 15 h; or Method B: R$_2$-I, Pd$_2$(dba)$_3$, RuPhos, KOtBu, dioxane, reflux, 19 h; C) Method A C) TMSI, NMM, DCM, rt; or Method B: TFA, CDM, rt; D) i) Triphosgene, DCM, 0° C.; ii) N,N-Bis(substituted aryl)piperidin-4-amine, DMAP, DCM, 0° C. to rt, 2.5 h; iii) R$_3$-H, DMAP, THF, rt.

Synthesis of 1-(4-(bis(4-fluorophenyl)amino)piperidine-1-carbonyl)-1H-benzo[d][1,2,3]triazole-6-carbonitrile (Example-61) and 1-(4-(bis(4-fluorophenyl)amino)piperidine-1-carbonyl)-1H-benzo[d][1,2,3]triazole-5-carbonitrile (Example-62)

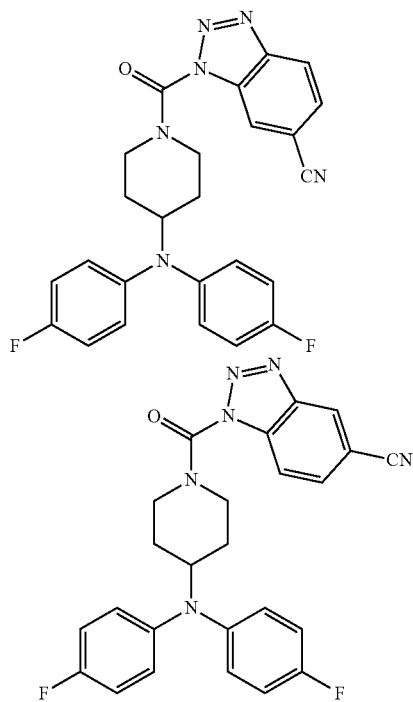

and

Step 1. Preparation of tert-butyl 4-((4-fluorophenyl)amino)piperidine-1-carboxylate General Procedure J

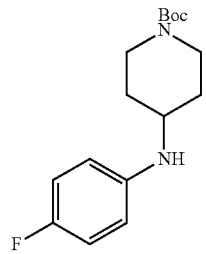 [SMILES: CC(C)(C)OC(=O)N1CCC(Nc2ccc(F)cc2)CC1]

A solution of 4-fluoroaniline (1.31 g, 11.8 mmol) in dichloromethane (60 mL) was stirred at ambient temperature while 1-(tert-butoxycarbonyl)-4-piperidone (2.58 g, 13.0 mmol) was added followed by acetic acid (0.67 mL) and sodium triacetoxyborohydride (5.00 g, 23.6 mmol). The mixture was stirred at ambient temperature under nitrogen atmosphere for 3 days then washed with 1N aqueous sodium hydroxide (60 mL) and water (20 mL). The organic layer was dried over anhydrous sodium sulfate, filtered and concentrated in vacuo, and the residue was purified by column chromatography, eluting with 5% to 15% ethyl acetate in dichloromethane to afford the title compound as a pale solid (3.15 g, 91% yield).

$^1$H NMR (400 MHz, CDCl$_3$) δ 6.88 (m, 2H), 6.54 (m, 2H), 4.04 (m, 2H), 3.35 (m, 2H), 2.90 (m, 2H), 2.02 (m, 2H), 1.46 (s, 9H), 1.35-1.25 (m, 2H).

Step 2. Preparation of tert-butyl 4-(bis(4-fluorophenyl)amino)piperidine-1-carboxylate General Procedure K

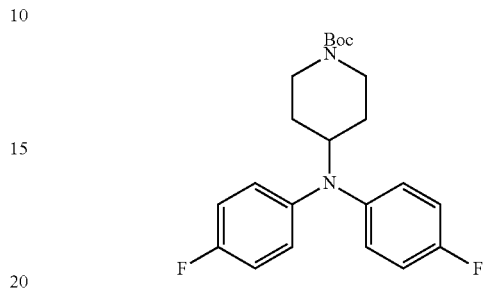

To a solution of tert-butyl 4-((4-fluorophenyl)amino)piperidine-1-carboxylate (504 mg, 1.71 mmol) and 4-fluoroiodobenzene (418 mg, 1.88 mmol) in anhydrous toluene (17 mL) was added (R)-(+)-2,2'-bis(diphenylphosphino)-1,1'-binaphthalene (107 mg, 0.172 mmol) followed by palladium(II) acetate (38 mg, 0.17 mmol) and potassium tert-butoxide (231 mg, 2.06 mmol). The mixture was degassed with nitrogen for 5 minutes then heated to 110° C. under nitrogen atmosphere for 15 hours. The mixture was allowed to cool to ambient temperature then ethyl acetate (20 mL) was added, and the mixture was filtered through Celite® 545. The filtrate was washed with 1N aqueous sodium hydroxide (15 mL) and brine (10 mL) then the organic layer was dried over anhydrous sodium sulfate, filtered and concentrated in vacuo. The residue was purified by column chromatography, eluting with 7% to 25% ethyl acetate in hexanes to afford the title compound as a yellow foam (176 mg, 26% yield).

$^1$H NMR (400 MHz, CDCl$_3$) δ 6.97 (m, 4H), 6.76 (m, 4H), 4.18 (m, 2H), 3.87 (m, 1H), 2.78 (m, 2H), 1.92 (m, 2H), 1.41 (s, 9H), 1.29 (m, 2H).

Step 3. Preparation of N,N-bis(4-fluorophenyl)piperidin-4-amine

General Procedure L

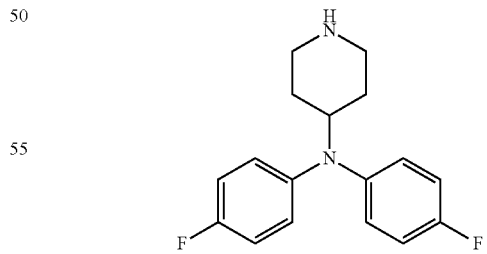

tert-Butyl 4-(bis(4-fluorophenyl)amino)piperidine-1-carboxylate (172 mg, 0.443 mmol) was dissolved in dichloromethane (4.4 mL) and stirred at ambient temperature while 4-methylmorpholine (0.19 mL, 1.7 mmol) was added followed by iodotrimethylsilane (0.16 mL, 1.1 mmol). The solution was stirred at ambient temperature for 55 minutes then diluted with dichloromethane (30 mL) and washed with saturated aqueous sodium bicarbonate (15 mL) followed by 1N aqueous sodium thiosulfate (15 mL) and water (2×15 mL). The organic layer was dried over anhydrous sodium sulfate, filtered and concentrated in vacuo. The residue was purified by column chromatography, eluting with 5% to 10% methanol (containing 10% aqueous ammonium hydroxide) in dichloromethane to afford the title compound as a colourless oil (109 mg, 85% yield).

$^1$H NMR (400 MHz, CDCl$_3$) δ 6.96 (m, 4H), 6.77 (m, 4H), 3.84 (m, 1H), 3.14 (m, 2H), 2.74 (m, 2H), 1.95 (m, 2H), 1.40-1.29 (m, 2H).

Step 4. Preparation of 1-(4-(bis(4-fluorophenyl)amino)piperidine-1-carbonyl)-1H-benzo[d][1,2,3]triazole-6-carbonitrile (Example-61) and 1-(4-(bis(4-fluorophenyl)amino)piperidine-1-carbonyl)-1H-benzo[d][1,2,3]triazole-5-carbonitrile Example-62

General Procedure M

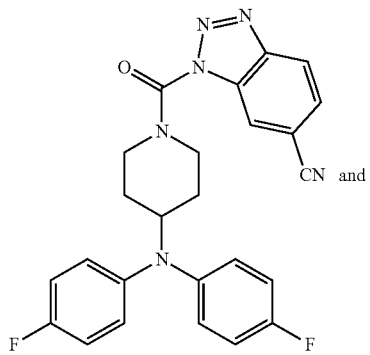

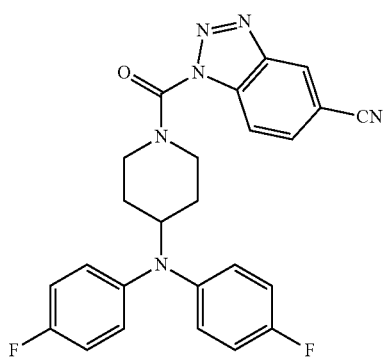

Triphosgene (108 mg, 0.364 mmol) was dissolved in anhydrous dichloromethane (1 mL), and the solution was cooled to 0° C. under nitrogen atmosphere. A solution of N,N-bis(4-fluorophenyl)piperidin-4-amine (105 mg, 0.364 mmol) and 4-(dimethylamino)pyridine (44 mL, 0.36 mmol) in anhydrous dichloromethane (2.6 mL) was added dropwise. The reaction vessel was sealed, and the mixture was stirred at ambient temperature for 2.5 hours then concentrated in vacuo. Anhydrous tetrahydrofuran (3.6 mL) was added followed by 4-(dimethylamino)pyridine (44 mg, 0.36 mmol) and 1H-1,2,3-benzotriazole-5-carbonitrile (52 mg, 0.36 mmol). The mixture was sealed and stirred at ambient temperature for 15.5 hours. The mixture was concentrated in vacuo then purified by column chromatography, eluting with 20% to 25% ethyl acetate in hexanes to afford the title compounds as a light yellow foam (33 mg, 20% yield) and a light yellow foam (53 mg, 32% yield), respectively.

The structure of 1-(4-(bis(4-fluorophenyl)amino)piperidine-1-carbonyl)-1H-benzo[d][1,2,3]triazole-6-carbonitrile was tentatively assigned.

$^1$H NMR (400 MHz, CDCl$_3$) δ 8.38 (s, 1H), 8.19 (d, J=8.6 Hz, 1H), 7.68 (m, 1H), 7.00 (m, 4H), 6.81 (m, 4H), 4.67 (m, 2H), 4.12 (m, 1H), 3.31 (m, 2H), 2.17 (m, 2H), 1.68-1.58 (m, 2H); $^{19}$F NMR (376 MHz, CDCl$_3$) δ −120.79 (s, 2F); MS (API-ES+) m/z 459.2 (M+1).

The structure of 1-(4-(bis(4-fluorophenyl)amino)piperidine-1-carbonyl)-1H-benzo[d][1,2,3]triazole-5-carbonitrile was tentatively assigned.

$^1$H NMR (400 MHz, CDCl$_3$) δ 8.46 (s, 1H), 8.08 (d, J=8.6 Hz, 1H), 7.80 (m, 1H), 7.00 (m, 4H), 6.81 (m, 4H), 4.65 (m, 2H), 4.12 (m, 1H), 3.30 (m, 2H), 2.17 (m, 2H), 1.68-1.58 (m, 2H); $^{19}$F NMR (376 MHz, CDCl$_3$) δ −120.78 (s, 2F); MS (API-ES+) m/z 459.0 (M+1); MS (API-ES+) m/z 459.0 (M+1).

Synthesis of 1-(4-(benzo[d][1,3]dioxol-5-yl(4-fluorophenyl)amino)piperidine-1-carbonyl)-1H-benzo[d][1,2,3]triazole-6-carbonitrile (Example-63) and 1-(4-(benzo[d][1,3]dioxol-5-yl(4-fluorophenyl)amino)piperidine-1-carbonyl)-1H-benzo[d][1,2,3]triazole-5-carbonitrile (Example-64)

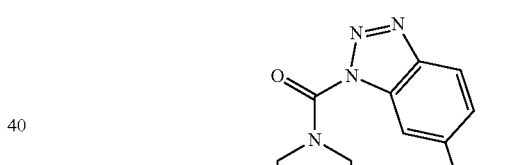

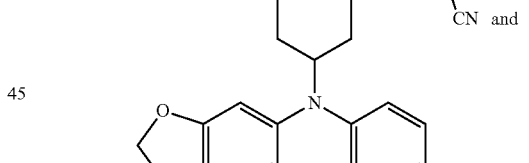

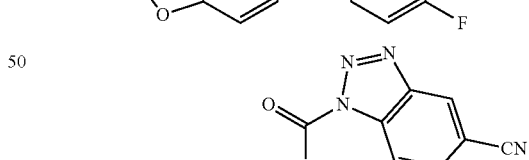

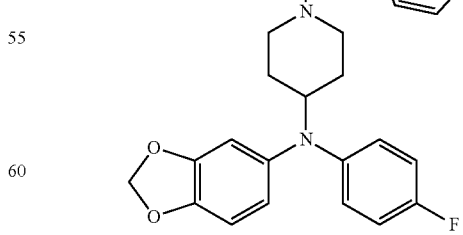

Step 1. Preparation of tert-butyl 4-(benzo[d][1,3]dioxol-5-yl(4-fluorophenyl)amino)piperidine-1-carboxylate

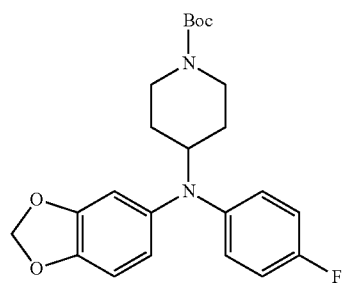 [SMILES: CC(C)(C)OC(=O)N1CCC(N(c2ccc(F)cc2)c2ccc3c(c2)OCO3)CC1]

Following General Procedure K and making non-critical variations as required to replace 4-fluoroiodobenzene with 1-iodo-3,4-methylenedioxybenzene, the title compound was obtained as a yellow foam (195 mg, 28% yield).

$^1$H NMR (400 MHz, CDCl$_3$) δ 6.91 (m, 2H), 6.76 (d, J=8.3 Hz, 1H), 6.65 (dd, J=8.9, 4.5 Hz, 2H), 6.43 (d, J=2.2 Hz, 1H), 6.40 (dd, J=8.2, 2.1 Hz, 1H), 5.96 (s, 2H), 4.18 (m, 2H), 3.83 (m, 1H), 2.78 (m, 2H), 1.91 (m, 2H), 1.42 (s, 9H), 1.32 (m, 2H).

Step 2. Preparation of N-(benzo[d][1,3]dioxol-5-yl)-N-(4-fluorophenyl)piperidin-4-amine General Procedure N

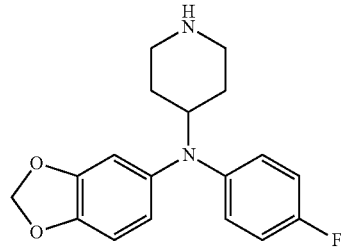 [SMILES: Fc1ccc(N(c2ccc3c(c2)OCO3)C2CCNCC2)cc1]

A solution of tert-butyl 4-(benzo[d][1,3]dioxol-5-yl(4-fluorophenyl)amino)piperidine-1 carboxylate (191 mg, 0.461 mmol) in dichloromethane (5 mL) was stirred at ambient temperature while trifluoroacetic acid (2.5 mL) was added. The solution was stirred for 1 hour then concentrated in vacuo followed by azeotropic removal of remaining trifluoroacetic acid using dichloromethane (2×10 mL). The residue was dissolved in dichloromethane (40 mL) and washed with 1N aqueous sodium hydroxide (30 mL) and water (20 mL) then dried over anhydrous sodium sulfate and concentrated in vacuo. The residue was purified by column chromatography, eluting with 5% to 7% methanol (containing 10% aqueous ammonium hydroxide) in dichloromethane to afford the title compound as a light yellow film (93 mg, 64% yield).

$^1$H NMR (400 MHz, CDCl$_3$) δ 6.90 (m, 2H), 6.76 (d, J=8.2 Hz, 1H), 6.66 (m, 2H), 6.44 (m, 1H), 6.41 (dd, J=8.3, 2.0 Hz, 1H), 5.95 (s, 2H), 3.81 (m, 1H), 3.15 (m, 2H), 2.73 (m, 2H), 1.95 (m, 2H), 1.38 (m, 2H) (NH not observed).

Step 3. Preparation of 1-(4-(benzo[d][1,3]dioxol-5-yl(4-fluorophenyl)amino)piperidine-1-carbonyl)-1H-benzo[d][1,2,3]triazole-6-carbonitrile (Example-63) and 1-(4-(benzo[d][1,3]dioxol-5-yl(4-fluorophenyl)amino)piperidine-1-carbonyl)-1H-benzo[d][1,2,3]triazole-5-carbonitrile (Example-64)

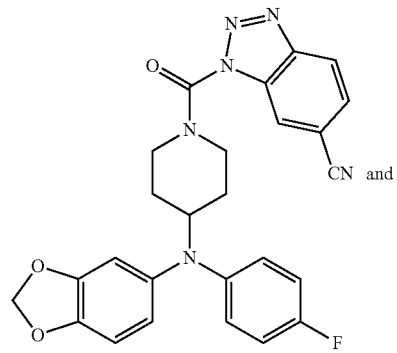

and

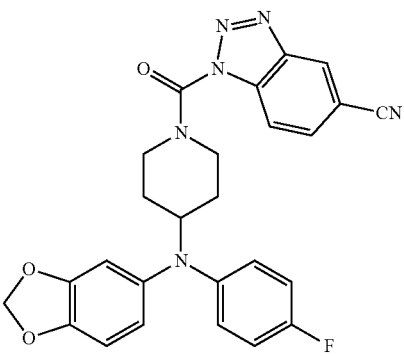

Following General Procedure M and making non-critical variations as required to replace N,N-bis(4-fluorophenyl)piperidin-4-amine with N-(benzo[d][1,3]dioxol-5-yl)-N-(4-fluorophenyl)piperidin-4-amine, the title compounds were obtained as a yellow foam (44 mg, 32% yield) and a yellow foam (49 mg, 36% yield), respectively.

The structure of 1-(4-(benzo[d][1,3]dioxol-5-yl(4-fluorophenyl)amino)piperidine-1-carbonyl)-1H-benzo[d][1,2,3]triazole-6-carbonitrile was tentatively assigned.

$^1$H NMR (400 MHz, CDCl$_3$) δ 8.38 (s, 1H), 8.19 (d, J=8.6 Hz, 1H), 7.67 (d, J=8.5 Hz, 1H), 6.94 (m, 2H), 6.79 (d, J=8.0 Hz, 1H), 6.69 (m, 2H), 6.46 (m, 2H), 5.97 (s, 2H), 4.67 (m, 2H), 4.08 (m, 1H), 3.41-3.18 (m, 2H), 2.15 (m, 2H), 1.66 (m, 2H); $^{19}$F NMR (376 MHz, CDCl$_3$) δ −124.19 (s, 1F).

The structure of 1-(4-(benzo[d][1,3]dioxol-5-yl(4-fluorophenyl)amino)piperidine-1-carbonyl)-1H-benzo[d][1,2,3]triazole-5-carbonitrile was tentatively assigned.

$^1$H NMR (400 MHz, CDCl$_3$) δ 8.46 (s, 1H), 8.09 (d, J=8.6 Hz, 1H), 7.80 (d, J=8.6 Hz, 1H), 6.94 (m, 2H), 6.78 (d, J=8.1 Hz, 1H), 6.69 (m, 2H), 6.46 (m, 2H), 5.97 (s, 2H), 4.64 (m, 2H), 4.08 (m, 1H), 3.43-3.16 (m, 2H), 2.15 (m, 2H), 1.66 (m, 2H); $^{19}$F NMR (376 MHz, CDCl$_3$) δ −124.15 (s, 1F).

Synthesis of 1-(4-((4-fluorophenyl)(4-methoxyphenyl)amino)piperidine-1-carbonyl)-1H-benzo[d][1,2,3]triazole-6-carbonitrile (Example-65) and 1-(4-((4-fluorophenyl)(4-methoxyphenyl)amino)piperidine-1-carbonyl)-1H-benzo[d][1,2,3]triazole-5-carbonitrile (Example-66)

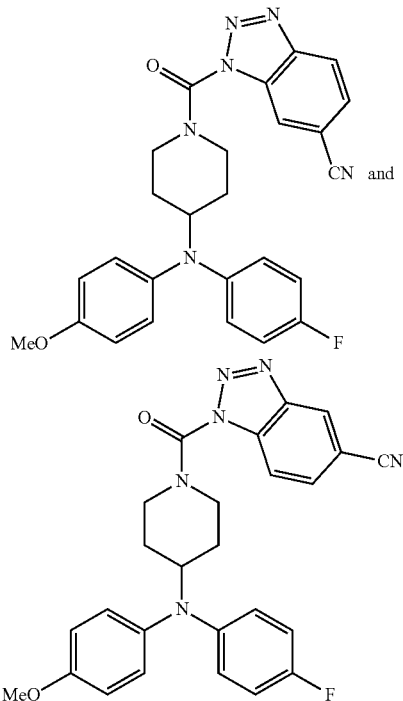

Step 1. Preparation of tert-butyl 4-((4-methoxyphenyl)amino)piperidine-1-carboxylate

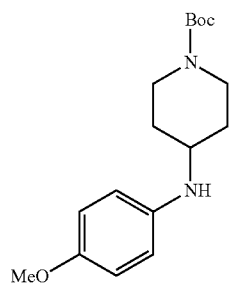

Following General Procedure J and making non-critical variations as required to replace 4-fluoroaniline with 4-methoxyaniline, the title compound was obtained as light yellow crystals (3.86 g, 99% yield).

$^1$H NMR (400 MHz, CDCl$_3$) δ 6.78 (m, 2H), 6.59 (m, 2H), 4.03 (m, 2H), 3.74 (s, 3H), 3.33 (m, 1H), 3.19 (br s, 1H), 2.90 (m, 2H), 2.02 (m, 2H), 1.46 (s, 9H), 1.34-1.24 (m, 2H).

Step 2. Preparation of tert-butyl 4-((4-fluorophenyl)(4-methoxyphenyl)amino)piperidine-1-carboxylate

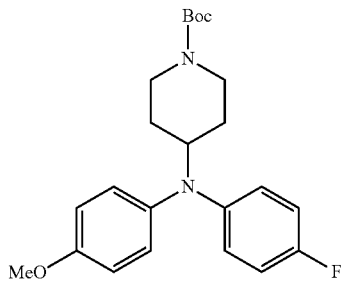

Following General Procedure K and making non-critical variations as required to replace tert-butyl 4-((4-fluorophenyl)amino)piperidine-1-carboxylate with tert-butyl 4-((4-methoxyphenyl)amino)piperidine-1-carboxylate, the title compound was obtained as a yellow film (65 mg, 13% yield).

$^1$H NMR (400 MHz, CDCl$_3$) δ 6.88 (m, 6H), 6.58 (m, 2H), 4.17 (m, 2H), 3.84 (m, 1H), 3.81 (s, 3H), 2.80 (m, 2H), 1.92 (m, 2H), 1.41 (s, 9H), 1.30 (m, 2H).

Step 3. Preparation of N-(4-fluorophenyl)-N-(4-methoxyphenyl)piperidin-4-amine Following General Procedure N and making non-critical variations as required to replace tert-butyl 4-(benzo[d][1,3]dioxol-5-yl(4-fluorophenyl)amino)piperidine-1 carboxylate with tert-butyl 4-((4-fluorophenyl)(4-methoxyphenyl)amino)piperidine-1-carboxylate, the title compound was obtained as a pale oil (127 mg, 96% yield).

$^1$H NMR (400 MHz, CDCl$_3$) δ 6.88 (m, 6H), 6.59 (m, 2H), 3.83 (m, 1H), 3.80 (s, 3H), 3.15 (m, 2H), 2.74 (m, 2H), 1.96 (m, 2H), 1.41-1.31 (m, 2H) (NH not observed).

Step 4. Preparation of 1-(4-((4-fluorophenyl)(4-methoxyphenyl)amino)piperidine-1-carbonyl)-1H-benzo[d][1,2,3]triazole-6-carbonitrile (Example-65) and 1-(4-((4-fluorophenyl)(4-methoxyphenyl)amino)piperidine-1-carbonyl)-1H-benzo[d][1,2,3]triazole-5-carbonitrile (Example-66)

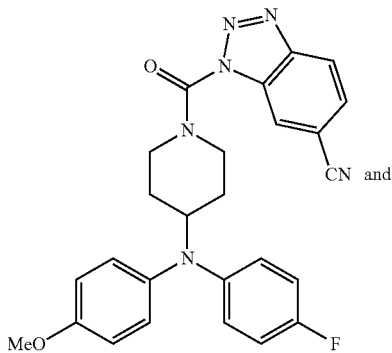

and

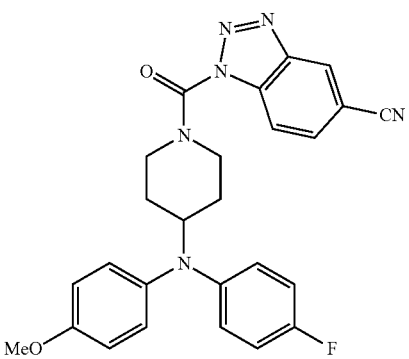

Following General Procedure M and making non-critical variations as required to replace N,N-bis(4-fluorophenyl) piperidin-4-amine with N-(4-fluorophenyl)-N-(4-methoxyphenyl)piperidin-4-amine, the title compounds were obtained as a yellow foam (40 mg, 21% yield) and a yellow foam (65 mg, 34% yield), respectively.

The structure of 1-(4-((4-fluorophenyl)(4-methoxyphenyl)amino)piperidine-1-carbonyl)-1H-benzo[d][1,2,3]triazole-6-carbonitrile was tentatively assigned.

$^1$H NMR (400 MHz, CDCl$_3$) δ 8.37 (s, 1H), 8.19 (d, J=8.5 Hz, 1H), 7.67 (dd, J=8.5, 1.5 Hz, 1H), 6.92 (m, 6H), 6.63 (m, 2H), 4.66 (m, 2H), 4.11 (m, 1H), 3.81 (s, 3H), 3.44-3.18 (m, 2H), 2.16 (m, 2H), 1.63 (m, 2H); $^{19}$F NMR (376 MHz, CDCl$_3$) δ −125.55 (s, 1F).

The structure of 1-(4-((4-fluorophenyl)(4-methoxyphenyl)amino)piperidine-1-carbonyl)-1H-benzo[d][1,2,3]triazole-5-carbonitrile was tentatively assigned.

$^1$H NMR (400 MHz, CDCl$_3$) δ 8.46 (s, 1H), 8.08 (d, J=8.6 Hz, 1H), 7.80 (dd, J=8.6, 1.4 Hz, 1H), 6.92 (m, 6H), 6.63 (m, 2H), 4.63 (m, 2H), 4.10 (m, 1H), 3.81 (s, 3H), 3.43-3.18 (m, 2H), 2.16 (m, 2H), 1.63 (m, 2H); $^{19}$F NMR (376 MHz, CDCl$_3$) δ −125.55 (s, 1F).

Synthesis of 1-(4-(bis(benzo[d][1,3]dioxol-5-yl)amino)piperidine-1-carbonyl)-1H-benzo[d][1,2,3]triazole-6-carbonitrile (Example-67) and 1-(4-(bis(benzo[d][1,3]dioxol-5-yl)amino)piperidine-1-carbonyl)-1H-benzo[d][1,2,3]triazole-5-carbonitrile (Example-68)

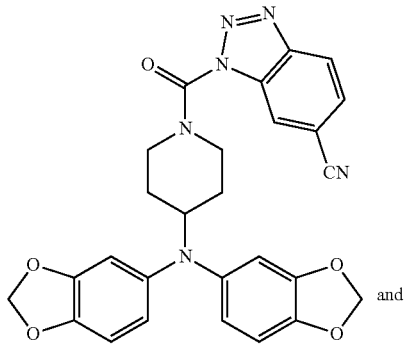

and

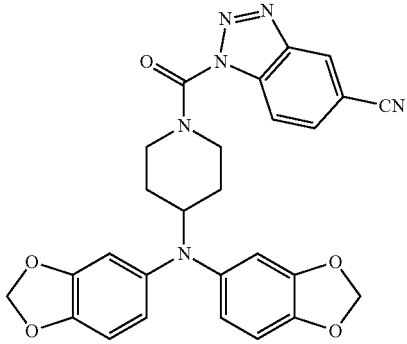

Step 1. Preparation of tert-butyl 4-(benzo[d][1,3]dioxol-5-ylamino)piperidine-1-carboxylate

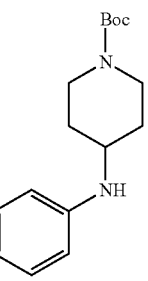

Following General Procedure J and making non-critical variations as required to replace 4-fluoroaniline with 3,4-(methylenedioxy)aniline, the title compound was obtained as pale crystals (3.8 g, 100% yield).

$^1$H NMR (400 MHz, CDCl$_3$) δ 6.65 (d, J=8.3 Hz, 1H), 6.24 (d, J=2.1 Hz, 1H), 6.05 (dd, J=8.3, 2.3 Hz, 1H), 5.85 (s, 2H), 4.03 (m, 2H), 3.29 (m, 2H), 2.88 (m, 2H), 2.01 (m, 2H), 1.46 (s, 9H), 1.33-1.23 (m, 2H).

Step 2. Preparation of tert-butyl 4-(bis(benzo[d][1,3]dioxol-5-yl)amino)piperidine-1-carboxylate

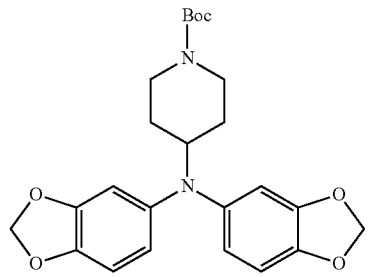 [SMILES: CC(C)(C)OC(=O)N1CCC(N(c2ccc3c(c2)OCO3)c2ccc3c(c2)OCO3)CC1]

A mixture of tert-butyl 4-(benzo[d][1,3]dioxol-5-ylamino)piperidine-1-carboxylate (193 mg, 0.602 mmol), 1-iodo-3,4-methylenedioxybenzene (134 mg, 0.540 mmol), tris(dibenzylideneacetone)-dipalladium(0) (11 mg, 0.012 mmol), 2-dicyclohexylphosphino-2',6'-diisopropoxybiphenyl (22 mg, 0.047 mmol) and potassium tert-butoxide (135 mg, 1.20 mmol) in anhydrous 1,4-dioxane (2 mL) was degassed with nitrogen for 5 minutes then heated to reflux under argon atmosphere for 19 hours. The mixture was allowed to cool to ambient temperature then ethyl acetate (10 mL) was added, and the mixture was filtered through Celite® 545. The filtrate was concentrated in vacuo, and the residue was purified by column chromatography, eluting with 12% ethyl acetate in hexanes to afford the title compound as a yellow film (93 mg, 39% yield).

$^1$H NMR (400 MHz, CDCl$_3$) δ 6.71 (d, J=8.4 Hz, 2H), 6.36 (d, J=2.1 Hz, 2H), 6.30 (dd, J=8.4, 2.0 Hz, 2H), 5.92 (s, 4H), 4.16 (m, 2H), 3.79 (m, 1H), 2.78 (m, 2H), 1.91 (m, 2H), 1.42 (s, 9H), 1.33 (m, 2H).

Step 3. Preparation of N,N-bis(benzo[d][1,3]dioxol-5-yl)piperidin-4-amine

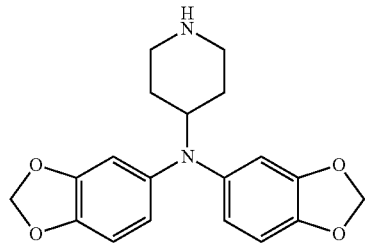 [SMILES: c1cc2c(cc1N(c1ccc3c(c1)OCO3)C1CCNCC1)OCO2]

Following General Procedure L and making non-critical variations as required to replace tert-butyl 4-(bis(4-fluorophenyl)amino)piperidine-1-carboxylate with tert-butyl 4-(bis(benzo[d][1,3]dioxol-5-yl)amino)piperidine-1-carboxylate, the title compound was obtained as a pale oil (104 mg, 100% yield).

$^1$H NMR (400 MHz, CDCl$_3$) δ 6.71 (d, J=8.3 Hz, 2H), 6.38 (d, J=2.1 Hz, 2H), 6.31 (dd, J=8.3, 2.1 Hz, 2H), 5.91 (s, 4H), 3.78 (m, 1H), 3.21 (m, 2H), 2.77 (m, 2H), 1.98 (m, 2H), 1.52-1.42 (m, 2H) (NH not observed).

Step 4. Preparation of 1-(4-(bis(benzo[d][1,3]dioxol-5-yl)amino)piperidine-1-carbonyl)-1H-benzo[d][1,2,3]triazole-6-carbonitrile (Example-67) and 1-(4-(bis(benzo[d][1,3]dioxol-5-yl)amino)piperidine-1-carbonyl)-1H-benzo[d][1,2,3]triazole-5-carbonitrile (Example-68)

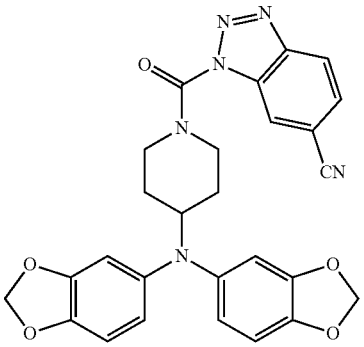 and

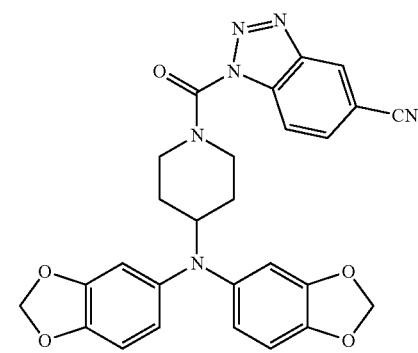

Following General Procedure M and making non-critical variations as required to replace N,N-bis(4-fluorophenyl)piperidin-4-amine with N,N-bis(benzo[d][1,3]dioxol-5-yl)piperidin-4-amine, the title compounds were obtained as a yellow foam (30 mg, 20% yield) and a yellow foam (43 mg, 29% yield), respectively.

The structure of 1-(4-(bis(benzo[d][1,3]dioxol-5-yl)amino)piperidine-1-carbonyl)-1H-benzo[d][1,2,3]triazole-6-carbonitrile was tentatively assigned.

$^1$H NMR (400 MHz, CDCl$_3$) δ 8.38 (s, 1H), 8.19 (d, J=8.5 Hz, 1H), 7.67 (dd, J=8.5, 1.5 Hz, 1H), 6.74 (d, J=8.4 Hz, 2H), 6.40 (d, J=2.1 Hz, 2H), 6.35 (dd, J=8.3, 2.2 Hz, 2H), 5.93 (s, 4H), 4.65 (m, 2H), 4.04 (m, 1H), 3.43-3.15 (m, 2H), 2.14 (m, 2H), 1.71-1.61 (m, 2H).

The structure of 1-(4-(bis(benzo[d][1,3]dioxol-5-yl)amino)piperidine-1-carbonyl)-1H-benzo[d][1,2,3]triazole-5-carbonitrile was tentatively assigned.

$^1$H NMR (400 MHz, CDCl$_3$) δ 8.46 (s, 1H), 8.09 (d, J=8.6 Hz, 1H), 7.80 (dd, J=8.6, 1.5 Hz, 1H), 6.74 (d, J=8.4 Hz, 2H), 6.40 (d, J=2.1 Hz, 2H), 6.35 (dd, J=8.3, 2.2 Hz, 2H), 5.93 (s, 4H), 4.62 (m, 2H), 4.03 (m, 1H), 3.42-3.16 (m, 2H), 2.15 (m, 2H), 1.66 (m, 2H).

Synthesis of 1-(4-(benzo[d][1,3]dioxol-5-yl(4-(trifluoromethyl)phenyl)amino)piperidine-1-carbonyl)-1H-benzo[d][1,2,3]triazole-6-carbonitrile (Example-69) and 1-(4-(benzo[d][1,3]dioxol-5-yl(4-(trifluoromethyl)phenyl)amino)piperidine-1-carbonyl)-1H-benzo[d][1,2,3]triazole-5-carbonitrile (Example-70)

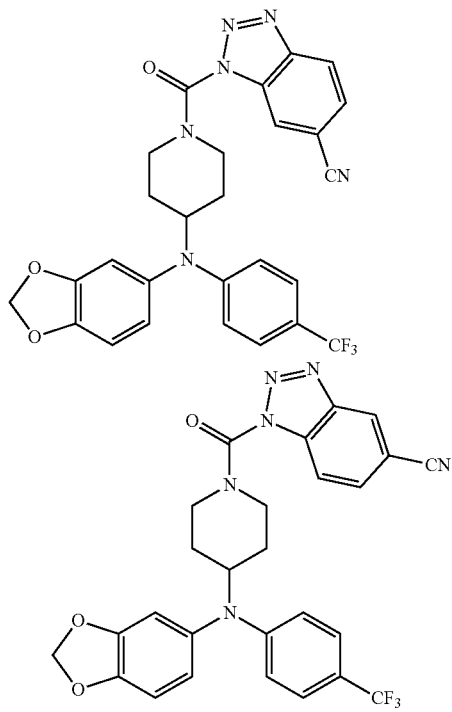

and

Step 1. Preparation of tert-butyl 4-(benzo[d][1,3]dioxol-5-yl(4-(trifluoromethyl)phenyl)amino)piperidine-1-carboxylate

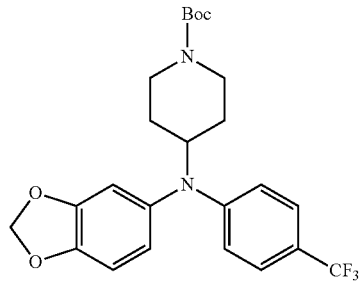 [SMILES: CC(C)(C)OC(=O)N1CCC(N(c2ccc(C(F)(F)F)cc2)c2ccc3c(c2)OCO3)CC1]

Following General Procedure O and making non-critical variations as required to replace 1-iodo-3,4-methylenedioxybenzene with 4-iodobenzotrifluoride, the title compound was obtained as a yellow solid (266 mg, 51% yield).

$^1$H NMR (400 MHz, CDCl$_3$) δ 7.35 (d, J=8.6 Hz, 2H), 6.85 (d, J=8.6 Hz, 1H), 6.55 (m, 4H), 6.04 (s, 2H), 4.20 (m, 2H), 3.95 (m, 1H), 2.81 (m, 2H), 1.92 (m, 2H), 1.43 (s, 9H), 1.36 (m, 2H).

Step 2. Preparation of N-(benzo[d][1,3]dioxol-5-yl)-N-(4-(trifluoromethyl)phenyl)piperidin-4-amine

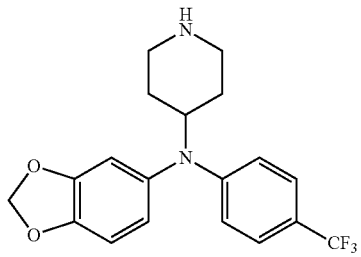 [SMILES: FC(F)(F)c1ccc(N(c2ccc3c(c2)OCO3)C2CCNCC2)cc1]

Following General Procedure N and making non-critical variations as required to replace tert-butyl 4-(benzo[d][1,3]dioxol-5-yl(4-fluorophenyl)amino)piperidine-1 carboxylate with tert-butyl 4-(benzo[d][1,3]dioxol-5-yl(4-(trifluoromethyl)phenyl)amino)piperidine-1-carboxylate, the title compound was obtained as a pale foam (195 mg, 95% yield).

$^1$H NMR (400 MHz, CDCl$_3$) δ 7.35 (d, J=8.6 Hz, 2H), 6.85 (d, J=8.7 Hz, 1H), 6.56 (m, 4H), 6.02 (s, 2H), 3.93 (m, 1H), 3.19 (m, 2H), 2.77 (m, 2H), 1.96 (m, 2H), 1.49-1.39 (m, 2H) (NH not observed).

Step 3. Preparation of 1-(4-(benzo[d][1,3]dioxol-5-yl(4-(trifluoromethyl)phenyl)amino)piperidine-1-carbonyl)-1H-benzo[d][1,2,3]triazole-6-carbonitrile (Example-69) and 1-(4-(benzo[d][1,3]dioxol-5-yl(4-(trifluoromethyl)phenyl)amino)piperidine-1-carbonyl)-1H-benzo[d][1,2,3]triazole-5-carbonitrile (Example-70)

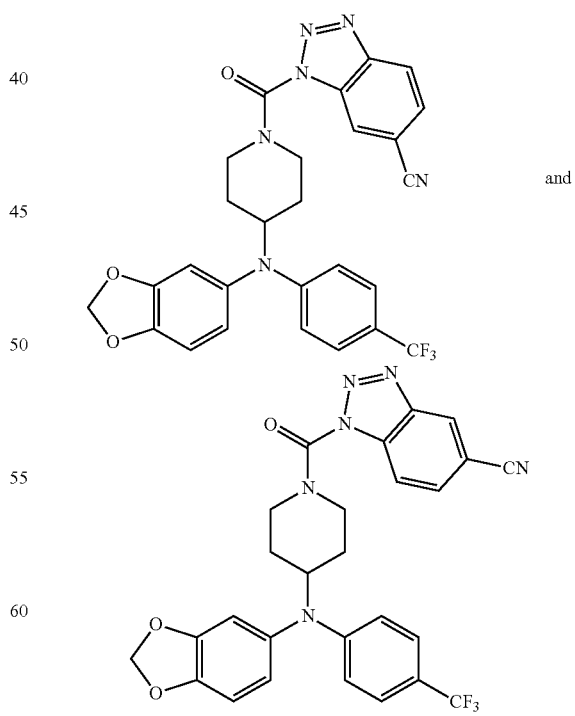

and

Following General Procedure M and making non-critical variations as required to replace N,N-bis(4-fluorophenyl)

piperidin-4-amine with N-(benzo[d][1,3]dioxol-5-yl)-N-(4-(trifluoromethyl)phenyl)piperidin-4-amine, the title compounds were obtained as a pale foam (56 mg, 33% yield) and a light yellow foam (60 mg, 35% yield), respectively.

The structure of 1-(4-(benzo[d][1,3]dioxol-5-yl(4-(trifluoromethyl)phenyl)amino)piperidine-1-carbonyl)-1H-benzo[d][1,2,3]triazole-6-carbonitrile was tentatively assigned.

$^{1}$H NMR (400 MHz, CDCl$_{3}$) δ 8.39 (d, J=1.3 Hz, 1H), 8.20 (d, J=8.5 Hz, 1H), 7.68 (dd, J=8.5, 1.4 Hz, 1H), 7.39 (d, J=8.5 Hz, 2H), 6.87 (d, J=7.9 Hz, 1H), 6.60 (m, 4H), 6.05 (s, 2H), 4.71 (m, 2H), 4.21 (m, 1H), 3.39-3.23 (m, 2H), 2.16 (m, 2H), 1.75-1.65 (m, 2H); $^{19}$F NMR (376 MHz, CDCl$_{3}$) δ −61.13 (s, 3F).

The structure of 1-(4-(benzo[d][1,3]dioxol-5-yl(4-(trifluoromethyl)phenyl)amino)piperidine-1-carbonyl)-1H-benzo[d][1,2,3]triazole-5-carbonitrile was tentatively assigned.

$^{1}$H NMR (400 MHz, CDCl$_{3}$) δ 8.47 (s, 1H), 8.10 (d, J=8.6 Hz, 1H), 7.81 (dd, J=8.6, 1.5 Hz, 1H), 7.39 (d, J=8.6 Hz, 2H), 6.87 (d, J=7.9 Hz, 1H), 6.59 (m, 4H), 6.05 (s, 2H), 4.68 (m, 2H), 4.20 (m, 1H), 3.40-3.22 (m, 2H), 2.16 (m, 2H), 1.70 (m, 2H); $^{19}$F NMR (376 MHz, CDCl$_{3}$) δ −61.13 (s, 3F).

Synthesis of 1-(4-(benzo[d][1,3]dioxol-5-yl(4-(trifluoromethyl)phenyl)amino)piperidine-1-carbonyl)-1H-1,2,4-triazole-3-carbonitrile Example-71

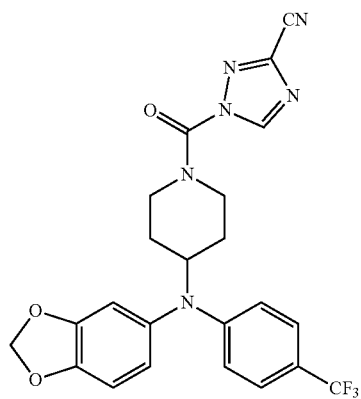 [SMILES: N#Cc1ncn(C(=O)N2CCC(N(c3ccc(C(F)(F)F)cc3)c3ccc4c(c3)OCO4)CC2)n1]

Following General Procedure M and making non-critical variations as required to replace N,N-bis(4-fluorophenyl)piperidin-4-amine with N-(benzo[d][1,3]dioxol-5-yl)-N-(4-(trifluoromethyl)phenyl)piperidin-4-amine and replace 1H-1,2,3-benzotriazole-5-carbonitrile with 2H-1,2,4-triazole-3-carbonitrile, the title compound was obtained as a pale foam (66 mg, 67% yield).

$^{1}$H NMR (400 MHz, CDCl$_{3}$) δ 8.82 (s, 1H), 7.38 (d, J=8.6 Hz, 2H), 6.88 (d, J=7.9 Hz, 1H), 6.57 (m, 4H), 6.05 (s, 2H), 4.67-4.57 (m, 2H), 4.15 (m, 1H), 3.29-3.11 (m, 2H), 2.13 (m, 2H), 1.58 (m, 2H).

Synthesis of 1-(4-(benzo[d][1,3]dioxol-5-yl(4-methoxyphenyl)amino)piperidine-1-carbonyl)-1H-benzo[d][1,2,3]triazole-6-carbonitrile (Example-72) and 1-(4-(benzo[d][1,3]dioxol-5-yl(4-methoxyphenyl)amino)piperidine-1-carbonyl)-1H-benzo[d][1,2,3]triazole-5-carbonitrile (Example-73)

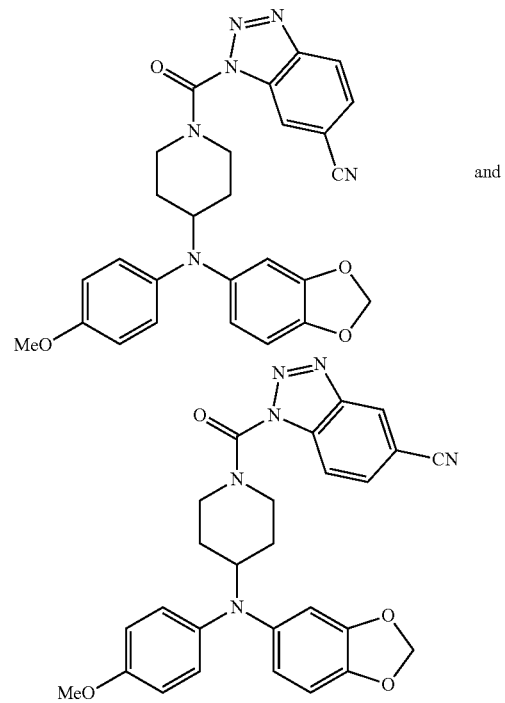

Step 1. Preparation of tert-butyl 4-(benzo[d][1,3]dioxol-5-yl(4-methoxyphenyl)amino)piperidine-1-carboxylate

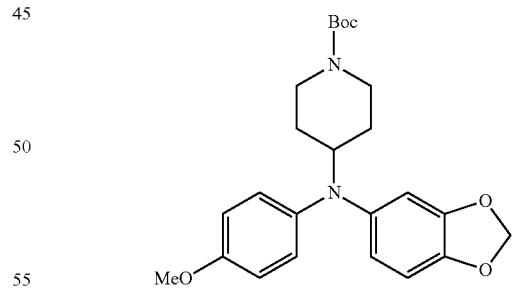

Following General Procedure O and making non-critical variations as required to replace tert-butyl 4-(benzo[d][1,3]dioxol-5-ylamino)piperidine-1-carboxylate with tert-butyl 4-((4-methoxyphenyl)amino)piperidine-1-carboxylate, the title compound was obtained as a yellow oil (108 mg, 28% yield).

$^{1}$H NMR (400 MHz, CDCl$_{3}$) δ 6.83 (m, 4H), 6.69 (d, J=8.6 Hz, 1H), 6.30 (d, J=2.2 Hz, 1H), 6.22 (dd, J=8.3, 2.3 Hz, 1H), 5.89 (s, 2H), 4.16 (m, 2H), 3.82 (m, 1H), 3.79 (s, 3H), 2.79 (m, 2H), 1.92 (m, 2H), 1.41 (s, 9H), 1.31 (m, 2H).

Step 2. Preparation of N-(benzo[d][1,3]dioxol-5-yl)-N-(4-methoxyphenyl)piperidin-4-amine

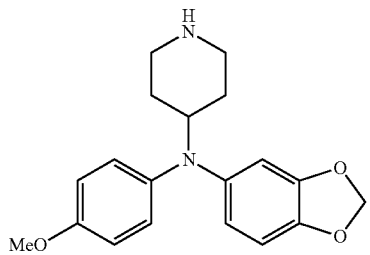 [SMILES: COc1ccc(N(c2ccc3c(c2)OCO3)C2CCNCC2)cc1]

Following General Procedure N and making non-critical variations as required to replace tert-butyl 4-(benzo[d][1,3]dioxol-5-yl(4-fluorophenyl)amino)piperidine-1 carboxylate with tert-butyl 4-(benzo[d][1,3]dioxol-5-yl(4-methoxyphenyl)amino)piperidine-1-carboxylate, the title compound was obtained as a yellow oil (80 mg, 100% yield).

$^1$H NMR (400 MHz, CDCl$_3$) δ 6.83 (m, 4H), 6.68 (d, J=8.4 Hz, 1H), 6.32 (d, J=2.1 Hz, 1H), 6.23 (dd, J=8.4, 2.3 Hz, 1H), 5.88 (s, 2H), 3.79 (m, 1H), 3.78 (s, 3H), 3.13 (m, 2H), 2.72 (m, 2H), 1.95 (m, 2H), 1.40-1.30 (m, 2H) (NH not observed).

Step 3. Preparation of 1-(4-(benzo[d][1,3]dioxol-5-yl(4-methoxyphenyl)amino)piperidine-1-carbonyl)-1H-benzo[d][1,2,3]triazole-6-carbonitrile (Example-72) and 1-(4-(benzo[d][1,3]dioxol-5-yl(4-methoxyphenyl)amino)piperidine-1-carbonyl)-1H-benzo[d][1,2,3]triazole-5-carbonitrile (Example-73)

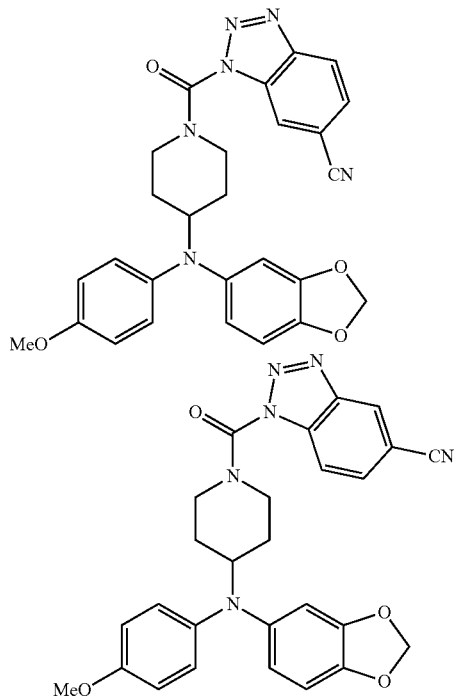

and

Following General Procedure M and making non-critical variations as required to replace N,N-bis(4-fluorophenyl)piperidin-4-amine with N-(benzo[d][1,3]dioxol-5-yl)-N-(4-methoxyphenyl)piperidin-4-amine, the title compounds were obtained as a yellow foam (35 mg, 30% yield) and a yellow foam (48 mg, 41% yield), respectively.

The structure of 1-(4-(benzo[d][1,3]dioxol-5-yl(4-methoxyphenyl)amino)piperidine-1-carbonyl)-1H-benzo[d][1,2,3]triazole-6-carbonitrile was tentatively assigned.

$^1$H NMR (400 MHz, CDCl$_3$) δ 8.38 (s, 1H), 8.19 (d, J=8.5 Hz, 1H), 7.67 (dd, J=8.5, 1.6 Hz, 1H), 6.86 (m, 4H), 6.71 (d, J=8.4 Hz, 1H), 6.34 (d, J=2.3 Hz, 1H), 6.28 (dd, J=8.4, 2.2 Hz, 1H), 5.91 (s, 2H), 4.65 (m, 2H), 4.07 (m, 1H), 3.79 (s, 3H), 3.42-3.19 (m, 2H), 2.15 (m, 2H), 1.69-1.59 (m, 2H).

The structure of 1-(4-(benzo[d][1,3]dioxol-5-yl(4-methoxyphenyl)amino)piperidine-1-carbonyl)-1H-benzo[d][1,2,3]triazole-5-carbonitrile was tentatively assigned.

$^1$H NMR (400 MHz, CDCl$_3$) δ 8.46 (s, 1H), 8.08 (d, J=8.6 Hz, 1H), 7.80 (dd, J=8.6, 1.5 Hz, 1H), 6.86 (m, 4H), 6.71 (d, J=8.5 Hz, 1H), 6.34 (d, J=2.3 Hz, 1H), 6.28 (dd, J=8.4, 2.3 Hz, 1H), 5.91 (s, 2H), 4.62 (m, 2H), 4.06 (m, 1H), 3.79 (s, 3H), 3.42-3.19 (m, 2H), 2.15 (m, 2H), 1.69-1.59 (m, 2H).

Synthesis of 1-(4-(benzo[d][1,3]dioxol-5-yl(pyridin-3-yl)amino)piperidine-1-carbonyl)-1H-benzo[d][1,2,3]triazole-6-carbonitrile (Example-74) and 1-(4-(benzo[d][1,3]dioxol-5-yl(pyridin-3-yl)amino)piperidine-1-carbonyl)-1H-benzo[d][1,2,3]triazole-5-carbonitrile (Example-75)

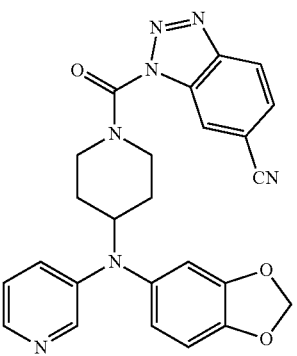 and

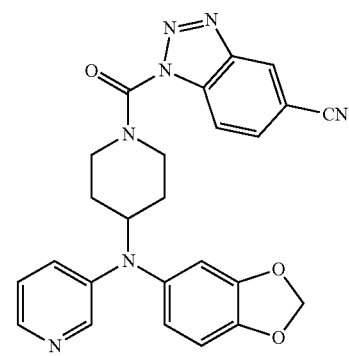

Step 1. Preparation of tert-butyl 4-(pyridin-3-ylamino)piperidine-1-carboxylate

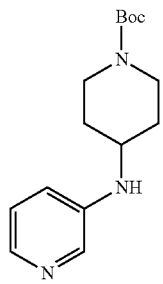 [SMILES: CC(C)(C)OC(=O)N1CCC(Nc2cccnc2)CC1]

Following General Procedure J and making non-critical variations as required to replace 4-fluoroaniline with 3-aminopyridine and in the absence of acetic acid, the title compound was obtained as a light green solid (1.56 g, 68% yield).

$^1$H NMR (400 MHz, CDCl$_3$) δ 8.01 (d, J=2.4 Hz, 1H), 7.95 (dd, J=4.6, 1.4 Hz, 1H), 7.08 (dd, J=8.3, 4.6 Hz, 1H), 6.87 (m, 1H), 4.06 (m, 2H), 3.55 (d, J=8.1 Hz, 1H), 3.42 (m, 1H), 2.92 (m, 2H), 2.03 (m, 2H), 1.46 (s, 9H), 1.39-1.29 (m, 2H).

Step 2. Preparation of tert-butyl 4-(benzo[d][1,3]dioxol-5-yl(pyridin-3-yl)amino)piperidine-1-carboxylate

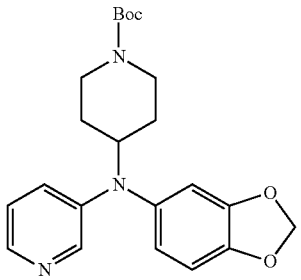 [SMILES: CC(C)(C)OC(=O)N1CCC(N(c2cccnc2)c2ccc3c(c2)OCO3)CC1]

Following General Procedure O and making non-critical variations as required to replace tert-butyl 4-(benzo[d][1,3]dioxol-5-ylamino)piperidine-1-carboxylate with tert-butyl 4-(pyridin-3-ylamino)piperidine-1-carboxylate, the title compound was obtained as a yellow film (119 mg, 22% yield).

$^1$H NMR (400 MHz, CDCl$_3$) δ 8.01 (d, J=2.9 Hz, 1H), 7.97 (dd, J=4.6, 1.3 Hz, 1H), 7.04 (dd, J=8.5, 4.6 Hz, 1H), 6.82 (m, 2H), 6.54 (m, 2H), 6.02 (s, 2H), 4.20 (m, 2H), 3.91 (m, 1H), 2.81 (m, 2H), 1.93 (m, 2H), 1.43 (s, 9H), 1.42-1.32 (m, 2H).

Step 3. Preparation of N-(benzo[d][1,3]dioxol-5-yl)-N-(piperidin-4-yl)pyridin-3-amine

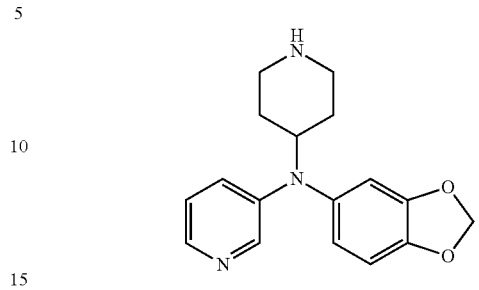

Following General Procedure N and making non-critical variations as required to replace tert-butyl 4-(benzo[d][1,3]dioxol-5-yl(4-fluorophenyl)amino)piperidine-1 carboxylate with tert-butyl 4-(benzo[d][1,3]dioxol-5-yl(pyridin-3-yl)amino)piperidine-1-carboxylate, the title compound was obtained as a light yellow film (70 mg, 81% yield).

$^1$H NMR (400 MHz, CDCl$_3$) δ 8.02 (d, J=3.0 Hz, 1H), 7.96 (dd, J=4.5, 1.3 Hz, 1H), 7.03 (dd, J=8.5, 4.6 Hz, 1H), 6.82 (m, 2H), 6.56 (m, 2H), 6.01 (s, 2H), 3.90 (m, 1H), 3.22 (m, 2H), 2.79 (m, 2H), 1.98 (m, 2H), 1.54-1.44 (m, 2H) (NH not observed).

Step 4. Preparation of 1-(4-(benzo[d][1,3]dioxol-5-yl(pyridin-3-yl)amino)piperidine-1-carbonyl)-1H-benzo[d][1,2,3]triazole-6-carbonitrile (Example-74) and 1-(4-(benzo[d][1,3]dioxol-5-yl(pyridin-3-yl)amino)piperidine-1-carbonyl)-1H-benzo[d][1,2,3]triazole-5-carbonitrile (Example-75)

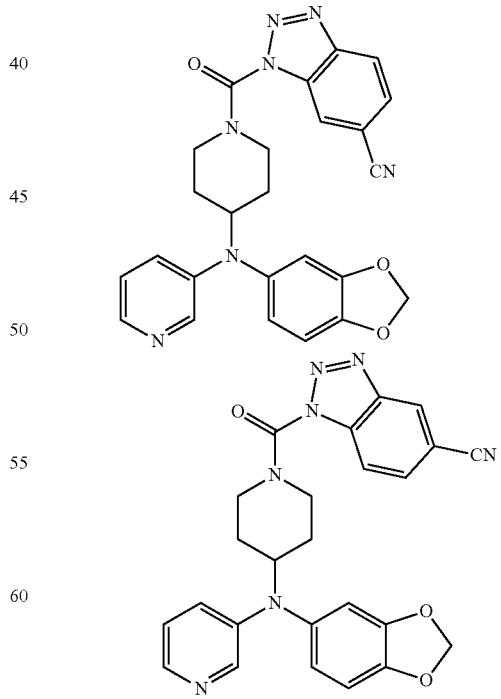

Following General Procedure M and making non-critical variations as required to replace N,N-bis(4-fluorophenyl)

piperidin-4-amine with N-(benzo[d][1,3]dioxol-5-yl)-N-(piperidin-4-yl)pyridin-3-amine and replace tetrahydrofuran with dichloromethane, the title compounds were obtained as a yellow foam (25 mg, 24% yield) and a yellow foam (25 mg, 24% yield), respectively.

The structure of 1-(4-(benzo[d][1,3]dioxol-5-yl(pyridin-3-yl)amino)piperidine-1-carbonyl)-1H-benzo[d][1,2,3]triazole-6-carbonitrile was tentatively assigned.

$^1$H NMR (400 MHz, CDCl$_3$) δ 8.39 (s, 1H), 8.20 (d, J=8.5 Hz, 1H), 8.08 (d, J=3.0 Hz, 1H), 8.01 (dd, J=4.6, 1.3 Hz, 1H), 7.68 (dd, J=8.6, 1.4 Hz, 1H), 7.07 (dd, J=8.5, 4.6 Hz, 1H), 6.85 (m, 2H), 6.59 (m, 2H), 6.03 (s, 2H), 4.71 (m, 2H), 4.17 (m, 1H), 3.40-3.22 (m, 2H), 2.17 (m, 2H), 1.70 (m, 2H).

The structure of 1-(4-(benzo[d][1,3]dioxol-5-yl(pyridin-3-yl)amino)piperidine-1-carbonyl)-1H-benzo[d][1,2,3]triazole-5-carbonitrile was tentatively assigned.

$^1$H NMR (400 MHz, CDCl$_3$) δ 8.47 (s, 1H), 8.09 (m, 2H), 8.01 (d, J=4.2 Hz, 1H), 7.81 (dd, J=8.6, 1.4 Hz, 1H), 7.08 (dd, J=8.5, 4.6 Hz, 1H), 6.85 (m, 2H), 6.59 (m, 2H), 6.03 (s, 2H), 4.68 (m, 2H), 4.16 (m, 1H), 3.39-3.22 (m, 2H), 2.17 (m, 2H), 1.71 (m, 2H).

Scheme IX

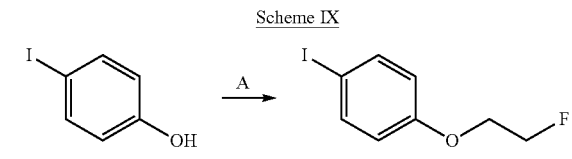

Reagents and conditions: A) 1-Fluoro-2-iodoethane, K$_2$CO$_3$, acetone, reflux, 36 h.

Synthesis of 1-(4-((4-fluorophenyl)(4-(vinyloxy)phenyl)amino)piperidine-1-carbonyl)-1H-benzo[d][1,2,3]triazole-6-carbonitrile (Example-76) and 1-(4-((4-fluorophenyl)(4-(vinyloxy)phenyl)amino)piperidine-1-carbonyl)-1H-benzo[d][1,2,3]triazole-5-carbonitrile (Example-77)

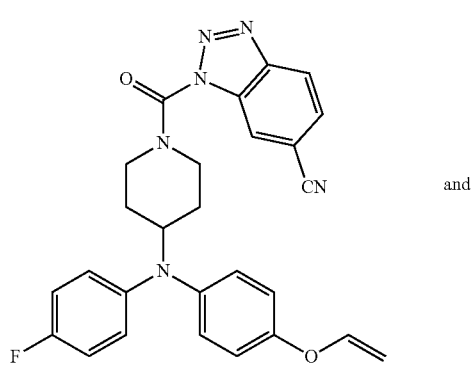

and

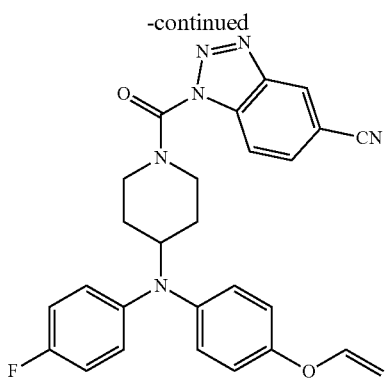

Step 1. Preparation of 1-(2-fluoroethoxy)-4-iodobenzene

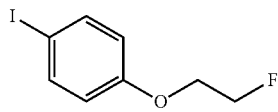 [SMILES: FCCOc1ccc(I)cc1]

To a solution of 4-iodophenol (1.55 g, 7.05 mmol) and 1-fluoro-2-iodoethane (1.47 g, 8.45 mmol) in acetone (28 mL) was added potassium carbonate (1.46 g, 10.6 mmol), and the mixture was heated to reflux under nitrogen atmosphere for 36 hours. The mixture was concentrated in vacuo, and the residue was partitioned between dichloromethane (30 mL) and water (20 mL). The aqueous phase was extracted with dichloromethane (20 mL), and the combined organic layers were dried over anhydrous sodium sulfate, filtered and concentrated in vacuo. The residue was purified by column chromatography, eluting with 0% to 5% ethyl acetate in hexanes to afford the title compound as colourless crystals (1.73 g, 93% yield).

$^1$H NMR (400 MHz, CDCl$_3$) δ 7.57 (d, J=9.0 Hz, 2H), 6.71 (d, J=9.1 Hz, 2H), 4.82-4.68 (m, 2H), 4.22-4.13 (m, 2H).

Step 2. Preparation of tert-butyl 4-((4-fluorophenyl)(4-(vinyloxy)phenyl)amino)piperidine-1-carboxylate

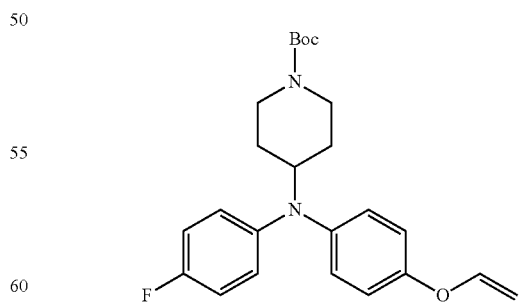

Following General Procedure O and making non-critical variations as required to replace tert-butyl 4-(benzo[d][1,3]dioxol-5-ylamino)piperidine-1-carboxylate with tert-butyl 4-((4-fluorophenyl)amino)piperidine-1-carboxylate and replace 1-iodo-3,4-methylenedioxybenzene with 1-(2-fluoroethoxy)-4-iodobenzene, the title compound was obtained as a yellow oil (162 mg, 32% yield).

$^{1}$H NMR (400 MHz, CDCl$_{3}$) δ 6.95 (m, 4H), 6.75 (m, 4H), 6.61 (dd, J=13.9, 6.1 Hz, 1H), 4.72 (dd, J=13.7, 1.7 Hz, 1H), 4.39 (dd, J=6.1, 1.6 Hz, 1H), 4.17 (m, 2H), 3.88 (m, 1H), 2.80 (m, 2H), 1.93 (m, 2H), 1.41 (s, 9H), 1.29 (m, 2H).

Step 3. Preparation of N-(4-fluorophenyl)-N-(4-(vinyloxy)phenyl)piperidin-4-amine

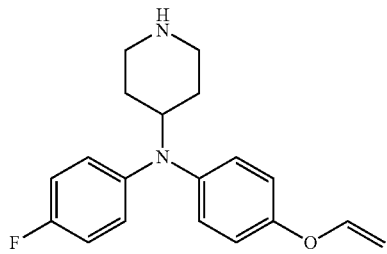 [SMILES: C=COc1ccc(N(c2ccc(F)cc2)C2CCNCC2)cc1]

Following General Procedure L and making non-critical variations as required to replace tert-butyl 4-(bis(4-fluorophenyl)amino)piperidine-1-carboxylate with tert-butyl 4-((4-fluorophenyl)(4-(vinyloxy)phenyl)amino)piperidine-1-carboxylate, the title compound was obtained as a pale oil (123 mg, 100% yield).

$^{1}$H NMR (400 MHz, CDCl$_{3}$) δ 6.94 (m, 4H), 6.76 (m, 4H), 6.60 (dd, J=13.7, 6.2 Hz, 1H), 4.71 (dd, J=13.7, 1.6 Hz, 1H), 4.38 (dd, J=6.1, 1.6 Hz, 1H), 3.85 (m, 1H), 3.15 (m, 2H), 2.74 (m, 2H), 1.96 (m, 2H), 1.40-1.30 (m, 2H) (NH not observed).

Step 4. Preparation of 1-(4-((4-fluorophenyl)(4-(vinyloxy)phenyl)amino)piperidine-1-carbonyl)-1H-benzo[d][1,2,3]triazole-6-carbonitrile (Example-76) and 1-(4-((4-fluorophenyl)(4-(vinyloxy)phenyl)amino)piperidine-1-carbonyl)-1H-benzo[d][1,2,3]triazole-5-carbonitrile (Example-77)

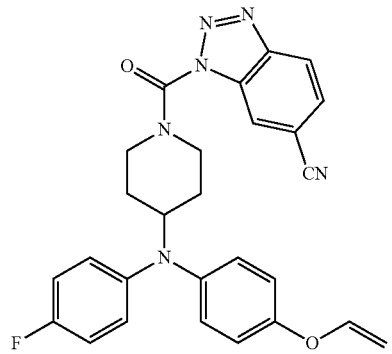

and

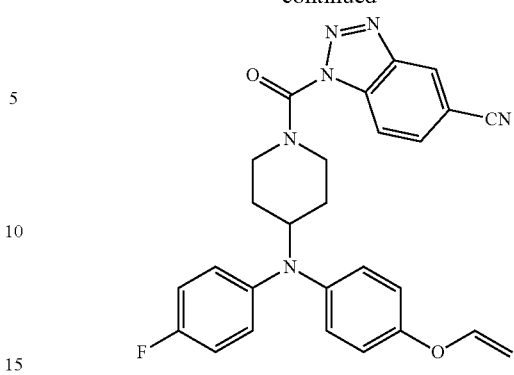

Following General Procedure M and making non-critical variations as required to replace N,N-bis(4-fluorophenyl)piperidin-4-amine with N-(4-fluorophenyl)-N-(4-(vinyloxy)phenyl)piperidin-4-amine, the title compounds were obtained as a yellow foam (42 mg, 24% yield) and a yellow foam (51 mg, 29% yield), respectively.

The structure of 1-(4-((4-fluorophenyl)(4-(vinyloxy)phenyl)amino)piperidine-1-carbonyl)-1H-benzo[d][1,2,3]triazole-6-carbonitrile was tentatively assigned.

$^{1}$H NMR (400 MHz, CDCl$_{3}$) δ 8.38 (s, 1H), 8.19 (d, J=8.5 Hz, 1H), 7.67 (dd, J=8.6, 1.5 Hz, 1H), 6.97 (m, 4H), 6.80 (m, 4H), 6.61 (dd, J=13.8, 6.1 Hz, 1H), 4.74 (dd, J=13.7, 1.6 Hz, 1H), 4.68 (m, 2H), 4.41 (dd, J=6.1, 1.6 Hz, 1H), 4.13 (m, 1H), 3.42-3.19 (m, 2H), 2.17 (m, 2H), 1.68-1.58 (m, 2H); $^{19}$F NMR (376 MHz, CDCl$_{3}$) δ −121.73 (s, 1F).

The structure of 1-(4-((4-fluorophenyl)(4-(vinyloxy)phenyl)amino)piperidine-1-carbonyl)-1H-benzo[d][1,2,3]triazole-5-carbonitrile was tentatively assigned.

$^{1}$H NMR (400 MHz, CDCl$_{3}$) δ 8.46 (s, 1H), 8.08 (d, J=8.6 Hz, 1H), 7.80 (dd, J=8.6, 1.4 Hz, 1H), 6.97 (m, 4H), 6.80 (m, 4H), 6.61 (dd, J=13.5, 6.0 Hz, 1H), 4.74 (dd, J=13.7, 1.6 Hz, 1H), 4.65 (m, 2H), 4.41 (dd, J=6.1, 1.6 Hz, 1H), 4.13 (m, 1H), 3.42-3.19 (m, 2H), 2.17 (m, 2H), 1.68-1.58 (m, 2H); $^{19}$F NMR (376 MHz, CDCl$_{3}$) δ −121.72 (s, 1F).

Scheme VII: Synthesis of (1S,4S)-(5-(bis(4H-benzo[d][1,3]dioxin-6-yl)methyl)-2,5-diazabicyclo[2.2.1]heptan-2-yl)methanone

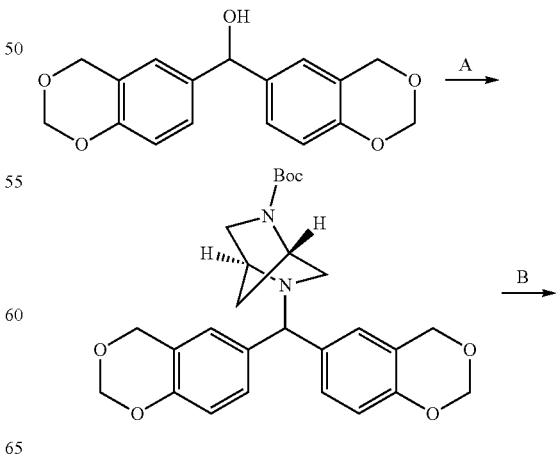

-continued

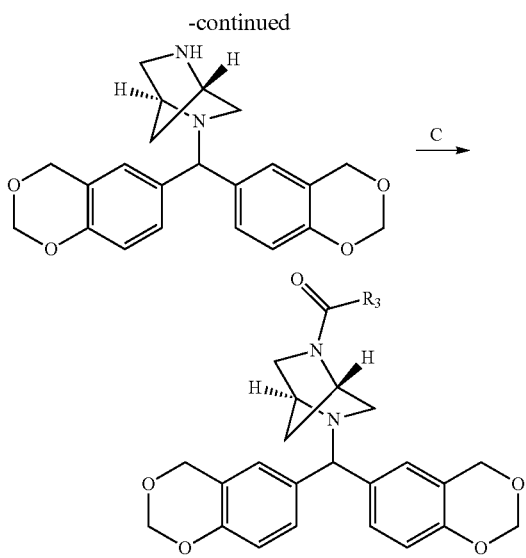

Reagents and conditions: A) i) SOCl₂, DCM, 0° C. to rt, 3 h; ii) (1S,4S)-2-Boc-2,5-diazabicyclo[2.2.1]heptane, Cs₂CO₃, DMF, 80° C., 17 h; B) TMSI, NMM, DCM, rt, 1 h; C) i) Triphosgene, DCM, 0° C.; ii) (1S,4S)-2-(Bis(4H-benzo[d][1,3]dioxin-6-yl)methyl)-2,5-diazabicyclo[2.2.1]heptane, Et₃N, DCM, 0° C. to rt, 75 min; iii) R₃-H, DMAP, THF, rt, 17 h.

Synthesis of 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-6-carbonitrile and 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-5-carbonitrile (unassigned ratio of 1:1) (Example-78)

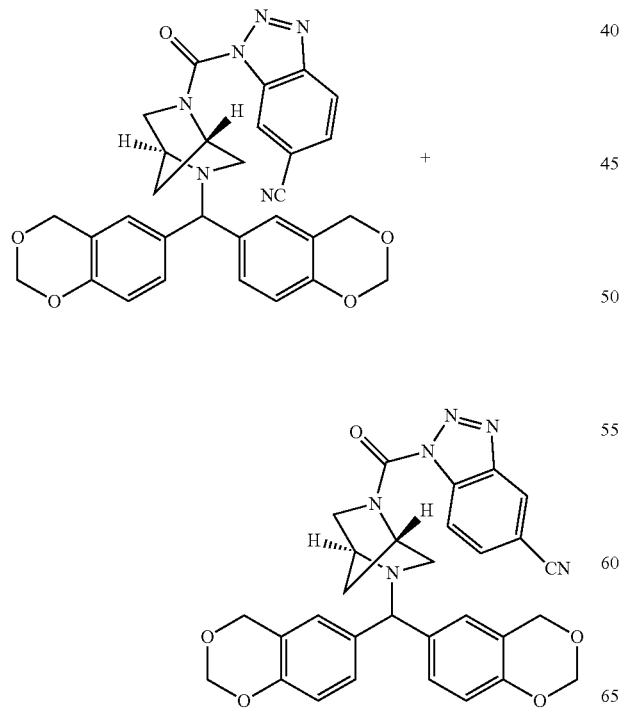

Step 1. Preparation of tert-butyl (1S,4S)-5-(bis(4H-benzo[d][1,3]dioxin-6-yl)methyl)-2,5-diazabicyclo[2.2.1]heptane-2-carboxylate

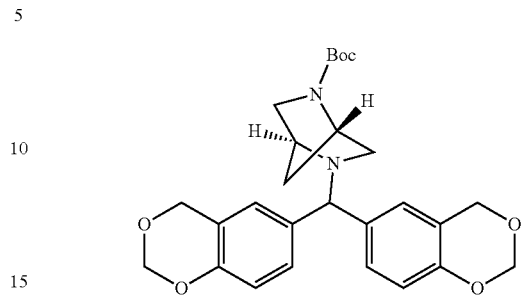

A solution of bis(4H-benzo[d][1,3]dioxin-6-yl)methanol (510 mg, 1.70 mmol) in anhydrous dichloromethane (5.7 mL) was cooled to 0° C. under nitrogen atmosphere and thionyl chloride (0.25 mL, 3.4 mmol) was added dropwise. The solution was stirred at 0° C. for 40 minutes then the reaction vessel was sealed, and the solution was stirred at ambient temperature for 3 hours.

The solution was concentrated in vacuo followed by azeotropic removal of thionyl chloride with dichloromethane (2×15 mL). The residue was dissolved in anhydrous N,N-dimethylformamide (5.7 mL) and cesium carbonate (1.11 g, 3.41 mmol) was added followed by tert-butyl (1S,4S)-2,5-diazabicyclo[2.2.1]heptane-2-carboxylate (505 mg, 2.55 mmol). The mixture was heated to 80° C. under nitrogen atmosphere for 17 hours then allowed to cool to ambient temperature. The residue was partitioned between ethyl acetate (40 mL) and water (15 mL), and the organic layer was washed with brine (5×16 mL) then dried over anhydrous sodium sulfate, filtered and concentrated in vacuo. The residue was semi-purified by column chromatography, eluting with 25% ethyl acetate in hexanes to provide a colourless foam (627 mg). Analysis by ¹H NMR (400 MHz, CDCl₃) indicated that the mixture contained a 10:1 ratio of the title compound and bis(4H-benzo[d][1,3]dioxin-6-yl)methanol, respectively.

¹H NMR (400 MHz, CDCl₃) δ 7.21 (m, 2H), 7.00 (br s, 2H), 6.77 (m, 2H), 5.19 (s, 4H), 4.86 (s, 4H), 4.43 (s, 0.6H), 4.38 (s, 0.4H), 4.35 (s, 0.4H), 4.21 (s, 0.6H), 3.59 (d, J=10.4 Hz, 0.6H), 3.44 (d, J=10.3 Hz, 0.4H), 3.38 (br s, 1H), 3.06 (d, J=10.3 Hz, 1H), 2.79 (d, J=9.9 Hz, 0.6H), 2.69 (d, J=10.0 Hz, 0.4H), 2.54 (d, J=10.0 Hz, 0.4H), 2.37 (d, J=9.9 Hz, 0.6H), 1.86 (m, 1H), 1.67 (d, J=9.6 Hz, 0.6H), 1.60 (m, 0.4H), 1.47 (s, 3.5H), 1.44 (s, 5.5H) (2 conformational isomers observed in a ratio of 8:5).

Step 2. Preparation of (1S,4S)-2-(bis(4H-benzo[d][1,3]dioxin-6-yl)methyl)-2,5-diazabicyclo[2.2.1]heptane

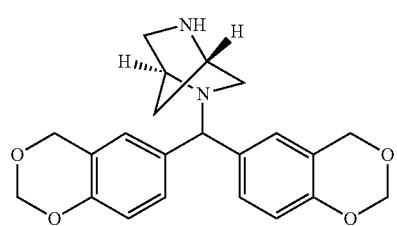 [SMILES: c1cc2c(cc1C(c1ccc3c(c1)COCO3)N1C[C@@H]3C[C@H]1CN3)COCO2]

tert-Butyl (1S,4S)-5-(bis(4H-benzo[d][1,3]dioxin-6-yl)methyl)-2,5-diazabicyclo[2.2.1]heptane-2-carboxylate (623 mg, containing bis(4H-benzo[d][1,3]dioxin-6-yl)methanol as specified above) was dissolved in dichloromethane (13 mL) and stirred at ambient temperature while 4-methylmorpholine (0.57 mL, 5.2 mmol) was added followed by iodotrimethylsilane (0.46 mL, 3.2 mmol). The solution was stirred at ambient temperature for 1 hour then diluted with dichloromethane (40 mL) and washed with saturated aqueous sodium bicarbonate (20 mL) followed by 1N aqueous sodium thiosulfate (20 mL) and water (2×20 mL). The organic layer was dried over anhydrous sodium sulfate, filtered and concentrated in vacuo. The residue was purified by column chromatography, eluting with 5% to 10% methanol (containing 10% aqueous ammonium hydroxide) in dichloromethane to afford the title compound as a colourless foam (401 mg, 62% yield over 2 steps).

$^1$H NMR (400 MHz, CDCl$_3$) δ 7.21 (m, 2H), 7.00 (s, 1H), 6.99 (s, 1H), 6.77 (d, J=8.4 Hz, 1H), 6.77 (d, J=8.4 Hz, 1H), 5.19 (s, 4H), 4.86 (s, 4H), 4.42 (s, 1H), 3.55 (s, 1H), 3.29 (s, 1H), 3.22 (d, J=10.3 Hz, 1H), 2.76 (m, 2H), 2.30 (d, J=10.2 Hz, 1H), 1.86 (d, J=9.8 Hz, 1H), 1.53 (d, J=9.7 Hz, 1H) (2 conformational isomers observed in a ratio of 1:1) (NH not observed).

Step 3. Preparation of 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-6-carbonitrile and 1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-5-carbonitrile (unassigned ratio of 1:1) (Example-78)

Triphosgene (62 mg, 0.21 mmol) was dissolved in anhydrous dichloromethane (0.5 mL), and the solution was cooled to 0° C. under nitrogen atmosphere. A solution of (1S,4S)-2-(bis(4H-benzo[d][1,3]dioxin-6-yl)methyl)-2,5-diazabicyclo[2.2.1]heptane (80 mg, 0.21 mmol) and triethylamine (0.03 mL, 0.2 mmol) in anhydrous dichloromethane (1.6 mL) was added dropwise. The reaction vessel was sealed, and the mixture was stirred at ambient temperature for 75 minutes then concentrated in vacuo. Anhydrous tetrahydrofuran (2.1 mL) was added followed by 4-(dimethylamino)pyridine (26 mg, 0.21 mmol) and 1H-1,2,3-benzotriazole-5-carbonitrile (30 mg, 0.21 mmol). The mixture was sealed and stirred at ambient temperature for 17 hours. The mixture was concentrated in vacuo then purified by column chromatography, eluting with 35% ethyl acetate in hexanes to afford the title compounds as a mixture in an unassigned ratio of 1:1 as a pale foam (51 mg, 63% yield).

$^1$H NMR (400 MHz, CDCl$_3$) δ 8.69 (s, 0.5H), 8.59 (s, 0.5H), 8.50 (s, 0.5H), 8.47 (s, 0.5H), 8.39 (d, J=8.7 Hz, 0.5H), 8.30 (d, J=8.6 Hz, 0.5H), 8.22 (d, J=8.5 Hz, 0.5H), 8.19 (d, J=8.6 Hz, 0.5H), 7.82 (m, 1H), 7.70 (m, 1H), 7.24 (m, 4H), 7.02 (s, 2H), 6.98 (s, 2H), 6.79 (m, 4H), 5.30 (s, 2H), 5.20 (m, 8H), 4.87 (m, 8H), 4.51 (s, 1H), 4.43 (s, 1H), 4.24 (d, J=11.1 Hz, 1H), 3.95 (m, 2H), 3.59 (m, 3H), 3.03 (d, J=10.5 Hz, 1H), 2.85 (m, 3H), 2.09 (m, 2H), 1.87 (d, J=10.2 Hz, 2H) (2 conformational isomers observed in a ratio of 1:1); MS (API-ES+) m/z 551.1 (M+1).

Scheme XI

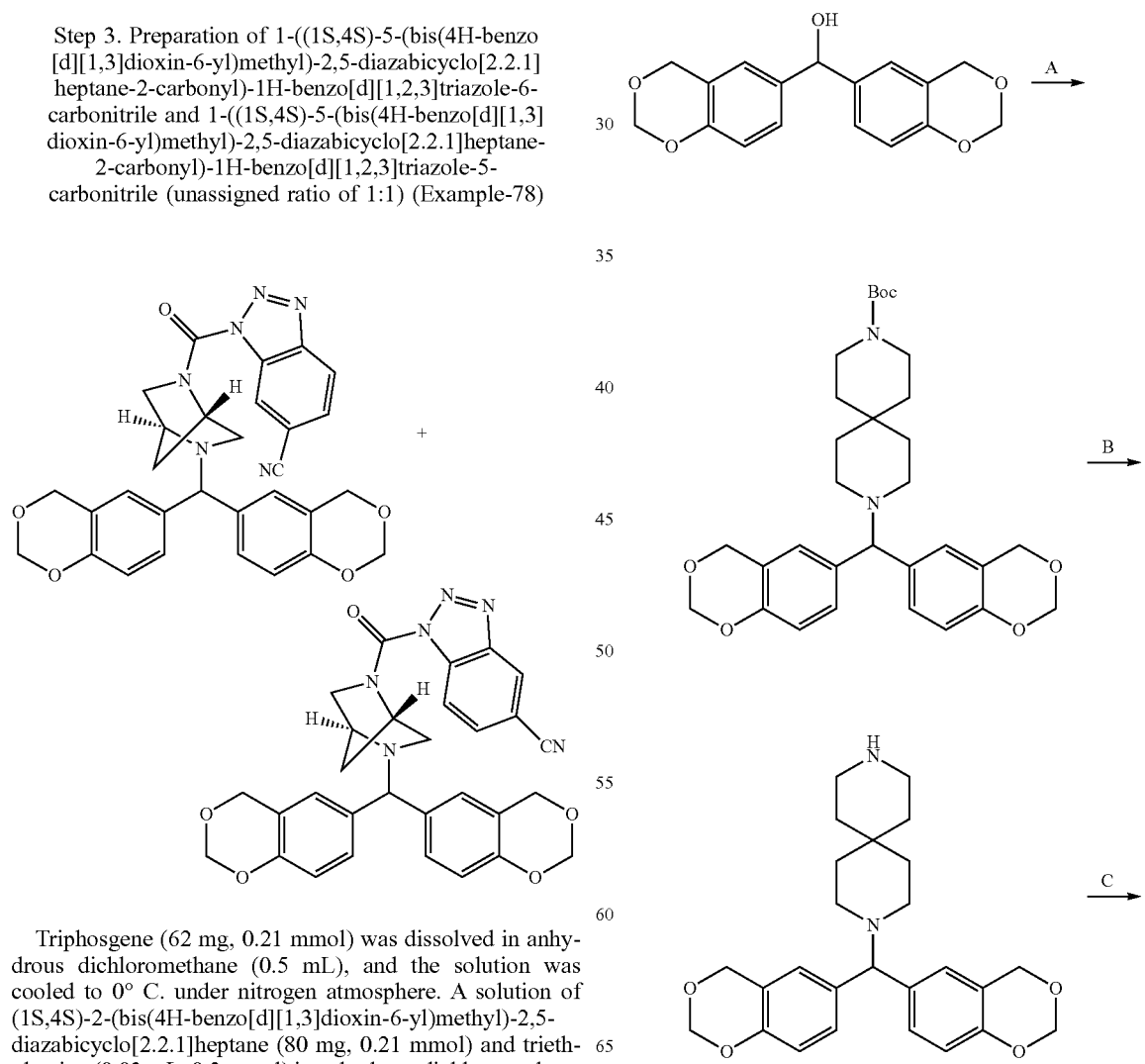

159

-continued

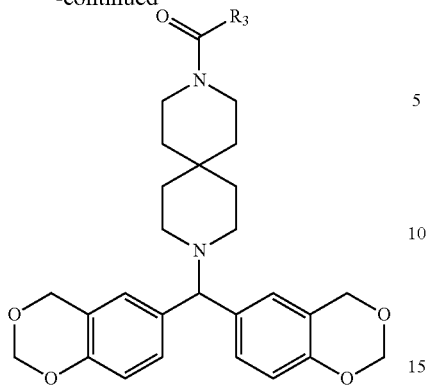

Reagents and conditions: A) i) SOCl₂, DCM, rt, 17 h; ii) tert-Butyl 3,9-diazaspiro[5.5]undecane-3-carboxylate, K₂CO₃, CH₃CN, 70° C., 36 h; B) TMSI, NMM, DCM, rt, 2 h; C) i) Triphosgene, DCM, 0° C.; ii) 3-(Bis(4H-benzo[d][1,3]dioxin-6-yl)methyl)-3,9-diazaspiro[5.5]undecane, DMAP, DCM, 0° C. to rt, 3 h; iii) R₃-H, DMAP, THF, rt, 17 h.

Synthesis of 1-(9-(bis(4H-benzo[d][1,3]dioxin-6-yl)methyl)-3,9-diazaspiro[5.5]undecane-3-carbonyl)-1H-1,2,4-triazole-3-carbonitrile (Example-79)

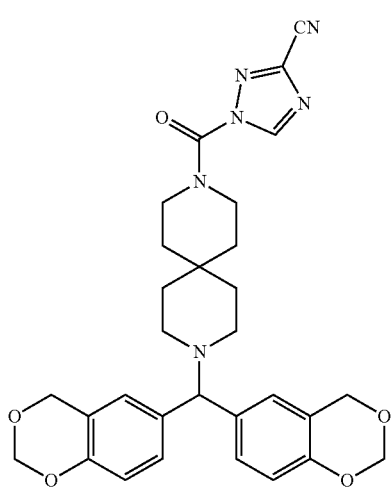 [SMILES: N#Cc1ncn(C(=O)N2CCC3(CC2)CCN(C(c2ccc4c(c2)COCO4)c2ccc4c(c2)COCO4)CC3)n1]

Step 1. Preparation of tert-butyl 9-(bis(4H-benzo[d][1,3]dioxin-6-yl)methyl)-3,9-diazaspiro[5.5]undecane-3-carboxylate

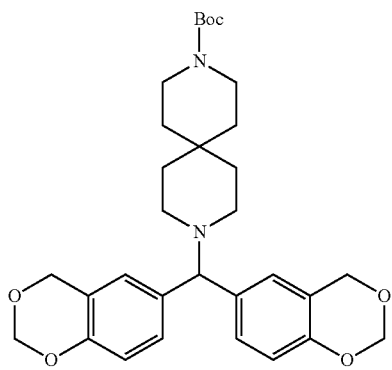 [SMILES: CC(C)(C)OC(=O)N1CCC2(CC1)CCN(C(c1ccc3c(c1)COCO3)c1ccc3c(c1)COCO3)CC2]

160

Following General Procedure Q and making non-critical variations as required to replace (4-methoxyphenyl)(pyridin-3-yl)methanol with bis(4H-benzo[d][1,3]dioxin-6-yl)methanol and replace tert-butyl piperazine-1-carboxylate with tert-butyl 3,9-diazaspiro[5.5]undecane-3-carboxylate, the title compound was obtained as a colourless foam (502 mg, 95% yield).

$^1$H NMR (400 MHz, CDCl$_3$) δ 7.15 (dd, J=8.4, 2.1 Hz, 2H), 6.92 (d, J=2.1 Hz, 2H), 6.78 (d, J=8.4 Hz, 2H), 5.20 (s, 4H), 4.86 (s, 4H), 4.05 (s, 1H), 3.33 (m, 4H), 2.28 (m, 4H), 1.48 (m, 4H), 1.44 (s, 9H), 1.39 (m, 4H).

Step 2. Preparation of 3-(bis(4H-benzo[d][1,3]dioxin-6-yl)methyl)-3,9-diazaspiro[5.5]undecane

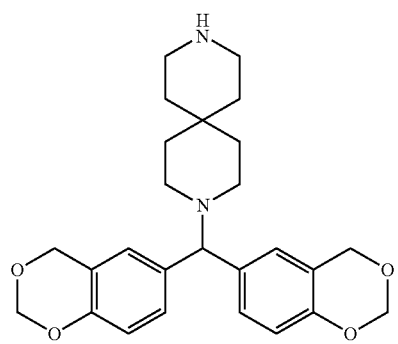 [SMILES: c1cc2c(cc1C(c1ccc3c(c1)COCO3)N1CCC3(CCNCC3)CC1)COCO2]

Following General Procedure S and making non-critical variations as required to replace tert-butyl 4-(bis(1-methyl-1H-indazol-5-yl)methyl)piperazine-1-carboxylate with 9-(bis(4H-benzo[d][1,3]dioxin-6-yl)methyl)-3,9-diazaspiro[5.5]undecane-3-carboxylate, the title compound was obtained as a colourless foam (398 mg, 98% yield).

$^1$H NMR (400 MHz, CDCl$_3$) δ 7.14 (dd, J=8.5, 2.1 Hz, 2H), 6.92 (d, J=2.1 Hz, 2H), 6.78 (d, J=8.4 Hz, 2H), 5.20 (s, 4H), 4.86 (s, 4H), 4.05 (s, 1H), 2.85 (m, 4H), 2.27 (m, 4H), 1.50 (m, 8H) (NH not observed).

Step 3. Preparation of 1-(9-(bis(4H-benzo[d][1,3]dioxin-6-yl)methyl)-3,9-diazaspiro[5.5]undecane-3-carbonyl)-1H-1,2,4-triazole-3-carbonitrile (Example-79)

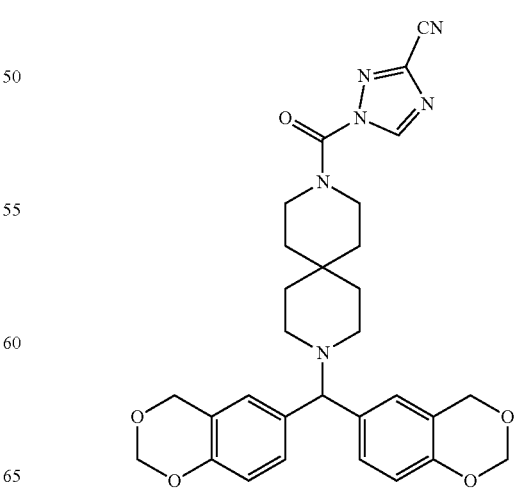

Following General Procedure M and making non-critical variations as required to replace N,N-bis(4-fluorophenyl)piperidin-4-amine with 3-(bis(4H-benzo[d][1,3]dioxin-6-yl)methyl)-3,9-diazaspiro[5.5]undecane, replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (28 mg, 34% yield).

$^1$H NMR (400 MHz, CDCl$_3$) δ 8.81 (s, 1H), 7.16 (dd, J=8.4, 2.1 Hz, 2H), 6.92 (d, J=2.1 Hz, 2H), 6.79 (d, J=8.4 Hz, 2H), 5.21 (s, 4H), 4.86 (s, 4H), 4.08 (s, 1H), 3.76-3.66 (m, 4H), 2.32 (m, 4H), 1.58 (m, 8H).

Scheme XIII

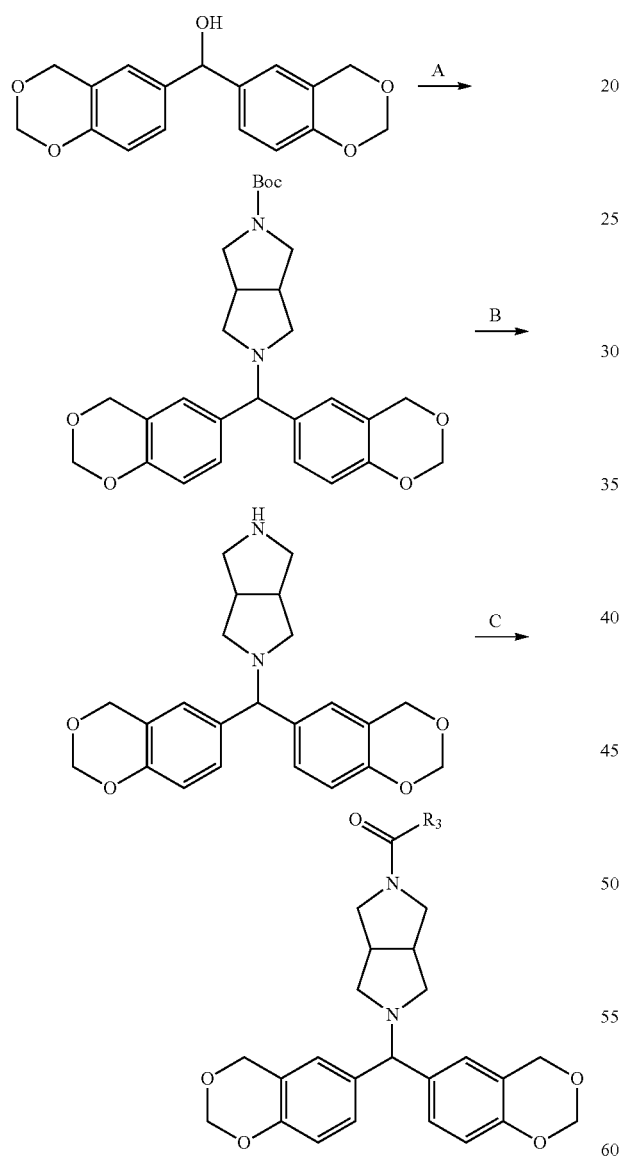

Reagents and conditions: A) i) SOCl$_2$, DCM, rt, 18 h; ii) meso-tert-Butyl hexahydropyrrolo[3,4-c]pyrrole-2(1H)-carboxylate, K$_2$CO$_3$, CH$_3$CN, 70° C., 21 h; B) TMSI, NMM, DCM, rt, 2 h; C) i) Triphosgene, DCM, 0° C.; ii) meso-2-(Bis(4H-benzo[d][1,3]dioxin-6-yl)methyl)octahydropyrrolo[3,4-c]pyrrole, DMAP, DCM, 0° C. to rt, 3 h; iii) R$_3$-H, DMAP, THF, rt, 21 h.

Synthesis of meso-1-(5-(bis(4H-benzo[d][1,3]dioxin-6-yl)methyl)octahydropyrrolo[3,4-c]pyrrole-2-carbonyl)-1H-1,2,4-triazole-3-carbonitrile (Example-81)

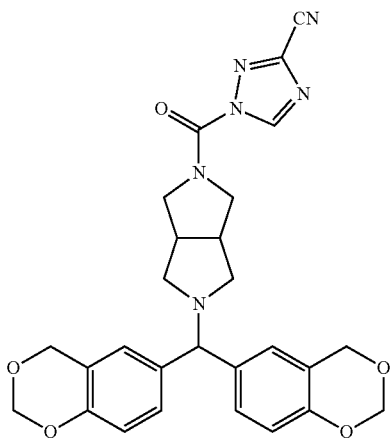

Step 1. Preparation of meso-tert-butyl 5-(bis(4H-benzo[d][1,3]dioxin-6-yl)methyl)hexahydropyrrolo[3,4-c]pyrrole-2(1H)-carboxylate

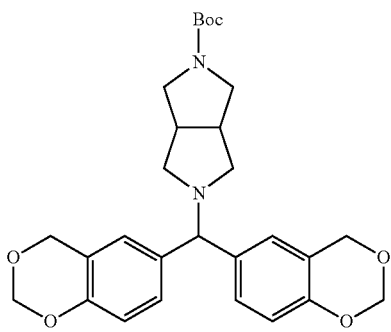

Following General Procedure Q and making non-critical variations as required to replace (4-methoxyphenyl)(pyridin-3-yl)methanol with bis(4H-benzo[d][1,3]dioxin-6-yl)methanol and replace tert-butyl piperazine-1-carboxylate with meso-tert-butyl hexahydropyrrolo[3,4-c]pyrrole-2(1H)-carboxylate, the title compound was obtained as a colourless foam (487 mg, 95% yield).

$^1$H NMR (400 MHz, CDCl$_3$) δ 7.19 (dd, J=8.5, 2.1 Hz, 2H), 6.95 (d, J=2.1 Hz, 2H), 6.78 (d, J=8.4 Hz, 2H), 5.20 (s, 4H), 4.86 (s, 4H), 3.98 (s, 1H), 3.55 (m, 2H), 3.22 (m, 2H), 2.75 (m, 2H), 2.47-2.33 (m, 4H), 1.48 (s, 9H).

Step 2. Preparation of meso-2-(bis(4H-benzo[d][1,3]dioxin-6-yl)methyl)octahydropyrrolo[3,4-c]pyrrole

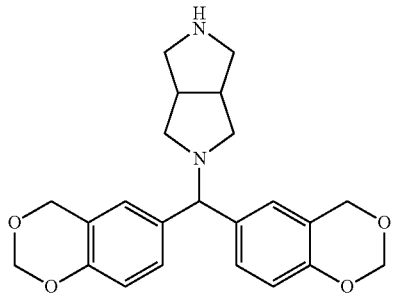

Following General Procedure S and making non-critical variations as required to replace tert-butyl 4-(bis(1-methyl-1H-indazol-5-yl)methyl)piperazine-1-carboxylate with meso-tert-butyl 5-(bis(4H-benzo[d][1,3]dioxin-6-yl)methyl)hexahydropyrrolo[3,4-c]pyrrole-2(1H)-carboxylate, the title compound was obtained as a colourless foam (351 mg, 91% yield).

$^1$H NMR (400 MHz, CDCl$_3$) δ 7.21 (m, 2H), 7.00 (d, J=2.1 Hz, 1.6H), 6.95 (d, J=2.1 Hz, 0.4H), 6.78 (d, J=8.4 Hz, 1.6H), 6.77 (d, J=8.4 Hz, 0.4H), 5.19 (s, 4H), 4.87 (s, 3.2H), 4.85 (s, 0.8H), 3.97 (s, 0.2H), 3.92 (s, 0.8H), 3.19 (m, 2H), 2.91 (m, 2H), 2.78 (m, 1.6H), 2.68 (s, 0.4H), 2.45 (m, 2H), 2.34 (m, 1.6H), 2.25 (m, 0.4H) (NH not observed) (2 conformational isomers observed in a ratio of 4:1).

Step 3. Preparation of meso-1-(5-(bis(4H-benzo[d][1,3]dioxin-6-yl)methyl)octahydropyrrolo[3,4-c]pyrrole-2-carbonyl)-1H-1,2,4-triazole-3-carbonitrile (Example-81)

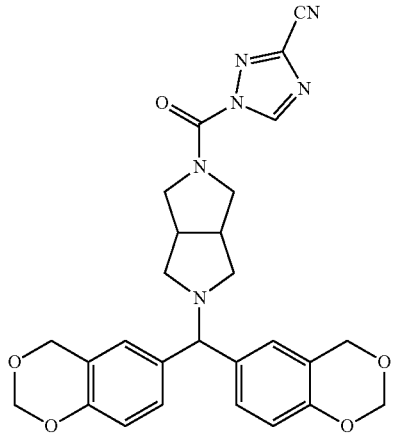 [SMILES: N#Cc1ncn(C(=O)N2CC3CN(C(c4ccc5c(c4)COCO5)c4ccc5c(c4)COCO5)CC3C2)n1]

Following General Procedure M and making non-critical variations as required to replace N,N-bis(4-fluorophenyl)piperidin-4-amine with meso-2-(bis(4H-benzo[d][1,3]dioxin-6-yl)methyl)octahydropyrrolo[3,4-c]pyrrole, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (52 mg, 60% yield).

$^1$H NMR (400 MHz, CDCl$_3$) δ 8.98 (s, 1H), 7.18 (m, 2H), 6.92 (m, 2H), 6.79 (d, J=8.4 Hz, 2H), 5.20 (s, 4H), 4.85 (s, 4H), 4.20 (m, 1H), 4.02 (s, 1H), 4.00 (m, 1H), 3.87 (m, 1H), 3.67 (m, 1H), 2.92 (m, 2H), 2.56-2.43 (m, 4H).

Scheme XIV

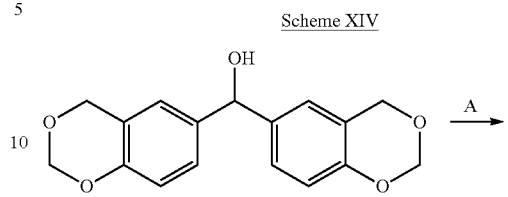

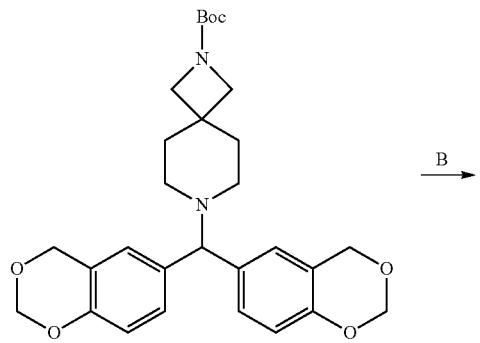

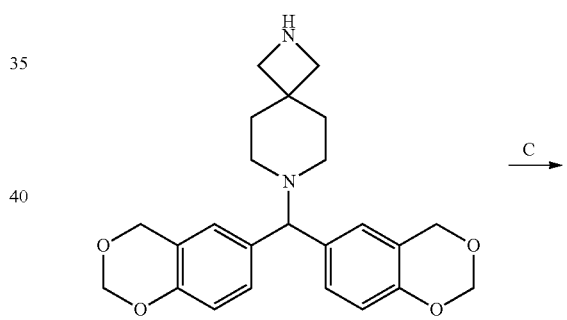

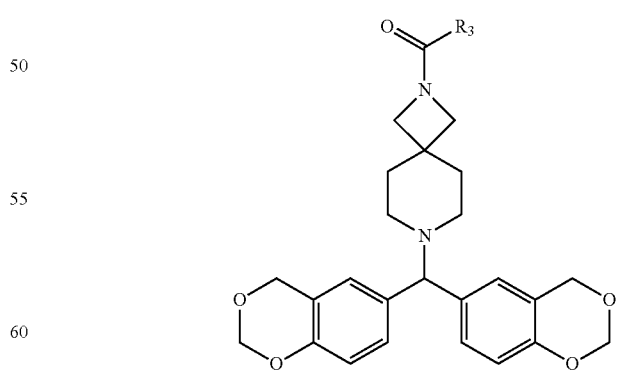

Reagents and conditions: A) i) SOCl$_2$, DCM, rt, 19 h; ii) 2-(tert-Butoxycarbonyl)-2,7-diazaspiro[3.5]nonane, K$_2$CO$_3$, CH$_3$CN, 70° C., 21 h; B) TMSI, NMM, DCM, rt, 2 h; C) i) Triphosgene, DCM, 0° C.; ii) 7-(Bis(4H-benzo[d][1,3]dioxin-6-yl)methyl)-2,7-diazaspiro[3.5]nonane, DMAP, DCM, 0° C. to rt, 3 h; iii) R$_3$-H, DMAP, THF, rt, 19 h.

Synthesis of 1-(7-(bis(4H-benzo[d][1,3]dioxin-6-yl)methyl)-2,7-diazaspiro[3.5]nonane-2-carbonyl)-1H-1,2,4-triazole-3-carbonitrile (Example-82)

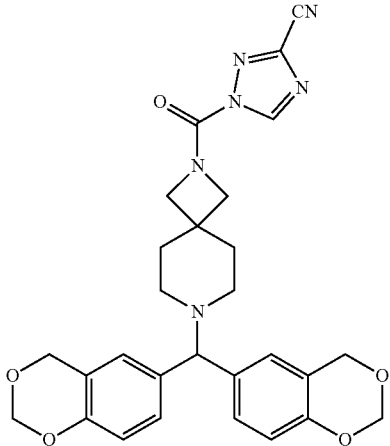 [SMILES: N#Cc1ncn(C(=O)N2CC3(CCN(C(c4ccc5c(c4)COCO5)c4ccc5c(c4)COCO5)CC3)C2)n1]

Step 1. Preparation of tert-butyl 7-(bis(4H-benzo[d][1,3]dioxin-6-yl)methyl)-2,7-diazaspiro[3.5]nonane-2-carboxylate

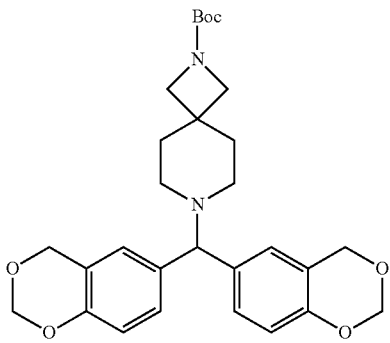 [SMILES: CC(C)(C)OC(=O)N1CC2(CCN(C(c3ccc4c(c3)COCO4)c3ccc4c(c3)COCO4)CC2)C1]

Following General Procedure Q and making non-critical variations as required to replace (4-methoxyphenyl)(pyridin-3-yl)methanol with bis(4H-benzo[d][1,3]dioxin-6-yl)methanol and replace tert-butyl piperazine-1-carboxylate with 2-(tert-butoxycarbonyl)-2,7-diazaspiro[3.5]nonane, the title compound was obtained as a colourless foam (519 mg, 91% yield).

$^1$H NMR (400 MHz, CDCl$_3$) δ 7.14 (dd, J=8.4, 2.2 Hz, 2H), 6.90 (d, J=2.1 Hz, 2H), 6.78 (d, J=8.4 Hz, 2H), 5.20 (s, 4H), 4.86 (s, 4H), 4.01 (s, 1H), 3.57 (s, 4H), 2.28-2.18 (m, 4H), 1.72 (m, 4H), 1.43 (s, 9H).

Step 2. Preparation of 7-(bis(4H-benzo[d][1,3]dioxin-6-yl)methyl)-2,7-diazaspiro[3.5]nonane

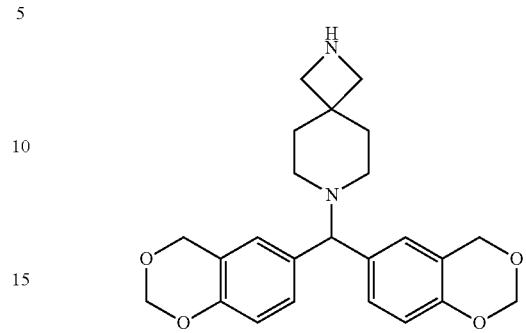

Following General Procedure S and making non-critical variations as required to replace tert-butyl 4-(bis(1-methyl-1H-indazol-5-yl)methyl)piperazine-1-carboxylate with tert-butyl 7-(bis(4H-benzo[d][1,3]dioxin-6-yl)methyl)-2,7-diazaspiro[3.5]nonane-2-carboxylate, the title compound was obtained as a pale foam (330 mg, 80% yield).

$^1$H NMR (400 MHz, CDCl$_3$) δ 7.13 (dd, J=8.4, 2.1 Hz, 2H), 6.89 (d, J=2.1 Hz, 2H), 6.78 (d, J=8.4 Hz, 2H), 5.20 (s, 4H), 4.85 (s, 4H), 4.01 (s, 1H), 3.48 (s, 4H), 2.21 (m, 4H), 1.80 (m, 4H) (NH not observed).

Step 3. Preparation of 1-(7-(bis(4H-benzo[d][1,3]dioxin-6-yl)methyl)-2,7-diazaspiro[3.5]nonane-2-carbonyl)-1H-1,2,4-triazole-3-carbonitrile (Example-82)

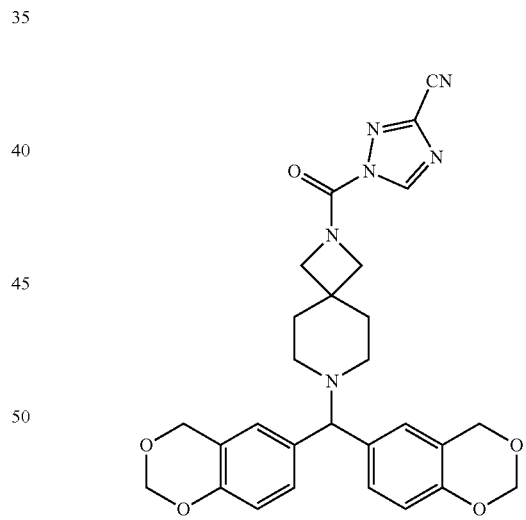

Following General Procedure M and making non-critical variations as required to replace N,N-bis(4-fluorophenyl)piperidin-4-amine with 7-(bis(4H-benzo[d][1,3]dioxin-6-yl)methyl)-2,7-diazaspiro[3.5]nonane, replace 1H-1,2,3-benzotriazole-5-carbonitrile with 2H-1,2,4-triazole-3-carbonitrile and replace triethylamine with 4-(dimethylamino)pyridine, the title compound was obtained as a yellow foam (44 mg, 50% yield).

$^1$H NMR (400 MHz, CDCl$_3$) δ 8.92 (s, 1H), 7.16 (dd, J=8.5, 2.1 Hz, 2H), 6.91 (d, J=2.1 Hz, 2H), 6.80 (d, J=8.4 Hz, 2H), 5.21 (s, 4H), 4.86 (s, 4H), 4.32 (s, 2H), 4.05 (s, 1H), 3.91 (s, 2H), 2.37-2.23 (m, 4H), 1.82 (m, 4H).

167

Scheme XV

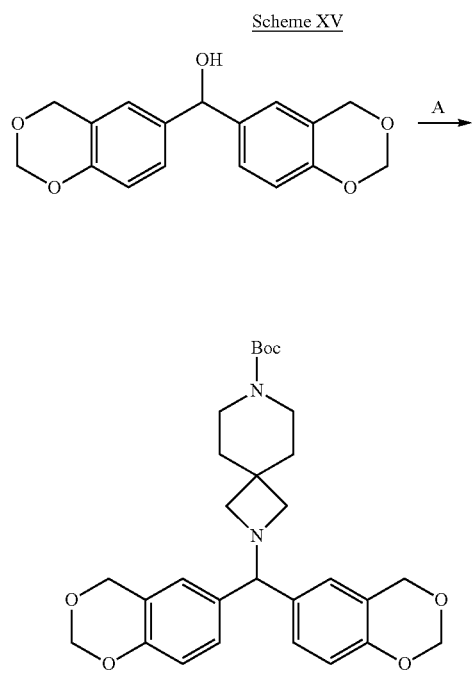

Reagents and conditions: A) i) SOCl₂, DCM, rt, 18 h; ii) tert-Butyl 2,7-diazaspiro[3.5]nonane-7-carboxylate, K₂CO₃, CH₃CN, 70° C., 36 h; B) TMSI, NMM, DCM, rt, 2 h; C) i) Triphosgene, DCM, 0° C.; ii) 2-(Bis(4H-benzo[d][1,3]dioxin-6-yl)methyl)-2,7-diazaspiro[3.5]nonane, DMAP, DCM, 0° C. to rt, 3 h; iii) R₃-H, DMAP, THF, rt, 16 h.

168

Synthesis of 1-(2-(bis(4H-benzo[d][1,3]dioxin-6-yl) methyl)-2,7-diazaspiro[3.5]nonane-7-carbonyl)-1H-1,2,4-triazole-3-carbonitrile (Example-83)

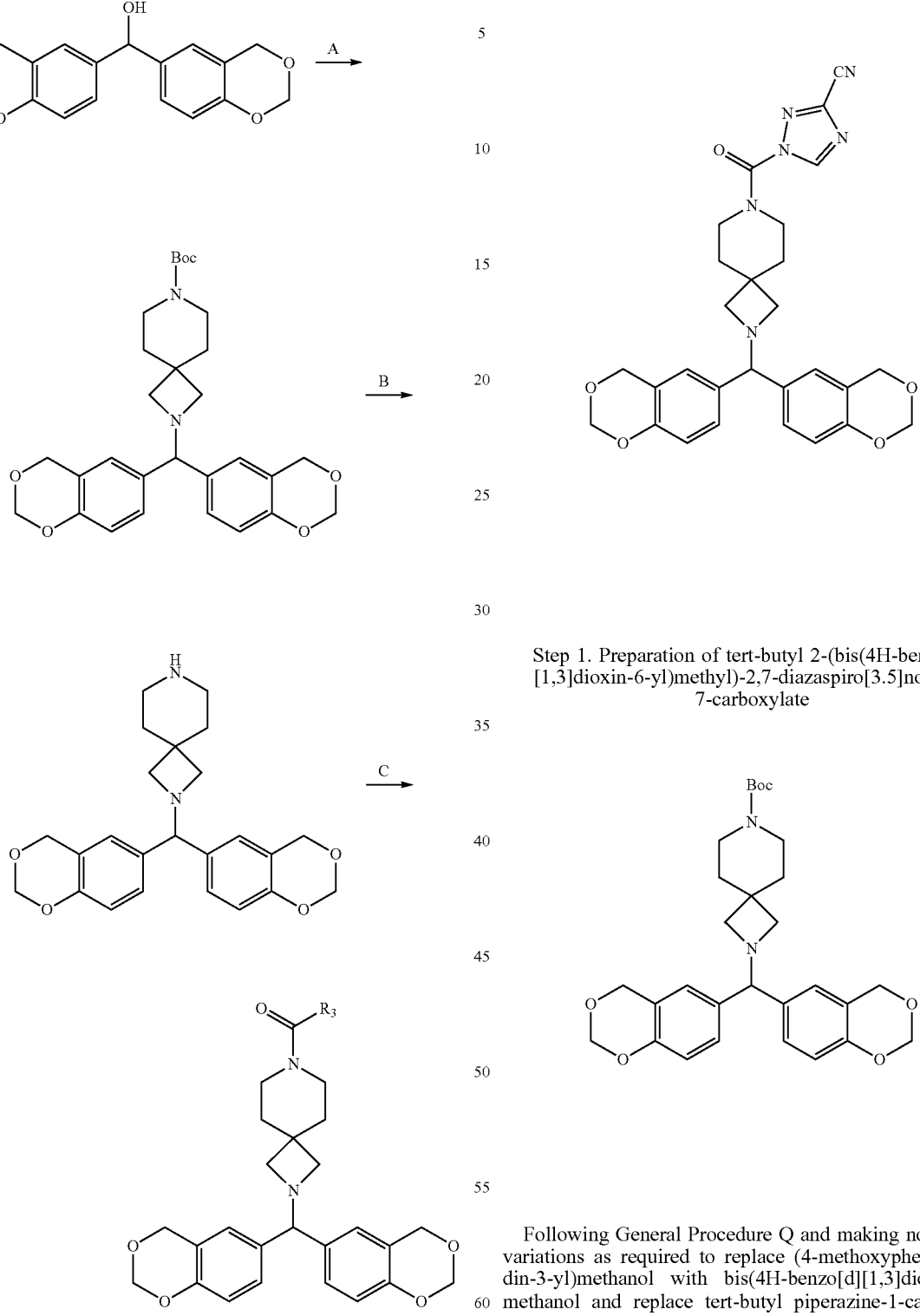

Step 1. Preparation of tert-butyl 2-(bis(4H-benzo[d][1,3]dioxin-6-yl)methyl)-2,7-diazaspiro[3.5]nonane-7-carboxylate Following General Procedure Q and making non-critical variations as required to replace (4-methoxyphenyl)(pyridin-3-yl)methanol with bis(4H-benzo[d][1,3]dioxin-6-yl) methanol and replace tert-butyl piperazine-1-carboxylate with tert-butyl 2,7-diazaspiro[3.5]nonane-7-carboxylate, the title compound was obtained as a colourless foam (531 mg, 99% yield).

¹H NMR (400 MHz, CDCl₃) δ 7.16 (dd, J=8.5, 2.1 Hz, 2H), 6.93 (d, J=2.1 Hz, 2H), 6.77 (d, J=8.4 Hz, 2H), 5.19 (s, 4H), 4.86 (s, 4H), 4.18 (s, 1H), 3.30 (m, 4H), 2.88 (s, 4H), 1.69 (m, 4H), 1.44 (s, 9H).

Step 2. Preparation of 2-(bis(4H-benzo[d][1,3]dioxin-6-yl)methyl)-2,7-diazaspiro[3.5]nonane

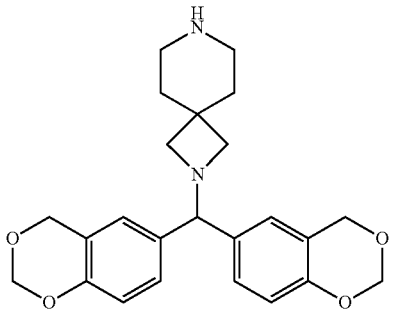 [SMILES: c1cc2c(cc1C(c1ccc3c(c1)COCO3)N1CC3(CCNCC3)C1)COCO2]

Following General Procedure S and making non-critical variations as required to replace tert-butyl 4-(bis(1-methyl-1H-indazol-5-yl)methyl)piperazine-1-carboxylate with tert-butyl 2-(bis(4H-benzo[d][1,3]dioxin-6-yl)methyl)-2,7-diazaspiro[3.5]nonane-7-carboxylate, the title compound was obtained as a colourless foam (411 mg, 97% yield).

$^1$H NMR (400 MHz, CDCl$_3$) δ 7.15 (dd, J=8.5, 2.1 Hz, 2H), 6.93 (d, J=2.1 Hz, 2H), 6.77 (d, J=8.5 Hz, 2H), 5.19 (s, 4H), 4.86 (s, 4H), 4.17 (s, 1H), 2.88 (s, 4H), 2.78 (m, 4H), 1.75 (m, 4H) (NH not observed).

Step 3. Preparation of 1-(2-(bis(4H-benzo[d][1,3]dioxin-6-yl)methyl)-2,7-diazaspiro[3.5]nonane-7-carbonyl)-1H-1,2,4-triazole-3-carbonitrile (Example-83)

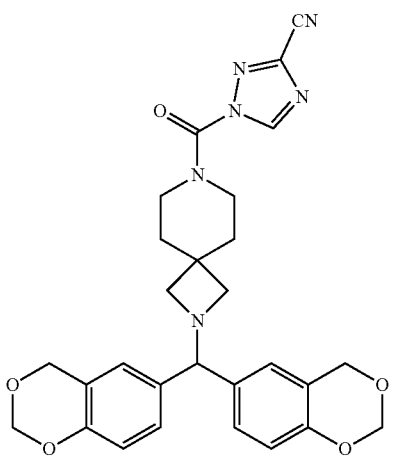 [SMILES: N#Cc1ncn(C(=O)N2CCC3(CC2)CN(C(c2ccc4c(c2)COCO4)c2ccc4c(c2)COCO4)C3)n1]

Following General Procedure M and making non-critical variations as required to replace N,N-bis(4-fluorophenyl)piperidin-4-amine with 2-(bis(4H-benzo[d][1,3]dioxin-6-yl)methyl)-2,7-diazaspiro[3.5]nonane, replace 1H-1,2,3-benzotriazole-5-carbonitrile with 2H-1,2,4-triazole-3-carbonitrile and replace triethylamine with 4-(dimethylamino)pyridine, the title compound was obtained as a yellow foam (54 mg, 64% yield).

$^1$H NMR (400 MHz, CDCl$_3$) δ 8.82 (s, 1H), 7.17 (dd, J=8.4, 2.1 Hz, 2H), 6.94 (d, J=2.1 Hz, 2H), 6.79 (d, J=8.4 Hz, 2H), 5.20 (s, 4H), 4.87 (s, 4H), 4.20 (s, 1H), 3.68 (m, 4H), 2.95 (s, 4H), 1.92 (m, 4H).

Scheme XVI

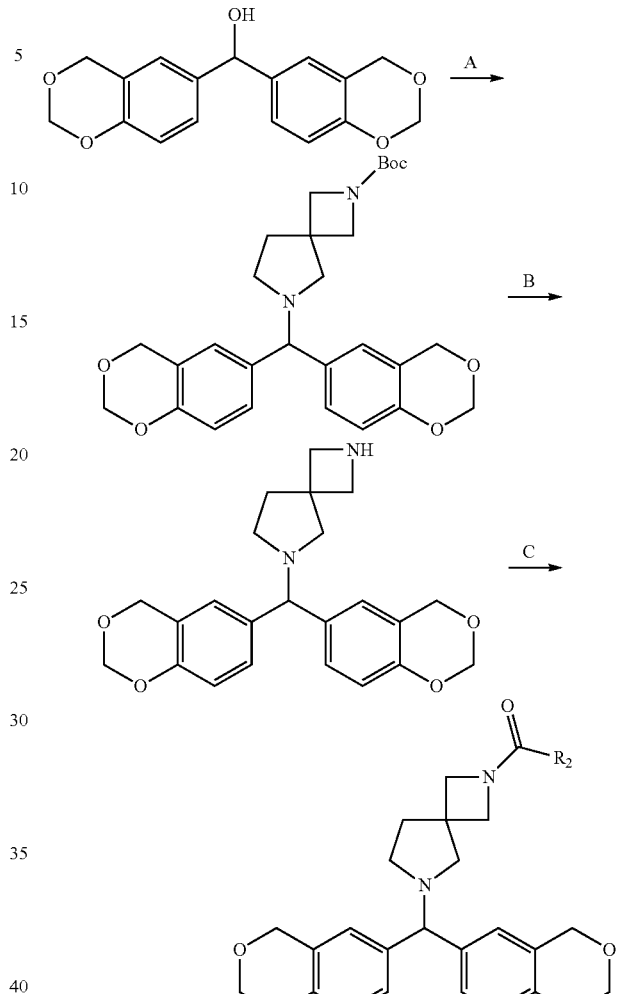

Reagents and conditions: A) i) SOCl$_2$, DCM, rt, 15 h; ii) tert-Butyl 2,6-diazaspiro[3.4]octane-2-carboxylate, K$_2$CO$_3$, CH$_3$CN, 70° C., 21 h; B) TMSI, NMM, DCM, rt, 2 h; C) i) Triphosgene, DCM, 0° C.; ii) 6-(Bis(4H-benzo[d][1,3]dioxin-6-yl)methyl)-2,6-diazaspiro[3.4]nonane, DMAP, DCM, 0° C. to rt, 3 h; iii) R$_3$-H, DMAP, THF, rt, 18 h.

Synthesis of 1-(6-(bis(4H-benzo[d][1,3]dioxin-6-yl)methyl)-2,6-diazaspiro[3.4]octane-2-carbonyl)-1H-1,2,4-triazole-3-carbonitrile (Example-84)

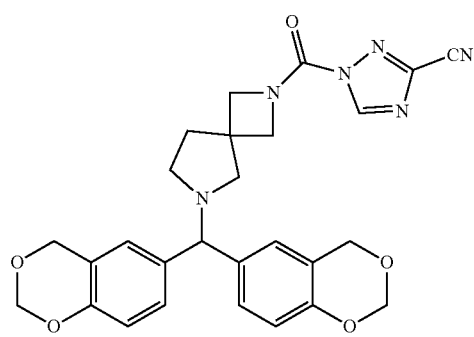 [SMILES: N#Cc1ncn(C(=O)N2CC3(CCN(C(c4ccc5c(c4)COCO5)c4ccc5c(c4)COCO5)C3)C2)n1]

Step 1. Preparation of tert-butyl 6-(bis(4H-benzo[d][1,3]dioxin-6-yl)methyl)-2,6-diazaspiro[3.4]octane-2-carboxylate

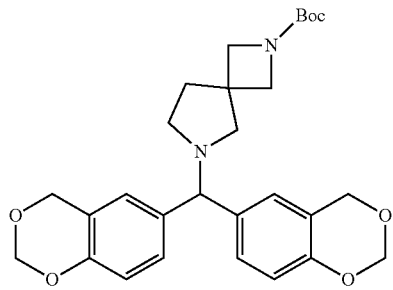 [SMILES: CC(C)(C)OC(=O)N1CC2(CCN(C(c3ccc4c(c3)COCO4)c3ccc4c(c3)COCO4)C2)C1]

Following General Procedure Q and making non-critical variations as required to replace (4-methoxyphenyl)(pyridin-3-yl)methanol with bis(4H-benzo[d][1,3]dioxin-6-yl)methanol and replace tert-butyl piperazine-1-carboxylate with tert-butyl 2,6-diazaspiro[3.4]octane-2-carboxylate, the title compound was obtained as a colourless foam (400 mg, 100% yield).

¹H NMR (400 MHz, CDCl₃) δ 7.19 (dd, J=8.4, 2.1 Hz, 2H), 6.95 (d, J=2.1 Hz, 2H), 6.78 (d, J=8.4 Hz, 2H), 5.20 (s, 4H), 4.86 (s, 4H), 4.00 (s, 1H), 3.82 (d, J=8.4 Hz, 2H), 3.79 (d, J=8.4 Hz, 2H), 2.58 (s, 2H), 2.44 (m, 2H), 2.01 (m, 2H), 1.42 (s, 9H).

Step 2. Preparation of 6-(bis(4H-benzo[d][1,3]dioxin-6-yl)methyl)-2,6-diazaspiro[3.4]octane

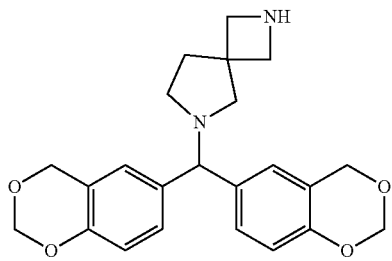 [SMILES: c1cc2c(cc1C(c1ccc3c(c1)COCO3)N1CCC3(CNC3)C1)COCO2]

Following General Procedure S and making non-critical variations as required to replace tert-butyl 4-(bis(1-methyl-1H-indazol-5-yl)methyl)piperazine-1-carboxylate with tert-butyl 6-(bis(4H-benzo[d][1,3]dioxin-6-yl)methyl)-2,6-diazaspiro[3.4]octane-2-carboxylate, the title compound was obtained as a colourless foam (261 mg, 83% yield).

¹H NMR (400 MHz, CDCl₃) δ 7.18 (dd, J=8.4, 2.1 Hz, 2H), 6.95 (d, J=2.1 Hz, 2H), 6.77 (d, J=8.4 Hz, 2H), 5.20 (s, 4H), 4.86 (s, 4H), 3.98 (s, 1H), 3.61 (d, J=7.9 Hz, 2H), 3.56 (d, J=7.9 Hz, 2H), 2.63 (s, 2H), 2.39 (m, 2H), 2.02 (m, 2H) (NH not observed).

Step 3. Preparation of 1-(6-(bis(4H-benzo[d][1,3]dioxin-6-yl)methyl)-2,6-diazaspiro[3.4]octane-2-carbonyl)-1H-1,2,4-triazole-3-carbonitrile (Example-84)

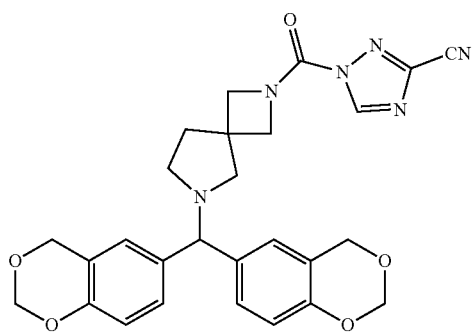 [SMILES: N#Cc1ncn(C(=O)N2CC3(CCN(C(c4ccc5c(c4)COCO5)c4ccc5c(c4)COCO5)C3)C2)n1]

Following General Procedure M and making non-critical variations as required to replace N,N-bis(4-fluorophenyl)piperidin-4-amine with 6-(bis(4H-benzo[d][1,3]dioxin-6-yl)methyl)-2,6-diazaspiro[3.4]octane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (50 mg, 59% yield).

¹H NMR (400 MHz, CDCl₃) δ 8.91 (s, 1H), 7.21 (m, 2H), 6.96 (m, 2H), 6.80 (d, J=8.4 Hz, 2H), 5.20 (s, 4H), 4.87 (s, 4H), 4.58 (d, J=10.5 Hz, 1H), 4.54 (d, J=10.5 Hz, 1H), 4.16 (d, J=10.2 Hz, 1H), 4.13 (d, J=10.2 Hz, 1H), 4.04 (s, 1H), 2.67 (d, J=9.7 Hz, 1H), 2.64 (d, J=9.7 Hz, 1H), 2.57-2.46 (m, 2H), 2.12 (m, 2H).

Scheme XVII

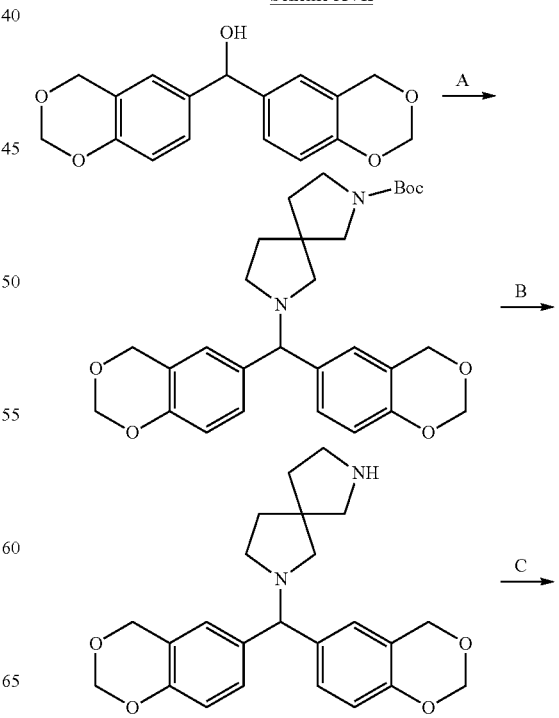

-continued

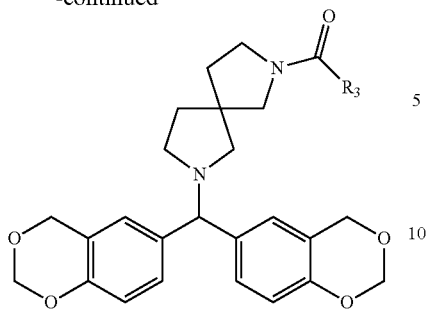

Reagents and conditions: A) i) SOCl₂, DCM, rt, 17 h; ii) tert-Butyl 2,7-diazaspiro[4.4]nonane-2-carboxylate, K₂CO₃, CH₃CN, 70° C., 21 h; B) TMSI, NMM, DCM, rt, 2 h; C) i) Triphosgene, DCM, 0° C.; ii) 2-(Bis(4H-benzo[d][1,3]dioxin-6-yl)methyl)-2,7-diazaspiro[4.4]nonane, DMAP, DCM, 0° C. to rt, 3 h; iii) R₃—H, DMAP, THF, rt, 17 h.

Synthesis of 1-(7-(bis(4H-benzo[d][1,3]dioxin-6-yl)methyl)-2,7-diazaspiro[4.4]nonane-2-carbonyl)-1H-1,2,4-triazole-3-carbonitrile (Example-85)

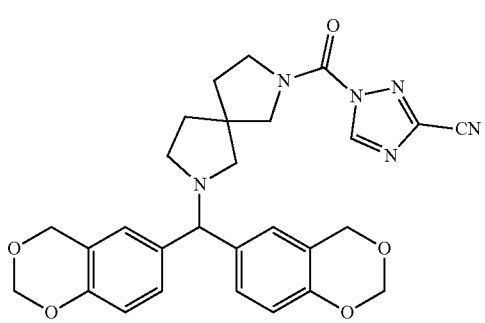 [SMILES: N#Cc1ncn(C(=O)N2CCC3(CCN(C(c4ccc5c(c4)COCO5)c4ccc5c(c4)COCO5)C3)C2)n1]

Step 1. Preparation of tert-butyl 7-(bis(4H-benzo[d][1,3]dioxin-6-yl)methyl)-2,7-diazaspiro[4.4]nonane-2-carboxylate

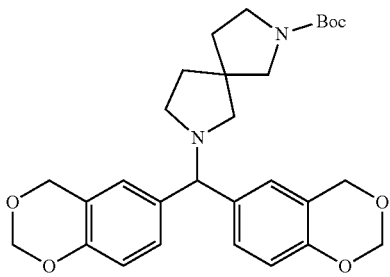 [SMILES: CC(C)(C)OC(=O)N1CCC2(CCN(C(c3ccc4c(c3)COCO4)c3ccc4c(c3)COCO4)C2)C1]

Following General Procedure Q and making non-critical variations as required to replace (4-methoxyphenyl)(pyridin-3-yl)methanol with bis(4H-benzo[d][1,3]dioxin-6-yl)methanol and replace tert-butyl piperazine-1-carboxylate with tert-butyl 2,7-diazaspiro[4.4]nonane-2-carboxylate, the title compound was obtained as a colourless foam (398 mg, 100% yield).

¹H NMR (400 MHz, CDCl₃) δ 7.20 (m, 2H), 6.96 (m, 2H), 6.78 (d, J=8.4 Hz, 2H), 5.20 (s, 4H), 4.86 (s, 4H), 4.02 (s, 0.5H), 4.01 (s, 0.5H), 3.40-3.16 (m, 4H), 2.55-2.39 (m, 3H), 2.29 (m, 1H), 1.86-1.67 (m, 4H), 1.46 (s, 4.5H), 1.44 (s, 4.5H) (2 conformational isomers observed in a ratio of 1:1).

Step 2. Preparation of 2-(bis(4H-benzo[d][1,3]dioxin-6-yl)methyl)-2,7-diazaspiro[4.4]nonane

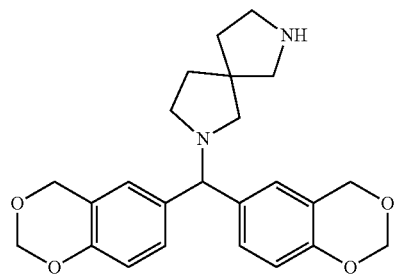 [SMILES: c1cc2c(cc1C(c1ccc3c(c1)COCO3)N1CCC3(CCNC3)C1)COCO2]

Following General Procedure S and making non-critical variations as required to replace tert-butyl 4-(bis(1-methyl-1H-indazol-5-yl)methyl)piperazine-1-carboxylate with tert-butyl 7-(bis(4H-benzo[d][1,3]dioxin-6-yl)methyl)-2,7-diazaspiro[4.4]nonane-2-carboxylate, the title compound was obtained as a colourless foam (291 mg, 92% yield).

¹H NMR (400 MHz, CDCl₃) δ 7.19 (m, 2H), 6.95 (d, J=2.1 Hz, 2H), 6.78 (d, J=8.4 Hz, 2H), 5.20 (s, 4H), 4.86 (s, 4H), 4.03 (s, 1H), 3.09-2.89 (m, 4H), 2.57-2.41 (m, 3H), 2.32 (m, 1H), 1.87-1.74 (m, 4H) (NH not observed).

Step 3. Preparation of 1-(7-(bis(4H-benzo[d][1,3]dioxin-6-yl)methyl)-2,7-diazaspiro[4.4]nonane-2-carbonyl)-1H-1,2,4-triazole-3-carbonitrile (Example-85)

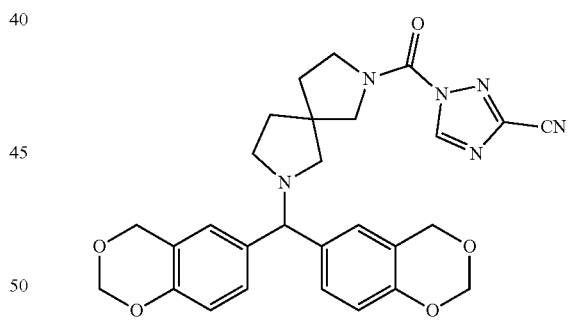

Following General Procedure M and making non-critical variations as required to replace N,N-bis(4-fluorophenyl)piperidin-4-amine with 2-(bis(4H-benzo[d][1,3]dioxin-6-yl)methyl)-2,7-diazaspiro[4.4]nonane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (38 mg, 48% yield).

¹H NMR (400 MHz, CDCl₃) δ 8.96 (s, 0.5H), 8.95 (s, 0.5H), 7.20 (m, 2H), 6.95 (m, 2H), 6.79 (m, 2H), 5.20 (m, 4H), 4.85 (m, 4H), 4.06-4.00 (m, 0.5H), 4.05 (s, 0.5H), 4.03 (s, 0.5H), 3.93-3.59 (m, 3.5H), 2.65-2.33 (m, 4H), 2.06-1.79 (m, 4H) (2 conformational isomers observed in a ratio of 1:1).

Scheme XVIII

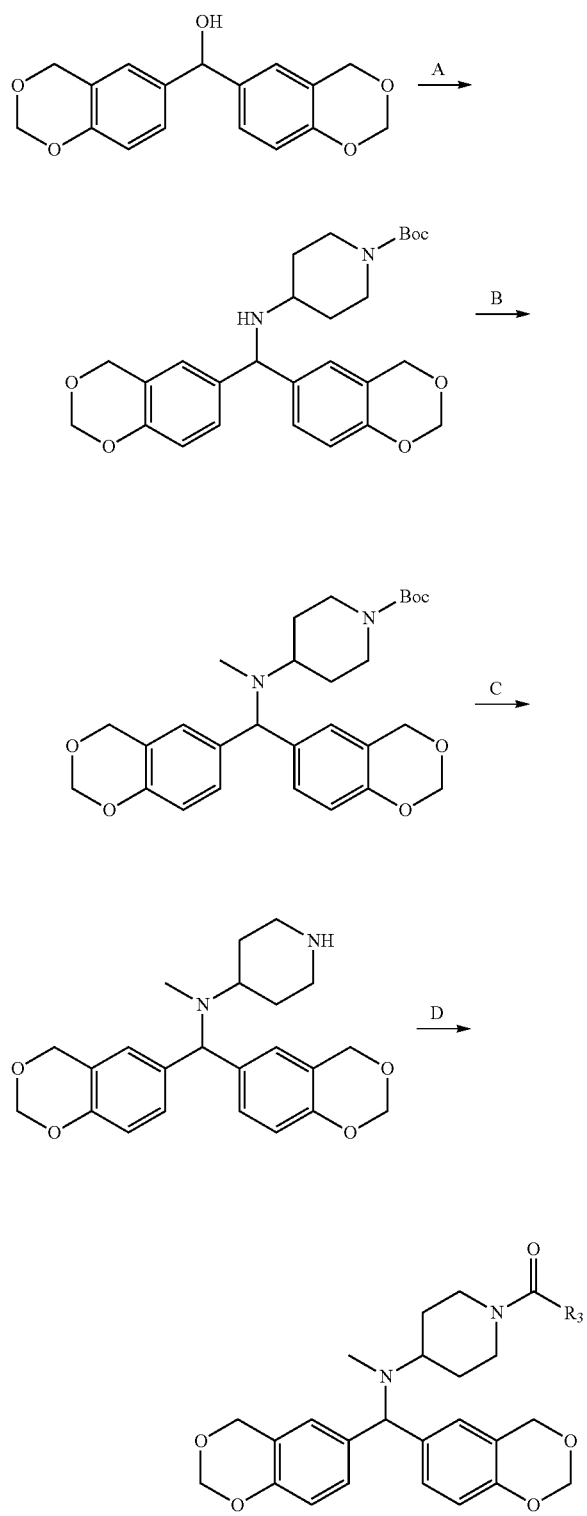

Reagents and conditions: A) i) SOCl₂, DCM, 0° C. to rt, 3 h; ii) tert-butyl 4-amino-1-piperidinecarboxylate, Cs₂CO₃, DMF, 80° C., 16 h; B) NaBH₃CN, HCHO (37%), THF, rt, 16 h; C) TMSI, NMM, DCM, rt, 1 h; D) i) Triphosgene, DCM, 0° C.; ii) N-(bis(4H-benzo[d][1,3]dioxin-6-yl)methyl)-N-methylpiperidin-4-amine, Et₃N, DCM, 0° C. to rt, 70 min; iii) R₃-H, DMAP, THF, rt.

Synthesis of 1-(4-((bis(4H-benzo[d][1,3]dioxin-6-yl)methyl)(methyl)amino)piperidine-1-carbonyl)-1H-benzo[d][1,2,3]triazole-6-carbonitrile and 1-(4-((bis(4H-benzo[d][1,3]dioxin-6-yl)methyl)(methyl)amino)piperidine-1-carbonyl)-1H-benzo[d][1,2,3]triazole-5-carbonitrile (unassigned ratio of 5:4) (Example-86)

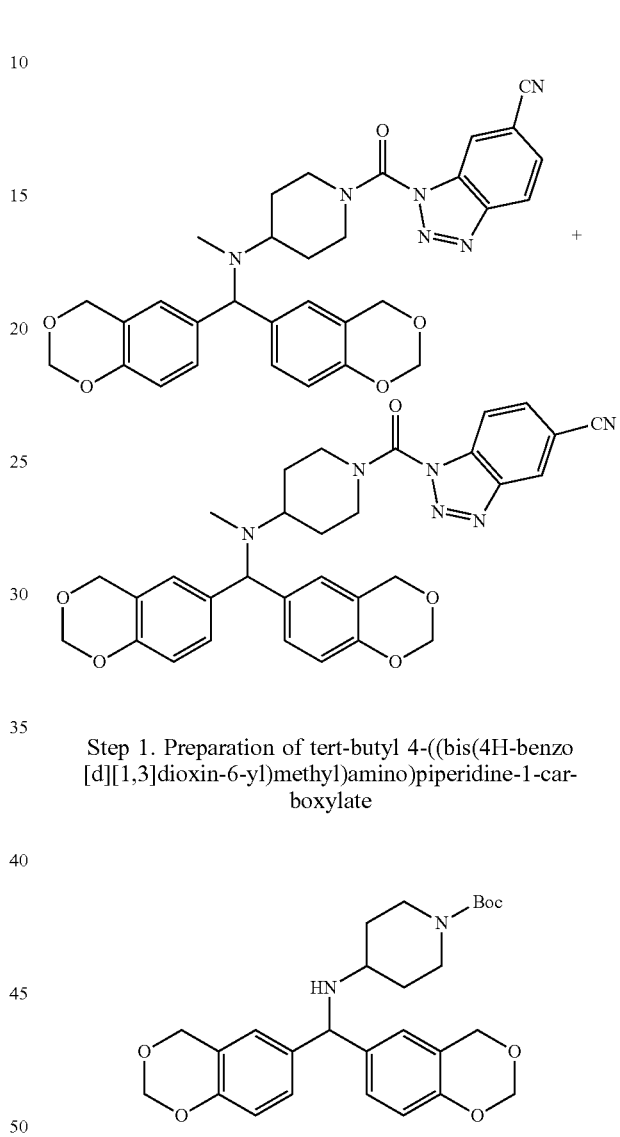

Step 1. Preparation of tert-butyl 4-((bis(4H-benzo[d][1,3]dioxin-6-yl)methyl)amino)piperidine-1-carboxylate A solution of bis(4H-benzo[d][1,3]dioxin-6-yl)methanol (1.03 g, 3.43 mmol) in anhydrous dichloromethane (11 mL) was cooled to 0° C. under nitrogen atmosphere and thionyl chloride (0.50 mL, 6.9 mmol) was added dropwise. The solution was stirred at 0° C. for 35 minutes then at ambient temperature for 3 hours. The solution was concentrated in vacuo followed by azeotropic removal of thionyl chloride with dichloromethane (2×15 mL). The residue was dissolved in anhydrous N,N-dimethylformamide (11 mL) and tert-butyl 4-amino-1-piperidinecarboxylate (1.03 g, 5.14 mmol) was added followed by cesium carbonate (2.23 g, 6.84 mmol). The mixture was heated to 80° C. under nitrogen atmosphere for 16 hours then allowed to cool to ambient temperature. The residue was partitioned between ethyl acetate (40 mL) and water (20 mL), and the organic layer was washed with brine (5×18 mL) then dried over anhydrous sodium sulfate, filtered and concentrated in vacuo. The residue was semi-purified by column chromatography, eluting with 30% ethyl acetate in hexanes to provide a colourless foam (889 mg). Analysis by $^1$H NMR (400 MHz, CDCl$_3$) indicated that the mixture contained a 3:2 ratio of the title compound and bis(4H-benzo[d][1,3]dioxin-6-yl)methanol, respectively.

$^1$H NMR (400 MHz, CDCl$_3$) δ 7.13 (m, 2H), 6.93 (s, 2H), 6.80 (d, J=8.3 Hz, 2H), 5.21 (s, 4H), 4.87 (s, 4H), 4.85 (s, 1H), 3.98 (m, 2H), 2.71 (m, 2H), 2.52 (m, 1H), 1.86 (m, 2H), 1.53 (m, 2H), 1.44 (s, 9H) (NH not observed).

Step 2. Preparation of tert-butyl 4-((bis(4H-benzo[d][1,3]dioxin-6-yl)methyl)(methyl)amino)piperidine-1-carboxylate

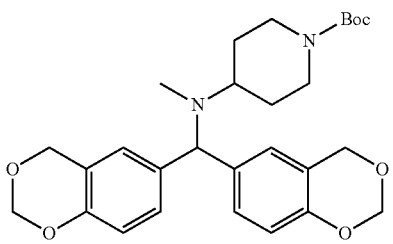 [SMILES: CN(C1CCN(C(=O)OC(C)(C)C)CC1)C(c1ccc2c(c1)COCO2)c1ccc2c(c1)COCO2]

tert-Butyl 4-((bis(4H-benzo[d][1,3]dioxin-6-yl)methyl)amino)piperidine-1-carboxylate (885 mg, containing bis(4H-benzo[d][1,3]dioxin-6-yl)methanol as specified above) was dissolved in tetrahydrofuran (18 mL) and stirred at ambient temperature while sodium cyanoborohydride (230 mg, 3.66 mmol) was added followed by 37% aqueous formaldehyde (0.82 mL, 11 mmol). The reaction vessel was sealed, and the mixture was stirred at ambient temperature for 16 hours then concentrated in vacuo to approximately one third volume. Ethyl acetate (30 mL) and saturated aqueous sodium bicarbonate (10 mL) were added, and the organic phase was washed with brine (10 mL) then dried over anhydrous sodium sulfate, filtered and concentrated in vacuo. The residue was purified by column chromatography, eluting with 20% ethyl acetate in hexanes to afford the title compound as a colourless foam (536 mg, 32% yield over 2 steps).

$^1$H NMR (400 MHz, CDCl$_3$) δ 7.17 (m, 2H), 6.92 (br s, 2H), 6.78 (d, J=8.4 Hz, 2H), 5.21 (s, 4H), 4.86 (s, 4H), 4.48 (s, 1H), 4.09 (m, 2H), 2.66 (m, 1H), 2.47 (m, 2H), 2.03 (s, 3H), 1.64-1.49 (m, 4H), 1.44 (s, 9H).

Step 3. Preparation of N-(bis(4H-benzo[d][1,3]dioxin-6-yl)methyl)-N-methylpiperidin-4-amine

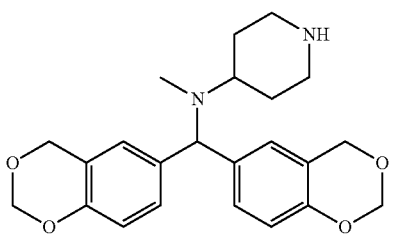 [SMILES: CN(C1CCNCC1)C(c1ccc2c(c1)COCO2)c1ccc2c(c1)COCO2]

tert-Butyl 4-((bis(4H-benzo[d][1,3]dioxin-6-yl)methyl)(methyl)amino)piperidine-1-carboxylate (532 mg, 1.07 mmol) was dissolved in dichloromethane (11 mL) and stirred at ambient temperature while 4-methylmorpholine (0.47 mL, 4.3 mmol) was added followed by iodotrimethylsilane (0.38 mL, 2.7 mmol). The solution was stirred at ambient temperature for 1 hour then diluted with dichloromethane (40 mL) and washed with saturated aqueous sodium bicarbonate (20 mL) followed by 1N aqueous sodium thiosulfate (20 mL) and water (2×20 mL). The organic layer was dried over anhydrous sodium sulfate, filtered and concentrated in vacuo. The residue was purified by column chromatography, eluting with 5% to 10% methanol (containing 10% aqueous ammonium hydroxide) in dichloromethane to afford the title compound as a colourless foam (398 mg, 94% yield).

$^1$H NMR (400 MHz, CDCl$_3$) δ 7.17 (m, 2H), 6.92 (br s, 2H), 6.78 (d, J=8.3 Hz, 2H), 5.21 (s, 4H), 4.86 (s, 4H), 4.48 (s, 1H), 3.12 (m, 2H), 2.64 (m, 1H), 2.43 (m, 2H), 2.06 (s, 3H), 1.70-1.57 (m, 4H) (NH not observed).

Step 4. Preparation of 1-(4-((bis(4H-benzo[d][1,3]dioxin-6-yl)methyl)(methyl)amino)piperidine-1-carbonyl)-1H-benzo[d][1,2,3]triazole-6-carbonitrile and 1-(4-((bis(4H-benzo[d][1,3]dioxin-6-yl)methyl)(methyl)amino)piperidine-1-carbonyl)-1H-benzo[d][1,2,3]triazole-5-carbonitrile (unassigned ratio of 5:4) (Example-86)

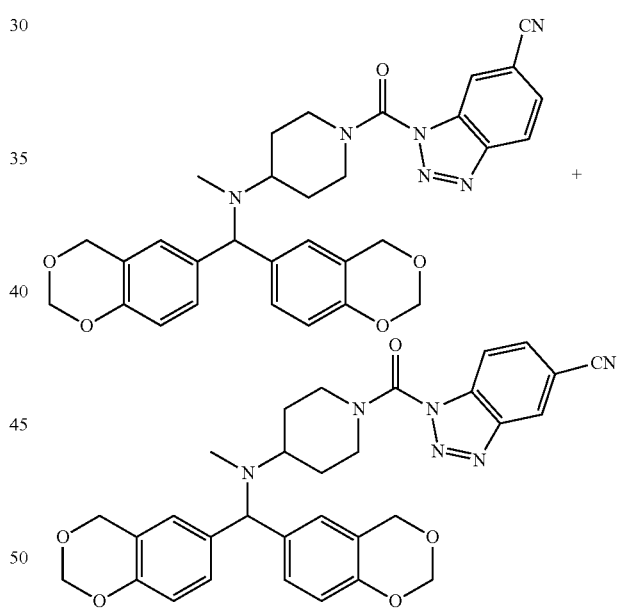

Triphosgene (70 mg, 0.24 mmol) was dissolved in anhydrous dichloromethane (0.6 mL), and the solution was cooled to 0° C. under nitrogen atmosphere. A solution of N-(bis(4H-benzo[d][1,3]dioxin-6-yl)methyl)-N-methylpiperidin-4-amine (93 mg, 0.23 mmol) and triethylamine (0.03 mL, 0.2 mmol) in anhydrous dichloromethane (1.7 mL) was added dropwise. The reaction vessel was sealed, and the mixture was stirred at ambient temperature for 70 minutes then concentrated in vacuo. Anhydrous tetrahydrofuran (2.3 mL) was added followed by 4-(dimethylamino)pyridine (29 mg, 0.24 mmol) and 1H-1,2,3-benzotriazole-5-carbonitrile (34 mg, 0.24 mmol). The mixture was sealed and stirred at ambient temperature for 21 hours. Ethyl acetate (25 mL) and water (8 mL) were added, and the organic phase was washed with water (8 mL) then dried over anhydrous sodium sulfate, filtered and concentrated in vacuo. The residue was purified by column chromatography, eluting with 35% ethyl acetate in hexanes to afford the title compounds as a mixture in an unassigned ratio of 5:4 as a light brown foam (13 mg, 10% yield).

$^1$H NMR (400 MHz, CDCl$_3$) δ 8.47 (s, 1H), 8.39 (s, 1H), 8.20 (d, J=8.6 Hz, 1H), 8.09 (d, J=8.6 Hz, 1H), 7.80 (m, 1H), 7.68 (m, 1H), 7.20 (d, J=8.4 Hz, 4H), 6.95 (s, 4H), 6.81 (d, J=8.4 Hz, 4H), 5.22 (s, 8H), 4.87 (s, 8H), 4.56 (m, 4H), 4.52 (s, 2H), 3.09-2.88 (m, 6H), 2.11 (s, 6H), 1.86 (m, 8H).

Step 1. Preparation of (4-fluorophenyl)(4-methoxyphenyl)methanol

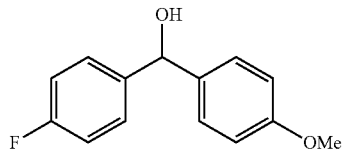

Diethyl ether (1.5 mL) was added to magnesium turnings (119 mg, 4.90 mmol), and the mixture was stirred at ambient Scheme XIX

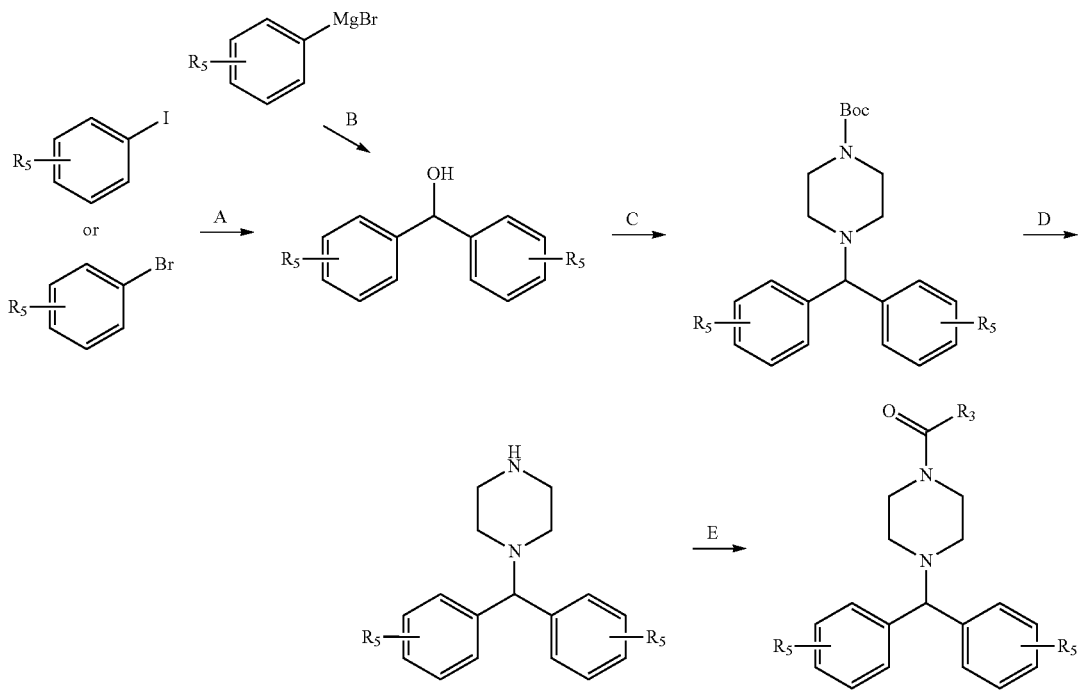

Reagents and conditions: A) Method A: i) Mg, I$_2$ (cat), Et$_2$O, rt, 2 h; ii) R$_5$—C$_6$H$_4$—CHO, Et$_2$O, 0° C. to rt, 1 h; or Method B: i-PrMgBr, THF, 0° C. to rt, 1 h; ii) R$_5$—C$_6$H$_4$—CHO, THF, 0° C. to rt, 16 h; or Method C: i) n-BuLi, THF, -78° C., 20 min to 1 h; ii) R$_5$—C$_6$H$_4$—CHO, THF, -78° C. or -78° C. to rt, 3 h; or Method D: i) n-BuLi, THF, -84° C., 30 min; ii) Ethyl formate, THF, -84° C. to rt, 3 h; B) THF, 0° C. to rt, 2 h; C) i) SOCl$_2$, DCM, 0° C. to rt, 3 h; ii) 1-Boc-piperazine, DMF or CH$_3$CN, Cs$_2$CO$_3$ or K$_2$CO$_3$, 70° C. or 80° C., 17 h; D) TMSI, NMM, DCM, rt, 55 min; E) Method A: i) Triphosgene, DCM, 0° C; ii) 1-(Bis(substituted phenyl)methyl)piperazine, DMAP, DCM, rt, 2 h; iii) R$_3$-H, DMAP, THF, rt, 15 h; or Method B: i) Triphosgene, DCM, 0° C.; ii) 1H-benzotriazole or 4-cyanopyrazole, DMAP, DCM, rt, 3 h; iii) 1-(Bis(substituted phenyl)methyl)piperazine, DMAP, THF, rt, 17 h Synthesis of 1-(4-((4-fluorophenyl)(4-methoxyphenyl)methyl)piperazine-1-carbonyl)-1H-benzo[d][1,2,3]triazole-5-carbonitrile (Example-87)

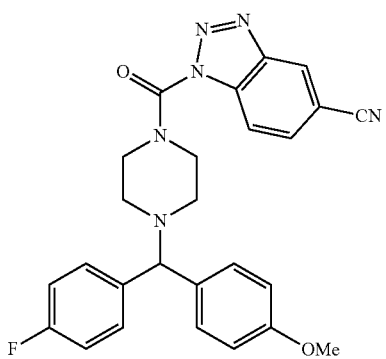 [SMILES: COc1ccc(C(c2ccc(F)cc2)N2CCN(C(=O)n3nnc4cc(C#N)ccc43)CC2)cc1]

temperature while iodine (catalytic amount) was added followed by a solution of 4-fluoroiodobenzene (985 mg, 4.44 mmol) in diethyl ether (2 mL). The mixture was heated to reflux under nitrogen atmosphere for 2 minutes then stirred at ambient temperature for 2 hours. The mixture was added to a solution of p-anisaldehyde (604 mg, 4.44 mmol) in diethyl ether (2.5 mL) at 0° C., and the mixture was stirred at ambient temperature for 1 hour then cooled to 0° C. Saturated aqueous ammonium chloride (5 mL) was added followed by dichloromethane (8 mL). The organic layer was dried over anhydrous sodium sulfate, filtered and concentrated in vacuo. The residue was purified by column chromatography, eluting with 10% to 20% ethyl acetate in hexanes to afford the title compound as a yellow oil (340 mg, 33% yield).

$^1$H NMR (400 MHz, CDCl$_3$) δ 7.34 (m, 2H), 7.26 (m, 2H), 7.02 (m, 2H), 6.87 (m, 2H), 5.80 (d, J=3.0 Hz, 1H), 3.80 (s, 3H), 2.14 (d, J=3.4 Hz, 1H).

Step 2. Preparation of tert-butyl 4-((4-fluorophenyl)(4-methoxyphenyl)methyl)piperazine-1-carboxylate

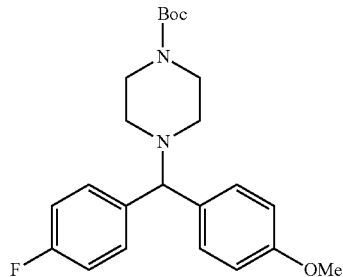 [SMILES: COc1ccc(C(c2ccc(F)cc2)N2CCN(C(=O)OC(C)(C)C)CC2)cc1]

A solution of (4-fluorophenyl)(4-methoxyphenyl)methanol (335 mg, 1.44 mmol) in anhydrous dichloromethane (4 mL) was cooled to 0° C. under nitrogen atmosphere and thionyl chloride (0.21 mL, 2.9 mmol) was added dropwise. The solution was stirred at 0° C. for 15 minutes then at ambient temperature for 4 hours. The solution was concentrated in vacuo followed by azeotropic removal of thionyl chloride with dichloromethane (3×10 mL). The residue was dissolved in anhydrous N,N-dimethylformamide (5 mL) and cesium carbonate (940 mg, 2.89 mmol) was added followed by tert-butyl piperazine-1-carboxylate (322 mg, 1.73 mmol). The mixture was heated to 80° C. under nitrogen atmosphere for 17 hours then allowed to cool to ambient temperature. The residue was partitioned between ethyl acetate (40 mL) and water (10 mL), and the organic layer was washed with brine (5×15 mL) then dried over anhydrous sodium sulfate, filtered and concentrated in vacuo. The residue was purified by column chromatography, eluting with 0% to 15% ethyl acetate in hexanes to provide the title compound as a colourless oil (343 mg, 59% yield).

$^1$H NMR (400 MHz, CDCl$_3$) δ 7.35 (m, 2H), 7.26 (m, 2H), 6.96 (m, 2H), 6.82 (m, 2H), 4.17 (s, 1H), 3.76 (s, 3H), 3.40 (m, 4H), 2.30 (m, 4H), 1.43 (s, 9H).

Step 3. Preparation of 1-((4-fluorophenyl)(4-methoxyphenyl)methyl)piperazine

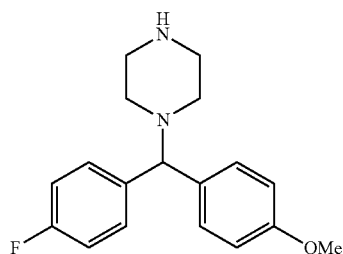 [SMILES: COc1ccc(C(c2ccc(F)cc2)N2CCNCC2)cc1]

Following General Procedure L and making non-critical variations as required to replace tert-butyl 4-(bis(4-fluorophenyl)amino)piperidine-1-carboxylate with tert-butyl 4-((4-fluorophenyl)(4-methoxyphenyl)methyl)piperazine-1-carboxylate, the title compound was obtained as a yellow oil (254 mg, 100% yield).

$^1$H NMR (400 MHz, CDCl$_3$) δ 7.35 (m, 2H), 7.27 (m, 2H), 6.95 (m, 2H), 6.81 (m, 2H), 4.17 (s, 1H), 3.76 (s, 3H), 2.92 (m, 4H), 2.37 (m, 4H) (NH not observed).

Step 4. Preparation of 1-(4-((4-fluorophenyl)(4-methoxyphenyl)methyl)piperazine-1-carbonyl)-1H-benzo[d][1,2,3]triazole-5-carbonitrile (Example-87)

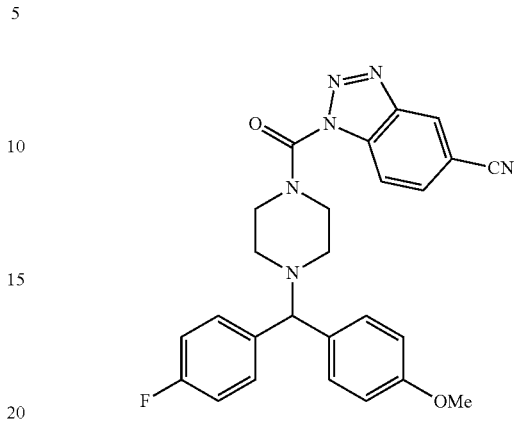

Following General Procedure M and making non-critical variations as required to replace N,N-bis(4-fluorophenyl)piperidin-4-amine with 1-((4-fluorophenyl)(4-methoxyphenyl)methyl)piperazine, the title compound was obtained as a pale foam (44 mg, 35% yield).

The structure of 1-(4-((4-fluorophenyl)(4-methoxyphenyl)methyl)piperazine-1-carbonyl)-1H-benzo[d][1,2,3]triazole-5-carbonitrile was tentatively assigned.

$^1$H NMR (400 MHz, CDCl$_3$) δ 8.46 (s, 1H), 8.11 (d, J=8.6 Hz, 1H), 7.80 (dd, J=8.6, 1.3 Hz, 1H), 7.39 (dd, J=8.5, 5.4 Hz, 2H), 7.29 (d, J=8.6 Hz, 2H), 6.99 (m, 2H), 6.85 (d, J=8.6 Hz, 2H), 4.30 (s, 1H), 3.92 (m, 4H), 3.78 (s, 3H), 2.57 (m, 4H).

Synthesis of 1-(4-(bis(4-methoxyphenyl)methyl)piperazine-1-carbonyl)-1H-benzo[d][1,2,3]triazole-6-carbonitrile (Example-88) and 1-(4-(bis(4-methoxyphenyl)methyl)piperazine-1-carbonyl)-1H-benzo[d][1,2,3]triazole-5-carbonitrile (Example-89)

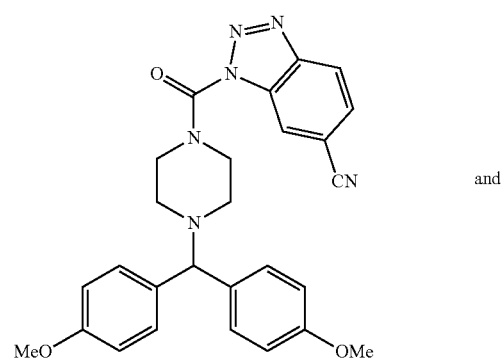 and

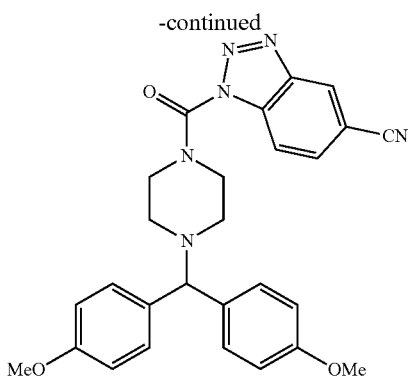

Step 1. Preparation of bis(4-methoxyphenyl)methanol

General Procedure P

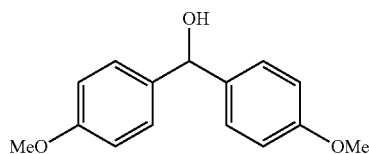 [SMILES: COc1ccc(C(O)c2ccc(OC)cc2)cc1]

A solution of 4-iodoanisole (1.06 g, 4.53 mmol) in anhydrous tetrahydrofuran (6 mL) was stirred at 0° C. under nitrogen atmosphere while isopropylmagnesium bromide (0.75 M in tetrahydrofuran, 6.04 mL, 4.5 mmol) was slowly added. The mixture was stirred at ambient temperature for 1 hour then added to a solution of p-anisaldehyde (617 mg, 4.53 mmol) in tetrahydrofuran (18 mL) at 0° C. under nitrogen atmosphere. The mixture was stirred at ambient temperature overnight then cooled to 0° C. and acidified using 1N hydrochloric acid. Ethyl acetate (15 mL) was added, and the organic layer was washed with brine (10 mL) then dried over anhydrous sodium sulfate, filtered and concentrated in vacuo. The residue was semi-purified by column chromatography, eluting with 0% to 15% ethyl acetate in hexanes to provide pale crystals (423 mg). Analysis by $^1$H NMR (400 MHz, CDCl$_3$) indicated that the mixture contained a 4:3 ratio of the title compound and an unidentified impurity, respectively.

$^1$H NMR (400 MHz, CDCl$_3$) δ 7.24 (m, 4H), 6.84 (m, 4H), 5.28 (s, 1H), 3.79 (s, 6H) (OH not observed).

Step 2. Preparation of tert-butyl 4-(bis(4-methoxyphenyl)methyl)piperazine-1-carboxylate

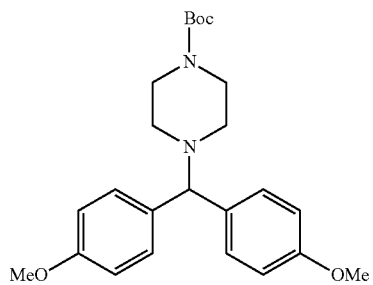 [SMILES: COc1ccc(C(c2ccc(OC)cc2)N2CCN(C(=O)OC(C)(C)C)CC2)cc1]

A solution of bis(4-methoxyphenyl)methanol (419 mg, containing an impurity as specified above) in anhydrous dichloromethane (4.3 mL) was cooled to 0° C. under nitrogen atmosphere and thionyl chloride (0.25 mL, 3.4 mmol) was added dropwise. The solution was stirred at 0° C. for 15 minutes then at ambient temperature for 3 hours. The solution was concentrated in vacuo followed by azeotropic removal of thionyl chloride with dichloromethane (3×10 mL). The residue was dissolved in anhydrous N,N-dimethylformamide (5.7 mL) and cesium carbonate (1.12 g, 3.44 mmol) was added followed by tert-butyl piperazine-1-carboxylate (383 mg, 2.06 mmol). The mixture was heated to 80° C. under nitrogen atmosphere for 18 hours then allowed to cool to ambient temperature. The residue was partitioned between ethyl acetate (30 mL) and water (20 mL), and the organic layer was washed with brine (5×15 mL) then dried over anhydrous sodium sulfate, filtered and concentrated in vacuo. The residue was purified by column chromatography, eluting with 0% to 5% ethyl acetate in dichloromethane to provide the title compound as a yellow oil (316 mg, 17% yield over 2 steps).

$^1$H NMR (400 MHz, CDCl$_3$) δ 7.29 (m, 4H), 6.81 (m, 4H), 4.14 (s, 1H), 3.76 (s, 6H), 3.40 (m, 4H), 2.31 (m, 4H), 1.43 (s, 9H).

Step 3. Preparation of 1-(bis(4-methoxyphenyl)methyl)piperazine

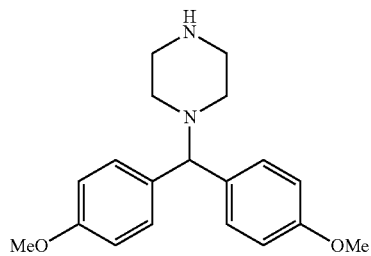 [SMILES: COc1ccc(C(c2ccc(OC)cc2)N2CCNCC2)cc1]

Following General Procedure L and making non-critical variations as required to replace tert-butyl 4-(bis(4-fluorophenyl)amino)piperidine-1-carboxylate with tert-butyl 4-(bis(4-methoxyphenyl)methyl)piperazine-1-carboxylate, the title compound was obtained as light yellow crystals (190 mg, 81% yield).

$^1$H NMR (400 MHz, CDCl$_3$) δ 7.29 (m, 4H), 6.81 (m, 4H), 4.14 (s, 1H), 3.75 (s, 6H), 2.90 (m, 4H), 2.36 (m, 4H) (NH not observed).

Step 4. Preparation of 1-(4-(bis(4-methoxyphenyl)methyl)piperazine-1-carbonyl)-1H-benzo[d][1,2,3]triazole-6-carbonitrile (Example-88) and 1-(4-(bis(4-methoxyphenyl)methyl)piperazine-1-carbonyl)-1H-benzo[d][1,2,3]triazole-5-carbonitrile (Example-89)

Synthesis of 1-(4-(bis(4-methoxyphenyl)methyl)piperazine-1-carbonyl)-1H-1,2,4-triazole-3-carbonitrile (Example-90)

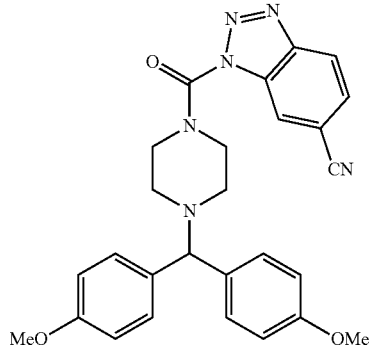

and

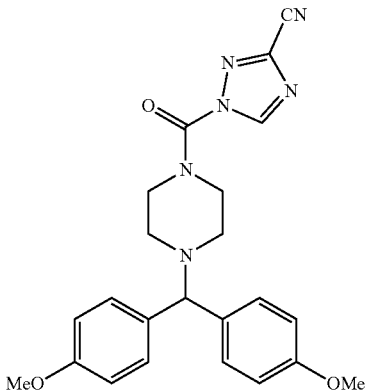 [SMILES: COc1ccc(C(c2ccc(OC)cc2)N2CCN(C(=O)n3cnc(C#N)n3)CC2)cc1]

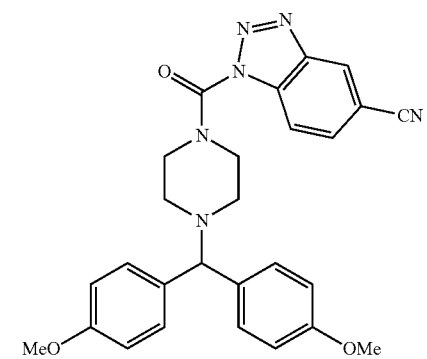

Following General Procedure M and making non-critical variations as required to replace N,N-bis(4-fluorophenyl)piperidin-4-amine with 1-(bis(4-methoxyphenyl)methyl)piperazine and replace triethylamine with 4-(dimethylamino)pyridine, the title compounds were obtained as a pale foam (44 mg, 31% yield) and a pale foam (54 mg, 38% yield), respectively.

The structure of 1-(4-(bis(4-methoxyphenyl)methyl)piperazine-1-carbonyl)-1H-benzo[d][1,2,3]triazole-6-carbonitrile was tentatively assigned.

$^1$H NMR (400 MHz, CDCl$_3$) δ 8.41 (dd, J=1.4, 0.8 Hz, 1H), 8.19 (dd, J=8.6, 0.9 Hz, 1H), 7.67 (dd, J=8.6, 1.4 Hz, 1H), 7.32 (m, 4H), 6.84 (m, 4H), 4.26 (s, 1H), 3.98-3.88 (m, 4H), 3.77 (s, 6H), 2.57 (m, 4H).

The structure of 1-(4-(bis(4-methoxyphenyl)methyl)piperazine-1-carbonyl)-1H-benzo[d][1,2,3]triazole-5-carbonitrile was tentatively assigned.

$^1$H NMR (400 MHz, CDCl$_3$) δ 8.46 (dd, J=1.4, 0.8 Hz, 1H), 8.11 (dd, J=8.7, 0.8 Hz, 1H), 7.80 (dd, J=8.6, 1.4 Hz, 1H), 7.32 (m, 4H), 6.84 (m, 4H), 4.26 (s, 1H), 3.96-3.86 (m, 4H), 3.77 (s, 6H), 2.58 (m, 4H).

Following General Procedure M and making non-critical variations as required to replace N,N-bis(4-fluorophenyl)piperidin-4-amine with 1-(bis(4-methoxyphenyl)methyl)piperazine, replace 1H-1,2,3-benzotriazole-5-carbonitrile with 4H-1,2,4-triazole-3-carbonitrile and replace triethylamine with 4-(dimethylamino)pyridine, the title compound was obtained as a pale foam (19 mg, 31% yield).

$^1$H NMR (400 MHz, CDCl$_3$) δ 8.83 (s, 1H), 7.30 (m, 4H), 6.83 (m, 4H), 4.23 (s, 1H), 3.88-3.77 (m, 4H), 3.77 (s, 6H), 2.51 (m, 4H).

Synthesis of 1-(4-(bis(2,3-dihydrobenzo[b][1,4]dioxin-6-yl)methyl)piperazine-1-carbonyl)-1H-benzo[d][1,2,3]triazole-6-carbonitrile and 1-(4-(bis(2,3-dihydrobenzo[b][1,4]dioxin-6-yl)methyl)piperazine-1-carbonyl)-1H-benzo[d][1,2,3]triazole-5-carbonitrile (unassigned ratio of 4:3) (Example-91)

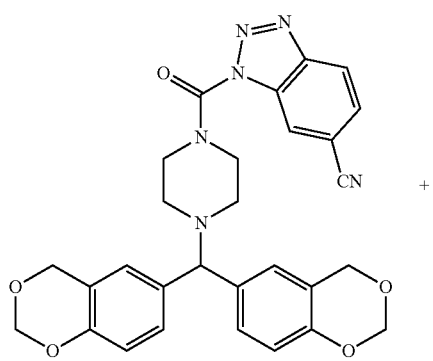 +

-continued

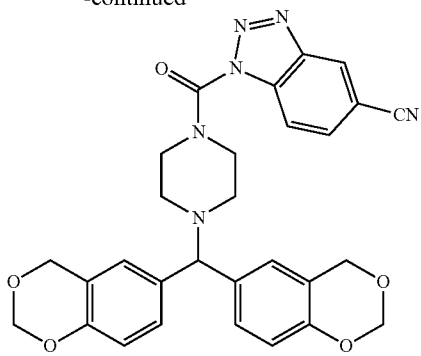

Step 1. Preparation of bis(2,3-dihydrobenzo[b][1,4]dioxin-6-yl)methanol

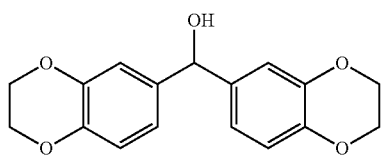 [SMILES: OC(c1ccc2c(c1)OCCO2)c1ccc2c(c1)OCCO2]

Following General Procedure P and making non-critical variations as required to replace 4-iodoanisole with 6-iodo-2,3-dihydro-1,4-benzodioxine and replace p-anisaldehyde with 2,3-dihydro-1,4-benzodioxine-6-carbaldehyde, a yellow oil (707 mg) was obtained containing the title compound plus unidentified impurities.

Step 2. Preparation of tert-butyl 4-(bis(2,3-dihydrobenzo[b][1,4]dioxin-6-yl)methyl)piperazine-1-carboxylate

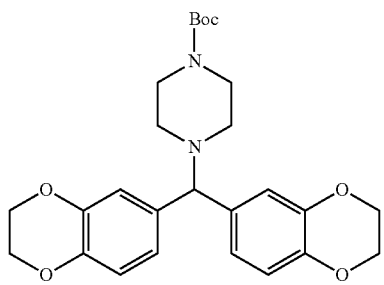 [SMILES: CC(C)(C)OC(=O)N1CCN(C(c2ccc3c(c2)OCCO3)c2ccc3c(c2)OCCO3)CC1]

A solution of bis(2,3-dihydrobenzo[b][1,4]dioxin-6-yl)methanol (702 mg, containing impurities as specified above) in anhydrous dichloromethane (6 mL) was cooled to 0° C. under nitrogen atmosphere and thionyl chloride (0.34 mL, 4.7 mmol) was added. The solution was stirred at 0° C. for 10 minutes then at ambient temperature for 3.5 hours. The solution was concentrated in vacuo followed by azeotropic removal of thionyl chloride with dichloromethane (3×10 mL). The residue was dissolved in anhydrous N,N-dimethylformamide (8 mL) and cesium carbonate (1.52 g, 4.67 mmol) was added followed by tert-butyl piperazine-1-carboxylate (522 mg, 2.80 mmol). The mixture was heated to 70° C. under nitrogen atmosphere for 3 days then allowed to cool to ambient temperature. The residue was partitioned between ethyl acetate (30 mL) and water (10 mL), and the organic layer was washed with brine (5×15 mL) then dried over anhydrous sodium sulfate, filtered and concentrated in vacuo. The residue was semi-purified by column chromatography, eluting with 0% to 5% ethyl acetate in dichloromethane to provide a yellow oil (480 mg). Analysis by $^1$H NMR (400 MHz, CDCl$_3$) indicated that the mixture contained the title compound and an unidentified impurity.

Step 3. Preparation of 1-(bis(2,3-dihydrobenzo[b][1,4]dioxin-6-yl)methyl)piperazine

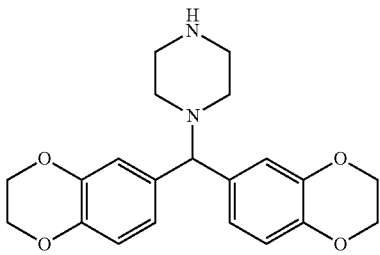 [SMILES: c1cc2c(cc1C(c1ccc3c(c1)OCCO3)N1CCNCC1)OCCO2]

Following General Procedure L and making non-critical variations as required to replace tert-butyl 4-(bis(4-fluorophenyl)amino)piperidine-1-carboxylate with tert-butyl 4-(bis(2,3-dihydrobenzo[b][1,4]dioxin-6-yl)methyl)piperazine-1-carboxylate, the title compound was obtained as a light yellow solid (193 mg, 15% yield over 3 steps).

$^1$H NMR (400 MHz, CDCl$_3$) δ 6.89 (m, 2H), 6.82 (m, 2H), 6.74 (m, 2H), 4.20 (m, 8H), 4.01 (s, 1H), 2.97 (m, 4H), 2.45 (m, 4H) (NH not observed).

Step 4. Preparation of 1-(4-(bis(2,3-dihydrobenzo[b][1,4]dioxin-6-yl)methyl)piperazine-1-carbonyl)-1H-benzo[d][1,2,3]triazole-6-carbonitrile and 1-(4-(bis(2,3-dihydrobenzo[b][1,4]dioxin-6-yl)methyl)piperazine-1-carbonyl)-1H-benzo[d][1,2,3]triazole-5-carbonitrile (unassigned ratio of 4:3) (Example-91)

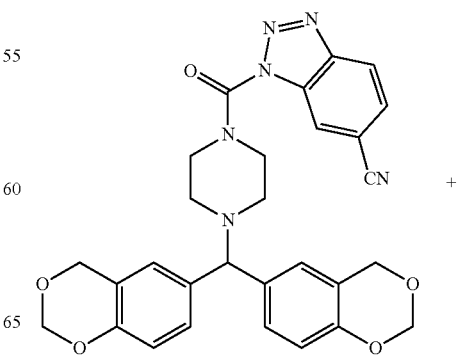

-continued

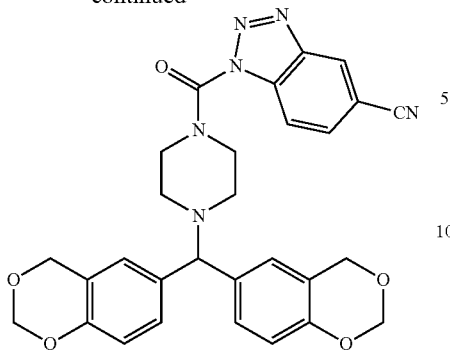

Following General Procedure M and making non-critical variations as required to replace N,N-bis(4-fluorophenyl)piperidin-4-amine with 1-(bis(2,3-dihydrobenzo[b][1,4]dioxin-6-yl)methyl)piperazine and replace triethylamine with 4-(dimethylamino)pyridine, the title compounds were obtained as a mixture in an unassigned ratio of 4:3 as a pale foam (93 mg, 70% yield).

$^1$H NMR (400 MHz, CDCl$_3$) δ 8.46 (m, 1H), 8.41 (m, 1H), 8.19 (m, 1H), 8.11 (m, 1H), 7.80 (m, 1H), 7.67 (m, 1H), 6.93 (m, 4H), 6.86 (m, 4H), 6.78 (m, 4H), 4.22 (m, 16H), 4.10 (s, 2H), 3.96-3.86 (s, 8H), 2.58 (m, 8H).

Synthesis of 1-(4-(bis(2,3-dihydrobenzo[b][1,4]dioxin-6-yl)methyl)piperazine-1-carbonyl)-1H-1,2,4-triazole-3-carbonitrile (Example-92)

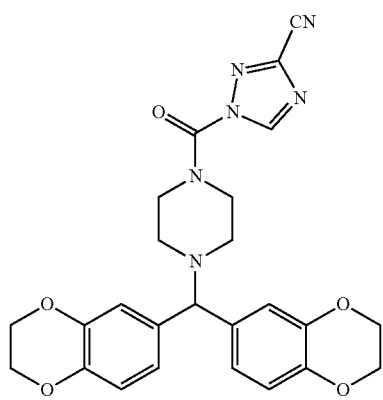 [SMILES: N#Cc1ncn(C(=O)N2CCN(C(c3ccc4c(c3)OCCO4)c3ccc4c(c3)OCCO4)CC2)n1]

Following General Procedure M and making non-critical variations as required to replace N,N-bis(4-fluorophenyl)piperidin-4-amine with 1-(bis(2,3-dihydrobenzo[b][1,4]dioxin-6-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a light yellow foam (41 mg, 66% yield).

$^1$H NMR (400 MHz, CDCl$_3$) δ 8.83 (s, 1H), 6.91 (d, J=2.1 Hz, 2H), 6.84 (dd, J=8.4, 2.0 Hz, 2H), 6.77 (d, J=8.3 Hz, 2H), 4.22 (m, 8H), 4.06 (s, 1H), 3.88-3.76 (m, 4H), 2.51 (m, 4H).

Synthesis of 1-(4-(bis(3,4-dimethoxyphenyl)methyl)piperazine-1-carbonyl)-1H-benzo[d][1,2,3]triazole-6-carbonitrile (Example-93) and 1-(4-(bis(3,4-dimethoxyphenyl)methyl)piperazine-1-carbonyl)-1H-benzo[d][1,2,3]triazole-5-carbonitrile (Example-94)

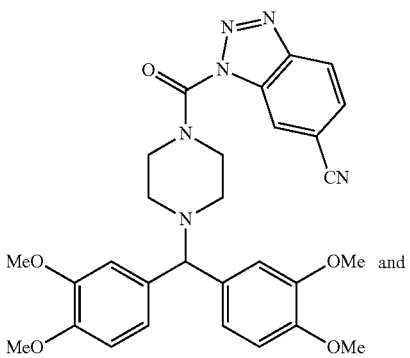

and

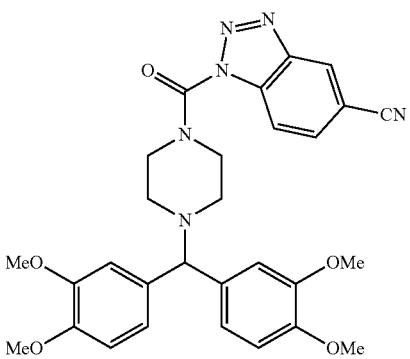

Step 1. Preparation of bis(3,4-dimethoxyphenyl)methanol

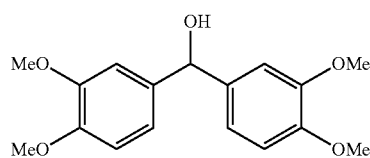 [SMILES: COc1ccc(C(O)c2ccc(OC)c(OC)c2)cc1OC]

Following General Procedure P and making non-critical variations as required to replace 4-iodoanisole with 3,4-dimethoxyiodobenzene and replace p-anisaldehyde with 3,4-dimethoxybenzaldehyde, a yellow oil (381 mg) was obtained containing the title compound plus unidentified impurities.

Step 2. Preparation of tert-butyl 4-(bis(3,4-dimethoxyphenyl)methyl)piperazine-1-carboxylate

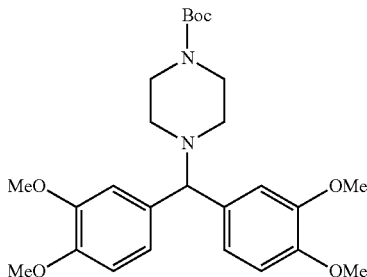 [SMILES: COc1ccc(C(c2ccc(OC)c(OC)c2)N2CCN(C(=O)OC(C)(C)C)CC2)cc1OC]

A solution of bis(3,4-dimethoxyphenyl)methanol (377 mg, containing impurities as specified above) in anhydrous dichloromethane (4.3 mL) was cooled to 0° C. under nitrogen atmosphere and thionyl chloride (0.18 mL, 2.5 mmol) was added dropwise. The solution was stirred at 0° C. for 15 minutes then at ambient temperature for 3 hours. The solution was concentrated in vacuo followed by azeotropic removal of thionyl chloride with dichloromethane (3×10 mL). The residue was dissolved in anhydrous N,N-dimethylformamide (6 mL) and cesium carbonate (807 mg, 2.48 mmol) was added followed by tert-butyl piperazine-1-carboxylate (277 mg, 1.49 mmol). The mixture was heated to 70° C. under nitrogen atmosphere overnight then allowed to cool to ambient temperature. The residue was partitioned between ethyl acetate (40 mL) and water (15 mL), and the organic layer was washed with brine (5×10 mL) then dried over anhydrous sodium sulfate, filtered and concentrated in vacuo. The residue was purified by column chromatography, eluting with 40% to 55% ethyl acetate in hexanes to provide the title compound as a yellow foam (220 mg, 14% yield over 2 steps).

$^1$H NMR (400 MHz, CDCl$_3$) δ 6.95 (d, J=2.0 Hz, 2H), 6.92 (dd, J=8.2, 2.0 Hz, 2H), 6.78 (d, J=8.2 Hz, 2H), 4.11 (s, 1H), 3.86 (s, 6H), 3.83 (s, 6H), 3.42 (m, 4H), 2.33 (m, 4H), 1.44 (s, 9H).

Step 3. Preparation of 1-(bis(3,4-dimethoxyphenyl)methyl)piperazine

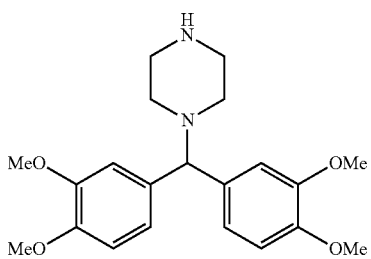 [SMILES: COc1ccc(C(c2ccc(OC)c(OC)c2)N2CCNCC2)cc1OC]

Following General Procedure L and making non-critical variations as required to replace tert-butyl 4-(bis(4-fluorophenyl)amino)piperidine-1-carboxylate with tert-butyl 4-(bis(3,4-dimethoxyphenyl)methyl)piperazine-1-carboxylate, the title compound was obtained as a pale foam (107 mg, 63% yield).

$^1$H NMR (400 MHz, CDCl$_3$) δ 6.95 (d, J=2.0 Hz, 2H), 6.92 (dd, J=8.2, 2.0 Hz, 2H), 6.77 (d, J=8.1 Hz, 2H), 4.11 (s, 1H), 3.86 (s, 6H), 3.83 (s, 6H), 2.93 (m, 4H), 2.40 (m, 4H) (NH not observed).

Step 4. Preparation of 1-(4-(bis(3,4-dimethoxyphenyl)methyl)piperazine-1-carbonyl)-1H-benzo[d][1,2,3]triazole-6-carbonitrile (Example-93) and 1-(4-(bis(3,4-dimethoxyphenyl)methyl)piperazine-1-carbonyl)-1H-benzo[d][1,2,3]triazole-5-carbonitrile (Example-94)

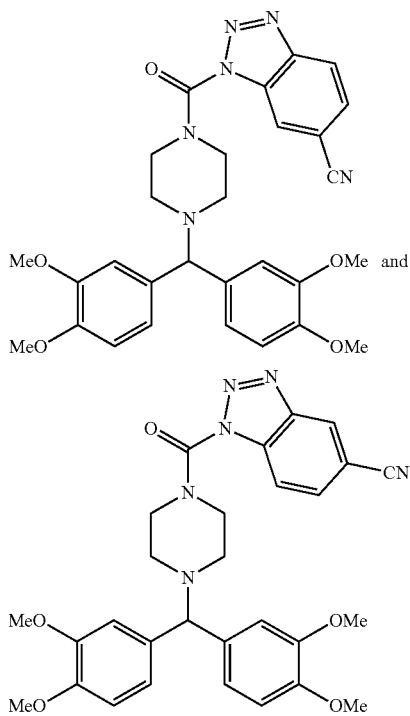

Following General Procedure M and making non-critical variations as required to replace N,N-bis(4-fluorophenyl)piperidin-4-amine with 1-(bis(3,4-dimethoxyphenyl)methyl)piperazine and replace triethylamine with 4-(dimethylamino)pyridine, the title compounds were obtained as a yellow foam (30 mg, 20% yield) and a yellow foam (41 mg, 27% yield), respectively.

The structure of 1-(4-(bis(3,4-dimethoxyphenyl)methyl)piperazine-1-carbonyl)-1H-benzo[d][1,2,3]triazole-6-carbonitrile was tentatively assigned.

$^1$H NMR (400 MHz, CDCl$_3$) δ 8.41 (dd, J=1.4, 0.8 Hz, 1H), 8.19 (dd, J=8.6, 0.9 Hz, 1H), 7.67 (dd, J=8.6, 1.4 Hz, 1H), 6.97 (m, 4H), 6.81 (m, 2H), 4.22 (s, 1H), 3.95 (m, 4H), 3.88 (s, 6H), 3.85 (s, 6H), 2.60 (m, 4H).

The structure of 1-(4-(bis(3,4-dimethoxyphenyl)methyl)piperazine-1-carbonyl)-1H-benzo[d][1,2,3]triazole-5-carbonitrile was tentatively assigned.

$^1$H NMR (400 MHz, CDCl$_3$) δ 8.46 (m, 1H), 8.11 (dd, J=8.6, 0.8 Hz, 1H), 7.81 (dd, J=8.6, 1.4 Hz, 1H), 6.96 (m, 4H), 6.81 (m, 2H), 4.22 (s, 1H), 3.93 (m, 4H), 3.87 (s, 6H), 3.85 (s, 6H), 2.60 (m, 4H).

Synthesis of 1-(4-(bis(3-methoxyphenyl)methyl)piperazine-1-carbonyl)-1H-benzo[d][1,2,3]triazole-6-carbonitrile (Example-95) and 1-(4-(bis(3-methoxyphenyl)methyl)piperazine-1-carbonyl)-1H-benzo[d][1,2,3]triazole-5-carbonitrile (Example-96)

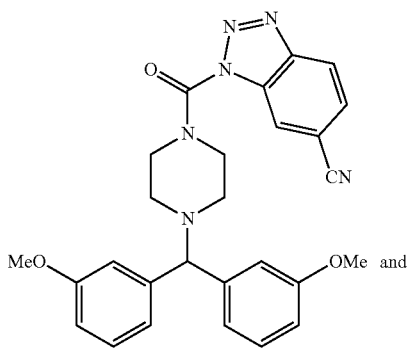

and

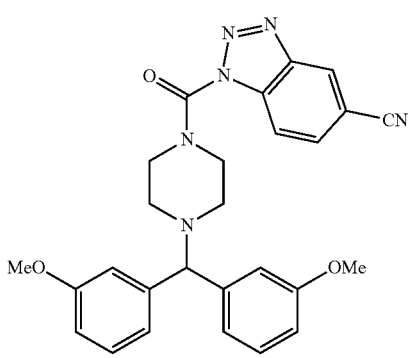

Step 1. Preparation of bis(3-methoxyphenyl)methanol

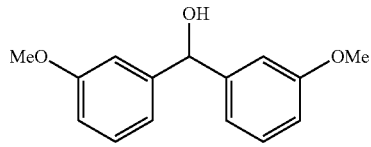 [SMILES: COc1cccc(C(O)c2cccc(OC)c2)c1]

Following General Procedure P and making non-critical variations as required to replace 4-iodoanisole with 3-iodoanisole and replace p-anisaldehyde with 3-methoxybenzaldehyde, the title compound was obtained as a yellow oil (549 mg, 54% yield).

$^1$H NMR (400 MHz, CDCl$_3$) δ 7.25 (m, 2H), 6.95 (m, 4H), 6.81 (m, 2H), 5.79 (s, 1H), 3.79 (s, 6H), 2.20 (br s, 1H).

Step 2. Preparation of tert-butyl 4-(bis(3-methoxyphenyl)methyl)piperazine-1-carboxylate

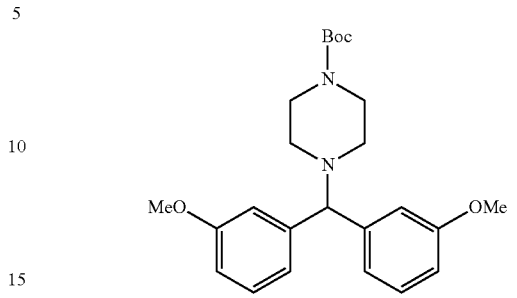

A solution of bis(3-methoxyphenyl)methanol (544 mg, 2.23 mmol) in anhydrous dichloromethane (11 mL) was stirred at ambient temperature while thionyl chloride (0.32 mL, 4.4 mmol) was added dropwise. The reaction vessel was sealed, and the mixture was stirred at ambient temperature for 19 hours. The mixture was concentrated in vacuo followed by azeotropic removal of thionyl chloride with dichloromethane (3×10 mL). The residue was dissolved in anhydrous acetonitrile (11 mL) and tert-butyl piperazine-1-carboxylate (830 mg, 4.46 mmol) was added. The mixture was heated to 70° C. under nitrogen atmosphere for 23 hours then allowed to cool to ambient temperature. The residue was partitioned between ethyl acetate (40 mL) and saturated aqueous sodium bicarbonate (10 mL). The organic layer was washed with saturated aqueous sodium bicarbonate (10 mL) and brine (10 mL) then dried over anhydrous sodium sulfate, filtered and concentrated in vacuo. The residue was purified by column chromatography, eluting with 10% to 15% ethyl acetate in hexanes to provide the title compound as a pale oil (565 mg, 61% yield).

$^1$H NMR (400 MHz, CDCl$_3$) δ 7.18 (m, 2H), 6.99 (m, 4H), 6.72 (m, 2H), 4.14 (s, 1H), 3.77 (s, 6H), 3.41 (m, 4H), 2.34 (m, 4H), 1.43 (s, 9H).

Step 3. Preparation of 1-(bis(3-methoxyphenyl)methyl)piperazine

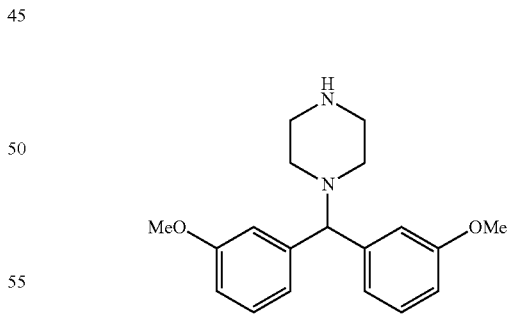

Following General Procedure L and making non-critical variations as required to replace tert-butyl 4-(bis(4-fluorophenyl)amino)piperidine-1-carboxylate with tert-butyl 4-(bis(3-methoxyphenyl)methyl)piperazine-1-carboxylate, the title compound was obtained as a pale oil (328 mg, 77% yield).

$^1$H NMR (400 MHz, CDCl$_3$) δ 7.17 (m, 2H), 6.99 (m, 4H), 6.72 (m, 2H), 4.14 (s, 1H), 3.77 (s, 6H), 2.92 (m, 4H), 2.40 (m, 4H) (NH not observed).

Step 4. Preparation of 1-(4-(bis(3-methoxyphenyl)methyl)piperazine-1-carbonyl)-1H-benzo[d][1,2,3]triazole-6-carbonitrile (Example-95) and 1-(4-(bis(3-methoxyphenyl)methyl)piperazine-1-carbonyl)-1H-benzo[d][1,2,3]triazole-5-carbonitrile (Example-96)

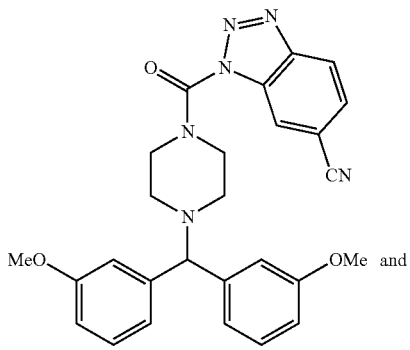

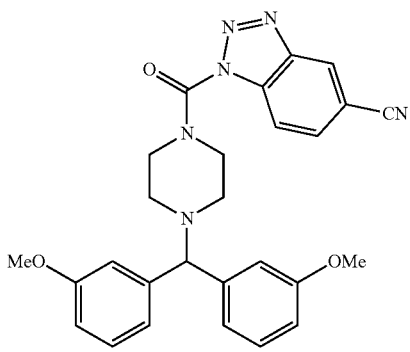

Following General Procedure M and making non-critical variations as required to replace N,N-bis(4-fluorophenyl)piperidin-4-amine with 1-(bis(3-methoxyphenyl)methyl)piperazine and replace triethylamine with 4-(dimethylamino)pyridine, the title compounds were obtained as a pale foam (22 mg, 18% yield) and a pale foam (36 mg, 29% yield), respectively.

The structure of 1-(4-(bis(3-methoxyphenyl)methyl)piperazine-1-carbonyl)-1H-benzo[d][1,2,3]triazole-6-carbonitrile was tentatively assigned.

$^1$H NMR (400 MHz, CDCl$_3$) δ 8.41 (m, 1H), 8.19 (dd, J=8.5, 0.8 Hz, 1H), 7.67 (dd, J=8.6, 1.4 Hz, 1H), 7.22 (m, 2H), 7.02 (m, 4H), 6.75 (m, 2H), 4.25 (s, 1H), 3.95 (m, 4H), 3.79 (s, 6H), 2.61 (m, 4H).

The structure of 1-(4-(bis(3-methoxyphenyl)methyl)piperazine-1-carbonyl)-1H-benzo[d][1,2,3]triazole-5-carbonitrile was tentatively assigned.

$^1$H NMR (400 MHz, CDCl$_3$) δ 8.46 (m, 1H), 8.11 (dd, J=8.6, 0.8 Hz, 1H), 7.80 (dd, J=8.6, 1.4 Hz, 1H), 7.22 (m, 2H), 7.02 (m, 4H), 6.75 (m, 2H), 4.25 (s, 1H), 3.93 (m, 4H), 3.79 (s, 6H), 2.61 (m, 4H).

Synthesis of 1-(4-(bis(3-methoxyphenyl)methyl)piperazine-1-carbonyl)-1H-1,2,4-triazole-3-carbonitrile (Example-97)

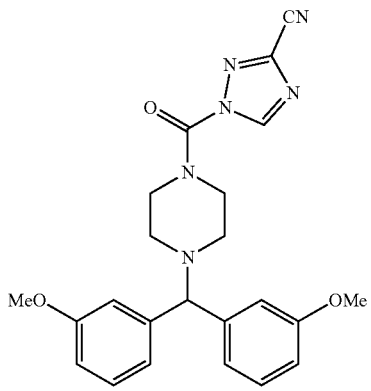 [SMILES: COc1cccc(C(c2cccc(OC)c2)N2CCN(C(=O)n3cnc(C#N)n3)CC2)c1]

Following General Procedure M and making non-critical variations as required to replace N,N-bis(4-fluorophenyl)piperidin-4-amine with 1-(bis(3-methoxyphenyl)methyl)piperazine, replace 1H-1,2,3-benzotriazole-5-carbonitrile with 4H-1,2,4-triazole-3-carbonitrile and replace triethylamine with 4-(dimethylamino)pyridine, the title compound was obtained as a colourless foam (48 mg, 59% yield).

$^1$H NMR (400 MHz, CDCl$_3$) δ 8.83 (s, 1H), 7.21 (m, 2H), 7.00 (m, 4H), 6.75 (ddd, J=8.2, 2.7, 1.0 Hz, 2H), 4.22 (s, 1H), 3.90-3.78 (m, 4H), 3.78 (s, 6H), 2.54 (m, 4H).

Synthesis of 1-(4-(bis(2,2-difluorobenzo[d][1,3]dioxol-5-yl)methyl)piperazine-1-carbonyl)-1H-benzo[d][1,2,3]triazole-6-carbonitrile (Example-98) and 1-(4-(bis(2,2-difluorobenzo[d][1,3]dioxol-5-yl)methyl)piperazine-1-carbonyl)-1H-benzo[d][1,2,3]triazole-5-carbonitrile (Example-99)

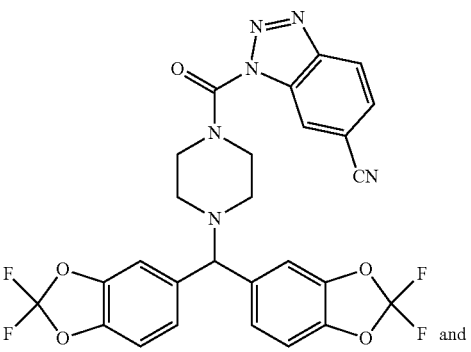

-continued

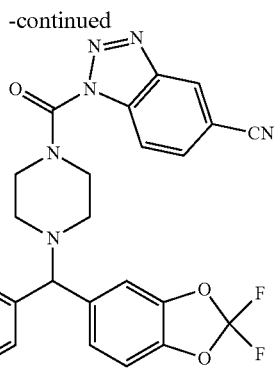

Step 1. Preparation of bis(2,2-difluorobenzo[d][1,3]dioxol-5-yl)methanol

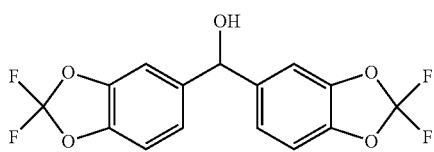 [SMILES: OC(c1ccc2c(c1)OC(F)(F)O2)c1ccc2c(c1)OC(F)(F)O2]

Following General Procedure P and making non-critical variations as required to replace 4-iodoanisole with 5-bromo-2,2-difluorobenzo[d][1,3]dioxole and replace p-anisaldehyde with 2,2-difluoro-1,3-benzodioxole-5-carbaldehyde, the title compound was obtained as a yellow oil (170 mg, 16% yield).

$^1$H NMR (400 MHz, CDCl$_3$) δ 7.08 (m, 4H), 7.02 (m, 2H), 5.81 (br s, 1H), 2.28 (d, J=3.3 Hz, 1H).

Step 2. Preparation of tert-butyl 4-(bis(2,2-difluorobenzo[d][1,3]dioxol-5-yl)methyl)piperazine-1-carboxylate

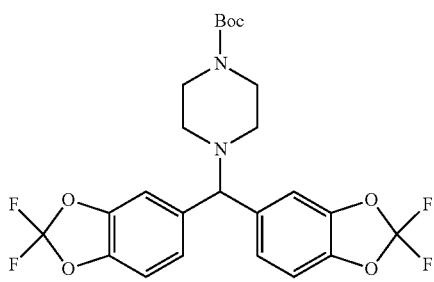 [SMILES: CC(C)(C)OC(=O)N1CCN(C(c2ccc3c(c2)OC(F)(F)O3)c2ccc3c(c2)OC(F)(F)O3)CC1]

A solution of bis(2,2-difluorobenzo[d][1,3]dioxol-5-yl)methanol (166 mg, 0.482 mmol) in anhydrous dichloromethane (5 mL) was stirred at ambient temperature while thionyl chloride (0.070 mL, 0.96 mmol) was added dropwise. The reaction vessel was sealed, and the mixture was stirred at ambient temperature for 19 hours. The mixture was concentrated in vacuo followed by azeotropic removal of thionyl chloride with dichloromethane (3×10 mL). The residue was dissolved in anhydrous acetonitrile (5 mL) and tert-butyl piperazine-1-carboxylate (180 mg, 0.966 mmol) was added. The mixture was heated to 70° C. under nitrogen atmosphere for 29 hours then allowed to cool to ambient temperature. The residue was partitioned between ethyl acetate (30 mL) and saturated aqueous sodium bicarbonate (10 mL). The organic layer was washed with brine (10 mL) then dried over anhydrous sodium sulfate, filtered and concentrated in vacuo. The residue was purified by column chromatography, eluting with 0% to 10% ethyl acetate in hexanes to provide the title compound as a pale foam (131 mg, 53% yield).

$^1$H NMR (400 MHz, CDCl$_3$) δ 7.13 (d, J=1.6 Hz, 2H), 7.06 (dd, J=8.3, 1.7 Hz, 2H), 6.96 (d, J=8.2 Hz, 2H), 4.20 (s, 1H), 3.43 (m, 4H), 2.32 (m, 4H), 1.44 (s, 9H).

Step 3. Preparation of 1-(bis(2,2-difluorobenzo[d][1,3]dioxol-5-yl)methyl)piperazine

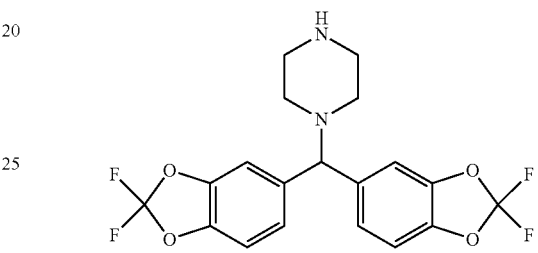

Following General Procedure L and making non-critical variations as required to replace tert-butyl 4-(bis(4-fluorophenyl)amino)piperidine-1-carboxylate with tert-butyl 4-(bis(2,2-difluorobenzo[d][1,3]dioxol-5-yl)methyl)piperazine-1-carboxylate, the title compound was obtained as a colourless solid (92 mg, 89% yield).

$^1$H NMR (400 MHz, CDCl$_3$) δ 7.13 (d, J=1.6 Hz, 2H), 7.06 (dd, J=8.3, 1.7 Hz, 2H), 6.96 (d, J=8.2 Hz, 2H), 4.20 (s, 1H), 2.92 (m, 4H), 2.37 (m, 4H) (NH not observed).

Step 4. Preparation of 1-(4-(bis(2,2-difluorobenzo[d][1,3]dioxol-5-yl)methyl)piperazine-1-carbonyl)-1H-benzo[d][1,2,3]triazole-6-carbonitrile (Example-98) and 1-(4-(bis(2,2-difluorobenzo[d][1,3]dioxol-5-yl)methyl)piperazine-1-carbonyl)-1H-benzo[d][1,2,3]triazole-5-carbonitrile (Example-99)

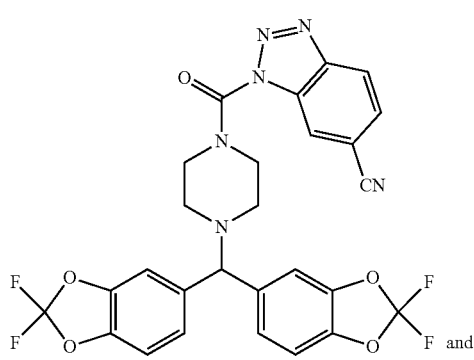

and

199

-continued

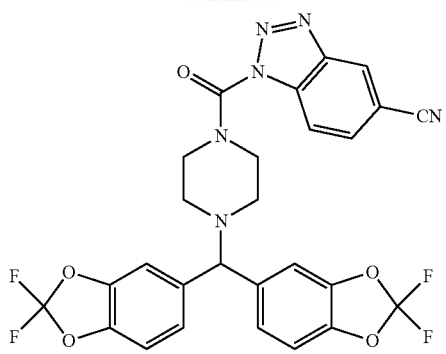

Following General Procedure M and making non-critical variations as required to replace N,N-bis(4-fluorophenyl) piperidin-4-amine with 1-(bis(2,2-difluorobenzo[d][1,3]dioxol-5-yl)methyl)piperazine and replace triethylamine with 4-(dimethylamino)pyridine, the title compounds were obtained as a pale foam (34 mg, 27% yield) and a pale foam (49 mg, 40% yield), respectively.

The structure of 1-(4-(bis(2,2-difluorobenzo[d][1,3]dioxol-5-yl)methyl)piperazine-1-carbonyl)-1H-benzo[d][1,2,3]triazole-6-carbonitrile was tentatively assigned.

$^1$H NMR (400 MHz, CDCl$_3$) δ 8.41 (m, 1H), 8.20 (dd, J=8.6, 0.9 Hz, 1H), 7.68 (dd, J=8.6, 1.4 Hz, 1H), 7.17 (d, J=1.7 Hz, 2H), 7.10 (dd, J=8.3, 1.7 Hz, 2H), 7.00 (d, J=8.2 Hz, 2H), 4.32 (s, 1H), 4.04-3.91 (m, 4H), 2.60 (m, 4H).

The structure of 1-(4-(bis(2,2-difluorobenzo[d][1,3]dioxol-5-yl)methyl)piperazine-1-carbonyl)-1H-benzo[d][1,2,3]triazole-5-carbonitrile was tentatively assigned.

$^1$H NMR (400 MHz, CDCl$_3$) δ 8.47 (m, 1H), 8.12 (dd, J=8.6, 0.9 Hz, 1H), 7.82 (dd, J=8.6, 1.4 Hz, 1H), 7.17 (d, J=1.7 Hz, 2H), 7.10 (dd, J=8.2, 1.7 Hz, 2H), 7.00 (d, J=8.2 Hz, 2H), 4.32 (s, 1H), 4.02-3.90 (m, 4H), 2.60 (m, 4H).

Synthesis of 4,4'-((4-(6-cyano-1H-benzo[d][1,2,3]triazole-1-carbonyl)piperazin-1-yl)methylene)dibenzonitrile (Example-100) and 4,4'-((4-(5-cyano-1H-benzo[d][1,2,3]triazole-1-carbonyl)piperazin-1-yl)methylene)dibenzonitrile (Example-101)

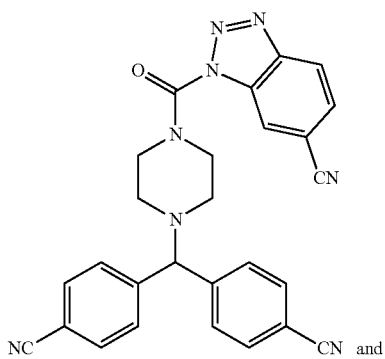

and

200

-continued

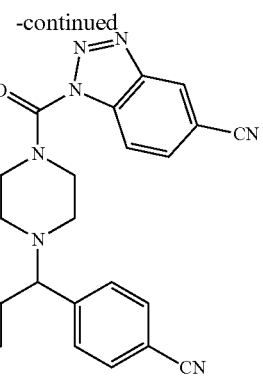

Step 1. Preparation of 4,4'-(hydroxymethylene)dibenzonitrile

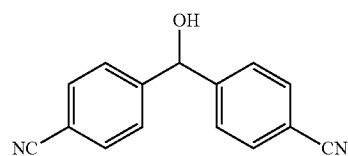 [SMILES: N#Cc1ccc(C(O)c2ccc(C#N)cc2)cc1]

Following General Procedure P and making non-critical variations as required to replace 4-iodoanisole with 4-iodobenzonitrile and replace p-anisaldehyde with 4-cyanobenzaldehyde, the title compound was obtained as a light yellow solid (603 mg, 59% yield).

$^1$H NMR (400 MHz, CDCl$_3$) δ 7.65 (m, 4H), 7.49 (m, 4H), 5.92 (d, J=3.4 Hz, 1H), 2.53 (d, J=3.5 Hz, 1H).

Step 2. Preparation of tert-butyl 4-(bis(4-cyanophenyl)methyl)piperazine-1-carboxylate

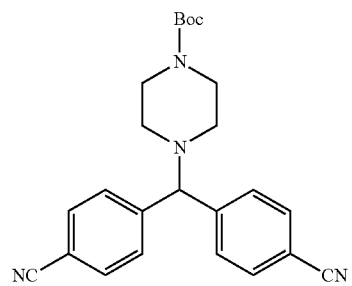 [SMILES: CC(C)(C)OC(=O)N1CCN(C(c2ccc(C#N)cc2)c2ccc(C#N)cc2)CC1]

A solution of 4,4'-(hydroxymethylene)dibenzonitrile (598 mg, 2.55 mmol) in anhydrous dichloromethane (13 mL) was stirred at ambient temperature while thionyl chloride (0.37 mL, 5.1 mmol) was added dropwise. The reaction vessel was sealed, and the mixture was stirred at ambient temperature for 16 hours. The mixture was concentrated in vacuo followed by azeotropic removal of thionyl chloride with dichloromethane (3×10 mL). The residue was dissolved in anhydrous acetonitrile (17 mL) and tert-butyl piperazine-1-carboxylate (951 mg, 5.11 mmol) was added. The mixture was heated to 70° C. under nitrogen atmosphere for 23 hours then allowed to cool to ambient temperature. The residue was partitioned between ethyl acetate (30 mL) and saturated aqueous sodium bicarbonate (20 mL). The organic layer was washed with brine (10 mL) then dried over anhydrous sodium sulfate, filtered and concentrated in vacuo. The residue was purified by column chromatography, eluting with 0% to 20% ethyl acetate in hexanes to provide the title compound as a light yellow oil (312 mg, 30% yield).

¹H NMR (400 MHz, CDCl₃) δ 7.61 (m, 4H), 7.50 (m, 4H), 4.36 (s, 1H), 3.44 (m, 4H), 2.32 (m, 4H), 1.44 (s, 9H).

Step 3. Preparation of 4,4'-(piperazin-1-ylmethylene)dibenzonitrile

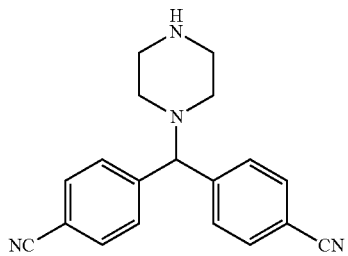 [SMILES: N#Cc1ccc(C(c2ccc(C#N)cc2)N2CCNCC2)cc1]

Following General Procedure L and making non-critical variations as required to replace tert-butyl 4-(bis(4-fluorophenyl)amino)piperidine-1-carboxylate with tert-butyl 4-(bis(4-cyanophenyl)methyl)piperazine-1-carboxylate, the title compound was obtained as a pale foam (128 mg, 55% yield).

¹H NMR (400 MHz, CDCl₃) δ 7.59 (m, 4H), 7.50 (m, 4H), 4.35 (s, 1H), 2.91 (m, 4H), 2.35 (m, 4H) (NH not observed).

Step 4. Preparation of 4,4'-((4-(6-cyano-1H-benzo[d][1,2,3]triazole-1-carbonyl)piperazin-1-yl)methylene)dibenzonitrile (Example-100) and 4,4'-((4-(5-cyano-1H-benzo[d][1,2,3]triazole-1-carbonyl)piperazin-1-yl)methylene)dibenzonitrile (Example-101)

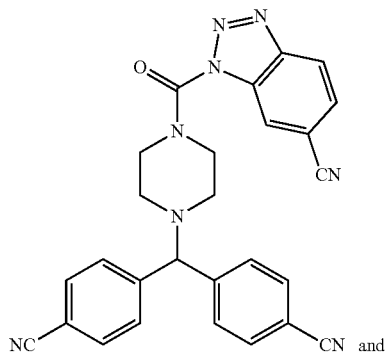

and

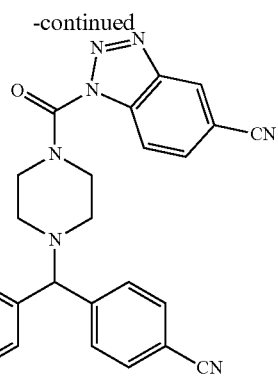

Following General Procedure M and making non-critical variations as required to replace N,N-bis(4-fluorophenyl)piperidin-4-amine with 4,4'-(piperazin-1-ylmethylene)dibenzonitrile and replace triethylamine with 4-(dimethylamino)pyridine, the title compounds were obtained as a light yellow foam (36 mg, 31% yield) and a pale foam (37 mg, 32% yield), respectively.

The structure of 4,4'-((4-(6-cyano-1H-benzo[d][1,2,3]triazole-1-carbonyl)piperazin-1-yl)methylene)dibenzonitrile was tentatively assigned.

¹H NMR (400 MHz, CDCl₃) δ 8.41 (dd, J=1.4, 0.8 Hz, 1H), 8.20 (dd, J=8.6, 0.9 Hz, 1H), 7.69 (dd, J=8.6, 1.4 Hz, 1H), 7.65 (m, 4H), 7.55 (m, 4H), 4.48 (s, 1H), 4.04-3.93 (m, 4H), 2.60 (m, 4H).

The structure of 4,4'-((4-(5-cyano-1H-benzo[d][1,2,3]triazole-1-carbonyl)piperazin-1-yl)methylene)dibenzonitrile was tentatively assigned.

¹H NMR (400 MHz, CDCl₃) δ 8.46 (dd, J=1.4, 0.9 Hz, 1H), 8.12 (dd, J=8.6, 0.9 Hz, 1H), 7.82 (dd, J=8.6, 1.4 Hz, 1H), 7.64 (m, 4H), 7.55 (m, 4H), 4.48 (s, 1H), 4.03-3.92 (m, 4H), 2.60 (m, 4H).

Synthesis of 4,4'-((4-(3-cyano-1H-1,2,4-triazole-1-carbonyl)piperazin-1-yl)methylene)dibenzonitrile (Example-102)

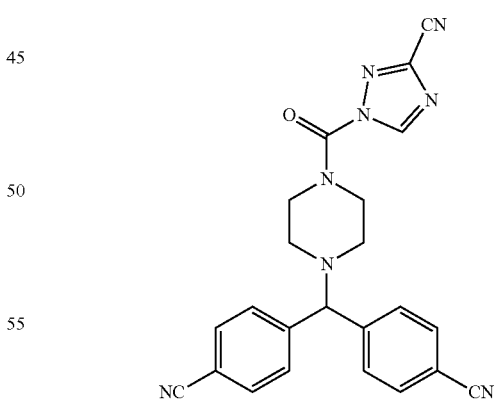

Following General Procedure M and making non-critical variations as required to replace N,N-bis(4-fluorophenyl)piperidin-4-amine with 4,4'-(piperazin-1-ylmethylene)dibenzonitrile, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (22 mg, 31% yield).

$^1$H NMR (400 MHz, CDCl$_3$) δ 8.85 (s, 1H), 7.64 (m, 4H), 7.53 (m, 4H), 4.45 (s, 1H), 3.96-3.83 (m, 4H), 2.54 (m, 4H).

Synthesis of 1-(4-((4-methoxyphenyl)(pyridin-3-yl)methyl)piperazine-1-carbonyl)-1H-benzo[d][1,2,3]triazole-6-carbonitrile and 1-(4-((4-methoxyphenyl)(pyridin-3-yl)methyl)piperazine-1-carbonyl)-1H-benzo[d][1,2,3]triazole-5-carbonitrile (unassigned ratio of 8:5) (Example-103)

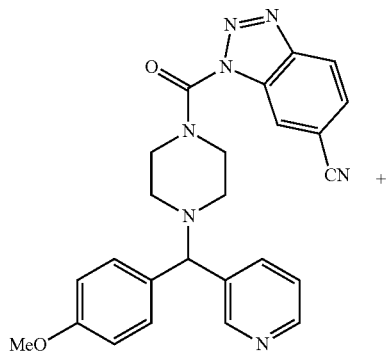

Step 1. Preparation of (4-methoxyphenyl)(pyridin-3-yl)methanol

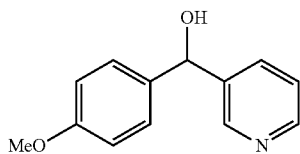

Following General Procedure P and making non-critical variations as required to replace p-anisaldehyde with 3-pyridinecarboxaldehyde, the title compound was obtained as yellow crystals (452 mg, 46% yield).

$^1$H NMR (400 MHz, CDCl$_3$) δ 8.59 (d, J=2.0 Hz, 1H), 8.47 (dd, J=4.8, 1.7 Hz, 1H), 7.69 (m, 1H), 7.26 (m, 3H), 6.88 (m, 2H), 5.84 (s, 1H), 3.80 (s, 3H), 2.66 (br s, 1H).

Step 2. Preparation of tert-butyl 4-((4-methoxyphenyl)(pyridin-3-yl)methyl)piperazine-1-carboxylate General Procedure Q

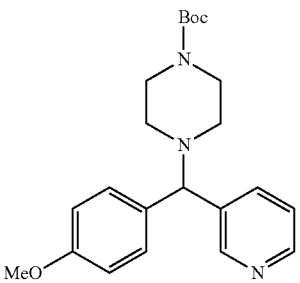 [SMILES: COc1ccc(C(c2cccnc2)N2CCN(C(=O)OC(C)(C)C)CC2)cc1]

A solution of (4-methoxyphenyl)(pyridin-3-yl)methanol (447 mg, 2.08 mmol) in anhydrous dichloromethane (10 mL) was stirred at ambient temperature while thionyl chloride (0.30 mL, 4.1 mmol) was added dropwise. The reaction vessel was sealed, and the mixture was stirred at ambient temperature for 16 hours. The mixture was concentrated in vacuo followed by azeotropic removal of thionyl chloride with dichloromethane (3×10 mL). The residue was dissolved in anhydrous acetonitrile (20 mL) and potassium carbonate (287 mg, 2.08 mmol) was added followed by tert-butyl piperazine-1-carboxylate (774 mg, 4.16 mmol). The mixture was heated to 70° C. under nitrogen atmosphere for 27 hours then allowed to cool to ambient temperature. The residue was partitioned between ethyl acetate (35 mL) and saturated aqueous sodium bicarbonate (20 mL). The organic layer was washed with brine (10 mL) then dried over anhydrous sodium sulfate, filtered and concentrated in vacuo. The residue was purified by column chromatography, eluting with 20% to 40% ethyl acetate in dichloromethane to provide the title compound as a yellow foam (738 mg, 93% yield).

$^1$H NMR (400 MHz, CDCl$_3$) δ 8.64 (d, J=2.0 Hz, 1H), 8.45 (dd, J=4.8, 1.6 Hz, 1H), 7.71 (m, 1H), 7.27 (m, 2H), 7.21 (m, 1H), 6.83 (m, 2H), 4.25 (s, 1H), 3.77 (s, 3H), 3.42 (m, 4H), 2.38-2.27 (m, 4H), 1.43 (s, 9H).

Step 3. Preparation of 1-((4-methoxyphenyl)(pyridin-3-yl)methyl)piperazine

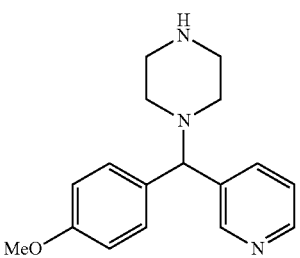 [SMILES: COc1ccc(C(c2cccnc2)N2CCNCC2)cc1]

Following General Procedure L and making non-critical variations as required to replace tert-Butyl 4-(bis(4-fluorophenyl)amino)piperidine-1-carboxylate with tert-butyl 4-((4-methoxyphenyl)(pyridin-3-yl)methyl)piperazine-1-carboxylate, the title compound was obtained as a yellow oil (461 mg, 85% yield).

¹H NMR (400 MHz, CDCl₃) δ 8.64 (d, J=1.6 Hz, 1H), 8.43 (dd, J=4.8, 1.7 Hz, 1H), 7.72 (m, 1H), 7.28 (m, 2H), 7.20 (m, 1H), 6.83 (m, 2H), 4.24 (s, 1H), 3.76 (s, 3H), 2.90 (m, 4H), 2.36 (m, 4H) (NH not observed).

Step 4. Preparation of 1-(4-((4-methoxyphenyl)(pyridin-3-yl)methyl)piperazine-1-carbonyl)-1H-benzo[d][1,2,3]triazole-6-carbonitrile and 1-(4-((4-methoxyphenyl)(pyridin-3-yl)methyl)piperazine-1-carbonyl)-1H-benzo[d][1,2,3]triazole-5-carbonitrile (unassigned ratio of 8:5) (Example-103)

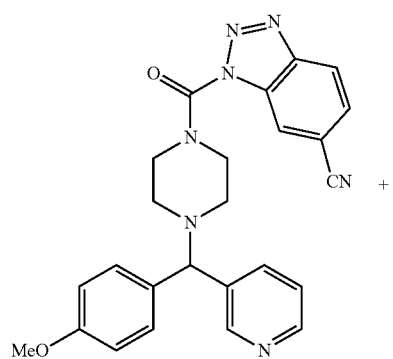

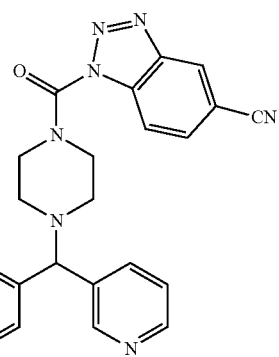

Following General Procedure M and making non-critical variations as required to replace N,N-bis(4-fluorophenyl) piperidin-4-amine with 1-((4-methoxyphenyl)(pyridin-3-yl)methyl)piperazine and replace triethylamine with 4-(dimethylamino)pyridine, the title compounds were obtained as a mixture in an unassigned ratio of 8:5 as a yellow foam (111 mg, 83% yield).

¹H NMR (400 MHz, CDCl₃) δ 8.70 (d, J=2.2 Hz, 2H), 8.48 (m 2H), 8.46 (m, 1H), 8.41 (m, 1H), 8.19 (dd, J=8.6, 0.8 Hz, 1H), 8.11 (dd, J=8.7, 0.8 Hz, 1H), 7.81 (dd, J=8.6, 1.4 Hz, 1H), 7.75 (m, 2H), 7.67 (dd, J=8.6, 1.4 Hz, 1H), 7.31 (m, 4H), 7.25 (m, 2H), 6.86 (m, 4H), 4.37 (s, 2H), 4.00-3.90 (m, 8H), 3.78 (s, 6H), 2.60 (m, 8H).

Synthesis of 1-(4-((4-methoxyphenyl)(pyridin-3-yl)methyl)piperazine-1-carbonyl)-1H-1,2,4-triazole-3-carbonitrile (Example-104)

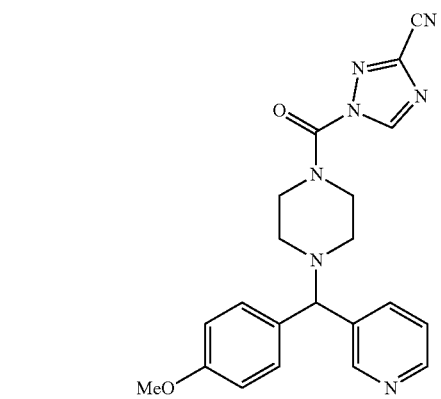 [SMILES: COc1ccc(C(c2cccnc2)N2CCN(C(=O)n3cnc(C#N)n3)CC2)cc1]

Following General Procedure M and making non-critical variations as required to replace N,N-bis(4-fluorophenyl) piperidin-4-amine with 1-((4-methoxyphenyl)(pyridin-3-yl)methyl)piperazine, replace 1H-1,2,3-benzotriazole-5-carbonitrile with 4H-1,2,4-triazole-3-carbonitrile and replace triethylamine with 4-(dimethylamino)pyridine, the title compound was obtained as a light yellow foam (43 mg, 51% yield).

¹H NMR (400 MHz, CDCl₃) δ 8.83 (s, 1H), 8.68 (d, J=2.2 Hz, 1H), 8.48 (dd, J=4.8, 1.7 Hz, 1H), 7.72 (m, 1H), 7.28 (m, 2H), 7.24 (m, 1H), 6.86 (m, 2H), 4.34 (s, 1H), 3.91 (m, 4H), 3.78 (s, 3H), 2.53 (m, 4H).

Synthesis of 1-(4-(di(pyridin-3-yl)methyl)piperazine-1-carbonyl)-1H-benzo[d][1,2,3]triazole-6-carbonitrile and 1-(4-(di(pyridin-3-yl)methyl)piperazine-1-carbonyl)-1H-benzo[d][1,2,3]triazole-5-carbonitrile (unassigned ratio of 5:3) (Example-105)

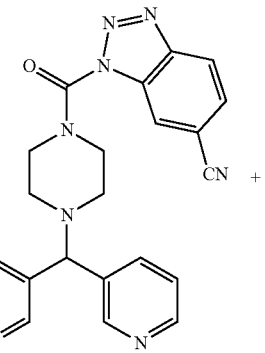

207
-continued

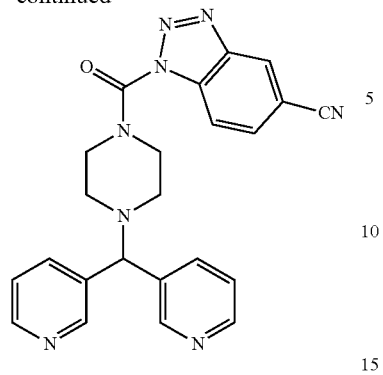

Step 1. Preparation of di(pyridin-3-yl)methanol

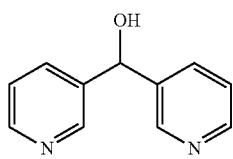 [SMILES: OC(c1cccnc1)c1cccnc1]

Following General Procedure P and making non-critical variations as required to replace 4-iodoanisole with 3-iodopyridine and replace p-anisaldehyde with 3-pyridinecarboxaldehyde, the title compound was obtained as a colourless film (168 mg, 17% yield).

$^1$H NMR (400 MHz, CDCl$_3$) δ 8.58 (d, J=2.3 Hz, 2H), 8.49 (dd, J=4.9, 1.7 Hz, 2H), 7.69 (m, 2H), 7.28 (m, 2H), 5.91 (s, 1H), 3.87 (br s, 1H).

Step 2. Preparation of tert-butyl 4-(di(pyridin-3-yl)methyl)piperazine-1-carboxylate

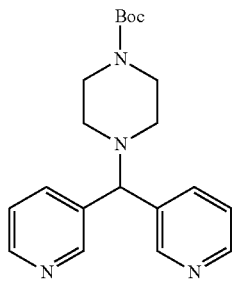 [SMILES: CC(C)(C)OC(=O)N1CCN(C(c2cccnc2)c2cccnc2)CC1]

Following General Procedure Q and making non-critical variations as required to replace (4-methoxyphenyl)(pyridin-3-yl)methanol with di(pyridin-3-yl)methanol, the title compound was obtained as a yellow film (85 mg, 27% yield).

$^1$H NMR (400 MHz, CDCl$_3$) δ 8.65 (d, J=2.0 Hz, 2H), 8.50 (dd, J=4.8, 1.6 Hz, 2H), 7.70 (m, 2H), 7.25 (m, 2H), 4.37 (s, 1H), 3.44 (m, 4H), 2.35 (m, 4H), 1.43 (s, 9H).

208
Step 3. Preparation of 1-(di(pyridin-3-yl)methyl)piperazine

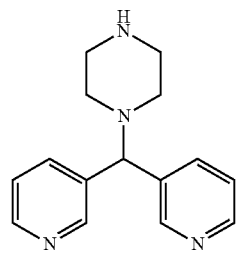 [SMILES: c1cncc(C(c2cccnc2)N2CCNCC2)c1]

tert-Butyl 4-(di(pyridin-3-yl)methyl)piperazine-1-carboxylate (80 mg, 0.23 mmol) was dissolved in dichloromethane (6 mL) and stirred at ambient temperature while 4-methylmorpholine (0.08 mL, 0.7 mmol) was added followed by iodotrimethylsilane (0.06 mL, 0.4 mmol). The solution was stirred at ambient temperature for 2 hours then concentrated in vacuo. The residue was semi-purified by column chromatography, eluting with 10% to 15% methanol (containing 10% aqueous ammonium hydroxide) in dichloromethane to provide a light yellow oil (154 mg) containing the title compound plus unidentified impurities that was used in the next step without further purification.

Step 4. Preparation of 1-(4-(di(pyridin-3-yl)methyl)piperazine-1-carbonyl)-1H-benzo[d][1,2,3]triazole-6-carbonitrile and 1-(4-(di(pyridin-3-yl)methyl)piperazine-1-carbonyl)-1H-benzo[d][1,2,3]triazole-5-carbonitrile (unassigned ratio of 5:3) (Example-105)

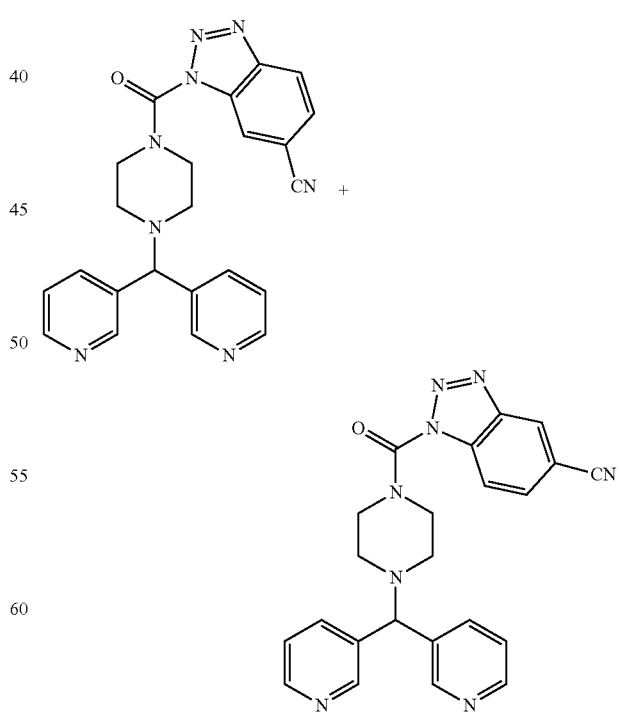

Following General Procedure M and making non-critical variations as required to replace N,N-bis(4-fluorophenyl)

piperidin-4-amine with 1-(di(pyridin-3-yl)methyl)piperazine and replace triethylamine with 4-(dimethylamino)pyridine, the title compounds were obtained as a mixture in an unassigned ratio of 5:3 as a yellow foam (40 mg, 42% yield over 2 steps).

¹H NMR (400 MHz, CDCl₃) δ 8.71 (d, J=2.3 Hz, 4H), 8.54 (dd, J=4.8, 1.6 Hz, 4H), 8.46 (m, 1H), 8.41 (m, 1H), 8.19 (dd, J=8.5, 0.8 Hz, 1H), 8.11 (dd, J=8.6, 0.8 Hz, 1H), 7.81 (dd, J=8.6, 1.4 Hz, 1H), 7.74 (m, 4H), 7.68 (dd, J=8.6, 1.5 Hz, 1H), 7.29 (dd, J=7.9, 4.8 Hz, 4H), 4.49 (s, 2H), 4.04-3.91 (m, 8H), 2.63 (m, 8H).

Synthesis of 1-(4-((2,3-dihydrobenzo[b][1,4]dioxin-6-yl)(4-methoxyphenyl)methyl)piperazine-1-carbonyl)-1H-benzo[d][1,2,3]triazole-6-carbonitrile and 1-(4-((2,3-dihydrobenzo[b][1,4]dioxin-6-yl)(4-methoxyphenyl)methyl)piperazine-1-carbonyl)-1H-benzo[d][1,2,3]triazole-5-carbonitrile (unassigned ratio of 4:3) (Example-106)

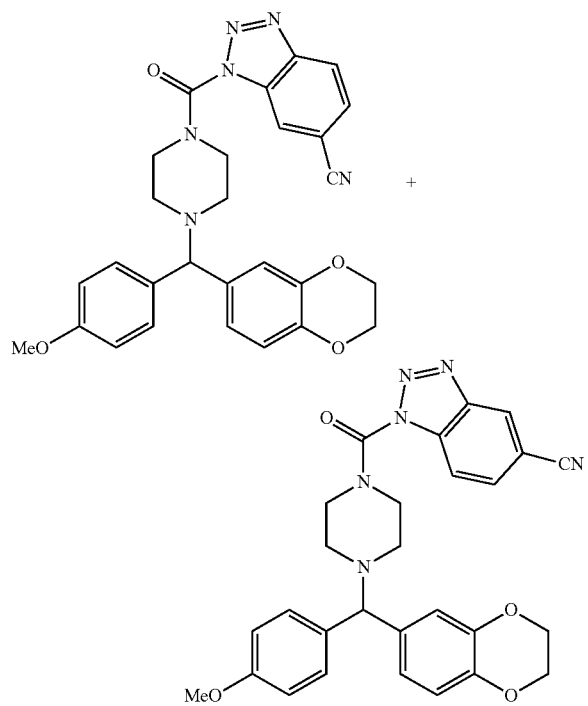

Step 1. Preparation of (2,3-dihydrobenzo[b][1,4]dioxin-6-yl)(4-methoxyphenyl)methanol

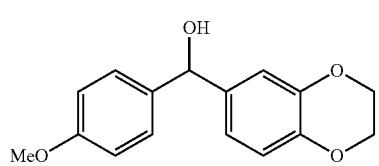 [SMILES: COc1ccc(C(O)c2ccc3c(c2)OCCO3)cc1]

Following General Procedure P and making non-critical variations as required to replace p-anisaldehyde with 2,3-dihydro-1,4-benzodioxine-6-carbaldehyde, a pale oil (165 mg) was obtained containing the title compound plus unidentified impurities.

Step 2. Preparation of tert-butyl 4-((2,3-dihydrobenzo[b][1,4]dioxin-6-yl)(4-methoxyphenyl)methyl)piperazine-1-carboxylate

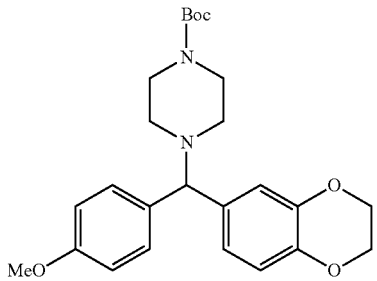 [SMILES: COc1ccc(C(c2ccc3c(c2)OCCO3)N2CCN(C(=O)OC(C)(C)C)CC2)cc1]

Following General Procedure Q and making non-critical variations as required to replace (4-methoxyphenyl)(pyridin-3-yl)methanol with (2,3-dihydrobenzo[b][1,4]dioxin-6-yl)(4-methoxyphenyl)methanol, a light yellow oil (155 mg) was obtained containing the title compound plus unidentified impurities.

Step 3. Preparation of 1-((2,3-dihydrobenzo[b][1,4]dioxin-6-yl)(4-methoxyphenyl)methyl)piperazine

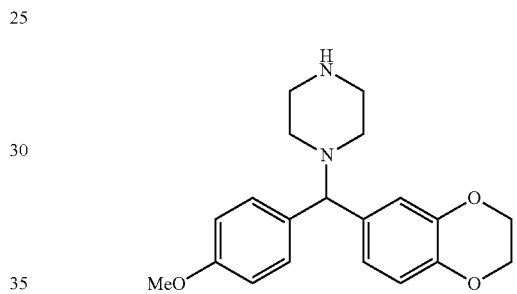

Following General Procedure L and making non-critical variations as required to replace tert-Butyl 4-(bis(4-fluorophenyl)amino)piperidine-1-carboxylate with tert-butyl 4-((2,3-dihydrobenzo[b][1,4]dioxin-6-yl)(4-methoxyphenyl)methyl)piperazine-1-carboxylate, a pale foam (35 mg) was obtained containing the title compound.

Step 4. Preparation of 1-(4-((2,3-dihydrobenzo[b][1,4]dioxin-6-yl)(4-methoxyphenyl)methyl)piperazine-1-carbonyl)-1H-benzo[d][1,2,3]triazole-6-carbonitrile and 1-(4-((2,3-dihydrobenzo[b][1,4]dioxin-6-yl)(4-methoxyphenyl)methyl)piperazine-1-carbonyl)-1H-benzo[d][1,2,3]triazole-5-carbonitrile (unassigned ratio of 4:3) (Example-106)

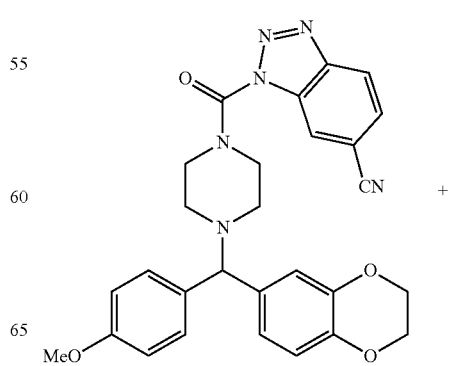

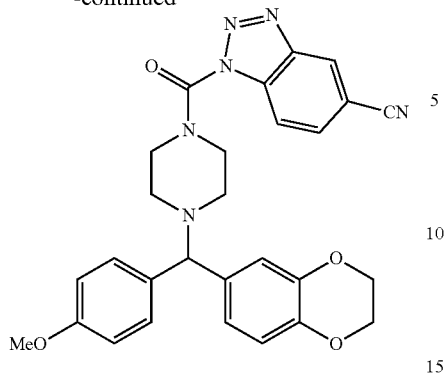

Following General Procedure M and making non-critical variations as required to replace N,N-bis(4-fluorophenyl)piperidin-4-amine with 1-((2,3-dihydrobenzo[b][1,4]dioxin-6-yl)(4-methoxyphenyl)methyl)piperazine and replace triethylamine with 4-(dimethylamino)pyridine, the title compounds were obtained as a mixture in an unassigned ratio of 4:3 as a light yellow foam (45 mg, 2% yield over 4 steps).

$^1$H NMR (400 MHz, CDCl$_3$) δ 8.46 (m, 1H), 8.41 (dd, J=1.4, 0.8 Hz, 1H), 8.19 (dd, J=8.5, 0.9 Hz, 1H), 8.11 (dd, J=8.6, 0.9 Hz, 1H), 7.80 (dd, J=8.6, 1.4 Hz, 1H), 7.67 (dd, J=8.6, 1.4 Hz, 1H), 7.31 (m, 4H), 6.94 (m, 2H), 6.85 (m, 6H), 6.78 (d, J=8.3 Hz, 2H), 4.22 (m, 8H), 4.18 (s, 2H), 3.97-3.87 (m, 8H), 3.77 (s, 6H), 2.58 (m, 8H).

Synthesis of 1-(4-(bis(2,3-dihydrobenzofuran-5-yl)methyl)piperazine-1-carbonyl)-1H-1,2,4-triazole-3-carbonitrile (Example-107)

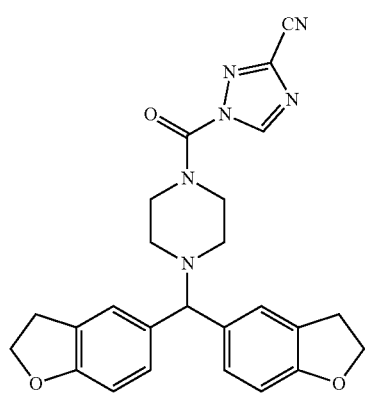 [SMILES: N#Cc1ncn(C(=O)N2CCN(C(c3ccc4c(c3)CCO4)c3ccc4c(c3)CCO4)CC2)n1]

Step 1. Preparation of bis(2,3-dihydrobenzofuran-5-yl)methanol

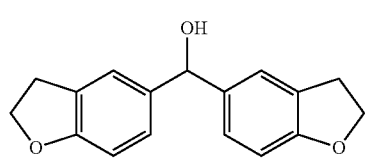 [SMILES: OC(c1ccc2c(c1)CCO2)c1ccc2c(c1)CCO2]

Following General Procedure P and making non-critical variations as required to replace 4-iodoanisole with 5-iodo-2,3-dihydro-1-benzofuran and replace p-anisaldehyde with 2,3-dihydrobenzofuran-5-carboxaldehyde, a yellow oil (146 mg) was obtained containing the title compound plus unidentified impurities.

Step 2. Preparation of tert-butyl 4-(bis(2,3-dihydrobenzofuran-5-yl)methyl)piperazine-1-carboxylate

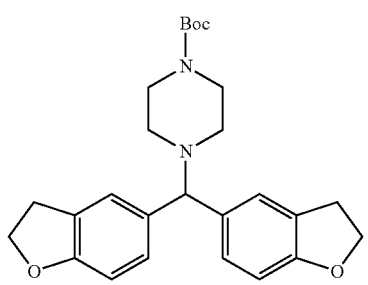 [SMILES: CC(C)(C)OC(=O)N1CCN(C(c2ccc3c(c2)CCO3)c2ccc3c(c2)CCO3)CC1]

Following General Procedure Q and making non-critical variations as required to replace (4-methoxyphenyl)(pyridin-3-yl)methanol with bis(2,3-dihydrobenzofuran-5-yl)methanol, the title compound was obtained as a yellow film (67 mg, 8% yield over 2 steps).

$^1$H NMR (400 MHz, CDCl$_3$) δ 7.20 (d, J=1.7 Hz, 2H), 7.11 (dd, J=8.3, 1.9 Hz, 2H), 6.68 (d, J=8.2 Hz, 2H), 4.52 (t, J=8.7 Hz, 4H), 4.07 (s, 1H), 3.40 (m, 4H), 3.16 (t, J=8.6 Hz, 4H), 2.32 (m, 4H), 1.43 (s, 9H).

Step 3. Preparation of 1-(bis(2,3-dihydrobenzofuran-5-yl)methyl)piperazine

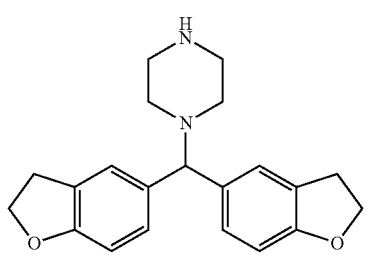 [SMILES: c1cc2c(cc1C(c1ccc3c(c1)CCO3)N1CCNCC1)CCO2]

The Following General Procedure S and making non-critical variations as required to replace tert-butyl 4-(bis(1-methyl-1H-indazol-5-yl)methyl)piperazine-1-carboxylate with tert-butyl 4-(bis(2,3-dihydrobenzofuran-5-yl)methyl)piperazine-1-carboxylate, the title compound was obtained as a pale oil (49 mg, 100% yield).

$^1$H NMR (400 MHz, CDCl$_3$) δ 7.19 (d, J=1.8 Hz, 2H), 7.11 (dd, J=8.3, 2.0 Hz, 2H), 6.68 (d, J=8.2 Hz, 2H), 4.51 (t, J=8.7 Hz, 4H), 4.09 (s, 1H), 3.15 (t, J=8.7 Hz, 4H), 2.96 (m, 4H), 2.44 (m, 4H) (NH not observed).

Step 4. Preparation of 1-(4-(bis(2,3-dihydrobenzo-furan-5-yl)methyl)piperazine-1-carbonyl)-1H-1,2,4-triazole-3-carbonitrile (Example-107)

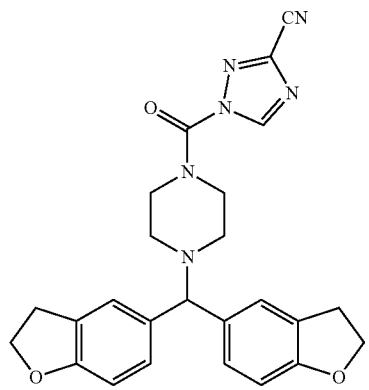 [SMILES: N#Cc1ncn(C(=O)N2CCN(C(c3ccc4c(c3)CCO4)c3ccc4c(c3)CCO4)CC2)n1]

Following General Procedure M and making non-critical variations as required to replace N,N-bis(4-fluorophenyl)piperidin-4-amine with 1-(bis(2,3-dihydrobenzofuran-5-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a yellow foam (32 mg, 52% yield).

$^1$H NMR (400 MHz, CDCl$_3$) δ 8.83 (s, 1H), 7.20 (d, J=1.8 Hz, 2H), 7.13 (dd, J=8.2, 1.9 Hz, 2H), 6.70 (d, J=8.2 Hz, 2H), 4.53 (t, J=8.7 Hz, 4H), 4.15 (s, 1H), 3.88-3.78 (m, 4H), 3.17 (t, J=8.7 Hz, 4H), 2.52 (m, 4H).

Synthesis of (1H-benzo[d][1,2,3]triazol-1-yl)(4-(bis(2,3-dihydrobenzofuran-5-yl)methyl)piperazin-1-yl)methanone (Example-108)

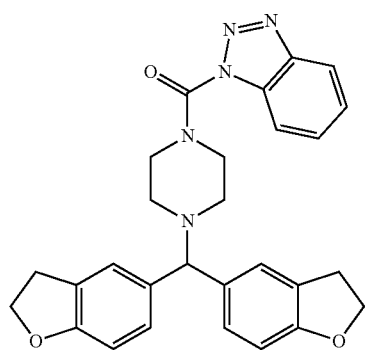 [SMILES: O=C(N1CCN(C(c2ccc3c(c2)CCO3)c2ccc3c(c2)CCO3)CC1)n1nnc2ccccc21]

Following General Procedure V and making non-critical variations as required to replace 6,6'-(piperazin-1-ylmethylene)diquinoline with 1-(bis(2,3-dihydrobenzofuran-5-yl)methyl)piperazine, the title compound was obtained as a light yellow foam (61 mg, 59% yield).

$^1$H NMR (400 MHz, CDCl$_3$) δ 8.07 (m, 1H), 7.98 (m, 1H), 7.59 (m, 1H), 7.44 (m, 1H), 7.23 (d, J=1.8 Hz, 2H), 7.15 (dd, J=8.2, 1.9 Hz, 2H), 6.70 (d, J=8.2 Hz, 2H), 4.53 (t, J=8.7 Hz, 4H), 4.18 (s, 1H), 3.91 (m, 4H), 3.17 (t, J=8.6 Hz, 4H), 2.57 (m, 4H).

Synthesis of (1H-benzo[d][1,2,3]triazol-1-yl)(4-(di(quinolin-6-yl)methyl)piperazin-1-yl)methanone (Example-109)

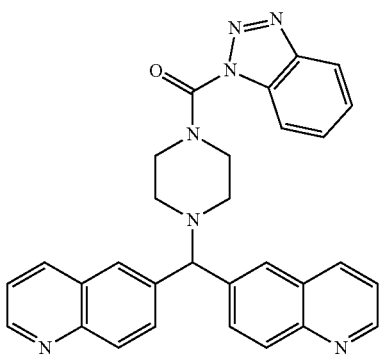 [SMILES: O=C(N1CCN(C(c2ccc3ncccc3c2)c2ccc3ncccc3c2)CC1)n1nnc2ccccc21]

Step 1. Preparation of di(quinolin-6-yl)methanol

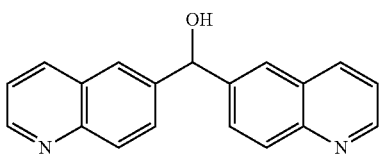 [SMILES: OC(c1ccc2ncccc2c1)c1ccc2ncccc2c1]

Following General Procedure P and making non-critical variations as required to replace 4-iodoanisole with 6-iodoquinoline and replace p-anisaldehyde with 6-quinolinecarbaldehyde, the title compound was obtained as a yellow solid (195 mg, 28% yield).

$^1$H NMR (400 MHz, CDCl$_3$) δ 8.88 (dd, J=4.3, 1.7 Hz, 2H), 8.15 (dd, J=8.0, 1.2 Hz, 2H), 8.05 (d, J=8.8 Hz, 2H), 7.93 (d, J=2.0 Hz, 2H), 7.70 (dd, J=8.8, 2.0 Hz, 2H), 7.40 (dd, J=8.3, 4.2 Hz, 2H), 6.22 (s, 1H), 3.11 (br s, 1H).

Step 2. Preparation of tert-butyl 4-(di(quinolin-6-yl)methyl)piperazine-1-carboxylate

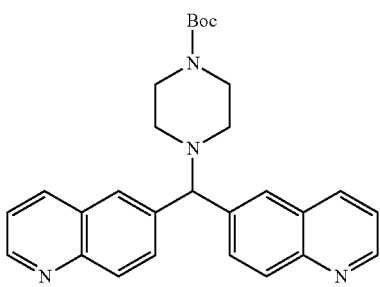 [SMILES: CC(C)(C)OC(=O)N1CCN(C(c2ccc3ncccc3c2)c2ccc3ncccc3c2)CC1]

Following General Procedure Q and making non-critical variations as required to replace (4-methoxyphenyl)(pyridin-3-yl)methanol with di(quinolin-6-yl)methanol, the title compound was obtained as a light yellow foam (305 mg, 61% yield).

¹H NMR (400 MHz, CDCl₃) δ 8.86 (dd, J=4.2, 1.7 Hz, 2H), 8.13 (m, 2H), 8.05 (d, J=9.3 Hz, 2H), 7.89 (m, 4H), 7.38 (dd, J=8.3, 4.2 Hz, 2H), 4.65 (s, 1H), 3.49 (m, 4H), 2.45 (m, 4H), 1.43 (s, 9H).

Step 3. Preparation of
6,6'-(piperazin-1-ylmethylene)diquinoline

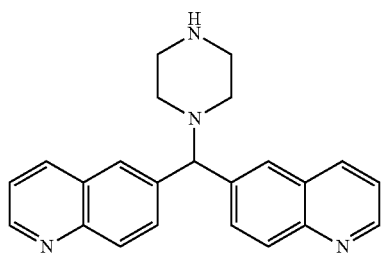 [SMILES: c1cnc2ccc(C(c3ccc4ncccc4c3)N3CCNCC3)cc2c1]

Following General Procedure S and making non-critical variations as required to replace tert-butyl 4-(bis(1-methyl-1H-indazol-5-yl)methyl)piperazine-1-carboxylate with tert-butyl 4-(di(quinolin-6-yl)methyl)piperazine-1-carboxylate, the title compound was obtained as a light yellow foam (196 mg, 84% yield).

¹H NMR (400 MHz, CDCl₃) δ 8.85 (dd, J=4.2, 1.7 Hz, 2H), 8.13 (m, 2H), 8.04 (d, J=9.4 Hz, 2H), 7.90 (m, 4H), 7.37 (dd, J=8.3, 4.2 Hz, 2H), 4.65 (s, 1H), 2.98 (m, 4H), 2.50 (m, 4H) (NH not observed).

Step 4. Preparation of (1H-benzo[d][1,2,3]triazol-1-yl)(4-(di(quinolin-6-yl)methyl)piperazin-1-yl)methanone (Example-109)

General Procedure V

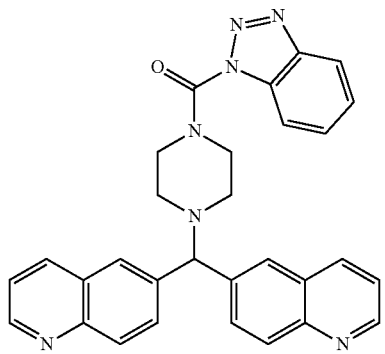 [SMILES: O=C(N1CCN(C(c2ccc3ncccc3c2)c2ccc3ncccc3c2)CC1)n1nnc2ccccc21]

Triphosgene (20 mg, 0.067 mmol) was dissolved in anhydrous dichloromethane (0.5 mL), and the solution was cooled to 0° C. under nitrogen atmosphere. A solution of 1H-benzotriazole (16 mg, 0.13 mmol) and 4-(dimethylamino)pyridine (16 mg, 0.13 mmol) in dichloromethane (1.5 mL) was added dropwise. The reaction vessel was sealed, and the mixture was stirred at ambient temperature for 3 hours then concentrated in vacuo. The residue was dissolved in dichloromethane (1 mL) and stirred at ambient temperature while a solution of 6,6'-(piperazin-1-ylmethylene)diquinoline (47 mg, 0.13 mmol) and 4-(dimethylamino)pyridine (16 mg, 0.13 mmol) in anhydrous tetrahydrofuran (1 mL) was added dropwise. The mixture was sealed and stirred at ambient temperature for 17 hours. Dichloromethane (10 mL) and water (10 mL) were added, and the aqueous phase was extracted with dichloromethane (10 mL). The combined organic layers were dried over anhydrous sodium sulfate, filtered and concentrated in vacuo. The residue was purified by column chromatography, eluting with 1% to 2% methanol in dichloromethane to afford the title compound as a pale foam (28 mg, 42% yield).

¹H NMR (400 MHz, CDCl₃) δ 8.88 (dd, J=4.3, 1.7 Hz, 2H), 8.15 (m, 2H), 8.08 (m, 3H), 7.98 (m, 1H), 7.93 (m, 4H), 7.59 (m, 1H), 7.44 (m, 1H), 7.40 (dd, J=8.3, 4.2 Hz, 2H), 4.76 (s, 1H), 4.00 (m, 4H), 2.71 (m, 4H).

Synthesis of 1-(4-(bis(1-methyl-1H-indazol-5-yl)methyl)piperazine-1-carbonyl)-1H-benzo[d][1,2,3]triazole-6-carbonitrile and 1-(4-(bis(1-methyl-1H-indazol-5-yl)methyl)piperazine-1-carbonyl)-1H-benzo[d][1,2,3]triazole-5-carbonitrile (unassigned ratio of 10:9) (Example-110)

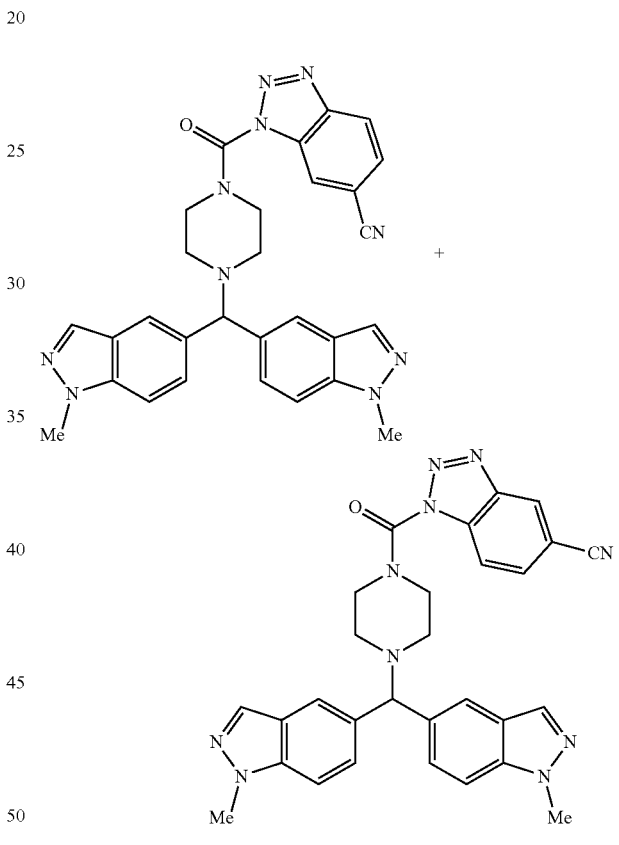

Step 1. Preparation of
bis(1-methyl-1H-indazol-5-yl)methanol

General Procedure R

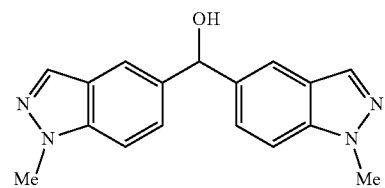 [SMILES: Cn1ncc2cc(C(O)c3ccc4c(cnn4C)c3)ccc21]

A solution of 5-bromo-1-methyl-1H-indazole (749 mg, 3.55 mmol) in anhydrous tetrahydrofuran (71 mL) was cooled to −78° C. and stirred under nitrogen atmosphere while n-butyllithium (1.5 M in hexanes, 2.6 mL, 3.9 mmol) was added dropwise. The mixture was stirred at −78° C. for 20 minutes then a solution of 1-methyl-1H-indazole-5-carbaldehyde (589 mg, 3.68 mmol) in anhydrous tetrahydrofuran (18 mL) was slowly added. The mixture was stirred at −78° C. for 10 minutes then at ambient temperature for 3 hours. Saturated aqueous ammonium chloride (35 mL) was added, and the aqueous phase was extracted with ethyl acetate (25 mL). The combined organic layers were dried over anhydrous sodium sulfate, filtered and concentrated in vacuo. The residue was purified by column chromatography, eluting with 10% to 40% ethyl acetate in dichloromethane to afford the title compound as a light yellow solid (199 mg, 19% yield).

$^1$H NMR (400 MHz, CDCl$_3$) δ 7.95 (d, J=1.0 Hz, 2H), 7.78 (m, 2H), 7.38 (dd, J=8.7, 1.6 Hz, 2H), 7.34 (m, 2H), 6.10 (s, 1H), 4.05 (s, 6H), 2.40 (br s, 1H).

Step 2. Preparation of tert-butyl 4-(bis(1-methyl-1H-indazol-5-yl)methyl)piperazine-1-carboxylate

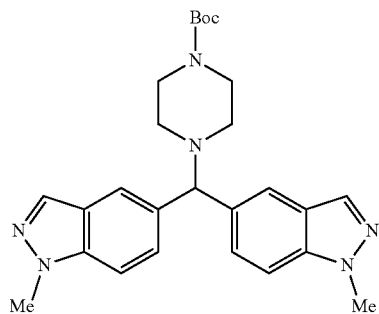 [SMILES: Cn1ncc2cc(C(c3ccc4c(cnn4C)c3)N3CCN(C(=O)OC(C)(C)C)CC3)ccc21]

Following General Procedure Q and making non-critical variations as required to replace (4-methoxyphenyl)(pyridin-3-yl)methanol with bis(1-methyl-1H-indazol-5-yl)methanol (2 equivalents) and in the absence of potassium carbonate, the title compound was obtained as a pale foam (275 mg, 90% yield).

$^1$H NMR (400 MHz, CDCl$_3$) δ 7.91 (d, J=0.9 Hz, 2H), 7.77 (s, 2H), 7.51 (dd, J=8.8, 1.5 Hz, 2H), 7.30 (d, J=8.9 Hz, 2H), 4.48 (s, 1H), 4.01 (s, 6H), 3.44 (m, 4H), 2.39 (m, 4H), 1.43 (s, 9H).

Step 3. Preparation of 5,5'-(piperazin-1-ylmethylene)bis(1-methyl-1H-indazole)

General Procedure S

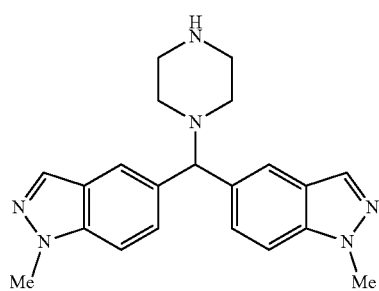 [SMILES: Cn1ncc2cc(C(c3ccc4c(cnn4C)c3)N3CCNCC3)ccc21]

tert-Butyl 4-(bis(1-methyl-1H-indazol-5-yl)methyl)piperazine-1-carboxylate (270 mg, 0.586 mmol) was dissolved in dichloromethane (6 mL) and stirred at ambient temperature while 4-methylmorpholine (0.21 mL, 1.9 mmol) was added followed by dropwise addition of iodotrimethylsilane (0.17 mL, 1.2 mmol). The reaction vessel was sealed, and the solution was stirred at ambient temperature for 2 hours then diluted with dichloromethane (20 mL) and washed with saturated aqueous sodium bicarbonate (20 mL). The aqueous phase was extracted with dichloromethane (10 mL), and the combined organic layers were dried over anhydrous sodium sulfate, filtered and concentrated in vacuo. The residue was purified by column chromatography, eluting with 6% to 10% methanol (containing 10% aqueous ammonium hydroxide) in dichloromethane to afford the title compound as a colourless foam (210 mg, 100% yield).

$^1$H NMR (400 MHz, CDCl$_3$) δ 7.90 (d, J=0.9 Hz, 2H), 7.77 (s, 2H), 7.52 (dd, J=8.8, 1.5 Hz, 2H), 7.29 (d, J=8.7 Hz, 2H), 4.47 (s, 1H), 4.00 (s, 6H), 2.94 (m, 4H), 2.43 (m, 4H).

Step 4. Preparation of 1-(4-(bis(1-methyl-1H-indazol-5-yl)methyl)piperazine-1-carbonyl)-1H-benzo[d][1,2,3]triazole-6-carbonitrile and 1-(4-(bis(1-methyl-1H-indazol-5-yl)methyl)piperazine-1-carbonyl)-1H-benzo[d][1,2,3]triazole-5-carbonitrile (unassigned ratio of 10:9) (Example-110)

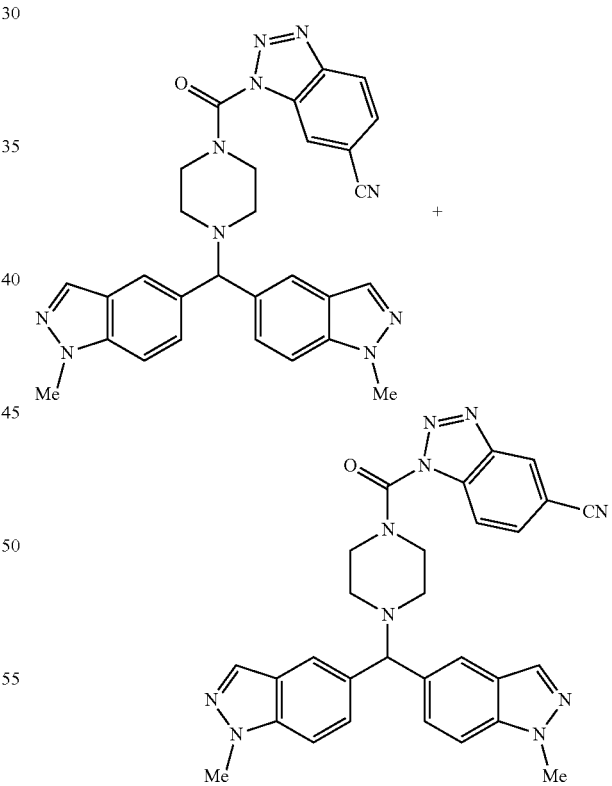

Following General Procedure M and making non-critical variations as required to replace N,N-bis(4-fluorophenyl)piperidin-4-amine with 5,5'-(piperazin-1-ylmethylene)bis(1-methyl-1H-indazole) and replace triethylamine with 4-(dimethylamino)pyridine, the title compounds were obtained as a mixture in an unassigned ratio of 10:9 as a yellow foam (19 mg, 18% yield).

¹H NMR (400 MHz, CDCl₃) δ 8.45 (m, 1H), 8.41 (m, 1H), 8.18 (dd, J=8.6, 0.8 Hz, 1H), 8.11 (dd, J=8.6, 0.8 Hz, 1H), 7.93 (m, 4H), 7.81 (m, 4H), 7.80 (m, 1H), 7.67 (dd, J=8.6, 1.4 Hz, 1H), 7.53 (m, 4H), 7.33 (m, 4H), 4.60 (s, 2H), 4.03 (s, 12H), 3.97 (m, 8H), 2.66 (m, 8H).

Synthesis of 1-(4-(bis(1-methyl-1H-indazol-5-yl)methyl)piperazine-1-carbonyl)-1H-1,2,4-triazole-3-carbonitrile (Example-111)

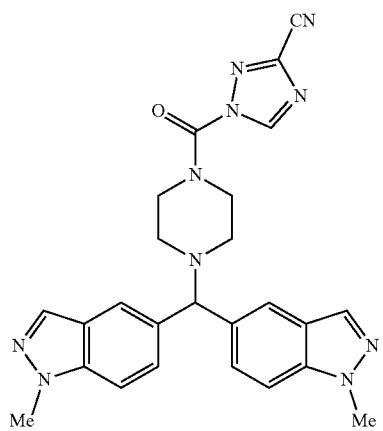 [SMILES: Cn1ncc2cc(C(c3ccc4c(cnn4C)c3)N3CCN(C(=O)n4cnc(C#N)n4)CC3)ccc21]

Following General Procedure M and making non-critical variations as required to replace N,N-bis(4-fluorophenyl)piperidin-4-amine with 5,5'-(piperazin-1-ylmethylene)bis(1-methyl-1H-indazole), replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (28 mg, 39% yield).

¹H NMR (400 MHz, CDCl₃) δ 8.83 (s, 1H), 7.92 (d, J=0.9 Hz, 2H), 7.79 (m, 2H), 7.51 (dd, J=8.7, 1.6 Hz, 2H), 7.33 (m, 2H), 4.56 (s, 1H), 4.02 (s, 6H), 3.93-3.82 (m, 4H), 2.59 (m, 4H).

Synthesis of (1H-benzo[d][1,2,3]triazol-1-yl)(4-(bis(1-methyl-1H-indazol-5-yl)methyl)piperazin-1-yl)methanone (Example-112)

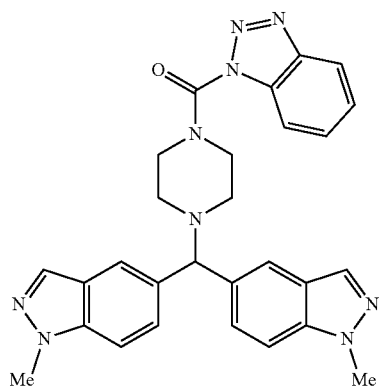 [SMILES: Cn1ncc2cc(C(c3ccc4c(cnn4C)c3)N3CCN(C(=O)n4nnc5ccccc54)CC3)ccc21]

Following General Procedure M and making non-critical variations as required to replace N,N-bis(4-fluorophenyl)piperidin-4-amine with 5,5'-(piperazin-1-ylmethylene)bis(1-methyl-1H-indazole), replace 1H-1,2,3-benzotriazole-5-carbonitrile with 1H-benzotriazole and replace triethylamine with 4-(dimethylamino)pyridine, the title compound was obtained as a yellow foam (74 mg, 65% yield).

¹H NMR (400 MHz, CDCl₃) δ 8.07 (m, 1H), 7.98 (m, 1H), 7.93 (d, J=0.9 Hz, 2H), 7.81 (m, 2H), 7.59 (m, 1H), 7.54 (dd, J=8.8, 1.6 Hz, 2H), 7.44 (m, 1H), 7.33 (d, J=8.7 Hz, 2H), 4.59 (s, 1H), 4.02 (s, 6H), 3.96 (m, 4H), 2.65 (m, 4H); MS (ESI) m/z 506.4 (M+1).

Synthesis of 1-(4-(bis(6-methoxypyridin-3-yl)methyl)piperazine-1-carbonyl)-1H-benzo[d][1,2,3]triazole-6-carbonitrile and 1-(4-(bis(6-methoxypyridin-3-yl)methyl)piperazine-1-carbonyl)-1H-benzo[d][1,2,3]triazole-5-carbonitrile (unassigned ratio of 3:2) (Example-113)

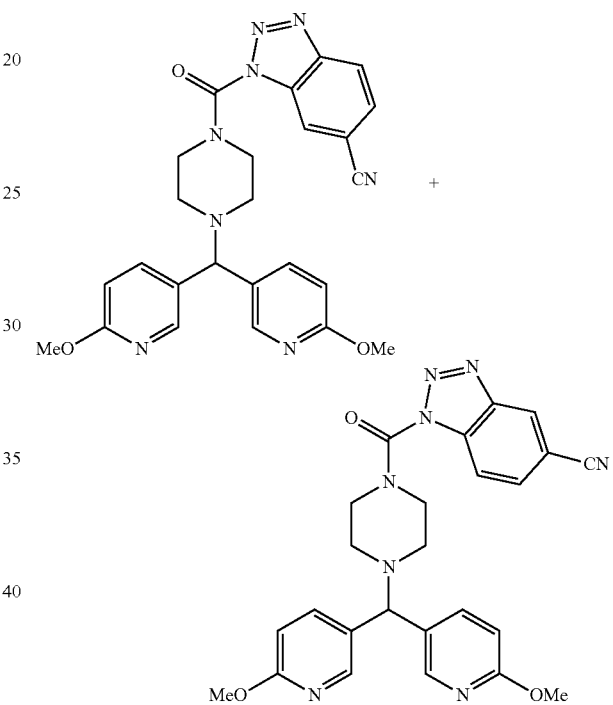

Step 1. Preparation of bis(6-methoxypyridin-3-yl)methanol

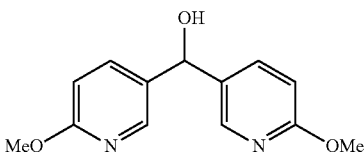 [SMILES: COc1ccc(C(O)c2ccc(OC)nc2)cn1]

Following General Procedure R and making non-critical variations as required to replace 5-bromo-1-methyl-1H-indazole with 5-bromo-2-methoxypyridine and replace 1-methyl-1H-indazole-5-carbaldehyde with 6-methoxynicotinaldehyde, the title compound was obtained as a colourless oil (873 mg, 81% yield).

¹H NMR (400 MHz, CDCl₃) δ 8.15 (d, J=2.6 Hz, 2H), 7.54 (dd, J=8.6, 2.5 Hz, 2H), 6.72 (d, J=8.6 Hz, 2H), 5.81 (d, J=3.3 Hz, 1H), 3.92 (s, 6H), 2.29 (d, J=3.4 Hz, 1H).

Step 2. Preparation of tert-butyl 4-(bis(6-methoxypyridin-3-yl)methyl)piperazine-1-carboxylate

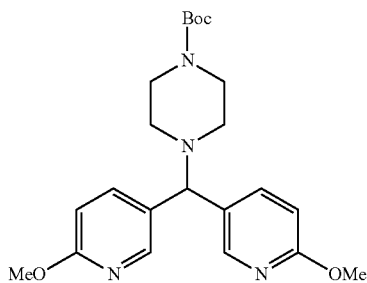 [SMILES: COc1ccc(C(c2ccc(OC)nc2)N2CCN(C(=O)OC(C)(C)C)CC2)cn1]

Following General Procedure Q and making non-critical variations as required to replace (4-methoxyphenyl)(pyridin-3-yl)methanol with bis(6-methoxypyridin-3-yl)methanol, the title compound was obtained as a yellow oil (189 mg, 13% yield).

$^1$H NMR (400 MHz, CDCl$_3$) δ 8.13 (d, J=2.4 Hz, 2H), 7.56 (dd, J=8.6, 2.5 Hz, 2H), 6.69 (d, J=8.6 Hz, 2H), 4.24 (s, 1H), 3.90 (s, 6H), 3.41 (m, 4H), 2.33 (m, 4H), 1.43 (s, 9H).

Step 3. Preparation of 1-(bis(6-methoxypyridin-3-yl)methyl)piperazine

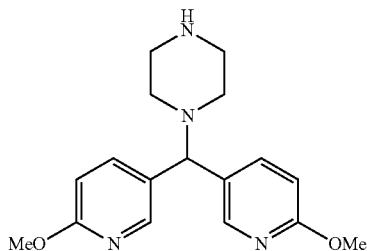 [SMILES: COc1ccc(C(c2ccc(OC)nc2)N2CCNCC2)cn1]

Following General Procedure S and making non-critical variations as required to replace tert-butyl 4-(bis(1-methyl-1H-indazol-5-yl)methyl)piperazine-1-carboxylate with tert-butyl 4-(bis(6-methoxypyridin-3-yl)methyl)piperazine-1-carboxylate, the title compound was obtained as a light yellow oil (110 mg, 79% yield).

$^1$H NMR (400 MHz, CDCl$_3$) δ 8.13 (d, J=2.4 Hz, 2H), 7.57 (dd, J=8.6, 2.5 Hz, 2H), 6.68 (d, J=8.6 Hz, 2H), 4.23 (s, 1H), 3.90 (s, 6H), 2.89 (m, 4H), 2.36 (m, 4H) (NH not observed).

Step 4. Preparation of 1-(4-(bis(6-methoxypyridin-3-yl)methyl)piperazine-1-carbonyl)-1H-benzo[d][1,2,3]triazole-6-carbonitrile and 1-(4-(bis(6-methoxypyridin-3-yl)methyl)piperazine-1-carbonyl)-1H-benzo[d][1,2,3]triazole-5-carbonitrile (unassigned ratio of 3:2) (Example-113)

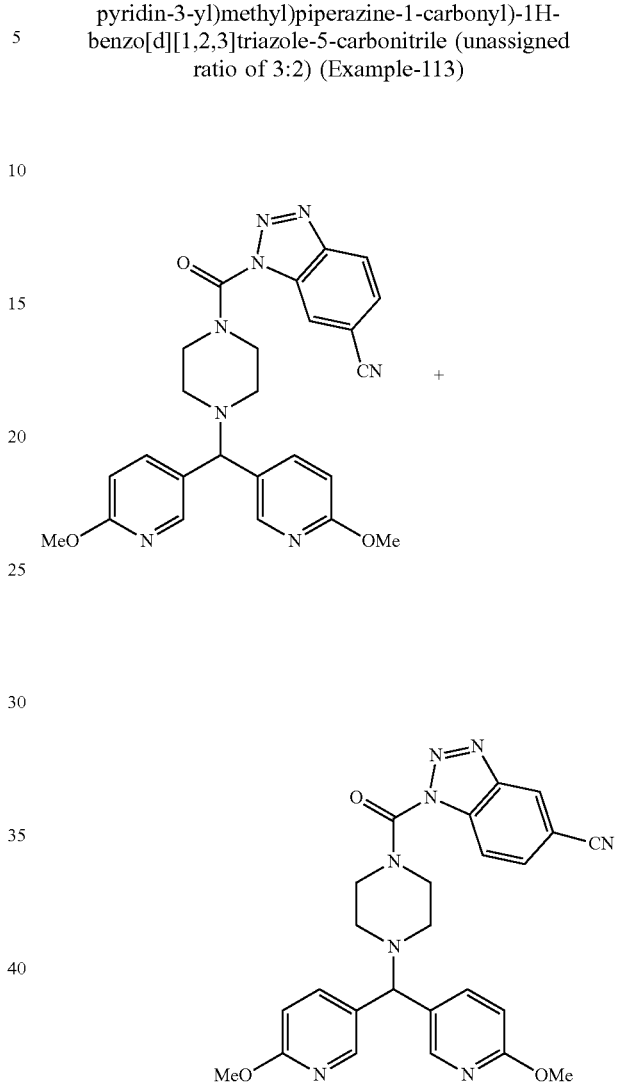

Following General Procedure M and making non-critical variations as required to replace N,N-bis(4-fluorophenyl)piperidin-4-amine with 1-(bis(6-methoxypyridin-3-yl)methyl)piperazine and replace triethylamine with 4-(dimethylamino)pyridine, the title compounds were obtained as a mixture in an unassigned ratio of 3:2 as a light yellow foam (65 mg, 76% yield).

$^1$H NMR (400 MHz, CDCl$_3$) δ 8.46 (m, 1H), 8.41 (m, 1H), 8.19 (m, 1H), 8.18 (d, J=2.5 Hz, 4H), 8.11 (dd, J=8.7, 0.8 Hz, 1H), 7.81 (dd, J=8.6, 1.4 Hz, 1H), 7.68 (dd, J=8.6, 1.4 Hz, 1H), 7.59 (m, 4H), 6.72 (d, J=8.6 Hz, 4H), 4.36 (s, 2H), 3.94 (m, 8H), 3.91 (s, 12H), 2.60 (m, 8H).

Synthesis of 1-(4-(bis(6-methoxypyridin-3-yl)methyl)piperazine-1-carbonyl)-1H-1,2,4-triazole-3-carbonitrile (Example-114)

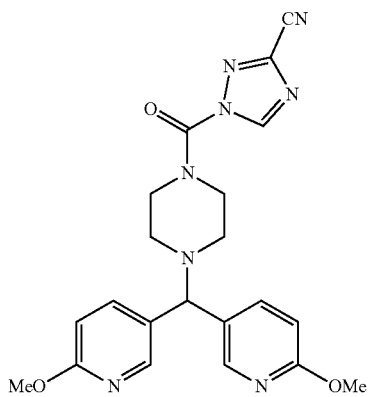 [SMILES: COc1ccc(C(c2ccc(OC)nc2)N2CCN(C(=O)n3cnc(C#N)n3)CC2)cn1]

Following General Procedure M and making non-critical variations as required to replace N,N-bis(4-fluorophenyl)piperidin-4-amine with 1-(bis(6-methoxypyridin-3-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a light yellow foam (31 mg, 45% yield).

$^1$H NMR (400 MHz, CDCl$_3$) δ 8.84 (s, 1H), 8.16 (d, J=2.4 Hz, 2H), 7.57 (dd, J=8.6, 2.5 Hz, 2H), 6.72 (d, J=8.6 Hz, 2H), 4.32 (s, 1H), 3.91 (s, 6H), 3.91-3.78 (m, 4H), 2.54 (s, 4H).

Synthesis of 1-(4-(bis(4-(1H-pyrazol-1-yl)phenyl)methyl)piperazine-1-carbonyl)-1H-benzo[d][1,2,3]triazole-6-carbonitrile and 1-(4-(bis(4-(1H-pyrazol-1-yl)phenyl)methyl)piperazine-1-carbonyl)-1H-benzo[d][1,2,3]triazole-5-carbonitrile (unassigned ratio of_3:2) (Example-115)

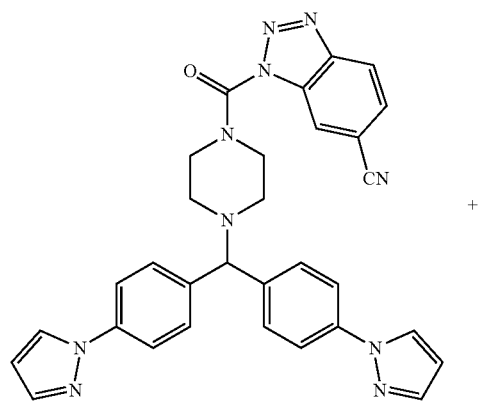

+

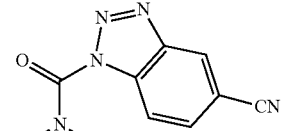

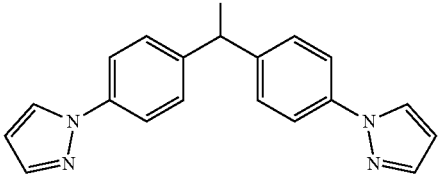

Step 1. Preparation of bis(4-(1H-pyrazol-1-yl)phenyl)methanol

General Procedure T

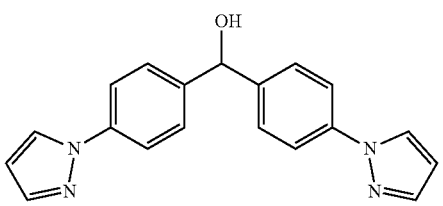 [SMILES: OC(c1ccc(-n2cccn2)cc1)c1ccc(-n2cccn2)cc1]

A solution of 1-(4-bromophenyl)-1H-pyrazole (743 mg, 3.33 mmol) in anhydrous tetrahydrofuran (66 mL) was cooled to −84° C. and stirred under nitrogen atmosphere while n-butyllithium (1.5 M in hexanes, 2.44 mL, 3.7 mmol) was added dropwise. The mixture was stirred at −84° C. for 30 minutes then a solution of ethyl formate (123 mg, 1.66 mmol) in anhydrous tetrahydrofuran (13 mL) was slowly added. The mixture was stirred at −84° C. for 10 minutes then at ambient temperature for 3 hours. Saturated aqueous ammonium chloride (20 mL) was added, and the aqueous phase was extracted with ethyl acetate (20 mL). The combined organic layers were dried over anhydrous sodium sulfate, filtered and concentrated in vacuo. The residue was purified by column chromatography, eluting with 20% to 50% ethyl acetate in hexanes to afford the title compound as a yellow oil (235 mg, 45% yield).

$^1$H NMR (400 MHz, CDCl$_3$) δ 7.62 (d, J=1.8 Hz, 2H), 7.32 (m, 6H), 7.18 (m, 4H), 6.46 (d, J=1.8 Hz, 2H), 5.78 (d, J=5.5 Hz, 1H), 2.54 (d, J=5.9 Hz, 1H).

Step 2. Preparation of tert-butyl 4-(bis(4-(1H-pyrazol-1-yl)phenyl)methyl)piperazine-1-carboxylate

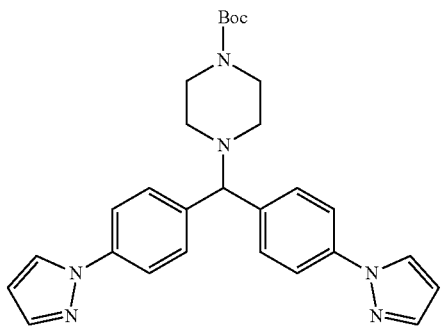 [SMILES: CC(C)(C)OC(=O)N1CCN(C(c2ccc(-n3cccn3)cc2)c2ccc(-n3cccn3)cc2)CC1]

Following General Procedure Q and making non-critical variations as required to replace (4-methoxyphenyl)(pyridin-3-yl)methanol with bis(4-(1H-pyrazol-1-yl)phenyl)methanol (2 equivalents) and in the absence of potassium carbonate, the title compound was obtained as a light yellow foam (266 mg, 75% yield).

$^1$H NMR (400 MHz, CDCl$_3$) δ 7.66 (d, J=1.9 Hz, 2H), 7.34 (m, 6H), 7.20 (m, 4H), 6.46 (d, J=1.9 Hz, 2H), 5.10 (s, 1H), 3.14 (m, 4H), 2.22 (m, 4H), 1.40 (s, 9H).

Step 3. Preparation of 1-(bis(4-(1H-pyrazol-1-yl)phenyl)methyl)piperazine

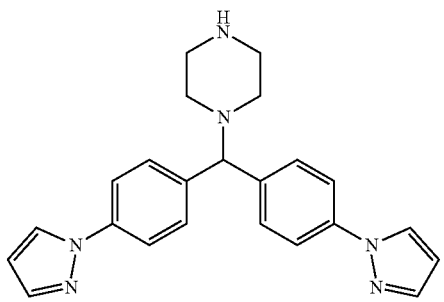 [SMILES: c1cnn(-c2ccc(C(c3ccc(-n4cccn4)cc3)N3CCNCC3)cc2)c1]

Following General Procedure S and making non-critical variations as required to replace tert-butyl 4-(bis(1-methyl-1H-indazol-5-yl)methyl)piperazine-1-carboxylate with tert-butyl 4-(bis(4-(1H-pyrazol-1-yl)phenyl)methyl)piperazine-1-carboxylate, the title compound was obtained as a colourless foam (141 mg, 68% yield).

$^1$H NMR (400 MHz, CDCl$_3$) δ 7.65 (d, J=1.9 Hz, 2H), 7.32 (m, 6H), 7.20 (m, 4H), 6.48 (d, J=1.9 Hz, 2H), 5.03 (s, 1H), 2.63 (m, 4H), 2.28 (m, 4H) (NH not observed).

Step 4. Preparation of 1-(4-(bis(4-(1H-pyrazol-1-yl)phenyl)methyl)piperazine-1-carbonyl)-1H-benzo[d][1,2,3]triazole-6-carbonitrile and 1-(4-(bis(4-(1H-pyrazol-1-yl)phenyl)methyl)piperazine-1-carbonyl)-1H-benzo[d][1,2,3]triazole-5-carbonitrile (unassigned ratio of 3:2) (Example-115)

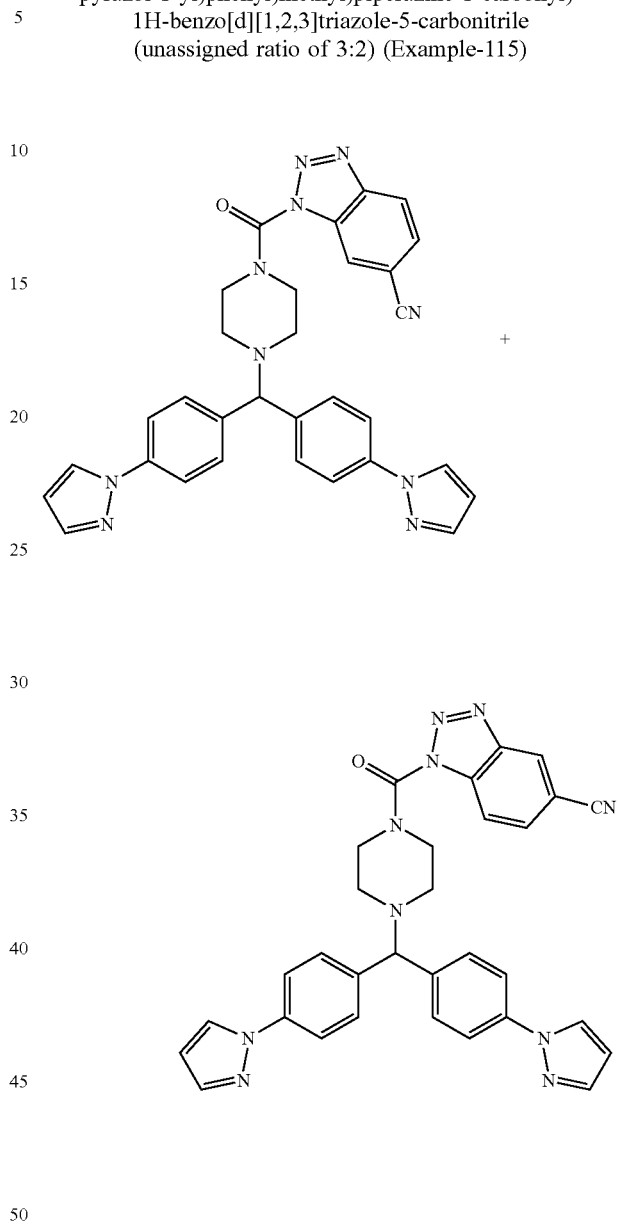

Following General Procedure M and making non-critical variations as required to replace N,N-bis(4-fluorophenyl)piperidin-4-amine with 1-(bis(4-(1H-pyrazol-1-yl)phenyl)methyl)piperazine and replace triethylamine with 4-(dimethylamino)pyridine, the title compounds were obtained as a mixture in an unassigned ratio of 3:2 as a pale foam (34 mg, 33% yield).

$^1$H NMR (400 MHz, CDCl$_3$) δ 8.45 (m, 1H), 8.36 (m, 1H), 8.18 (dd, J=8.6, 0.9 Hz, 1H), 8.06 (dd, J=8.6, 0.8 Hz, 1H), 7.79 (dd, J=8.6, 1.4 Hz, 1H), 7.69 (d, J=1.9 Hz, 4H), 7.67 (dd, J=8.6, 1.4 Hz, 1H), 7.38 (m, 12H), 7.22 (m, 8H), 6.50 (d, J=1.9 Hz, 4H), 5.24 (s, 2H), 3.68-3.55 (m, 8H), 2.45 (m, 8H).

Synthesis of 1-(4-(bis(4-(1H-pyrazol-1-yl)phenyl)methyl)piperazine-1-carbonyl)-1H-1,2,4-triazole-3-carbonitrile (Example-116)

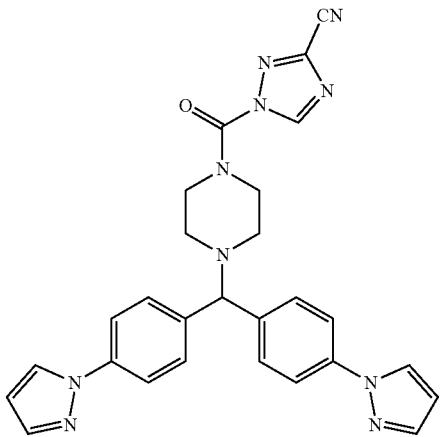 [SMILES: N#Cc1ncn(C(=O)N2CCN(C(c3ccc(-n4cccn4)cc3)c3ccc(-n4cccn4)cc3)CC2)n1]

Following General Procedure M and making non-critical variations as required to replace N,N-bis(4-fluorophenyl)piperidin-4-amine with 1-(bis(4-(1H-pyrazol-1-yl)phenyl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (23 mg, 25% yield).

$^1$H NMR (400 MHz, CDCl$_3$) δ 8.78 (s, 1H), 7.69 (d, J=2.0 Hz, 2H), 7.38 (m, 6H), 7.21 (m, 4H), 6.49 (d, J=1.9 Hz, 2H), 5.23 (s, 1H), 3.58-3.45 (m, 4H), 2.37 (m, 4H).

Synthesis of 1-(4-(di(benzofuran-5-yl)methyl)piperazine-1-carbonyl)-1H-1,2,4-triazole-3-carbonitrile (Example-117)

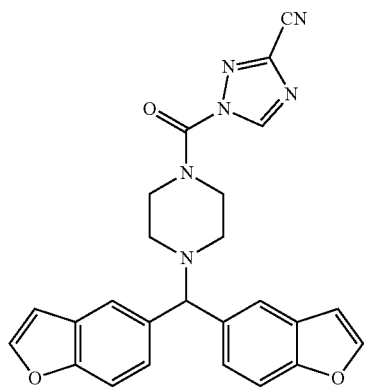 [SMILES: N#Cc1ncn(C(=O)N2CCN(C(c3ccc4occc4c3)c3ccc4occc4c3)CC2)n1]

Step 1. Preparation of di(benzofuran-5-yl)methanol

General Procedure U

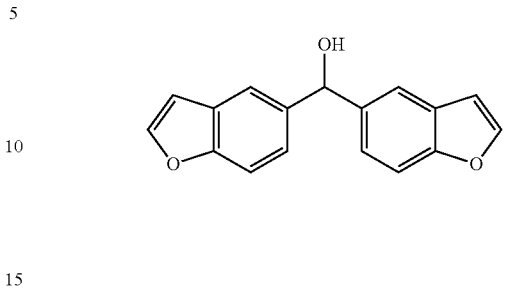

A solution of n-butyllithium (1.5 M in hexanes, 2.3 mL, 3.5 mmol) in anhydrous tetrahydrofuran (16 mL) was cooled to −78° C. and stirred under nitrogen atmosphere while a solution of 5-bromobenzofuran (617 mg, 3.13 mmol) in anhydrous tetrahydrofuran (5 mL) was added dropwise. The mixture was stirred at −78° C. for 1 hour then a solution of 1-benzofuran-5-carbaldehyde (458 mg, 3.13 mmol) in anhydrous tetrahydrofuran (4 mL) was slowly added. The mixture was stirred at −78° C. for 2 hours then saturated aqueous ammonium chloride (15 mL) was added. The mixture was stirred at ambient temperature for 1 hour then water (10 mL) was added, and the aqueous phase was extracted with dichloromethane (15 mL). The combined organic layers were dried over anhydrous sodium sulfate, filtered and concentrated in vacuo. The residue was purified by column chromatography, eluting with 10% to 15% ethyl acetate in hexanes to afford the title compound as a pale oil (616 mg, 74% yield).

$^1$H NMR (400 MHz, CDCl$_3$) δ 7.65 (m, 2H), 7.62 (d, J=2.2 Hz, 2H), 7.46 (m, 2H), 7.32 (dd, J=8.5, 1.8 Hz, 2H), 6.74 (dd, J=2.2, 1.0 Hz, 2H), 6.08 (d, J=3.3 Hz, 1H), 2.28 (d, J=3.4 Hz, 1H).

Step 2. Preparation of tert-butyl 4-(di(benzofuran-5-yl)methyl)piperazine-1-carboxylate

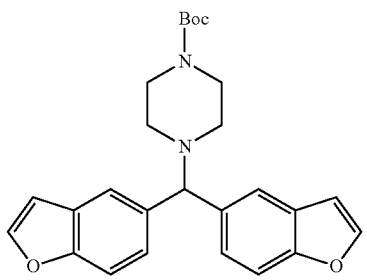

Following General Procedure Q and making non-critical variations as required to replace (4-methoxyphenyl)(pyridin-3-yl)methanol with di(benzofuran-5-yl)methanol, the title compound was obtained as a colourless foam (270 mg, 83% yield).

$^1$H NMR (400 MHz, CDCl$_3$) δ 7.66 (m, 2H), 7.57 (d, J=2.2 Hz, 2H), 7.40 (m, 4H), 6.71 (d, J=2.2 Hz, 2H), 4.43 (s, 1H), 3.44 (m, 4H), 2.38 (m, 4H), 1.43 (s, 9H).

Step 3. Preparation of 1-(di(benzofuran-5-yl)methyl)piperazine

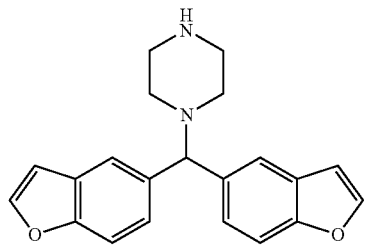 [SMILES: c1cc2cc(C(c3ccc4occc4c3)N3CCNCC3)ccc2o1]

Following General Procedure S and making non-critical variations as required to replace tert-butyl 4-(bis(1-methyl-1H-indazol-5-yl)methyl)piperazine-1-carboxylate with tert-butyl 4-(di(benzofuran-5-yl)methyl)piperazine-1-carboxylate, the title compound was obtained as a colourless foam (144 mg, 71% yield).

$^1$H NMR (400 MHz, CDCl$_3$) δ 7.67 (m, 2H), 7.56 (d, J=2.2 Hz, 2H), 7.40 (m, 4H), 6.71 (dd, J=2.2, 0.6 Hz, 2H), 4.41 (s, 1H), 2.91 (m, 4H), 2.41 (m, 4H) (NH not observed).

Step 4. Preparation of 1-(4-(di(benzofuran-5-yl)methyl)piperazine-1-carbonyl)-1H-1,2,4-triazole-3-carbonitrile (Example-117)

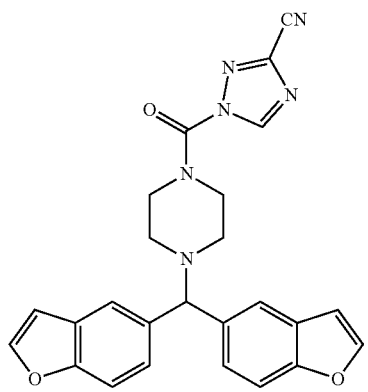 [SMILES: N#Cc1ncn(C(=O)N2CCN(C(c3ccc4occc4c3)c3ccc4occc4c3)CC2)n1]

Following General Procedure M and making non-critical variations as required to replace N,N-bis(4-fluorophenyl)piperidin-4-amine with 1-(di(benzofuran-5-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (61 mg, 70% yield).

$^1$H NMR (400 MHz, CDCl$_3$) δ 8.83 (s, 1H), 7.67 (m, 2H), 7.59 (d, J=2.2 Hz, 2H), 7.42 (m, 4H), 6.72 (dd, J=2.2, 0.8 Hz, 2H), 4.51 (s, 1H), 3.92-3.81 (m, 4H), 2.58 (m, 4H).

Synthesis of 1-(4-((4H-benzo[d][1,3]dioxin-6-yl)(6-methoxypyridin-3-yl)methyl)piperazine-1-carbonyl)-1H-1,2,4-triazole-3-carbonitrile (Example-118)

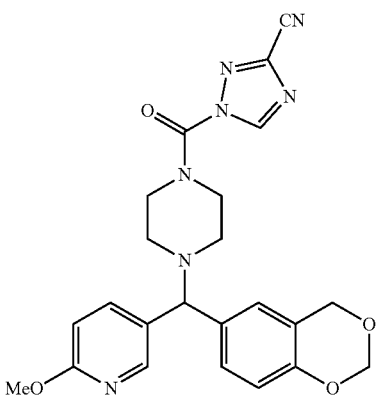 [SMILES: COc1ccc(C(c2ccc3c(c2)COCO3)N2CCN(C(=O)n3cnc(C#N)n3)CC2)cn1]

Step 1. Preparation of (4H-benzo[d][1,3]dioxin-6-yl)(6-methoxypyridin-3-yl)methanol

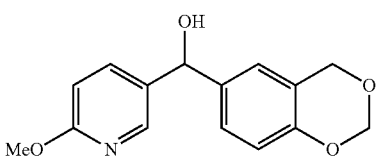 [SMILES: COc1ccc(C(O)c2ccc3c(c2)COCO3)cn1]

Following General Procedure U and making non-critical variations as required to replace 5-bromobenzofuran with 5-bromo-2-methoxypyridine and replace 1-benzofuran-5-carbaldehyde with 4H-benzo[d][1,3]dioxine-6-carbaldehyde, the title compound was obtained as a yellow oil (442 mg, 60% yield).

$^1$H NMR (400 MHz, CDCl$_3$) δ 8.14 (d, J=2.4 Hz, 1H), 7.53 (dd, J=8.6, 2.5 Hz, 1H), 7.14 (dd, J=8.5, 2.2 Hz, 1H), 6.98 (m, 1H), 6.85 (d, J=8.4 Hz, 1H), 6.71 (d, J=8.6 Hz, 1H), 5.75 (d, J=3.2 Hz, 1H), 5.23 (s, 2H), 4.88 (s, 2H), 3.92 (s, 3H), 2.18 (d, J=3.4 Hz, 1H).

Step 2. Preparation of tert-butyl 4-((4H-benzo[d][1,3]dioxin-6-yl)(6-methoxypyridin-3-yl)methyl)piperazine-1-carboxylate

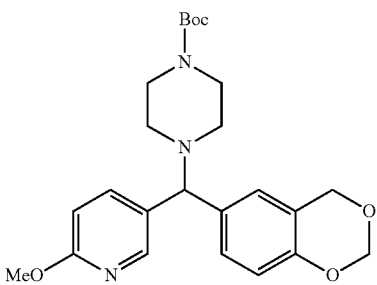 [SMILES: COc1ccc(C(c2ccc3c(c2)COCO3)N2CCN(C(=O)OC(C)(C)C)CC2)cn1]

Following General Procedure Q and making non-critical variations as required to replace (4-methoxyphenyl)(pyridin-3-yl)methanol with (4H-benzo[d][1,3]dioxin-6-yl)(6-methoxypyridin-3-yl)methanol, the title compound was obtained as a light yellow foam (393 mg, 56% yield).

¹H NMR (400 MHz, CDCl₃) δ 8.11 (d, J=2.4 Hz, 1H), 7.56 (dd, J=8.6, 2.5 Hz, 1H), 7.17 (dd, J=8.4, 2.1 Hz, 1H), 6.93 (d, J=2.1 Hz, 1H), 6.80 (d, J=8.4 Hz, 1H), 6.68 (d, J=8.5 Hz, 1H), 5.20 (s, 2H), 4.86 (s, 2H), 4.14 (s, 1H), 3.90 (s, 3H), 3.40 (m, 4H), 2.36-2.26 (m, 4H), 1.43 (s, 9H).

Step 3. Preparation of 1-((4H-benzo[d][1,3]dioxin-6-yl)(6-methoxypyridin-3-yl)methyl)piperazine

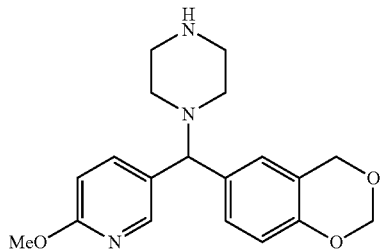 [SMILES: COc1ccc(C(c2ccc3c(c2)COCO3)N2CCNCC2)cn1]

Following General Procedure S and making non-critical variations as required to replace tert-butyl 4-(bis(1-methyl-1H-indazol-5-yl)methyl)piperazine-1-carboxylate with tert-butyl 4-((4H-benzo[d][1,3]dioxin-6-yl)(6-methoxypyridin-3-yl)methyl)piperazine-1-carboxylate, the title compound was obtained as a colourless foam (243 mg, 81% yield).

¹H NMR (400 MHz, CDCl₃) δ 8.11 (d, J=2.4 Hz, 1H), 7.56 (dd, J=8.6, 2.5 Hz, 1H), 7.17 (dd, J=8.5, 2.1 Hz, 1H), 6.94 (d, J=2.1 Hz, 1H), 6.80 (d, J=8.4 Hz, 1H), 6.67 (d, J=8.6 Hz, 1H), 5.20 (s, 2H), 4.86 (s, 2H), 4.13 (s, 1H), 3.89 (s, 3H), 2.89 (m, 4H), 2.36 (m, 4H) (NH not observed).

Step 4. Preparation of 1-(4-((4H-benzo[d][1,3]dioxin-6-yl)(6-methoxypyridin-3-yl)methyl)piperazine-1-carbonyl)-1H-1,2,4-triazole-3-carbonitrile (Example-118)

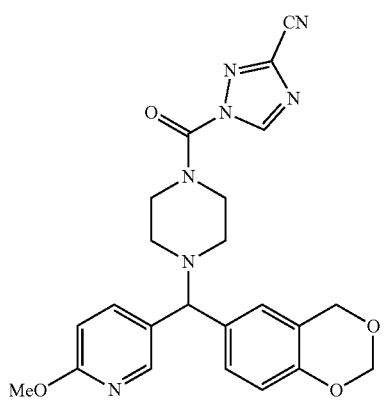

Following General Procedure M and making non-critical variations as required to replace N,N-bis(4-fluorophenyl)piperidin-4-amine with 1-((4H-benzo[d][1,3]dioxin-6-yl)(6-methoxypyridin-3-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (38 mg, 40% yield); MS (ESI) m/z 462.3 (M+1).

¹H NMR (400 MHz, CDCl₃) δ 8.84 (s, 1H), 8.14 (d, J=2.4 Hz, 1H), 7.57 (dd, J=8.6, 2.5 Hz, 1H), 7.19 (dd, J=8.5, 2.1 Hz, 1H), 6.94 (d, J=2.1 Hz, 1H), 6.83 (d, J=8.4 Hz, 1H), 6.70 (d, J=8.6 Hz, 1H), 5.21 (s, 2H), 4.87 (s, 2H), 4.22 (s, 1H), 3.91 (s, 3H), 3.91-3.78 (m, 4H), 2.52 (m, 4H).

Synthesis of 1-(4-((4H-benzo[d][1,3]dioxin-6-yl)(6-methoxypyridin-3-yl)methyl)piperazine-1-carbonyl)-1H-pyrazole-4-carbonitrile (Example-119)

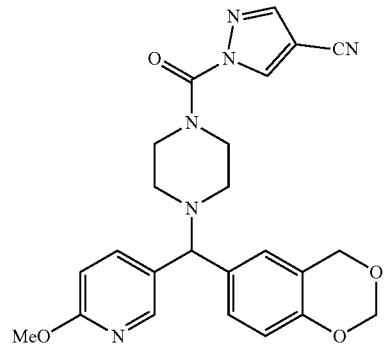 [SMILES: COc1ccc(C(c2ccc3c(c2)COCO3)N2CCN(C(=O)n3cc(C#N)cn3)CC2)cn1]

Following General Procedure V and making non-critical variations as required to replace 1H-benzotriazole with 4-cyanopyrazole and replace 6,6'-(piperazin-1-ylmethylene)diquinoline with 1-((4H-benzo[d][1,3]dioxin-6-yl)(6-methoxypyridin-3-yl)methyl)piperazine, the title compound was obtained as a pale foam (90 mg, 90% yield).

¹H NMR (400 MHz, CDCl₃) δ 8.51 (d, J=0.8 Hz, 1H), 8.14 (d, J=2.4 Hz, 1H), 7.83 (d, J=0.7 Hz, 1H), 7.57 (dd, J=8.6, 2.5 Hz, 1H), 7.19 (dd, J=8.5, 2.2 Hz, 1H), 6.94 (d, J=2.1 Hz, 1H), 6.82 (d, J=8.4 Hz, 1H), 6.69 (d, J=8.5 Hz, 1H), 5.21 (s, 2H), 4.86 (s, 2H), 4.20 (s, 1H), 3.90 (s, 3H), 3.90-3.78 (m, 4H), 2.49 (m, 4H); MS (ESI) m/z 461.4 (M+1).

Scheme XX

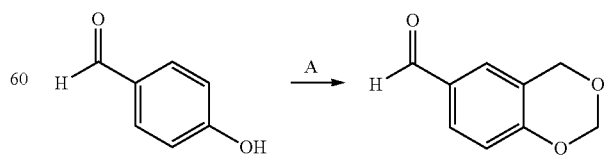

Reagents and conditions: A) HCHO (37%), HClO₄/CH₃COOH, rt to 75° C., 3 h.

Synthesis of 1-(4-((4-(1H-pyrazol-1-yl)phenyl)(4H-benzo[d][1,3]dioxin-6-yl)methyl)piperazine-1-carbonyl)-1H-1,2,4-triazole-3-carbonitrile (Example-120)

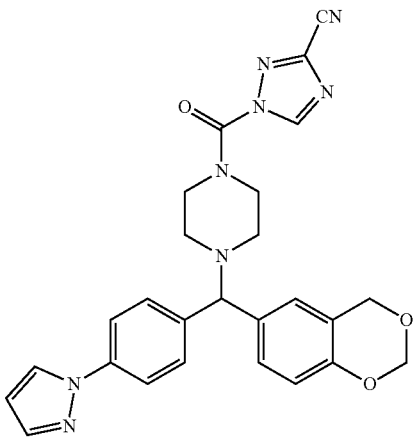 [SMILES: N#Cc1ncn(C(=O)N2CCN(C(c3ccc(-n4cccn4)cc3)c3ccc4c(c3)COCO4)CC2)n1]

Step 1. Preparation of 4H-benzo[d][1,3]dioxine-6-carbaldehyde

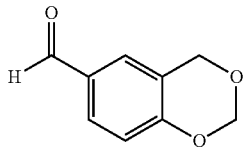 [SMILES: O=Cc1ccc2c(c1)COCO2]

A solution of 4-hydroxybenzaldehyde (2.05 g, 16.8 mmol) in 37% aqueous formaldehyde (47 mL) was stirred at ambient temperature while a solution of 70% aqueous perchloric acid (22 mL) in acetic acid (120 mL) was added dropwise over 2.5 hours. The mixture was heated to 75° C. for 3 hours then allowed to cool to ambient temperature. The mixture was concentrated in vacuo to reduce the volume by approximately 90 mL. Water (50 mL) was added, and the mixture was extracted with dichloromethane (25 mL then 2×20 mL). The combined organic layers were washed with saturated aqueous sodium bicarbonate until the washings remained basic then dried over anhydrous sodium sulfate, filtered and concentrated in vacuo to provide the title compound as colourless crystals (1.96 g, 71% yield) that were used in the next step without further purification.

$^1$H NMR (400 MHz, CDCl$_3$) δ 9.87 (s, 1H), 7.71 (dd, J=8.5, 2.0 Hz, 1H), 7.54 (m, 1H), 7.00 (d, J=8.4 Hz, 1H), 5.32 (s, 2H), 4.96 (s, 2H).

Step 2. Preparation of (4-(1H-pyrazol-1-yl)phenyl)(4H-benzo[d][1,3]dioxin-6-yl)methanol

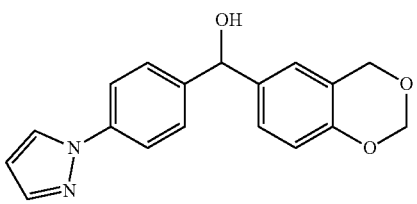 [SMILES: OC(c1ccc(-n2cccn2)cc1)c1ccc2c(c1)COCO2]

Following General Procedure R and making non-critical variations as required to replace 5-bromo-1-methyl-1H-indazole with 1-(4-bromophenyl)-1H-pyrazole and replace 1-methyl-1H-indazole-5-carbaldehyde with 4H-benzo[d][1,3]dioxine-6-carbaldehyde, the title compound was obtained as a yellow oil (390 mg, 46% yield).

$^1$H NMR (400 MHz, CDCl$_3$) δ 7.62 (d, J=1.9 Hz, 1H), 7.42 (m, 5H), 7.07 (dd, J=8.4, 2.2 Hz, 1H), 6.88 (d, J=2.2 Hz, 1H), 6.82 (d, J=8.5 Hz, 1H), 6.33 (d, J=1.9 Hz, 1H), 5.78 (d, J=4.6 Hz, 1H), 5.23 (s, 2H), 4.84 (s, 2H), 2.26 (d, J=4.6 Hz, 1H).

Step 3. Preparation of tert-butyl 4-((4-(1H-pyrazol-1-yl)phenyl)(4H-benzo[d][1,3]dioxin-6-yl)methyl)piperazine-1-carboxylate

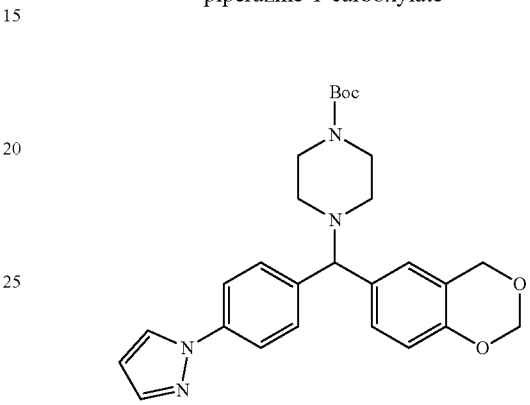

Following General Procedure Q and making non-critical variations as required to replace (4-methoxyphenyl)(pyridin-3-yl)methanol with (4-(1H-pyrazol-1-yl)phenyl)(4H-benzo[d][1,3]dioxin-6-yl)methanol, the title compound was obtained as a colourless foam (477 mg, 80% yield).

$^1$H NMR (400 MHz, CDCl$_3$) δ 7.64 (d, J=1.8 Hz, 1H), 7.44 (m, 3H), 7.24 (m, 2H), 7.01 (dd, J=8.4, 2.1 Hz, 1H), 6.80 (d, J=2.1 Hz, 1H), 6.78 (d, J=8.4 Hz, 1H), 6.46 (d, J=1.9 Hz, 1H), 5.23 (d, J=5.7 Hz, 1H), 5.22 (d, J=5.7 Hz, 1H), 4.83 (s, 2H), 4.42 (s, 1H), 3.34 (m, 4H), 2.34-2.16 (m, 4H), 1.42 (s, 9H).

Step 4. Preparation of 1-((4-(1H-pyrazol-1-yl)phenyl)(4H-benzo[d][1,3]dioxin-6-yl)methyl)piperazine

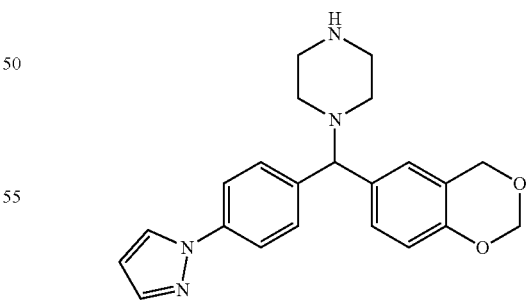

Following General Procedure S and making non-critical variations as required to replace tert-butyl 4-(bis(1-methyl-1H-indazol-5-yl)methyl)piperazine-1-carboxylate with tert-butyl 4-((4-(1H-pyrazol-1-yl)phenyl)(4H-benzo[d][1,3]dioxin-6-yl)methyl)piperazine-1-carboxylate, the title compound was obtained as a colourless foam (329 mg, 88% yield).

¹H NMR (400 MHz, CDCl₃) δ 7.63 (d, J=1.7 Hz, 1H), 7.44 (m, 3H), 7.24 (m, 2H), 7.01 (dd, J=8.5, 2.2 Hz, 1H), 6.80 (d, J=2.1 Hz, 1H), 6.77 (d, J=8.4 Hz, 1H), 6.46 (d, J=1.9 Hz, 1H), 5.23 (d, J=5.7 Hz, 1H), 5.22 (d, J=5.7 Hz, 1H), 4.82 (s, 2H), 4.40 (s, 1H), 2.82 (m, 4H), 2.37-2.21 (m, 4H) (NH not observed).

Step 5. Preparation of 1-(4-((4-(1H-pyrazol-1-yl)phenyl)(4H-benzo[d][1,3]dioxin-6-yl)methyl)piperazine-1-carbonyl)-1H-1,2,4-triazole-3-carbonitrile (Example-120)

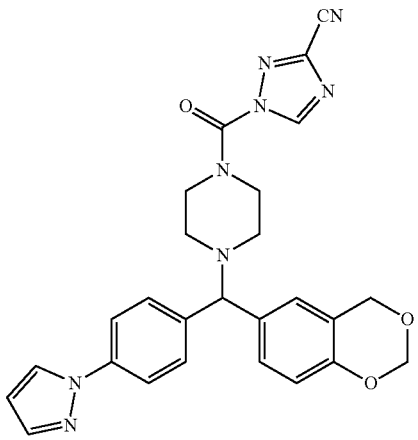 [SMILES: N#Cc1ncn(C(=O)N2CCN(C(c3ccc(-n4cccn4)cc3)c3ccc4c(c3)COCO4)CC2)n1]

Following General Procedure M and making non-critical variations as required to replace N,N-bis(4-fluorophenyl)piperidin-4-amine with 1-((4-(1H-pyrazol-1-yl)phenyl)(4H-benzo[d][1,3]dioxin-6-yl)methyl)piperazine, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (47 mg, 47% yield).

¹H NMR (400 MHz, CDCl₃) δ 8.81 (s, 1H), 7.67 (d, J=1.7 Hz, 1H), 7.46 (m, 3H), 7.24 (m, 2H), 7.05 (dd, J=8.6, 2.2 Hz, 1H), 6.82 (m, 2H), 6.48 (d, J=1.8 Hz, 1H), 5.25 (d, J=5.7 Hz, 1H), 5.23 (d, J=5.7 Hz, 1H), 4.84 (s, 2H), 4.51 (s, 1H), 3.82-3.70 (m, 4H), 2.51-2.35 (m, 4H); MS (ESI) m/z 497.3 (M+1).

Synthesis of 1-(4-(bis(4-fluorophenyl)methyl)piperazine-1-carbonyl)-1H-benzo[d][1,2,3]triazole-5-carbonitrile (Example-121)

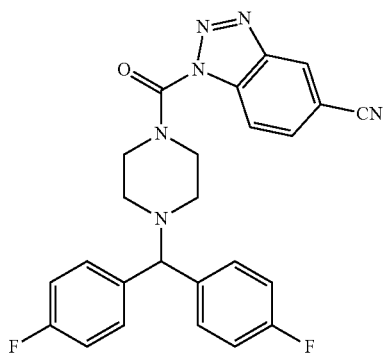 [SMILES: N#Cc1ccc2c(c1)nnn2C(=O)N1CCN(C(c2ccc(F)cc2)c2ccc(F)cc2)CC1]

Step 1. Preparation of bis(4-fluorophenyl)methanol

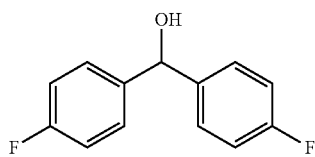 [SMILES: OC(c1ccc(F)cc1)c1ccc(F)cc1]

A solution of 4-fluorophenylmagnesium bromide (1.0 M in tetrahydrofuran, 4.50 mL, 4.50 mmol) was slowly added to a solution of 4-fluorobenzaldehyde (558 mg, 4.50 mmol) in anhydrous tetrahydrofuran (20 mL) at 0° C. under nitrogen atmosphere. The mixture was stirred at ambient temperature for 2 hours then acidified using 1N hydrochloric acid. Ethyl acetate (20 mL) was added, and the organic layer was washed with brine (10 mL) then dried over anhydrous sodium sulfate, filtered and concentrated in vacuo. The residue was purified by column chromatography, eluting with 10% to 15% ethyl acetate in hexanes to provide the title compound as a pale oil (807 mg, 82% yield).

¹H NMR (400 MHz, CDCl₃) δ 7.32 (m, 4H), 7.03 (m, 4H), 5.82 (d, J=3.2 Hz, 1H), 2.18 (d, J=3.4 Hz, 1H).

Step 2. Preparation of tert-butyl 4-(bis(4-fluorophenyl)methyl)piperazine-1-carboxylate

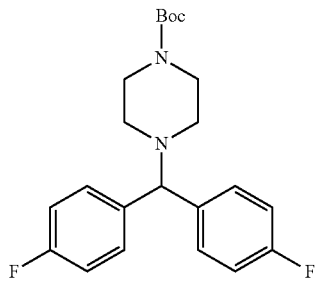 [SMILES: CC(C)(C)OC(=O)N1CCN(C(c2ccc(F)cc2)c2ccc(F)cc2)CC1]

A solution of bis(4-fluorophenyl)methanol (802 mg, 3.64 mmol) in anhydrous dichloromethane (9 mL) was cooled to 0° C. under nitrogen atmosphere and thionyl chloride (0.53 mL, 7.3 mmol) was added dropwise. The solution was stirred at 0° C. for 15 minutes then at ambient temperature for 3 hours. The solution was concentrated in vacuo followed by azeotropic removal of thionyl chloride with dichloromethane (3×10 mL). The residue was dissolved in anhydrous N,N-dimethylformamide (12 mL) and cesium carbonate (2.37 g, 7.27 mmol) was added followed by tert-butyl piperazine-1-carboxylate (678 mg, 3.64 mmol). The mixture was heated to 80° C. under nitrogen atmosphere for 16 hours then allowed to cool to ambient temperature. The residue was partitioned between ethyl acetate (40 mL) and water (20 mL), and the organic layer was washed with brine (5×12 mL) then dried over anhydrous sodium sulfate, filtered and concentrated in vacuo. The residue was purified by column chromatography, eluting with 0% to 10% ethyl acetate in hexanes to provide the title compound as colourless crystals (304 mg, 22% yield).

¹H NMR (400 MHz, CDCl₃) δ 7.33 (m, 4H), 6.97 (m, 4H), 4.21 (s, 1H), 3.41 (m, 4H), 2.30 (m, 4H), 1.43 (s, 9H).

Step 3. Preparation of 1-(bis(4-fluorophenyl)methyl)piperazine

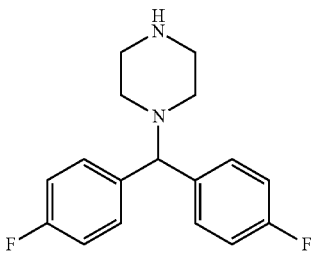 [SMILES: Fc1ccc(C(c2ccc(F)cc2)N2CCNCC2)cc1]

Following General Procedure L and making non-critical variations as required to replace tert-butyl 4-(bis(4-fluorophenyl)amino)piperidine-1-carboxylate with 4-(bis(4-fluorophenyl)methyl)piperazine-1-carboxylate, the title compound was obtained as a yellow oil (222 mg, 100% yield).

$^1$H NMR (400 MHz, CDCl$_3$) δ 7.34 (m, 4H), 6.96 (m, 4H), 4.21 (s, 1H), 2.90 (m, 4H), 2.35 (m, 4H) (NH not observed).

Step 4. Preparation of 1-(4-(bis(4-fluorophenyl)methyl)piperazine-1-carbonyl)-1H-benzo[d][1,2,3]triazole-5-carbonitrile (Example-121)

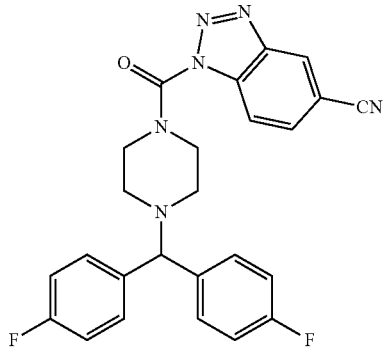 [SMILES: N#Cc1ccc2c(c1)nnn2C(=O)N1CCN(C(c2ccc(F)cc2)c2ccc(F)cc2)CC1]

Following General Procedure M and making non-critical variations as required to replace N,N-bis(4-fluorophenyl)piperidin-4-amine with 1-(bis(4-fluorophenyl)methyl)piperazine, the title compound was obtained as a pale foam (29 mg, 22% yield).

The structure of 1-(4-(bis(4-fluorophenyl)methyl)piperazine-1-carbonyl)-1H-benzo[d][1,2,3]triazole-5-carbonitrile was tentatively assigned.

$^1$H NMR (400 MHz, CDCl$_3$) δ 8.46 (s, 1H), 8.11 (d, J=8.6 Hz, 1H), 7.81 (dd, J=8.6, 1.4 Hz, 1H), 7.37 (m, 4H), 7.01 (m, 4H), 4.33 (s, 1H), 3.93 (m, 4H), 2.58 (m, 4H).

Scheme XXI

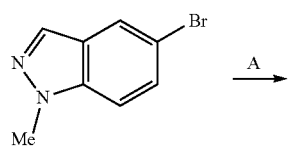

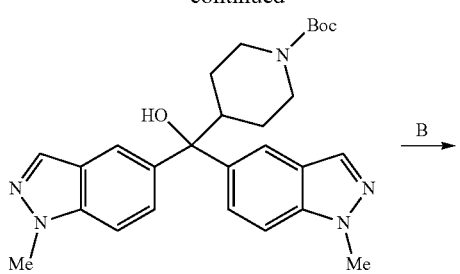

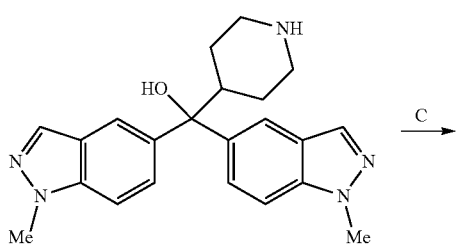

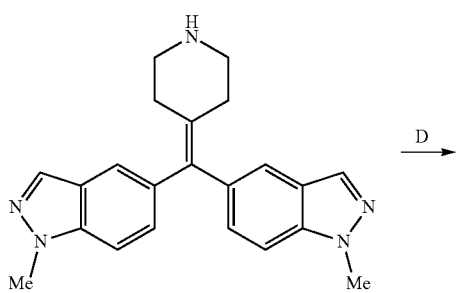

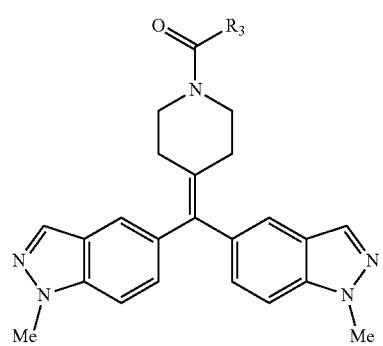

Reagents and conditions: A) i) n-BuLi, THF, -78° C., 2 h; ii) Ethyl 1-(tert-butoxycarbonyl)-4-piperidinecarboxylate, THF, -78° C. to rt, 21 h; B) TMSI, NMM, DCM, rt, 2 h; C) p-TsOH•H$_2$O, toluene, 70° C.; D) Method A: i) Triphosgene, DCM, 0° C.; ii) 5,5'-(Piperidin-4-ylidenemethylene)bis(1-methyl-1H-indazole), DMAP, DCM, rt, 2 h; iii) R$_3$—H, DMAP, THF, rt, 3 d; or Method B: i) Triphosgene, DCM, 0° C.; ii) 1H-benzotriazole, DMAP, DCM, rt, 3 h; iii) 5,5'-(Piperidin-4-ylidenemethylene)bis(1-methyl-1H-indazole), DMAP, THF, rt, 3 d.

Synthesis of (1H-benzo[d][1,2,3]triazol-1-yl)(4-(bis (1-methyl-1H-indazol-5-yl)methylene)piperidin-1-yl)methanone (Example-122)

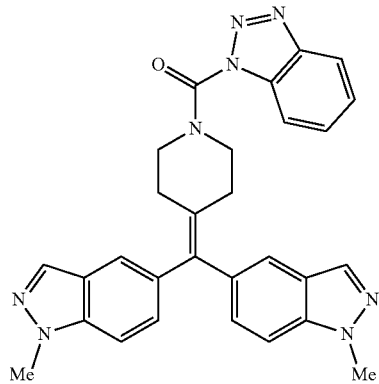 [SMILES: Cn1ncc2cc(C(=C3CCN(C(=O)n4nnc5ccccc54)CC3)c3ccc4c(cnn4C)c3)ccc21]

Step 1. Preparation of tert-butyl 4-(hydroxybis(1-methyl-1H-indazol-5-yl)methyl)piperidine-1-carboxylate

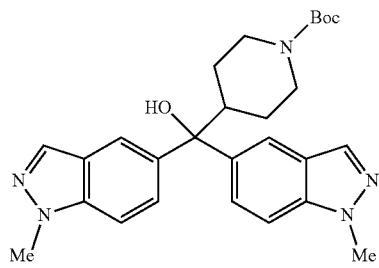 [SMILES: Cn1ncc2cc(C(O)(c3ccc4c(cnn4C)c3)C3CCN(C(=O)OC(C)(C)C)CC3)ccc21]

Following General Procedure T and making non-critical variations as required to replace 1-(4-bromophenyl)-1H-pyrazole with 5-bromo-1-methyl-1H-indazole and replace ethyl formate with ethyl 1-(tert-butoxycarbonyl)-4-piperidinecarboxylate, the title compound was obtained as a yellow gummy solid (531 mg, 83% yield).

$^{1}$H NMR (400 MHz, CDCl$_3$) δ 7.94 (d, J=0.9 Hz, 2H), 7.89 (m, 2H), 7.45 (dd, J=8.9, 1.7 Hz, 2H), 7.29 (m, 2H), 4.21-4.10 (m, 2H), 4.02 (s, 6H), 2.79-2.65 (m, 3H), 2.18 (s, 1H), 1.58 (m, 2H), 1.42 (s, 9H), 1.40-1.30 (m, 2H).

Step 2. Preparation of bis(1-methyl-1H-indazol-5-yl)(piperidin-4-yl)methanol

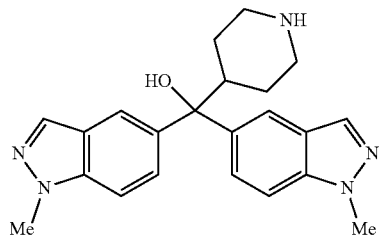 [SMILES: Cn1ncc2cc(C(O)(c3ccc4c(cnn4C)c3)C3CCNCC3)ccc21]

Following General Procedure S and making non-critical variations as required to replace tert-butyl 4-(bis(1-methyl-1H-indazol-5-yl)methyl)piperazine-1-carboxylate with tert-butyl 4-(hydroxybis(1-methyl-1H-indazol-5-yl)methyl)piperidine-1-carboxylate, pale crystals (274 mg) were obtained containing the title compound plus unidentified impurities.

Step 3. Preparation of 5,5'-(piperidin-4-ylidenemethylene)bis(1-methyl-1H-indazole)

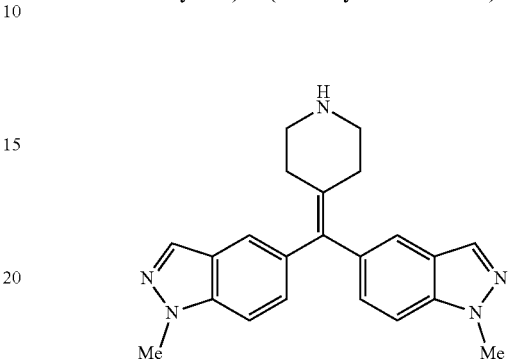

p-Toluenesulfonic acid monohydrate (164 mg, 0.862 mmol) was added to a solution of bis(1-methyl-1H-indazol-5-yl)(piperidin-4-yl)methanol (270 mg, containing impurities as specified above) in toluene (20 mL), and the mixture was heated to 70° C. under nitrogen atmosphere for 21 hours. The mixture was allowed to cool to ambient temperature, and 1N aqueous sodium hydroxide (20 mL) was added then stirred until all material dissolved. The aqueous phase was extracted with ethyl acetate (2×15 mL), and the combined organic layers were dried over anhydrous sodium sulfate, filtered and concentrated in vacuo. The residue was purified by column chromatography, eluting with 6% to 8% methanol (containing 10% aqueous ammonium hydroxide) in dichloromethane to afford the title compound as a pale foam (185 mg, 64% yield over 2 steps).

$^{1}$H NMR (400 MHz, CDCl$_3$) δ 7.92 (d, J=1.0 Hz, 2H), 7.50 (m, 2H), 7.29 (m, 2H), 7.15 (dd, J=8.6, 1.5 Hz, 2H), 4.04 (s, 6H), 2.98 (m, 4H), 2.43 (m, 4H) (NH not observed).

Step 4. Preparation of (1H-benzo[d][1,2,3]triazol-1-yl)(4-(bis(1-methyl-1H-indazol-5-yl)methylene)piperidin-1-yl)methanone (Example-122)

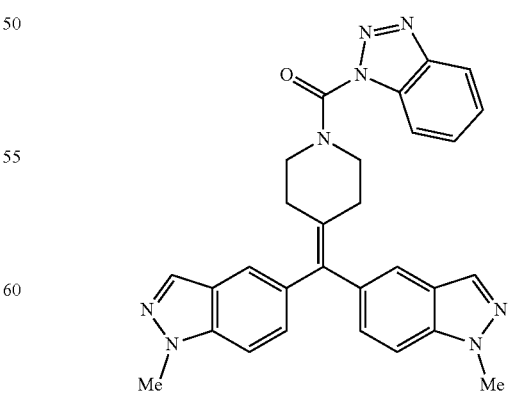

Following General Procedure V and making non-critical variations as required to replace 6,6'-(piperazin-1-ylmethylene)diquinoline with 5,5'-(piperidin-4-ylidenemethylene)bis(1-methyl-1H-indazole), the title compound was obtained as a pale foam (56 mg, 80% yield).

¹H NMR (400 MHz, CDCl₃) δ 8.09 (m, 1H), 8.00 (m, 1H), 7.94 (br s, 2H), 7.60 (m, 1H), 7.54 (br s, 2H), 7.45 (m, 1H), 7.32 (d, J=8.6 Hz, 2H), 7.17 (dd, J=8.6, 1.5 Hz, 2H), 4.06 (s, 6H), 3.94 (m, 4H), 2.69 (m, 4H); MS (ESI) m/z 503.4 (M+1); MS (ESI) m/z 503.4 (M+1).

Synthesis of 1-(4-(bis(1-methyl-1H-indazol-5-yl)methylene)piperidine-1-carbonyl)-1H-1,2,4-triazole-3-carbonitrile (Example-123)

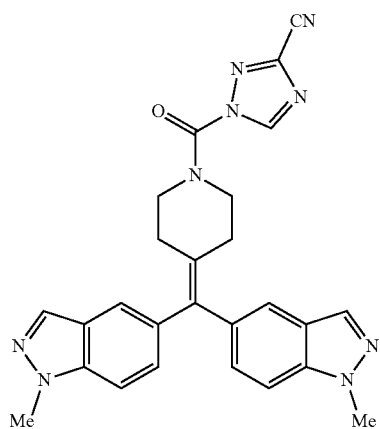 [SMILES: Cn1ncc2cc(C(=C3CCN(C(=O)n4cnc(C#N)n4)CC3)c3ccc4c(cnn4C)c3)ccc21]

Following General Procedure M and making non-critical variations as required to replace N,N-bis(4-fluorophenyl)piperidin-4-amine with 5,5'-(piperidin-4-ylidenemethylene)bis(1-methyl-1H-indazole), replace 1H-1,2,3-benzotriazole-5-carbonitrile with 2H-1,2,4-triazole-3-carbonitrile and replace triethylamine with 4-(dimethylamino)pyridine, the title compound was obtained as a light yellow foam (16 mg, 20% yield).

¹H NMR (400 MHz, CDCl₃) δ 8.86 (s, 1H), 7.94 (d, J=1.0 Hz, 2H), 7.52 (br s, 2H), 7.33 (d, J=8.7 Hz, 2H), 7.15 (dd, J=8.6, 1.5 Hz, 2H), 4.06 (s, 6H), 3.90-3.80 (m, 4H), 2.63 (m, 4H).

Scheme XXII

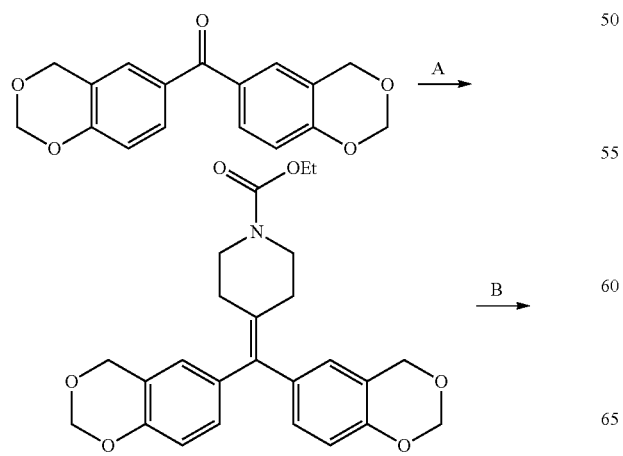

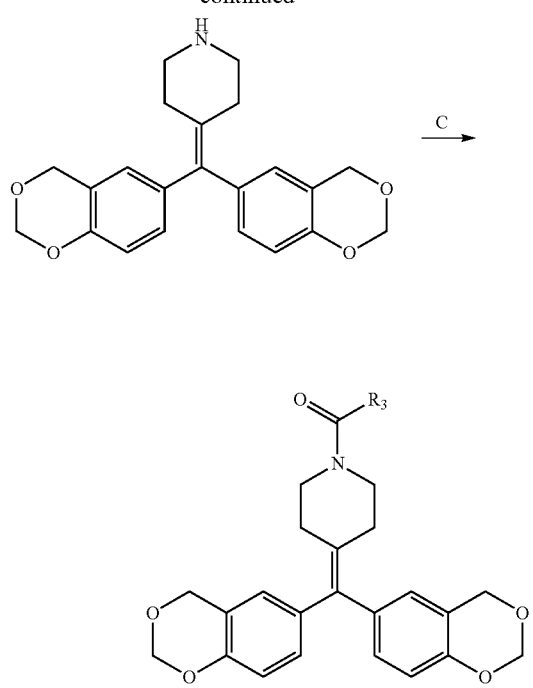

Reagents and conditions: A) i) TiCl₄, Zn, THF, reflux, 2 h; ii) Bis(4H-benzo[d][1,3]dioxin-6-yl)methanone, ethyl 4-oxo-1-piperidinecarboxylate, THF, reflux, 16 h; B) KOH, EtOH/H₂O, reflux, 4 d; C) i) Triphosgene, DCM, 0° C.; ii) 4-(Bis(4H-benzo[d][1,3]dioxin-6-yl)methylene)piperidine, DMAP, DCM, 0° C. to rt, 3 h; iii) R₃=H, DMAP, THF, rt, 19 h.

Synthesis of 1-(4-(bis(4H-benzo[d][1,3]dioxin-6-yl)methylene)piperidine-1-carbonyl)-1H-1,2,4-triazole-3-carbonitrile (Example-124)

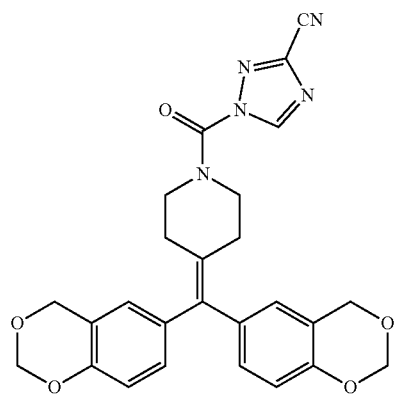 [SMILES: N#Cc1ncn(C(=O)N2CCC(=C(c3ccc4c(c3)COCO4)c3ccc4c(c3)COCO4)CC2)n1]

Step 1. Preparation of ethyl 4-(bis(4H-benzo[d][1,3]dioxin-6-yl)methylene)piperidine-1-carboxylate General Procedure W

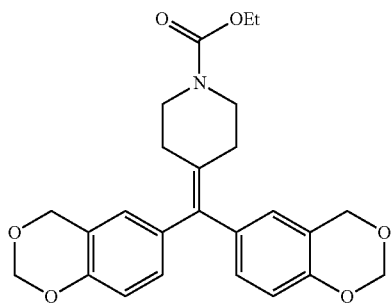 [SMILES: CCOC(=O)N1CCC(=C(c2ccc3c(c2)COCO3)c2ccc3c(c2)COCO3)CC1]

Titanium tetrachloride (0.46 mL, 4.2 mmol) was slowly added to a stirred suspension of zinc powder (546 mg, 8.35 mmol) in anhydrous tetrahydrofuran (6 mL) under nitrogen atmosphere, and the mixture was heated to reflux for 2 hours. The mixture was allowed to cool to ambient temperature then stirred while a suspension of bis(4H-benzo[d][1,3]dioxin-6-yl)methanone (356 mg, 1.19 mmol) and ethyl 4-oxo-1-piperidinecarboxylate (204 mg, 1.19 mmol) in tetrahydrofuran (6 mL) was added. The mixture was heated to reflux under nitrogen atmosphere for 16 hours then allowed to cool to ambient temperature. Saturated aqueous sodium bicarbonate (20 mL) was slowly added, and the mixture was stirred at ambient temperature for 20 minutes then filtered through Celite® 545 and the Celite rinsed with ethyl acetate. The aqueous phase was extracted with ethyl acetate (20 mL), and the combined organic layers were dried over anhydrous sodium sulfate, filtered and concentrated in vacuo. The residue was purified by column chromatography, eluting with 15% to 20% ethyl acetate in hexanes to afford the title compound as a pale oil (242 mg, 46% yield).

$^1$H NMR (400 MHz, CDCl$_3$) δ 6.90 (dd, J=8.4, 2.1 Hz, 2H), 6.80 (d, J=8.4 Hz, 2H), 6.64 (d, J=2.0 Hz, 2H), 5.24 (s, 4H), 4.85 (s, 4H), 4.14 (q, J=7.1 Hz, 2H), 3.48 (m, 4H), 2.32 (m, 4H), 1.26 (t, J=7.1 Hz, 3H).

Step 2. Preparation of 4-(bis(4H-benzo[d][1,3]dioxin-6-yl)methylene)piperidine

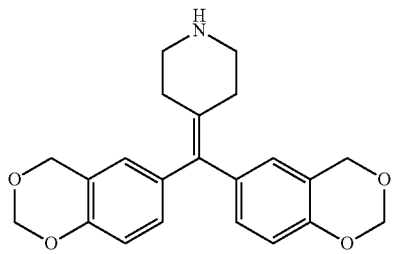

To a solution of ethyl 4-(bis(4H-benzo[d][1,3]dioxin-6-yl)methylene)piperidine-1-carboxylate (237 mg, 0.542 mmol) in ethanol (20 mL) was added potassium hydroxide (1.04 g, 18.5 mmol) and water (1 mL), and the mixture was heated to reflux for 4 days. The mixture was allowed to cool to ambient temperature then concentrated in vacuo. Dichloromethane (20 mL) and water (15 mL) were added, and the aqueous phase was extracted with dichloromethane (10 mL). The combined organic layers were dried over anhydrous sodium sulfate, filtered and concentrated in vacuo. The residue was purified by column chromatography, eluting with 5% to 8% methanol (containing 10% aqueous ammonium hydroxide) in dichloromethane to afford the title compound as a colourless foam (153 mg, 77% yield).

$^1$H NMR (400 MHz, CDCl$_3$) δ 6.90 (dd, J=8.4, 2.1 Hz, 2H), 6.79 (d, J=8.3 Hz, 2H), 6.64 (m, 2H), 5.23 (s, 4H), 4.85 (s, 4H), 2.93 (m, 4H), 2.35 (m, 4H) (NH not observed).

Step 3. Preparation of 1-(4-(bis(4H-benzo[d][1,3]dioxin-6-yl)methylene)piperidine-1-carbonyl)-1H-1,2,4-triazole-3-carbonitrile (Example-124)

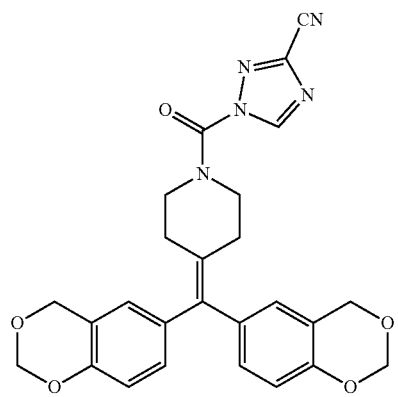 [SMILES: N#Cc1ncn(C(=O)N2CCC(=C(c3ccc4c(c3)COCO4)c3ccc4c(c3)COCO4)CC2)n1]

Following General Procedure M and making non-critical variations as required to replace N,N-bis(4-fluorophenyl)piperidin-4-amine with 4-(bis(4H-benzo[d][1,3]dioxin-6-yl)methylene)piperidine, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (48 mg, 50% yield).

$^1$H NMR (400 MHz, CDCl$_3$) δ 8.85 (s, 1H), 6.91 (m, 2H), 6.83 (d, J=8.4 Hz, 2H), 6.66 (d, J=2.0 Hz, 2H), 5.25 (s, 4H), 4.86 (s, 4H), 3.85-3.74 (m, 4H), 2.54 (m, 4H); MS (ESI) m/z 508.2 (M+Na).

Scheme XXIII

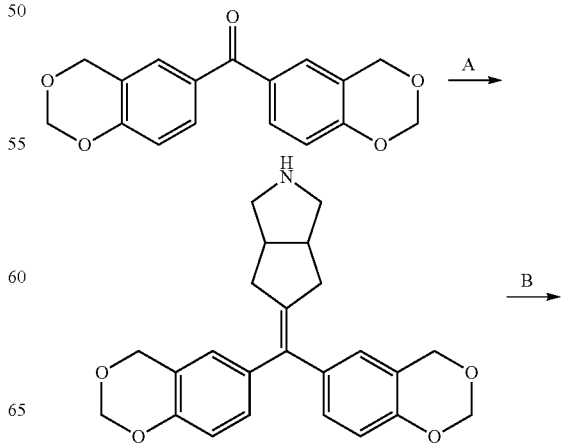

-continued

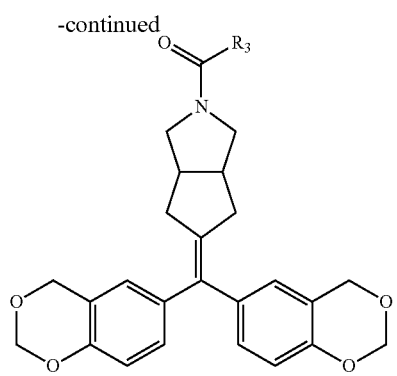

Reagents and conditions: A) i) TiCl₄, Zn, THF, reflux, 2.5 h; ii) Bis(4H-benzo[d][1,3]dioxin-6-yl)methanone, cis-tert-butyl 5-oxohexahydrocyclopenta[c]pyrrole-2(1H)-carboxylate, THF, reflux, 16 h; B) i) Triphosgene, DCM, 0° C.; 5-(Bis(4H-benzo[d][1,3]dioxin-6-yl)methylene)octahydrocyclopenta[c]pyrrole, DMAP, DCM, 0° C. to rt, 3 h; iii) R₃—H, DMAP, THF, rt, 16 h.

Synthesis of meso-1-(5-(bis(4H-benzo[d][1,3]dioxin-6-yl)methylene)octahydrocyclopenta[c]pyrrole-2-carbonyl)-1H-1,2,4-triazole-3-carbonitrile

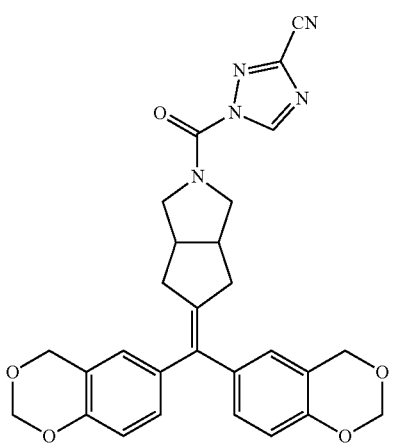 [SMILES: N#Cc1ncn(C(=O)N2CC3CC(=C(c4ccc5c(c4)COCO5)c4ccc5c(c4)COCO5)CC3C2)n1]

Step 1. Preparation of 5-(bis(4H-benzo[d][1,3]dioxin-6-yl)methylene)octahydrocyclopenta[c]pyrrole

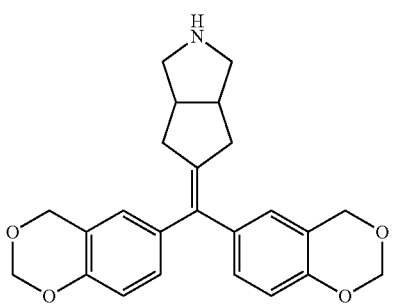 [SMILES: c1cc2c(cc1C(=C1CC3CNCC3C1)c1ccc3c(c1)COCO3)COCO2]

Following General Procedure W and making non-critical variations as required to replace ethyl 4-oxo-1-piperidinecarboxylate with cis-tert-butyl 5-oxohexahydrocyclopenta[c]pyrrole-2(1H)-carboxylate, the title compound was obtained as a light yellow foam (442 mg, 41% yield).

¹H NMR (400 MHz, CDCl₃) δ 6.95 (dd, J=8.4, 2.1 Hz, 2H), 6.80 (d, J=8.5 Hz, 2H), 6.72 (d, J=2.0 Hz, 2H), 5.24 (s, 4H), 4.86 (s, 4H), 3.26 (m, 2H), 2.81-2.61 (m, 6H), 2.31 (m, 2H) (NH not observed).

Step 2. Preparation of meso-1-(5-(bis(4H-benzo[d][1,3]dioxin-6-yl)methylene)octahydrocyclopenta[c]pyrrole-2-carbonyl)-1H-1,2,4-triazole-3-carbonitrile (Example-125)

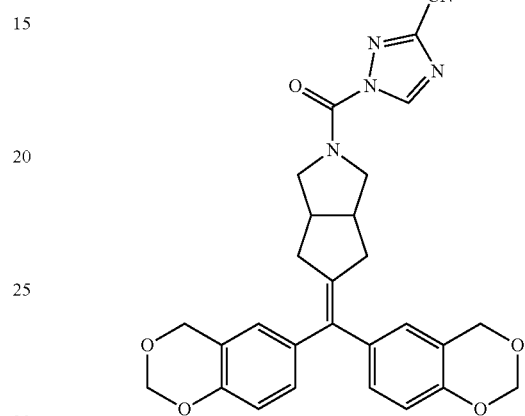

Following General Procedure M and making non-critical variations as required to replace N,N-bis(4-fluorophenyl)piperidin-4-amine with 5-(bis(4H-benzo[d][1,3]dioxin-6-yl)methylene)octahydrocyclopenta[c]pyrrole, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (10 mg, 11% yield).

¹H NMR (400 MHz, CDCl₃) δ 8.97 (s, 1H), 6.97 (d, J=9.4 Hz, 2H), 6.82 (dd, J=8.5, 1.7 Hz, 2H), 6.70 (br s, 2H), 5.25 (s, 2H), 5.24 (s, 2H), 4.85 (s, 4H), 4.13 (dd, J=12.3, 7.3 Hz, 1H), 3.90 (dd, J=12.5, 6.9 Hz, 1H), 3.78 (dd, J=12.3, 5.3 Hz, 1H), 3.56 (dd, J=12.5, 4.7 Hz, 1H), 2.90-2.72 (m, 4H), 2.37 (m, 2H); MS (ESI) m/z 534.3 (M+Na).

Scheme XXIV

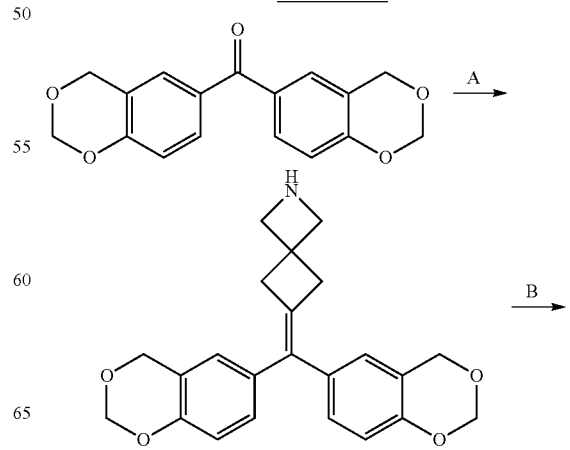

-continued

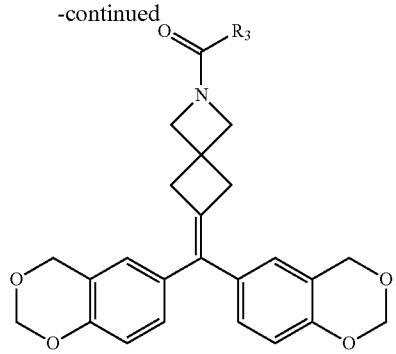

Reagents and conditions: A) i) TiCl₄, Zn, THF, reflux, 2.5 h; ii) Bis(4H-benzo[d][1,3]dioxin-6-yl)methanone, tert-butyl 6-oxo-2-azaspiro[3.3]heptane-2-carboxylate, THF, reflux, 18 h; B) i) Triphosgene, DCM, 0° C.; ii) 6-(Bis(4H-benzo[d][1,3]dioxin-6-yl)methylene)-2-azaspiro[3.3]heptane, DMAP, DCM, 0° C. to rt, 3 h; iii) R₃—H, DMAP, THF, rt, 3 d.

Synthesis of 1-(6-(bis(4H-benzo[d][1,3]dioxin-6-yl)methylene)-2-azaspiro[3.3]heptane-2-carbonyl)-1H-1,2,4-triazole-3-carbonitrile (Example-126)

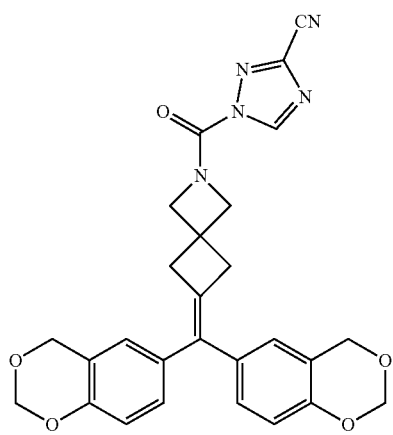 [SMILES: N#Cc1ncn(C(=O)N2CC3(CC(=C(c4ccc5c(c4)COCO5)c4ccc5c(c4)COCO5)C3)C2)n1]

Step 1. Preparation of 6-(bis(4H-benzo[d][1,3]dioxin-6-yl)methylene)-2-azaspiro[3.3]heptane

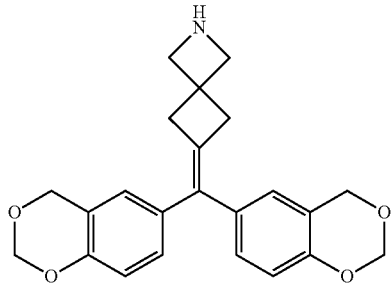 [SMILES: c1cc2c(cc1C(=C1CC3(CNC3)C1)c1ccc3c(c1)COCO3)COCO2]

Following General Procedure W and making non-critical variations as required to replace ethyl 4-oxo-1-piperidinecarboxylate with tert-butyl 6-oxo-2-azaspiro[3.3]heptane-2-carboxylate, the title compound was obtained as a light yellow foam (415 mg, 40% yield).

¹H NMR (400 MHz, CDCl₃) δ 6.92 (dd, J=8.4, 2.1 Hz, 2H), 6.81 (d, J=8.4 Hz, 2H), 6.66 (d, J=2.1 Hz, 2H), 5.25 (s, 4H), 4.84 (s, 4H), 3.99 (s, 4H), 3.12 (s, 4H) (NH not observed).

Step 2. Preparation of 1-(6-(bis(4H-benzo[d][1,3]dioxin-6-yl)methylene)-2-azaspiro[3.3]heptane-2-carbonyl)-1H-1,2,4-triazole-3-carbonitrile (Example-126)

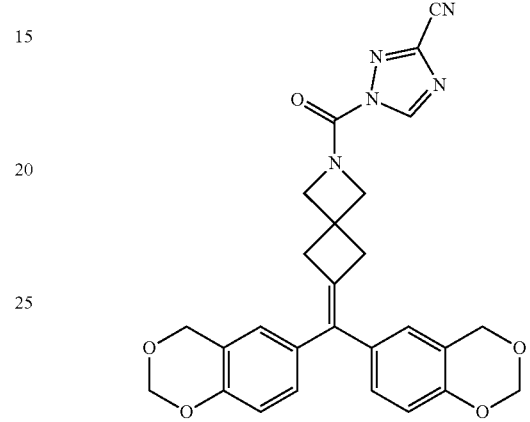

Following General Procedure M and making non-critical variations as required to replace N,N-bis(4-fluorophenyl)piperidin-4-amine with 6-(bis(4H-benzo[d][1,3]dioxin-6-yl)methylene)-2-azaspiro[3.3]heptane, replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (25 mg, 25% yield).

¹H NMR (400 MHz, CDCl₃) δ 8.93 (s, 1H), 6.96 (dd, J=8.4, 2.1 Hz, 2H), 6.83 (d, J=8.4 Hz, 2H), 6.69 (d, J=2.1 Hz, 2H), 5.26 (s, 4H), 4.85 (s, 4H), 4.73 (s, 2H), 4.31 (s, 2H), 3.15 (s, 4H); MS (ESI) m/z 497.3 (M+).

Scheme XXV

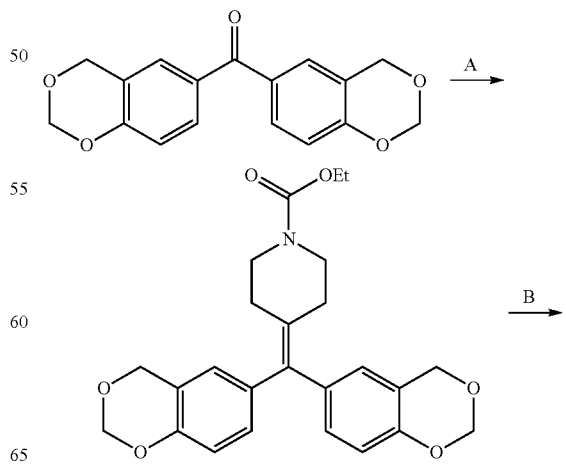

249
-continued

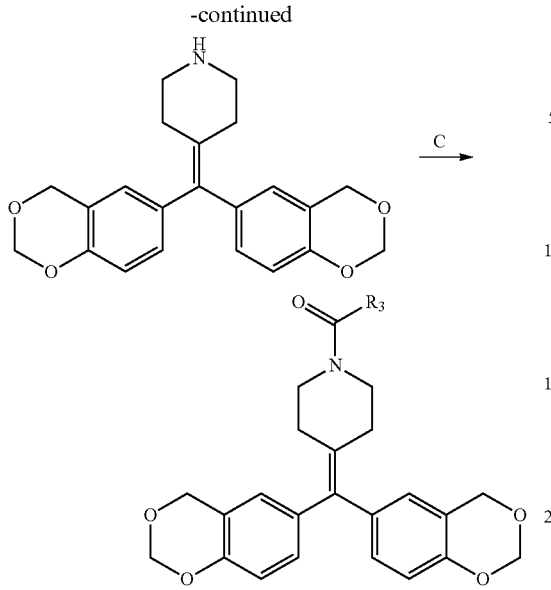

Reagents and conditions: A) i) TiCl₄, Zn, THF, reflux, 2 h; ii) Bis(4H-benzo[d][1,3]dioxin-6-yl)methanone, ethyl 4-oxo-1-piperidinecarboxylate, THF, reflux, 16 h; B) KOH, EtOH/H₂O, reflux, 4 d; C) i) Triphosgene, DCM, 0° C.; ii) 4-(Bis(4H-benzo[d][1,3]dioxin-6-yl)methylene)piperidine, DMAP, DCM, 0° C. to rt, 3 h; iii) R₃—H, DMAP, THF, rt, 19 h.

Scheme XXVI

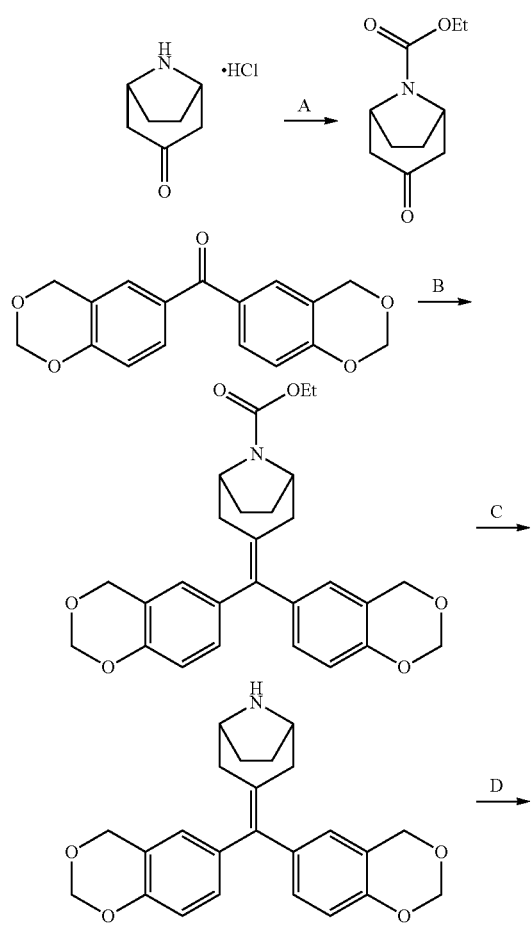

250
-continued

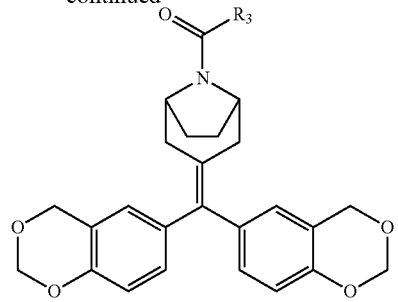

Reagents and conditions: A) Ethyl chloroformate, Et₃N, DCM, 0° C. to rt, 5 h; B) i) TiCl₄, Zn, THF, reflux, 2 h; ii) Bis(4H-benzo[d][1,3]dioxin-6-yl)methanone, ethyl 3-oxo-8-azabicyclo[3.2.1]octane-8-carboxylate, THF, reflux, 17 h; C) TMSI, NMM, DCM, rt, 23 h; D) i) Triphosgene, DCM, 0° C.; ii) 3-(Bis(4H-benzo[d][1,3]dioxin-6-yl)methylene-8-azabicyclo[3.2.1]octane, DMAP, DCM, 0° C. to rt, 2.5 h; iii) R₃—H, DMAP, THF, rt, 42 h.

Synthesis of 1-(3-(bis(4H-benzo[d][1,3]dioxin-6-yl)methylene)-8-azabicyclo[3.2.1]octane-8-carbonyl)-1H-1,2,4-triazole-3-carbonitrile (Example-127)

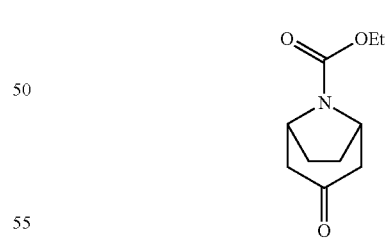

Step 1. Preparation of ethyl 3-oxo-8-azabicyclo[3.2.1]octane-8-carboxylate

A suspension of 8-azabicyclo[3.2.1]octan-3-one hydrochloride (2.02 g, 12.5 mmol) in dichloromethane (50 mL) was cooled to 0° C. under nitrogen atmosphere and triethylamine (4.35 mL, 31.2 mmol) was added. The mixture was stirred at 0° C. for 5 minutes then ethyl chloroformate (1.31 mL, 13.7 mmol) was slowly added. The mixture was stirred at ambient temperature for 5 hours then water (40 mL) was added, and the aqueous phase was extracted with dichloromethane (20 mL). The combined organic layers were dried over anhydrous sodium sulfate, filtered and concentrated in vacuo. The residue was purified by column chromatography, eluting with 25% ethyl acetate in hexanes to afford the title compound as a pale oil (1.17 g, 48% yield).

¹H NMR (400 MHz, CDCl₃) δ 4.55 (m, 2H), 4.21 (q, J=7.1 Hz, 2H), 2.73-2.61 (m, 2H), 2.35 (m, 2H), 2.10 (m, 2H), 1.69 (m, 2H), 1.30 (t, J=7.1 Hz, 3H).

Step 2. Preparation of ethyl 3-(bis(4H-benzo[d][1,3]dioxin-6-yl)methylene)-8-azabicyclo[3.2.1]octane-8-carboxylate

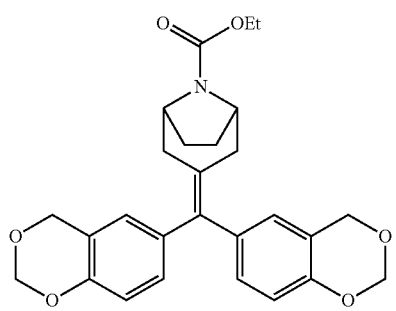 [SMILES: CCOC(=O)N1C2CCC1CC(=C(c1ccc3c(c1)COCO3)c1ccc3c(c1)COCO3)C2]

Following General Procedure W and making non-critical variations as required to replace ethyl 4-oxo-1-piperidinecarboxylate with ethyl 3-oxo-8-azabicyclo[3.2.1]octane-8-carboxylate, the title compound was obtained as a colourless foam (691 mg, 55% yield).

¹H NMR (400 MHz, CDCl₃) δ 6.91 (dd, J=8.4, 2.1 Hz, 2H), 6.80 (d, J=8.3 Hz, 2H), 6.65 (d, J=2.0 Hz, 2H), 5.23 (s, 4H), 4.85 (s, 4H), 4.26 (m, 2H), 4.16 (q, J=7.1 Hz, 2H), 2.37 (m, 4H), 1.91 (m, 2H), 1.65 (m, 2H), 1.26 (t, J=7.1 Hz, 3H).

Step 3. Preparation of 3-(bis(4H-benzo[d][1,3]dioxin-6-yl)methylene)-8-azabicyclo[3.2.1]octane

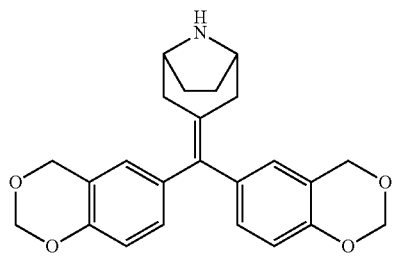 [SMILES: c1cc2c(cc1C(=C1CC3CCC(C1)N3)c1ccc3c(c1)COCO3)COCO2]

Following General Procedure S and making non-critical variations as required to replace tert-butyl 4-(bis(1-methyl-1H-indazol-5-yl)methyl)piperazine-1-carboxylate with ethyl 3-(bis(4H-benzo[d][1,3]dioxin-6-yl)methylene)-8-azabicyclo[3.2.1]octane-8-carboxylate, the title compound was obtained as a pale foam (165 mg, 63% yield).

¹H NMR (400 MHz, CDCl₃) δ 6.92 (dd, J=8.4, 2.1 Hz, 2H), 6.80 (d, J=8.3 Hz, 2H), 6.65 (d, J=2.0 Hz, 2H), 5.23 (s, 4H), 4.85 (s, 4H), 3.61 (m, 2H), 2.43-2.29 (m, 4H), 1.82 (m, 2H), 1.67 (m, 2H) (NH not observed).

Step 4. Preparation of 1-(3-(bis(4H-benzo[d][1,3]dioxin-6-yl)methylene)-8-azabicyclo[3.2.1]octane-8-carbonyl)-1H-1,2,4-triazole-3-carbonitrile (Example-127)

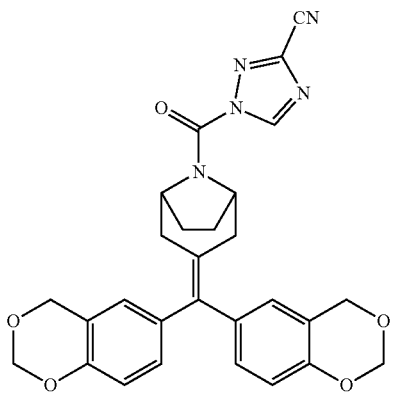 [SMILES: N#Cc1ncn(C(=O)N2C3CCC2CC(=C(c2ccc4c(c2)COCO4)c2ccc4c(c2)COCO4)C3)n1]

Following General Procedure M and making non-critical variations as required to replace N,N-bis(4-fluorophenyl)piperidin-4-amine with 3-(bis(4H-benzo[d][1,3]dioxin-6-yl)methylene)-8-azabicyclo[3.2.1]octane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (38 mg, 36% yield).

¹H NMR (400 MHz, CDCl₃) δ 8.95 (s, 1H), 6.93 (d, J=8.4 Hz, 2H), 6.83 (d, J=8.4 Hz, 2H), 6.66 (br s, 2H), 5.24 (s, 4H), 5.20 (m, 1H), 4.86 (s, 4H), 4.73 (m, 1H), 2.57 (m, 4H), 2.05 (m, 2H), 1.82 (m, 2H); MS (ESI) m/z 534.3 (M+Na).

Scheme XXVII

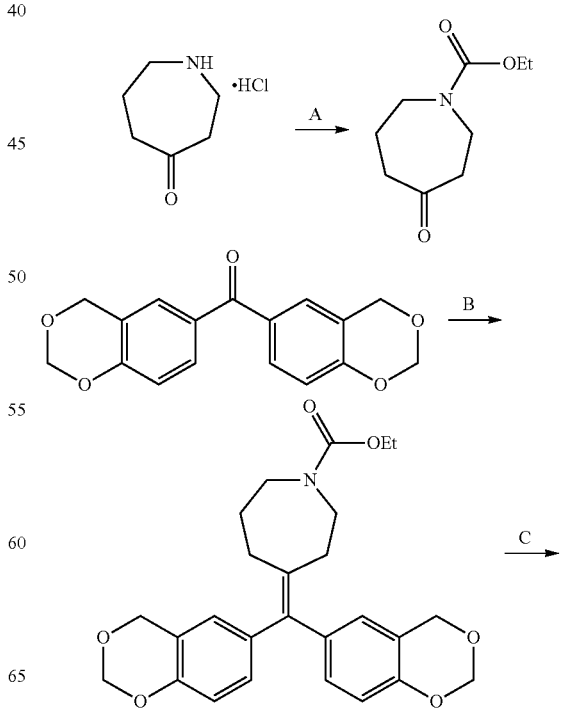

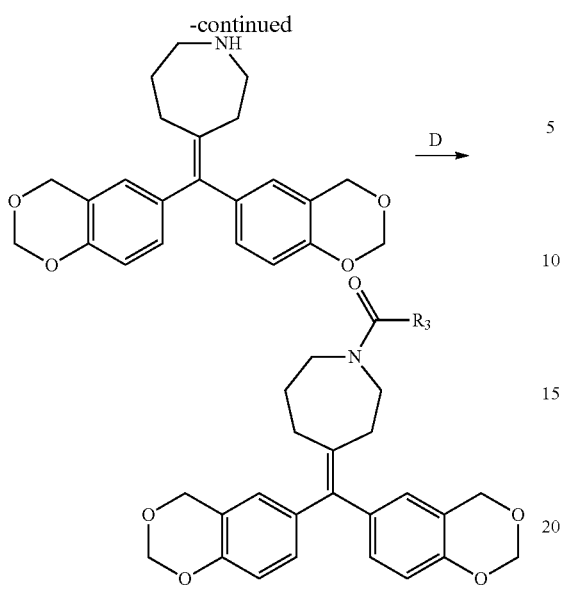

Reagents and conditions: A) Ethyl chloroformate, Et₃N, DCM, 0° C. to rt, 2 h; B) i) TiCl₄, Zn, THF, reflux, 2 h; ii) Bis(4H-benzo[d][1,3]dioxin-6-yl)methanone, ethyl 4-oxoazepane-1-carboxylate, THF, reflux, 16 h; C) TMSI, NMM, DCM, rt, 3 d; D) i) Triphosgene, DCM, 0° C.; ii) 4-(Bis(4H-benzo[d][1,3]dioxin-6-yl)methylene)azepane, DMAP, DCM, 0° C. to rt, 4.5 h; iii) R₃—H, DMAP, THF, rt, 18 h.

Synthesis of 1-(4-(bis(4H-benzo[d][1,3]dioxin-6-yl)methylene)azepane-1-carbonyl)-1H-1,2,4-triazole-3-carbonitrile (Example-128)

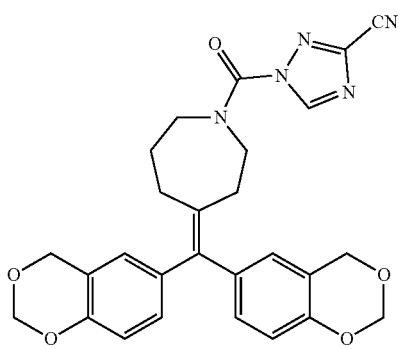 [SMILES: N#Cc1ncn(C(=O)N2CCCC(=C(c3ccc4c(c3)COCO4)c3ccc4c(c3)COCO4)CC2)n1]

Step 1. Preparation of ethyl 4-oxoazepane-1-carboxylate

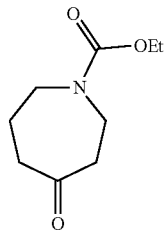 [SMILES: CCOC(=O)N1CCCC(=O)CC1]

A suspension of 4-perhydroazepinone hydrochloride (2.03 g, 13.6 mmol) in dichloromethane (54 mL) was cooled to 0° C. under nitrogen atmosphere and triethylamine (4.73 mL, 33.9 mmol) was added. The mixture was stirred at 0° C. for 5 minutes then ethyl chloroformate (1.43 mL, 15.0 mmol) was slowly added. The mixture was stirred at ambient temperature for 2 hours then water (40 mL) was added, and the aqueous phase was extracted with dichloromethane (20 mL). The combined organic layers were dried over anhydrous sodium sulfate, filtered and concentrated in vacuo. The residue was purified by column chromatography, eluting with 30% ethyl acetate in hexanes to afford the title compound as a light yellow oil (2.14 g, 85% yield).

¹H NMR (400 MHz, CDCl₃) δ 4.14 (q, J=7.1 Hz, 2H), 3.62 (m, 4H), 2.64 (m, 4H), 1.80 (m, 2H), 1.25 (t, J=7.1 Hz, 3H).

Step 2. Preparation of ethyl 4-(bis(4H-benzo[d][1,3]dioxin-6-yl)methylene)azepane-1-carboxylate

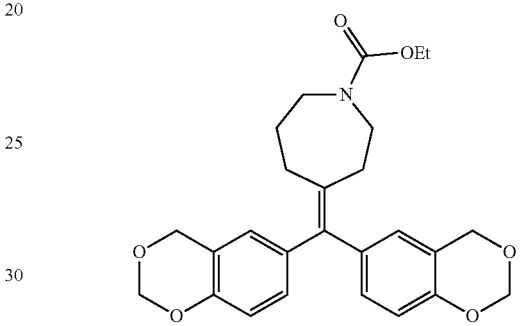

Following General Procedure W and making non-critical variations as required to replace ethyl 4-oxo-1-piperidinecarboxylate with ethyl 4-oxoazepane-1-carboxylate, the title compound was obtained as a colourless foam (604 mg, 50% yield).

¹H NMR (400 MHz, CDCl₃) δ 6.91 (dd, J=8.3, 2.1 Hz, 2H), 6.79 (d, J=8.4 Hz, 2H), 6.67 (br s, 2H), 5.23 (s, 4H), 4.85 (s, 4H), 4.14 (m, 2H), 3.49-3.40 (m, 4H), 2.43 (m, 2H), 2.26 (m, 2H), 1.66 (m, 2H), 1.29-1.19 (m, 3H).

Step 3. Preparation of 4-(bis(4H-benzo[d][1,3]dioxin-6-yl)methylene)azepane

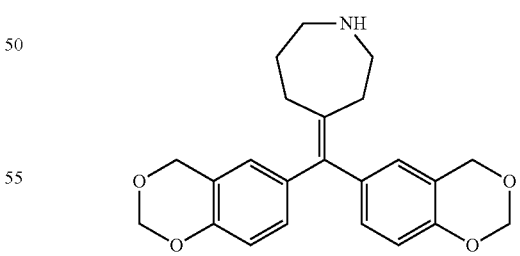

Following General Procedure S and making non-critical variations as required to replace tert-butyl 4-(bis(1-methyl-1H-indazol-5-yl)methyl)piperazine-1-carboxylate with ethyl 4-(bis(4H-benzo[d][1,3]dioxin-6-yl)methylene)azepane-1-carboxylate, the title compound was obtained as a pale foam (85 mg, 49% yield).

¹H NMR (400 MHz, CDCl₃) δ 6.95 (m, Hz, 2H), 6.80 (d, J=2.3 Hz, 1H), 6.78 (d, J=2.3 Hz, 1H), 6.70 (d, J=2.0 Hz,

2H), 5.23 (s, 2H), 5.23 (s, 2H), 4.85 (s, 2H), 4.85 (s, 2H), 3.00-2.92 (m, 4H), 2.51-2.38 (m, 4H), 1.74 (m, 2H) (NH not observed).

Step 4. Preparation of 1-(4-(bis(4H-benzo[d][1,3]dioxin-6-yl)methylene)azepane-1-carbonyl)-1H-1,2,4-triazole-3-carbonitrile (Example-128)

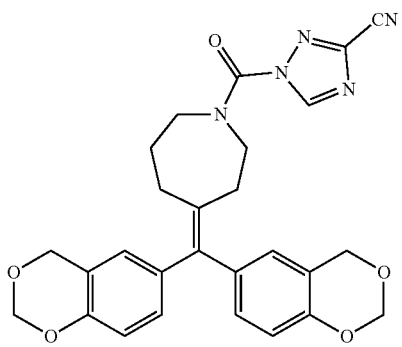 [SMILES: N#Cc1ncn(C(=O)N2CCCC(=C(c3ccc4c(c3)COCO4)c3ccc4c(c3)COCO4)CC2)n1]

Following General Procedure M and making non-critical variations as required to replace N,N-bis(4-fluorophenyl)piperidin-4-amine with 4-(bis(4H-benzo[d][1,3]dioxin-6-yl)methylene)azepane, replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (24 mg, 23% yield).

$^1$H NMR (400 MHz, CDCl$_3$) δ 8.89 (s, 1H), 6.91 (m, 1.5H), 6.80 (m, 2.5H), 6.66 (m, 1.5H), 6.54 (br s, 0.5H), 5.24 (s, 4H), 4.84 (m, 4H), 3.86-3.70 (m, 4H), 2.62 (m, 2H), 2.37 (m, 2H), 1.88 (m, 2H) (2 conformational isomers observed in a ratio of 3:1); MS (ESI) m/z 522.4 (M+Na).

Scheme XXVIII

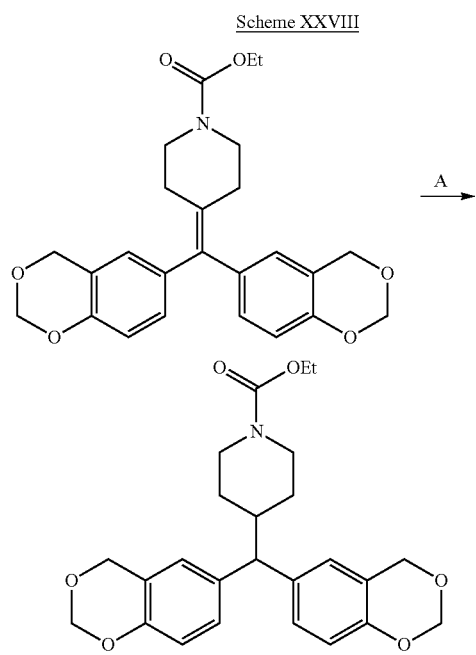

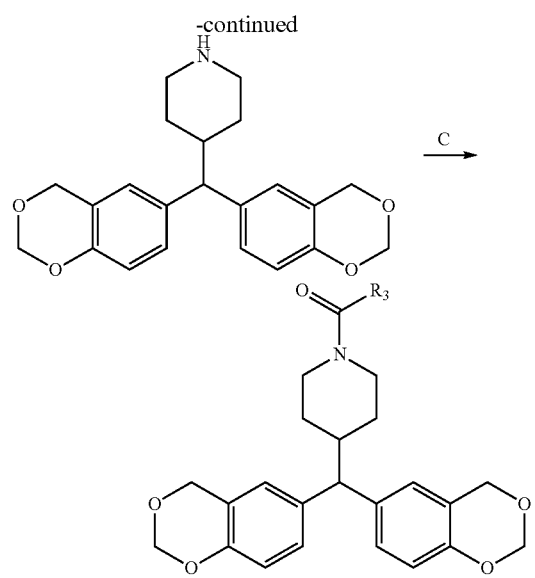

Reagents and conditions: A) H$_2$(g), 10% Pd/C, EtOH, 55° C., 21 h; B) KOH, EtOH/H$_2$O, reflux, 4 d; C) i) Triphosgene, DCM, 0° C.; ii) 4-(Bis(4H-benzo[d][1,3]dioxin-6-yl)methyl)piperidine, DMAP, DCM, 0° C. to rt, 2 h; iii) R$_3$—H, DMAP, THF, rt, 21 h.

Synthesis of 1-(4-(bis(4H-benzo[d][1,3]dioxin-6-yl)methyl)piperidine-1-carbonyl)-1H-1,2,4-triazole-3-carbonitrile (Example-129)

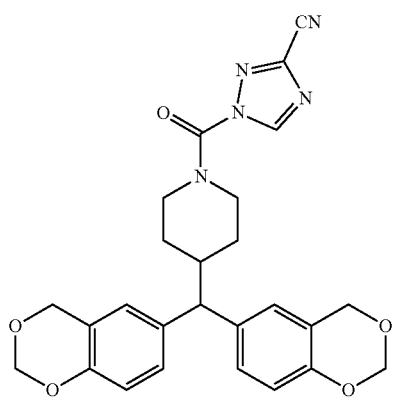 [SMILES: N#Cc1ncn(C(=O)N2CCC(C(c3ccc4c(c3)COCO4)c3ccc4c(c3)COCO4)CC2)n1]

Step 1. Preparation of ethyl 4-(bis(4H-benzo[d][1,3]dioxin-6-yl)methyl)piperidine-1-carboxylate General Procedure X

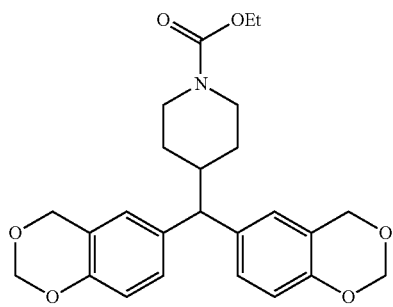 [SMILES: CCOC(=O)N1CCC(C(c2ccc3c(c2)COCO3)c2ccc3c(c2)COCO3)CC1]

A solution of ethyl 4-(bis(4H-benzo[d][1,3]dioxin-6-yl)methylene)piperidine-1-carboxylate (323 mg, 0.738 mmol) in ethanol (10 mL) was stirred with a suspension of 10% palladium on activated carbon (65 mg) under hydrogen atmosphere (1 atm) and heated to 55° C. for 21 hours. The mixture was filtered through Celite® 545 and the Celite rinsed with ethyl acetate. The filtrate was concentrated in vacuo to provide the title compound as a colourless foam (314 mg, 97% yield) that was used in the next step without further purification.

$^1$H NMR (400 MHz, CDCl$_3$) δ 7.03 (dd, J=8.4, 2.2 Hz, 2H), 6.79 (d, J=8.4 Hz, 2H), 6.77 (d, J=2.0 Hz, 2H), 5.20 (s, 4H), 4.86 (s, 4H), 4.10 (m, 4H), 3.30 (d, J=10.9 Hz, 1H), 2.70 (m, 2H), 2.16-2.03 (m, 1H), 1.54 (m, 2H), 1.23 (t, J=7.1 Hz, 3H), 1.09-0.99 (m, 2H).

Step 2. Preparation of 4-(bis(4H-benzo[d][1,3]dioxin-6-yl)methyl)piperidine

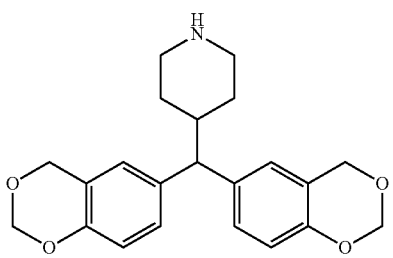 [SMILES: c1cc2c(cc1C(c1ccc3c(c1)COCO3)C1CCNCC1)COCO2]

To a solution of ethyl 4-(bis(4H-benzo[d][1,3]dioxin-6-yl)methyl)piperidine-1-carboxylate (309 mg, 0.703 mmol) in ethanol (18 mL) was added potassium hydroxide (986 mg, 17.6 mmol) and water (2 mL), and the mixture was heated to reflux for 4 days. The mixture was allowed to cool to ambient temperature then concentrated in vacuo. Dichloromethane (20 mL) and water (20 mL) were added, and the aqueous phase was extracted with dichloromethane (15 mL). The combined organic layers were dried over anhydrous sodium sulfate, filtered and concentrated in vacuo. The residue was purified by column chromatography, eluting with 7% to 8% methanol (containing 10% aqueous ammonium hydroxide) in dichloromethane to afford the title compound as a colourless foam (210 mg, 81% yield).

$^1$H NMR (400 MHz, CDCl$_3$) δ 7.04 (dd, J=8.5, 2.2 Hz, 2H), 6.78 (m, 4H), 5.19 (s, 4H), 4.86 (s, 4H), 3.33 (d, J=10.9 Hz, 1H), 3.09 (m, 2H), 2.60 (m, 2H), 2.11-2.01 (m, 1H), 1.57 (m, 2H), 1.17-1.07 (m, 2H) (NH not observed).

Step 3. Preparation of 1-(4-(bis(4H-benzo[d][1,3]dioxin-6-yl)methyl)piperidine-1-carbonyl)-1H-1,2,4-triazole-3-carbonitrile (Example-129)

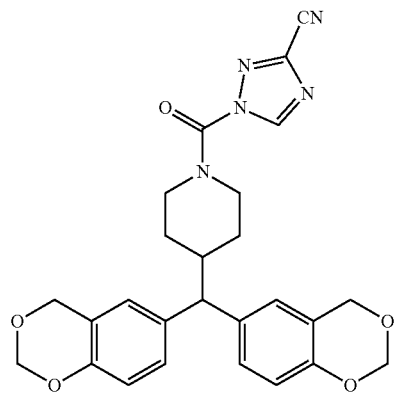 [SMILES: N#Cc1ncn(C(=O)N2CCC(C(c3ccc4c(c3)COCO4)c3ccc4c(c3)COCO4)CC2)n1]

Following General Procedure M and making non-critical variations as required to replace N,N-bis(4-fluorophenyl)piperidin-4-amine with 4-(bis(4H-benzo[d][1,3]dioxin-6-yl)methyl)piperidine, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (37 mg, 39% yield).

$^1$H NMR (400 MHz, CDCl$_3$) δ 8.81 (s, 1H), 7.06 (dd, J=8.5, 2.2 Hz, 2H), 6.82 (d, J=8.4 Hz, 2H), 6.80 (d, J=2.1 Hz, 2H), 5.21 (s, 4H), 4.87 (s, 4H), 4.41 (m, 2H), 3.36 (d, J=10.9 Hz, 1H), 3.10-2.96 (m, 2H), 2.33-2.23 (m, 1H), 1.73 (m, 2H), 1.33-1.22 (m, 2H); MS (ESI) m/z 510.3 (M+Na).

Scheme XXIX

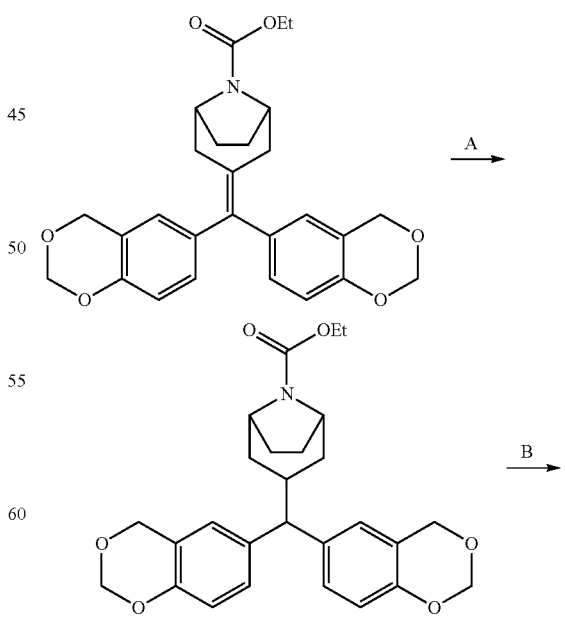

-continued

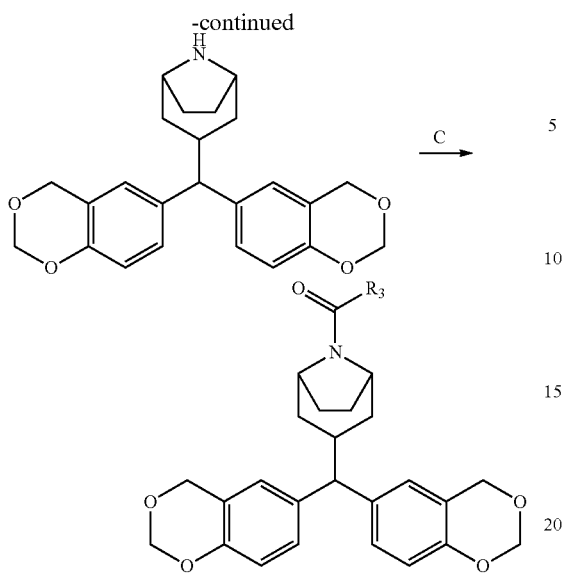

Reagents and conditions: A) H₂(g), 10% Pd/C, EtOH, 40° C., 3 d; B) TMSI, NMM, DCM, rt, 21 h; C) i) Triphosgene, DCM, 0° C.; ii) 3-(Bis(4H-benzo[d][1,3]dioxin-6-yl)methyl)-8-azabicyclo[3.2.1]octane, DMAP, DCM, 0° C. to rt, 2 h; iii) R₃—H, DMAP, THF, rt, 20 h.

Synthesis of 1-(3-(bis(4H-benzo[d][1,3]dioxin-6-yl)methyl)-8-azabicyclo[3.2.1]octane-8-carbonyl)-1H-1,2,4-triazole-3-carbonitrile (Example-130)

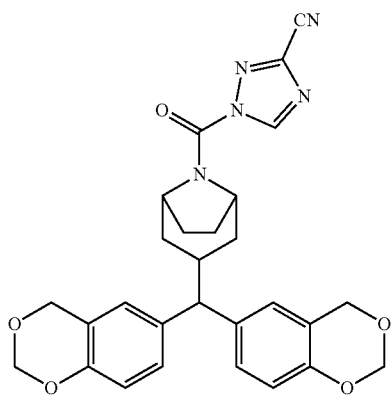 [SMILES: N#Cc1ncn(C(=O)N2C3CCC2CC(C(c2ccc4c(c2)COCO4)c2ccc4c(c2)COCO4)C3)n1]

Step 1. Preparation of ethyl 3-(bis(4H-benzo[d][1,3]dioxin-6-yl)methyl)-8-azabicyclo[3.2.1]octane-8-carboxylate

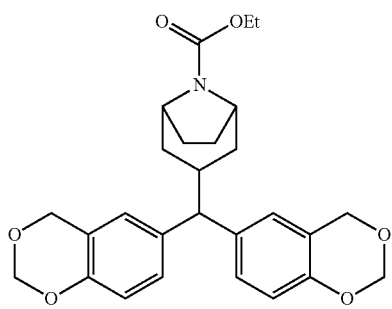 [SMILES: CCOC(=O)N1C2CCC1CC(C(c1ccc3c(c1)COCO3)c1ccc3c(c1)COCO3)C2]

Following General Procedure X and making non-critical variations as required to replace ethyl 4-(bis(4H-benzo[[d] [1,3]dioxin-6-yl)methylene)piperidine-1-carboxylate with ethyl 3-(bis(4H-benzo[d]1,3]dioxin-6-yl)methylene)-8-azabicyclo[3.2.1]octane-8-carboxylate followed by purification by column chromatography, eluting with 20% to 25% ethyl acetate in hexanes, the title compound was obtained as a colourless foam (282 mg, 76% yield).

¹H NMR (400 MHz, CDCl₃) δ 7.02 (m, 2H), 6.77 (m, 4H), 5.19 (s, 4H), 4.85 (s, 4H), 4.21 (m, 2H), 4.13 (q, J=7.1 Hz, 2H), 3.66 (d, J=12.4 Hz, 0.2H), 3.25 (d, J=10.9 Hz, 0.8H), 2.53-2.42 (in, 0.8H), 2.38-2.29 (in, 0.2H), 1.97 (m, 2H), 1.66 (m, 2H), 1.42-1.14 (in, 7H) (2 conformational isomers observed in a ratio of 4:1).

Step 2. Preparation of 3-(bis(4H-benzo[d][1,3]dioxin-6-yl)methyl)-8-azabicyclo[d3.2.1]octane

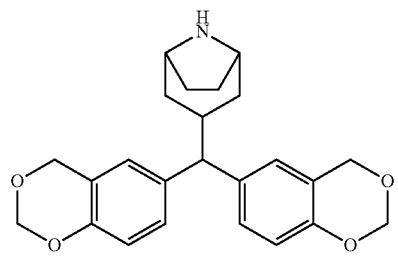 [SMILES: c1cc2c(cc1C(c1ccc3c(c1)COCO3)C1CC3CCC(C1)N3)COCO2]

Following General Procedure S and making non-critical variations as required to replace tert-butyl 4-(bis(1-methyl-1H-indazol-5-yl)methyl)piperazine-1-carboxylate with ethyl 3-(bis(4H-benzo[d][1,3]dioxin-6-yl)methyl)-8-azabicyclo[3.2.1]octane-8-carboxylate, the title compound was obtained as a colourless foam (161 mg, 69% yield).

¹H NMR (400 MHz, CDCl₃) δ 7.04 (m, 2H), 6.78 (m, 4H), 5.19 (s, 4H), 4.85 (s, 4H), 3.61 (d, J=12.4 Hz, 0.2H), 3.49 (m, 2H), 3.28 (d, J=10.9 Hz, 0.8H), 2.55-2.46 (m, 0.2H), 2.39-2.28 (m, 0.8H), 1.97-1.62 (m, 5H), 1.45-1.13 (m, 3H) (NH not observed) (2 conformational isomers observed in a ratio of 4:1).

Step 3. Preparation of 1-(3-(bis(4H-benzo[d][1,3]dioxin-6-yl)methyl)-8-azabicyclo[3.2.1]octane-8-carbonyl)-1H-1,2,4-triazole-3-carbonitrile (Example-130)

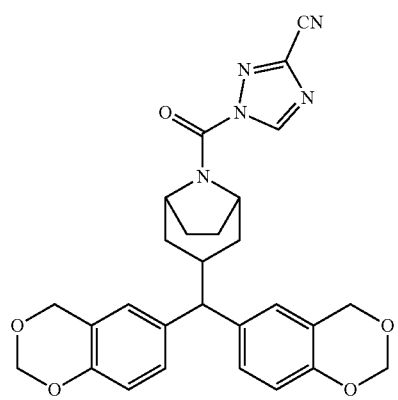

Following General Procedure M and making non-critical variations as required to replace N,N-bis(4-fluorophenyl)

piperidin-4-amine with 3-(bis(4H-benzo[d][1,3]dioxin-6-yl)methyl)-8-azabicyclo[3.2.1]octane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (37 mg, 38% yield).

$^1$H NMR (400 MHz, CDCl$_3$) δ 8.93 (s, 0.8H), 8.93 (s, 0.2H), 7.04 (m, 2H), 6.79 (m, 4H), 5.20 (s, 4H), 5.15 (s, 1H), 4.86 (s, 4H), 4.66 (s, 1H), 3.72 (d, J=12.4 Hz, 0.2H), 3.29 (d, J=11.0 Hz, 0.8H), 2.66-2.54 (m, 0.8H), 2.51-2.41 (m, 0.2H), 2.34-1.81 (m, 4H), 1.65-1.40 (m, 4H) (2 conformational isomers observed in a ratio of 4:1); MS (ESI) n/z 536.4 (M+Na).

Scheme XXX

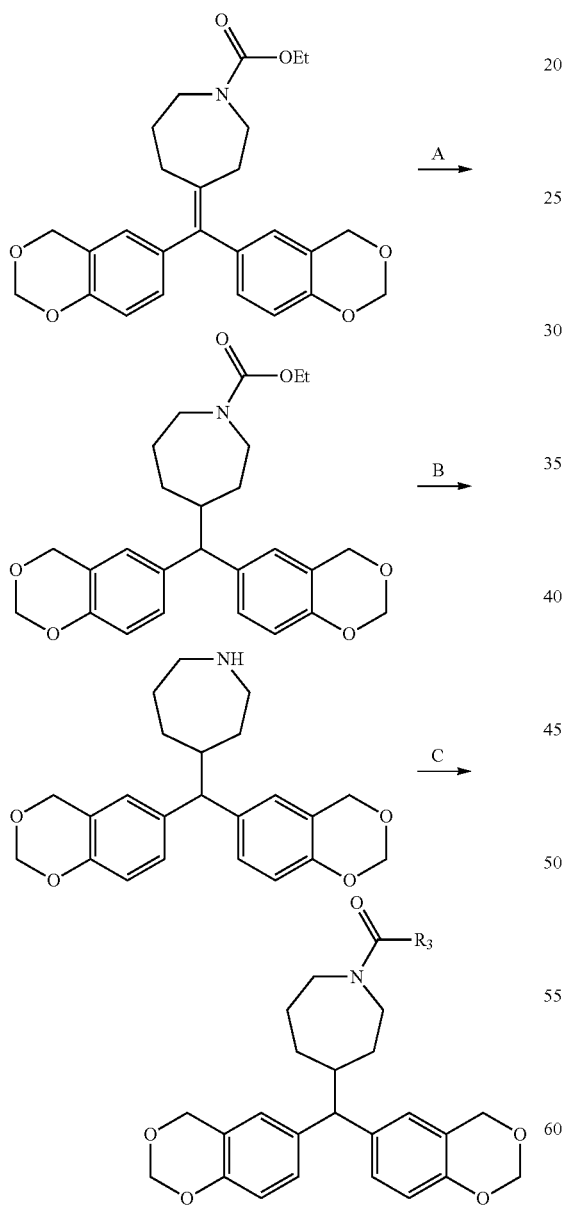

Reagents and conditions: A) H$_2$(g), 10% Pd/C, EtOH, 55° C., 21 h; B) TMSI, NMM, DCM, rt, 20 h; C) i) Triphosgene, DCM, 0° C.; ii) 4-(Bis(4H-benzo[d][1,3]dioxin-6-yl)methyl)azepane, DMAP, DCM, 0° C. to rt, 3 h; iii) R$_3$—H, DMAP, THF, rt, 19 h.

Synthesis of 1-(4-(bis(4H-benzo[d][1,3]dioxin-6-yl)methyl)azepane-1-carbonyl)-1H-1,2,4-triazole-3-carbonitrile (Example-131)

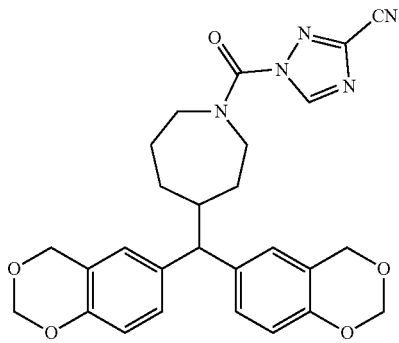 [SMILES: N#Cc1ncn(C(=O)N2CCCC(C(c3ccc4c(c3)COCO4)c3ccc4c(c3)COCO4)CC2)n1]

Step 1. Preparation of ethyl 4-(bis(4H-benzo[d][1,3]dioxin-6-yl)methyl)azepane-1-carboxylate

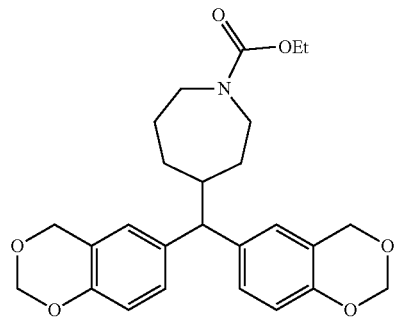 [SMILES: CCOC(=O)N1CCCC(C(c2ccc3c(c2)COCO3)c2ccc3c(c2)COCO3)CC1]

Following General Procedure X and making non-critical variations as required to replace ethyl 4-(bis(4H-benzo[d][1,3]dioxin-6-yl)methylene)piperidine-1-carboxylate with ethyl 4-(bis(4H-benzo[d][1,3]dioxin-6-yl)methylene)azepane-1-carboxylate followed by purification by column chromatography, eluting with 20% to 25% ethyl acetate in hexanes, the title compound was obtained as a colourless foam (284 mg, 90% yield).

$^1$H NMR (400 MHz, CDCl$_3$) δ 7.03 (dd, J=8.4, 2.2 Hz, 2H), 6.77 (m, 4H), 5.20 (s, 4H), 4.85 (s, 4H), 4.14 (m, 2H), 3.60-3.44 (m, 2H), 3.40 (d, J=11.0 Hz, 1H), 3.38-3.16 (m, 2H), 2.16 (m, 1H), 1.82-1.67 (m, 3H), 1.50 (m, 1H), 1.33-1.00 (m, 5H).

Step 2. Preparation of 4-(bis(4H-benzo[d][1,3]dioxin-6-yl)methyl)azepane

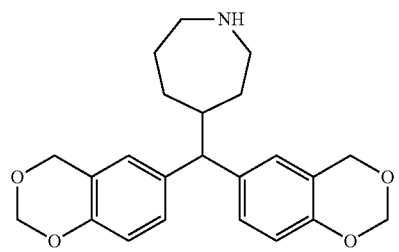 [SMILES: c1cc2c(cc1C(c1ccc3c(c1)COCO3)C1CCCNCC1)COCO2]

Following General Procedure S and making non-critical variations as required to replace tert-butyl 4-(bis(1-methyl-1H-indazol-5-yl)methyl)piperazine-1-carboxylate with ethyl 4-(bis(4H-benzo[d][1,3]dioxin-6-yl)methyl)azepane-1-carboxylate, the title compound was obtained as a pale foam (166 mg, 70% yield).

$^1$H NMR (400 MHz, CDCl$_3$) δ 7.05 (m, 2H), 6.78 (m, 4H), 5.20 (s, 2H), 5.19 (s, 2H), 4.86 (s, 2H), 4.85 (s, 2H), 3.44 (d, J=11.0 Hz, 1H), 3.03-2.76 (m, 4H), 2.42-2.33 (m, 1H), 1.79-1.49 (m, 4H), 1.31-1.18 (m, 2H) (NH not observed).

Step 3. Preparation of 1-(4-(bis(4H-benzo[d][1,3]dioxin-6-yl)methyl)azepane-1-carbonyl)-1H-1,2,4-triazole-3-carbonitrile (Example-131)

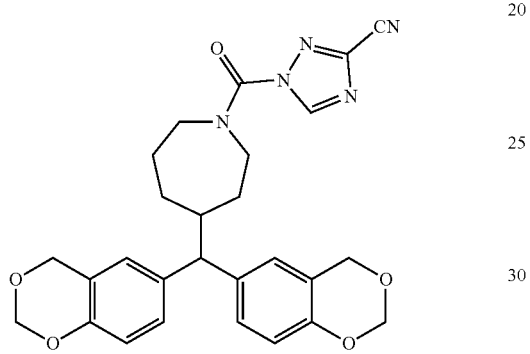

Following General Procedure M and making non-critical variations as required to replace N,N-bis(4-fluorophenyl)piperidin-4-amine with 4-(bis(4H-benzo[d][1,3]dioxin-6-yl)methyl)azepane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (35 mg, 34% yield).

$^1$H NMR (400 MHz, CDCl$_3$) δ 8.88 (s, 1H), 7.04 (m, 2H), 6.79 (m, 4H), 5.20 (s, 4H), 4.86 (s, 4H), 3.94-3.77 (m, 2H), 3.64-3.46 (m, 2H), 3.43 (d, J=11.0 Hz, 1H), 2.25 (m, 1H), 2.01-1.65 (m, 4H), 1.53-1.40 (m, 1H), 1.22-1.09 (m, 1H); MS (ESI) m/z 524.4 (M+Na).

Scheme XXXI

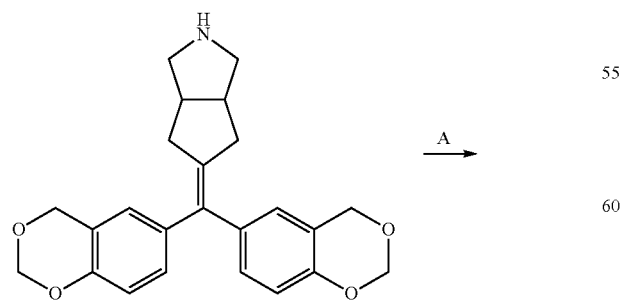

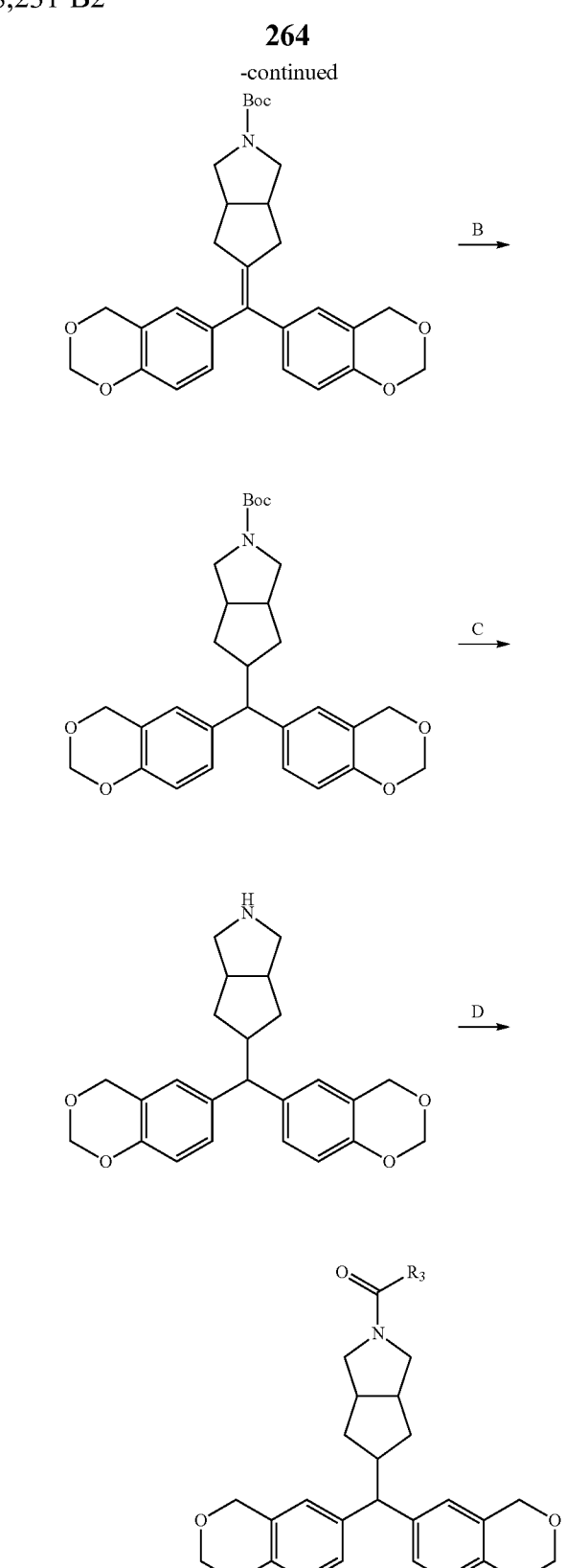

Reagents and conditions: A) Boc$_2$O, Et$_3$N, DCM, rt, 22 h; B) H$_2$(g), 10% Pd/C, EtOH, 55° C., 3 d; C) TMSI, NMM, DCM, rt, 3 h; D) i) Triphosgene, DCM, 0° C.; ii) 5-(Bis(4H-benzo[d][1,3]dioxin-6-yl)methyl)octahydrocyclopenta[c]pyrrole, DMAP, DCM, 0° C. to rt, 4.5 h; iii) R$_3$—H, DMAP, THF, rt, 21 h.

Synthesis of 1-(5-(bis(4H-benzo[d][1,3]dioxin-6-yl)methyl)octahydrocyclopenta[c]pyrrole-2-carbonyl)-1H-1,2,4-triazole-3-carbonitrile (Example-132)

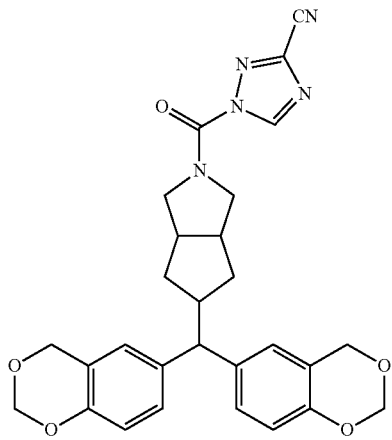 [SMILES: N#Cc1ncn(C(=O)N2CC3CC(C(c4ccc5c(c4)COCO5)c4ccc5c(c4)COCO5)CC3C2)n1]

Step 1. Preparation of tert-butyl 5-(bis(4H-benzo[d][1,3]dioxin-6-yl)methylene)hexahydrocyclopenta[c]pyrrole-2(1H)-carboxylate

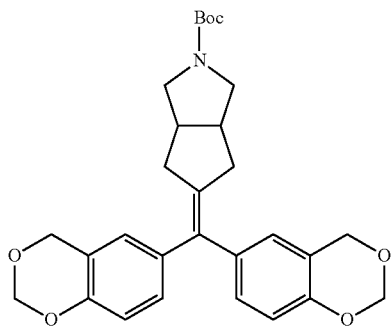 [SMILES: CC(C)(C)OC(=O)N1CC2CC(=C(c3ccc4c(c3)COCO4)c3ccc4c(c3)COCO4)CC2C1]

A solution of 5-(bis(4H-benzo[d][1,3]dioxin-6-yl)methylene)octahydrocyclopenta[c]pyrrole (163 mg, 0.416 mmol) in dichloromethane (5 mL) was stirred at ambient temperature while triethylamine (0.12 mL, 0.86 mmol) was added followed by a solution of di-tert-butyl dicarbonate (136 mg, 0.623 mmol) in dichloromethane (1 mL). The reaction vessel was sealed, and the mixture was stirred at ambient temperature for 22 hours. The mixture was diluted with dichloromethane (15 mL) and washed with saturated aqueous sodium bicarbonate (15 mL). The aqueous phase was extracted with dichloromethane (10 mL), and the combined organic layers were dried over anhydrous sodium sulfate, filtered and concentrated in vacuo. The residue was purified by column chromatography, eluting with 20% ethyl acetate in hexanes to afford the title compound as a colourless foam (166 mg, 81% yield).

$^1$H NMR (400 MHz, CDCl$_3$) δ 6.96 (m, 2H), 6.80 (d, J=8.4 Hz, 2H), 6.70 (d, J=2.1 Hz, 2H), 5.24 (s, 4H), 4.85 (s, 4H), 3.50 (m, 2H), 3.14 (m, 2H), 2.64 (m, 4H), 2.30 (m, 2H), 1.46 (s, 9H).

Step 2. Preparation of tert-butyl 5-(bis(4H-benzo[d][1,3]dioxin-6-yl)methyl)hexahydrocyclopenta[c]pyrrole-2(1H)-carboxylate

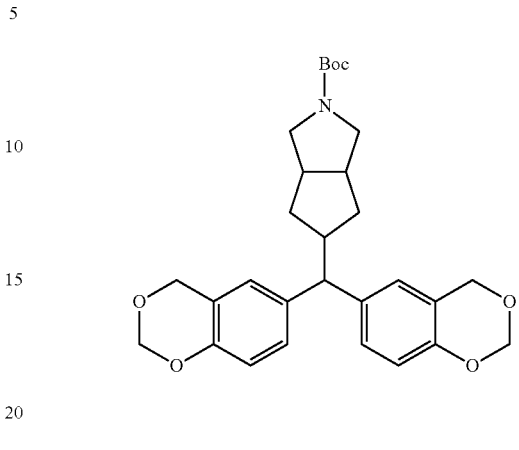

Following General Procedure X and making non-critical variations as required to replace ethyl 4-(bis(4H-benzo[d][1,3]dioxin-6-yl)methylene)piperidine-1-carboxylate with tert-butyl 5-(bis(4H-benzo[d][1,3]dioxin-6-yl)methylene)hexahydrocyclopenta[c]pyrrole-2(1H)-carboxylate, the title compound was obtained as a colourless foam (163 mg, 100% yield) that was used in the next step without further purification.

$^1$H NMR (400 MHz, CDCl$_3$) δ 7.04 (m, 2H), 6.77 (m, 4H), 5.20 (s, 4H), 4.86 (s, 4H), 3.44 (d, J=11.1 Hz, 1H), 3.40 (m, 2H), 3.19 (m, 2H), 2.71-2.55 (m, 3H), 1.88 (m, 2H), 1.45 (s, 9H), 1.05 (m, 2H).

Step 3. Preparation of 5-(bis(4H-benzo[d][1,3]dioxin-6-yl)methyl)octahydrocyclopenta[c]pyrrole

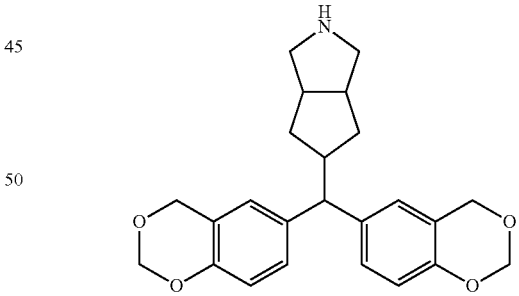

Following General Procedure S and making non-critical variations as required to replace tert-butyl 4-(bis(1-methyl-1H-indazol-5-yl)methyl)piperazine-1-carboxylate with tert-butyl 5-(bis(4H-benzo[d][1,3]dioxin-6-yl)methyl)hexahydrocyclopenta[c]pyrrole-2(1H)-carboxylate, the title compound was obtained as a colourless foam (117 mg, 92% yield).

$^1$H NMR (400 MHz, CDCl$_3$) δ 7.05 (dd, J=8.4, 2.2 Hz, 2H), 6.77 (m, 4H), 5.19 (s, 4H), 4.85 (s, 4H), 3.46 (d, J=10.9 Hz, 1H), 2.78 (m, 4H), 2.60-2.42 (m, 3H), 1.89 (m, 2H), 0.91 (m, 2H) (NH not observed).

267

Step 4. Preparation of 1-(5-(bis(4H-benzo[d][1,3]dioxin-6-yl)methyl)octahydrocyclopenta[c]pyrrole-2-carbonyl)-1H-1,2,4-triazole-3-carbonitrile (Example-132)

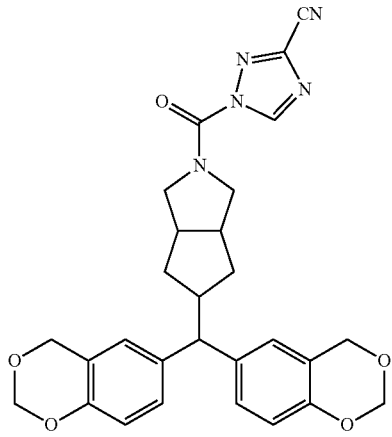 [SMILES: N#Cc1ncn(C(=O)N2CC3CC(C(c4ccc5c(c4)COCO5)c4ccc5c(c4)COCO5)CC3C2)n1]

Following General Procedure M and making non-critical variations as required to replace N,N-bis(4-fluorophenyl)piperidin-4-amine with 5-(bis(4H-benzo[d][1,3]dioxin-6-yl)methyl)octahydrocyclopenta[c]pyrrole, replace 1H-1,2,3-benzotriazole-5-carbonitrile with 2H-1,2,4-triazole-3-carbonitrile and replace triethylamine with 4-(dimethylamino)pyridine, the title compound was obtained as a pale foam (12 mg, 12% yield).

$^1$H NMR (400 MHz, CDCl$_3$) δ 8.95 (s, 1H), 7.04 (dd, J=8.5, 2.2 Hz, 2H), 6.78 (m, 4H), 5.20 (s, 4H), 4.86 (s, 4H), 4.01 (dd, J=12.4, 7.8 Hz, 1H), 3.83 (m, 2H), 3.62 (dd, J=12.7, 4.1 Hz, 1H), 3.47 (d, J=11.2 Hz, 1H), 2.83-2.69 (m, 3H), 1.98 (m, 2H), 1.18-1.08 (m, 2H); MS (ESI) m/z 536.4 (M+Na).

268

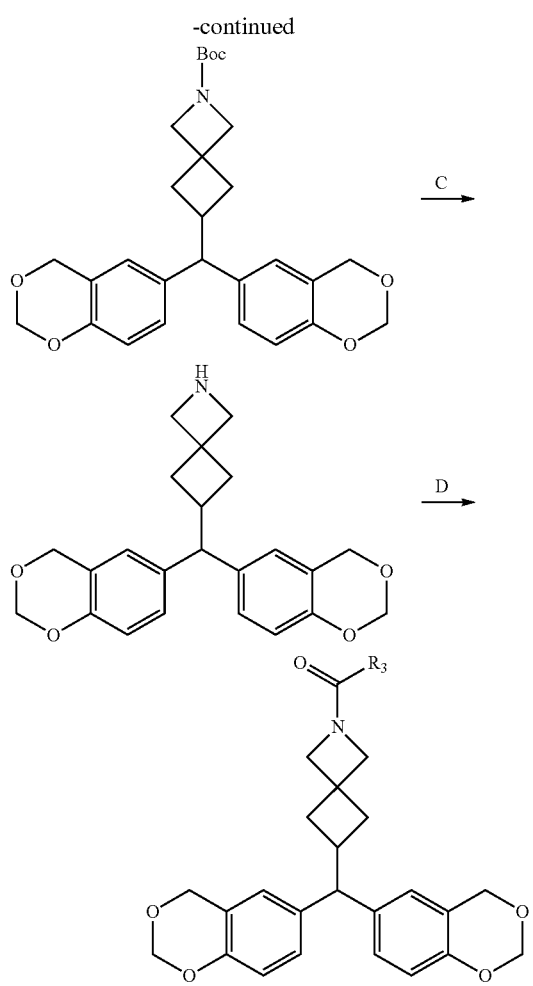

Reagents and conditions: A) Boc$_2$O, Et$_3$N, DCM, rt, 21 h; B) H$_2$(g), 10% Pd/C, EtOH, 70° C., 2 d; C) TMSI, NMM, DCM, rt, 3 h; D) Triphosgene, DCM, 0° C.; ii) 6-(Bis(4H-benzo[d][1,3]dioxin-6-yl)methyl)-2-azaspiro[3.3]heptane, DMAP, DCM, 0° C. to rt, 4 h; iii) R$_3$ — H, DMAP, THF, rt, 18 h.

Scheme XXXII

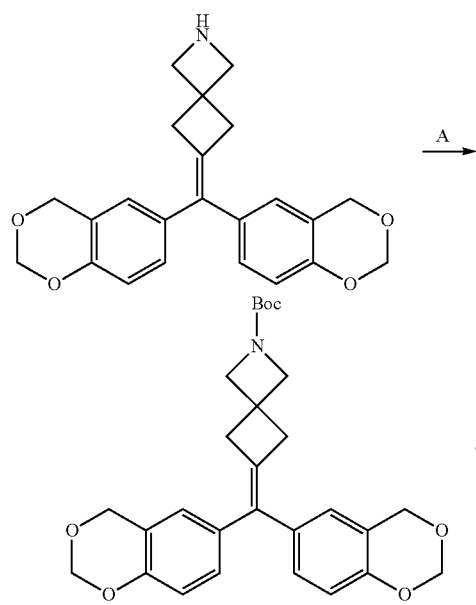

Synthesis of 1-(6-(bis(4H-benzo[d][1,3]dioxin-6-yl)methyl)-2-azaspiro[3.3]heptane-2-carbonyl)-1H-1,2,4-triazole-3-carbonitrile (Example-133)

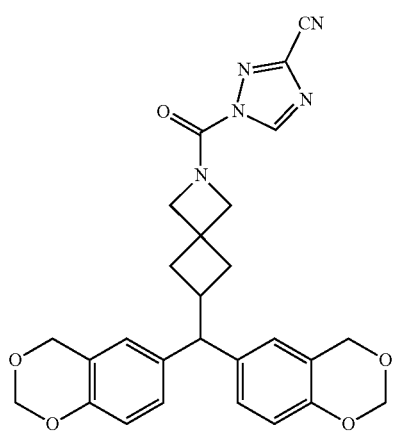 [SMILES: N#Cc1ncn(C(=O)N2CC3(CC(C(c4ccc5c(c4)COCO5)c4ccc5c(c4)COCO5)C3)C2)n1]

Step 1. Preparation of tert-butyl 6-(bis(4H-benzo[d][1,3]dioxin-6-yl)methylene)-2-azaspiro[3.3]heptane-2-carboxylate

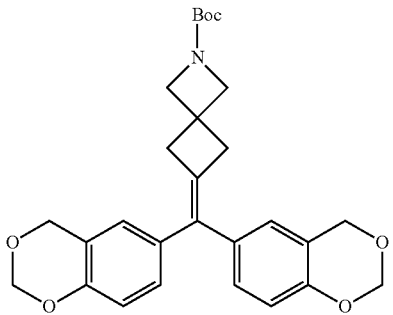 [SMILES: CC(C)(C)OC(=O)N1CC2(CC(=C(c3ccc4c(c3)COCO4)c3ccc4c(c3)COCO4)C2)C1]

A solution of 6-(bis(4H-benzo[d][1,3]dioxin-6-yl)methylene)-2-azaspiro[3.3]heptane (250 mg, 0.662 mmol) in dichloromethane (4 mL) was stirred at ambient temperature while triethylamine (0.18 mL, 1.3 mmol) was added followed by a solution of di-tert-butyl dicarbonate (217 mg, 0.994 mmol) in dichloromethane (3 mL). The reaction vessel was sealed, and the mixture was stirred at ambient temperature for 21 hours. The mixture was diluted with dichloromethane (15 mL) and washed with saturated aqueous sodium bicarbonate (20 mL). The aqueous phase was extracted with dichloromethane (2×10 mL), and the combined organic layers were dried over anhydrous sodium sulfate, filtered and concentrated in vacuo. The residue was purified by column chromatography, eluting with 15% to 20% ethyl acetate in hexanes to afford the title compound as a colourless foam (248 mg, 78% yield).

$^1$H NMR (400 MHz, CDCl$_3$) δ 6.95 (dd, J=8.5, 2.1 Hz, 2H), 6.82 (d, J=8.5 Hz, 2H), 6.68 (d, J=2.1 Hz, 2H), 5.25 (s, 4H), 4.85 (s, 4H), 3.96 (s, 4H), 3.04 (s, 4H), 1.43 (s, 9H).

Step 2. Preparation of tert-butyl 6-(bis(4H-benzo[d][1,3]dioxin-6-yl)methyl)-2-azaspiro[3.3]heptane-2-carboxylate

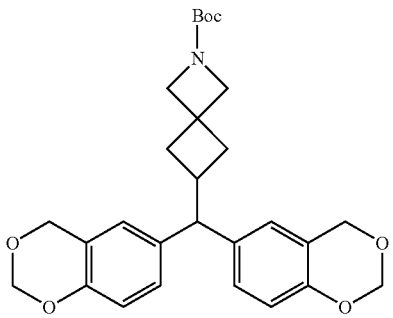 [SMILES: CC(C)(C)OC(=O)N1CC2(CC(C(c3ccc4c(c3)COCO4)c3ccc4c(c3)COCO4)C2)C1]

Following General Procedure X and making non-critical variations as required to replace ethyl 4-(bis(4H-benzo[d][1,3]dioxin-6-yl)methylene)piperidine-1-carboxylate with tert-butyl 6-(bis(4H-benzo[d][1,3]dioxin-6-yl)methylene)-2-azaspiro[3.3]heptane-2-carboxylate, the title compound was obtained as a colourless foam (245 mg, 100% yield) that was used in the next step without further purification.

$^1$H NMR (400 MHz, CDCl$_3$) δ 6.93 (dd, J=8.5, 2.2 Hz, 2H), 6.77 (d, J=8.4 Hz, 2H), 6.68 (d, J=2.2 Hz, 2H), 5.21 (s, 4H), 4.85 (s, 4H), 3.92 (s, 2H), 3.79 (s, 2H), 3.56 (d, J=11.0 Hz, 1H), 2.78-2.67 (m, 1H), 2.21 (m, 2H), 1.83 (m, 2H), 1.42 (s, 9H).

Step 3. Preparation of 6-(bis(4H-benzo[d][1,3]dioxin-6-yl)methyl)-2-azaspiro[3.3]heptane

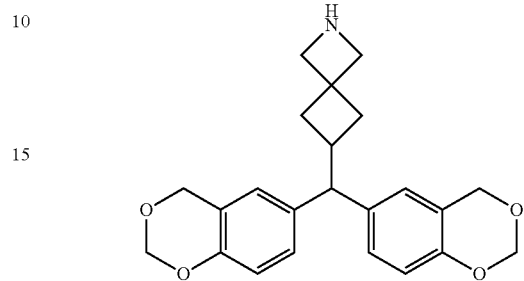

Following General Procedure S and making non-critical variations as required to replace tert-butyl 4-(bis(1-methyl-1H-indazol-5-yl)methyl)piperazine-1-carboxylate with tert-butyl 6-(bis(4H-benzo[d][1,3]dioxin-6-yl)methyl)-2-azaspiro[3.3]heptane-2-carboxylate, the title compound was obtained as a colourless foam (165 mg, 86% yield).

$^1$H NMR (400 MHz, CDCl$_3$) δ 6.91 (dd, J=8.5, 2.1 Hz, 2H), 6.77 (d, J=8.3 Hz, 2H), 6.66 (d, J=2.1 Hz, 2H), 5.21 (s, 4H), 4.84 (s, 4H), 3.82 (s, 2H), 3.67 (s, 2H), 3.54 (d, J=10.8 Hz, 1H), 2.76-2.66 (m, 1H), 2.28 (m, 2H), 1.84 (m, 2H) (NH not observed).

Step 4. Preparation of 1-(6-(bis(4H-benzo[d][1,3]dioxin-6-yl)methyl)-2-azaspiro[3.3]heptane-2-carbonyl 1H-1,2,4-triazole-3-carbonitrile (Example-133)

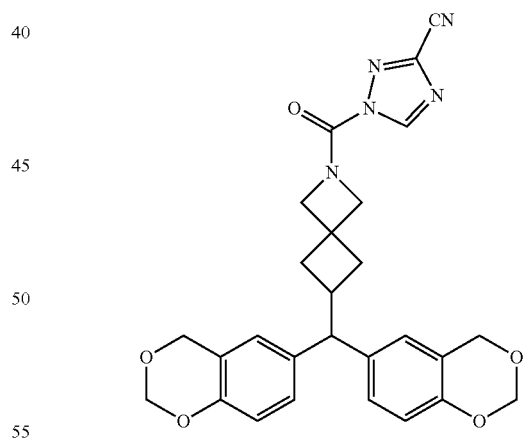

Following General Procedure M and making non-critical variations as required to replace N,N-bis(4-fluorophenyl)piperidin-4-amine with 6-(bis(4H-benzo[d][1,3]dioxin-6-yl)methyl)-2-azaspiro[3.3]heptane, replace 1H-1,2,3-benzotriazole-5-carbonitrile with 2H-1,2,4-triazole-3-carbonitrile and replace triethylamine with 4-(dimethylamino)pyridine, the title compound was obtained as a colourless foam (66 mg, 63% yield).

$^1$H NMR (400 MHz, CDCl$_3$) δ 8.91 (s, 1H), 6.95 (m, 2H), 6.79 (m, 2H), 6.70 (m, 2H), 5.21 (s, 4H), 4.85 (s, 4H), 4.70 (s, 1H), 4.54 (s, 1H), 4.26 (s, 1H), 4.13 (s, 1H), 3.59 (d,

J=11.0 Hz, 1H), 2.88-2.76 (m, 1H), 2.32 (m, 2H), 1.95 (m, 2H); MS (ESI) m/z 522.4 (M+Na).

Example 2: In vitro inhibition on MAGL and FAAH activity

The inhibitory effect of the synthetic chemicals on activity of human recombinant MAGL was studied using commercial inhibitor screening kit (Cayman Chemical). In brief, MAGL hydrolyzes 4-nitrophenylacetate resulting in a yellow product, 4-nitrophenol, with an absorbance at 405-412 nm, while the inhibitor will inhibit the MAGL activity and thus reduce the intensity of yellow signal. The absorbance of the yellow product can be analyzed using the plate reader.

Inhibition is calculated as a percentage of the treated sample over the non-treated MAGL control based on the signal values, and where possible, series of concentrations of chemicals were tested to determine the IC50 value (Inhibitory Concentration 50%), which is the concentration of the chemicals that inhibited 50% of the non-treated MAGL activity. The inhibitory effect of the test chemicals on activity of human recombinant FAAH was also studied for their selectivity using commercial FAAH inhibitor screening kit (Cayman Chemical, Muccioli et al, Chembiochem. 2008 Nov. 3; 9(16):2704-10)). In brief, FAAH hydrolyzes AMC arachidonoyl amide resulting in the release of the fluorescent product, while the inhibitor will inhibit the FAAH activity and thus reduce the fluorescent signal. The resulting fluorophore can be analyzed using an excitation wavelength of 340-360 nm and an emission wavelength of 450-465 nm by a plate reader (Synergy $H_1$, BioTek). Inhibition is calculated as a percentage of the treated sample over the non-treated control based on the signal values, and where possible, series of concentrations of chemicals were tested to find the IC50 value, which is the concentration of the chemicals that inhibited 50% of the non-treated FAAH activity.

TABLE 1

In vitro inhibitory efficacy of MAGL inhibitors on human recombinant MAGL and FAAH activity.

| Compound | Inhibition on MAGL activity ($IC_{50}$, nM) | Inhibition on FAAH activity ($IC_{50}$, nM) |
|---|---|---|
| Example 1 | >100 | >50,000 |
| Example 2 | 1-10 | >10,000 |
| Example 3 | 1-20 | >50,000 |
| Example 4 | 100-1,000 | >10,000 |
| Example 5 | >100 | >50,000 |
| Example 6 | >100 | >50,000 |
| Example 7 | >100 | >10,000 |
| Example 8 | 1-20 | >20,000 |
| Example 9 | >100 | >10,000 |
| Example 10 | 10-100 | 1,000-10,000 |
| Example 11 | >100 | >50,000 |
| Example 12 | >100 | >10,000 |
| Example 13 | >100 | >10,000 |
| Example 14 | >100 | >50,000 |
| Example 15 | >100 | >50,000 |
| Example 16 | >100 | >50,000 |
| Example 17 | >100 | >50,000 |
| Example 18 | >100 | >50,000 |
| Example 19 | >100 | >50,000 |
| Example 20 | >100 | >50,000 |
| Example 21 | >100 | >50,000 |
| Example 22 | >100 | >50,000 |
| Example 23 | >100 | >10,000 |
| Example 24 | 1-10 | 1,000-10,000 |
| Example 25 | 10-100 | >10,000 |
| Example 26 | 10-100 | 1,000-10,000 |
| Example 27 | 10-100 | >10,000 |
| Example 28 | 1-20 | >20,000 |

TABLE 1-continued

In vitro inhibitory efficacy of MAGL inhibitors on human recombinant MAGL and FAAH activity.

| Compound | Inhibition on MAGL activity ($IC_{50}$, nM) | Inhibition on FAAH activity ($IC_{50}$, nM) |
|---|---|---|
| Example 29 | >100 | >50,000 |
| Example 30 | >10,000 | >50,000 |
| Example 31 | 1-10 | ~20,000 |
| Example 32 | 1-10 | 1,000-10,000 |
| Example 33 | 1-10 | >20,000 |
| Example 34 | 1-10 | >20,000 |
| Example 35 | >100 | >50,000 |
| Example 36 | 10-100 | >10,000 |
| Example 37 | 1-10 | >50,000 |
| Example 38 | 10-100 | >50,000 |
| Example 39 | 1-10 | ~50,000 |
| Example 40 | 10-100 | 1,000-20,000 |
| Example 41 | 1-10 (~10) | >50,000 |
| Example 42 | 1-10 | >20,000 |
| Example 43 | >100 | >50,000 |
| Example 44 | 1-10 | >10,000 |
| Example 45 | 10-100 | >1,000 |
| Example 46 | 10-100 | >10,000 |
| Example 47 | 10-100 | 1,000-10,000 |
| Example 48 | 1-10 | >20,000 |
| Example 49 | 10-100 | >20,000 |
| Example 50 | >100 | >50,000 |
| Example 51 | 10-100 | >10,000 |
| Example 52 | >100 | >50,000 |
| Example 53 | >100 | >50,000 |
| Example 54 | >100 | >50,000 |
| Example 55 | 1-10 | 1,000-10,000 |
| Example 56 | 1-10 | >10,000 |
| Example 57 | 1-10 | 100-1,000 |
| Example 58 | 10-100 | >10,000 |
| Example 59 | 10-100 | ~10,000 |
| Example 60 | 10-100 | <10,000 |
| Example 61 | 1-10 | 100-1,000 |
| Example 63 | 1-10 | 100-1,000 (~100) |
| Example 64 | 1-10 | 10-100 (~100) |
| Example 65 | 1-10 | 100-1,000 |
| Example 66 | 1-10 | 100-1,000 |
| Example 67 | 1-10 | 100-1,000 |
| Example 68 | 1-10 | 100-1,000 |
| Example 69 | 1-10 | 100-1,000 |
| Example 70 | 1-10 | 100-1,000 |
| Example 71 | 1-10 | 100-1,000 |
| Example 72 | 1-10 | 100-1,000 |
| Example 73 | 1-10 | 100-1,000 |
| Example 74 | 1-10 | 100-1,000 (~1,000) |
| Example 75 | 1-10 | 100-1,000 |
| Example 76 | 1-10 | 100-1,000 |
| Example 77 | 1-10 | 100-1,000 |
| Example 78 | >100 | >10,000 |
| Example 79 | 1-10 | ~50,000 |
| Example 80 | 10-100 | 10,000-50,000 |
| Example 81 | 1-10 | 1,000-10,000 |
| Example 82 | 10-100 | >50,000 |
| Example 83 | 1-10 | 10,000-50,000 |
| Example 84 | 1-10 | 1,000-10,000 |
| Example 85 | 10-100 | 1,000-10,000 |
| Example 86 | 1-10 (~10) | 100-1,000 (~1,000) |
| Example 87 | 1-10 | 100-1,000 |
| Example 88 | 1-10 | ~50,000 |
| Example 89 | 10-100 | 1,000-10,000 |
| Example 90 | 1-10 | 1,000-10,000 |
| Example 91 | 1-10 | >50,000 |
| Example 92 | 1-10 | ~10,000 |
| Example 93 | 10-100 | >50,000 |
| Example 94 | 10-100 | >50,000 |
| Example 95 | 1-10 | 10,000-50,000 |
| Example 96 | 1-10 | 1,000-10,000 |
| Example 97 | 1-10 | 1,000-10,000 |
| Example 98 | 1-10 | >50,000 |
| Example 99 | 1-10 | >50,000 |
| Example 100 | 1-10 | >50,000 |
| Example 101 | 1-10 | >50,000 |
| Example 102 | 1-10 | 1,000-10,000 |
| Example 103 | 1-10 | 1,000-10,000 |

TABLE 1-continued

In vitro inhibitory efficacy of MAGL inhibitors on human recombinant MAGL and FAAH activity.

| Compound | Inhibition on MAGL activity ($IC_{50}$, nM) | Inhibition on FAAH activity ($IC_{50}$, nM) |
|---|---|---|
| Example 104 | 1-10 | 1,000-10,000 |
| Example 105 | 10-1,000 | >10,000 |
| Example 106 | 1-10 | ~10,000 |
| Example 107 | 1-10 | 1,000-10,000 |
| Example 108 | 1-10 | ~10,000 |
| Example 109 | 10-100 | ~50,000 |
| Example 110 | 1-10 | >10,000 |
| Example 111 | 1-10 | ~10,000 |
| Example 112 | 10-100 | ~50,000 |
| Example 113 | 1-10 | 10,000-50,000 |
| Example 114 | 1-10 | ~10,000 |
| Example 115 | 1-10 | 10,000-50,000 |
| Example 116 | 1-10 | 10,000-50,000 |
| Example 117 | 1-10 | 100-1,000 |
| Example 118 | 1-10 | ~10,000 |
| Example 120 | 1-10 | >50,000 |
| Example 121 | 1-10 | ~100 |
| Example 122 | 10-100 | ~50,000 |
| Example 123 | 1-10 | ~10,000 |
| Example 124 | 1-10 | 1,000-10,000 |
| Example 125 | 1-10 | 1,000-10,000 |
| Example 126 | 1-10 | 1,000-10,000 |
| Example 127 | 1-10 | >50,000 |
| Example 128 | 1-10 | 1,000-10,000 |
| Example 129 | 1-10 | 1,000-10,000 |
| Example 130 | 1-10 | >50,000 |
| Reference | | |
| ABX-1431 | 1-10 | >50,000 |
| URB597 | >50,000 | 87.7 |
| JNJ-42165279 | >50,000 | 105.6 |
| PF-04457845 | >10,000 | 1.9 |

Results of in vitro inhibition on MAGL and FAAH and activity: The MAGL inhibitory activity (nM) of the molecules is listed in Table 1. Multiple tested molecules have $IC_{50}$ values around 1-10 nM, while demonstrating selectivity over FAAH with $IC_{50}$ values over 20-50 μM.

REFERENCES

1. Lu H C, Mackie K. An Introduction to the Endogenous Cannabinoid System. Biol Psychiatry. 2016; 79(7):516-525. doi:10.1016/j.biopsych.2015.07.028
2. Howlett A C, Barth F, Bonner T I, Cabral G, Casellas P, Devane W A, Felder C C, Herkenham M, Mackie K, Martin B R, Mechoulam R, Pertwee R G. International Union of Pharmacology. XXVII. Classification of cannabinoid receptors. Pharmacol Rev. 2002 June; 54(2): 161-202. doi: 10.1124/pr.54.2.161. PMID: 12037135.
3. Ulugöl A. The endocannabinoid system as a potential therapeutic target for pain modulation. Balkan Med J. 2014 June; 31(2):115-20. doi: 10.5152/balkanmedj.2014.13103. Epub 2014 Jun. 1. PMID: 25207181; PMCID: PMC4115931.
4. Sugiura T, Kondo S, Sukagawa A, Nakane S, Shinoda A, Itoh K, Yamashita A, Waku K. 2-Arachidonoylglycerol: a possible endogenous cannabinoid receptor ligand in brain. Biochem Biophys Res Commun. 1995 Oct. 4; 215(1):89-97. doi: 10.1006/bbrc.1995.2437. PMID: 7575630.
5. Devane W A, Hanus L, Breuer A, Pertwee R G, Stevenson L A, Griffin G, Gibson D, Mandelbaum A, Etinger A, Mechoulam R. Isolation and structure of a brain constituent that binds to the cannabinoid receptor. Science. 1992 Dec. 18; 258(5090):1946-9. doi: 10.1126/science.1470919. PMID: 1470919.
6. Patel S, Hillard C J. Role of endocannabinoid signaling in anxiety and depression. Curr Top Behav Neurosci. 2009; 1:347-371. doi:10.1007/978-3-540-88955-7_14
7. Griebel, G., Pichat, P., Beeské, S., Leroy, T., Redon, N., Jacquet, A., Frangon, D., Bert, L., Even, L., Lopez-Grancha, M., Tolstykh, T., Sun, F., Yu, Q., Brittain, S., Arlt, H., He, T., Zhang, B., Wiederschain, D., Bertrand, T., Houtmann, J., . . . Escoubet, J. (2015). Selective blockade of the hydrolysis of the endocannabinoid 2-arachidonoylglycerol impairs learning and memory performance while producing antinociceptive activity in rodents. Scientific reports, 5, 7642. https://doi.org/10.1038/srep07642
8. Zanfirescu A, Ungurianu A, Mihai D P, Radulescu D, Nitulescu G M. Targeting Monoacylglycerol Lipase in Pursuiit of Therapies for Neurological and Neurodegenerative Diseases. Molecules. 2021 Sep. 18; 26(18):5668. doi: 10.3390/molecules26185668. PMID: 34577139; PMCID: PMC8468992.
9. Stasiulewicz A, Znajdek K, Grudzien M, Pawinski T, Sulkowska A J I. A Guide to Targeting the Endocannabinoid System in Drug Design. Int J Mol Sci. 2020 Apr. 16; 21(8):2778.
10. Deng H, Li W. Monoacylglycerol lipase inhibitors: modulators for lipid metabolism in cancer malignancy, neurological and metabolic disorders. Acta Pharm Sin B. 2020 April; 10(4):582-602. doi: 10.1016/j.apsb.2019.10.006. Epub 2019 Oct. 18. Karlsson M, Contreras J A, Hellman U, Tornqvist H, Holm C. cDNA cloning, tissue distribution, and identification of the catalytic triad of monoglyceride lipase. Evolutionary relationship to esterases, lysophospholipases, and haloperoxidases. J Biol Chem. 1997 Oct. 24; 272(43):27218-23. doi: 10.1074/jbc.272.43.27218. PMID: 9341166.
11. Remington, J. P. and A. R. Gennaro, Remington's pharmaceutical sciences. 1990, Easton, Pa.: Mack Pub. Co.
12. Muccioli G G, Labar G, Lambert D M. CAY10499, a novel monoglyceride lipase inhibitor evidenced by an expeditious MGL assay. Chembiochem. 2008 Nov. 3; 9(16):2704-10. doi: 10.1002/cbic.200800428. PMID: 18855964.
13. O'Brien J, Wilson I, Orton T, Pognan F. Investigation of the Alamar Blue (resazurin) fluorescent dye for the assessment of mammalian cell cytotoxicity. Eur J Biochem. 2000 September; 267(17):5421-6. doi: 10.1046/j.1432-1327.2000.01606.x. PMID: 10951200.
14. A. F. Almeida-Santos, P. H. Gobira, L. C. Rosa, F. S. Guimaraes, and D. C. Aguiar. Modulation of anxiety-like behavior by the endocannabinoid 2-arachidonoylglycerol (2-AG) in the dorsolateral periaqueductal gray. Behav. Brain Res. 2013; 252:10-17
15. Zanfirescu A, Ungurianu A, Mihai D P, Radulescu D, Nitulescu G M. Targeting Monoacylglycerol Lipase in Pursuit of Therapies for Neurological and Neurodegenerative Diseases. Molecules 2021; 26: 5668.

The invention claimed is:
1. A compound having the Formula I:

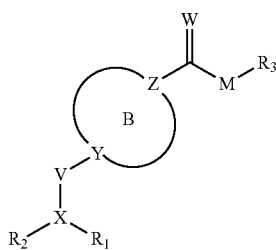

Formula I a prodrug thereof, or a pharmaceutically acceptable salt thereof,
wherein:
a. X is C, CH, or N;
b. V is O, N (CH₃), or none, wherein when V is none, X is directly attached to Y by single or double bond;
C. Y is C, CH, or N;
d. Z is C, CH, or N;
e. W is O or S;
f. M is O, N, or none, wherein when M is none, C═W is directly attached to R₃;
g. B is $C_{4-10}$ heterocycloalkyl, $C_{6-12}$ fused heterocycloalkyl, $C_{6-12}$ spirocycloalkyl, azetidinyl, azepanyl, piperazinyl, piperidinyl, diazepanyl, 2-azaspiro[3.3]heptane, 2,5-diazabicyclo[2.2.1]heptane, 8-azabicyclo[3.2.1]octane, 2,6-diazaspiro[3.4]octane, 2,7-diazaspiro[3.5]nonane, 2,7-diazaspiro[4.4]nonane, or 3,9-diazaspiro[5.5]undecane, wherein:
(i) when B is azetidinyl, then Y is CH, and Z is N:

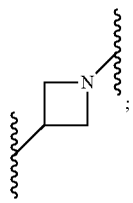 [SMILES: *C1CN(*)C1 ; ";"]

(ii) when B is piperazinyl, then Y is N and Z is N:

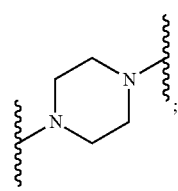 [SMILES: *N1CCN(*)CC1]

(iii) when B is piperidinyl, then Y is CH and Z is N:

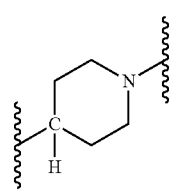 [SMILES: *C1CCN(*)CC1]

(iv) when B is piperid-4,4-diyl, then Y is C and Z is N:

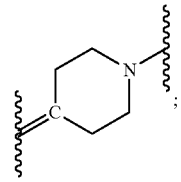 [SMILES: *N1CCC(=*)CC1]

(v) when B is azepanyl, then Y is CH and Z is N:

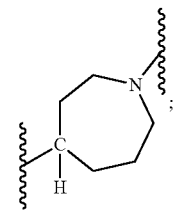 [SMILES: *C1CCCN(*)CC1]

(vi) when B is diazepanyl, then Y is N and Z is N:

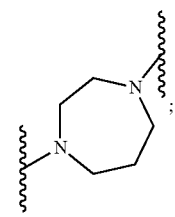 [SMILES: *N1CCCN(*)CC1]

(vii) when B is 2-azaspiro[3.3]heptane, then Y is CH and Z is N:

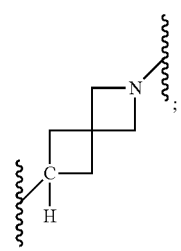 [SMILES: *C1CC2(C1)CN(*)C2 ; ";"]

(viii) when B is 2,6-diazaspiro[3.3]heptane, then Y is N and Z is N:

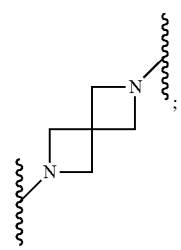 [SMILES: *N1CC2(C1)CN(*)C2 ; ";"]

(ix) when B is 2,5-diazabicyclo[2.2.1]heptane, Y is N and Z is N:

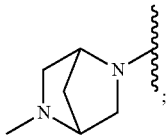 [SMILES: *N1CC2CC1CN2C]

(x) when B is 8-azabicyclo[3.2.1]octane, then Y is N and Z is N:

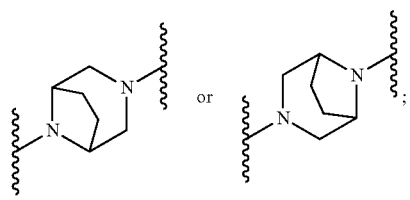 [SMILES: *N1CC2CCC(C1)N2* ; *N1CC2CCC(C1)N2*]

(xi) when B is 2,6-diazaspiro[3.4]octane, then Y is N and Z is N:

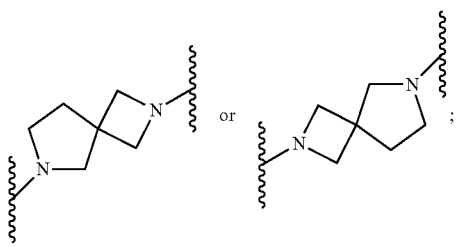 [SMILES: *N1CCC2(C1)CN(*)C2 ; *N1CCC2(C1)CN(*)C2]

(xii) when B is 2,7-diazaspiro[3.5]nonane, then Y is N and Z is N:

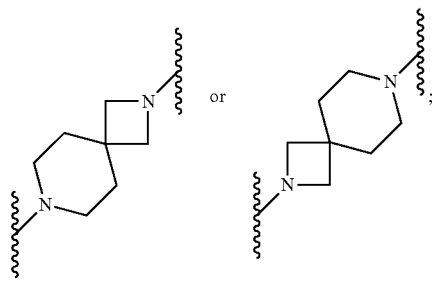 [SMILES: *N1CCC2(CC1)CN(*)C2 ; "or" ; *N1CCC2(CC1)CN(*)C2 ; ";"]

(xiii) when B is 2,7-diazaspiro[4.4]nonane, then Y is N and Z is N:

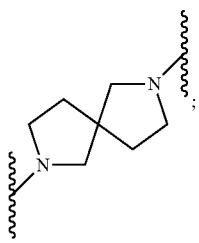 [SMILES: *N1CCC2(CCN(*)C2)C1]

or (xiv) when B is 3,9-diazaspiro[5.5]undecane, then Y is N and Z is N:

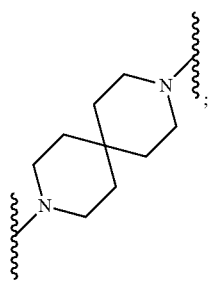 [SMILES: *N1CCC2(CC1)CCN(*)CC2 ; ";"]

h. $R_1$ and $R_2$ are each independently aryl, heteroaryl, heterocyclyl, phenyl, pyridyl, benzo-1,3-dioxanyl, benzo-1,4-dioxanyl, benzofuranyl, dihydrobenzofuranyl, benzopyrazolyl, or quinolinyl, wherein each group may be unsubstituted, monosubstituted or disubstituted with an $R_5$ group; wherein $R_5$ may be one of the following moieties: alkyl, alkoxy, alkenoxy, halogen, cyano, or pyrazolyl; and i. $R_3$ is $C_1$-$C_6$ alkyl, $C_3$-$C_6$ cycloalkyl, $C_4$-$C_8$ heterocycloalkyl, aryl, heteroaryl, piperidinyl, piperazinyl, morpholinyl, phenyl, pyridinyl, imidazolyl, pyrazolyl, benzopyrazolyl, triazolyl, benzotriazolyl, pyridotriazolyl, or indanyl, and $R_3$ may be unsubstituted or substituted with a $R_4$ group; wherein $R_4$ may be one of the following moieties: F, Cl, Br, $CF_3$, $NO_2$, CN, O, $OCH_3$, $OCF_3$, $C_1$-$C_6$ alkyl, $C_1$-$C_6$ alkyloxy, $C_6H_5$, $OC_6H_5$, or $C(O)OCH_3$, or j. wherein M and $R_3$ together form a leaving group; wherein at least one of $R_1$ and $R_2$ is a benzo-1,3-dioxanyl.

2. The compound of claim 1, having Formula II

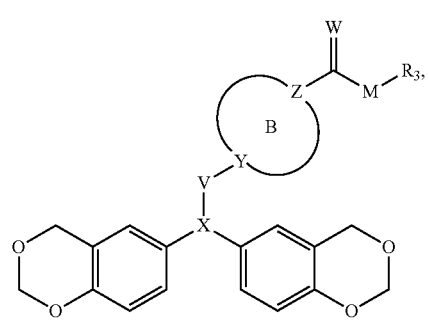

II a prodrug thereof, or a pharmaceutically acceptable salt thereof.

3. The compound of claim 1, wherein:
$R_1$ is benzo-1,3-dioxanyl; and
$R_2$ is aryl, heteroaryl, phenyl, pyridyl, benzo-1,4-dioxanyl, benzofuranyl, dihydrobenzofuranyl, benzopyrazolyl, or quinolinyl, wherein $R_2$ may be unsubstituted, monosubstituted, or disubstituted with an $R_5$ group; wherein $R_5$ may be one of the following moieties: alkyl, alkoxy, alkenoxy, halogen, cyano, or pyrazolyl.

4. The compound of claim 1, wherein $R_1$ is benzo-1,3-dioxanyl and $R_2$ is pyridyl, having the Formula III:

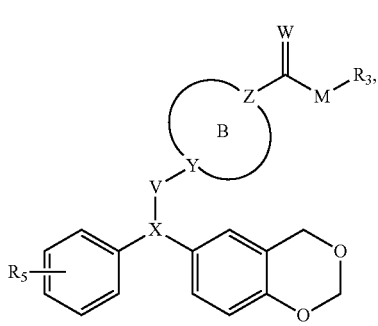

III a prodrug thereof, or a pharmaceutically acceptable salt thereof.

5. The compound of claim 1, wherein X is nitrogen, having Formula IV

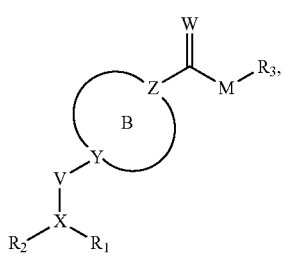

IV a prodrug thereof, or a pharmaceutically acceptable salt thereof.

6. The compound of claim 1, wherein X is carbon.

7. The compound of claim 1, wherein X and Y are carbon, V is none, and X is directly attached to Y by double bond, having Formula V

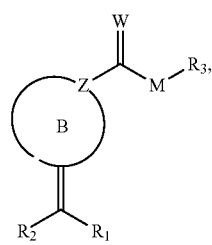

V a prodrug thereof, or a pharmaceutically acceptable salt thereof.

8. The compound of claim 1, wherein Z is nitrogen.

9. The compound of claim 1, wherein B is piperazinyl or piperidinyl.

10. The compound of claim 1, wherein W is O.
11. The compound of claim 1, wherein W is S.
12. The compound of claim 1, wherein M is O.
13. The compound of claim 1, wherein M is N.
14. The compound of claim 1, wherein V is O.
15. The compound of claim 1, wherein
$R_3$ may be $C_1$-$C_6$ alkyl, $C_3$-$C_6$ cycloalkyl, $C_4$-$C_8$ heterocycloalkyl, aryl, heteroaryl, piperidinyl, piperazinyl, morpholinyl, phenyl, pyridinyl, imidazolyl, pyrazolyl, benzopyrazolyl, triazolyl, benzotriazolyl, pyridotriazolyl, or indanyl;
wherein $R_3$ may be unsubstituted or substituted with an $R_4$ group; wherein $R_4$ may be one of the following moieties: F, Cl, Br, $CF_3$, $NO_2$, CN, O, $OCH_3$, $OCF_3$, $C_1$-$C_6$ alkyl, $C_1$-$C_6$ alkyloxy, $C_6H_5$, $OC_6H_5$, or $C(O)OCH_3$.

16. The compound of claim 1, wherein the compound is
(4-(bis(4H-benzo[d][1,3]dioxin-6-yl)methyl)piperazin-1-yl)(1H-pyrazol-1-yl)methanone,
(4-(bis(4H-benzo[d][1,3]dioxin-6-yl)methyl)piperazin-1-yl)(3-chloro-1H-1,2,4-triazol-1-yl)methanone,
1,1,1,3,3,3-hexafluoropropan-2-yl 4-(bis(4H-benzo[d][1,3]dioxin-6-yl)methyl)piperazine-1-carboxylate,
4-nitrophenyl 4-(bis(4H-benzo[d][1,3]dioxin-6-yl)methyl)piperazine-1-carboxylate,
4-fluorophenyl 4-(bis(4H-benzo[d][1,3]dioxin-6-yl)methyl)piperazine-1-carboxylate,
2,5-dioxopyrrolidin-1-yl 4-(bis(4H-benzo[d][1,3]dioxin-6-yl)methyl)piperazine-1-carboxylate,
4-phenoxyphenyl 4-(bis(4H-benzo[d][1,3]dioxin-6-yl)methyl)piperazine-1-carboxylate,
(1H-benzo[d][1,2,3]triazol-1-yl)(4-(bis(4H-benzo[d][1,3]dioxin-6-yl)methyl)piperazin-1-yl)methanone,
(4-(bis(4H-benzo[d][1,3]dioxin-6-yl)methyl)piperazin-1-yl)(1H-imidazol-1-yl)methanone,
(4-(bis(4H-benzo[d][1,3]dioxin-6-yl)methyl)piperazin-1-yl)(1H-1,2,4-triazol-1-yl)methanone,
4-(bis(4H-benzo[d][1,3]dioxin-6-yl)methyl)-N-ethyl-N-isopropylpiperazine-1-carboxamide,
2,3-dihydro-1H-inden-5-yl 4-(bis(4H-benzo[d][1,3]dioxin-6-yl)methyl)piperazine-1-carboxylate,
2,4-dinitrophenyl 4-(bis(4H-benzo[d][1,3]dioxin-6-yl)methyl)piperazine-1-carboxylate,
4-methoxyphenyl 4-(bis(4H-benzo[d][1,3]dioxin-6-yl)methyl)piperazine carboxylate,
pentan-3-yl 4-(bis(4H-benzo[d][1,3]dioxin-6-yl)methyl)piperazine-1-carboxylate,
cyclohexyl 4-(bis(4H-benzo[d][1,3]dioxin-6-yl)methyl)piperazine-1-carboxylate,
(4-(bis(4H-benzo[d][1,3]dioxin-6-yl)methyl)piperazin-1-yl)(piperidin-1-yl)methanone,
4-(bis(4H-benzo[d][1,3]dioxin-6-yl)methyl)-N,N-diethylpiperazine-1-carboxamide,
2-fluoro-4-nitrophenyl 4-(bis(4H-benzo[d][1,3]dioxin-6-yl)methyl)piperazine-1-carboxylate,
pyridin-2-yl 4-(bis(4H-benzo[d][1,3]dioxin-6-yl)methyl)piperazine-1-carboxylate,
(4-(bis(4H-benzo[d][1,3]dioxin-6-yl)methyl)piperazin-1-yl)(1H-1,2,4-triazol-1-yl) methanethione,
6-(trifluoromethyl)-1H-benzo[d][1,2,3]triazol-1-yl 4-(bis(4H-benzo[d][1,3]dioxin-6-yl)methyl)piperazine-1-carboxylate,
3H-[1,2,3]triazolo[4,5-b]pyridin-3-yl 4-(bis(4H-benzo[d][1,3]dioxin-6-yl)methyl)piperazine-1-carboxylate,
1-(4-(bis(4H-benzo[d][1,3]dioxin-6-yl)methyl)piperazine-1-carbonyl)-1H-pyrazole-4-carbonitrile,
4-(bis(4H-benzo[d][1,3]dioxin-6-yl)methyl)piperazin-1-yl)(4-phenyl-1H-1,2,3-triazol-1-yl)methanone, (4-(bis(4H-benzo[d][1,3]dioxin-6-yl)methyl)piperazin-1-yl)(4-phenyl-2H-1,2,3-triazol-2-yl)methanone,
1H-benzo[d][1,2,3]triazol-1-yl 4-(bis(4H-benzo[d][1,3]dioxin-6-yl)methyl)piperazine-1-carboxylate,
(4-(bis(4H-benzo[d][1,3]dioxin-6-yl)methyl)piperazin-1-yl)(3-methyl-1H-1,2,4-triazol-1-yl)methanone,
pentaflurophenyl 4-(bis(4H-benzo[d][1,3]dioxin-6-yl)methyl)piperazine-1-carboxylate,
propan-2-one O-(4-(bis(4H-benzo[d][1,3]dioxin-6-yl)methyl)piperazine-1-carbonyl) oxime,
4-(bis(4H-benzo[d][1,3]dioxin-6-yl)methyl)piperazin-1-yl)(1H-1,2,3-triazol-1-yl)methanone,
(4-(bis(4H-benzo[d][1,3]dioxin-6-yl)methyl)piperazin-1-yl)(2H-1,2,3-triazol-2-yl)methanone,
(3H-[1,2,3]triazolo[4,5-b]pyridin-3-yl)(4-(bis(4H-benzo[d][1,3]dioxin-6-yl)methyl)piperazin-1-yl)methanone,
(1H-[1,2,3]triazolo[4,5-b]pyridin-1-yl)(4-(bis(4H-benzo[d][1,3]dioxin-6-yl)methyl)piperazin-1-yl)methanone,
4-(bis(4H-benzo[d][1,3]dioxin-6-yl)methyl)piperazin-1-yl)(5-chloro-1H-benzo[d][1,2,3]triazol-1-yl)methanone,
(4-(bis(4H-benzo[d][1,3]dioxin-6-yl)methyl)piperazin-1-yl)(6-chloro-1H-benzo[d][1,2,3]triazol-1-yl)methanone,
4-(bis(4H-benzo[d][1,3]dioxin-6-yl)methyl)piperazin-1-yl)(5-methyl-1H-benzo[d][1,2,3]triazol-1-yl)methanone,
(4-(bis(4H-benzo[d][1,3]dioxin-6-yl)methyl)piperazin-1-yl)(6-methyl-1H-benzo[d][1,2,3]triazol-1-yl)methanone,
(4-(bis(4H-benzo[d][1,3]dioxin-6-yl)methyl)piperazin-1-yl)(1H-indazol-1-yl)methanone,
1-(4-(bis(4H-benzo[d][1,3]dioxin-6-yl)methyl)piperazine-1-carbonyl)-1H-1,2,4-triazole-3-carbonitrile,
(4-(bis(4H-benzo[d][1,3]dioxin-6-yl)methyl)piperazin-1-yl)(6-bromo-1H-benzo[d][1,2,3]triazol-1-yl)methanone,
(4-(bis(4H-benzo[d][1,3]dioxin-6-yl)methyl)piperazin-1-yl)(5-bromo-1H-benzo[d][1,2,3]triazol-1-yl)methanone,
(4-(bis(4H-benzo[d][1,3]dioxin-6-yl)methyl)piperazin-1-yl)(6-fluoro-1H-benzo[d][1,2,3]triazol-1-yl)methanone,
(4-(bis(4H-benzo[d][1,3]dioxin-6-yl)methyl)piperazin-1-yl)(5-fluoro-1H-benzo[d][1,2,3]triazol-1-yl)methanone,
methyl 1-(4-(bis(4H-benzo[d][1,3]dioxin-6-yl)methyl)piperazine-1-carbonyl)-1H-benzo[d][1,2,3]triazole-5-carboxylate,
methyl 1-(4-(bis(4H-benzo[d][1,3]dioxin-6-yl)methyl)piperazine-1-carbonyl)-1H-benzo[d][1,2,3]triazole-6-carboxylate,
(4-(bis(4H-benzo[d][1,3]dioxin-6-yl)methyl)piperazin-1-yl)(4-chloro-6-(trifluoromethyl)-1H-benzo[d][1,2,3]triazol-1-yl)methanone,
4-(bis(4H-benzo[d][1,3]dioxin-6-yl)methyl)-N-(pyridin-3-yl) piperazine-1-carboxamide,
(4-(bis(4H-benzo[d][1,3]dioxin-6-yl)methyl)piperazin-1-yl)(6-(trifluoromethyl)-1H-benzo[d][1,2,3]triazol-1-yl)methanone,
(4-(bis(4H-benzo[d][1,3]dioxin-6-yl)methyl)piperazin-1-yl)(5-(trifluoromethyl)-1H-benzo[d][1,2,3]triazol-1-yl)methanone,
(4-(bis(4H-benzo[d][1,3]dioxin-6-yl)methyl)piperazin-1-yl)(6,7-dihydro-1H-[1,4]dioxino[2',3':4,5]benzo[1,2-d][1,2,3]triazol-1-yl)methanone,
(3H-[1,2,3]triazolo[4,5-c]pyridin-3-yl)(4-(bis(4H-benzo[d][1,3]dioxin-6-yl)methyl)piperazin-1-yl)methanone,
(1H-[1,2,3]triazolo[4,5-c]pyridin-1-yl)(4-(bis(4H-benzo[d][1,3]dioxin-6-yl)methyl)piperazin-1-yl)methanone,
1-(4-(bis(4H-benzo[d][1,3]dioxin-6-yl)methyl)piperazine-1-carbonyl)-1H-benzo[d][1,2,3]triazole-6-carbonitrile,
1-(4-(bis(4H-benzo[d][1,3]dioxin-6-yl)methyl)piperazine-1-carbonyl)-1H-benzo[d][1,2,3]triazole-5-carbonitrile,
2-(4-(bis(4H-benzo[d][1,3]dioxin-6-yl)methyl)piperazine-1-carbonyl)-[1,2,4]triazolo[4,3-a]pyridin-3(2H)-one,
1-(4-(bis(4H-benzo[d][1,3]dioxin-6-yl)methyl)-1,4-diazepane-1-carbonyl)-1H-benzo[d][1,2,3]triazole-6-carbonitrile,
(1H-benzo[d][1,2,3]triazol-1-yl)(1-(bis(4H-benzo[d][1,3]dioxin-6-yl)methyl) piperidin-4-yl)methanone,
1,1,1,3,3,3-hexafluoropropan-2-yl 1-(bis(4H-benzo[d][1,3]dioxin-6-yl)methyl) piperidine-4-carboxylate,
pentafluorophenyl 1-(bis(4H-benzo[d][1,3]dioxin-6-yl)methyl) piperidine-4-carboxylate,
1-(4-(bis(4H-benzo[d][1,3]dioxin-6-yl) methoxy) piperidine-1-carbonyl)-1H-benzo[d][1,2,3]triazole-6-carbonitrile,
1-(4-(bis(4H-benzo[d][1,3]dioxin-6-yl) methoxy) piperidine-1-carbonyl)-1H-benzo[d][1,2,3]triazole-5-carbonitrile,
1-(3-(bis(4H-benzo[d][1,3]dioxin-6-yl) methoxy) azetidine-1-carbonyl)-1H-benzo[d][1,2,3]triazole-6-carbonitrile,
1-(3-(bis(4H-benzo[d][1,3]dioxin-6-yl) methoxy) azetidine-1-carbonyl)-1H-benzo[d][1,2,3]triazole-5-carbonitrile,
1-(6-(bis(4H-benzo[d][1,3]dioxin-6-yl) methoxy)-2-azaspiro[3.3]heptane-2-carbonyl)-1H-benzo[d][1,2,3]triazole-6-carbonitrile,
1-(6-(bis(4H-benzo[d][1,3]dioxin-6-yl) methoxy)-2-azaspiro[3.3]heptane-2-carbonyl)-1H-benzo[d][1,2,3]triazole-5-carbonitrile,
1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-6-carbonitrile,
1-((1S,4S)-5-(bis(4H-benzo[d][1,3]dioxin-6-yl)methyl)-2,5-diazabicyclo[2.2.1]heptane-2-carbonyl)-1H-benzo[d][1,2,3]triazole-5-carbonitrile,
1-(9-(bis(4H-benzo[d][1,3]dioxin-6-yl)methyl)-3,9-diazaspiro[5.5]undecane-3-carbonyl)-1H-1,2,4-triazole-3-carbonitrile,
1-(6-(bis(4H-benzo[d][1,3]dioxin-6-yl)methyl)-2,6-diazaspiro[3.3]heptane-2-carbonyl)-1H-1,2,4-triazole-3-carbonitrile,
meso-1-(5-(bis(4H-benzo[d][1,3]dioxin-6-yl)methyl) octahydropyrrolo[3,4-c]pyrrole-2-carbonyl)-1H-1,2,4-triazole-3-carbonitrile,
1-(7-(bis(4H-benzo[d][1,3]dioxin-6-yl)methyl)-2,7-diazaspiro[3.5]nonane-2-carbonyl)-1H-1,2,4-triazole-3-carbonitrile,
1-(2-(bis(4H-benzo[d][1,3]dioxin-6-yl)methyl)-2,7-diazaspiro[3.5]nonane-7-carbonyl)-1H-1,2,4-triazole-3-carbonitrile,
1-(6-(bis(4H-benzo[d][1,3]dioxin-6-yl)methyl)-2,6-diazaspiro[3.4]octane-2-carbonyl)-1H-1,2,4-triazole-3-carbonitrile,
1-(7-(bis(4H-benzo[d][1,3]dioxin-6-yl)methyl)-2, 7-diazaspiro[4.4]nonane-2-carbonyl)-1H-1,2,4-triazole-3-carbonitrile, 1-(4-((bis(4H-benzo[d][1,3]dioxin-6-yl)methyl)(methyl)
amino) piperidine-1-carbonyl)-1H-benzo[d][1,2,3]tri-
azole-6-carbonitrile, 1-(4-((bis(4H-benzo[d][1,3]dioxin-6-yl)methyl)(methyl)
amino) piperidine-1-carbonyl)-1H-benzo[d][1,2,3]tri-
azole-5-carbonitrile, 1-(4-(bis(4H-benzo[d][1,3]dioxin-6-yl)methyl) piperi-
dine-1-carbonyl)-1H-1,2,4-triazole-3-carbonitrile, 1-(3-(bis(4H-benzo[d][1,3]dioxin-6-yl)methyl)-8-azabi-
cyclo[3.2.1]octane-8-carbonyl)-1H-1,2,4-triazole-3-
carbonitrile, 1-(4-(bis(4H-benzo[d][1,3]dioxin-6-yl)methyl) azepane-
1-carbonyl)-1H-1,2,4-triazole-3-carbonitrile, 1-(5-(bis(4H-benzo[d][1,3]dioxin-6-yl)methyl) octahy-
drocyclopenta[c]pyrrole-2-carbonyl)-1H-1,2,4-triaz-
ole-3-carbonitrile, or 1-(6-(bis(4H-benzo[d][1,3]dioxin-6-yl)methyl)-2-
azaspiro[3.3]heptane-2-carbonyl)-1H-1,2,4-triazole-3-
carbonitrile.

17. A pharmaceutical composition comprising at least one compound of claim 1 and optionally one or more pharmaceutically acceptable excipients or adjuvants.

18. The pharmaceutical composition of claim 17, comprising an effective amount of the compound, wherein the effective amount is between about 0.0001 to about 1,000 mg.

19. The pharmaceutical composition of claim 17, further comprising one or more additional therapeutic agent.

20. The pharmaceutical composition of claim 19, wherein the one or more additional therapeutic agent is selected from the group consisting of: FAAH inhibitors; CB1 cannabinoid receptor agonists; CB2 cannabinoid receptor agonists; phytocannabinoids; non-steroidal anti-inflammatory drugs (NSAIDs); cyclooxygenase-II (COX-II) inhibitors; anti-anxiety agents; antidepressants; antiepileptic drugs; anti-Alzheimer's agents; antipsychotic drugs; antihemorrhagic agents; benzodiazepines; acetylcholinesterase inhibitors; alpha-adrenoreceptor antagonists; alpha-adrenergic receptor agonists; β-blockers; angiotensin-converting enzymes inhibitors (ACEI); serotonin (5-HT) reuptake inhibitors; serotonin and noradrenaline reuptake inhibitors (SNRIs); serotonin 1A (5-HT1A) agonists or antagonists; antibody medicament; antirheumatic drug; therapeutic monoclonal antibodies; and anticancer medications.

21. The pharmaceutical composition of claim 17 formulated for oral, parenteral, and/or transmucosal administration.

22. A method of inhibiting or modulating an endocannabinoid hydrolase, comprising contacting the endocannabinoid hydrolase with the compound of claim 1.

23. The method of claim 22, wherein the endocannabinoid hydrolase is a serine hydrolase enzyme.

24. The method of claim 23, wherein the serine hydrolase enzyme is a monoacylglycerol lipase (MAGL) enzyme.

25. A method of modulating or inhibiting monoacylglycerol lipase (MAGL) in a subject in need thereof, comprising administering to the subject the compound of claim 1.

26. A method of treating a disease, disorder, or condition which benefits from inhibition or modulation of monoacylglycerol lipase (MAGL) activity, comprising administering to a subject in need thereof the compound of claim 1.

27. The method according to claim 26, wherein the disease, disorder, or condition is selected from the group consisting of: a neurodegenerative disorder; primary tauopathies; neuropathy; withdrawal syndrome; metabolic disorder; burning feet syndrome; ischemia; nausea; vomiting or emesis; an eating disorder; a kidney disease; an eye disease; a lung disorder; osteoarthritis; osteoporosis; bipolar disease; depression; schizophrenia; sleeping sickness; cerebral palsy; cerebral edema; meningitis; cachexia; sleep apnea; De Vivo disease; spasticity; dystonia; progressive multifocal leukoencephalopathy; dyskinesia; tremor; hearing loss; insomnia; Tourette's syndrome; autism, bladder dysfunction, chronic motor or vocal tic disorder; trichotillomania; cognitive impairment; an inflammatory disorder; an autoimmune disease; a demyelinating disease; neuromyelitis optica; a disorder of the immune system; post-traumatic stress disorder (PTSD); acute stress disorder; panic disorder; substance-induced anxiety; obsessive-compulsive disorder (OCD); agoraphobia; a specific phobia; social phobia; anxiety disorder; attention deficit disorder (ADD); attention deficit hyperactivity disorder (ADHD); and Asperger's syndrome.

\* \* \* \* \*